US010960008B2

(12) United States Patent
Zhao et al.

(10) Patent No.: US 10,960,008 B2

(45) Date of Patent: Mar. 30, 2021

(54) METHODS FOR TREATING PTEN DEFICIENT EPITHELIAL CANCERS USING A COMBINATION OF ANTI-PI3KBETA AND ANTI-IMMUNE CHECKPOINT AGENTS

(71) Applicant: Dana-Farber Cancer Institute, Inc., Boston, MA (US)

(72) Inventors: Jean Zhao, Brookline, MA (US); Johann Bergholz, Cambridge, MA (US); Gordon J. Freeman, Brookline, MA (US); Thomas M. Roberts, Cambridge, MA (US)

(73) Assignee: Dana-Farber Cancer Institute, Inc., Boston, MA (US)

(*) Notice: Subject to any disclaimer, the term of this patent is extended or adjusted under 35 U.S.C. 154(b) by 4 days.

(21) Appl. No.: 16/315,298

(22) PCT Filed: Jul. 11, 2017

(86) PCT No.: PCT/US2017/041490

§ 371 (c)(1),
(2) Date: Jan. 4, 2019

(87) PCT Pub. No.: WO2018/013534

PCT Pub. Date: Jan. 18, 2018

(65) Prior Publication Data

US 2019/0298728 A1 Oct. 3, 2019

Related U.S. Application Data

(60) Provisional application No. 62/360,596, filed on Jul. 11, 2016.

(51) Int. Cl.

| | |
|---|---|
| ***A61K 31/5377*** | (2006.01) |
| ***A61K 47/68*** | (2017.01) |
| ***A61P 35/04*** | (2006.01) |
| ***A01K 67/027*** | (2006.01) |
| ***A61K 31/7105*** | (2006.01) |
| ***A61K 31/713*** | (2006.01) |
| ***C07K 16/32*** | (2006.01) |
| ***C12Q 1/6827*** | (2018.01) |
| ***C12Q 1/6886*** | (2018.01) |
| ***A61K 45/06*** | (2006.01) |

(52) U.S. Cl.

CPC ...... *A61K 31/5377* (2013.01); *A01K 67/0278* (2013.01); *A61K 31/713* (2013.01); *A61K 31/7105* (2013.01); *A61K 47/6803* (2017.08); *A61P 35/04* (2018.01); *C07K 16/32* (2013.01); *C12Q 1/6827* (2013.01); *C12Q 1/6886* (2013.01); *A01K 2227/105* (2013.01); *A01K 2267/0331* (2013.01); *A61K 45/06* (2013.01)

(58) Field of Classification Search

CPC ........... A61K 31/5377; A61K 31/7105; A61K 31/713; A61K 47/6803; A61K 45/06; A61P 35/00; A61P 35/04; C07K 16/32; C12Q 1/6886; C12Q 1/6827; A01K 2227/105; A01K 2267/0331; A01K 67/0278

See application file for complete search history.

(56) References Cited

U.S. PATENT DOCUMENTS

| | | | |
|---|---|---|---|
| 9,399,028 B2 * | 7/2016 | Tavazoie | A61P 43/00 |
| 2012/0088767 A1 * | 4/2012 | Qu | C07D 403/04 514/234.5 |
| 2015/0118222 A1 | 4/2015 | Levy et al. | |
| 2015/0361095 A1 | 12/2015 | Du et al. | |
| 2017/0049790 A1 * | 2/2017 | Altieri | A61K 31/4745 |

FOREIGN PATENT DOCUMENTS

| | | |
|---|---|---|
| WO | WO-2015/184061 A2 | 12/2015 |
| WO | WO-2016/024228 A1 | 2/2016 |

OTHER PUBLICATIONS

Shepherd et al. (Cancer Discovery, May 2012, p. 393-394) (Year: 2012).*

Ni et al. (Cancer Discov, 2, 5, OF1-OF9, 2012) (Year: 2012).*

PTEN, Cancer Genetics Web (PTEN, Cancer genetics web, http://www.cancerindex.org/geneweb/PTEN.htm, 2019) (Year: 2019).*

Cetintas, (J Transl Med, 2020, 18:45, p. 1-11). (Year: 2020).*

Alfieri, Frontiers in Oncology, vol. 7, Aug. 9, 2017, p. 1-8 (Year: 2017).*

Golub et al. (Science, 1999, 286, 531-537). (Year: 1999).*

Notification of Transmittal of the International Search Report and the Written Opinion and the International Search Report and Written Opinion for International Application No. PCT/US2017/041490 dated Oct. 20, 2017, 11 pages.

Labanca et al., "A Combinatorial Investigation of the Response to Anti-angiogenic Therapy in Breast Cancer: New Strategies for Patient Selection and Opportunities for Reconsidering Anti-VEGF, Anti-PI3K and Checkpoint Inhibition," EBioMedicine, 10:13-14 (2016).

Peng et al., "Loss of PTEN promotes resistance to T cell-mediated immunotherapy," Cancer Discov, 6(2):202-216 (2016).

Bradford et al,. "Assessing the efficacy of targeting the phosphatidylinositol 3-kinase/AKT/mTOR signaling pathway in endometrial cancer," Gynecologic Oncology, 133(2): 346-352 (2014).

Extended European Search Report for EP Application No. EP 17828280.2 dated Mar. 4, 2020.

Hyman et al., "Parallel phase Ib studies of two schedules of buparlisib (BKM120) plus carboplatin and paclitaxel (q21 days or q28 days) for patients with advanced solid tumors," Cancer Chemotherapy and Pharmacology, 75(4): 747-755 (2015).

(Continued)

*Primary Examiner* — Umamaheswari Ramachandran

(74) *Attorney, Agent, or Firm* — Foley Hoag LLP

(57) ABSTRACT

The present invention relates to methods for treating PTEN deficient epithelial cancers using a combination of anti-PI3Kbeta and anti-immune checkpoint agents.

18 Claims, 18 Drawing Sheets

Specification includes a Sequence Listing.

(56) References Cited

OTHER PUBLICATIONS

Shee et al., "MP88-18 A Novel, Integrated Gene Expression and Drug Sensitivity Approach Reveals Unique Sensitivity of Squamous Cell Carcinoma-Like Bladder Cancers to PI3Kβ Inhibitor AZD6482," The Journal of Urology, 197(4S): e1181 (2017).
Smyth et al., "A phase 1b dose expansion study of the pan-class I PI3K inhibitor buparlisib (BKM120) plus carboplatin and paclitaxel in PTEN deficient tumors and with dose intensified carboplatin and paclitaxel", Investigational New Drugs, 35(6): 742-750 (2017).
Zhang et al,. "Addition of the p110α inhibitor BYL719 overcomes targeted therapy resistance in cells from Her2-positive-PTEN-loss breast cancer," Tumor Biology, 37(11): 14831-14839 (2016).

* cited by examiner a)

b)

c)

a)

b)

A

B

SEQUENCE LISTING

<160> NUMBER OF SEQ ID NOS: 54

<210> SEQ ID NO 1
<211> LENGTH: 3207
<212> TYPE: DNA
<213> ORGANISM: Homo sapiens

<400> SEQUENCE: 1

```
atgcctccac gaccatcatc aggtgaactg tggggcatcc acttgatgcc cccaagaatc      60
ctagtagaat gtttactacc aaatggaatg atagtgactt tagaatgcct ccgtgaggct     120
acattaataa ccataaagca tgaactattt aaagaagcaa gaaaataccc cctccatcaa     180
cttcttcaag atgaatcttc ttacattttc gtaagtgtta ctcaagaagc agaaagggaa     240
gaattttttg atgaaacaag acgactttgt gaccttcggc tttttcaacc ctttttaaaa     300
gtaattgaac cagtaggcaa ccgtgaagaa aagatcctca atcgagaaat tggttttgct     360
atcggcatgc cagtgtgtga atttgatatg gttaaagatc cagaagtaca ggacttccga     420
agaaatattc tgaacgtttg taaagaagct gtggatctta gggacctcaa ttcacctcat     480
agtagagcaa tgtatgtcta tcctccaaat gtagaatctt caccagaatt gccaaagcac     540
atatataata aattagataa agggcaaata atagtggtga tctgggtaat agtttctcca     600
aataatgaca agcagaagta tactctgaaa atcaaccatg actgtgtacc agaacaagta     660
attgctgaag caatcaggaa aaaaactcga agtatgttgc tatcctctga acaactaaaa     720
ctctgtgttt tagaatatca gggcaagtat attttaaaag tgtgtggatg tgatgaatac     780
ttcctagaaa aatatcctct gagtcagtat aagtatataa gaagctgtat aatgcttggg     840
aggatgccca atttgatgtt gatggctaaa gaaagccttt attctcaact gccaatggac     900
tgttttacaa tgccatctta ttccagacgc atttccacag ctacaccata tatgaatgga     960
gaaacatcta caaaatccct ttgggttata aatagtgcac tcagaataaa aattctttgt    1020
gcaacctacg tgaatgtaaa tattcgagac attgataaga tctatgttcg aacaggtatc    1080
taccatggag gagaaccctt atgtgacaat gtgaacactc aaagagtacc ttgttccaat    1140
cccaggtgga atgaatggct gaattatgat atatacattc ctgatcttcc tcgtgctgct    1200
cgactttgcc tttccatttg ctctgttaaa ggccgaaagg gtgctaaaga ggaacactgt    1260
ccattggcat ggggaaatat aaacttgttt gattacacag acactctagt atctggaaaa    1320
atggctttga atctttggcc agtacctcat ggattagaag atttgctgaa ccctattggt    1380
gttactggat caaatccaaa taaagaaact ccatgcttag agttggagtt tgactggttc    1440
agcagtgtgg taaagttccc agatatgtca gtgattgaag agcatgccaa ttggtctgta    1500
tcccgagaag caggatttag ctattcccac gcaggactga gtaacagact agctagagac    1560
aatgaattaa gggaaaatga caaagaacag ctcaaagcaa tttctacacg agatcctctc    1620
tctgaaatca ctgagcagga gaaagatttt ctatggagtc acagacacta ttgtgtaact    1680
atccccgaaa ttctacccaa attgcttctg tctgttaaat ggaattctag agatgaagta    1740
gcccagatgt attgcttggt aaaagattgg cctccaatca aacctgaaca ggctatggaa    1800
cttctggact gtaattaccc agatcctatg gttcgaggtt ttgctgttcg gtgcttggaa    1860
aaatatttaa cagatgacaa actttctcag tatttaattc agctagtaca ggtcctaaaa    1920
tatgaacaat atttggataa cttgcttgtg agatttttac tgaagaaagc attgactaat    1980
caaaggattg ggcacttttt cttttggcat ttaaaatctg agatgcacaa taaaacagtt    2040
agccagaggt ttggcctgct tttggagtcc tattgtcgtg catgtgggat gtatttgaag    2100
```

```
cacctgaata ggcaagtcga ggcaatggaa aagctcatta acttaactga cattctcaaa   2160

caggagaaga aggatgaaac acaaaaggta cagatgaagt ttttagttga gcaaatgagg   2220

cgaccagatt tcatggatgc tctacagggc tttctgtctc ctctaaaccc tgctcatcaa   2280

ctaggaaacc tcaggcttga agagtgtcga attatgtcct ctgcaaaaag gccactgtgg   2340

ttgaattggg agaacccaga catcatgtca gagttactgt ttcagaacaa tgagatcatc   2400

tttaaaaatg gggatgattt acggcaagat atgctaacac ttcaaattat tcgtattatg   2460

gaaaatatct ggcaaaatca aggtcttgat cttcgaatgt taccttatgg ttgtctgtca   2520

atcggtgact gtgtgggact tattgaggtg gtgcgaaatt ctcacactat tatgcaaatt   2580

cagtgcaaag gcggcttgaa aggtgcactg cagttcaaca gccacacact acatcagtgg   2640

ctcaaagaca agaacaaagg agaaatatat gatgcagcca ttgacctgtt tacacgttca   2700

tgtgctggat actgtgtagc taccttcatt ttgggaattg gagatcgtca caatagtaac   2760

atcatggtga aagacgatgg acaactgttt catatagatt ttggacactt tttggatcac   2820

aagaagaaaa aatttggtta taaacgagaa cgtgtgccat ttgttttgac acaggatttc   2880

ttaatagtga ttagtaaagg agcccaagaa tgcacaaaga caagagaatt tgagaggttt   2940

caggagatgt gttacaaggc ttatctagct attcgacagc atgccaatct cttcataaat   3000

cttttctcaa tgatgcttgg ctctggaatg ccagaactac aatcttttga tgacattgca   3060

tacattcgaa agaccctagc cttagataaa actgagcaag aggctttgga gtatttcatg   3120

aaacaaatga atgatgcaca tcatggtggc tggacaacaa aaatggattg gatcttccac   3180

acaattaaac agcatgcatt gaactga                                      3207
```

```
<210> SEQ ID NO 2
<211> LENGTH: 1068
<212> TYPE: PRT
<213> ORGANISM: Homo sapiens

<400> SEQUENCE: 2

Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Ile Thr Ile Lys His Glu
        35                  40                  45

Leu Phe Lys Glu Ala Arg Lys Tyr Pro Leu His Gln Leu Leu Gln Asp
    50                  55                  60

Glu Ser Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
            100                 105                 110

Leu Asn Arg Glu Ile Gly Phe Ala Ile Gly Met Pro Val Cys Glu Phe
        115                 120                 125

Asp Met Val Lys Asp Pro Glu Val Gln Asp Phe Arg Arg Asn Ile Leu
    130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175
```

```
Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
        195                 200                 205

Leu Lys Ile Asn His Asp Cys Val Pro Glu Gln Val Ile Ala Glu Ala
    210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                245                 250                 255

Cys Asp Glu Tyr Phe Leu Glu Lys Tyr Pro Leu Ser Gln Tyr Lys Tyr
            260                 265                 270

Ile Arg Ser Cys Ile Met Leu Gly Arg Met Pro Asn Leu Met Leu Met
        275                 280                 285

Ala Lys Glu Ser Leu Tyr Ser Gln Leu Pro Met Asp Cys Phe Thr Met
    290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
                325                 330                 335

Lys Ile Leu Cys Ala Thr Tyr Val Asn Val Asn Ile Arg Asp Ile Asp
            340                 345                 350

Lys Ile Tyr Val Arg Thr Gly Ile Tyr His Gly Gly Glu Pro Leu Cys
        355                 360                 365

Asp Asn Val Asn Thr Gln Arg Val Pro Cys Ser Asn Pro Arg Trp Asn
    370                 375                 380

Glu Trp Leu Asn Tyr Asp Ile Tyr Ile Pro Asp Leu Pro Arg Ala Ala
385                 390                 395                 400

Arg Leu Cys Leu Ser Ile Cys Ser Val Lys Gly Arg Lys Gly Ala Lys
                405                 410                 415

Glu Glu His Cys Pro Leu Ala Trp Gly Asn Ile Asn Leu Phe Asp Tyr
            420                 425                 430

Thr Asp Thr Leu Val Ser Gly Lys Met Ala Leu Asn Leu Trp Pro Val
        435                 440                 445

Pro His Gly Leu Glu Asp Leu Leu Asn Pro Ile Gly Val Thr Gly Ser
    450                 455                 460

Asn Pro Asn Lys Glu Thr Pro Cys Leu Glu Leu Glu Phe Asp Trp Phe
465                 470                 475                 480

Ser Ser Val Val Lys Phe Pro Asp Met Ser Val Ile Glu Glu His Ala
                485                 490                 495

Asn Trp Ser Val Ser Arg Glu Ala Gly Phe Ser Tyr Ser His Ala Gly
            500                 505                 510

Leu Ser Asn Arg Leu Ala Arg Asp Asn Glu Leu Arg Glu Asn Asp Lys
        515                 520                 525

Glu Gln Leu Lys Ala Ile Ser Thr Arg Asp Pro Leu Ser Glu Ile Thr
    530                 535                 540

Glu Gln Glu Lys Asp Phe Leu Trp Ser His Arg His Tyr Cys Val Thr
545                 550                 555                 560

Ile Pro Glu Ile Leu Pro Lys Leu Leu Leu Ser Val Lys Trp Asn Ser
                565                 570                 575

Arg Asp Glu Val Ala Gln Met Tyr Cys Leu Val Lys Asp Trp Pro Pro
            580                 585                 590
```

```
Ile Lys Pro Glu Gln Ala Met Glu Leu Leu Asp Cys Asn Tyr Pro Asp
        595                 600                 605

Pro Met Val Arg Gly Phe Ala Val Arg Cys Leu Glu Lys Tyr Leu Thr
    610                 615                 620

Asp Asp Lys Leu Ser Gln Tyr Leu Ile Gln Leu Val Gln Val Leu Lys
625                 630                 635                 640

Tyr Glu Gln Tyr Leu Asp Asn Leu Leu Val Arg Phe Leu Leu Lys Lys
                645                 650                 655

Ala Leu Thr Asn Gln Arg Ile Gly His Phe Phe Phe Trp His Leu Lys
            660                 665                 670

Ser Glu Met His Asn Lys Thr Val Ser Gln Arg Phe Gly Leu Leu Leu
        675                 680                 685

Glu Ser Tyr Cys Arg Ala Cys Gly Met Tyr Leu Lys His Leu Asn Arg
    690                 695                 700

Gln Val Glu Ala Met Glu Lys Leu Ile Asn Leu Thr Asp Ile Leu Lys
705                 710                 715                 720

Gln Glu Lys Lys Asp Glu Thr Gln Lys Val Gln Met Lys Phe Leu Val
                725                 730                 735

Glu Gln Met Arg Arg Pro Asp Phe Met Asp Ala Leu Gln Gly Phe Leu
            740                 745                 750

Ser Pro Leu Asn Pro Ala His Gln Leu Gly Asn Leu Arg Leu Glu Glu
        755                 760                 765

Cys Arg Ile Met Ser Ser Ala Lys Arg Pro Leu Trp Leu Asn Trp Glu
    770                 775                 780

Asn Pro Asp Ile Met Ser Glu Leu Leu Phe Gln Asn Asn Glu Ile Ile
785                 790                 795                 800

Phe Lys Asn Gly Asp Asp Leu Arg Gln Asp Met Leu Thr Leu Gln Ile
                805                 810                 815

Ile Arg Ile Met Glu Asn Ile Trp Gln Asn Gln Gly Leu Asp Leu Arg
            820                 825                 830

Met Leu Pro Tyr Gly Cys Leu Ser Ile Gly Asp Cys Val Gly Leu Ile
        835                 840                 845

Glu Val Val Arg Asn Ser His Thr Ile Met Gln Ile Gln Cys Lys Gly
    850                 855                 860

Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu
                885                 890                 895

Phe Thr Arg Ser Cys Ala Gly Tyr Cys Val Ala Thr Phe Ile Leu Gly
            900                 905                 910

Ile Gly Asp Arg His Asn Ser Asn Ile Met Val Lys Asp Asp Gly Gln
        915                 920                 925

Leu Phe His Ile Asp Phe Gly His Phe Leu Asp His Lys Lys Lys Lys
    930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Cys Thr Lys Thr Arg Glu
                965                 970                 975

Phe Glu Arg Phe Gln Glu Met Cys Tyr Lys Ala Tyr Leu Ala Ile Arg
            980                 985                 990

Gln His Ala Asn Leu Phe Ile Asn  Leu Phe Ser Met Met  Leu Gly Ser
        995                 1000                 1005

Gly Met  Pro Glu Leu Gln Ser  Phe Asp Asp Ile Ala  Tyr Ile Arg
```

```
    1010                1015                1020

Lys Thr  Leu Ala Leu Asp Lys  Thr Glu Gln Glu Ala  Leu Glu Tyr
    1025                1030                1035

Phe Met  Lys Gln Met Asn Asp  Ala His His Gly Gly  Trp Thr Thr
    1040                1045                1050

Lys Met  Asp Trp Ile Phe His  Thr Ile Lys Gln His  Ala Leu Asn
    1055                1060                1065
```

<210> SEQ ID NO 3
<211> LENGTH: 3207
<212> TYPE: DNA
<213> ORGANISM: Mus musculus

<400> SEQUENCE: 3

```
atgcctccac gaccatcttc gggtgaactg tggggcatcc acttgatgcc cccacgaatc     60
ctagtggaat gtttactccc caatggaatg atagtgactt tagaatgcct ccgtgaggcc    120
acactcgtca ccatcaaaca tgaactgttc agagaggcca ggaaataccc tctccatcag    180
cttctgcaag acgaaacttc ttacattttc gtaagtgtca cccaagaagc agaaagggaa    240
gaatttttg atgaaacaag acgactttgt gaccttcggc tttttcaacc ctttttaaaa     300
gttattgaac cagtaggcaa ccgtgaagaa aagatcctca atcgagaaat tggttttgtt    360
attggcatgc cagtgtgtga atttgatatg gttaaagatc cagaagtcca agactttcga    420
aggaacattc tgaatgtttg caaagaagct gtggacctgc gggatctcaa ctcgcctcat    480
agcagagcaa tgtatgtcta ccctccaaat gtcgagtctt ccccagaact gccaaagcac    540
atctacaaca agttagataa aggacaaatc atagtggtga tttgggtaat agtctctcca    600
aacaacgaca agcagaagta cactctgaag atcaatcatg actgtgtgcc agagcaagtc    660
attgctgaag ccatcaggaa aaagactcgg agcatgttgt tgtcctctga gcagctgaaa    720
ctctgtgtct tagaatatca gggcaagtat attctgaaag tgtgtggctg tgacgaatac    780
ttcctggaaa agtaccctct gagtcagtac aagtacataa gaagctgtat aatgctgggg    840
aggatgccca acttgatgct gatggccaaa gaaagcctat actctcagct gccgattgat    900
agcttcacca tgccgtcata ctccaggcgc atctccacag ccacacccta catgaatgga    960
gagacatcta cgaaatccct ctgggtcata aatagtgcgc tcagaataaa aattctttgt   1020
gcaacctatg taaatgtaaa tattcgagac attgataaga tctatgttcg aacaggtatc   1080
taccatggag gagaaccctt atgtgacaat gtgaacactc aaagagtacc ttgttccaat   1140
cctaggtgga atgaatggct gaattatgat atatacattc ctgatcttcc tcgtgctgcg   1200
cgcctttgcc tttcaatctg ctctgttaaa ggccgaaagg gtgctaagga ggagcactgt   1260
ccgttggcct ggggaaacat aaacttgttt gattatacag acaccctagt gtccgggaaa   1320
atggctttga atctctggcc tgtaccgcat gggttagaag atctgctgaa ccctattggt   1380
gttactgggt caaatccaaa taaagaaact ccatgcttag agttggagtt tgattggttc   1440
agcagtgtgg tgaagtttcc agacatgtct gtgatcgaag aacatgccaa ttggtccgtg   1500
tcccgagaag ctggattcag ttactcccat acaggactga gtaacagact agccagagac   1560
aatgagttaa gagaaaatga caaggaacag ctccgagcac tttgcacccg ggacccacta   1620
tctgaaatca ctgaacaaga gaaagacttc ctatggagcc acagacacta ctgcgtaact   1680
attcctgaaa tcctacccaa attgcttctg tctgtcaagt ggaattccag agacgaagtg   1740
gcccagatgt actgcttagt aaaagattgg cctccaatca aaccagagca agccatggaa   1800
```

```
ctcctggact gtaactatcc agatcctatg gttcggagtt ttgctgttcg gtgcttagaa   1860

aaatatttaa cagatgacaa actttctcag tacctcattc aacttgtaca ggtcttaaaa   1920

tatgaacagt atttggataa cctgcttgtg agatttttac tcaagaaagc attgacaaat   1980

caaaggattg gccatttttt cttttggcat ttaaaatctg agatgcacaa taagactgtc   2040

agtcagaggt ttggcctgct attggagtcc tactgccgtg cctgtgggat gtatctgaag   2100

cacctgaaca gacaagtaga ggccatggag aagctcatca acctaacgga catccttaag   2160

caggagaaga aggatgagac acaaaaggta cagatgaagt tttggttga acagatgaga    2220

cagccagact tcatggatgc tttgcagggt tttctgtccc ctctgaatcc tgctcaccaa   2280

ctaggaaacc tcaggcttga agagtgtcga attatgtcct ctgcaaaaag gccactgtgg   2340

ttgaattggg agaacccaga catcatgtca gagctactgt ttcagaacaa tgagatcatc   2400

tttaaaaatg gcgacgactt acggcaagat atgttaaccc ttcagatcat ccgaatcatg   2460

gagaacatct ggcaaaacca aggccttgac cttcgcatgc taccttatgg ctgtctatcc   2520

attggggact gtgtgggtct catcgaggtg gtgagaaact ctcacaccat catgcaaatc   2580

cagtgcaaag gaggcctgaa gggggcgctg cagttcaaca gccacacact gcatcaatgg   2640

ctcaaggaca agaacaaggg cgagatatat gatgcagcca ttgacctgtt cactcggtcc   2700

tgcgctgggt actgcgtggc aacctttatc ttgggaattg gagaccggca caacagcaac   2760

atcatggtga aagatgacgg acagctgttt catatagatt ttgggcactt tttggatcac   2820

aagaagaaaa aatttggcta taagcgggaa cgtgtgccat ttgtgttgac acaggatttc   2880

ttgattgtga ttagtaaggg agcacaagag tacaccaaga ccagagagtt tgagaggttt   2940

caggagatgt gttacaaggc ttacctagca attcggcagc atgccaatct cttcatcaac   3000

ctttttttcaa tgatgcttgg ctctggaatg ccagaactac aatcttttga tgacattgca  3060

tatatccgaa agactctagc cttggacaaa actgagcaag aagctttgga atatttcaca   3120

aagcaaatga atgatgcaca tcatggtgga tggacgacaa aaatggattg gatcttccac   3180

accatcaagc agcatgcttt gaactga                                       3207
```

```
<210> SEQ ID NO 4
<211> LENGTH: 1068
<212> TYPE: PRT
<213> ORGANISM: Mus musculus

<400> SEQUENCE: 4

Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Val Thr Ile Lys His Glu
        35                  40                  45

Leu Phe Arg Glu Ala Arg Lys Tyr Pro Leu His Gln Leu Leu Gln Asp
    50                  55                  60

Glu Thr Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
            100                 105                 110

Leu Asn Arg Glu Ile Gly Phe Val Ile Gly Met Pro Val Cys Glu Phe
        115                 120                 125
```

```
Asp Met Val Lys Asp Pro Glu Val Gln Asp Phe Arg Arg Asn Ile Leu
    130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
        195                 200                 205

Leu Lys Ile Asn His Asp Cys Val Pro Glu Gln Val Ile Ala Glu Ala
    210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                245                 250                 255

Cys Asp Glu Tyr Phe Leu Glu Lys Tyr Pro Leu Ser Gln Tyr Lys Tyr
            260                 265                 270

Ile Arg Ser Cys Ile Met Leu Gly Arg Met Pro Asn Leu Met Leu Met
        275                 280                 285

Ala Lys Glu Ser Leu Tyr Ser Gln Leu Pro Ile Asp Ser Phe Thr Met
    290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
                325                 330                 335

Lys Ile Leu Cys Ala Thr Tyr Val Asn Val Asn Ile Arg Asp Ile Asp
            340                 345                 350

Lys Ile Tyr Val Arg Thr Gly Ile Tyr His Gly Gly Glu Pro Leu Cys
        355                 360                 365

Asp Asn Val Asn Thr Gln Arg Val Pro Cys Ser Asn Pro Arg Trp Asn
    370                 375                 380

Glu Trp Leu Asn Tyr Asp Ile Tyr Ile Pro Asp Leu Pro Arg Ala Ala
385                 390                 395                 400

Arg Leu Cys Leu Ser Ile Cys Ser Val Lys Gly Arg Lys Gly Ala Lys
                405                 410                 415

Glu Glu His Cys Pro Leu Ala Trp Gly Asn Ile Asn Leu Phe Asp Tyr
            420                 425                 430

Thr Asp Thr Leu Val Ser Gly Lys Met Ala Leu Asn Leu Trp Pro Val
        435                 440                 445

Pro His Gly Leu Glu Asp Leu Leu Asn Pro Ile Gly Val Thr Gly Ser
    450                 455                 460

Asn Pro Asn Lys Glu Thr Pro Cys Leu Glu Leu Glu Phe Asp Trp Phe
465                 470                 475                 480

Ser Ser Val Val Lys Phe Pro Asp Met Ser Val Ile Glu Glu His Ala
                485                 490                 495

Asn Trp Ser Val Ser Arg Glu Ala Gly Phe Ser Tyr Ser His Thr Gly
            500                 505                 510

Leu Ser Asn Arg Leu Ala Arg Asp Asn Glu Leu Arg Glu Asn Asp Lys
        515                 520                 525

Glu Gln Leu Arg Ala Leu Cys Thr Arg Asp Pro Leu Ser Glu Ile Thr
    530                 535                 540
```

```
Glu Gln Glu Lys Asp Phe Leu Trp Ser His Arg His Tyr Cys Val Thr
545                 550                 555                 560

Ile Pro Glu Ile Leu Pro Lys Leu Leu Leu Ser Val Lys Trp Asn Ser
                565                 570                 575

Arg Asp Glu Val Ala Gln Met Tyr Cys Leu Val Lys Asp Trp Pro Pro
            580                 585                 590

Ile Lys Pro Glu Gln Ala Met Glu Leu Leu Asp Cys Asn Tyr Pro Asp
        595                 600                 605

Pro Met Val Arg Ser Phe Ala Val Arg Cys Leu Glu Lys Tyr Leu Thr
    610                 615                 620

Asp Asp Lys Leu Ser Gln Tyr Leu Ile Gln Leu Val Gln Val Leu Lys
625                 630                 635                 640

Tyr Glu Gln Tyr Leu Asp Asn Leu Leu Val Arg Phe Leu Leu Lys Lys
                645                 650                 655

Ala Leu Thr Asn Gln Arg Ile Gly His Phe Phe Phe Trp His Leu Lys
            660                 665                 670

Ser Glu Met His Asn Lys Thr Val Ser Gln Arg Phe Gly Leu Leu Leu
        675                 680                 685

Glu Ser Tyr Cys Arg Ala Cys Gly Met Tyr Leu Lys His Leu Asn Arg
    690                 695                 700

Gln Val Glu Ala Met Glu Lys Leu Ile Asn Leu Thr Asp Ile Leu Lys
705                 710                 715                 720

Gln Glu Lys Lys Asp Glu Thr Gln Lys Val Gln Met Lys Phe Leu Val
                725                 730                 735

Glu Gln Met Arg Gln Pro Asp Phe Met Asp Ala Leu Gln Gly Phe Leu
            740                 745                 750

Ser Pro Leu Asn Pro Ala His Gln Leu Gly Asn Leu Arg Leu Glu Glu
        755                 760                 765

Cys Arg Ile Met Ser Ser Ala Lys Arg Pro Leu Trp Leu Asn Trp Glu
    770                 775                 780

Asn Pro Asp Ile Met Ser Glu Leu Leu Phe Gln Asn Asn Glu Ile Ile
785                 790                 795                 800

Phe Lys Asn Gly Asp Asp Leu Arg Gln Asp Met Leu Thr Leu Gln Ile
                805                 810                 815

Ile Arg Ile Met Glu Asn Ile Trp Gln Asn Gln Gly Leu Asp Leu Arg
            820                 825                 830

Met Leu Pro Tyr Gly Cys Leu Ser Ile Gly Asp Cys Val Gly Leu Ile
        835                 840                 845

Glu Val Val Arg Asn Ser His Thr Ile Met Gln Ile Gln Cys Lys Gly
    850                 855                 860

Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu
                885                 890                 895

Phe Thr Arg Ser Cys Ala Gly Tyr Cys Val Ala Thr Phe Ile Leu Gly
            900                 905                 910

Ile Gly Asp Arg His Asn Ser Asn Ile Met Val Lys Asp Asp Gly Gln
        915                 920                 925

Leu Phe His Ile Asp Phe Gly His Phe Leu Asp His Lys Lys Lys Lys
    930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Tyr Thr Lys Thr Arg Glu
```

```
                965                 970                 975

Phe Glu Arg Phe Gln Glu Met Cys Tyr Lys Ala Tyr Leu Ala Ile Arg
            980                 985                 990

Gln His Ala Asn Leu Phe Ile Asn  Leu Phe Ser Met Met  Leu Gly Ser
        995                 1000                 1005

Gly Met  Pro Glu Leu Gln Ser  Phe Asp Asp Ile Ala  Tyr Ile Arg
    1010                 1015                 1020

Lys Thr  Leu Ala Leu Asp Lys  Thr Glu Gln Glu Ala  Leu Glu Tyr
    1025                 1030                 1035

Phe Thr  Lys Gln Met Asn Asp  Ala His His Gly Gly  Trp Thr Thr
    1040                 1045                 1050

Lys Met  Asp Trp Ile Phe His  Thr Ile Lys Gln His  Ala Leu Asn
    1055                 1060                 1065
```

<210> SEQ ID NO 5
<211> LENGTH: 3207
<212> TYPE: DNA
<213> ORGANISM: Mus musculus

<400> SEQUENCE: 5

```
atgcctccac gaccatcttc gggtgaactg tggggcatcc acttgatgcc cccacgaatc     60
ctagtggaat gtttactccc caatggaatg atagtgactt tagaatgcct ccgtgaggcc    120
acactcgtca ccatcaaaca tgaactgttc agagaggcca ggaaataccc tctccatcag    180
cttctgcaag acgaaacttc ttacattttc gtaagtgtca cccaagaagc agaaagggaa    240
gaatttttg atgaaacaag acgactttgt gaccttcggc tttttcaacc ctttttaaaa     300
gttattgaac cagtaggcaa ccgtgaagaa aagatcctca atcgagaaat tggttttgtt    360
attggcatgc cagtgtgtga atttgatatg gttaaagatc cagaagtcca agactttcga    420
aggaacattc tgaatgtttg caaagaagct gtggacctgc gggatctcaa ctcgcctcat    480
agcagagcaa tgtatgtcta ccctccaaat gtcgagtctt ccccagaact gccaaagcac    540
atctacaaca agttagataa aggacaaatc atagtggtga tttgggtaat agtctctcca    600
aacaacgaca agcagaagta cactctgaag atcaatcatg actgtgtgcc agagcaagtc    660
attgctgaag ccatcaggaa aaagactcgg agcatgttgt tgtcctctga gcagctgaaa    720
ctctgtgtct tagaatatca gggcaagtat attctgaaag tgtgtggctg tgacgaatac    780
ttcctggaaa agtaccctct gagtcagtac aagtacataa gaagctgtat aatgctgggg    840
aggatgccca acttgatgct gatggccaaa gaaagcctat actctcagct gccgattgat    900
agcttcacca tgccgtcata ctccaggcgc atctccacag ccacacccta catgaatgga    960
gagacatcta cgaaatccct ctgggtcata aatagtgcgc tcagaataaa aattctttgt   1020
gcaacctatg taaatgtaaa tattcgagac attgataaga tctatgttcg aacaggtatc   1080
taccatggag gagaaccctt atgtgacaat gtgaacactc aaagagtacc ttgttccaat   1140
cctaggtgga atgaatggct gaattatgat atatacattc ctgatcttcc tcgtgctgcg   1200
cgcctttgcc tttcaatctg ctctgttaaa ggccgaaagg gtgctaagga ggagcactgt   1260
ccgttggcct ggggaaacat aaacttgttt gattatacag acaccctagt gtccgggaaa   1320
atggctttga atctctggcc tgtaccgcat gggttagaag atctgctgaa ccctattggt   1380
gttactgggt caaatccaaa taaagaaact ccatgcttag agttggagtt tgattggttc   1440
agcagtgtgg tgaagtttcc agacatgtct gtgatcgaag aacatgccaa ttggtccgtg   1500
tcccgagaag ctggattcag ttactcccat acaggactga gtaacagact agccagagac   1560
```

```
aatgagttaa gagaaaatga caaggaacag ctccgagcac tttgcacccg ggacccacta   1620

tctgaaatca ctgaacaaga gaaagacttc ctatggagcc acagacacta ctgcgtaact   1680

attcctgaaa tcctacccaa attgcttctg tctgtcaagt ggaattccag agacgaagtg   1740

gcccagatgt actgcttagt aaaagattgg cctccaatca aaccagagca agccatggaa   1800

ctcctggact gtaactatcc agatcctatg gttcggagtt ttgctgttcg gtgcttagaa   1860

aaatatttaa cagatgacaa actttctcag tacctcattc aacttgtaca ggtcttaaaa   1920

tatgaacagt atttggataa cctgcttgtg agatttttac tcaagaaagc attgacaaat   1980

caaaggattg gccatttttt cttttggcat ttaaaatctg agatgcacaa taagactgtc   2040

agtcagaggt ttggcctgct attggagtcc tactgccgtg cctgtgggat gtatctgaag   2100

cacctgaaca gacaagtaga ggccatggag aagctcatca acctaacgga catccttaag   2160

caggagaaga aggatgagac acaaaaggta cagatgaagt tttggttga acagatgaga   2220

cagccagact tcatggatgc tttgcagggt tttctgtccc ctctgaatcc tgctcaccaa   2280

ctaggaaacc tcaggcttga agagtgtcga attatgtcct ctgcaaaaag gccactgtgg   2340

ttgaattggg agaacccaga catcatgtca gagctactgt ttcagaacaa tgagatcatc   2400

tttaaaaatg gcgacgactt acggcaagat atgttaaccc ttcagatcat ccgaatcatg   2460

gagaacatct ggcaaaacca aggccttgac cttcgcatgc taccttatgg ctgtctatcc   2520

attggggact gtgtgggtct catcgaggtg gtgagaaact ctcacaccat catgcaaatc   2580

cagtgcaaag gaggcctgaa gggggcgctg cagttcaaca gccacacact gcatcaatgg   2640

ctcaaggaca agaacaaggg cgagatatat gatgcagcca ttgacctgtt cactcggtcc   2700

tgcgctgggt actgcgtggc aacctttatc ttgggaattg gagaccggca caacagcaac   2760

atcatggtga aagatgacgg acagctgttt catatagatt ttgggcactt tttggatcac   2820

aagaagaaaa aatttggcta taagcgggaa cgtgtgccat ttgtgttgac acaggatttc   2880

ttgattgtga ttagtaaggg agcacaagag tacaccaaga ccagagagtt tgagaggttt   2940

caggagatgt gttacaaggc ttacctagca attcggcagc atgccaatct cttcatcaac   3000

ctttttttcaa tgatgcttgg ctctggaatg ccagaactac aatcttttga tgacattgca   3060

tatatccgaa agactctagc cttggacaaa actgagcaag aagctttgga atatttcaca   3120

aagcaaatga atgatgcaca tcatggtgga tggacgacaa aaatggattg gatcttccac   3180

accatcaagc agcatgcttt gaactga                                      3207
```

<210> SEQ ID NO 6
<211> LENGTH: 1068
<212> TYPE: PRT
<213> ORGANISM: Mus musculus

<400> SEQUENCE: 6

```
Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Val Thr Ile Lys His Glu
        35                  40                  45

Leu Phe Arg Glu Ala Arg Lys Tyr Pro Leu His Gln Leu Leu Gln Asp
    50                  55                  60

Glu Thr Ser Tyr Ile Phe Val Ser Val Thr Gln Glu Ala Glu Arg Glu
65                  70                  75                  80
```

```
Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
            100                 105                 110

Leu Asn Arg Glu Ile Gly Phe Val Ile Gly Met Pro Val Cys Glu Phe
        115                 120                 125

Asp Met Val Lys Asp Pro Glu Val Gln Asp Phe Arg Arg Asn Ile Leu
    130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
        195                 200                 205

Leu Lys Ile Asn His Asp Cys Val Pro Glu Gln Val Ile Ala Glu Ala
    210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                245                 250                 255

Cys Asp Glu Tyr Phe Leu Glu Lys Tyr Pro Leu Ser Gln Tyr Lys Tyr
            260                 265                 270

Ile Arg Ser Cys Ile Met Leu Gly Arg Met Pro Asn Leu Met Leu Met
        275                 280                 285

Ala Lys Glu Ser Leu Tyr Ser Gln Leu Pro Ile Asp Ser Phe Thr Met
    290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
                325                 330                 335

Lys Ile Leu Cys Ala Thr Tyr Val Asn Val Asn Ile Arg Asp Ile Asp
            340                 345                 350

Lys Ile Tyr Val Arg Thr Gly Ile Tyr His Gly Gly Glu Pro Leu Cys
        355                 360                 365

Asp Asn Val Asn Thr Gln Arg Val Pro Cys Ser Asn Pro Arg Trp Asn
    370                 375                 380

Glu Trp Leu Asn Tyr Asp Ile Tyr Ile Pro Asp Leu Pro Arg Ala Ala
385                 390                 395                 400

Arg Leu Cys Leu Ser Ile Cys Ser Val Lys Gly Arg Lys Gly Ala Lys
                405                 410                 415

Glu Glu His Cys Pro Leu Ala Trp Gly Asn Ile Asn Leu Phe Asp Tyr
            420                 425                 430

Thr Asp Thr Leu Val Ser Gly Lys Met Ala Leu Asn Leu Trp Pro Val
        435                 440                 445

Pro His Gly Leu Glu Asp Leu Leu Asn Pro Ile Gly Val Thr Gly Ser
    450                 455                 460

Asn Pro Asn Lys Glu Thr Pro Cys Leu Glu Leu Glu Phe Asp Trp Phe
465                 470                 475                 480

Ser Ser Val Val Lys Phe Pro Asp Met Ser Val Ile Glu Glu His Ala
                485                 490                 495
```

```
Asn Trp Ser Val Ser Arg Glu Ala Gly Phe Ser Tyr Ser His Thr Gly
            500                 505                 510

Leu Ser Asn Arg Leu Ala Arg Asp Asn Glu Leu Arg Glu Asn Asp Lys
        515                 520                 525

Glu Gln Leu Arg Ala Leu Cys Thr Arg Asp Pro Leu Ser Glu Ile Thr
    530                 535                 540

Glu Gln Glu Lys Asp Phe Leu Trp Ser His Arg His Tyr Cys Val Thr
545                 550                 555                 560

Ile Pro Glu Ile Leu Pro Lys Leu Leu Leu Ser Val Lys Trp Asn Ser
                565                 570                 575

Arg Asp Glu Val Ala Gln Met Tyr Cys Leu Val Lys Asp Trp Pro Pro
            580                 585                 590

Ile Lys Pro Glu Gln Ala Met Glu Leu Leu Asp Cys Asn Tyr Pro Asp
        595                 600                 605

Pro Met Val Arg Ser Phe Ala Val Arg Cys Leu Glu Lys Tyr Leu Thr
    610                 615                 620

Asp Asp Lys Leu Ser Gln Tyr Leu Ile Gln Leu Val Gln Val Leu Lys
625                 630                 635                 640

Tyr Glu Gln Tyr Leu Asp Asn Leu Leu Val Arg Phe Leu Leu Lys Lys
                645                 650                 655

Ala Leu Thr Asn Gln Arg Ile Gly His Phe Phe Phe Trp His Leu Lys
            660                 665                 670

Ser Glu Met His Asn Lys Thr Val Ser Gln Arg Phe Gly Leu Leu Leu
        675                 680                 685

Glu Ser Tyr Cys Arg Ala Cys Gly Met Tyr Leu Lys His Leu Asn Arg
    690                 695                 700

Gln Val Glu Ala Met Glu Lys Leu Ile Asn Leu Thr Asp Ile Leu Lys
705                 710                 715                 720

Gln Glu Lys Lys Asp Glu Thr Gln Lys Val Gln Met Lys Phe Leu Val
                725                 730                 735

Glu Gln Met Arg Gln Pro Asp Phe Met Asp Ala Leu Gln Gly Phe Leu
            740                 745                 750

Ser Pro Leu Asn Pro Ala His Gln Leu Gly Asn Leu Arg Leu Glu Glu
        755                 760                 765

Cys Arg Ile Met Ser Ser Ala Lys Arg Pro Leu Trp Leu Asn Trp Glu
    770                 775                 780

Asn Pro Asp Ile Met Ser Glu Leu Leu Phe Gln Asn Asn Glu Ile Ile
785                 790                 795                 800

Phe Lys Asn Gly Asp Asp Leu Arg Gln Asp Met Leu Thr Leu Gln Ile
                805                 810                 815

Ile Arg Ile Met Glu Asn Ile Trp Gln Asn Gln Gly Leu Asp Leu Arg
            820                 825                 830

Met Leu Pro Tyr Gly Cys Leu Ser Ile Gly Asp Cys Val Gly Leu Ile
        835                 840                 845

Glu Val Val Arg Asn Ser His Thr Ile Met Gln Ile Gln Cys Lys Gly
    850                 855                 860

Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu
                885                 890                 895

Phe Thr Arg Ser Cys Ala Gly Tyr Cys Val Ala Thr Phe Ile Leu Gly
            900                 905                 910

Ile Gly Asp Arg His Asn Ser Asn Ile Met Val Lys Asp Asp Gly Gln
```

```
        915                 920                 925

Leu Phe His Ile Asp Phe Gly His Phe Leu Asp His Lys Lys Lys Lys
    930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Tyr Thr Lys Thr Arg Glu
                965                 970                 975

Phe Glu Arg Phe Gln Glu Met Cys Tyr Lys Ala Tyr Leu Ala Ile Arg
            980                 985                 990

Gln His Ala Asn Leu Phe Ile Asn  Leu Phe Ser Met Met  Leu Gly Ser
        995                 1000                1005

Gly Met  Pro Glu Leu Gln Ser  Phe Asp Asp Ile Ala  Tyr Ile Arg
    1010                1015                1020

Lys Thr  Leu Ala Leu Asp Lys  Thr Glu Gln Glu Ala  Leu Glu Tyr
    1025                1030                1035

Phe Thr  Lys Gln Met Asn Asp  Ala His His Gly Gly  Trp Thr Thr
    1040                1045                1050

Lys Met  Asp Trp Ile Phe His  Thr Ile Lys Gln His  Ala Leu Asn
    1055                1060                1065


<210> SEQ ID NO 7
<211> LENGTH: 3213
<212> TYPE: DNA
<213> ORGANISM: Homo sapiens

<400> SEQUENCE: 7

atgtgcttca gtttcataat gcctcctgct atggcagaca tccttgacat ctgggcggtg     60

gattcacaga tagcatctga tggctccata cctgtggatt tcctttttgcc cactgggatt    120

tatatccagt tggaggtacc tcgggaagct accatttctt atattaagca gatgttatgg    180

aagcaagttc acaattaccc aatgttcaac ctccttatgg atattgactc ctatatgttt    240

gcatgtgtga atcagactgc tgtatatgag gagcttgaag atgaaacacg aagactctgt    300

gatgtcagac cttttcttcc agttctcaaa ttagtgacaa gaagttgtga cccaggggaa    360

aaattagact caaaaattgg agtccttata ggaaaaggtc tgcatgaatt tgattccttg    420

aaggatcctg aagtaaatga atttcgaaga aaaatgcgca aattcagcga ggaaaaaatc    480

ctgtcacttg tgggattgtc ttggatggac tggctaaaac aaacatatcc accagagcat    540

gaaccatcca tccctgaaaa cttagaagat aaactttatg gggaaagct catcgtagct    600

gttcattttg aaaactgcca ggacgtgttt agctttcaag tgtctcctaa tatgaatcct    660

atcaaagtaa atgaattggc aatccaaaaa cgtttgacta ttcatgggaa ggaagatgaa    720

gttagcccct atgattatgt gttgcaagtc agcgggagag tagaatatgt tttggtgat    780

catccactaa ttcagttcca gtatatccgg aactgtgtga tgaacagagc cctgccccat    840

tttatacttg tggaatgctg caagatcaag aaaatgtatg aacaagaaat gattgccata    900

gaggctgcca taaatcgaaa ttcatctaat cttcctcttc cattaccacc aaagaaaaca    960

cgaattattt ctcatgtttg ggaaaataac aaccctttcc aaattgtctt ggttaaggga   1020

aataaactta acacagagga aactgtaaaa gttcatgtca gggctggtct ttttcatggt   1080

actgagctcc tgtgtaaaac catcgtaagc tcagaggtat cagggaaaaa tgatcatatt   1140

tggaatgaac cactggaatt tgatattaat atttgtgact taccaagaat ggctcgatta   1200

tgttttgctg tttatgcagt tttggataaa gtaaaaacga agaaatcaac gaaaactatt   1260
```

```
aatccctcta aatatcagac catcaggaaa gctggaaaag tgcattatcc tgtagcgtgg   1320

gtaaatacga tggtttttga ctttaaagga caattgagaa ctggagacat aatattacac   1380

agctggtctt catttcctga tgaactcgaa gaaatgttga atccaatggg aactgttcaa   1440

acaaatccat atactgaaaa tgcaacagct ttgcatgtta aatttccaga gaataaaaaa   1500

caaccttatt attaccctcc cttcgataag attattgaaa aggcagctga gattgcaagc   1560

agtgatagtg ctaatgtgtc aagtcgaggt ggaaaaaagt ttcttcctgt attgaaagaa   1620

atcttggaca gggatccctt gtctcaactg tgtgaaaatg aaatggatct tatttggact   1680

ttgcgacaag actgccgaga gattttccca caatcactgc caaaattact gctgtcaatc   1740

aagtggaata aacttgagga tgttgctcag cttcaggcgc tgcttcagat ttggcctaaa   1800

ctgccccccc gggaggccct agagcttctg gatttcaact atccagacca gtacgttcga   1860

gaatatgctg taggctgcct gcgacagatg agtgatgaag aactttctca atatctttta   1920

caactggtgc aagtgttaaa atatgagcct tttcttgatt gtgccctctc tagattccta   1980

ttagaaagag cacttggtaa tcggaggata gggcagtttc tattttggca tcttaggtca   2040

gaagtgcaca ttcctgctgt ctcagtacaa tttggtgtca tccttgaagc atactgccgg   2100

ggaagtgtgg ggcacatgaa agtgctttct aagcaggttg aagcactcaa taagttaaaa   2160

actttaaata gtttaatcaa actgaatgcc gtgaagttaa acagagccaa agggaaggag   2220

gccatgcata cctgtttaaa acagagtgct taccgggaag ccctctctga cctgcagtca   2280

cccctgaacc catgtgttat cctctcagaa ctctatgttg aaaagtgcaa atacatggat   2340

tccaaaatga agcctttgtg gctggtatac aataacaagg tatttggtga ggattcagtt   2400

ggagtgattt ttaaaaatgg tgatgattta cgacaggata tgttgacact ccaaatgttg   2460

cgcttgatgg atttactctg gaaagaagct ggtttggatc ttcggatgtt gccttatggc   2520

tgtttagcaa caggagatcg ctctggcctc attgaagttg tgagcacctc tgaaacaatt   2580

gctgacattc agctgaacag tagcaatgtg gctgctgcag cagccttcaa caaagatgcc   2640

cttctgaact ggcttaaaga atacaactct ggggatgacc tggaccgagc cattgaggaa   2700

tttacactgt cctgtgctgg ctactgtgta gcttcttatg tccttgggat tggtgacaga   2760

catagtgaca acatcatggt caaaaaaact ggccagctct tccacattga ctttggacat   2820

attcttggaa atttcaaatc taagtttggc attaaaaggg agcgagtgcc ttttattctt   2880

acctatgatt tcatccatgt cattcaacaa ggaaaaacag gaaatacaga aaagtttggc   2940

cggttccgcc agtgttgtga ggatgcatat ctgattttac gacggcatgg gaatctcttc   3000

atcactctct ttgcgctgat gttgactgca gggcttcctg aactcacatc agtcaaagat   3060

atacagtatc ttaaggactc tcttgcatta gggaagagtg aagaagaagc actcaaacag   3120

tttaagcaaa aatttgatga ggcgctcagg gaaagctgga ctactaaagt gaactggatg   3180

gcccacacag ttcggaaaga ctacagatct taa                                3213
```

<210> SEQ ID NO 8
<211> LENGTH: 1070
<212> TYPE: PRT
<213> ORGANISM: Homo sapiens

<400> SEQUENCE: 8

```
Met Cys Phe Ser Phe Ile Met Pro Pro Ala Met Ala Asp Ile Leu Asp
1               5                   10                  15

Ile Trp Ala Val Asp Ser Gln Ile Ala Ser Asp Gly Ser Ile Pro Val
            20                  25                  30
```

```
Asp Phe Leu Leu Pro Thr Gly Ile Tyr Ile Gln Leu Glu Val Pro Arg
        35                  40                  45

Glu Ala Thr Ile Ser Tyr Ile Lys Gln Met Leu Trp Lys Gln Val His
    50                  55                  60

Asn Tyr Pro Met Phe Asn Leu Leu Met Asp Ile Asp Ser Tyr Met Phe
65                  70                  75                  80

Ala Cys Val Asn Gln Thr Ala Val Tyr Glu Glu Leu Glu Asp Glu Thr
                85                  90                  95

Arg Arg Leu Cys Asp Val Arg Pro Phe Leu Pro Val Leu Lys Leu Val
            100                 105                 110

Thr Arg Ser Cys Asp Pro Gly Glu Lys Leu Asp Ser Lys Ile Gly Val
        115                 120                 125

Leu Ile Gly Lys Gly Leu His Glu Phe Asp Ser Leu Lys Asp Pro Glu
    130                 135                 140

Val Asn Glu Phe Arg Arg Lys Met Arg Lys Phe Ser Glu Glu Lys Ile
145                 150                 155                 160

Leu Ser Leu Val Gly Leu Ser Trp Met Asp Trp Leu Lys Gln Thr Tyr
                165                 170                 175

Pro Pro Glu His Glu Pro Ser Ile Pro Glu Asn Leu Glu Asp Lys Leu
            180                 185                 190

Tyr Gly Gly Lys Leu Ile Val Ala Val His Phe Glu Asn Cys Gln Asp
        195                 200                 205

Val Phe Ser Phe Gln Val Ser Pro Asn Met Asn Pro Ile Lys Val Asn
    210                 215                 220

Glu Leu Ala Ile Gln Lys Arg Leu Thr Ile His Gly Lys Glu Asp Glu
225                 230                 235                 240

Val Ser Pro Tyr Asp Tyr Val Leu Gln Val Ser Gly Arg Val Glu Tyr
                245                 250                 255

Val Phe Gly Asp His Pro Leu Ile Gln Phe Gln Tyr Ile Arg Asn Cys
            260                 265                 270

Val Met Asn Arg Ala Leu Pro His Phe Ile Leu Val Glu Cys Cys Lys
        275                 280                 285

Ile Lys Lys Met Tyr Glu Gln Glu Met Ile Ala Ile Glu Ala Ala Ile
    290                 295                 300

Asn Arg Asn Ser Ser Asn Leu Pro Leu Pro Leu Pro Pro Lys Lys Thr
305                 310                 315                 320

Arg Ile Ile Ser His Val Trp Glu Asn Asn Asn Pro Phe Gln Ile Val
                325                 330                 335

Leu Val Lys Gly Asn Lys Leu Asn Thr Glu Glu Thr Val Lys Val His
            340                 345                 350

Val Arg Ala Gly Leu Phe His Gly Thr Glu Leu Leu Cys Lys Thr Ile
        355                 360                 365

Val Ser Ser Glu Val Ser Gly Lys Asn Asp His Ile Trp Asn Glu Pro
    370                 375                 380

Leu Glu Phe Asp Ile Asn Ile Cys Asp Leu Pro Arg Met Ala Arg Leu
385                 390                 395                 400

Cys Phe Ala Val Tyr Ala Val Leu Asp Lys Val Lys Thr Lys Lys Ser
                405                 410                 415

Thr Lys Thr Ile Asn Pro Ser Lys Tyr Gln Thr Ile Arg Lys Ala Gly
            420                 425                 430

Lys Val His Tyr Pro Val Ala Trp Val Asn Thr Met Val Phe Asp Phe
        435                 440                 445
```

```
Lys Gly Gln Leu Arg Thr Gly Asp Ile Ile Leu His Ser Trp Ser Ser
    450                 455                 460

Phe Pro Asp Glu Leu Glu Glu Met Leu Asn Pro Met Gly Thr Val Gln
465                 470                 475                 480

Thr Asn Pro Tyr Thr Glu Asn Ala Thr Ala Leu His Val Lys Phe Pro
                485                 490                 495

Glu Asn Lys Lys Gln Pro Tyr Tyr Tyr Pro Pro Phe Asp Lys Ile Ile
            500                 505                 510

Glu Lys Ala Ala Glu Ile Ala Ser Ser Asp Ser Ala Asn Val Ser Ser
        515                 520                 525

Arg Gly Gly Lys Lys Phe Leu Pro Val Leu Lys Glu Ile Leu Asp Arg
    530                 535                 540

Asp Pro Leu Ser Gln Leu Cys Glu Asn Glu Met Asp Leu Ile Trp Thr
545                 550                 555                 560

Leu Arg Gln Asp Cys Arg Glu Ile Phe Pro Gln Ser Leu Pro Lys Leu
                565                 570                 575

Leu Leu Ser Ile Lys Trp Asn Lys Leu Glu Asp Val Ala Gln Leu Gln
            580                 585                 590

Ala Leu Leu Gln Ile Trp Pro Lys Leu Pro Pro Arg Glu Ala Leu Glu
        595                 600                 605

Leu Leu Asp Phe Asn Tyr Pro Asp Gln Tyr Val Arg Glu Tyr Ala Val
    610                 615                 620

Gly Cys Leu Arg Gln Met Ser Asp Glu Glu Leu Ser Gln Tyr Leu Leu
625                 630                 635                 640

Gln Leu Val Gln Val Leu Lys Tyr Glu Pro Phe Leu Asp Cys Ala Leu
                645                 650                 655

Ser Arg Phe Leu Leu Glu Arg Ala Leu Gly Asn Arg Arg Ile Gly Gln
            660                 665                 670

Phe Leu Phe Trp His Leu Arg Ser Glu Val His Ile Pro Ala Val Ser
        675                 680                 685

Val Gln Phe Gly Val Ile Leu Glu Ala Tyr Cys Arg Gly Ser Val Gly
    690                 695                 700

His Met Lys Val Leu Ser Lys Gln Val Glu Ala Leu Asn Lys Leu Lys
705                 710                 715                 720

Thr Leu Asn Ser Leu Ile Lys Leu Asn Ala Val Lys Leu Asn Arg Ala
                725                 730                 735

Lys Gly Lys Glu Ala Met His Thr Cys Leu Lys Gln Ser Ala Tyr Arg
            740                 745                 750

Glu Ala Leu Ser Asp Leu Gln Ser Pro Leu Asn Pro Cys Val Ile Leu
        755                 760                 765

Ser Glu Leu Tyr Val Glu Lys Cys Lys Tyr Met Asp Ser Lys Met Lys
    770                 775                 780

Pro Leu Trp Leu Val Tyr Asn Asn Lys Val Phe Gly Glu Asp Ser Val
785                 790                 795                 800

Gly Val Ile Phe Lys Asn Gly Asp Asp Leu Arg Gln Asp Met Leu Thr
                805                 810                 815

Leu Gln Met Leu Arg Leu Met Asp Leu Leu Trp Lys Glu Ala Gly Leu
            820                 825                 830

Asp Leu Arg Met Leu Pro Tyr Gly Cys Leu Ala Thr Gly Asp Arg Ser
        835                 840                 845

Gly Leu Ile Glu Val Val Ser Thr Ser Glu Thr Ile Ala Asp Ile Gln
    850                 855                 860

Leu Asn Ser Ser Asn Val Ala Ala Ala Ala Ala Phe Asn Lys Asp Ala
```

```
865                 870                 875                 880

Leu Leu Asn Trp Leu Lys Glu Tyr Asn Ser Gly Asp Asp Leu Asp Arg
                885                 890                 895

Ala Ile Glu Glu Phe Thr Leu Ser Cys Ala Gly Tyr Cys Val Ala Ser
            900                 905                 910

Tyr Val Leu Gly Ile Gly Asp Arg His Ser Asp Asn Ile Met Val Lys
        915                 920                 925

Lys Thr Gly Gln Leu Phe His Ile Asp Phe Gly His Ile Leu Gly Asn
    930                 935                 940

Phe Lys Ser Lys Phe Gly Ile Lys Arg Glu Arg Val Pro Phe Ile Leu
945                 950                 955                 960

Thr Tyr Asp Phe Ile His Val Ile Gln Gln Gly Lys Thr Gly Asn Thr
                965                 970                 975

Glu Lys Phe Gly Arg Phe Arg Gln Cys Cys Glu Asp Ala Tyr Leu Ile
            980                 985                 990

Leu Arg Arg His Gly Asn Leu Phe  Ile Thr Leu Phe Ala  Leu Met Leu
        995                 1000                1005

Thr Ala  Gly Leu Pro Glu Leu  Thr Ser Val Lys Asp  Ile Gln Tyr
    1010                1015                1020

Leu Lys  Asp Ser Leu Ala Leu  Gly Lys Ser Glu Glu  Glu Ala Leu
    1025                1030                1035

Lys Gln  Phe Lys Gln Lys Phe  Asp Glu Ala Leu Arg  Glu Ser Trp
    1040                1045                1050

Thr Thr  Lys Val Asn Trp Met  Ala His Thr Val Arg  Lys Asp Tyr
    1055                1060                1065

Arg Ser
    1070
```

<210> SEQ ID NO 9
<211> LENGTH: 1749
<212> TYPE: DNA
<213> ORGANISM: Homo sapiens

<400> SEQUENCE: 9

```
atgttgaatc caatgggaac tgttcaaaca aatccatata ctgaaaatgc aacagctttg      60

catgttaaat ttccagagaa taaaaaacaa ccttattatt accctccctt cgataagagt     120

cgaggtggaa aaaagtttct tcctgtattg aaagaaatct tggacaggga tcccttgtct     180

caactgtgtg aaaatgaaat ggatcttatt tggactttgc gacaagactg ccgagagatt     240

ttcccacaat cactgccaaa attactgctg tcaatcaagt ggaataaact tgaggatgtt     300

gctcagcttc aggcgctgct tcagatttgg cctaaactgc ccccccggga ggccctagag     360

cttctggatt tcaactatcc agaccagtac gttcgagaat atgctgtagg ctgcctgcga     420

cagatgagtg atgaagaact ttctcaatat cttttacaac tggtgcaagt gttaaaatat     480

gagccttttc ttgattgtgc cctctctaga ttcctattag aaagagcact tggtaatcgg     540

aggatagggc agtttctatt ttggcatctt aggtcagaag tgcacattcc tgctgtctca     600

gtacaatttg gtgtcatcct tgaagcatac tgccggggaa gtgtggggca catgaaagtg     660

ctttctaagc aggttgaagc actcaataag ttaaaaactt taaatagttt aatcaaactg     720

aatgccgtga agttaaacag agccaaaggg aaggaggcca tgcatacctg tttaaaacag     780

agtgcttacc gggaagccct ctctgacctg cagtcacccc tgaacccatg tgttatcctc     840

tcagaactct atgttgaaaa gtgcaaatac atggattcca aaatgaagcc tttgtggctg     900
```

```
gtatacaata acaaggtatt tggtgaggat tcagttggag tgattttttaa aaatggtgat    960

gatttacgac aggatatgtt gacactccaa atgttgcgct tgatggattt actctggaaa   1020

gaagctggtt tggatcttcg gatgttgcct tatggctgtt tagcaacagg agatcgctct   1080

ggcctcattg aagttgtgag cacctctgaa acaattgctg acattcagct gaacagtagc   1140

aatgtggctg ctgcagcagc cttcaacaaa gatgcccttc tgaactggct taaagaatac   1200

aactctgggg atgacctgga ccgagccatt gaggaattta cactgtcctg tgctggctac   1260

tgtgtagctt cttatgtcct tgggattggt gacagacata gtgacaacat catggtcaaa   1320

aaaactggcc agctcttcca cattgacttt ggacatattc ttggaaattt caaatctaag   1380

tttggcatta aaagggagcg agtgcctttt attcttacct atgatttcat ccatgtcatt   1440

caacaaggaa aaacaggaaa tacagaaaag tttggccggt tccgccagtg ttgtgaggat   1500

gcatatctga ttttacgacg gcatgggaat ctcttcatca ctctctttgc gctgatgttg   1560

actgcagggc ttcctgaact cacatcagtc aaagatatac agtatcttaa ggactctctt   1620

gcattaggga agagtgaaga agaagcactc aaacagttta agcaaaaatt tgatgaggcg   1680

ctcagggaaa gctggactac taaagtgaac tggatggccc acacagttcg gaaagactac   1740

agatcttaa                                                           1749
```

<210> SEQ ID NO 10
<211> LENGTH: 582
<212> TYPE: PRT
<213> ORGANISM: Homo sapiens

<400> SEQUENCE: 10

```
Met Leu Asn Pro Met Gly Thr Val Gln Thr Asn Pro Tyr Thr Glu Asn
1               5                   10                  15

Ala Thr Ala Leu His Val Lys Phe Pro Glu Asn Lys Lys Gln Pro Tyr
            20                  25                  30

Tyr Tyr Pro Pro Phe Asp Lys Ser Arg Gly Gly Lys Lys Phe Leu Pro
        35                  40                  45

Val Leu Lys Glu Ile Leu Asp Arg Asp Pro Leu Ser Gln Leu Cys Glu
    50                  55                  60

Asn Glu Met Asp Leu Ile Trp Thr Leu Arg Gln Asp Cys Arg Glu Ile
65                  70                  75                  80

Phe Pro Gln Ser Leu Pro Lys Leu Leu Leu Ser Ile Lys Trp Asn Lys
                85                  90                  95

Leu Glu Asp Val Ala Gln Leu Gln Ala Leu Leu Gln Ile Trp Pro Lys
            100                 105                 110

Leu Pro Pro Arg Glu Ala Leu Glu Leu Leu Asp Phe Asn Tyr Pro Asp
        115                 120                 125

Gln Tyr Val Arg Glu Tyr Ala Val Gly Cys Leu Arg Gln Met Ser Asp
    130                 135                 140

Glu Glu Leu Ser Gln Tyr Leu Leu Gln Leu Val Gln Val Leu Lys Tyr
145                 150                 155                 160

Glu Pro Phe Leu Asp Cys Ala Leu Ser Arg Phe Leu Leu Glu Arg Ala
                165                 170                 175

Leu Gly Asn Arg Arg Ile Gly Gln Phe Leu Phe Trp His Leu Arg Ser
            180                 185                 190

Glu Val His Ile Pro Ala Val Ser Val Gln Phe Gly Val Ile Leu Glu
        195                 200                 205

Ala Tyr Cys Arg Gly Ser Val Gly His Met Lys Val Leu Ser Lys Gln
    210                 215                 220
```

```
Val Glu Ala Leu Asn Lys Leu Lys Thr Leu Asn Ser Leu Ile Lys Leu
225                 230                 235                 240

Asn Ala Val Lys Leu Asn Arg Ala Lys Gly Lys Glu Ala Met His Thr
                245                 250                 255

Cys Leu Lys Gln Ser Ala Tyr Arg Glu Ala Leu Ser Asp Leu Gln Ser
            260                 265                 270

Pro Leu Asn Pro Cys Val Ile Leu Ser Glu Leu Tyr Val Glu Lys Cys
        275                 280                 285

Lys Tyr Met Asp Ser Lys Met Lys Pro Leu Trp Leu Val Tyr Asn Asn
    290                 295                 300

Lys Val Phe Gly Glu Asp Ser Val Gly Val Ile Phe Lys Asn Gly Asp
305                 310                 315                 320

Asp Leu Arg Gln Asp Met Leu Thr Leu Gln Met Leu Arg Leu Met Asp
                325                 330                 335

Leu Leu Trp Lys Glu Ala Gly Leu Asp Leu Arg Met Leu Pro Tyr Gly
            340                 345                 350

Cys Leu Ala Thr Gly Asp Arg Ser Gly Leu Ile Glu Val Val Ser Thr
        355                 360                 365

Ser Glu Thr Ile Ala Asp Ile Gln Leu Asn Ser Ser Asn Val Ala Ala
    370                 375                 380

Ala Ala Ala Phe Asn Lys Asp Ala Leu Leu Asn Trp Leu Lys Glu Tyr
385                 390                 395                 400

Asn Ser Gly Asp Asp Leu Asp Arg Ala Ile Glu Glu Phe Thr Leu Ser
                405                 410                 415

Cys Ala Gly Tyr Cys Val Ala Ser Tyr Val Leu Gly Ile Gly Asp Arg
            420                 425                 430

His Ser Asp Asn Ile Met Val Lys Lys Thr Gly Gln Leu Phe His Ile
        435                 440                 445

Asp Phe Gly His Ile Leu Gly Asn Phe Lys Ser Lys Phe Gly Ile Lys
    450                 455                 460

Arg Glu Arg Val Pro Phe Ile Leu Thr Tyr Asp Phe Ile His Val Ile
465                 470                 475                 480

Gln Gln Gly Lys Thr Gly Asn Thr Glu Lys Phe Gly Arg Phe Arg Gln
                485                 490                 495

Cys Cys Glu Asp Ala Tyr Leu Ile Leu Arg Arg His Gly Asn Leu Phe
            500                 505                 510

Ile Thr Leu Phe Ala Leu Met Leu Thr Ala Gly Leu Pro Glu Leu Thr
        515                 520                 525

Ser Val Lys Asp Ile Gln Tyr Leu Lys Asp Ser Leu Ala Leu Gly Lys
    530                 535                 540

Ser Glu Glu Glu Ala Leu Lys Gln Phe Lys Gln Lys Phe Asp Glu Ala
545                 550                 555                 560

Leu Arg Glu Ser Trp Thr Thr Lys Val Asn Trp Met Ala His Thr Val
                565                 570                 575

Arg Lys Asp Tyr Arg Ser
            580
```

<210> SEQ ID NO 11
<211> LENGTH: 3195
<212> TYPE: DNA
<213> ORGANISM: Mus musculus

<400> SEQUENCE: 11

```
atgcctcctg ctatggcaga caaccttgac atctgggcag tggactcaca gattgcatcc      60
```

-continued

```
gatggcgcca tatccgtcga tttccttctg cccaccggga tttatatcca gttggaagta    120
cctcgggaag ctaccatttc ttatattaaa cagatgttat ggaagcaagt tcacaactac    180
ccgatgttta acctcctcat ggacattgac tcgtatatgt ttgcatgtgt gaatcaaact    240
gctgtatatg aggaactgga agacgaaaca cgaagacttt gtgatgtcag accttttctt    300
ccagttctca aactagtgac tagaagctgt gacccccgcag aaaaattgga ctcaaaaatt    360
ggggttctta taggaaaagg tcttcatgag tttgatgcct tgaaggatcc cgaagtgaat    420
gaatttagaa gaaaaatgcg caaattcagt gaggccaaga ttcagtctct ggtagggttg    480
tcttggatcg actggctaaa gcacacgtat ccgcctgagc acgagccgtc cgtcctggag    540
aacttggaag ataaacttta tggaggaaag ctggttgtgg ctgtgcactt tgaaaatagc    600
caggatgtat ttagttttca agtgtctccc aatttgaatc ctataaaaat aaatgaattg    660
gcaatccaga aacgcctcac tattcgtgga aaggaagatg aagctagccc ctgtgactat    720
gtgttacagg tcagtgggag agtggagtat gtgtttggcg atcatccact aattcagttc    780
cagtacatcc ggaattgtgt gatgaataga accctgcccc acttcatcct tgtggaatgt    840
tgtaagatca agaaaatgta tgaacaagaa atgattgcca tagaggctgc catcaaccga    900
aactcatcca accttcctct ccctttacca ccaaagaaaa cgcgagttat ttctcatatc    960
tgggacaaca acaacccttt ccaaattacc ttggttaaag gaaataagct taatacagaa   1020
gaaactgtga aagttcatgt ccgagctggg ctttttcacg gaaccgagct cctgtgtaaa   1080
accgtcgtaa gctcagagat atcaggaaag aacgaccata tttggaatga acaactggaa   1140
tttgatatta atatttgtga cttaccaaga atggctcgat tatgttttgc tgtttatgca   1200
gttttggata aagtaaaaac gaagaaatca acaaagacta ttaatccctc taagtatcag   1260
accatcagga aagccgggaa agtgcattat cctgtcgcat gggtaaatac catggttttt   1320
gacttcaaag gacagctgag gtctggagac gtcatattgc atagctggtc ttcgtttcct   1380
gatgagctgg aagaaatgct gaatcccatg gggactgtgc agacgaaccc atatgctgag   1440
aacgccaccg ccttgcacat tacgttccca gagaataaga agcagccgtg ttattatccc   1500
cccttcgata agatcattga gaaggcagct gagcttgcca gcggagacag tgctaatgtg   1560
tcaagtcgtg gtggaaaaaa atttcttgct gtgctgaaag aaatcttgga cagggacccc   1620
ctgtctcagc tgtgtgagaa cgaaatggac cttatttgga ctctacggca agactgccga   1680
gaaaatttcc ctcagtcact gccaaaacta ctcttgtcaa tcaagtggaa taaacttgaa   1740
gatgttgctc agcttcaggc gctcctgcag atatggccca aactgccccc cagggaagcc   1800
ctggaactcc tggatttcaa ctatccagac cagtatgtcc gggaatacgc tgtaggctgc   1860
cttcgacaga tgagtgatga agaactctct cagtatcttt tacaattggt gcaagttttg   1920
aaatatgagc cttttctcga ttgtgccctc tccagattcc tattagaaag agcacttgat   1980
aatcggagga ttgggcagtt tctgttttgg catcttaggt cagaggtgca cactcctgct   2040
gtgtccgtac agtttggtgt catcctggaa gcatactgtc gaggaagcgt ggggcacatg   2100
aaagtgcttt ccaaacaggt ggaagcactc aataagttaa aaactttaaa tagcttaatc   2160
aaactgaatg cggtgaagct gagcagagct aagggaaagg aggccatgca cacgtgcctg   2220
aaacagagtg cttaccggga ggcgctctct gacctgcagt cgccgctgaa cccctgcgtc   2280
atcctctcag agctctatgt tgaaaagtgc aaatacatgg actccaagat gaagcccctg   2340
tggctggtct acagcagcag agcctttgga gaggactcgg ttggagtgat ctttaaaaat   2400
```

```
ggtgacgatt tgcggcagga catgctgacg ctgcagatgt tgcgcctgat ggatctgctt   2460

tggaaagaag ctggcttgga cctgcggatg ctcccctatg gctgcttagc aacaggagat   2520

cgctctggcc tcattgaggt tgtgagcacc tctgagacaa tcgctgacat tcagctgaac   2580

agtagtaacg tggctgccac ggcagccttc aacaaagacg cactcctgaa ctggctcaag   2640

gagtacaact ctggggatga cctggaccga gcgattgagg agtttacctt gtcctgtgct   2700

ggctactgtg tagcctctta tgtcctcggc attggtgaca ggcacagtga caacatcatg   2760

gtgaagaaaa ccggccagct cttccacata gattttgggc atattcttgg aaatttcaaa   2820

tctaaatttg gcattaaaag ggagcgagta ccttttattc ttacttatga cttcattcat   2880

gtcattcaac aaggaaaaac gggaaacact gaaaaatttg gcagattccg ccagtgctgt   2940

gaagatgcgt atctgatttt acggcggcat gggaatctct tcatcaccct gtttgccctg   3000

atgttgactg cagggctgcc tgagctcaca tcggtcaaag atatacagta tcttaaggac   3060

tcgcttgcct tagggaagag cgaggaggaa gcactgaagc agttcaagca gaagtttgac   3120

gaggccctca gggaaagctg gactactaaa gtgaactgga tggctcacac agtacggaaa   3180

gactacaggt cctag                                                    3195
```

<210> SEQ ID NO 12
<211> LENGTH: 1064
<212> TYPE: PRT
<213> ORGANISM: Mus musculus

<400> SEQUENCE: 12

```
Met Pro Pro Ala Met Ala Asp Asn Leu Asp Ile Trp Ala Val Asp Ser
1               5                   10                  15

Gln Ile Ala Ser Asp Gly Ala Ile Ser Val Asp Phe Leu Leu Pro Thr
            20                  25                  30

Gly Ile Tyr Ile Gln Leu Glu Val Pro Arg Glu Ala Thr Ile Ser Tyr
        35                  40                  45

Ile Lys Gln Met Leu Trp Lys Gln Val His Asn Tyr Pro Met Phe Asn
    50                  55                  60

Leu Leu Met Asp Ile Asp Ser Tyr Met Phe Ala Cys Val Asn Gln Thr
65                  70                  75                  80

Ala Val Tyr Glu Glu Leu Glu Asp Glu Thr Arg Arg Leu Cys Asp Val
                85                  90                  95

Arg Pro Phe Leu Pro Val Leu Lys Leu Val Thr Arg Ser Cys Asp Pro
            100                 105                 110

Ala Glu Lys Leu Asp Ser Lys Ile Gly Val Leu Ile Gly Lys Gly Leu
        115                 120                 125

His Glu Phe Asp Ala Leu Lys Asp Pro Glu Val Asn Glu Phe Arg Arg
    130                 135                 140

Lys Met Arg Lys Phe Ser Glu Ala Lys Ile Gln Ser Leu Val Gly Leu
145                 150                 155                 160

Ser Trp Ile Asp Trp Leu Lys His Thr Tyr Pro Pro Glu His Glu Pro
                165                 170                 175

Ser Val Leu Glu Asn Leu Glu Asp Lys Leu Tyr Gly Gly Lys Leu Val
            180                 185                 190

Val Ala Val His Phe Glu Asn Ser Gln Asp Val Phe Ser Phe Gln Val
        195                 200                 205

Ser Pro Asn Leu Asn Pro Ile Lys Ile Asn Glu Leu Ala Ile Gln Lys
    210                 215                 220

Arg Leu Thr Ile Arg Gly Lys Glu Asp Glu Ala Ser Pro Cys Asp Tyr
```

```
225                 230                 235                 240

Val Leu Gln Val Ser Gly Arg Val Glu Tyr Val Phe Gly Asp His Pro
                245                 250                 255

Leu Ile Gln Phe Gln Tyr Ile Arg Asn Cys Val Met Asn Arg Thr Leu
            260                 265                 270

Pro His Phe Ile Leu Val Glu Cys Cys Lys Ile Lys Lys Met Tyr Glu
        275                 280                 285

Gln Glu Met Ile Ala Ile Glu Ala Ala Ile Asn Arg Asn Ser Ser Asn
    290                 295                 300

Leu Pro Leu Pro Leu Pro Pro Lys Lys Thr Arg Val Ile Ser His Ile
305                 310                 315                 320

Trp Asp Asn Asn Asn Pro Phe Gln Ile Thr Leu Val Lys Gly Asn Lys
                325                 330                 335

Leu Asn Thr Glu Glu Thr Val Lys Val His Val Arg Ala Gly Leu Phe
            340                 345                 350

His Gly Thr Glu Leu Leu Cys Lys Thr Val Val Ser Ser Glu Ile Ser
        355                 360                 365

Gly Lys Asn Asp His Ile Trp Asn Glu Gln Leu Glu Phe Asp Ile Asn
    370                 375                 380

Ile Cys Asp Leu Pro Arg Met Ala Arg Leu Cys Phe Ala Val Tyr Ala
385                 390                 395                 400

Val Leu Asp Lys Val Lys Thr Lys Lys Ser Thr Lys Thr Ile Asn Pro
                405                 410                 415

Ser Lys Tyr Gln Thr Ile Arg Lys Ala Gly Lys Val His Tyr Pro Val
            420                 425                 430

Ala Trp Val Asn Thr Met Val Phe Asp Phe Lys Gly Gln Leu Arg Ser
        435                 440                 445

Gly Asp Val Ile Leu His Ser Trp Ser Ser Phe Pro Asp Glu Leu Glu
    450                 455                 460

Glu Met Leu Asn Pro Met Gly Thr Val Gln Thr Asn Pro Tyr Ala Glu
465                 470                 475                 480

Asn Ala Thr Ala Leu His Ile Thr Phe Pro Glu Asn Lys Lys Gln Pro
                485                 490                 495

Cys Tyr Tyr Pro Pro Phe Asp Lys Ile Ile Glu Lys Ala Ala Glu Leu
            500                 505                 510

Ala Ser Gly Asp Ser Ala Asn Val Ser Ser Arg Gly Gly Lys Lys Phe
        515                 520                 525

Leu Ala Val Leu Lys Glu Ile Leu Asp Arg Asp Pro Leu Ser Gln Leu
    530                 535                 540

Cys Glu Asn Glu Met Asp Leu Ile Trp Thr Leu Arg Gln Asp Cys Arg
545                 550                 555                 560

Glu Asn Phe Pro Gln Ser Leu Pro Lys Leu Leu Leu Ser Ile Lys Trp
                565                 570                 575

Asn Lys Leu Glu Asp Val Ala Gln Leu Gln Ala Leu Leu Gln Ile Trp
            580                 585                 590

Pro Lys Leu Pro Pro Arg Glu Ala Leu Glu Leu Leu Asp Phe Asn Tyr
        595                 600                 605

Pro Asp Gln Tyr Val Arg Glu Tyr Ala Val Gly Cys Leu Arg Gln Met
    610                 615                 620

Ser Asp Glu Glu Leu Ser Gln Tyr Leu Leu Gln Leu Val Gln Val Leu
625                 630                 635                 640

Lys Tyr Glu Pro Phe Leu Asp Cys Ala Leu Ser Arg Phe Leu Leu Glu
                645                 650                 655
```

```
Arg Ala Leu Asp Asn Arg Arg Ile Gly Gln Phe Leu Phe Trp His Leu
            660                 665                 670

Arg Ser Glu Val His Thr Pro Ala Val Ser Val Gln Phe Gly Val Ile
        675                 680                 685

Leu Glu Ala Tyr Cys Arg Gly Ser Val Gly His Met Lys Val Leu Ser
    690                 695                 700

Lys Gln Val Glu Ala Leu Asn Lys Leu Lys Thr Leu Asn Ser Leu Ile
705                 710                 715                 720

Lys Leu Asn Ala Val Lys Leu Ser Arg Ala Lys Gly Lys Glu Ala Met
                725                 730                 735

His Thr Cys Leu Lys Gln Ser Ala Tyr Arg Glu Ala Leu Ser Asp Leu
            740                 745                 750

Gln Ser Pro Leu Asn Pro Cys Val Ile Leu Ser Glu Leu Tyr Val Glu
        755                 760                 765

Lys Cys Lys Tyr Met Asp Ser Lys Met Lys Pro Leu Trp Leu Val Tyr
    770                 775                 780

Ser Ser Arg Ala Phe Gly Glu Asp Ser Val Gly Val Ile Phe Lys Asn
785                 790                 795                 800

Gly Asp Asp Leu Arg Gln Asp Met Leu Thr Leu Gln Met Leu Arg Leu
                805                 810                 815

Met Asp Leu Leu Trp Lys Glu Ala Gly Leu Asp Leu Arg Met Leu Pro
            820                 825                 830

Tyr Gly Cys Leu Ala Thr Gly Asp Arg Ser Gly Leu Ile Glu Val Val
        835                 840                 845

Ser Thr Ser Glu Thr Ile Ala Asp Ile Gln Leu Asn Ser Ser Asn Val
    850                 855                 860

Ala Ala Thr Ala Ala Phe Asn Lys Asp Ala Leu Leu Asn Trp Leu Lys
865                 870                 875                 880

Glu Tyr Asn Ser Gly Asp Asp Leu Asp Arg Ala Ile Glu Glu Phe Thr
                885                 890                 895

Leu Ser Cys Ala Gly Tyr Cys Val Ala Ser Tyr Val Leu Gly Ile Gly
            900                 905                 910

Asp Arg His Ser Asp Asn Ile Met Val Lys Lys Thr Gly Gln Leu Phe
        915                 920                 925

His Ile Asp Phe Gly His Ile Leu Gly Asn Phe Lys Ser Lys Phe Gly
    930                 935                 940

Ile Lys Arg Glu Arg Val Pro Phe Ile Leu Thr Tyr Asp Phe Ile His
945                 950                 955                 960

Val Ile Gln Gln Gly Lys Thr Gly Asn Thr Glu Lys Phe Gly Arg Phe
                965                 970                 975

Arg Gln Cys Cys Glu Asp Ala Tyr Leu Ile Leu Arg Arg His Gly Asn
            980                 985                 990

Leu Phe Ile Thr Leu Phe Ala Leu  Met Leu Thr Ala Gly  Leu Pro Glu
        995                 1000                1005

Leu Thr  Ser Val Lys Asp Ile  Gln Tyr Leu Lys Asp  Ser Leu Ala
    1010                 1015                 1020

Leu Gly  Lys Ser Glu Glu Glu  Ala Leu Lys Gln Phe  Lys Gln Lys
    1025                 1030                 1035

Phe Asp  Glu Ala Leu Arg Glu  Ser Trp Thr Thr Lys  Val Asn Trp
    1040                 1045                 1050

Met Ala  His Thr Val Arg Lys  Asp Tyr Arg Ser
    1055                 1060
```

<210> SEQ ID NO 13
<211> LENGTH: 3309
<212> TYPE: DNA
<213> ORGANISM: Homo sapiens

<400> SEQUENCE: 13

```
atggagctgg agaactataa acagcccgtg gtgctgagag aggacaactg ccgaaggcgc     60
cggaggatga agccgcgcag tgctgcggcc agcctgtcct ccatggagct catccccatc    120
gagttcgtgc tgcccaccag ccagcgcaaa tgcaagagcc ccgaaacggc gctgctgcac    180
gtggccggcc acggcaacgt ggagcagatg aaggcccagg tgtggctgcg agcgctggag    240
accagcgtgg cggcggactt ctaccaccgg ctgggaccgc atcacttcct cctgctctat    300
cagaagaagg ggcagtggta cgagatctac gacaagtacc aggtggtgca gactctggac    360
tgcctgcgct actggaaggc cacgcaccgg agcccgggcc agatccacct ggtgcagcgg    420
cacccgccct ccgaggagtc ccaagccttc cagcggcagc tcacggcgct gattggctat    480
gacgtcactg acgtcagcaa cgtgcacgac gatgagctgg agttcacgcg ccgtggcttg    540
gtgaccccgc gcatggcgga ggtggccagc cgcgacccca agctctacgc catgcacccg    600
tgggtgacgt ccaagcccct cccggagtac ctgtggaaga agattgccaa caactgcatc    660
ttcatcgtca ttcaccgcag caccaccagc cagaccatta aggtctcacc cgacgacacc    720
cccggcgcca tcctgcagag cttcttcacc aagatggcca agaagaaatc tctgatggat    780
attcccgaaa gccaaagcga acaggatttt gtgctgcgcg tctgtggccg ggatgagtac    840
ctggtgggcg aaacgcccat caaaaacttc cagtgggtga ggcactgcct caagaacgga    900
gaagagattc acgtggtact ggacacgcct ccagacccgg ccctagacga ggtgaggaag    960
gaagagtggc cactggtgga tgactgcacg ggagtcaccg gctaccatga gcagcttacc   1020
atccacggca aggaccacga gagtgtgttc accgtgtccc tgtgggactg cgaccgcaag   1080
ttcagggtca agatcagagg cattgatatc cccgtcctgc ctcggaacac cgacctcaca   1140
gtttttgtag aggcaaacat ccagcatggg caacaagtcc tttgccaaag gagaaccagc   1200
cccaaaccct tcacagagga ggtgctgtgg aatgtgtggc ttgagttcag tatcaaaatc   1260
aaagacttgc ccaaaggggc tctactgaac ctccagatct actgcggtaa agctccagca   1320
ctgtccagca aggcctctgc agagtccccc agttctgagt ccaagggcaa agttcagctt   1380
ctctattatg tgaacctgct gctgatagac caccgtttcc tcctgcgccg tggagaatac   1440
gtcctccaca tgtggcagat atctgggaag ggagaagacc aaggaagctt caatgctgac   1500
aaactcacgt ctgcaactaa cccagacaag gagaactcaa tgtccatctc cattcttctg   1560
gacaattact gccacccgat agccctgcct aagcatcagc ccacccctga cccggaaggg   1620
gaccgggttc gagcagaaat gcccaaccag cttcgcaagc aattggaggc gatcatagcc   1680
actgatccac ttaaccctct cacagcagag gacaaagaat tgctctggca ttttagatac   1740
gaaagcctta agcacccaaa agcatatcct aagctattta gttcagtgaa atggggacag   1800
caagaaattg tggccaaaac ataccaattg ttggccagaa gggaagtctg ggatcaaagt   1860
gctttggatg ttgggttaac aatgcagctc ctggactgca acttctcaga tgaaaatgta   1920
agagccattg cagttcagaa actggagagc ttggaggacg atgatgttct gcattacctt   1980
ctacaattgg tccaggctgt gaaatttgaa ccataccatg atagcgccct tgccagattt   2040
ctgctgaagc gtggtttaag aaacaaaaga attggtcact tttgttttg gttcttgaga    2100
agtgagatag cccagtccag acactatcag cagaggttcg ctgtgattct ggaagcctat   2160
```

```
ctgaggggct gtggcacagc catgctgcac gactttaccc aacaagtcca agtaatcgag   2220

atgttacaaa aagtcaccct tgatattaaa tcgctctctg ctgaaaagta tgacgtcagt   2280

tcccaagtta tttcacaact taaacaaaag cttgaaaacc tgcagaattc tcaactcccc   2340

gaaagcttta gagttccata tgatcctgga ctgaaagcag gagcgctggc aattgaaaaa   2400

tgtaaagtaa tggcctccaa gaaaaaacca ctatggcttg agtttaaatg tgccgatcct   2460

acagccctat caaatgaaac aattggaatt atctttaaac atggtgatga tctgcgccaa   2520

gacatgctta ttttacagat tctacgaatc atggagtcta tttgggagac tgaatctttg   2580

gatctatgcc tcctgccata tggttgcatt tcaactggtg acaaaatagg aatgatcgag   2640

attgtgaaag acgccacgac aattgccaaa attcagcaaa gcacagtggg caacacggga   2700

gcatttaaag atgaagtcct gaatcactgg ctcaaagaaa aatcccctac tgaagaaaag   2760

tttcaggcag cagtggagag atttgtttat tcctgtgcag gctactgtgt ggcaaccttt   2820

gttcttggaa taggcgacag acacaatgac aatattatga tcaccgagac aggaaaccta   2880

tttcatattg acttcgggca cattcttggg aattacaaaa gtttcctggg cattaataaa   2940

gagagagtgc catttgtgct aacccctgac ttcctctttg tgatgggaac ttctggaaag   3000

aagacaagcc cacacttcca gaaatttcag gacatctgtg ttaaggctta tctagccctt   3060

cgtcatcaca caaacctact gatcatcctg ttctccatga tgctgatgac aggaatgccc   3120

cagttaacaa gcaaagaaga cattgaatat atccgggatg ccctcacagt ggggaaaaat   3180

gaggaggatg ctaaaaagta ttttcttgat cagatcgaag tttgcagaga caaaggatgg   3240

actgtgcagt ttaattggtt tctacatctt gttcttggca tcaaacaagg agagaaacat   3300

tcagcctaa                                                           3309
```

<210> SEQ ID NO 14
<211> LENGTH: 1102
<212> TYPE: PRT
<213> ORGANISM: Homo sapiens

<400> SEQUENCE: 14

```
Met Glu Leu Glu Asn Tyr Lys Gln Pro Val Val Leu Arg Glu Asp Asn
1               5                   10                  15

Cys Arg Arg Arg Arg Arg Met Lys Pro Arg Ser Ala Ala Ala Ser Leu
            20                  25                  30

Ser Ser Met Glu Leu Ile Pro Ile Glu Phe Val Leu Pro Thr Ser Gln
        35                  40                  45

Arg Lys Cys Lys Ser Pro Glu Thr Ala Leu Leu His Val Ala Gly His
    50                  55                  60

Gly Asn Val Glu Gln Met Lys Ala Gln Val Trp Leu Arg Ala Leu Glu
65                  70                  75                  80

Thr Ser Val Ala Ala Asp Phe Tyr His Arg Leu Gly Pro His His Phe
                85                  90                  95

Leu Leu Leu Tyr Gln Lys Lys Gly Gln Trp Tyr Glu Ile Tyr Asp Lys
            100                 105                 110

Tyr Gln Val Val Gln Thr Leu Asp Cys Leu Arg Tyr Trp Lys Ala Thr
        115                 120                 125

His Arg Ser Pro Gly Gln Ile His Leu Val Gln Arg His Pro Pro Ser
    130                 135                 140

Glu Glu Ser Gln Ala Phe Gln Arg Gln Leu Thr Ala Leu Ile Gly Tyr
145                 150                 155                 160
```

```
Asp Val Thr Asp Val Ser Asn Val His Asp Asp Glu Leu Glu Phe Thr
                165                 170                 175

Arg Arg Gly Leu Val Thr Pro Arg Met Ala Glu Val Ala Ser Arg Asp
            180                 185                 190

Pro Lys Leu Tyr Ala Met His Pro Trp Val Thr Ser Lys Pro Leu Pro
        195                 200                 205

Glu Tyr Leu Trp Lys Lys Ile Ala Asn Asn Cys Ile Phe Ile Val Ile
    210                 215                 220

His Arg Ser Thr Thr Ser Gln Thr Ile Lys Val Ser Pro Asp Asp Thr
225                 230                 235                 240

Pro Gly Ala Ile Leu Gln Ser Phe Phe Thr Lys Met Ala Lys Lys Lys
                245                 250                 255

Ser Leu Met Asp Ile Pro Glu Ser Gln Ser Glu Gln Asp Phe Val Leu
            260                 265                 270

Arg Val Cys Gly Arg Asp Glu Tyr Leu Val Gly Glu Thr Pro Ile Lys
        275                 280                 285

Asn Phe Gln Trp Val Arg His Cys Leu Lys Asn Gly Glu Glu Ile His
    290                 295                 300

Val Val Leu Asp Thr Pro Pro Asp Pro Ala Leu Asp Glu Val Arg Lys
305                 310                 315                 320

Glu Glu Trp Pro Leu Val Asp Asp Cys Thr Gly Val Thr Gly Tyr His
                325                 330                 335

Glu Gln Leu Thr Ile His Gly Lys Asp His Glu Ser Val Phe Thr Val
            340                 345                 350

Ser Leu Trp Asp Cys Asp Arg Lys Phe Arg Val Lys Ile Arg Gly Ile
        355                 360                 365

Asp Ile Pro Val Leu Pro Arg Asn Thr Asp Leu Thr Val Phe Val Glu
    370                 375                 380

Ala Asn Ile Gln His Gly Gln Gln Val Leu Cys Gln Arg Arg Thr Ser
385                 390                 395                 400

Pro Lys Pro Phe Thr Glu Glu Val Leu Trp Asn Val Trp Leu Glu Phe
                405                 410                 415

Ser Ile Lys Ile Lys Asp Leu Pro Lys Gly Ala Leu Leu Asn Leu Gln
            420                 425                 430

Ile Tyr Cys Gly Lys Ala Pro Ala Leu Ser Ser Lys Ala Ser Ala Glu
        435                 440                 445

Ser Pro Ser Ser Glu Ser Lys Gly Lys Val Gln Leu Leu Tyr Tyr Val
    450                 455                 460

Asn Leu Leu Leu Ile Asp His Arg Phe Leu Leu Arg Arg Gly Glu Tyr
465                 470                 475                 480

Val Leu His Met Trp Gln Ile Ser Gly Lys Gly Glu Asp Gln Gly Ser
                485                 490                 495

Phe Asn Ala Asp Lys Leu Thr Ser Ala Thr Asn Pro Asp Lys Glu Asn
            500                 505                 510

Ser Met Ser Ile Ser Ile Leu Leu Asp Asn Tyr Cys His Pro Ile Ala
        515                 520                 525

Leu Pro Lys His Gln Pro Thr Pro Asp Pro Glu Gly Asp Arg Val Arg
    530                 535                 540

Ala Glu Met Pro Asn Gln Leu Arg Lys Gln Leu Glu Ala Ile Ile Ala
545                 550                 555                 560

Thr Asp Pro Leu Asn Pro Leu Thr Ala Glu Asp Lys Glu Leu Leu Trp
                565                 570                 575

His Phe Arg Tyr Glu Ser Leu Lys His Pro Lys Ala Tyr Pro Lys Leu
```

```
            580                 585                 590

Phe Ser Ser Val Lys Trp Gly Gln Gln Glu Ile Val Ala Lys Thr Tyr
        595                 600                 605

Gln Leu Leu Ala Arg Arg Glu Val Trp Asp Gln Ser Ala Leu Asp Val
    610                 615                 620

Gly Leu Thr Met Gln Leu Leu Asp Cys Asn Phe Ser Asp Glu Asn Val
625                 630                 635                 640

Arg Ala Ile Ala Val Gln Lys Leu Glu Ser Leu Glu Asp Asp Asp Val
                645                 650                 655

Leu His Tyr Leu Leu Gln Leu Val Gln Ala Val Lys Phe Glu Pro Tyr
            660                 665                 670

His Asp Ser Ala Leu Ala Arg Phe Leu Leu Lys Arg Gly Leu Arg Asn
        675                 680                 685

Lys Arg Ile Gly His Phe Leu Phe Trp Phe Leu Arg Ser Glu Ile Ala
    690                 695                 700

Gln Ser Arg His Tyr Gln Gln Arg Phe Ala Val Ile Leu Glu Ala Tyr
705                 710                 715                 720

Leu Arg Gly Cys Gly Thr Ala Met Leu His Asp Phe Thr Gln Gln Val
                725                 730                 735

Gln Val Ile Glu Met Leu Gln Lys Val Thr Leu Asp Ile Lys Ser Leu
            740                 745                 750

Ser Ala Glu Lys Tyr Asp Val Ser Ser Gln Val Ile Ser Gln Leu Lys
        755                 760                 765

Gln Lys Leu Glu Asn Leu Gln Asn Ser Gln Leu Pro Glu Ser Phe Arg
    770                 775                 780

Val Pro Tyr Asp Pro Gly Leu Lys Ala Gly Ala Leu Ala Ile Glu Lys
785                 790                 795                 800

Cys Lys Val Met Ala Ser Lys Lys Lys Pro Leu Trp Leu Glu Phe Lys
                805                 810                 815

Cys Ala Asp Pro Thr Ala Leu Ser Asn Glu Thr Ile Gly Ile Ile Phe
            820                 825                 830

Lys His Gly Asp Asp Leu Arg Gln Asp Met Leu Ile Leu Gln Ile Leu
        835                 840                 845

Arg Ile Met Glu Ser Ile Trp Glu Thr Glu Ser Leu Asp Leu Cys Leu
    850                 855                 860

Leu Pro Tyr Gly Cys Ile Ser Thr Gly Asp Lys Ile Gly Met Ile Glu
865                 870                 875                 880

Ile Val Lys Asp Ala Thr Thr Ile Ala Lys Ile Gln Gln Ser Thr Val
                885                 890                 895

Gly Asn Thr Gly Ala Phe Lys Asp Glu Val Leu Asn His Trp Leu Lys
            900                 905                 910

Glu Lys Ser Pro Thr Glu Glu Lys Phe Gln Ala Ala Val Glu Arg Phe
        915                 920                 925

Val Tyr Ser Cys Ala Gly Tyr Cys Val Ala Thr Phe Val Leu Gly Ile
    930                 935                 940

Gly Asp Arg His Asn Asp Asn Ile Met Ile Thr Glu Thr Gly Asn Leu
945                 950                 955                 960

Phe His Ile Asp Phe Gly His Ile Leu Gly Asn Tyr Lys Ser Phe Leu
                965                 970                 975

Gly Ile Asn Lys Glu Arg Val Pro Phe Val Leu Thr Pro Asp Phe Leu
            980                 985                 990

Phe Val Met Gly Thr Ser Gly Lys  Lys Thr Ser Pro His  Phe Gln Lys
        995                 1000                1005
```

```
Phe Gln  Asp Ile Cys Val Lys  Ala Tyr Leu Ala Leu  Arg His His
    1010                 1015                 1020

Thr Asn  Leu Leu Ile Ile Leu  Phe Ser Met Met Leu  Met Thr Gly
    1025                 1030                 1035

Met Pro  Gln Leu Thr Ser Lys  Glu Asp Ile Glu Tyr  Ile Arg Asp
    1040                 1045                 1050

Ala Leu  Thr Val Gly Lys Asn  Glu Glu Asp Ala Lys  Lys Tyr Phe
    1055                 1060                 1065

Leu Asp  Gln Ile Glu Val Cys  Arg Asp Lys Gly Trp  Thr Val Gln
    1070                 1075                 1080

Phe Asn  Trp Phe Leu His Leu  Val Leu Gly Ile Lys  Gln Gly Glu
    1085                 1090                 1095

Lys His  Ser Ala
    1100
```

<210> SEQ ID NO 15
<211> LENGTH: 3309
<212> TYPE: DNA
<213> ORGANISM: Homo sapiens

<400> SEQUENCE: 15

```
atggagctgg agaactataa acagcccgtg gtgctgagag aggacaactg ccgaaggcgc     60

cggaggatga agccgcgcag tgctgcggcc agcctgtcct ccatggagct catccccatc    120

gagttcgtgc tgcccaccag ccagcgcaaa tgcaagagcc ccgaaacggc gctgctgcac    180

gtggccggcc acggcaacgt ggagcagatg aaggcccagg tgtggctgcg agcgctggag    240

accagcgtgg cggcggactt ctaccaccgg ctgggaccgc atcacttcct cctgctctat    300

cagaagaagg ggcagtggta cgagatctac gacaagtacc aggtggtgca gactctggac    360

tgcctgcgct actggaaggc cacgcaccgg agcccgggcc agatccacct ggtgcagcgg    420

cacccgccct ccgaggagtc ccaagccttc cagcggcagc tcacggcgct gattggctat    480

gacgtcactg acgtcagcaa cgtgcacgac gatgagctgg agttcacgcg ccgtggcttg    540

gtgaccccgc gcatggcgga ggtggccagc cgcgacccca agctctacgc catgcacccg    600

tgggtgacgt ccaagcccct cccggagtac ctgtggaaga agattgccaa caactgcatc    660

ttcatcgtca ttcaccgcag caccaccagc cagaccatta aggtctcacc cgacgacacc    720

cccggcgcca tcctgcagag cttcttcacc aagatggcca agaagaaatc tctgatggat    780

attcccgaaa gccaaagcga acaggatttt gtgctgcgcg tctgtggccg ggatgagtac    840

ctggtgggcg aaacgcccat caaaaacttc cagtgggtga ggcactgcct caagaacgga    900

gaagagattc acgtggtact ggacacgcct ccagacccgg ccctagacga ggtgaggaag    960

gaagagtggc cactggtgga tgactgcacg ggagtcaccg gctaccatga gcagcttacc   1020

atccacggca aggaccacga gagtgtgttc accgtgtccc tgtgggactg cgaccgcaag   1080

ttcagggtca agatcagagg cattgatatc cccgtcctgc ctcggaacac cgacctcaca   1140

gtttttgtag aggcaaacat ccagcatggg caacaagtcc tttgccaaag gagaaccagc   1200

cccaaaccct tcacagagga ggtgctgtgg aatgtgtggc ttgagttcag tatcaaaatc   1260

aaagacttgc ccaaaggggc tctactgaac ctccagatct actgcggtaa agctccagca   1320

ctgtccagca aggcctctgc agagtccccc agttctgagt ccaagggcaa agttcagctt   1380

ctctattatg tgaacctgct gctgatagac caccgtttcc tcctgcgccg tggagaatac   1440

gtcctccaca tgtggcagat atctgggaag ggagaagacc aaggaagctt caatgctgac   1500
```

aaactcacgt ctgcaactaa cccagacaag gagaactcaa tgtccatctc cattcttctg 1560
gacaattact gccacccgat agccctgcct aagcatcagc ccacccctga cccggaaggg 1620
gaccgggttc gagcagaaat gcccaaccag cttcgcaagc aattggaggc gatcatagcc 1680
actgatccac ttaaccctct cacagcagag gacaaagaat tgctctggca ttttagatac 1740
gaaagcctta agcacccaaa agcatatcct aagctattta gttcagtgaa atggggacag 1800
caagaaattg tggccaaaac ataccaattg ttggccagaa gggaagtctg ggatcaaagt 1860
gctttggatg ttgggttaac aatgcagctc ctggactgca acttctcaga tgaaaatgta 1920
agagccattg cagttcagaa actggagagc ttggaggacg atgatgttct gcattacctt 1980
ctacaattgg tccaggctgt gaaatttgaa ccataccatg atagcgccct tgccagattt 2040
ctgctgaagc gtggtttaag aaacaaaaga attggtcact tttgttttg gttcttgaga 2100 agtgagatag cccagtccag acactatcag cagaggttcg ctgtgattct ggaagcctat 2160
ctgaggggct gtggcacagc catgctgcac gactttaccc aacaagtcca agtaatcgag 2220
atgttacaaa aagtcaccct tgatattaaa tcgctctctg ctgaaaagta tgacgtcagt 2280
tcccaagtta tttcacaact taaacaaaag cttgaaaacc tgcagaattc tcaactcccc 2340
gaaagcttta gagttccata tgatcctgga ctgaaagcag gagcgctggc aattgaaaaa 2400
tgtaaagtaa tggcctccaa gaaaaaacca ctatggcttg agtttaaatg tgccgatcct 2460
acagccctat caaatgaaac aattggaatt atctttaaac atggtgatga tctgcgccaa 2520
gacatgctta ttttacagat tctacgaatc atggagtcta tttgggagac tgaatctttg 2580
gatctatgcc tcctgccata tggttgcatt tcaactggtg acaaaatagg aatgatcgag 2640
attgtgaaag acgccacgac aattgccaaa attcagcaaa gcacagtggg caacacggga 2700
gcatttaaag atgaagtcct gaatcactgg ctcaaagaaa aatcccctac tgaagaaaag 2760
tttcaggcag cagtggagag atttgtttat tcctgtgcag gctactgtgt ggcaaccttt 2820
gttcttggaa taggcgacag acacaatgac aatattatga tcaccgagac aggaaaccta 2880
tttcatattg acttcgggca cattcttggg aattacaaaa gtttcctggg cattaataaa 2940
gagagagtgc catttgtgct aacccctgac ttcctctttg tgatgggaac ttctggaaag 3000
aagacaagcc cacacttcca gaaatttcag gacatctgtg ttaaggctta tctagccctt 3060
cgtcatcaca caaacctact gatcatcctg ttctccatga tgctgatgac aggaatgccc 3120
cagttaacaa gcaaagaaga cattgaatat atccgggatg ccctcacagt ggggaaaaat 3180
gaggaggatg ctaaaaagta ttttcttgat cagatcgaag tttgcagaga caaaggatgg 3240
actgtgcagt ttaattggtt tctacatctt gttcttggca tcaaacaagg agagaaacat 3300
tcagcctaa 3309

<210> SEQ ID NO 16
<211> LENGTH: 1102
<212> TYPE: PRT
<213> ORGANISM: Homo sapiens

<400> SEQUENCE: 16

Met Glu Leu Glu Asn Tyr Lys Gln Pro Val Val Leu Arg Glu Asp Asn
1 5 10 15

Cys Arg Arg Arg Arg Arg Met Lys Pro Arg Ser Ala Ala Ala Ser Leu
20 25 30

Ser Ser Met Glu Leu Ile Pro Ile Glu Phe Val Leu Pro Thr Ser Gln
35 40 45

```
Arg Lys Cys Lys Ser Pro Glu Thr Ala Leu Leu His Val Ala Gly His
    50                  55                  60

Gly Asn Val Glu Gln Met Lys Ala Gln Val Trp Leu Arg Ala Leu Glu
65                  70                  75                  80

Thr Ser Val Ala Ala Asp Phe Tyr His Arg Leu Gly Pro His His Phe
                85                  90                  95

Leu Leu Leu Tyr Gln Lys Lys Gly Gln Trp Tyr Glu Ile Tyr Asp Lys
            100                 105                 110

Tyr Gln Val Val Gln Thr Leu Asp Cys Leu Arg Tyr Trp Lys Ala Thr
        115                 120                 125

His Arg Ser Pro Gly Gln Ile His Leu Val Gln Arg His Pro Pro Ser
    130                 135                 140

Glu Glu Ser Gln Ala Phe Gln Arg Gln Leu Thr Ala Leu Ile Gly Tyr
145                 150                 155                 160

Asp Val Thr Asp Val Ser Asn Val His Asp Asp Glu Leu Glu Phe Thr
                165                 170                 175

Arg Arg Gly Leu Val Thr Pro Arg Met Ala Glu Val Ala Ser Arg Asp
            180                 185                 190

Pro Lys Leu Tyr Ala Met His Pro Trp Val Thr Ser Lys Pro Leu Pro
        195                 200                 205

Glu Tyr Leu Trp Lys Lys Ile Ala Asn Asn Cys Ile Phe Ile Val Ile
    210                 215                 220

His Arg Ser Thr Thr Ser Gln Thr Ile Lys Val Ser Pro Asp Asp Thr
225                 230                 235                 240

Pro Gly Ala Ile Leu Gln Ser Phe Phe Thr Lys Met Ala Lys Lys Lys
                245                 250                 255

Ser Leu Met Asp Ile Pro Glu Ser Gln Ser Glu Gln Asp Phe Val Leu
            260                 265                 270

Arg Val Cys Gly Arg Asp Glu Tyr Leu Val Gly Glu Thr Pro Ile Lys
        275                 280                 285

Asn Phe Gln Trp Val Arg His Cys Leu Lys Asn Gly Glu Glu Ile His
    290                 295                 300

Val Val Leu Asp Thr Pro Pro Asp Pro Ala Leu Asp Glu Val Arg Lys
305                 310                 315                 320

Glu Glu Trp Pro Leu Val Asp Asp Cys Thr Gly Val Thr Gly Tyr His
                325                 330                 335

Glu Gln Leu Thr Ile His Gly Lys Asp His Glu Ser Val Phe Thr Val
            340                 345                 350

Ser Leu Trp Asp Cys Asp Arg Lys Phe Arg Val Lys Ile Arg Gly Ile
        355                 360                 365

Asp Ile Pro Val Leu Pro Arg Asn Thr Asp Leu Thr Val Phe Val Glu
    370                 375                 380

Ala Asn Ile Gln His Gly Gln Gln Val Leu Cys Gln Arg Arg Thr Ser
385                 390                 395                 400

Pro Lys Pro Phe Thr Glu Glu Val Leu Trp Asn Val Trp Leu Glu Phe
                405                 410                 415

Ser Ile Lys Ile Lys Asp Leu Pro Lys Gly Ala Leu Leu Asn Leu Gln
            420                 425                 430

Ile Tyr Cys Gly Lys Ala Pro Ala Leu Ser Ser Lys Ala Ser Ala Glu
        435                 440                 445

Ser Pro Ser Ser Glu Ser Lys Gly Lys Val Gln Leu Leu Tyr Tyr Val
    450                 455                 460
```

```
Asn Leu Leu Leu Ile Asp His Arg Phe Leu Leu Arg Arg Gly Glu Tyr
465                 470                 475                 480

Val Leu His Met Trp Gln Ile Ser Gly Lys Gly Glu Asp Gln Gly Ser
                485                 490                 495

Phe Asn Ala Asp Lys Leu Thr Ser Ala Thr Asn Pro Asp Lys Glu Asn
            500                 505                 510

Ser Met Ser Ile Ser Ile Leu Leu Asp Asn Tyr Cys His Pro Ile Ala
        515                 520                 525

Leu Pro Lys His Gln Pro Thr Pro Asp Pro Glu Gly Asp Arg Val Arg
    530                 535                 540

Ala Glu Met Pro Asn Gln Leu Arg Lys Gln Leu Glu Ala Ile Ile Ala
545                 550                 555                 560

Thr Asp Pro Leu Asn Pro Leu Thr Ala Glu Asp Lys Glu Leu Leu Trp
                565                 570                 575

His Phe Arg Tyr Glu Ser Leu Lys His Pro Lys Ala Tyr Pro Lys Leu
            580                 585                 590

Phe Ser Ser Val Lys Trp Gly Gln Gln Glu Ile Val Ala Lys Thr Tyr
        595                 600                 605

Gln Leu Leu Ala Arg Arg Glu Val Trp Asp Gln Ser Ala Leu Asp Val
    610                 615                 620

Gly Leu Thr Met Gln Leu Leu Asp Cys Asn Phe Ser Asp Glu Asn Val
625                 630                 635                 640

Arg Ala Ile Ala Val Gln Lys Leu Glu Ser Leu Glu Asp Asp Asp Val
                645                 650                 655

Leu His Tyr Leu Leu Gln Leu Val Gln Ala Val Lys Phe Glu Pro Tyr
            660                 665                 670

His Asp Ser Ala Leu Ala Arg Phe Leu Leu Lys Arg Gly Leu Arg Asn
        675                 680                 685

Lys Arg Ile Gly His Phe Leu Phe Trp Phe Leu Arg Ser Glu Ile Ala
    690                 695                 700

Gln Ser Arg His Tyr Gln Gln Arg Phe Ala Val Ile Leu Glu Ala Tyr
705                 710                 715                 720

Leu Arg Gly Cys Gly Thr Ala Met Leu His Asp Phe Thr Gln Gln Val
                725                 730                 735

Gln Val Ile Glu Met Leu Gln Lys Val Thr Leu Asp Ile Lys Ser Leu
            740                 745                 750

Ser Ala Glu Lys Tyr Asp Val Ser Ser Gln Val Ile Ser Gln Leu Lys
        755                 760                 765

Gln Lys Leu Glu Asn Leu Gln Asn Ser Gln Leu Pro Glu Ser Phe Arg
    770                 775                 780

Val Pro Tyr Asp Pro Gly Leu Lys Ala Gly Ala Leu Ala Ile Glu Lys
785                 790                 795                 800

Cys Lys Val Met Ala Ser Lys Lys Lys Pro Leu Trp Leu Glu Phe Lys
                805                 810                 815

Cys Ala Asp Pro Thr Ala Leu Ser Asn Glu Thr Ile Gly Ile Ile Phe
            820                 825                 830

Lys His Gly Asp Asp Leu Arg Gln Asp Met Leu Ile Leu Gln Ile Leu
        835                 840                 845

Arg Ile Met Glu Ser Ile Trp Glu Thr Glu Ser Leu Asp Leu Cys Leu
    850                 855                 860

Leu Pro Tyr Gly Cys Ile Ser Thr Gly Asp Lys Ile Gly Met Ile Glu
865                 870                 875                 880

Ile Val Lys Asp Ala Thr Thr Ile Ala Lys Ile Gln Gln Ser Thr Val
```

```
                885                 890                 895

Gly Asn Thr Gly Ala Phe Lys Asp Glu Val Leu Asn His Trp Leu Lys
            900                 905                 910

Glu Lys Ser Pro Thr Glu Glu Lys Phe Gln Ala Ala Val Glu Arg Phe
        915                 920                 925

Val Tyr Ser Cys Ala Gly Tyr Cys Val Ala Thr Phe Val Leu Gly Ile
    930                 935                 940

Gly Asp Arg His Asn Asp Asn Ile Met Ile Thr Glu Thr Gly Asn Leu
945                 950                 955                 960

Phe His Ile Asp Phe Gly His Ile Leu Gly Asn Tyr Lys Ser Phe Leu
                965                 970                 975

Gly Ile Asn Lys Glu Arg Val Pro Phe Val Leu Thr Pro Asp Phe Leu
            980                 985                 990

Phe Val Met Gly Thr Ser Gly Lys  Lys Thr Ser Pro His  Phe Gln Lys
        995                 1000                1005

Phe Gln  Asp Ile Cys Val Lys  Ala Tyr Leu Ala Leu  Arg His His
    1010                1015                1020

Thr Asn  Leu Leu Ile Ile Leu  Phe Ser Met Met Leu  Met Thr Gly
    1025                1030                1035

Met Pro  Gln Leu Thr Ser Lys  Glu Asp Ile Glu Tyr  Ile Arg Asp
    1040                1045                1050

Ala Leu  Thr Val Gly Lys Asn  Glu Glu Asp Ala Lys  Lys Tyr Phe
    1055                1060                1065

Leu Asp  Gln Ile Glu Val Cys  Arg Asp Lys Gly Trp  Thr Val Gln
    1070                1075                1080

Phe Asn  Trp Phe Leu His Leu  Val Leu Gly Ile Lys  Gln Gly Glu
    1085                1090                1095

Lys His  Ser Ala
    1100
```

<210> SEQ ID NO 17
<211> LENGTH: 3309
<212> TYPE: DNA
<213> ORGANISM: Homo sapiens

<400> SEQUENCE: 17

```
atggagctgg agaactataa acagcccgtg gtgctgagag aggacaactg ccgaaggcgc      60

cggaggatga agccgcgcag tgctgcggcc agcctgtcct ccatggagct catccccatc     120

gagttcgtgc tgcccaccag ccagcgcaaa tgcaagagcc ccgaaacggc gctgctgcac     180

gtggccggcc acggcaacgt ggagcagatg aaggcccagg tgtggctgcg agcgctggag     240

accagcgtgg cggcggactt ctaccaccgg ctgggaccgc atcacttcct cctgctctat     300

cagaagaagg ggcagtggta cgagatctac gacaagtacc aggtggtgca gactctggac     360

tgcctgcgct actggaaggc cacgcaccgg agcccgggcc agatccacct ggtgcagcgg     420

cacccgccct ccgaggagtc ccaagccttc cagcggcagc tcacggcgct gattggctat     480

gacgtcactg acgtcagcaa cgtgcacgac gatgagctgg agttcacgcg ccgtggcttg     540

gtgaccccgc gcatggcgga ggtggccagc cgcgacccca agctctacgc catgcacccg     600

tgggtgacgt ccaagcccct cccggagtac ctgtggaaga agattgccaa caactgcatc     660

ttcatcgtca ttcaccgcag caccaccagc cagaccatta aggtctcacc cgacgacacc     720

cccggcgcca tcctgcagag cttcttcacc aagatggcca agaagaaatc tctgatggat     780

attcccgaaa gccaaagcga acaggatttt gtgctgcgcg tctgtggccg ggatgagtac     840
```

```
ctggtgggcg aaacgcccat caaaaacttc cagtgggtga ggcactgcct caagaacgga    900
gaagagattc acgtggtact ggacacgcct ccagacccgg ccctagacga ggtgaggaag    960
gaagagtggc cactggtgga tgactgcacg ggagtcaccg gctaccatga gcagcttacc   1020
atccacggca aggaccacga gagtgtgttc accgtgtccc tgtgggactg cgaccgcaag   1080
ttcagggtca agatcagagg cattgatatc cccgtcctgc ctcggaacac cgacctcaca   1140
gtttttgtag aggcaaacat ccagcatggg caacaagtcc tttgccaaag gagaaccagc   1200
cccaaaccct tcacagagga ggtgctgtgg aatgtgtggc ttgagttcag tatcaaaatc   1260
aaagacttgc ccaaaggggc tctactgaac ctccagatct actgcggtaa agctccagca   1320
ctgtccagca aggcctctgc agagtccccc agttctgagt ccaagggcaa agttcagctt   1380
ctctattatg tgaacctgct gctgatagac caccgtttcc tcctgcgccg tggagaatac   1440
gtcctccaca tgtggcagat atctgggaag ggagaagacc aaggaagctt caatgctgac   1500
aaactcacgt ctgcaactaa cccagacaag gagaactcaa tgtccatctc cattcttctg   1560
gacaattact gccacccgat agccctgcct aagcatcagc ccacccctga cccggaaggg   1620
gaccgggttc gagcagaaat gcccaaccag cttcgcaagc aattggaggc gatcatagcc   1680
actgatccac ttaaccctct cacagcagag gacaaagaat tgctctggca ttttagatac   1740
gaaagcctta agcacccaaa agcatatcct aagctattta gttcagtgaa atggggacag   1800
caagaaattg tggccaaaac ataccaattg ttggccagaa gggaagtctg ggatcaaagt   1860
gctttggatg ttgggttaac aatgcagctc ctggactgca acttctcaga tgaaaatgta   1920
agagccattg cagttcagaa actggagagc ttggaggacg atgatgttct gcattacctt   1980
ctacaattgg tccaggctgt gaaatttgaa ccataccatg atagcgccct tgccagattt   2040
ctgctgaagc gtggtttaag aaacaaaaga attggtcact tttgttttg gttcttgaga   2100
agtgagatag cccagtccag acactatcag cagaggttcg ctgtgattct ggaagcctat   2160
ctgaggggct gtggcacagc catgctgcac gactttaccc aacaagtcca agtaatcgag   2220
atgttacaaa aagtcaccct tgatattaaa tcgctctctg ctgaaaagta tgacgtcagt   2280
tcccaagtta tttcacaact taaacaaaag cttgaaaacc tgcagaattc tcaactcccc   2340
gaaagcttta gagttccata tgatcctgga ctgaaagcag gagcgctggc aattgaaaaa   2400
tgtaaagtaa tggcctccaa gaaaaaacca ctatggcttg agtttaaatg tgccgatcct   2460
acagccctat caaatgaaac aattggaatt atctttaaac atggtgatga tctgcgccaa   2520
gacatgctta ttttacagat tctacgaatc atggagtcta tttgggagac tgaatctttg   2580
gatctatgcc tcctgccata tggttgcatt tcaactggtg acaaaatagg aatgatcgag   2640
attgtgaaag acgccacgac aattgccaaa attcagcaaa gcacagtggg caacacggga   2700
gcatttaaag atgaagtcct gaatcactgg ctcaaagaaa aatcccctac tgaagaaaag   2760
tttcaggcag cagtggagag atttgtttat tcctgtgcag gctactgtgt ggcaaccttt   2820
gttcttggaa taggcgacag acacaatgac aatattatga tcaccgagac aggaaaccta   2880
tttcatattg acttcgggca cattcttggg aattacaaaa gtttcctggg cattaataaa   2940
gagagagtgc catttgtgct aacccctgac ttcctctttg tgatgggaac ttctggaaag   3000
aagacaagcc cacacttcca gaaatttcag gacatctgtg ttaaggctta tctagccctt   3060
cgtcatcaca caaacctact gatcatcctg ttctccatga tgctgatgac aggaatgccc   3120
cagttaacaa gcaaagaaga cattgaatat atccgggatg ccctcacagt ggggaaaaat   3180
```

gaggaggatg ctaaaaagta ttttcttgat cagatcgaag tttgcagaga caaaggatgg 3240
actgtgcagt ttaattggtt tctacatctt gttcttggca tcaaacaagg agagaaacat 3300
tcagcctaa 3309

<210> SEQ ID NO 18
<211> LENGTH: 1102
<212> TYPE: PRT
<213> ORGANISM: Homo sapiens

<400> SEQUENCE: 18

Met Glu Leu Glu Asn Tyr Lys Gln Pro Val Val Leu Arg Glu Asp Asn
1 5 10 15

Cys Arg Arg Arg Arg Arg Met Lys Pro Arg Ser Ala Ala Ala Ser Leu
20 25 30

Ser Ser Met Glu Leu Ile Pro Ile Glu Phe Val Leu Pro Thr Ser Gln
35 40 45

Arg Lys Cys Lys Ser Pro Glu Thr Ala Leu Leu His Val Ala Gly His
50 55 60

Gly Asn Val Glu Gln Met Lys Ala Gln Val Trp Leu Arg Ala Leu Glu
65 70 75 80

Thr Ser Val Ala Ala Asp Phe Tyr His Arg Leu Gly Pro His His Phe
85 90 95

Leu Leu Leu Tyr Gln Lys Lys Gly Gln Trp Tyr Glu Ile Tyr Asp Lys
100 105 110

Tyr Gln Val Val Gln Thr Leu Asp Cys Leu Arg Tyr Trp Lys Ala Thr
115 120 125

His Arg Ser Pro Gly Gln Ile His Leu Val Gln Arg His Pro Pro Ser
130 135 140

Glu Glu Ser Gln Ala Phe Gln Arg Gln Leu Thr Ala Leu Ile Gly Tyr
145 150 155 160

Asp Val Thr Asp Val Ser Asn Val His Asp Asp Glu Leu Glu Phe Thr
165 170 175

Arg Arg Gly Leu Val Thr Pro Arg Met Ala Glu Val Ala Ser Arg Asp
180 185 190

Pro Lys Leu Tyr Ala Met His Pro Trp Val Thr Ser Lys Pro Leu Pro
195 200 205

Glu Tyr Leu Trp Lys Lys Ile Ala Asn Asn Cys Ile Phe Ile Val Ile
210 215 220

His Arg Ser Thr Thr Ser Gln Thr Ile Lys Val Ser Pro Asp Asp Thr
225 230 235 240

Pro Gly Ala Ile Leu Gln Ser Phe Phe Thr Lys Met Ala Lys Lys Lys
245 250 255

Ser Leu Met Asp Ile Pro Glu Ser Gln Ser Glu Gln Asp Phe Val Leu
260 265 270

Arg Val Cys Gly Arg Asp Glu Tyr Leu Val Gly Glu Thr Pro Ile Lys
275 280 285

Asn Phe Gln Trp Val Arg His Cys Leu Lys Asn Gly Glu Glu Ile His
290 295 300

Val Val Leu Asp Thr Pro Pro Asp Pro Ala Leu Asp Glu Val Arg Lys
305 310 315 320

Glu Glu Trp Pro Leu Val Asp Asp Cys Thr Gly Val Thr Gly Tyr His
325 330 335

Glu Gln Leu Thr Ile His Gly Lys Asp His Glu Ser Val Phe Thr Val
340 345 350

```
Ser Leu Trp Asp Cys Asp Arg Lys Phe Arg Val Lys Ile Arg Gly Ile
        355                 360                 365

Asp Ile Pro Val Leu Pro Arg Asn Thr Asp Leu Thr Val Phe Val Glu
    370                 375                 380

Ala Asn Ile Gln His Gly Gln Gln Val Leu Cys Gln Arg Arg Thr Ser
385                 390                 395                 400

Pro Lys Pro Phe Thr Glu Glu Val Leu Trp Asn Val Trp Leu Glu Phe
                405                 410                 415

Ser Ile Lys Ile Lys Asp Leu Pro Lys Gly Ala Leu Leu Asn Leu Gln
            420                 425                 430

Ile Tyr Cys Gly Lys Ala Pro Ala Leu Ser Ser Lys Ala Ser Ala Glu
        435                 440                 445

Ser Pro Ser Ser Glu Ser Lys Gly Lys Val Gln Leu Leu Tyr Tyr Val
    450                 455                 460

Asn Leu Leu Leu Ile Asp His Arg Phe Leu Leu Arg Arg Gly Glu Tyr
465                 470                 475                 480

Val Leu His Met Trp Gln Ile Ser Gly Lys Gly Glu Asp Gln Gly Ser
                485                 490                 495

Phe Asn Ala Asp Lys Leu Thr Ser Ala Thr Asn Pro Asp Lys Glu Asn
            500                 505                 510

Ser Met Ser Ile Ser Ile Leu Leu Asp Asn Tyr Cys His Pro Ile Ala
        515                 520                 525

Leu Pro Lys His Gln Pro Thr Pro Asp Pro Glu Gly Asp Arg Val Arg
    530                 535                 540

Ala Glu Met Pro Asn Gln Leu Arg Lys Gln Leu Glu Ala Ile Ile Ala
545                 550                 555                 560

Thr Asp Pro Leu Asn Pro Leu Thr Ala Glu Asp Lys Glu Leu Leu Trp
                565                 570                 575

His Phe Arg Tyr Glu Ser Leu Lys His Pro Lys Ala Tyr Pro Lys Leu
            580                 585                 590

Phe Ser Ser Val Lys Trp Gly Gln Gln Glu Ile Val Ala Lys Thr Tyr
        595                 600                 605

Gln Leu Leu Ala Arg Arg Glu Val Trp Asp Gln Ser Ala Leu Asp Val
    610                 615                 620

Gly Leu Thr Met Gln Leu Leu Asp Cys Asn Phe Ser Asp Glu Asn Val
625                 630                 635                 640

Arg Ala Ile Ala Val Gln Lys Leu Glu Ser Leu Glu Asp Asp Asp Val
                645                 650                 655

Leu His Tyr Leu Leu Gln Leu Val Gln Ala Val Lys Phe Glu Pro Tyr
            660                 665                 670

His Asp Ser Ala Leu Ala Arg Phe Leu Leu Lys Arg Gly Leu Arg Asn
        675                 680                 685

Lys Arg Ile Gly His Phe Leu Phe Trp Phe Leu Arg Ser Glu Ile Ala
    690                 695                 700

Gln Ser Arg His Tyr Gln Gln Arg Phe Ala Val Ile Leu Glu Ala Tyr
705                 710                 715                 720

Leu Arg Gly Cys Gly Thr Ala Met Leu His Asp Phe Thr Gln Gln Val
                725                 730                 735

Gln Val Ile Glu Met Leu Gln Lys Val Thr Leu Asp Ile Lys Ser Leu
            740                 745                 750

Ser Ala Glu Lys Tyr Asp Val Ser Ser Gln Val Ile Ser Gln Leu Lys
        755                 760                 765
```

```
Gln Lys Leu Glu Asn Leu Gln Asn Ser Gln Leu Pro Glu Ser Phe Arg
    770                 775                 780

Val Pro Tyr Asp Pro Gly Leu Lys Ala Gly Ala Leu Ala Ile Glu Lys
785                 790                 795                 800

Cys Lys Val Met Ala Ser Lys Lys Lys Pro Leu Trp Leu Glu Phe Lys
                805                 810                 815

Cys Ala Asp Pro Thr Ala Leu Ser Asn Glu Thr Ile Gly Ile Ile Phe
            820                 825                 830

Lys His Gly Asp Asp Leu Arg Gln Asp Met Leu Ile Leu Gln Ile Leu
        835                 840                 845

Arg Ile Met Glu Ser Ile Trp Glu Thr Glu Ser Leu Asp Leu Cys Leu
    850                 855                 860

Leu Pro Tyr Gly Cys Ile Ser Thr Gly Asp Lys Ile Gly Met Ile Glu
865                 870                 875                 880

Ile Val Lys Asp Ala Thr Thr Ile Ala Lys Ile Gln Gln Ser Thr Val
                885                 890                 895

Gly Asn Thr Gly Ala Phe Lys Asp Glu Val Leu Asn His Trp Leu Lys
            900                 905                 910

Glu Lys Ser Pro Thr Glu Glu Lys Phe Gln Ala Ala Val Glu Arg Phe
        915                 920                 925

Val Tyr Ser Cys Ala Gly Tyr Cys Val Ala Thr Phe Val Leu Gly Ile
    930                 935                 940

Gly Asp Arg His Asn Asp Asn Ile Met Ile Thr Glu Thr Gly Asn Leu
945                 950                 955                 960

Phe His Ile Asp Phe Gly His Ile Leu Gly Asn Tyr Lys Ser Phe Leu
                965                 970                 975

Gly Ile Asn Lys Glu Arg Val Pro Phe Val Leu Thr Pro Asp Phe Leu
            980                 985                 990

Phe Val Met Gly Thr Ser Gly Lys  Lys Thr Ser Pro His  Phe Gln Lys
        995                 1000                1005

Phe Gln  Asp Ile Cys Val Lys  Ala Tyr Leu Ala Leu  Arg His His
    1010                 1015                1020

Thr Asn  Leu Leu Ile Ile Leu  Phe Ser Met Met Leu  Met Thr Gly
    1025                 1030                1035

Met Pro  Gln Leu Thr Ser Lys  Glu Asp Ile Glu Tyr  Ile Arg Asp
    1040                 1045                1050

Ala Leu  Thr Val Gly Lys Asn  Glu Glu Asp Ala Lys  Lys Tyr Phe
    1055                 1060                1065

Leu Asp  Gln Ile Glu Val Cys  Arg Asp Lys Gly Trp  Thr Val Gln
    1070                 1075                1080

Phe Asn  Trp Phe Leu His Leu  Val Leu Gly Ile Lys  Gln Gly Glu
    1085                 1090                1095

Lys His  Ser Ala
    1100


<210> SEQ ID NO 19
<211> LENGTH: 3309
<212> TYPE: DNA
<213> ORGANISM: Mus musculus

<400> SEQUENCE: 19

atggagctgg agaactatga acaaccggtg gttctaagag aggacaacct ccgccggcgc     60

cggaggatga agccacgcag cgcagcaggc agcctgtctt ccatggagct catccccatt    120

gagttcgtac tgcccaccag ccagcgcatc agcaagactc cagaaacagc gctgctgcat    180
```

```
gtggctggcc atggcaatgt ggaacagatg aaagctcagg tgtggctgcg cgcactggag    240
accagtgtgg ctgcggagtt ctaccaccga ttgggcccgg accaattcct cctgctctac    300
cagaagaaag gacaatggta tgagatctat gacaggtacc aagtggtgca gaccctagac    360
tgcctgcatt actggaagtt gatgcacaag agccctggcc agatccacgt ggtacagcga    420
cacgtacctt ctgaggagac cttggctttc cagaagcagc tcacctccct gattggctat    480
gacgtcactg acatcagcaa tgtgcacgat gatgagctag agttcactcg ccgccgtctg    540
gttacgcccc gcatggctga agtggctggc cgggatgcca aactctatgc tatgcaccct    600
tgggtaacgt ccaaacctct cccagactac ctgtcaaaaa agattgccaa caactgcatc    660
ttcatcgtca tccaccgcgg taccaccagc caaaccatca aggtctccgc agatgatact    720
cctggtacca tcctccagag cttcttcacc aagatggcca agaagaagtc cctaatgaat    780
atctcagaaa gtcaaagtga gcaggatttt gtattgcggg tttgtggccg cgatgagtac    840
ctggtgggtg aaacacccct caaaaatttc cagtgggtga ggcagtgcct caagaacgga    900
gatgaaatac acctggtgct cgacacgcct ccagacccag cccttgatga ggtgaggaag    960
gaagaatggc cgctggtgga tgactgcact ggagtcaccg gctaccacga gcagctgacc   1020
atccatggca aggaccacga gagtgtgttc acagtgtctt tgtgggactg cgaccgaaag   1080
ttcagggtca agatcagagg cattgatatc cctgtcctgc ctcggaacac cgacctcact   1140
gtgtttgtgg aagcgaacat ccagcacggg caacaagtcc tctgccaaag gagaaccagc   1200
cctaagccct tcgcagaaga ggtactctgg aatgtgtggc tggagtttgg catcaaaatc   1260
aaagacttgc ccaaaggggc tctattgaac ctacagatct actgctgcaa aaccccatca   1320
ctgtccagca aggcttctgc agagactcca ggctccgagt ccaagggcaa agcccagctt   1380
ctctattacg tgaacttgct gttaatagac caccgtttcc tcctccgcca cggggactat   1440
gtgctccaca tgtggcagat atctggcaag gcagaggagc agggcagctt caatgctgac   1500
aagctcacat ccgcaaccaa tcctgacaag gagaactcaa tgtccatttc catcctgctg   1560
gacaattact gtcaccccat agctttgcct aagcaccggc ccacccctga cccagaggga   1620
gacagggttc gggctgaaat gcccaatcag cttcgaaagc aattggaggc gatcatagcc   1680
acagatccac ttaacccccct cacagcagag gacaaagaat tgctctggca ttttcgatat   1740
gaaagcctga agcatccgaa ggcttaccct aagctattca gctcagtgaa atgggggcag   1800
caagaaattg ttgccaaaac gtaccagctg ttagccagaa gggagatctg ggatcaaagt   1860
gctttggacg ttggcttaac catgcagctc ctggactgca acttttcaga cgagaatgtc   1920
cgggccattg cagttcagaa actggagagc ttagaggacg atgacgtttt acattacctt   1980
ctccagctgg tacaggctgt gaaatttgaa ccgtaccacg acagtgcgct ggccagattc   2040
ctgctgaagc gtggcttgag gaacaaaaga atcggtcact tcttgttctg gttcctgcga   2100
agtgagatcg cacagtccag acactatcag cagaggttcg ctgtgatcct ggaggcgtac   2160
ctgcgaggct gtggcacagc catgttgcag gacttcacac agcaggtcca tgtgattgag   2220
atgttacaga aagtcaccat tgatattaaa tcgctctcgg cagagaagta tgacgtcagt   2280
tcccaagtta tttcacagct taagcaaaag cttgaaagcc ttcagaactc caatctcccc   2340
gagagcttta gagttcccta tgatcctgga ctaaaagccg gtaccctggt gatcgagaaa   2400
tgcaaagtga tggcctccaa gaagaagccc ctgtggcttg agtttaagtg tgctgatccc   2460
acagtcctat ccaacgaaac cattggaatc atctttaaac atggtgatga tctgcgccaa   2520
```

```
gacatgttga tcttgcagat tctacgcatc atggagtcca tttgggagac tgaatctctg   2580

gacctgtgcc ttctgcctta cggttgcatc tcaactggtg acaaaatagg aatgatcgag   2640

attgtaaagg atgccacaac gatcgctcaa attcagcaaa gcacagtggg taacacgggg   2700

gcattcaaag atgaagtcct gaatcactgg ctcaaggaaa aatgtcctat tgaagaaaag   2760

tttcaggccg cagtggaaag gtttgtttac tcctgtgcag gctactgtgt ggccacattt   2820

gttcttggga tcggtgacag gcacaacgac aacattatga tctcagagac aggaaaccta   2880

tttcatatag acttcggaca cattcttggg aattacaaga gtttcctggg catcaataaa   2940

gagagagtgc ccttcgtcct aaccccagac ttcttgtttg tgatgggatc ttctggaaaa   3000

aagacaagtc cacacttcca gaaattccag gatgtctgtg ttagagctta cctagctctt   3060

cgccatcaca caaacctgtt gatcatcttg ttctccatga tgctgatgac aggaatgccc   3120

cagctgacaa gcaaagagga cattgaatat atccgggatg ccctcaccgt gggaaaaagc   3180

gaggaggacg ctaagaaata tttccttgat cagatcgaag tctgcagaga caaaggatgg   3240

actgtgcagt ttaactggtt cctacatctt gttcttggca tcaaacaagg agaaaagcac   3300

tccgcttga                                                           3309
```

```
<210> SEQ ID NO 20
<211> LENGTH: 1102
<212> TYPE: PRT
<213> ORGANISM: Mus musculus

<400> SEQUENCE: 20

Met Glu Leu Glu Asn Tyr Glu Gln Pro Val Val Leu Arg Glu Asp Asn
1               5                   10                  15

Leu Arg Arg Arg Arg Arg Met Lys Pro Arg Ser Ala Ala Gly Ser Leu
            20                  25                  30

Ser Ser Met Glu Leu Ile Pro Ile Glu Phe Val Leu Pro Thr Ser Gln
        35                  40                  45

Arg Ile Ser Lys Thr Pro Glu Thr Ala Leu Leu His Val Ala Gly His
    50                  55                  60

Gly Asn Val Glu Gln Met Lys Ala Gln Val Trp Leu Arg Ala Leu Glu
65                  70                  75                  80

Thr Ser Val Ala Ala Glu Phe Tyr His Arg Leu Gly Pro Asp Gln Phe
                85                  90                  95

Leu Leu Leu Tyr Gln Lys Lys Gly Gln Trp Tyr Glu Ile Tyr Asp Arg
            100                 105                 110

Tyr Gln Val Val Gln Thr Leu Asp Cys Leu His Tyr Trp Lys Leu Met
        115                 120                 125

His Lys Ser Pro Gly Gln Ile His Val Val Gln Arg His Val Pro Ser
    130                 135                 140

Glu Glu Thr Leu Ala Phe Gln Lys Gln Leu Thr Ser Leu Ile Gly Tyr
145                 150                 155                 160

Asp Val Thr Asp Ile Ser Asn Val His Asp Asp Glu Leu Glu Phe Thr
                165                 170                 175

Arg Arg Arg Leu Val Thr Pro Arg Met Ala Glu Val Ala Gly Arg Asp
            180                 185                 190

Ala Lys Leu Tyr Ala Met His Pro Trp Val Thr Ser Lys Pro Leu Pro
        195                 200                 205

Asp Tyr Leu Ser Lys Lys Ile Ala Asn Asn Cys Ile Phe Ile Val Ile
    210                 215                 220

His Arg Gly Thr Thr Ser Gln Thr Ile Lys Val Ser Ala Asp Asp Thr
```

```
225                 230                 235                 240

Pro Gly Thr Ile Leu Gln Ser Phe Phe Thr Lys Met Ala Lys Lys Lys
                245                 250                 255

Ser Leu Met Asn Ile Ser Glu Ser Gln Ser Glu Gln Asp Phe Val Leu
            260                 265                 270

Arg Val Cys Gly Arg Asp Glu Tyr Leu Val Gly Glu Thr Pro Leu Lys
        275                 280                 285

Asn Phe Gln Trp Val Arg Gln Cys Leu Lys Asn Gly Asp Glu Ile His
    290                 295                 300

Leu Val Leu Asp Thr Pro Pro Asp Pro Ala Leu Asp Glu Val Arg Lys
305                 310                 315                 320

Glu Glu Trp Pro Leu Val Asp Asp Cys Thr Gly Val Thr Gly Tyr His
                325                 330                 335

Glu Gln Leu Thr Ile His Gly Lys Asp His Glu Ser Val Phe Thr Val
            340                 345                 350

Ser Leu Trp Asp Cys Asp Arg Lys Phe Arg Val Lys Ile Arg Gly Ile
        355                 360                 365

Asp Ile Pro Val Leu Pro Arg Asn Thr Asp Leu Thr Val Phe Val Glu
    370                 375                 380

Ala Asn Ile Gln His Gly Gln Gln Val Leu Cys Gln Arg Arg Thr Ser
385                 390                 395                 400

Pro Lys Pro Phe Ala Glu Glu Val Leu Trp Asn Val Trp Leu Glu Phe
                405                 410                 415

Gly Ile Lys Ile Lys Asp Leu Pro Lys Gly Ala Leu Leu Asn Leu Gln
            420                 425                 430

Ile Tyr Cys Cys Lys Thr Pro Ser Leu Ser Ser Lys Ala Ser Ala Glu
        435                 440                 445

Thr Pro Gly Ser Glu Ser Lys Gly Lys Ala Gln Leu Leu Tyr Tyr Val
    450                 455                 460

Asn Leu Leu Leu Ile Asp His Arg Phe Leu Leu Arg His Gly Asp Tyr
465                 470                 475                 480

Val Leu His Met Trp Gln Ile Ser Gly Lys Ala Glu Glu Gln Gly Ser
                485                 490                 495

Phe Asn Ala Asp Lys Leu Thr Ser Ala Thr Asn Pro Asp Lys Glu Asn
            500                 505                 510

Ser Met Ser Ile Ser Ile Leu Leu Asp Asn Tyr Cys His Pro Ile Ala
        515                 520                 525

Leu Pro Lys His Arg Pro Thr Pro Asp Pro Glu Gly Asp Arg Val Arg
    530                 535                 540

Ala Glu Met Pro Asn Gln Leu Arg Lys Gln Leu Glu Ala Ile Ile Ala
545                 550                 555                 560

Thr Asp Pro Leu Asn Pro Leu Thr Ala Glu Asp Lys Glu Leu Leu Trp
                565                 570                 575

His Phe Arg Tyr Glu Ser Leu Lys His Pro Lys Ala Tyr Pro Lys Leu
            580                 585                 590

Phe Ser Ser Val Lys Trp Gly Gln Gln Glu Ile Val Ala Lys Thr Tyr
        595                 600                 605

Gln Leu Leu Ala Arg Arg Glu Ile Trp Asp Gln Ser Ala Leu Asp Val
    610                 615                 620

Gly Leu Thr Met Gln Leu Leu Asp Cys Asn Phe Ser Asp Glu Asn Val
625                 630                 635                 640

Arg Ala Ile Ala Val Gln Lys Leu Glu Ser Leu Glu Asp Asp Asp Val
                645                 650                 655
```

```
Leu His Tyr Leu Leu Gln Leu Val Gln Ala Val Lys Phe Glu Pro Tyr
            660                 665                 670

His Asp Ser Ala Leu Ala Arg Phe Leu Leu Lys Arg Gly Leu Arg Asn
        675                 680                 685

Lys Arg Ile Gly His Phe Leu Phe Trp Phe Leu Arg Ser Glu Ile Ala
    690                 695                 700

Gln Ser Arg His Tyr Gln Gln Arg Phe Ala Val Ile Leu Glu Ala Tyr
705                 710                 715                 720

Leu Arg Gly Cys Gly Thr Ala Met Leu Gln Asp Phe Thr Gln Gln Val
                725                 730                 735

His Val Ile Glu Met Leu Gln Lys Val Thr Ile Asp Ile Lys Ser Leu
            740                 745                 750

Ser Ala Glu Lys Tyr Asp Val Ser Ser Gln Val Ile Ser Gln Leu Lys
        755                 760                 765

Gln Lys Leu Glu Ser Leu Gln Asn Ser Asn Leu Pro Glu Ser Phe Arg
    770                 775                 780

Val Pro Tyr Asp Pro Gly Leu Lys Ala Gly Thr Leu Val Ile Glu Lys
785                 790                 795                 800

Cys Lys Val Met Ala Ser Lys Lys Lys Pro Leu Trp Leu Glu Phe Lys
                805                 810                 815

Cys Ala Asp Pro Thr Val Leu Ser Asn Glu Thr Ile Gly Ile Ile Phe
            820                 825                 830

Lys His Gly Asp Asp Leu Arg Gln Asp Met Leu Ile Leu Gln Ile Leu
        835                 840                 845

Arg Ile Met Glu Ser Ile Trp Glu Thr Glu Ser Leu Asp Leu Cys Leu
    850                 855                 860

Leu Pro Tyr Gly Cys Ile Ser Thr Gly Asp Lys Ile Gly Met Ile Glu
865                 870                 875                 880

Ile Val Lys Asp Ala Thr Thr Ile Ala Gln Ile Gln Gln Ser Thr Val
                885                 890                 895

Gly Asn Thr Gly Ala Phe Lys Asp Glu Val Leu Asn His Trp Leu Lys
            900                 905                 910

Glu Lys Cys Pro Ile Glu Glu Lys Phe Gln Ala Ala Val Glu Arg Phe
        915                 920                 925

Val Tyr Ser Cys Ala Gly Tyr Cys Val Ala Thr Phe Val Leu Gly Ile
    930                 935                 940

Gly Asp Arg His Asn Asp Asn Ile Met Ile Ser Glu Thr Gly Asn Leu
945                 950                 955                 960

Phe His Ile Asp Phe Gly His Ile Leu Gly Asn Tyr Lys Ser Phe Leu
                965                 970                 975

Gly Ile Asn Lys Glu Arg Val Pro Phe Val Leu Thr Pro Asp Phe Leu
            980                 985                 990

Phe Val Met Gly Ser Ser Gly Lys  Lys Thr Ser Pro His  Phe Gln Lys
        995                 1000                1005

Phe Gln  Asp Val Cys Val Arg  Ala Tyr Leu Ala Leu  Arg His His
    1010                1015                1020

Thr Asn  Leu Leu Ile Ile Leu  Phe Ser Met Met Leu  Met Thr Gly
    1025                1030                1035

Met Pro  Gln Leu Thr Ser Lys  Glu Asp Ile Glu Tyr  Ile Arg Asp
    1040                1045                1050

Ala Leu  Thr Val Gly Lys Ser  Glu Glu Asp Ala Lys  Lys Tyr Phe
    1055                1060                1065
```

```
Leu Asp  Gln Ile Glu Val Cys  Arg Asp Lys Gly Trp  Thr Val Gln
    1070                 1075                 1080

Phe Asn  Trp Phe Leu His Leu  Val Leu Gly Ile Lys  Gln Gly Glu
    1085                 1090                 1095

Lys His  Ser Ala
    1100


<210> SEQ ID NO 21
<211> LENGTH: 3309
<212> TYPE: DNA
<213> ORGANISM: Mus musculus

<400> SEQUENCE: 21

atggagctgg agaactatga acaaccggtg gttctaagag aggacaacct ccgccggcgc     60

cggaggatga agccacgcag cgcagcaggc agcctgtctt ccatggagct catccccatt    120

gagttcgtac tgcccaccag ccagcgcatc agcaagactc cagaaacagc gctgctgcat    180

gtggctggcc atggcaatgt ggaacagatg aaagctcagg tgtggctgcg cgcactggag    240

accagtgtgg ctgcggagtt ctaccaccga ttgggcccgg accaattcct cctgctctac    300

cagaagaaag gacaatggta tgagatctat gacaggtacc aagtggtgca gaccctagac    360

tgcctgcatt actggaagtt gatgcacaag agccctggcc agatccacgt ggtacagcga    420

cacgtacctt ctgaggagac cttggctttc cagaagcagc tcacctccct gattggctat    480

gacgtcactg acatcagcaa tgtgcacgat gatgagctag agttcactcg ccgccgtctg    540

gttacgcccc gcatggctga agtggctggc cgggatgcca aactctatgc tatgcaccct    600

tgggtaacgt ccaaacctct cccagactac ctgtcaaaaa agattgccaa caactgcatc    660

ttcatcgtca tccaccgcgg taccaccagc caaaccatca aggtctccgc agatgatact    720

cctggtacca tcctccagag cttcttcacc aagatggcca agaagaagtc cctaatgaat    780

atctcagaaa gtcaaagtga gcaggatttt gtattgcggg tttgtggccg cgatgagtac    840

ctggtgggtg aaacacccct caaaaatttc cagtgggtga ggcagtgcct caagaacgga    900

gatgaaatac acctggtgct cgacacgcct ccagacccag cccttgatga ggtgaggaag    960

gaagaatggc cgctggtgga tgactgcact ggagtcaccg gctaccacga gcagctgacc   1020

atccatggca aggaccacga gagtgtgttc acagtgtctt tgtgggactg cgaccgaaag   1080

ttcagggtca agatcagagg cattgatatc cctgtcctgc ctcggaacac cgacctcact   1140

gtgtttgtgg aagcgaacat ccagcacggg caacaagtcc tctgccaaag gagaaccagc   1200

cctaagccct tcgcagaaga ggtactctgg aatgtgtggc tggagtttgg catcaaaatc   1260

aaagacttgc ccaaaggggc tctattgaac ctacagatct actgctgcaa aaccccatca   1320

ctgtccagca aggcttctgc agagactcca ggctccgagt ccaagggcaa agcccagctt   1380

ctctattacg tgaacttgct gttaatagac caccgtttcc tcctccgcca cggggactat   1440

gtgctccaca tgtggcagat atctggcaag gcagaggagc agggcagctt caatgctgac   1500

aagctcacat ccgcaaccaa tcctgacaag gagaactcaa tgtccatttc catcctgctg   1560

gacaattact gtcaccccat agctttgcct aagcaccggc ccacccctga cccagaggga   1620

gacagggttc gggctgaaat gcccaatcag cttcgaaagc aattggaggc gatcatagcc   1680

acagatccac ttaaccccct cacagcagag gacaaagaat tgctctggca ttttcgatat   1740

gaaagcctga agcatccgaa ggcttaccct aagctattca gctcagtgaa atgggggcag   1800

caagaaattg ttgccaaaac gtaccagctg ttagccagaa gggagatctg ggatcaaagt   1860
```

```
gctttggacg ttggcttaac catgcagctc ctggactgca acttttcaga cgagaatgtc   1920

cgggccattg cagttcagaa actggagagc ttagaggacg atgacgtttt acattacctt   1980

ctccagctgg tacaggctgt gaaatttgaa ccgtaccacg acagtgcgct ggccagattc   2040

ctgctgaagc gtggcttgag gaacaaaaga atcggtcact tcttgttctg gttcctgcga   2100

agtgagatcg cacagtccag acactatcag cagaggttcg ctgtgatcct ggaggcgtac   2160

ctgcgaggct gtggcacagc catgttgcag gacttcacac agcaggtcca tgtgattgag   2220

atgttacaga aagtcaccat tgatattaaa tcgctctcgg cagagaagta tgacgtcagt   2280

tcccaagtta tttcacagct taagcaaaag cttgaaagcc ttcagaactc caatctcccc   2340

gagagcttta gagttcccta tgatcctgga ctaaaagccg gtaccctggt gatcgagaaa   2400

tgcaaagtga tggcctccaa gaagaagccc ctgtggcttg agtttaagtg tgctgatccc   2460

acagtcctat ccaacgaaac cattggaatc atctttaaac atggtgatga tctgcgccaa   2520

gacatgttga tcttgcagat tctacgcatc atggagtcca tttgggagac tgaatctctg   2580

gacctgtgcc ttctgcctta cggttgcatc tcaactggtg acaaaatagg aatgatcgag   2640

attgtaaagg atgccacaac gatcgctcaa attcagcaaa gcacagtggg taacacgggg   2700

gcattcaaag atgaagtcct gaatcactgg ctcaaggaaa aatgtcctat tgaagaaaag   2760

tttcaggccg cagtggaaag gtttgtttac tcctgtgcag gctactgtgt ggccacattt   2820

gttcttggga tcggtgacag gcacaacgac aacattatga tctcagagac aggaaaccta   2880

tttcatatag acttcggaca cattcttggg aattacaaga gtttcctggg catcaataaa   2940

gagagagtgc ccttcgtcct aaccccagac ttcttgtttg tgatgggatc ttctggaaaa   3000

aagacaagtc cacacttcca gaaattccag gatgtctgtg ttagagctta cctagctctt   3060

cgccatcaca caaacctgtt gatcatcttg ttctccatga tgctgatgac aggaatgccc   3120

cagctgacaa gcaaagagga cattgaatat atccgggatg ccctcaccgt gggaaaaagc   3180

gaggaggacg ctaagaaata tttccttgat cagatcgaag tctgcagaga caaaggatgg   3240

actgtgcagt ttaactggtt cctacatctt gttcttggca tcaaacaagg agaaaagcac   3300

tccgcttga                                                          3309
```

<210> SEQ ID NO 22
<211> LENGTH: 1102
<212> TYPE: PRT
<213> ORGANISM: Mus musculus

<400> SEQUENCE: 22

```
Met Glu Leu Glu Asn Tyr Glu Gln Pro Val Val Leu Arg Glu Asp Asn
1               5                   10                  15

Leu Arg Arg Arg Arg Arg Met Lys Pro Arg Ser Ala Ala Gly Ser Leu
            20                  25                  30

Ser Ser Met Glu Leu Ile Pro Ile Glu Phe Val Leu Pro Thr Ser Gln
        35                  40                  45

Arg Ile Ser Lys Thr Pro Glu Thr Ala Leu Leu His Val Ala Gly His
    50                  55                  60

Gly Asn Val Glu Gln Met Lys Ala Gln Val Trp Leu Arg Ala Leu Glu
65                  70                  75                  80

Thr Ser Val Ala Ala Glu Phe Tyr His Arg Leu Gly Pro Asp Gln Phe
                85                  90                  95

Leu Leu Leu Tyr Gln Lys Lys Gly Gln Trp Tyr Glu Ile Tyr Asp Arg
            100                 105                 110
```

```
Tyr Gln Val Val Gln Thr Leu Asp Cys Leu His Tyr Trp Lys Leu Met
        115                 120                 125

His Lys Ser Pro Gly Gln Ile His Val Val Gln Arg His Val Pro Ser
    130                 135                 140

Glu Glu Thr Leu Ala Phe Gln Lys Gln Leu Thr Ser Leu Ile Gly Tyr
145                 150                 155                 160

Asp Val Thr Asp Ile Ser Asn Val His Asp Asp Glu Leu Glu Phe Thr
                165                 170                 175

Arg Arg Arg Leu Val Thr Pro Arg Met Ala Glu Val Ala Gly Arg Asp
            180                 185                 190

Ala Lys Leu Tyr Ala Met His Pro Trp Val Thr Ser Lys Pro Leu Pro
        195                 200                 205

Asp Tyr Leu Ser Lys Lys Ile Ala Asn Asn Cys Ile Phe Ile Val Ile
    210                 215                 220

His Arg Gly Thr Thr Ser Gln Thr Ile Lys Val Ser Ala Asp Asp Thr
225                 230                 235                 240

Pro Gly Thr Ile Leu Gln Ser Phe Phe Thr Lys Met Ala Lys Lys Lys
                245                 250                 255

Ser Leu Met Asn Ile Ser Glu Ser Gln Ser Glu Gln Asp Phe Val Leu
            260                 265                 270

Arg Val Cys Gly Arg Asp Glu Tyr Leu Val Gly Glu Thr Pro Leu Lys
        275                 280                 285

Asn Phe Gln Trp Val Arg Gln Cys Leu Lys Asn Gly Asp Glu Ile His
    290                 295                 300

Leu Val Leu Asp Thr Pro Pro Asp Pro Ala Leu Asp Glu Val Arg Lys
305                 310                 315                 320

Glu Glu Trp Pro Leu Val Asp Asp Cys Thr Gly Val Thr Gly Tyr His
                325                 330                 335

Glu Gln Leu Thr Ile His Gly Lys Asp His Glu Ser Val Phe Thr Val
            340                 345                 350

Ser Leu Trp Asp Cys Asp Arg Lys Phe Arg Val Lys Ile Arg Gly Ile
        355                 360                 365

Asp Ile Pro Val Leu Pro Arg Asn Thr Asp Leu Thr Val Phe Val Glu
    370                 375                 380

Ala Asn Ile Gln His Gly Gln Gln Val Leu Cys Gln Arg Arg Thr Ser
385                 390                 395                 400

Pro Lys Pro Phe Ala Glu Glu Val Leu Trp Asn Val Trp Leu Glu Phe
                405                 410                 415

Gly Ile Lys Ile Lys Asp Leu Pro Lys Gly Ala Leu Leu Asn Leu Gln
            420                 425                 430

Ile Tyr Cys Cys Lys Thr Pro Ser Leu Ser Ser Lys Ala Ser Ala Glu
        435                 440                 445

Thr Pro Gly Ser Glu Ser Lys Gly Lys Ala Gln Leu Leu Tyr Tyr Val
    450                 455                 460

Asn Leu Leu Leu Ile Asp His Arg Phe Leu Leu Arg His Gly Asp Tyr
465                 470                 475                 480

Val Leu His Met Trp Gln Ile Ser Gly Lys Ala Glu Glu Gln Gly Ser
                485                 490                 495

Phe Asn Ala Asp Lys Leu Thr Ser Ala Thr Asn Pro Asp Lys Glu Asn
            500                 505                 510

Ser Met Ser Ile Ser Ile Leu Leu Asp Asn Tyr Cys His Pro Ile Ala
        515                 520                 525

Leu Pro Lys His Arg Pro Thr Pro Asp Pro Glu Gly Asp Arg Val Arg
```

```
    530                 535                 540

Ala Glu Met Pro Asn Gln Leu Arg Lys Gln Leu Glu Ala Ile Ile Ala
545                 550                 555                 560

Thr Asp Pro Leu Asn Pro Leu Thr Ala Glu Asp Lys Glu Leu Leu Trp
                565                 570                 575

His Phe Arg Tyr Glu Ser Leu Lys His Pro Lys Ala Tyr Pro Lys Leu
            580                 585                 590

Phe Ser Ser Val Lys Trp Gly Gln Gln Glu Ile Val Ala Lys Thr Tyr
        595                 600                 605

Gln Leu Leu Ala Arg Arg Glu Ile Trp Asp Gln Ser Ala Leu Asp Val
    610                 615                 620

Gly Leu Thr Met Gln Leu Leu Asp Cys Asn Phe Ser Asp Glu Asn Val
625                 630                 635                 640

Arg Ala Ile Ala Val Gln Lys Leu Glu Ser Leu Glu Asp Asp Asp Val
                645                 650                 655

Leu His Tyr Leu Leu Gln Leu Val Gln Ala Val Lys Phe Glu Pro Tyr
            660                 665                 670

His Asp Ser Ala Leu Ala Arg Phe Leu Leu Lys Arg Gly Leu Arg Asn
        675                 680                 685

Lys Arg Ile Gly His Phe Leu Phe Trp Phe Leu Arg Ser Glu Ile Ala
    690                 695                 700

Gln Ser Arg His Tyr Gln Gln Arg Phe Ala Val Ile Leu Glu Ala Tyr
705                 710                 715                 720

Leu Arg Gly Cys Gly Thr Ala Met Leu Gln Asp Phe Thr Gln Gln Val
                725                 730                 735

His Val Ile Glu Met Leu Gln Lys Val Thr Ile Asp Ile Lys Ser Leu
            740                 745                 750

Ser Ala Glu Lys Tyr Asp Val Ser Ser Gln Val Ile Ser Gln Leu Lys
        755                 760                 765

Gln Lys Leu Glu Ser Leu Gln Asn Ser Asn Leu Pro Glu Ser Phe Arg
    770                 775                 780

Val Pro Tyr Asp Pro Gly Leu Lys Ala Gly Thr Leu Val Ile Glu Lys
785                 790                 795                 800

Cys Lys Val Met Ala Ser Lys Lys Lys Pro Leu Trp Leu Glu Phe Lys
                805                 810                 815

Cys Ala Asp Pro Thr Val Leu Ser Asn Glu Thr Ile Gly Ile Ile Phe
            820                 825                 830

Lys His Gly Asp Asp Leu Arg Gln Asp Met Leu Ile Leu Gln Ile Leu
        835                 840                 845

Arg Ile Met Glu Ser Ile Trp Glu Thr Glu Ser Leu Asp Leu Cys Leu
    850                 855                 860

Leu Pro Tyr Gly Cys Ile Ser Thr Gly Asp Lys Ile Gly Met Ile Glu
865                 870                 875                 880

Ile Val Lys Asp Ala Thr Thr Ile Ala Gln Ile Gln Gln Ser Thr Val
                885                 890                 895

Gly Asn Thr Gly Ala Phe Lys Asp Glu Val Leu Asn His Trp Leu Lys
            900                 905                 910

Glu Lys Cys Pro Ile Glu Glu Lys Phe Gln Ala Ala Val Glu Arg Phe
        915                 920                 925

Val Tyr Ser Cys Ala Gly Tyr Cys Val Ala Thr Phe Val Leu Gly Ile
    930                 935                 940

Gly Asp Arg His Asn Asp Asn Ile Met Ile Ser Glu Thr Gly Asn Leu
945                 950                 955                 960
```

```
Phe His Ile Asp Phe Gly His Ile Leu Gly Asn Tyr Lys Ser Phe Leu
                965                 970                 975

Gly Ile Asn Lys Glu Arg Val Pro Phe Val Leu Thr Pro Asp Phe Leu
            980                 985                 990

Phe Val Met Gly Ser Ser Gly Lys  Lys Thr Ser Pro His  Phe Gln Lys
        995                 1000                1005

Phe Gln  Asp Val Cys Val Arg  Ala Tyr Leu Ala Leu  Arg His His
    1010                 1015                1020

Thr Asn  Leu Leu Ile Ile Leu  Phe Ser Met Met Leu  Met Thr Gly
    1025                 1030                1035

Met Pro  Gln Leu Thr Ser Lys  Glu Asp Ile Glu Tyr  Ile Arg Asp
    1040                 1045                1050

Ala Leu  Thr Val Gly Lys Ser  Glu Glu Asp Ala Lys  Lys Tyr Phe
    1055                 1060                1065

Leu Asp  Gln Ile Glu Val Cys  Arg Asp Lys Gly Trp  Thr Val Gln
    1070                 1075                1080

Phe Asn  Trp Phe Leu His Leu  Val Leu Gly Ile Lys  Gln Gly Glu
    1085                 1090                1095

Lys His  Ser Ala
    1100
```

<210> SEQ ID NO 23
<211> LENGTH: 3309
<212> TYPE: DNA
<213> ORGANISM: Mus musculus

<400> SEQUENCE: 23

```
atggagctgg agaactatga acaaccggtg gttctaagag aggacaacct ccgccggcgc     60
cggaggatga agccacgcag cgcagcaggc agcctgtctt ccatggagct catccccatt    120
gagttcgtac tgcccaccag ccagcgcatc agcaagactc cagaaacagc gctgctgcat    180
gtggctggcc atggcaatgt ggaacagatg aaagctcagg tgtggctgcg cgcactggag    240
accagtgtgg ctgcggagtt ctaccaccga ttgggcccgg accaattcct cctgctctac    300
cagaagaaag gacaatggta tgagatctat gacaggtacc aagtggtgca gaccctagac    360
tgcctgcatt actggaagtt gatgcacaag agccctggcc agatccacgt ggtacagcga    420
cacgtacctt ctgaggagac cttggctttc cagaagcagc tcacctccct gattggctat    480
gacgtcactg acatcagcaa tgtgcacgat gatgagctag agttcactcg ccgccgtctg    540
gttacgcccc gcatggctga agtggctggc cgggatgcca aactctatgc tatgcaccct    600
tgggtaacgt ccaaacctct cccagactac ctgtcaaaaa agattgccaa caactgcatc    660
ttcatcgtca tccaccgcgg taccaccagc caaaccatca aggtctccgc agatgatact    720
cctggtacca tcctccagag cttcttcacc aagatggcca agaagaagtc cctaatgaat    780
atctcagaaa gtcaaagtga gcaggatttt gtattgcggg tttgtggccg cgatgagtac    840
ctggtgggtg aaacacccct caaaaatttc cagtgggtga ggcagtgcct caagaacgga    900
gatgaaatac acctggtgct cgacacgcct ccagacccag cccttgatga ggtgaggaag    960
gaagaatggc cgctggtgga tgactgcact ggagtcaccg gctaccacga gcagctgacc   1020
atccatggca aggaccacga gagtgtgttc acagtgtctt tgtgggactg cgaccgaaag   1080
ttcagggtca agatcagagg cattgatatc cctgtcctgc ctcggaacac cgacctcact   1140
gtgtttgtgg aagcgaacat ccagcacggg caacaagtcc tctgccaaag gagaaccagc   1200
```

```
cctaagccct tcgcagaaga ggtactctgg aatgtgtggc tggagtttgg catcaaaatc   1260
aaagacttgc ccaaaggggc tctattgaac ctacagatct actgctgcaa aaccccatca   1320
ctgtccagca aggcttctgc agagactcca ggctccgagt ccaagggcaa agcccagctt   1380
ctctattacg tgaacttgct gttaatagac caccgtttcc tcctccgcca cggggactat   1440
gtgctccaca tgtggcagat atctggcaag gcagaggagc agggcagctt caatgctgac   1500
aagctcacat ccgcaaccaa tcctgacaag gagaactcaa tgtccatttc catcctgctg   1560
gacaattact gtcaccccat agctttgcct aagcaccggc ccacccctga cccagaggga   1620
gacagggttc gggctgaaat gcccaatcag cttcgaaagc aattggaggc gatcatagcc   1680
acagatccac ttaacccccct cacagcagag gacaaagaat tgctctggca ttttcgatat   1740
gaaagcctga agcatccgaa ggcttaccct aagctattca gctcagtgaa atgggggcag   1800
caagaaattg ttgccaaaac gtaccagctg ttagccagaa gggagatctg ggatcaaagt   1860
gctttggacg ttggcttaac catgcagctc ctggactgca acttttcaga cgagaatgtc   1920
cgggccattg cagttcagaa actggagagc ttagaggacg atgacgtttt acattacctt   1980
ctccagctgg tacaggctgt gaaatttgaa ccgtaccacg acagtgcgct ggccagattc   2040
ctgctgaagc gtggcttgag gaacaaaaga atcggtcact tcttgttctg gttcctgcga   2100
agtgagatcg cacagtccag acactatcag cagaggttcg ctgtgatcct ggaggcgtac   2160
ctgcgaggct gtggcacagc catgttgcag gacttcacac agcaggtcca tgtgattgag   2220
atgttacaga aagtcaccat tgatattaaa tcgctctcgg cagagaagta tgacgtcagt   2280
tcccaagtta tttcacagct taagcaaaag cttgaaagcc ttcagaactc caatctcccc   2340
gagagcttta gagttcccta tgatcctgga ctaaaagccg gtaccctggt gatcgagaaa   2400
tgcaaagtga tggcctccaa gaagaagccc ctgtggcttg agtttaagtg tgctgatccc   2460
acagtcctat ccaacgaaac cattggaatc atctttaaac atggtgatga tctgcgccaa   2520
gacatgttga tcttgcagat tctacgcatc atggagtcca tttgggagac tgaatctctg   2580
gacctgtgcc ttctgcctta cggttgcatc tcaactggtg acaaaatagg aatgatcgag   2640
attgtaaagg atgccacaac gatcgctcaa attcagcaaa gcacagtggg taacacgggg   2700
gcattcaaag atgaagtcct gaatcactgg ctcaaggaaa aatgtcctat tgaagaaaag   2760
tttcaggccg cagtggaaag gtttgtttac tcctgtgcag gctactgtgt ggccacattt   2820
gttcttggga tcggtgacag gcacaacgac aacattatga tctcagagac aggaaaccta   2880
tttcatatag acttcggaca cattcttggg aattacaaga gtttcctggg catcaataaa   2940
gagagagtgc ccttcgtcct aaccccagac ttcttgtttg tgatgggatc ttctggaaaa   3000
aagacaagtc cacacttcca gaaattccag gatgtctgtg ttagagctta cctagctctt   3060
cgccatcaca caaacctgtt gatcatcttg ttctccatga tgctgatgac aggaatgccc   3120
cagctgacaa gcaaagagga cattgaatat atccgggatg ccctcaccgt gggaaaaagc   3180
gaggaggacg ctaagaaata tttccttgat cagatcgaag tctgcagaga caaaggatgg   3240
actgtgcagt ttaactggtt cctacatctt gttcttggca tcaaacaagg agaaaagcac   3300
tccgcttga                                                           3309
```

<210> SEQ ID NO 24
<211> LENGTH: 1102
<212> TYPE: PRT
<213> ORGANISM: Mus musculus

<400> SEQUENCE: 24

```
Met Glu Leu Glu Asn Tyr Glu Gln Pro Val Val Leu Arg Glu Asp Asn
1               5                   10                  15

Leu Arg Arg Arg Arg Arg Met Lys Pro Arg Ser Ala Ala Gly Ser Leu
            20                  25                  30

Ser Ser Met Glu Leu Ile Pro Ile Glu Phe Val Leu Pro Thr Ser Gln
        35                  40                  45

Arg Ile Ser Lys Thr Pro Glu Thr Ala Leu Leu His Val Ala Gly His
    50                  55                  60

Gly Asn Val Glu Gln Met Lys Ala Gln Val Trp Leu Arg Ala Leu Glu
65                  70                  75                  80

Thr Ser Val Ala Ala Glu Phe Tyr His Arg Leu Gly Pro Asp Gln Phe
                85                  90                  95

Leu Leu Leu Tyr Gln Lys Lys Gly Gln Trp Tyr Glu Ile Tyr Asp Arg
            100                 105                 110

Tyr Gln Val Val Gln Thr Leu Asp Cys Leu His Tyr Trp Lys Leu Met
        115                 120                 125

His Lys Ser Pro Gly Gln Ile His Val Val Gln Arg His Val Pro Ser
    130                 135                 140

Glu Glu Thr Leu Ala Phe Gln Lys Gln Leu Thr Ser Leu Ile Gly Tyr
145                 150                 155                 160

Asp Val Thr Asp Ile Ser Asn Val His Asp Asp Glu Leu Glu Phe Thr
                165                 170                 175

Arg Arg Arg Leu Val Thr Pro Arg Met Ala Glu Val Ala Gly Arg Asp
            180                 185                 190

Ala Lys Leu Tyr Ala Met His Pro Trp Val Thr Ser Lys Pro Leu Pro
        195                 200                 205

Asp Tyr Leu Ser Lys Lys Ile Ala Asn Asn Cys Ile Phe Ile Val Ile
    210                 215                 220

His Arg Gly Thr Thr Ser Gln Thr Ile Lys Val Ser Ala Asp Asp Thr
225                 230                 235                 240

Pro Gly Thr Ile Leu Gln Ser Phe Phe Thr Lys Met Ala Lys Lys Lys
                245                 250                 255

Ser Leu Met Asn Ile Ser Glu Ser Gln Ser Glu Gln Asp Phe Val Leu
            260                 265                 270

Arg Val Cys Gly Arg Asp Glu Tyr Leu Val Gly Glu Thr Pro Leu Lys
        275                 280                 285

Asn Phe Gln Trp Val Arg Gln Cys Leu Lys Asn Gly Asp Glu Ile His
    290                 295                 300

Leu Val Leu Asp Thr Pro Pro Asp Pro Ala Leu Asp Glu Val Arg Lys
305                 310                 315                 320

Glu Glu Trp Pro Leu Val Asp Asp Cys Thr Gly Val Thr Gly Tyr His
                325                 330                 335

Glu Gln Leu Thr Ile His Gly Lys Asp His Glu Ser Val Phe Thr Val
            340                 345                 350

Ser Leu Trp Asp Cys Asp Arg Lys Phe Arg Val Lys Ile Arg Gly Ile
        355                 360                 365

Asp Ile Pro Val Leu Pro Arg Asn Thr Asp Leu Thr Val Phe Val Glu
    370                 375                 380

Ala Asn Ile Gln His Gly Gln Gln Val Leu Cys Gln Arg Arg Thr Ser
385                 390                 395                 400

Pro Lys Pro Phe Ala Glu Glu Val Leu Trp Asn Val Trp Leu Glu Phe
                405                 410                 415
```

```
Gly Ile Lys Ile Lys Asp Leu Pro Lys Gly Ala Leu Leu Asn Leu Gln
            420                 425                 430

Ile Tyr Cys Cys Lys Thr Pro Ser Leu Ser Ser Lys Ala Ser Ala Glu
        435                 440                 445

Thr Pro Gly Ser Glu Ser Lys Gly Lys Ala Gln Leu Leu Tyr Tyr Val
    450                 455                 460

Asn Leu Leu Leu Ile Asp His Arg Phe Leu Leu Arg His Gly Asp Tyr
465                 470                 475                 480

Val Leu His Met Trp Gln Ile Ser Gly Lys Ala Glu Glu Gln Gly Ser
                485                 490                 495

Phe Asn Ala Asp Lys Leu Thr Ser Ala Thr Asn Pro Asp Lys Glu Asn
            500                 505                 510

Ser Met Ser Ile Ser Ile Leu Leu Asp Asn Tyr Cys His Pro Ile Ala
        515                 520                 525

Leu Pro Lys His Arg Pro Thr Pro Asp Pro Glu Gly Asp Arg Val Arg
    530                 535                 540

Ala Glu Met Pro Asn Gln Leu Arg Lys Gln Leu Glu Ala Ile Ile Ala
545                 550                 555                 560

Thr Asp Pro Leu Asn Pro Leu Thr Ala Glu Asp Lys Glu Leu Leu Trp
                565                 570                 575

His Phe Arg Tyr Glu Ser Leu Lys His Pro Lys Ala Tyr Pro Lys Leu
            580                 585                 590

Phe Ser Ser Val Lys Trp Gly Gln Gln Glu Ile Val Ala Lys Thr Tyr
        595                 600                 605

Gln Leu Leu Ala Arg Arg Glu Ile Trp Asp Gln Ser Ala Leu Asp Val
    610                 615                 620

Gly Leu Thr Met Gln Leu Leu Asp Cys Asn Phe Ser Asp Glu Asn Val
625                 630                 635                 640

Arg Ala Ile Ala Val Gln Lys Leu Glu Ser Leu Glu Asp Asp Asp Val
                645                 650                 655

Leu His Tyr Leu Leu Gln Leu Val Gln Ala Val Lys Phe Glu Pro Tyr
            660                 665                 670

His Asp Ser Ala Leu Ala Arg Phe Leu Leu Lys Arg Gly Leu Arg Asn
        675                 680                 685

Lys Arg Ile Gly His Phe Leu Phe Trp Phe Leu Arg Ser Glu Ile Ala
    690                 695                 700

Gln Ser Arg His Tyr Gln Gln Arg Phe Ala Val Ile Leu Glu Ala Tyr
705                 710                 715                 720

Leu Arg Gly Cys Gly Thr Ala Met Leu Gln Asp Phe Thr Gln Gln Val
                725                 730                 735

His Val Ile Glu Met Leu Gln Lys Val Thr Ile Asp Ile Lys Ser Leu
            740                 745                 750

Ser Ala Glu Lys Tyr Asp Val Ser Ser Gln Val Ile Ser Gln Leu Lys
        755                 760                 765

Gln Lys Leu Glu Ser Leu Gln Asn Ser Asn Leu Pro Glu Ser Phe Arg
    770                 775                 780

Val Pro Tyr Asp Pro Gly Leu Lys Ala Gly Thr Leu Val Ile Glu Lys
785                 790                 795                 800

Cys Lys Val Met Ala Ser Lys Lys Lys Pro Leu Trp Leu Glu Phe Lys
                805                 810                 815

Cys Ala Asp Pro Thr Val Leu Ser Asn Glu Thr Ile Gly Ile Ile Phe
            820                 825                 830

Lys His Gly Asp Asp Leu Arg Gln Asp Met Leu Ile Leu Gln Ile Leu
```

```
        835                 840                 845

Arg Ile Met Glu Ser Ile Trp Glu Thr Glu Ser Leu Asp Leu Cys Leu
    850                 855                 860

Leu Pro Tyr Gly Cys Ile Ser Thr Gly Asp Lys Ile Gly Met Ile Glu
865                 870                 875                 880

Ile Val Lys Asp Ala Thr Thr Ile Ala Gln Ile Gln Gln Ser Thr Val
                885                 890                 895

Gly Asn Thr Gly Ala Phe Lys Asp Glu Val Leu Asn His Trp Leu Lys
            900                 905                 910

Glu Lys Cys Pro Ile Glu Glu Lys Phe Gln Ala Ala Val Glu Arg Phe
        915                 920                 925

Val Tyr Ser Cys Ala Gly Tyr Cys Val Ala Thr Phe Val Leu Gly Ile
    930                 935                 940

Gly Asp Arg His Asn Asp Asn Ile Met Ile Ser Glu Thr Gly Asn Leu
945                 950                 955                 960

Phe His Ile Asp Phe Gly His Ile Leu Gly Asn Tyr Lys Ser Phe Leu
                965                 970                 975

Gly Ile Asn Lys Glu Arg Val Pro Phe Val Leu Thr Pro Asp Phe Leu
            980                 985                 990

Phe Val Met Gly Ser Ser Gly Lys  Lys Thr Ser Pro His  Phe Gln Lys
        995                 1000                1005

Phe Gln  Asp Val Cys Val Arg  Ala Tyr Leu Ala Leu  Arg His His
    1010                1015                1020

Thr Asn  Leu Leu Ile Ile Leu  Phe Ser Met Met Leu  Met Thr Gly
    1025                1030                1035

Met Pro  Gln Leu Thr Ser Lys  Glu Asp Ile Glu Tyr  Ile Arg Asp
    1040                1045                1050

Ala Leu  Thr Val Gly Lys Ser  Glu Glu Asp Ala Lys  Lys Tyr Phe
    1055                1060                1065

Leu Asp  Gln Ile Glu Val Cys  Arg Asp Lys Gly Trp  Thr Val Gln
    1070                1075                1080

Phe Asn  Trp Phe Leu His Leu  Val Leu Gly Ile Lys  Gln Gly Glu
    1085                1090                1095

Lys His  Ser Ala
    1100


<210> SEQ ID NO 25
<211> LENGTH: 3135
<212> TYPE: DNA
<213> ORGANISM: Homo sapiens

<400> SEQUENCE: 25

atgccccctg gggtggactg ccccatggaa ttctggacca aggaggagaa tcagagcgtt      60

gtggttgact tcctgctgcc cacaggggtc tacctgaact tccctgtgtc ccgcaatgcc     120

aacctcagca ccatcaagca gctgctgtgg caccgcgccc agtatgagcc gctcttccac     180

atgctcagtg gccccgaggc ctatgtgttc acctgcatca accagacagc ggagcagcaa     240

gagctggagg acgagcaacg gcgtctgtgt gacgtgcagc ccttcctgcc cgtcctgcgc     300

ctggtggccc gtgagggcga ccgcgtgaag aagctcatca actcacagat cagcctcctc     360

atcggcaaag gcctccacga gtttgactcc ttgtgcgacc cagaagtgaa cgactttcgc     420

gccaagatgt gccaattctg cgaggaggcg gccgcccgcc ggcagcagct gggctgggag     480

gcctggctgc agtacagttt cccccctgcag ctggagccct cggctcaaac ctgggggcct     540
```

```
ggtaccctgc ggctcccgaa ccgggccctt ctggtcaacg ttaagtttga gggcagcgag    600
gagagcttca ccttccaggt gtccaccaag gacgtgccgc tggcgctgat ggcctgtgcc    660
ctgcggaaga aggccacagt gttccggcag ccgctggtgg agcagccgga agactacacg    720
ctgcaggtga acggcaggca tgagtacctg tatggcagct acccgctctg ccagttccag    780
tacatctgca gctgcctgca cagtgggttg accccctcacc tgaccatggt ccattcctcc    840
tccatcctcg ccatgcggga tgagcagagc aaccctgccc cccaggtcca gaaaccgcgt    900
gccaaaccac ctcccattcc tgcgaagaag ccttcctctg tgtccctgtg gtccctggag    960
cagccgttcc gcatcgagct catccagggc agcaaagtga acgccgacga gcggatgaag   1020
ctggtggtgc aggccgggct tttccacggc aacgagatgc tgtgcaagac ggtgtccagc   1080
tcggaggtga gcgtgtgctc ggagcccgtg tggaagcagc ggctggagtt cgacatcaac   1140
atctgcgacc tgccccgcat ggcccgtctc tgctttgcgc tgtacgccgt gatcgagaaa   1200
gccaagaagg ctcgctccac caagaagaag tccaagaagg cggactgccc cattgcctgg   1260
gccaacctca tgctgtttga ctacaaggac cagcttaaga ccggggaacg ctgcctctac   1320
atgtggccct ccgtcccaga tgagaagggc gagctgctga accccacggg cactgtgcgc   1380
agtaacccca acacggatag cgccgctgcc ctgctcatct gcctgcccga ggtggccccg   1440
caccccgtgt actaccccgc cctggagaag atcttggagc tggggcgaca cagcgagtgt   1500
gtgcatgtca ccgaggagga gcagctgcag ctgcgggaaa tcctggagcg gcgggggtct   1560
ggggagctgt atgagcacga gaaggacctg gtgtggaagc tgcggcatga agtccaggag   1620
cacttcccgg aggcgctagc ccggctgctg ctggtcacca agtggaacaa gcatgaggat   1680
gtggcccaga tgctctacct gctgtgctcc tggccggagc tgcccgtcct gagcgccctg   1740
gagctgctag acttcagctt ccccgattgc cacgtaggct ccttcgccat caagtcgctg   1800
cggaaactga cggacgatga gctgttccag tacctgctgc agctggtgca ggtgctcaag   1860
tacgagtcct acctggactg cgagctgacc aaattcctgc tggaccgggc cctggccaac   1920
cgcaagatcg gccacttcct tttctggcac ctccgctccg agatgcacgt gccgtcggtg   1980
gccctgcgct tcggcctcat cctggaggcc tactgcaggg gcagcaccca ccacatgaag   2040
gtgctgatga agcaggggga agcactgagc aaactgaagg ccctgaatga cttcgtcaag   2100
ctgagctctc agaagacccc caagccccag accaaggagc tgatgcactt gtgcatgcgg   2160
caggaggcct acctagaggc cctctcccac ctgcagtccc cactcgaccc cagcaccctg   2220
ctggctgaag tctgcgtgga gcagtgcacc ttcatggact ccaagatgaa gcccctgtgg   2280
atcatgtaca gcaacgagga ggcaggcagc ggcggcagcg tgggcatcat ctttaagaac   2340
ggggatgacc tccggcagga catgctgacc ctgcagatga tccagctcat ggacgtcctg   2400
tggaagcagg aggggctgga cctgaggatg accccctatg gctgcctccc caccggggac   2460
cgcacaggcc tcattgaggt ggtactccgt tcagacacca tcgccaacat ccaactcaac   2520
aagagcaaca tggcagccac agccgccttc aacaaggatg ccctgctcaa ctggctgaag   2580
tccaagaacc cgggggaggc cctggatcga gccattgagg agttcaccct ctcctgtgct   2640
ggctattgtg tggccacata tgtgctgggc attggcgatc ggcacagcga caacatcatg   2700
atccgagaga gtgggcagct gttccacatt gattttggcc actttctggg gaatttcaag   2760
accaagtttg gaatcaaccg cgagcgtgtc ccattcatcc tcacctacga ctttgtccat   2820
gtgattcagc aggggaagac taataatagt gagaaatttg aacggttccg ggctactgt   2880
gaaagggcct acaccatcct gcggcgccac gggcttctct tcctccacct ctttgccctg   2940
```

```
atgcgggcgg caggcctgcc tgagctcagc tgctccaaag acatccagta tctcaaggac   3000

tccctggcac tggggaaaac agaggaggag gcactgaagc acttccgagt gaagtttaac   3060

gaagccctcc gtgagagctg gaaaaccaaa gtgaactggc tggcccacaa cgtgtccaaa   3120

gacaacaggc agtag                                                    3135


<210> SEQ ID NO 26
<211> LENGTH: 1044
<212> TYPE: PRT
<213> ORGANISM: Homo sapiens

<400> SEQUENCE: 26

Met Pro Pro Gly Val Asp Cys Pro Met Glu Phe Trp Thr Lys Glu Glu
1               5                   10                  15

Asn Gln Ser Val Val Val Asp Phe Leu Leu Pro Thr Gly Val Tyr Leu
            20                  25                  30

Asn Phe Pro Val Ser Arg Asn Ala Asn Leu Ser Thr Ile Lys Gln Leu
        35                  40                  45

Leu Trp His Arg Ala Gln Tyr Glu Pro Leu Phe His Met Leu Ser Gly
    50                  55                  60

Pro Glu Ala Tyr Val Phe Thr Cys Ile Asn Gln Thr Ala Glu Gln Gln
65                  70                  75                  80

Glu Leu Glu Asp Glu Gln Arg Arg Leu Cys Asp Val Gln Pro Phe Leu
                85                  90                  95

Pro Val Leu Arg Leu Val Ala Arg Glu Gly Asp Arg Val Lys Lys Leu
            100                 105                 110

Ile Asn Ser Gln Ile Ser Leu Leu Ile Gly Lys Gly Leu His Glu Phe
        115                 120                 125

Asp Ser Leu Cys Asp Pro Glu Val Asn Asp Phe Arg Ala Lys Met Cys
    130                 135                 140

Gln Phe Cys Glu Glu Ala Ala Ala Arg Arg Gln Gln Leu Gly Trp Glu
145                 150                 155                 160

Ala Trp Leu Gln Tyr Ser Phe Pro Leu Gln Leu Glu Pro Ser Ala Gln
                165                 170                 175

Thr Trp Gly Pro Gly Thr Leu Arg Leu Pro Asn Arg Ala Leu Leu Val
            180                 185                 190

Asn Val Lys Phe Glu Gly Ser Glu Glu Ser Phe Thr Phe Gln Val Ser
        195                 200                 205

Thr Lys Asp Val Pro Leu Ala Leu Met Ala Cys Ala Leu Arg Lys Lys
    210                 215                 220

Ala Thr Val Phe Arg Gln Pro Leu Val Glu Gln Pro Glu Asp Tyr Thr
225                 230                 235                 240

Leu Gln Val Asn Gly Arg His Glu Tyr Leu Tyr Gly Ser Tyr Pro Leu
                245                 250                 255

Cys Gln Phe Gln Tyr Ile Cys Ser Cys Leu His Ser Gly Leu Thr Pro
            260                 265                 270

His Leu Thr Met Val His Ser Ser Ser Ile Leu Ala Met Arg Asp Glu
        275                 280                 285

Gln Ser Asn Pro Ala Pro Gln Val Gln Lys Pro Arg Ala Lys Pro Pro
    290                 295                 300

Pro Ile Pro Ala Lys Lys Pro Ser Ser Val Ser Leu Trp Ser Leu Glu
305                 310                 315                 320

Gln Pro Phe Arg Ile Glu Leu Ile Gln Gly Ser Lys Val Asn Ala Asp
                325                 330                 335
```

```
Glu Arg Met Lys Leu Val Val Gln Ala Gly Leu Phe His Gly Asn Glu
            340                 345                 350

Met Leu Cys Lys Thr Val Ser Ser Ser Glu Val Ser Val Cys Ser Glu
        355                 360                 365

Pro Val Trp Lys Gln Arg Leu Glu Phe Asp Ile Asn Ile Cys Asp Leu
    370                 375                 380

Pro Arg Met Ala Arg Leu Cys Phe Ala Leu Tyr Ala Val Ile Glu Lys
385                 390                 395                 400

Ala Lys Lys Ala Arg Ser Thr Lys Lys Lys Ser Lys Lys Ala Asp Cys
                405                 410                 415

Pro Ile Ala Trp Ala Asn Leu Met Leu Phe Asp Tyr Lys Asp Gln Leu
            420                 425                 430

Lys Thr Gly Glu Arg Cys Leu Tyr Met Trp Pro Ser Val Pro Asp Glu
        435                 440                 445

Lys Gly Glu Leu Leu Asn Pro Thr Gly Thr Val Arg Ser Asn Pro Asn
    450                 455                 460

Thr Asp Ser Ala Ala Ala Leu Leu Ile Cys Leu Pro Glu Val Ala Pro
465                 470                 475                 480

His Pro Val Tyr Tyr Pro Ala Leu Glu Lys Ile Leu Glu Leu Gly Arg
                485                 490                 495

His Ser Glu Cys Val His Val Thr Glu Glu Glu Gln Leu Gln Leu Arg
            500                 505                 510

Glu Ile Leu Glu Arg Arg Gly Ser Gly Glu Leu Tyr Glu His Glu Lys
        515                 520                 525

Asp Leu Val Trp Lys Leu Arg His Glu Val Gln Glu His Phe Pro Glu
    530                 535                 540

Ala Leu Ala Arg Leu Leu Leu Val Thr Lys Trp Asn Lys His Glu Asp
545                 550                 555                 560

Val Ala Gln Met Leu Tyr Leu Leu Cys Ser Trp Pro Glu Leu Pro Val
                565                 570                 575

Leu Ser Ala Leu Glu Leu Leu Asp Phe Ser Phe Pro Asp Cys His Val
            580                 585                 590

Gly Ser Phe Ala Ile Lys Ser Leu Arg Lys Leu Thr Asp Asp Glu Leu
        595                 600                 605

Phe Gln Tyr Leu Leu Gln Leu Val Gln Val Leu Lys Tyr Glu Ser Tyr
    610                 615                 620

Leu Asp Cys Glu Leu Thr Lys Phe Leu Leu Asp Arg Ala Leu Ala Asn
625                 630                 635                 640

Arg Lys Ile Gly His Phe Leu Phe Trp His Leu Arg Ser Glu Met His
                645                 650                 655

Val Pro Ser Val Ala Leu Arg Phe Gly Leu Ile Leu Glu Ala Tyr Cys
            660                 665                 670

Arg Gly Ser Thr His His Met Lys Val Leu Met Lys Gln Gly Glu Ala
        675                 680                 685

Leu Ser Lys Leu Lys Ala Leu Asn Asp Phe Val Lys Leu Ser Ser Gln
    690                 695                 700

Lys Thr Pro Lys Pro Gln Thr Lys Glu Leu Met His Leu Cys Met Arg
705                 710                 715                 720

Gln Glu Ala Tyr Leu Glu Ala Leu Ser His Leu Gln Ser Pro Leu Asp
                725                 730                 735

Pro Ser Thr Leu Leu Ala Glu Val Cys Val Glu Gln Cys Thr Phe Met
            740                 745                 750
```

```
Asp Ser Lys Met Lys Pro Leu Trp Ile Met Tyr Ser Asn Glu Glu Ala
        755                 760                 765

Gly Ser Gly Gly Ser Val Gly Ile Ile Phe Lys Asn Gly Asp Asp Leu
    770                 775                 780

Arg Gln Asp Met Leu Thr Leu Gln Met Ile Gln Leu Met Asp Val Leu
785                 790                 795                 800

Trp Lys Gln Glu Gly Leu Asp Leu Arg Met Thr Pro Tyr Gly Cys Leu
                805                 810                 815

Pro Thr Gly Asp Arg Thr Gly Leu Ile Glu Val Val Leu Arg Ser Asp
            820                 825                 830

Thr Ile Ala Asn Ile Gln Leu Asn Lys Ser Asn Met Ala Ala Thr Ala
        835                 840                 845

Ala Phe Asn Lys Asp Ala Leu Leu Asn Trp Leu Lys Ser Lys Asn Pro
    850                 855                 860

Gly Glu Ala Leu Asp Arg Ala Ile Glu Glu Phe Thr Leu Ser Cys Ala
865                 870                 875                 880

Gly Tyr Cys Val Ala Thr Tyr Val Leu Gly Ile Gly Asp Arg His Ser
                885                 890                 895

Asp Asn Ile Met Ile Arg Glu Ser Gly Gln Leu Phe His Ile Asp Phe
            900                 905                 910

Gly His Phe Leu Gly Asn Phe Lys Thr Lys Phe Gly Ile Asn Arg Glu
        915                 920                 925

Arg Val Pro Phe Ile Leu Thr Tyr Asp Phe Val His Val Ile Gln Gln
    930                 935                 940

Gly Lys Thr Asn Asn Ser Glu Lys Phe Glu Arg Phe Arg Gly Tyr Cys
945                 950                 955                 960

Glu Arg Ala Tyr Thr Ile Leu Arg Arg His Gly Leu Leu Phe Leu His
                965                 970                 975

Leu Phe Ala Leu Met Arg Ala Ala Gly Leu Pro Glu Leu Ser Cys Ser
            980                 985                 990

Lys Asp Ile Gln Tyr Leu Lys Asp  Ser Leu Ala Leu Gly  Lys Thr Glu
        995                 1000                1005

Glu Glu  Ala Leu Lys His Phe  Arg Val Lys Phe Asn  Glu Ala Leu
    1010                1015                1020

Arg Glu  Ser Trp Lys Thr Lys  Val Asn Trp Leu Ala  His Asn Val
    1025                1030                1035

Ser Lys  Asp Asn Arg Gln
    1040


<210> SEQ ID NO 27
<211> LENGTH: 3132
<212> TYPE: DNA
<213> ORGANISM: Mus musculus

<400> SEQUENCE: 27

atgccccctg ggtggactg ccccatggag ttctggacca aagaggagag ccagagcgtg      60

gttgttgact tcttgctgcc cacaggggtc tacttgaact tccccgtgtc ccgcaatgcc    120

aacctcagca ccatcaagca ggtgctgtgg caccgtgcac agtatgagcc actcttccac    180

atgctcagtg accccgaggc ctatgtgttc acctgtgtga accagacggc ggagcagcag    240

gagttggagg atgagcagcg gaggctgtgc gacatccagc ccttcctgcc cgtgctgcgc    300

ctcgtggccc gagaggggga ccgcgtgaag aagctcatta actcccagat cagcctcctc    360

attggcaaag gtctccatga gtttgattcc ctgcgggacc cggaagtaaa cgacttccgc    420
```

```
actaagatgc gccagttttg tgaagaggct gctgctcacc gccagcagct gggctgggtg    480

gaatggctgc agtacagctt ccccctgcag ctggagccct cagcaagggg ttggcgggcc    540

ggcttattgc gtgtcagcaa ccgagccctg ctggtcaacg tgaagttcga gggcagtgag    600

gagagcttca ccttccaggt atccaccaag gacatgcccc tggcactgat ggcctgtgcc    660

ctccgaaaaa aggccacagt gttccggcag cctctggtgg agcagcctga ggaatatgcc    720

ctgcaggtga acgggaggca cgaatacctc tacggcaact acccgctctg ccactttcag    780

tacatctgca gctgcctaca cagcgggctg acccctcatc tgaccatggt ccactcctcc    840

tccatccttg ctatgcggga tgagcagagc aatcctgccc cccaagtaca gaaaccacgt    900

gccaaacctc ccccgatccc tgccaagaag ccctcctctg tgtccctgtg gtccctggaa    960

cagccattct ccattgagct gatcgagggc cgaaaagtga atgctgacga gcggatgaag   1020

ctggttgttc aggccgggct cttccatggc aatgagatgc tgtgcaagac tgtgtcaagc   1080

tcggaggtga atgtatgctc agagcccgtg tggaagcagc gactggagtt cgatatcagc   1140

gtctgtgacc tcccgcgcat ggctcgactc tgttttgctc tctatgccgt cgtggagaag   1200

gctaagaagg cacgctccac aaagaagaag tctaagaagg cggactgccc catcgcttgg   1260

gccaacctca tgctattcga ctacaaagat cagctcaaga cgggggagcg ctgcctctac   1320

atgtggccct ctgtcccaga tgagaaggga gagctgctga atcctgcggg tacagtgcgc   1380

gggaacccca acacggagag tgccgctgcc ctggtcatct acctgcctga ggtggccccc   1440

caccctgtgt acttccccgc tctggagaag atcctggagc tggggcgtca cggggagcgt   1500

gggcgcatca cggaggagga gctgcagctg cgggagatcc tggaacggcg ggatccgggg   1560

gaactgtacg aacatgagaa ggacctggtg tggaagatgc gccacgaagt ccaggagcat   1620

ttcccagagg cgctggcccg cctgctgctg gtcaccaagt ggaataaaca cgaggatgtg   1680

gcccagatgc tctatttgct gtgctcctgg cccgagctgc ctgtgctgag cgccctggaa   1740

cttctggact ttagctttcc cgactgctac gtgggctcct tcgccatcaa gtcccttcgg   1800

aagctgacgg acgatgagct cttccagtac cttctgcagc tggtgcaagt gctcaaatat   1860

gagtcctacc tggactgcga gctgaccaaa ttcttgctgg gccgagccct ggctaaccgc   1920

aagatcggac acttcctgtt ctggcacctc cgctctgaga tgcacgtacc atcagtggct   1980

ctgcggtttg gtctcatcat ggaagcctac tgcagaggca gcacccacca catgaaggtg   2040

ctgatgaagc agggggaagc actgagcaag cttaaggcac tgaatgactt tgtgaaggtg   2100

agttcccaga agaccaccaa gccccaaacc aaggagatga tgcatatgtg catgcgccag   2160

gagacctaca tggaggccct gtcccacctg cagtctccac tcgaccccag caccctgctg   2220

gaggaagtct gtgtggagca gtgcaccttc atggactcca aaatgaagcc cctgtggatc   2280

atgtacagca gcgaggaggc gggcagtgct ggcaacgtgg gcatcatctt taagaacggg   2340

gatgacctcc gccaggacat gctgactctg cagatgatcc agctcatgga cgtcctgtgg   2400

aagcaggagg gcctggacct gaggatgacg ccctacggct gcctccccac cggggaccgc   2460

acaggtctca tcgaggtggt cctccactcg gacaccatcg ccaacatcca gctgaacaaa   2520

agcaacatgg cggccacagc tgccttcaac aaggacgccc tgctcaactg gctcaagtcc   2580

aagaaccctg gggaggccct ggatcgggcc attgaggaat tcaccctctc ctgtgctggc   2640

tactgtgtgg ccacatatgt tctgggcatc ggtgaccggc acagcgacaa catcatgatc   2700

agagagagtg ggcagctctt ccacattgat tttggccact ttctggggaa cttcaagacc   2760

aagtttggaa tcaaccgaga gcgcgtcccc ttcattctca cctacgactt tgtccacgtg   2820
```

```
atccagcagg ggaagactaa caacagtgag aagtttgaaa ggttccgcgg ctactgtgaa   2880

cgagcctata ccatcctgcg gcgccacggg ctgcttttcc tccatctctt cgccctgatg   2940

cgggccgcag gtctgcctga gcttagctgc tccaaagata tccagtatct caaggactct   3000

ctggcactgg ggaagacgga ggaagaggcg ctaaagcact tccgggtgaa gttcaacgaa   3060

gctctccgag aaagctggaa aaccaaagtc aactggctgg cgcacaatgt gtccaaggat   3120

aaccgacagt ag                                                        3132
```

<210> SEQ ID NO 28
<211> LENGTH: 1043
<212> TYPE: PRT
<213> ORGANISM: Mus musculus

<400> SEQUENCE: 28

```
Met Pro Pro Gly Val Asp Cys Pro Met Glu Phe Trp Thr Lys Glu Glu
1               5                   10                  15

Ser Gln Ser Val Val Val Asp Phe Leu Leu Pro Thr Gly Val Tyr Leu
            20                  25                  30

Asn Phe Pro Val Ser Arg Asn Ala Asn Leu Ser Thr Ile Lys Gln Val
        35                  40                  45

Leu Trp His Arg Ala Gln Tyr Glu Pro Leu Phe His Met Leu Ser Asp
    50                  55                  60

Pro Glu Ala Tyr Val Phe Thr Cys Val Asn Gln Thr Ala Glu Gln Gln
65                  70                  75                  80

Glu Leu Glu Asp Glu Gln Arg Arg Leu Cys Asp Ile Gln Pro Phe Leu
                85                  90                  95

Pro Val Leu Arg Leu Val Ala Arg Glu Gly Asp Arg Val Lys Lys Leu
            100                 105                 110

Ile Asn Ser Gln Ile Ser Leu Leu Ile Gly Lys Gly Leu His Glu Phe
        115                 120                 125

Asp Ser Leu Arg Asp Pro Glu Val Asn Asp Phe Arg Thr Lys Met Arg
    130                 135                 140

Gln Phe Cys Glu Glu Ala Ala Ala His Arg Gln Gln Leu Gly Trp Val
145                 150                 155                 160

Glu Trp Leu Gln Tyr Ser Phe Pro Leu Gln Leu Glu Pro Ser Ala Arg
                165                 170                 175

Gly Trp Arg Ala Gly Leu Leu Arg Val Ser Asn Arg Ala Leu Leu Val
            180                 185                 190

Asn Val Lys Phe Glu Gly Ser Glu Glu Ser Phe Thr Phe Gln Val Ser
        195                 200                 205

Thr Lys Asp Met Pro Leu Ala Leu Met Ala Cys Ala Leu Arg Lys Lys
    210                 215                 220

Ala Thr Val Phe Arg Gln Pro Leu Val Glu Gln Pro Glu Glu Tyr Ala
225                 230                 235                 240

Leu Gln Val Asn Gly Arg His Glu Tyr Leu Tyr Gly Asn Tyr Pro Leu
                245                 250                 255

Cys His Phe Gln Tyr Ile Cys Ser Cys Leu His Ser Gly Leu Thr Pro
            260                 265                 270

His Leu Thr Met Val His Ser Ser Ser Ile Leu Ala Met Arg Asp Glu
        275                 280                 285

Gln Ser Asn Pro Ala Pro Gln Val Gln Lys Pro Arg Ala Lys Pro Pro
    290                 295                 300

Pro Ile Pro Ala Lys Lys Pro Ser Ser Val Ser Leu Trp Ser Leu Glu
```

```
305                 310                 315                 320

Gln Pro Phe Ser Ile Glu Leu Ile Glu Gly Arg Lys Val Asn Ala Asp
                325                 330                 335

Glu Arg Met Lys Leu Val Val Gln Ala Gly Leu Phe His Gly Asn Glu
            340                 345                 350

Met Leu Cys Lys Thr Val Ser Ser Ser Glu Val Asn Val Cys Ser Glu
        355                 360                 365

Pro Val Trp Lys Gln Arg Leu Glu Phe Asp Ile Ser Val Cys Asp Leu
    370                 375                 380

Pro Arg Met Ala Arg Leu Cys Phe Ala Leu Tyr Ala Val Val Glu Lys
385                 390                 395                 400

Ala Lys Lys Ala Arg Ser Thr Lys Lys Lys Ser Lys Lys Ala Asp Cys
                405                 410                 415

Pro Ile Ala Trp Ala Asn Leu Met Leu Phe Asp Tyr Lys Asp Gln Leu
            420                 425                 430

Lys Thr Gly Glu Arg Cys Leu Tyr Met Trp Pro Ser Val Pro Asp Glu
        435                 440                 445

Lys Gly Glu Leu Leu Asn Pro Ala Gly Thr Val Arg Gly Asn Pro Asn
    450                 455                 460

Thr Glu Ser Ala Ala Ala Leu Val Ile Tyr Leu Pro Glu Val Ala Pro
465                 470                 475                 480

His Pro Val Tyr Phe Pro Ala Leu Glu Lys Ile Leu Glu Leu Gly Arg
                485                 490                 495

His Gly Glu Arg Gly Arg Ile Thr Glu Glu Glu Leu Gln Leu Arg Glu
            500                 505                 510

Ile Leu Glu Arg Arg Gly Ser Gly Glu Leu Tyr Glu His Glu Lys Asp
        515                 520                 525

Leu Val Trp Lys Met Arg His Glu Val Gln Glu His Phe Pro Glu Ala
    530                 535                 540

Leu Ala Arg Leu Leu Leu Val Thr Lys Trp Asn Lys His Glu Asp Val
545                 550                 555                 560

Ala Gln Met Leu Tyr Leu Leu Cys Ser Trp Pro Glu Leu Pro Val Leu
                565                 570                 575

Ser Ala Leu Glu Leu Leu Asp Phe Ser Phe Pro Asp Cys Tyr Val Gly
            580                 585                 590

Ser Phe Ala Ile Lys Ser Leu Arg Lys Leu Thr Asp Asp Glu Leu Phe
        595                 600                 605

Gln Tyr Leu Leu Gln Leu Val Gln Val Leu Lys Tyr Glu Ser Tyr Leu
    610                 615                 620

Asp Cys Glu Leu Thr Lys Phe Leu Leu Gly Arg Ala Leu Ala Asn Arg
625                 630                 635                 640

Lys Ile Gly His Phe Leu Phe Trp His Leu Arg Ser Glu Met His Val
                645                 650                 655

Pro Ser Val Ala Leu Arg Phe Gly Leu Ile Met Glu Ala Tyr Cys Arg
            660                 665                 670

Gly Ser Thr His His Met Lys Val Leu Met Lys Gln Gly Glu Ala Leu
        675                 680                 685

Ser Lys Leu Lys Ala Leu Asn Asp Phe Val Lys Val Ser Ser Gln Lys
    690                 695                 700

Thr Thr Lys Pro Gln Thr Lys Glu Met Met His Met Cys Met Arg Gln
705                 710                 715                 720

Glu Thr Tyr Met Glu Ala Leu Ser His Leu Gln Ser Pro Leu Asp Pro
                725                 730                 735
```

```
Ser Thr Leu Leu Glu Glu Val Cys Val Glu Gln Cys Thr Phe Met Asp
            740                 745                 750

Ser Lys Met Lys Pro Leu Trp Ile Met Tyr Ser Ser Glu Glu Ala Gly
        755                 760                 765

Ser Ala Gly Asn Val Gly Ile Ile Phe Lys Asn Gly Asp Asp Leu Arg
    770                 775                 780

Gln Asp Met Leu Thr Leu Gln Met Ile Gln Leu Met Asp Val Leu Trp
785                 790                 795                 800

Lys Gln Glu Gly Leu Asp Leu Arg Met Thr Pro Tyr Gly Cys Leu Pro
                805                 810                 815

Thr Gly Asp Arg Thr Gly Leu Ile Glu Val Val Leu His Ser Asp Thr
            820                 825                 830

Ile Ala Asn Ile Gln Leu Asn Lys Ser Asn Met Ala Ala Thr Ala Ala
        835                 840                 845

Phe Asn Lys Asp Ala Leu Leu Asn Trp Leu Lys Ser Lys Asn Pro Gly
    850                 855                 860

Glu Ala Leu Asp Arg Ala Ile Glu Glu Phe Thr Leu Ser Cys Ala Gly
865                 870                 875                 880

Tyr Cys Val Ala Thr Tyr Val Leu Gly Ile Gly Asp Arg His Ser Asp
                885                 890                 895

Asn Ile Met Ile Arg Glu Ser Gly Gln Leu Phe His Ile Asp Phe Gly
            900                 905                 910

His Phe Leu Gly Asn Phe Lys Thr Lys Phe Gly Ile Asn Arg Glu Arg
        915                 920                 925

Val Pro Phe Ile Leu Thr Tyr Asp Phe Val His Val Ile Gln Gln Gly
    930                 935                 940

Lys Thr Asn Asn Ser Glu Lys Phe Glu Arg Phe Arg Gly Tyr Cys Glu
945                 950                 955                 960

Arg Ala Tyr Thr Ile Leu Arg Arg His Gly Leu Leu Phe Leu His Leu
                965                 970                 975

Phe Ala Leu Met Arg Ala Ala Gly Leu Pro Glu Leu Ser Cys Ser Lys
            980                 985                 990

Asp Ile Gln Tyr Leu Lys Asp Ser  Leu Ala Leu Gly Lys  Thr Glu Glu
        995                 1000                 1005

Glu Ala  Leu Lys His Phe Arg  Val Lys Phe Asn Glu  Ala Leu Arg
    1010                 1015                 1020

Glu Ser  Trp Lys Thr Lys Val  Asn Trp Leu Ala His  Asn Val Ser
    1025                 1030                 1035

Lys Asp  Asn Arg Gln
    1040
```

<210> SEQ ID NO 29
<211> LENGTH: 3144
<212> TYPE: DNA
<213> ORGANISM: Mus musculus

<400> SEQUENCE: 29

```
atgccccctg ggtggactg ccccatggag ttctggacca aagaggagag ccagagcgtg      60

gttgttgact tcttgctgcc cacaggggtc tacttgaact tccccgtgtc ccgcaatgcc    120

aacctcagca ccatcaagca ggtgctgtgg caccgtgcac agtatgagcc actcttccac    180

atgctcagtg accccgaggc ctatgtgttc acctgtgtga accagacggc ggagcagcag    240

gagttggagg atgagcagcg gaggctgtgc gacatccagc ccttcctgcc cgtgctgcgc    300
```

```
ctcgtggccc gagaggggga ccgcgtgaag aagctcatta actcccagat cagcctcctc    360
attggcaaag gtctccatga gtttgattcc ctgcgggacc cggaagtaaa cgacttccgc    420
actaagatgc gccagttttg tgaagaggct gctgctcacc gccagcagct gggctgggtg    480
gaatggctgc agtacagctt cccccctgcag ctggagccct cagcaagggg ttggcgggcc    540
ggcttattgc gtgtcagcaa ccgagccctg ctggtcaacg tgaagttcga gggcagtgag    600
gagagcttca ccttccaggt atccaccaag gacatgcccc tggcactgat ggcctgtgcc    660
ctccgaaaaa aggccacagt gttccggcag cctctggtgg agcagcctga ggaatatgcc    720
ctgcaggtga acgggaggca cgaatacctc tacggcaact acccgctctg ccactttcag    780
tacatctgca gctgcctaca cagcgggctg acccctcatc tgaccatggt ccactcctcc    840
tccatccttg ctatgcggga tgagcagagc aatcctgccc cccaagtaca gaaaccacgt    900
gccaaacctc ccccgatccc tgccaagaag ccctcctctg tgtccctgtg gtccctggaa    960
cagccattct ccattgagct gatcgagggc cgaaaagtga atgctgacga gcggatgaag   1020
ctggttgttc aggccgggct cttccatggc aatgagatgc tgtgcaagac tgtgtcaagc   1080
tcggaggtga atgtatgctc agagcccgtg tggaagcagc gactggagtt cgatatcagc   1140
gtctgtgacc tcccgcgcat ggctcgactc tgttttgctc tctatgccgt cgtggagaag   1200
gctaagaagg cacgctccac aaagaagaag tctaagaagg cggactgccc catcgcttgg   1260
gccaacctca tgctattcga ctacaaagat cagctcaaga cgggggagcg ctgcctctac   1320
atgtggccct ctgtcccaga tgagaaggga gagctgctga atcctgcggg tacagtgcgc   1380
gggaacccca acacggagag tgccgctgcc ctggtcatct acctgcctga ggtggccccc   1440
caccctgtgt acttccccgc tctggagaag atcctggagc tggggcgtca cggggagcgt   1500
gggcgcatca cggaggagga gcagctgcag ctgcgggaga tcctggaacg gcggggatcc   1560
ggggaactgt acgaacatga gaaggacctg gtgtggaaga tgcgccacga agtccaggag   1620
catttcccag aggcgctggc ccgcctgctg ctggtcacca agtggaataa acacgaggat   1680
gtggcccagc tgtcccagat gctctatttg ctgtgctcct ggcccgagct gcctgtgctg   1740
agcgccctgg aacttctgga ctttagcttt cccgactgct acgtgggctc cttcgccatc   1800
aagtcccttc ggaagctgac ggacgatgag ctcttccagt accttctgca gctggtgcaa   1860
gtgctcaaat atgagtccta cctggactgc gagctgacca aattcttgct gggccgagcc   1920
ctggctaacc gcaagatcgg acacttcctg ttctggcacc tccgctctga gatgcacgta   1980
ccatcagtgg ctctgcggtt tggtctcatc atggaagcct actgcagagg cagcacccac   2040
cacatgaagg tgctgatgaa gcagggggaa gcactgagca agcttaaggc actgaatgac   2100
tttgtgaagg tgagttccca gaagaccacc aagccccaaa ccaaggagat gatgcatatg   2160
tgcatgcgcc aggagaccta catggaggcc ctgtcccacc tgcagtctcc actcgacccc   2220
agcaccctgc tggaggaagt ctgtgtggag cagtgcacct tcatggactc caaaatgaag   2280
cccctgtgga tcatgtacag cagcgaggag gcgggcagtg ctggcaacgt gggcatcatc   2340
tttaagaacg gggatgacct ccgccaggac atgctgactc tgcagatgat ccagctcatg   2400
gacgtcctgt ggaagcagga gggcctggac ctgaggatga cgccctacgg ctgcctcccc   2460
accggggacc gcacaggtct catcgaggtg gtcctccact cggacaccat cgccaacatc   2520
cagctgaaca aaagcaacat ggcggccaca gctgccttca acaaggacgc cctgctcaac   2580
tggctcaagt ccaagaaccc tggggaggcc ctggatcggg ccattgagga attcaccctc   2640
tcctgtgctg gctactgtgt ggccacatat gttctgggca tcggtgaccg gcacagcgac   2700
```

```
aacatcatga tcagagagag tgggcagctc ttccacattg attttggcca ctttctgggg   2760

aacttcaaga ccaagtttgg aatcaaccga gagcgcgtcc ccttcattct cacctacgac   2820

tttgtccacg tgatccagca ggggaagact aacaacagtg agaagtttga aaggttccgc   2880

ggctactgtg aacgagccta taccatcctg cggcgccacg ggctgctttt cctccatctc   2940

ttcgccctga tgcgggccgc aggtctgcct gagcttagct gctccaaaga tatccagtat   3000

ctcaaggact ctctggcact ggggaagacg gaggaagagg cgctaaagca cttccgggtg   3060

aagttcaacg aagctctccg agaaagctgg aaaaccaaag tcaactggct ggcgcacaat   3120

gtgtccaagg ataaccgaca gtag                                          3144


<210> SEQ ID NO 30
<211> LENGTH: 1047
<212> TYPE: PRT
<213> ORGANISM: Mus musculus

<400> SEQUENCE: 30

Met Pro Pro Gly Val Asp Cys Pro Met Glu Phe Trp Thr Lys Glu Glu
1               5                   10                  15

Ser Gln Ser Val Val Val Asp Phe Leu Leu Pro Thr Gly Val Tyr Leu
            20                  25                  30

Asn Phe Pro Val Ser Arg Asn Ala Asn Leu Ser Thr Ile Lys Gln Val
        35                  40                  45

Leu Trp His Arg Ala Gln Tyr Glu Pro Leu Phe His Met Leu Ser Asp
    50                  55                  60

Pro Glu Ala Tyr Val Phe Thr Cys Val Asn Gln Thr Ala Glu Gln Gln
65                  70                  75                  80

Glu Leu Glu Asp Glu Gln Arg Arg Leu Cys Asp Ile Gln Pro Phe Leu
                85                  90                  95

Pro Val Leu Arg Leu Val Ala Arg Glu Gly Asp Arg Val Lys Lys Leu
            100                 105                 110

Ile Asn Ser Gln Ile Ser Leu Leu Ile Gly Lys Gly Leu His Glu Phe
        115                 120                 125

Asp Ser Leu Arg Asp Pro Glu Val Asn Asp Phe Arg Thr Lys Met Arg
    130                 135                 140

Gln Phe Cys Glu Glu Ala Ala Ala His Arg Gln Gln Leu Gly Trp Val
145                 150                 155                 160

Glu Trp Leu Gln Tyr Ser Phe Pro Leu Gln Leu Glu Pro Ser Ala Arg
                165                 170                 175

Gly Trp Arg Ala Gly Leu Leu Arg Val Ser Asn Arg Ala Leu Leu Val
            180                 185                 190

Asn Val Lys Phe Glu Gly Ser Glu Glu Ser Phe Thr Phe Gln Val Ser
        195                 200                 205

Thr Lys Asp Met Pro Leu Ala Leu Met Ala Cys Ala Leu Arg Lys Lys
    210                 215                 220

Ala Thr Val Phe Arg Gln Pro Leu Val Glu Gln Pro Glu Glu Tyr Ala
225                 230                 235                 240

Leu Gln Val Asn Gly Arg His Glu Tyr Leu Tyr Gly Asn Tyr Pro Leu
                245                 250                 255

Cys His Phe Gln Tyr Ile Cys Ser Cys Leu His Ser Gly Leu Thr Pro
            260                 265                 270

His Leu Thr Met Val His Ser Ser Ser Ile Leu Ala Met Arg Asp Glu
        275                 280                 285
```

```
Gln Ser Asn Pro Ala Pro Gln Val Gln Lys Pro Arg Ala Lys Pro Pro
    290                 295                 300

Pro Ile Pro Ala Lys Lys Pro Ser Ser Val Ser Leu Trp Ser Leu Glu
305                 310                 315                 320

Gln Pro Phe Ser Ile Glu Leu Ile Glu Gly Arg Lys Val Asn Ala Asp
                325                 330                 335

Glu Arg Met Lys Leu Val Val Gln Ala Gly Leu Phe His Gly Asn Glu
            340                 345                 350

Met Leu Cys Lys Thr Val Ser Ser Ser Glu Val Asn Val Cys Ser Glu
        355                 360                 365

Pro Val Trp Lys Gln Arg Leu Glu Phe Asp Ile Ser Val Cys Asp Leu
    370                 375                 380

Pro Arg Met Ala Arg Leu Cys Phe Ala Leu Tyr Ala Val Val Glu Lys
385                 390                 395                 400

Ala Lys Lys Ala Arg Ser Thr Lys Lys Lys Ser Lys Lys Ala Asp Cys
                405                 410                 415

Pro Ile Ala Trp Ala Asn Leu Met Leu Phe Asp Tyr Lys Asp Gln Leu
            420                 425                 430

Lys Thr Gly Glu Arg Cys Leu Tyr Met Trp Pro Ser Val Pro Asp Glu
        435                 440                 445

Lys Gly Glu Leu Leu Asn Pro Ala Gly Thr Val Arg Gly Asn Pro Asn
    450                 455                 460

Thr Glu Ser Ala Ala Ala Leu Val Ile Tyr Leu Pro Glu Val Ala Pro
465                 470                 475                 480

His Pro Val Tyr Phe Pro Ala Leu Glu Lys Ile Leu Glu Leu Gly Arg
                485                 490                 495

His Gly Glu Arg Gly Arg Ile Thr Glu Glu Gln Leu Gln Leu Arg
            500                 505                 510

Glu Ile Leu Glu Arg Arg Gly Ser Gly Glu Leu Tyr Glu His Glu Lys
        515                 520                 525

Asp Leu Val Trp Lys Met Arg His Glu Val Gln Glu His Phe Pro Glu
    530                 535                 540

Ala Leu Ala Arg Leu Leu Leu Val Thr Lys Trp Asn Lys His Glu Asp
545                 550                 555                 560

Val Ala Gln Leu Ser Gln Met Leu Tyr Leu Leu Cys Ser Trp Pro Glu
                565                 570                 575

Leu Pro Val Leu Ser Ala Leu Glu Leu Leu Asp Phe Ser Phe Pro Asp
            580                 585                 590

Cys Tyr Val Gly Ser Phe Ala Ile Lys Ser Leu Arg Lys Leu Thr Asp
        595                 600                 605

Asp Glu Leu Phe Gln Tyr Leu Leu Gln Leu Val Gln Val Leu Lys Tyr
    610                 615                 620

Glu Ser Tyr Leu Asp Cys Glu Leu Thr Lys Phe Leu Leu Gly Arg Ala
625                 630                 635                 640

Leu Ala Asn Arg Lys Ile Gly His Phe Leu Phe Trp His Leu Arg Ser
                645                 650                 655

Glu Met His Val Pro Ser Val Ala Leu Arg Phe Gly Leu Ile Met Glu
            660                 665                 670

Ala Tyr Cys Arg Gly Ser Thr His His Met Lys Val Leu Met Lys Gln
        675                 680                 685

Gly Glu Ala Leu Ser Lys Leu Lys Ala Leu Asn Asp Phe Val Lys Val
    690                 695                 700

Ser Ser Gln Lys Thr Thr Lys Pro Gln Thr Lys Glu Met Met His Met
```

```
705                 710                 715                 720

Cys Met Arg Gln Glu Thr Tyr Met Glu Ala Leu Ser His Leu Gln Ser
                725                 730                 735

Pro Leu Asp Pro Ser Thr Leu Leu Glu Glu Val Cys Val Glu Gln Cys
            740                 745                 750

Thr Phe Met Asp Ser Lys Met Lys Pro Leu Trp Ile Met Tyr Ser Ser
        755                 760                 765

Glu Glu Ala Gly Ser Ala Gly Asn Val Gly Ile Ile Phe Lys Asn Gly
    770                 775                 780

Asp Asp Leu Arg Gln Asp Met Leu Thr Leu Gln Met Ile Gln Leu Met
785                 790                 795                 800

Asp Val Leu Trp Lys Gln Glu Gly Leu Asp Leu Arg Met Thr Pro Tyr
                805                 810                 815

Gly Cys Leu Pro Thr Gly Asp Arg Thr Gly Leu Ile Glu Val Val Leu
            820                 825                 830

His Ser Asp Thr Ile Ala Asn Ile Gln Leu Asn Lys Ser Asn Met Ala
        835                 840                 845

Ala Thr Ala Ala Phe Asn Lys Asp Ala Leu Leu Asn Trp Leu Lys Ser
    850                 855                 860

Lys Asn Pro Gly Glu Ala Leu Asp Arg Ala Ile Glu Glu Phe Thr Leu
865                 870                 875                 880

Ser Cys Ala Gly Tyr Cys Val Ala Thr Tyr Val Leu Gly Ile Gly Asp
                885                 890                 895

Arg His Ser Asp Asn Ile Met Ile Arg Glu Ser Gly Gln Leu Phe His
            900                 905                 910

Ile Asp Phe Gly His Phe Leu Gly Asn Phe Lys Thr Lys Phe Gly Ile
        915                 920                 925

Asn Arg Glu Arg Val Pro Phe Ile Leu Thr Tyr Asp Phe Val His Val
    930                 935                 940

Ile Gln Gln Gly Lys Thr Asn Asn Ser Glu Lys Phe Glu Arg Phe Arg
945                 950                 955                 960

Gly Tyr Cys Glu Arg Ala Tyr Thr Ile Leu Arg Arg His Gly Leu Leu
                965                 970                 975

Phe Leu His Leu Phe Ala Leu Met Arg Ala Ala Gly Leu Pro Glu Leu
            980                 985                 990

Ser Cys Ser Lys Asp Ile Gln Tyr  Leu Lys Asp Ser Leu  Ala Leu Gly
        995                 1000                 1005

Lys Thr  Glu Glu Glu Ala Leu  Lys His Phe Arg Val  Lys Phe Asn
    1010                 1015                 1020

Glu Ala  Leu Arg Glu Ser Trp  Lys Thr Lys Val Asn  Trp Leu Ala
    1025                 1030                 1035

His Asn  Val Ser Lys Asp Asn  Arg Gln
    1040                 1045


<210> SEQ ID NO 31
<211> LENGTH: 3144
<212> TYPE: DNA
<213> ORGANISM: Mus musculus

<400> SEQUENCE: 31

atgccccctg gggtggactg ccccatggag ttctggacca aagaggagag ccagagcgtg      60

gttgttgact tcttgctgcc cacaggggtc tacttgaact tccccgtgtc ccgcaatgcc     120

aacctcagca ccatcaagca ggtgctgtgg caccgtgcac agtatgagcc actcttccac     180
```

```
atgctcagtg accccgaggc ctatgtgttc acctgtgtga accagacggc ggagcagcag    240
gagttggagg atgagcagcg gaggctgtgc gacatccagc ccttcctgcc cgtgctgcgc    300
ctcgtggccc gagaggggga ccgcgtgaag aagctcatta actcccagat cagcctcctc    360
attggcaaag gtctccatga gtttgattcc ctgcgggacc cggaagtaaa cgacttccgc    420
actaagatgc gccagttttg tgaagaggct gctgctcacc gccagcagct gggctgggtg    480
gaatggctgc agtacagctt cccccctgcag ctggagccct cagcaagggg ttggcgggcc    540
ggcttattgc gtgtcagcaa ccgagccctg ctggtcaacg tgaagttcga gggcagtgag    600
gagagcttca ccttccaggt atccaccaag gacatgcccc tggcactgat ggcctgtgcc    660
ctccgaaaaa aggccacagt gttccggcag cctctggtgg agcagcctga ggaatatgcc    720
ctgcaggtga acgggaggca cgaatacctc tacggcaact acccgctctg ccactttcag    780
tacatctgca gctgcctaca cagcgggctg acccctcatc tgaccatggt ccactcctcc    840
tccatccttg ctatgcggga tgagcagagc aatcctgccc cccaagtaca gaaaccacgt    900
gccaaacctc ccccgatccc tgccaagaag ccctcctctg tgtccctgtg gtccctggaa    960
cagccattct ccattgagct gatcgagggc cgaaaagtga atgctgacga gcggatgaag   1020
ctggttgttc aggccgggct cttccatggc aatgagatgc tgtgcaagac tgtgtcaagc   1080
tcggaggtga atgtatgctc agagcccgtg tggaagcagc gactggagtt cgatatcagc   1140
gtctgtgacc tcccgcgcat ggctcgactc tgttttgctc tctatgccgt cgtggagaag   1200
gctaagaagg cacgctccac aaagaagaag tctaagaagg cggactgccc catcgcttgg   1260
gccaacctca tgctattcga ctacaaagat cagctcaaga cgggggagcg ctgcctctac   1320
atgtggccct ctgtcccaga tgagaaggga gagctgctga atcctgcggg tacagtgcgc   1380
gggaacccca acacggagag tgccgctgcc ctggtcatct acctgcctga ggtggccccc   1440
caccctgtgt acttccccgc tctggagaag atcctggagc tggggcgtca cggggagcgt   1500
gggcgcatca cggaggagga gcagctgcag ctgcgggaga tcctggaacg gcggggatcc   1560
ggggaactgt acgaacatga gaaggacctg gtgtggaaga tgcgccacga agtccaggag   1620
catttcccag aggcgctggc ccgcctgctg ctggtcacca agtggaataa acacgaggat   1680
gtggcccagc tgtcccagat gctctatttg ctgtgctcct ggcccgagct gcctgtgctg   1740
agcgccctgg aacttctgga ctttagcttt cccgactgct acgtgggctc cttcgccatc   1800
aagtcccttc ggaagctgac ggacgatgag ctcttccagt accttctgca gctggtgcaa   1860
gtgctcaaat atgagtccta cctggactgc gagctgacca aattcttgct gggccgagcc   1920
ctggctaacc gcaagatcgg acacttcctg ttctggcacc tccgctctga gatgcacgta   1980
ccatcagtgg ctctgcggtt tggtctcatc atggaagcct actgcagagg cagcacccac   2040
cacatgaagg tgctgatgaa gcagggggaa gcactgagca agcttaaggc actgaatgac   2100
tttgtgaagg tgagttccca gaagaccacc aagccccaaa ccaaggagat gatgcatatg   2160
tgcatgcgcc aggagaccta catggaggcc ctgtcccacc tgcagtctcc actcgacccc   2220
agcaccctgc tggaggaagt ctgtgtggag cagtgcacct tcatggactc caaaatgaag   2280
cccctgtgga tcatgtacag cagcgaggag gcgggcagtg ctggcaacgt gggcatcatc   2340
tttaagaacg gggatgacct ccgccaggac atgctgactc tgcagatgat ccagctcatg   2400
gacgtcctgt ggaagcagga gggcctggac ctgaggatga cgccctacgg ctgcctcccc   2460
accggggacc gcacaggtct catcgaggtg gtcctccact cggacaccat cgccaacatc   2520
cagctgaaca aaagcaacat ggcggccaca gctgccttca acaaggacgc cctgctcaac   2580
```

```
tggctcaagt ccaagaaccc tggggaggcc ctggatcggg ccattgagga attcaccctc   2640

tcctgtgctg gctactgtgt ggccacatat gttctgggca tcggtgaccg gcacagcgac   2700

aacatcatga tcagagagag tgggcagctc ttccacattg attttggcca ctttctgggg   2760

aacttcaaga ccaagtttgg aatcaaccga gagcgcgtcc ccttcattct cacctacgac   2820

tttgtccacg tgatccagca ggggaagact aacaacagtg agaagtttga aaggttccgc   2880

ggctactgtg aacgagccta taccatcctg cggcgccacg ggctgctttt cctccatctc   2940

ttcgccctga tgcgggccgc aggtctgcct gagcttagct gctccaaaga tatccagtat   3000

ctcaaggact ctctggcact ggggaagacg gaggaagagg cgctaaagca cttccgggtg   3060

aagttcaacg aagctctccg agaaagctgg aaaaccaaag tcaactggct ggcgcacaat   3120

gtgtccaagg ataaccgaca gtag                                          3144
```

<210> SEQ ID NO 32
<211> LENGTH: 1047
<212> TYPE: PRT
<213> ORGANISM: Mus musculus

<400> SEQUENCE: 32

```
Met Pro Pro Gly Val Asp Cys Pro Met Glu Phe Trp Thr Lys Glu Glu
1               5                   10                  15

Ser Gln Ser Val Val Val Asp Phe Leu Leu Pro Thr Gly Val Tyr Leu
            20                  25                  30

Asn Phe Pro Val Ser Arg Asn Ala Asn Leu Ser Thr Ile Lys Gln Val
        35                  40                  45

Leu Trp His Arg Ala Gln Tyr Glu Pro Leu Phe His Met Leu Ser Asp
    50                  55                  60

Pro Glu Ala Tyr Val Phe Thr Cys Val Asn Gln Thr Ala Glu Gln Gln
65                  70                  75                  80

Glu Leu Glu Asp Glu Gln Arg Arg Leu Cys Asp Ile Gln Pro Phe Leu
                85                  90                  95

Pro Val Leu Arg Leu Val Ala Arg Glu Gly Asp Arg Val Lys Lys Leu
            100                 105                 110

Ile Asn Ser Gln Ile Ser Leu Leu Ile Gly Lys Gly Leu His Glu Phe
        115                 120                 125

Asp Ser Leu Arg Asp Pro Glu Val Asn Asp Phe Arg Thr Lys Met Arg
    130                 135                 140

Gln Phe Cys Glu Glu Ala Ala Ala His Arg Gln Gln Leu Gly Trp Val
145                 150                 155                 160

Glu Trp Leu Gln Tyr Ser Phe Pro Leu Gln Leu Glu Pro Ser Ala Arg
                165                 170                 175

Gly Trp Arg Ala Gly Leu Leu Arg Val Ser Asn Arg Ala Leu Leu Val
            180                 185                 190

Asn Val Lys Phe Glu Gly Ser Glu Glu Ser Phe Thr Phe Gln Val Ser
        195                 200                 205

Thr Lys Asp Met Pro Leu Ala Leu Met Ala Cys Ala Leu Arg Lys Lys
    210                 215                 220

Ala Thr Val Phe Arg Gln Pro Leu Val Glu Gln Pro Glu Glu Tyr Ala
225                 230                 235                 240

Leu Gln Val Asn Gly Arg His Glu Tyr Leu Tyr Gly Asn Tyr Pro Leu
                245                 250                 255

Cys His Phe Gln Tyr Ile Cys Ser Cys Leu His Ser Gly Leu Thr Pro
            260                 265                 270
```

```
His Leu Thr Met Val His Ser Ser Ser Ile Leu Ala Met Arg Asp Glu
        275                 280                 285

Gln Ser Asn Pro Ala Pro Gln Val Gln Lys Pro Arg Ala Lys Pro Pro
    290                 295                 300

Pro Ile Pro Ala Lys Lys Pro Ser Ser Val Ser Leu Trp Ser Leu Glu
305                 310                 315                 320

Gln Pro Phe Ser Ile Glu Leu Ile Glu Gly Arg Lys Val Asn Ala Asp
                325                 330                 335

Glu Arg Met Lys Leu Val Val Gln Ala Gly Leu Phe His Gly Asn Glu
            340                 345                 350

Met Leu Cys Lys Thr Val Ser Ser Ser Glu Val Asn Val Cys Ser Glu
        355                 360                 365

Pro Val Trp Lys Gln Arg Leu Glu Phe Asp Ile Ser Val Cys Asp Leu
    370                 375                 380

Pro Arg Met Ala Arg Leu Cys Phe Ala Leu Tyr Ala Val Val Glu Lys
385                 390                 395                 400

Ala Lys Lys Ala Arg Ser Thr Lys Lys Lys Ser Lys Lys Ala Asp Cys
                405                 410                 415

Pro Ile Ala Trp Ala Asn Leu Met Leu Phe Asp Tyr Lys Asp Gln Leu
            420                 425                 430

Lys Thr Gly Glu Arg Cys Leu Tyr Met Trp Pro Ser Val Pro Asp Glu
        435                 440                 445

Lys Gly Glu Leu Leu Asn Pro Ala Gly Thr Val Arg Gly Asn Pro Asn
    450                 455                 460

Thr Glu Ser Ala Ala Ala Leu Val Ile Tyr Leu Pro Glu Val Ala Pro
465                 470                 475                 480

His Pro Val Tyr Phe Pro Ala Leu Glu Lys Ile Leu Glu Leu Gly Arg
                485                 490                 495

His Gly Glu Arg Gly Arg Ile Thr Glu Glu Glu Gln Leu Gln Leu Arg
            500                 505                 510

Glu Ile Leu Glu Arg Arg Gly Ser Gly Glu Leu Tyr Glu His Glu Lys
        515                 520                 525

Asp Leu Val Trp Lys Met Arg His Glu Val Gln Glu His Phe Pro Glu
    530                 535                 540

Ala Leu Ala Arg Leu Leu Leu Val Thr Lys Trp Asn Lys His Glu Asp
545                 550                 555                 560

Val Ala Gln Leu Ser Gln Met Leu Tyr Leu Leu Cys Ser Trp Pro Glu
                565                 570                 575

Leu Pro Val Leu Ser Ala Leu Glu Leu Leu Asp Phe Ser Phe Pro Asp
            580                 585                 590

Cys Tyr Val Gly Ser Phe Ala Ile Lys Ser Leu Arg Lys Leu Thr Asp
        595                 600                 605

Asp Glu Leu Phe Gln Tyr Leu Leu Gln Leu Val Gln Val Leu Lys Tyr
    610                 615                 620

Glu Ser Tyr Leu Asp Cys Glu Leu Thr Lys Phe Leu Leu Gly Arg Ala
625                 630                 635                 640

Leu Ala Asn Arg Lys Ile Gly His Phe Leu Phe Trp His Leu Arg Ser
                645                 650                 655

Glu Met His Val Pro Ser Val Ala Leu Arg Phe Gly Leu Ile Met Glu
            660                 665                 670

Ala Tyr Cys Arg Gly Ser Thr His His Met Lys Val Leu Met Lys Gln
        675                 680                 685
```

```
Gly Glu Ala Leu Ser Lys Leu Lys Ala Leu Asn Asp Phe Val Lys Val
    690                 695                 700

Ser Ser Gln Lys Thr Thr Lys Pro Gln Thr Lys Glu Met Met His Met
705                 710                 715                 720

Cys Met Arg Gln Glu Thr Tyr Met Glu Ala Leu Ser His Leu Gln Ser
                725                 730                 735

Pro Leu Asp Pro Ser Thr Leu Leu Glu Glu Val Cys Val Glu Gln Cys
            740                 745                 750

Thr Phe Met Asp Ser Lys Met Lys Pro Leu Trp Ile Met Tyr Ser Ser
        755                 760                 765

Glu Glu Ala Gly Ser Ala Gly Asn Val Gly Ile Ile Phe Lys Asn Gly
    770                 775                 780

Asp Asp Leu Arg Gln Asp Met Leu Thr Leu Gln Met Ile Gln Leu Met
785                 790                 795                 800

Asp Val Leu Trp Lys Gln Glu Gly Leu Asp Leu Arg Met Thr Pro Tyr
                805                 810                 815

Gly Cys Leu Pro Thr Gly Asp Arg Thr Gly Leu Ile Glu Val Val Leu
            820                 825                 830

His Ser Asp Thr Ile Ala Asn Ile Gln Leu Asn Lys Ser Asn Met Ala
        835                 840                 845

Ala Thr Ala Ala Phe Asn Lys Asp Ala Leu Leu Asn Trp Leu Lys Ser
    850                 855                 860

Lys Asn Pro Gly Glu Ala Leu Asp Arg Ala Ile Glu Glu Phe Thr Leu
865                 870                 875                 880

Ser Cys Ala Gly Tyr Cys Val Ala Thr Tyr Val Leu Gly Ile Gly Asp
                885                 890                 895

Arg His Ser Asp Asn Ile Met Ile Arg Glu Ser Gly Gln Leu Phe His
            900                 905                 910

Ile Asp Phe Gly His Phe Leu Gly Asn Phe Lys Thr Lys Phe Gly Ile
        915                 920                 925

Asn Arg Glu Arg Val Pro Phe Ile Leu Thr Tyr Asp Phe Val His Val
    930                 935                 940

Ile Gln Gln Gly Lys Thr Asn Asn Ser Glu Lys Phe Glu Arg Phe Arg
945                 950                 955                 960

Gly Tyr Cys Glu Arg Ala Tyr Thr Ile Leu Arg Arg His Gly Leu Leu
                965                 970                 975

Phe Leu His Leu Phe Ala Leu Met Arg Ala Ala Gly Leu Pro Glu Leu
            980                 985                 990

Ser Cys Ser Lys Asp Ile Gln Tyr  Leu Lys Asp Ser Leu  Ala Leu Gly
        995                 1000                 1005

Lys Thr  Glu Glu Glu Ala Leu  Lys His Phe Arg Val  Lys Phe Asn
    1010                 1015                 1020

Glu Ala  Leu Arg Glu Ser Trp  Lys Thr Lys Val Asn  Trp Leu Ala
    1025                 1030                 1035

His Asn  Val Ser Lys Asp Asn  Arg Gln
    1040                 1045
```

<210> SEQ ID NO 33
<211> LENGTH: 3135
<212> TYPE: DNA
<213> ORGANISM: Mus musculus

<400> SEQUENCE: 33

```
atgccccctg ggtggactg ccccatggag ttctggacca aagaggagag ccagagcgtg     60
```

```
gttgttgact tcttgctgcc cacaggggtc tacttgaact tccccgtgtc ccgcaatgcc    120
aacctcagca ccatcaagca ggtgctgtgg caccgtgcac agtatgagcc actcttccac    180
atgctcagtg accccgaggc ctatgtgttc acctgtgtga accagacggc ggagcagcag    240
gagttggagg atgagcagcg gaggctgtgc gacatccagc ccttcctgcc cgtgctgcgc    300
ctcgtggccc gagaggggga ccgcgtgaag aagctcatta actcccagat cagcctcctc    360
attggcaaag gtctccatga gtttgattcc ctgcgggacc cggaagtaaa cgacttccgc    420
actaagatgc gccagttttg tgaagaggct gctgctcacc gccagcagct gggctgggtg    480
gaatggctgc agtacagctt cccccctgcag ctggagccct cagcaagggg ttggcgggcc    540
ggcttattgc gtgtcagcaa ccgagccctg ctggtcaacg tgaagttcga gggcagtgag    600
gagagcttca ccttccaggt atccaccaag gacatgcccc tggcactgat ggcctgtgcc    660
ctccgaaaaa aggccacagt gttccggcag cctctggtgg agcagcctga ggaatatgcc    720
ctgcaggtga acgggaggca cgaatacctc tacggcaact acccgctctg ccactttcag    780
tacatctgca gctgcctaca cagcgggctg accctcatc tgaccatggt ccactcctcc    840
tccatccttg ctatgcggga tgagcagagc aatcctgccc cccaagtaca gaaaccacgt    900
gccaaacctc ccccgatccc tgccaagaag ccctcctctg tgtccctgtg gtccctggaa    960
cagccattct ccattgagct gatcgagggc cgaaaagtga atgctgacga gcggatgaag   1020
ctggttgttc aggccgggct cttccatggc aatgagatgc tgtgcaagac tgtgtcaagc   1080
tcggaggtga atgtatgctc agagcccgtg tggaagcagc gactggagtt cgatatcagc   1140
gtctgtgacc tcccgcgcat ggctcgactc tgttttgctc tctatgccgt cgtggagaag   1200
gctaagaagg cacgctccac aaagaagaag tctaagaagg cggactgccc catcgcttgg   1260
gccaacctca tgctattcga ctacaaagat cagctcaaga cgggggagcg ctgcctctac   1320
atgtggccct ctgtcccaga tgagaaggga gagctgctga atcctgcggg tacagtgcgc   1380
gggaacccca acacggagag tgccgctgcc ctggtcatct acctgcctga ggtggccccc   1440
caccctgtgt acttccccgc tctggagaag atcctggagc tggggcgtca cggggagcgt   1500
gggcgcatca cggaggagga gcagctgcag ctgcgggaga tcctggaacg gcggggatcc   1560
ggggaactgt acgaacatga gaaggacctg gtgtggaaga tgcgccacga agtccaggag   1620
catttcccag aggcgctggc ccgcctgctg ctggtcacca agtggaataa acacgaggat   1680
gtggcccaga tgctctattt gctgtgctcc tggcccgagc tgcctgtgct gagcgccctg   1740
gaacttctgg actttagctt tcccgactgc tacgtgggct ccttcgccat caagtccctt   1800
cggaagctga cggacgatga gctcttccag taccttctgc agctggtgca agtgctcaaa   1860
tatgagtcct acctggactg cgagctgacc aaattcttgc tgggccgagc cctggctaac   1920
cgcaagatcg gacacttcct gttctggcac ctccgctctg agatgcacgt accatcagtg   1980
gctctgcggt ttggtctcat catggaagcc tactgcagag gcagcaccca ccacatgaag   2040
gtgctgatga agcaggggga agcactgagc aagcttaagg cactgaatga ctttgtgaag   2100
gtgagttccc agaagaccac caagccccaa accaaggaga tgatgcatat gtgcatgcgc   2160
caggagacct acatggaggc cctgtcccac ctgcagtctc cactcgaccc cagcaccctg   2220
ctggaggaag tctgtgtgga gcagtgcacc ttcatggact ccaaaatgaa gcccctgtgg   2280
atcatgtaca gcagcgagga ggcgggcagt gctggcaacg tgggcatcat ctttaagaac   2340
ggggatgacc tccgccagga catgctgact ctgcagatga tccagctcat ggacgtcctg   2400
tggaagcagg agggcctgga cctgaggatg acgccctacg gctgcctccc caccggggac   2460
```

```
cgcacaggtc tcatcgaggt ggtcctccac tcggacacca tcgccaacat ccagctgaac   2520

aaaagcaaca tggcggccac agctgccttc aacaaggacg ccctgctcaa ctggctcaag   2580

tccaagaacc ctggggaggc cctggatcgg gccattgagg aattcaccct ctcctgtgct   2640

ggctactgtg tggccacata tgttctgggc atcggtgacc ggcacagcga caacatcatg   2700

atcagagaga gtgggcagct cttccacatt gattttggcc actttctggg gaacttcaag   2760

accaagtttg gaatcaaccg agagcgcgtc cccttcattc tcacctacga ctttgtccac   2820

gtgatccagc aggggaagac taacaacagt gagaagtttg aaaggttccg cggctactgt   2880

gaacgagcct ataccatcct gcggcgccac gggctgcttt tcctccatct cttcgccctg   2940

atgcgggccg caggtctgcc tgagcttagc tgctccaaag atatccagta tctcaaggac   3000

tctctggcac tggggaagac ggaggaagag gcgctaaagc acttccgggt gaagttcaac   3060

gaagctctcc gagaaagctg gaaaaccaaa gtcaactggc tggcgcacaa tgtgtccaag   3120

gataaccgac agtag                                                    3135
```

```
<210> SEQ ID NO 34
<211> LENGTH: 1044
<212> TYPE: PRT
<213> ORGANISM: Mus musculus

<400> SEQUENCE: 34

Met Pro Pro Gly Val Asp Cys Pro Met Glu Phe Trp Thr Lys Glu Glu
1               5                   10                  15

Ser Gln Ser Val Val Val Asp Phe Leu Leu Pro Thr Gly Val Tyr Leu
            20                  25                  30

Asn Phe Pro Val Ser Arg Asn Ala Asn Leu Ser Thr Ile Lys Gln Val
        35                  40                  45

Leu Trp His Arg Ala Gln Tyr Glu Pro Leu Phe His Met Leu Ser Asp
    50                  55                  60

Pro Glu Ala Tyr Val Phe Thr Cys Val Asn Gln Thr Ala Glu Gln Gln
65                  70                  75                  80

Glu Leu Glu Asp Glu Gln Arg Arg Leu Cys Asp Ile Gln Pro Phe Leu
                85                  90                  95

Pro Val Leu Arg Leu Val Ala Arg Glu Gly Asp Arg Val Lys Lys Leu
            100                 105                 110

Ile Asn Ser Gln Ile Ser Leu Leu Ile Gly Lys Gly Leu His Glu Phe
        115                 120                 125

Asp Ser Leu Arg Asp Pro Glu Val Asn Asp Phe Arg Thr Lys Met Arg
    130                 135                 140

Gln Phe Cys Glu Glu Ala Ala Ala His Arg Gln Gln Leu Gly Trp Val
145                 150                 155                 160

Glu Trp Leu Gln Tyr Ser Phe Pro Leu Gln Leu Glu Pro Ser Ala Arg
                165                 170                 175

Gly Trp Arg Ala Gly Leu Leu Arg Val Ser Asn Arg Ala Leu Leu Val
            180                 185                 190

Asn Val Lys Phe Glu Gly Ser Glu Glu Ser Phe Thr Phe Gln Val Ser
        195                 200                 205

Thr Lys Asp Met Pro Leu Ala Leu Met Ala Cys Ala Leu Arg Lys Lys
    210                 215                 220

Ala Thr Val Phe Arg Gln Pro Leu Val Glu Gln Pro Glu Glu Tyr Ala
225                 230                 235                 240

Leu Gln Val Asn Gly Arg His Glu Tyr Leu Tyr Gly Asn Tyr Pro Leu
```

```
                245                 250                 255

Cys His Phe Gln Tyr Ile Cys Ser Cys Leu His Ser Gly Leu Thr Pro
            260                 265                 270

His Leu Thr Met Val His Ser Ser Ser Ile Leu Ala Met Arg Asp Glu
        275                 280                 285

Gln Ser Asn Pro Ala Pro Gln Val Gln Lys Pro Arg Ala Lys Pro Pro
    290                 295                 300

Pro Ile Pro Ala Lys Lys Pro Ser Ser Val Ser Leu Trp Ser Leu Glu
305                 310                 315                 320

Gln Pro Phe Ser Ile Glu Leu Ile Glu Gly Arg Lys Val Asn Ala Asp
                325                 330                 335

Glu Arg Met Lys Leu Val Val Gln Ala Gly Leu Phe His Gly Asn Glu
            340                 345                 350

Met Leu Cys Lys Thr Val Ser Ser Ser Glu Val Asn Val Cys Ser Glu
        355                 360                 365

Pro Val Trp Lys Gln Arg Leu Glu Phe Asp Ile Ser Val Cys Asp Leu
    370                 375                 380

Pro Arg Met Ala Arg Leu Cys Phe Ala Leu Tyr Ala Val Val Glu Lys
385                 390                 395                 400

Ala Lys Lys Ala Arg Ser Thr Lys Lys Lys Ser Lys Lys Ala Asp Cys
                405                 410                 415

Pro Ile Ala Trp Ala Asn Leu Met Leu Phe Asp Tyr Lys Asp Gln Leu
            420                 425                 430

Lys Thr Gly Glu Arg Cys Leu Tyr Met Trp Pro Ser Val Pro Asp Glu
        435                 440                 445

Lys Gly Glu Leu Leu Asn Pro Ala Gly Thr Val Arg Gly Asn Pro Asn
    450                 455                 460

Thr Glu Ser Ala Ala Ala Leu Val Ile Tyr Leu Pro Glu Val Ala Pro
465                 470                 475                 480

His Pro Val Tyr Phe Pro Ala Leu Glu Lys Ile Leu Glu Leu Gly Arg
                485                 490                 495

His Gly Glu Arg Gly Arg Ile Thr Glu Glu Glu Gln Leu Gln Leu Arg
            500                 505                 510

Glu Ile Leu Glu Arg Arg Gly Ser Gly Glu Leu Tyr Glu His Glu Lys
        515                 520                 525

Asp Leu Val Trp Lys Met Arg His Glu Val Gln Glu His Phe Pro Glu
    530                 535                 540

Ala Leu Ala Arg Leu Leu Leu Val Thr Lys Trp Asn Lys His Glu Asp
545                 550                 555                 560

Val Ala Gln Met Leu Tyr Leu Leu Cys Ser Trp Pro Glu Leu Pro Val
                565                 570                 575

Leu Ser Ala Leu Glu Leu Leu Asp Phe Ser Phe Pro Asp Cys Tyr Val
            580                 585                 590

Gly Ser Phe Ala Ile Lys Ser Leu Arg Lys Leu Thr Asp Asp Glu Leu
        595                 600                 605

Phe Gln Tyr Leu Leu Gln Leu Val Gln Val Leu Lys Tyr Glu Ser Tyr
    610                 615                 620

Leu Asp Cys Glu Leu Thr Lys Phe Leu Leu Gly Arg Ala Leu Ala Asn
625                 630                 635                 640

Arg Lys Ile Gly His Phe Leu Phe Trp His Leu Arg Ser Glu Met His
                645                 650                 655

Val Pro Ser Val Ala Leu Arg Phe Gly Leu Ile Met Glu Ala Tyr Cys
            660                 665                 670
```

```
Arg Gly Ser Thr His His Met Lys Val Leu Met Lys Gln Gly Glu Ala
        675                 680                 685

Leu Ser Lys Leu Lys Ala Leu Asn Asp Phe Val Lys Val Ser Ser Gln
    690                 695                 700

Lys Thr Thr Lys Pro Gln Thr Lys Glu Met Met His Met Cys Met Arg
705                 710                 715                 720

Gln Glu Thr Tyr Met Glu Ala Leu Ser His Leu Gln Ser Pro Leu Asp
                725                 730                 735

Pro Ser Thr Leu Leu Glu Glu Val Cys Val Glu Gln Cys Thr Phe Met
            740                 745                 750

Asp Ser Lys Met Lys Pro Leu Trp Ile Met Tyr Ser Ser Glu Glu Ala
        755                 760                 765

Gly Ser Ala Gly Asn Val Gly Ile Ile Phe Lys Asn Gly Asp Asp Leu
    770                 775                 780

Arg Gln Asp Met Leu Thr Leu Gln Met Ile Gln Leu Met Asp Val Leu
785                 790                 795                 800

Trp Lys Gln Glu Gly Leu Asp Leu Arg Met Thr Pro Tyr Gly Cys Leu
                805                 810                 815

Pro Thr Gly Asp Arg Thr Gly Leu Ile Glu Val Val Leu His Ser Asp
            820                 825                 830

Thr Ile Ala Asn Ile Gln Leu Asn Lys Ser Asn Met Ala Ala Thr Ala
        835                 840                 845

Ala Phe Asn Lys Asp Ala Leu Leu Asn Trp Leu Lys Ser Lys Asn Pro
    850                 855                 860

Gly Glu Ala Leu Asp Arg Ala Ile Glu Glu Phe Thr Leu Ser Cys Ala
865                 870                 875                 880

Gly Tyr Cys Val Ala Thr Tyr Val Leu Gly Ile Gly Asp Arg His Ser
                885                 890                 895

Asp Asn Ile Met Ile Arg Glu Ser Gly Gln Leu Phe His Ile Asp Phe
            900                 905                 910

Gly His Phe Leu Gly Asn Phe Lys Thr Lys Phe Gly Ile Asn Arg Glu
        915                 920                 925

Arg Val Pro Phe Ile Leu Thr Tyr Asp Phe Val His Val Ile Gln Gln
    930                 935                 940

Gly Lys Thr Asn Asn Ser Glu Lys Phe Glu Arg Phe Arg Gly Tyr Cys
945                 950                 955                 960

Glu Arg Ala Tyr Thr Ile Leu Arg Arg His Gly Leu Leu Phe Leu His
                965                 970                 975

Leu Phe Ala Leu Met Arg Ala Ala Gly Leu Pro Glu Leu Ser Cys Ser
            980                 985                 990

Lys Asp Ile Gln Tyr Leu Lys Asp  Ser Leu Ala Leu Gly  Lys Thr Glu
        995                 1000                1005

Glu Glu  Ala Leu Lys His Phe  Arg Val Lys Phe Asn  Glu Ala Leu
    1010                1015                1020

Arg Glu  Ser Trp Lys Thr Lys  Val Asn Trp Leu Ala  His Asn Val
    1025                1030                1035

Ser Lys  Asp Asn Arg Gln
    1040
```

<210> SEQ ID NO 35
<211> LENGTH: 3138
<212> TYPE: DNA
<213> ORGANISM: Mus musculus

<400> SEQUENCE: 35

```
atgccccctg ggtggactg ccccatggag ttctggacca aagaggagag ccagagcgtg     60
gttgttgact tcttgctgcc cacaggggtc tacttgaact tccccgtgtc ccgcaatgcc    120
aacctcagca ccatcaagca ggtgctgtgg caccgtgcac agtatgagcc actcttccac    180
atgctcagtg accccgaggc ctatgtgttc acctgtgtga accagacggc ggagcagcag    240
gagttggagg atgagcagcg gaggctgtgc gacatccagc ccttcctgcc cgtgctgcgc    300
ctcgtggccc gagaggggga ccgcgtgaag aagctcatta actcccagat cagcctcctc    360
attggcaaag gtctccatga gtttgattcc ctgcgggacc cggaagtaaa cgacttccgc    420
actaagatgc gccagttttg tgaagaggct gctgctcacc gccagcagct gggctgggtg    480
gaatggctgc agtacagctt cccccctgcag ctggagccct cagcaagggg ttggcgggcc    540
ggcttattgc gtgtcagcaa ccgagccctg ctggtcaacg tgaagttcga gggcagtgag    600
gagagcttca ccttccaggt atccaccaag gacatgcccc tggcactgat ggcctgtgcc    660
ctccgaaaaa aggccacagt gttccggcag cctctggtgg agcagcctga ggaatatgcc    720
ctgcaggtga acgggaggca cgaatacctc tacggcaact acccgctctg ccactttcag    780
tacatctgca gctgcctaca cagcgggctg accccctcatc tgaccatggt ccactcctcc    840
tccatccttg ctatgcggga tgagcagagc aatcctgccc cccaagtaca gaaaccacgt    900
gccaaacctc ccccgatccc tgccaagaag ccctcctctg tgtccctgtg gtccctggaa    960
cagccattct ccattgagct gatcgagggc cgaaaagtga atgctgacga gcggatgaag   1020
ctggttgttc aggccgggct cttccatggc aatgagatgc tgtgcaagac tgtgtcaagc   1080
tcggaggtga atgtatgctc agagcccgtg tggaagcagc gactggagtt cgatatcagc   1140
gtctgtgacc tcccgcgcat ggctcgactc tgttttgctc tctatgccgt cgtggagaag   1200
gctaagaagg cacgctccac aaagaagaag tctaagaagg cggactgccc catcgcttgg   1260
gccaacctca tgctattcga ctacaaagat cagctcaaga cgggggagcg ctgcctctac   1320
atgtggccct ctgtcccaga tgagaaggga gagctgctga atcctgcggg tacagtgcgc   1380
gggaacccca acacggagag tgccgctgcc ctggtcatct acctgcctga ggtggccccc   1440
caccctgtgt acttccccgc tctggagaag atcctggagc tggggcgtca cggggagcgt   1500
gggcgcatca cggaggagga gcagctgcag ctgcgggaga tcctggaacg gcggggatcc   1560
ggggaactgt acgaacatga gaaggacctg gtgtggaaga tgcgccacga agtccaggag   1620
catttcccag aggcgctggc ccgcctgctg ctggtcacca agtggaataa acacgaggat   1680
gtggcccaga tgctctattt gctgtgctcc tggcccgagc tgcctgtgct gagcgccctg   1740
gaacttctgg actttagctt tcccgactgc tacgtgggct ccttcgccat caagtccctt   1800
cggaagctga cggacgatga gctcttccag taccttctgc agctggtgca agtgctcaaa   1860
tatgagtcct acctggactg cgagctgacc aaattcttgc tgggccgagc cctggctaac   1920
cgcaagatcg gacacttcct gttctggcac ctccgctctg agatgcacgt accatcagtg   1980
gctctgcggt ttggtctcat catggaagcc tactgcagag gcagcaccca ccacatgaag   2040
gtgctgatga agcaggggga agcactgagc aagcttaagg cactgaatga ctttgtgaag   2100
gtgagttccc agaagaccac caagccccaa accaaggaga tgatgcatat gtgcatgcgc   2160
caggagacct acatggaggc cctgtcccac ctgcagtctc cactcgaccc cagcaccctg   2220
ctggaggaag tctgcagtgt ggagcagtgc accttcatgg actccaaaat gaagcccctg   2280
tggatcatgt acagcagcga ggaggcgggc agtgctggca acgtgggcat catctttaag   2340
```

```
aacggggatg acctccgcca ggacatgctg actctgcaga tgatccagct catggacgtc   2400

ctgtggaagc aggagggcct ggacctgagg atgacgccct acggctgcct ccccaccggg   2460

gaccgcacag gtctcatcga ggtggtcctc cactcggaca ccatcgccaa catccagctg   2520

aacaaaagca acatggcggc cacagctgcc ttcaacaagg acgccctgct caactggctc   2580

aagtccaaga accctgggga ggccctggat cgggccattg aggaattcac cctctcctgt   2640

gctggctact gtgtggccac atatgttctg ggcatcggtg accggcacag cgacaacatc   2700

atgatcagag agagtgggca gctcttccac attgattttg gccactttct ggggaacttc   2760

aagaccaagt ttggaatcaa ccgagagcgc gtccccttca ttctcaccta cgactttgtc   2820

cacgtgatcc agcaggggaa gactaacaac agtgagaagt ttgaaaggtt ccgcggctac   2880

tgtgaacgag cctataccat cctgcggcgc cacgggctgc ttttcctcca tctcttcgcc   2940

ctgatgcggg ccgcaggtct gcctgagctt agctgctcca aagatatcca gtatctcaag   3000

gactctctgg cactggggaa gacggaggaa gaggcgctaa agcacttccg ggtgaagttc   3060

aacgaagctc tccgagaaag ctggaaaacc aaagtcaact ggctggcgca caatgtgtcc   3120

aaggataacc gacagtag                                                 3138
```

```
<210> SEQ ID NO 36
<211> LENGTH: 1045
<212> TYPE: PRT
<213> ORGANISM: Mus musculus

<400> SEQUENCE: 36

Met Pro Pro Gly Val Asp Cys Pro Met Glu Phe Trp Thr Lys Glu Glu
1               5                   10                  15

Ser Gln Ser Val Val Val Asp Phe Leu Leu Pro Thr Gly Val Tyr Leu
            20                  25                  30

Asn Phe Pro Val Ser Arg Asn Ala Asn Leu Ser Thr Ile Lys Gln Val
        35                  40                  45

Leu Trp His Arg Ala Gln Tyr Glu Pro Leu Phe His Met Leu Ser Asp
    50                  55                  60

Pro Glu Ala Tyr Val Phe Thr Cys Val Asn Gln Thr Ala Glu Gln Gln
65                  70                  75                  80

Glu Leu Glu Asp Glu Gln Arg Arg Leu Cys Asp Ile Gln Pro Phe Leu
                85                  90                  95

Pro Val Leu Arg Leu Val Ala Arg Glu Gly Asp Arg Val Lys Lys Leu
            100                 105                 110

Ile Asn Ser Gln Ile Ser Leu Leu Ile Gly Lys Gly Leu His Glu Phe
        115                 120                 125

Asp Ser Leu Arg Asp Pro Glu Val Asn Asp Phe Arg Thr Lys Met Arg
    130                 135                 140

Gln Phe Cys Glu Glu Ala Ala Ala His Arg Gln Gln Leu Gly Trp Val
145                 150                 155                 160

Glu Trp Leu Gln Tyr Ser Phe Pro Leu Gln Leu Glu Pro Ser Ala Arg
                165                 170                 175

Gly Trp Arg Ala Gly Leu Leu Arg Val Ser Asn Arg Ala Leu Leu Val
            180                 185                 190

Asn Val Lys Phe Glu Gly Ser Glu Glu Ser Phe Thr Phe Gln Val Ser
        195                 200                 205

Thr Lys Asp Met Pro Leu Ala Leu Met Ala Cys Ala Leu Arg Lys Lys
    210                 215                 220
```

-continued

```
Ala Thr Val Phe Arg Gln Pro Leu Val Glu Gln Pro Glu Glu Tyr Ala
225                 230                 235                 240

Leu Gln Val Asn Gly Arg His Glu Tyr Leu Tyr Gly Asn Tyr Pro Leu
                245                 250                 255

Cys His Phe Gln Tyr Ile Cys Ser Cys Leu His Ser Gly Leu Thr Pro
            260                 265                 270

His Leu Thr Met Val His Ser Ser Ser Ile Leu Ala Met Arg Asp Glu
        275                 280                 285

Gln Ser Asn Pro Ala Pro Gln Val Gln Lys Pro Arg Ala Lys Pro Pro
    290                 295                 300

Pro Ile Pro Ala Lys Lys Pro Ser Ser Val Ser Leu Trp Ser Leu Glu
305                 310                 315                 320

Gln Pro Phe Ser Ile Glu Leu Ile Glu Gly Arg Lys Val Asn Ala Asp
                325                 330                 335

Glu Arg Met Lys Leu Val Val Gln Ala Gly Leu Phe His Gly Asn Glu
            340                 345                 350

Met Leu Cys Lys Thr Val Ser Ser Ser Glu Val Asn Val Cys Ser Glu
        355                 360                 365

Pro Val Trp Lys Gln Arg Leu Glu Phe Asp Ile Ser Val Cys Asp Leu
    370                 375                 380

Pro Arg Met Ala Arg Leu Cys Phe Ala Leu Tyr Ala Val Val Glu Lys
385                 390                 395                 400

Ala Lys Lys Ala Arg Ser Thr Lys Lys Lys Ser Lys Lys Ala Asp Cys
                405                 410                 415

Pro Ile Ala Trp Ala Asn Leu Met Leu Phe Asp Tyr Lys Asp Gln Leu
            420                 425                 430

Lys Thr Gly Glu Arg Cys Leu Tyr Met Trp Pro Ser Val Pro Asp Glu
        435                 440                 445

Lys Gly Glu Leu Leu Asn Pro Ala Gly Thr Val Arg Gly Asn Pro Asn
    450                 455                 460

Thr Glu Ser Ala Ala Ala Leu Val Ile Tyr Leu Pro Glu Val Ala Pro
465                 470                 475                 480

His Pro Val Tyr Phe Pro Ala Leu Glu Lys Ile Leu Glu Leu Gly Arg
                485                 490                 495

His Gly Glu Arg Gly Arg Ile Thr Glu Glu Glu Gln Leu Gln Leu Arg
            500                 505                 510

Glu Ile Leu Glu Arg Arg Gly Ser Gly Glu Leu Tyr Glu His Glu Lys
        515                 520                 525

Asp Leu Val Trp Lys Met Arg His Glu Val Gln Glu His Phe Pro Glu
    530                 535                 540

Ala Leu Ala Arg Leu Leu Leu Val Thr Lys Trp Asn Lys His Glu Asp
545                 550                 555                 560

Val Ala Gln Met Leu Tyr Leu Leu Cys Ser Trp Pro Glu Leu Pro Val
                565                 570                 575

Leu Ser Ala Leu Glu Leu Leu Asp Phe Ser Phe Pro Asp Cys Tyr Val
            580                 585                 590

Gly Ser Phe Ala Ile Lys Ser Leu Arg Lys Leu Thr Asp Asp Glu Leu
        595                 600                 605

Phe Gln Tyr Leu Leu Gln Leu Val Gln Val Leu Lys Tyr Glu Ser Tyr
    610                 615                 620

Leu Asp Cys Glu Leu Thr Lys Phe Leu Leu Gly Arg Ala Leu Ala Asn
625                 630                 635                 640

Arg Lys Ile Gly His Phe Leu Phe Trp His Leu Arg Ser Glu Met His
```

```
                645                 650                 655

Val Pro Ser Val Ala Leu Arg Phe Gly Leu Ile Met Glu Ala Tyr Cys
            660                 665                 670

Arg Gly Ser Thr His His Met Lys Val Leu Met Lys Gln Gly Glu Ala
        675                 680                 685

Leu Ser Lys Leu Lys Ala Leu Asn Asp Phe Val Lys Val Ser Ser Gln
    690                 695                 700

Lys Thr Thr Lys Pro Gln Thr Lys Glu Met Met His Met Cys Met Arg
705                 710                 715                 720

Gln Glu Thr Tyr Met Glu Ala Leu Ser His Leu Gln Ser Pro Leu Asp
                725                 730                 735

Pro Ser Thr Leu Leu Glu Glu Val Cys Ser Val Glu Gln Cys Thr Phe
            740                 745                 750

Met Asp Ser Lys Met Lys Pro Leu Trp Ile Met Tyr Ser Ser Glu Glu
        755                 760                 765

Ala Gly Ser Ala Gly Asn Val Gly Ile Ile Phe Lys Asn Gly Asp Asp
    770                 775                 780

Leu Arg Gln Asp Met Leu Thr Leu Gln Met Ile Gln Leu Met Asp Val
785                 790                 795                 800

Leu Trp Lys Gln Glu Gly Leu Asp Leu Arg Met Thr Pro Tyr Gly Cys
                805                 810                 815

Leu Pro Thr Gly Asp Arg Thr Gly Leu Ile Glu Val Val Leu His Ser
            820                 825                 830

Asp Thr Ile Ala Asn Ile Gln Leu Asn Lys Ser Asn Met Ala Ala Thr
        835                 840                 845

Ala Ala Phe Asn Lys Asp Ala Leu Leu Asn Trp Leu Lys Ser Lys Asn
    850                 855                 860

Pro Gly Glu Ala Leu Asp Arg Ala Ile Glu Glu Phe Thr Leu Ser Cys
865                 870                 875                 880

Ala Gly Tyr Cys Val Ala Thr Tyr Val Leu Gly Ile Gly Asp Arg His
                885                 890                 895

Ser Asp Asn Ile Met Ile Arg Glu Ser Gly Gln Leu Phe His Ile Asp
            900                 905                 910

Phe Gly His Phe Leu Gly Asn Phe Lys Thr Lys Phe Gly Ile Asn Arg
        915                 920                 925

Glu Arg Val Pro Phe Ile Leu Thr Tyr Asp Phe Val His Val Ile Gln
    930                 935                 940

Gln Gly Lys Thr Asn Asn Ser Glu Lys Phe Glu Arg Phe Arg Gly Tyr
945                 950                 955                 960

Cys Glu Arg Ala Tyr Thr Ile Leu Arg Arg His Gly Leu Leu Phe Leu
                965                 970                 975

His Leu Phe Ala Leu Met Arg Ala Ala Gly Leu Pro Glu Leu Ser Cys
            980                 985                 990

Ser Lys Asp Ile Gln Tyr Leu Lys  Asp Ser Leu Ala Leu  Gly Lys Thr
        995                 1000                1005

Glu Glu  Glu Ala Leu Lys His  Phe Arg Val Lys Phe  Asn Glu Ala
    1010                1015                1020

Leu Arg  Glu Ser Trp Lys Thr  Lys Val Asn Trp Leu  Ala His Asn
    1025                1030                1035

Val Ser  Lys Asp Asn Arg Gln
    1040                1045
```

<210> SEQ ID NO 37

<211> LENGTH: 3141
<212> TYPE: DNA
<213> ORGANISM: Mus musculus

<400> SEQUENCE: 37

```
atgccccctg gggtggactg ccccatggag ttctggacca aagaggagag ccagagcgtg      60
gttgttgact tcttgctgcc cacaggggtc tacttgaact tccccgtgtc ccgcaatgcc     120
aacctcagca ccatcaagca ggtgctgtgg caccgtgcac agtatgagcc actcttccac     180
atgctcagtg accccgaggc ctatgtgttc acctgtgtga accagacggc ggagcagcag     240
gagttggagg atgagcagcg gaggctgtgc gacatccagc ccttcctgcc cgtgctgcgc     300
ctcgtggccc gagaggggga ccgcgtgaag aagctcatta actcccagat cagcctcctc     360
attggcaaag gtctccatga gtttgattcc ctgcgggacc cggaagtaaa cgacttccgc     420
actaagatgc gccagttttg tgaagaggct gctgctcacc gccagcagct gggctgggtg     480
gaatggctgc agtacagctt cccccctgcag ctggagccct cagcaagggg ttggcgggcc     540
ggcttattgc gtgtcagcaa ccgagccctg ctggtcaacg tgaagttcga gggcagtgag     600
gagagcttca ccttccaggt atccaccaag gacatgcccc tggcactgat ggcctgtgcc     660
ctccgaaaaa aggccacagt gttccggcag cctctggtgg agcagcctga ggaatatgcc     720
ctgcaggtga acgggaggca cgaatacctc tacggcaact acccgctctg ccactttcag     780
tacatctgca gctgcctaca cagcgggctg acccctcatc tgaccatggt ccactcctcc     840
tccatccttg ctatgcggga tgagcagagc aatcctgccc cccaagtaca gaaaccacgt     900
gccaaacctc ccccgatccc tgccaagaag ccctcctctg tgtccctgtg gtccctggaa     960
cagccattct ccattgagct gatcgagggc cgaaaagtga atgctgacga gcggatgaag    1020
ctggttgttc aggccgggct cttccatggc aatgagatgc tgtgcaagac tgtgtcaagc    1080
tcggaggtga atgtatgctc agagcccgtg tggaagcagc gactggagtt cgatatcagc    1140
gtctgtgacc tcccgcgcat ggctcgactc tgttttgctc tctatgccgt cgtggagaag    1200
gctaagaagg cacgctccac aaagaagaag tctaagaagg cggactgccc catcgcttgg    1260
gccaacctca tgctattcga ctacaaagat cagctcaaga cgggggagcg ctgcctctac    1320
atgtggccct ctgtcccaga tgagaaggga gagctgctga atcctgcggg tacagtgcgc    1380
gggaacccca acacggagag tgccgctgcc ctggtcatct acctgcctga ggtggccccc    1440
caccctgtgt acttccccgc tctggagaag atcctggagc tggggcgtca cggggagcgt    1500
gggcgcatca cggaggagga gctgcagctg cgggagatcc tggaacggcg ggatccgggg    1560
gaactgtacg aacatgagaa ggacctggtg tggaagatgc gccacgaagt ccaggagcat    1620
ttcccagagg cgctggcccg cctgctgctg gtcaccaagt ggaataaaca cgaggatgtg    1680
gcccagctgt cccagatgct ctatttgctg tgctcctggc ccgagctgcc tgtgctgagc    1740
gccctggaac ttctggactt tagctttccc gactgctacg tgggctcctt cgccatcaag    1800
tcccttcgga agctgacgga cgatgagctc ttccagtacc ttctgcagct ggtgcaagtg    1860
ctcaaatatg agtcctacct ggactgcgag ctgaccaaat tcttgctggg ccgagccctg    1920
gctaaccgca agatcggaca cttcctgttc tggcacctcc gctctgagat gcacgtacca    1980
tcagtggctc tgcggtttgg tctcatcatg gaagcctact gcagaggcag cacccaccac    2040
atgaaggtgc tgatgaagca gggggaagca ctgagcaagc ttaaggcact gaatgacttt    2100
gtgaaggtga gttcccagaa gaccaccaag ccccaaacca aggagatgat gcatatgtgc    2160
atgcgccagg agacctacat ggaggccctg tcccacctgc agtctccact cgaccccagc    2220
```

```
accctgctgg aggaagtctg tgtggagcag tgcaccttca tggactccaa aatgaagccc   2280

ctgtggatca tgtacagcag cgaggaggcg ggcagtgctg gcaacgtggg catcatcttt   2340

aagaacgggg atgacctccg ccaggacatg ctgactctgc agatgatcca gctcatggac   2400

gtcctgtgga agcaggaggg cctggacctg aggatgacgc cctacggctg cctccccacc   2460

ggggaccgca caggtctcat cgaggtggtc ctccactcgg acaccatcgc caacatccag   2520

ctgaacaaaa gcaacatggc ggccacagct gccttcaaca aggacgccct gctcaactgg   2580

ctcaagtcca agaaccctgg ggaggccctg gatcgggcca ttgaggaatt caccctctcc   2640

tgtgctggct actgtgtggc cacatatgtt ctgggcatcg gtgaccggca cagcgacaac   2700

atcatgatca gagagagtgg gcagctcttc cacattgatt ttggccactt tctggggaac   2760

ttcaagacca agtttggaat caaccgagag cgcgtcccct tcattctcac ctacgacttt   2820

gtccacgtga tccagcaggg gaagactaac aacagtgaga agtttgaaag gttccgcggc   2880

tactgtgaac gagcctatac catcctgcgg cgccacgggc tgcttttcct ccatctcttc   2940

gccctgatgc gggccgcagg tctgcctgag cttagctgct ccaaagatat ccagtatctc   3000

aaggactctc tggcactggg gaagacggag gaagaggcgc taaagcactt ccgggtgaag   3060

ttcaacgaag ctctccgaga aagctggaaa accaaagtca actggctggc gcacaatgtg   3120

tccaaggata accgacagta g                                             3141
```

```
<210> SEQ ID NO 38
<211> LENGTH: 1046
<212> TYPE: PRT
<213> ORGANISM: Mus musculus

<400> SEQUENCE: 38

Met Pro Pro Gly Val Asp Cys Pro Met Glu Phe Trp Thr Lys Glu Glu
1               5                   10                  15

Ser Gln Ser Val Val Val Asp Phe Leu Leu Pro Thr Gly Val Tyr Leu
            20                  25                  30

Asn Phe Pro Val Ser Arg Asn Ala Asn Leu Ser Thr Ile Lys Gln Val
        35                  40                  45

Leu Trp His Arg Ala Gln Tyr Glu Pro Leu Phe His Met Leu Ser Asp
    50                  55                  60

Pro Glu Ala Tyr Val Phe Thr Cys Val Asn Gln Thr Ala Glu Gln Gln
65                  70                  75                  80

Glu Leu Glu Asp Glu Gln Arg Arg Leu Cys Asp Ile Gln Pro Phe Leu
                85                  90                  95

Pro Val Leu Arg Leu Val Ala Arg Glu Gly Asp Arg Val Lys Lys Leu
            100                 105                 110

Ile Asn Ser Gln Ile Ser Leu Leu Ile Gly Lys Gly Leu His Glu Phe
        115                 120                 125

Asp Ser Leu Arg Asp Pro Glu Val Asn Asp Phe Arg Thr Lys Met Arg
    130                 135                 140

Gln Phe Cys Glu Glu Ala Ala Ala His Arg Gln Gln Leu Gly Trp Val
145                 150                 155                 160

Glu Trp Leu Gln Tyr Ser Phe Pro Leu Gln Leu Glu Pro Ser Ala Arg
                165                 170                 175

Gly Trp Arg Ala Gly Leu Leu Arg Val Ser Asn Arg Ala Leu Leu Val
            180                 185                 190

Asn Val Lys Phe Glu Gly Ser Glu Glu Ser Phe Thr Phe Gln Val Ser
        195                 200                 205
```

```
Thr Lys Asp Met Pro Leu Ala Leu Met Ala Cys Ala Leu Arg Lys Lys
    210                 215                 220

Ala Thr Val Phe Arg Gln Pro Leu Val Glu Gln Pro Glu Glu Tyr Ala
225                 230                 235                 240

Leu Gln Val Asn Gly Arg His Glu Tyr Leu Tyr Gly Asn Tyr Pro Leu
                245                 250                 255

Cys His Phe Gln Tyr Ile Cys Ser Cys Leu His Ser Gly Leu Thr Pro
            260                 265                 270

His Leu Thr Met Val His Ser Ser Ser Ile Leu Ala Met Arg Asp Glu
        275                 280                 285

Gln Ser Asn Pro Ala Pro Gln Val Gln Lys Pro Arg Ala Lys Pro Pro
    290                 295                 300

Pro Ile Pro Ala Lys Lys Pro Ser Ser Val Ser Leu Trp Ser Leu Glu
305                 310                 315                 320

Gln Pro Phe Ser Ile Glu Leu Ile Glu Gly Arg Lys Val Asn Ala Asp
                325                 330                 335

Glu Arg Met Lys Leu Val Val Gln Ala Gly Leu Phe His Gly Asn Glu
            340                 345                 350

Met Leu Cys Lys Thr Val Ser Ser Ser Glu Val Asn Val Cys Ser Glu
        355                 360                 365

Pro Val Trp Lys Gln Arg Leu Glu Phe Asp Ile Ser Val Cys Asp Leu
    370                 375                 380

Pro Arg Met Ala Arg Leu Cys Phe Ala Leu Tyr Ala Val Val Glu Lys
385                 390                 395                 400

Ala Lys Lys Ala Arg Ser Thr Lys Lys Lys Ser Lys Lys Ala Asp Cys
                405                 410                 415

Pro Ile Ala Trp Ala Asn Leu Met Leu Phe Asp Tyr Lys Asp Gln Leu
            420                 425                 430

Lys Thr Gly Glu Arg Cys Leu Tyr Met Trp Pro Ser Val Pro Asp Glu
        435                 440                 445

Lys Gly Glu Leu Leu Asn Pro Ala Gly Thr Val Arg Gly Asn Pro Asn
    450                 455                 460

Thr Glu Ser Ala Ala Ala Leu Val Ile Tyr Leu Pro Glu Val Ala Pro
465                 470                 475                 480

His Pro Val Tyr Phe Pro Ala Leu Glu Lys Ile Leu Glu Leu Gly Arg
                485                 490                 495

His Gly Glu Arg Gly Arg Ile Thr Glu Glu Glu Leu Gln Leu Arg Glu
            500                 505                 510

Ile Leu Glu Arg Arg Gly Ser Gly Glu Leu Tyr Glu His Glu Lys Asp
        515                 520                 525

Leu Val Trp Lys Met Arg His Glu Val Gln Glu His Phe Pro Glu Ala
    530                 535                 540

Leu Ala Arg Leu Leu Leu Val Thr Lys Trp Asn Lys His Glu Asp Val
545                 550                 555                 560

Ala Gln Leu Ser Gln Met Leu Tyr Leu Leu Cys Ser Trp Pro Glu Leu
                565                 570                 575

Pro Val Leu Ser Ala Leu Glu Leu Leu Asp Phe Ser Phe Pro Asp Cys
            580                 585                 590

Tyr Val Gly Ser Phe Ala Ile Lys Ser Leu Arg Lys Leu Thr Asp Asp
        595                 600                 605

Glu Leu Phe Gln Tyr Leu Leu Gln Leu Val Gln Val Leu Lys Tyr Glu
    610                 615                 620
```

```
Ser Tyr Leu Asp Cys Glu Leu Thr Lys Phe Leu Leu Gly Arg Ala Leu
625                 630                 635                 640

Ala Asn Arg Lys Ile Gly His Phe Leu Phe Trp His Leu Arg Ser Glu
                645                 650                 655

Met His Val Pro Ser Val Ala Leu Arg Phe Gly Leu Ile Met Glu Ala
            660                 665                 670

Tyr Cys Arg Gly Ser Thr His His Met Lys Val Leu Met Lys Gln Gly
        675                 680                 685

Glu Ala Leu Ser Lys Leu Lys Ala Leu Asn Asp Phe Val Lys Val Ser
    690                 695                 700

Ser Gln Lys Thr Thr Lys Pro Gln Thr Lys Glu Met Met His Met Cys
705                 710                 715                 720

Met Arg Gln Glu Thr Tyr Met Glu Ala Leu Ser His Leu Gln Ser Pro
                725                 730                 735

Leu Asp Pro Ser Thr Leu Leu Glu Glu Val Cys Val Glu Gln Cys Thr
            740                 745                 750

Phe Met Asp Ser Lys Met Lys Pro Leu Trp Ile Met Tyr Ser Ser Glu
        755                 760                 765

Glu Ala Gly Ser Ala Gly Asn Val Gly Ile Ile Phe Lys Asn Gly Asp
    770                 775                 780

Asp Leu Arg Gln Asp Met Leu Thr Leu Gln Met Ile Gln Leu Met Asp
785                 790                 795                 800

Val Leu Trp Lys Gln Glu Gly Leu Asp Leu Arg Met Thr Pro Tyr Gly
                805                 810                 815

Cys Leu Pro Thr Gly Asp Arg Thr Gly Leu Ile Glu Val Val Leu His
            820                 825                 830

Ser Asp Thr Ile Ala Asn Ile Gln Leu Asn Lys Ser Asn Met Ala Ala
        835                 840                 845

Thr Ala Ala Phe Asn Lys Asp Ala Leu Leu Asn Trp Leu Lys Ser Lys
    850                 855                 860

Asn Pro Gly Glu Ala Leu Asp Arg Ala Ile Glu Glu Phe Thr Leu Ser
865                 870                 875                 880

Cys Ala Gly Tyr Cys Val Ala Thr Tyr Val Leu Gly Ile Gly Asp Arg
                885                 890                 895

His Ser Asp Asn Ile Met Ile Arg Glu Ser Gly Gln Leu Phe His Ile
            900                 905                 910

Asp Phe Gly His Phe Leu Gly Asn Phe Lys Thr Lys Phe Gly Ile Asn
        915                 920                 925

Arg Glu Arg Val Pro Phe Ile Leu Thr Tyr Asp Phe Val His Val Ile
    930                 935                 940

Gln Gln Gly Lys Thr Asn Asn Ser Glu Lys Phe Glu Arg Phe Arg Gly
945                 950                 955                 960

Tyr Cys Glu Arg Ala Tyr Thr Ile Leu Arg Arg His Gly Leu Leu Phe
                965                 970                 975

Leu His Leu Phe Ala Leu Met Arg Ala Ala Gly Leu Pro Glu Leu Ser
            980                 985                 990

Cys Ser Lys Asp Ile Gln Tyr Leu  Lys Asp Ser Leu Ala  Leu Gly Lys
        995                 1000                1005

Thr Glu  Glu Glu Ala Leu Lys  His Phe Arg Val Lys  Phe Asn Glu
    1010                1015                1020

Ala Leu  Arg Glu Ser Trp Lys  Thr Lys Val Asn Trp  Leu Ala His
    1025                1030                1035

Asn Val  Ser Lys Asp Asn Arg  Gln
```

```
    1040                1045


<210> SEQ ID NO 39
<211> LENGTH: 921
<212> TYPE: DNA
<213> ORGANISM: Homo sapiens
<220> FEATURE:
<221> NAME/KEY: CDS
<222> LOCATION: (25)..(888)

<400> SEQUENCE: 39

cactctggtg ggctgctcc aggc atg cag atc cca cag gcg ccc tgg cca       51
                          Met Gln Ile Pro Gln Ala Pro Trp Pro
                          1               5

gtc gtc tgg gcg gtg cta caa ctg ggc tgg cgg cca gga tgg ttc tta      99
Val Val Trp Ala Val Leu Gln Leu Gly Trp Arg Pro Gly Trp Phe Leu
10                  15                  20                  25

gac tcc cca gac agg ccc tgg aac ccc ccc acc ttc tcc cca gcc ctg     147
Asp Ser Pro Asp Arg Pro Trp Asn Pro Pro Thr Phe Ser Pro Ala Leu
                30                  35                  40

ctc gtg gtg acc gaa ggg gac aac gcc acc ttc acc tgc agc ttc tcc     195
Leu Val Val Thr Glu Gly Asp Asn Ala Thr Phe Thr Cys Ser Phe Ser
            45                  50                  55

aac aca tcg gag agc ttc gtg cta aac tgg tac cgc atg agc ccc agc     243
Asn Thr Ser Glu Ser Phe Val Leu Asn Trp Tyr Arg Met Ser Pro Ser
        60                  65                  70

aac cag acg gac aag ctg gcc gcc ttc ccc gag gac cgc agc cag ccc     291
Asn Gln Thr Asp Lys Leu Ala Ala Phe Pro Glu Asp Arg Ser Gln Pro
    75                  80                  85

ggc cag gac tgc cgc ttc cgt gtc aca caa ctg ccc aac ggg cgt gac     339
Gly Gln Asp Cys Arg Phe Arg Val Thr Gln Leu Pro Asn Gly Arg Asp
90                  95                  100                 105

ttc cac atg agc gtg gtc agg gcc cgg cgc aat gac agc ggc acc tac     387
Phe His Met Ser Val Val Arg Ala Arg Arg Asn Asp Ser Gly Thr Tyr
                110                 115                 120

ctc tgt ggg gcc atc tcc ctg gcc ccc aag gcg cag atc aaa gag agc     435
Leu Cys Gly Ala Ile Ser Leu Ala Pro Lys Ala Gln Ile Lys Glu Ser
            125                 130                 135

ctg cgg gca gag ctc agg gtg aca gag aga agg gca gaa gtg ccc aca     483
Leu Arg Ala Glu Leu Arg Val Thr Glu Arg Arg Ala Glu Val Pro Thr
        140                 145                 150

gcc cac ccc agc ccc tca ccc agg tca gcc ggc cag ttc caa acc ctg     531
Ala His Pro Ser Pro Ser Pro Arg Ser Ala Gly Gln Phe Gln Thr Leu
    155                 160                 165

gtg gtt ggt gtc gtg ggc ggc ctg ctg ggc agc ctg gtg ctg cta gtc     579
Val Val Gly Val Val Gly Gly Leu Leu Gly Ser Leu Val Leu Leu Val
170                 175                 180                 185

tgg gtc ctg gcc gtc atc tgc tcc cgg gcc gca cga ggg aca ata gga     627
Trp Val Leu Ala Val Ile Cys Ser Arg Ala Ala Arg Gly Thr Ile Gly
                190                 195                 200

gcc agg cgc acc ggc cag ccc ctg aag gag gac ccc tca gcc gtg cct     675
Ala Arg Arg Thr Gly Gln Pro Leu Lys Glu Asp Pro Ser Ala Val Pro
            205                 210                 215

gtg ttc tct gtg gac tat ggg gag ctg gat ttc cag tgg cga gag aag     723
Val Phe Ser Val Asp Tyr Gly Glu Leu Asp Phe Gln Trp Arg Glu Lys
        220                 225                 230

acc ccg gag ccc ccc gtg ccc tgt gtc cct gag cag acg gag tat gcc     771
Thr Pro Glu Pro Pro Val Pro Cys Val Pro Glu Gln Thr Glu Tyr Ala
    235                 240                 245

acc att gtc ttt cct agc gga atg ggc acc tca tcc ccc gcc cgc agg     819
Thr Ile Val Phe Pro Ser Gly Met Gly Thr Ser Ser Pro Ala Arg Arg
```

```
250                 255                 260                 265

ggc tca gct gac ggc cct cgg agt gcc cag cca ctg agg cct gag gat      867
Gly Ser Ala Asp Gly Pro Arg Ser Ala Gln Pro Leu Arg Pro Glu Asp
                270                 275                 280

gga cac tgc tct tgg ccc ctc tgaccggctt ccttggccac cagtgttctg cag     921
Gly His Cys Ser Trp Pro Leu
            285


<210> SEQ ID NO 40
<211> LENGTH: 288
<212> TYPE: PRT
<213> ORGANISM: Homo sapiens

<400> SEQUENCE: 40

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Ser Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285


<210> SEQ ID NO 41
<211> LENGTH: 968
<212> TYPE: DNA
<213> ORGANISM: Homo sapiens
<220> FEATURE:
<221> NAME/KEY: CDS
```

```
<222> LOCATION: (59)..(793)

<400> SEQUENCE: 41

gcttcccgag gctccgcacc agccgcgctt ctgtccgcct gcagggcatt ccagaaag       58

atg agg ata ttt gct gtc ttt ata ttc atg acc tac tgg cat ttg ctg      106
Met Arg Ile Phe Ala Val Phe Ile Phe Met Thr Tyr Trp His Leu Leu
1               5                   10                  15

aac gca ttt act gtc acg gtt ccc aag gac cta tat gtg gta gag tat      154
Asn Ala Phe Thr Val Thr Val Pro Lys Asp Leu Tyr Val Val Glu Tyr
            20                  25                  30

ggt agc aat atg aca att gaa tgc aaa ttc cca gta gaa aaa caa tta      202
Gly Ser Asn Met Thr Ile Glu Cys Lys Phe Pro Val Glu Lys Gln Leu
        35                  40                  45

gac ctg gct gca cta att gtc tat tgg gaa atg gag gat aag aac att      250
Asp Leu Ala Ala Leu Ile Val Tyr Trp Glu Met Glu Asp Lys Asn Ile
    50                  55                  60

att caa ttt gtg cat gga gag gaa gac ctg aag gtt cag cat agt agc      298
Ile Gln Phe Val His Gly Glu Glu Asp Leu Lys Val Gln His Ser Ser
65                  70                  75                  80

tac aga cag agg gcc cgg ctg ttg aag gac cag ctc tcc ctg gga aat      346
Tyr Arg Gln Arg Ala Arg Leu Leu Lys Asp Gln Leu Ser Leu Gly Asn
                85                  90                  95

gct gca ctt cag atc aca gat gtg aaa ttg cag gat gca ggg gtg tac      394
Ala Ala Leu Gln Ile Thr Asp Val Lys Leu Gln Asp Ala Gly Val Tyr
            100                 105                 110

cgc tgc atg atc agc tat ggt ggt gcc gac tac aag cga att act gtg      442
Arg Cys Met Ile Ser Tyr Gly Gly Ala Asp Tyr Lys Arg Ile Thr Val
        115                 120                 125

aaa gtc aat gcc cca tac aac aaa atc aac caa aga att ttg gtt gtg      490
Lys Val Asn Ala Pro Tyr Asn Lys Ile Asn Gln Arg Ile Leu Val Val
    130                 135                 140

gat cca gtc acc tct gaa cat gaa ctg aca tgt cag gct gag ggc tac      538
Asp Pro Val Thr Ser Glu His Glu Leu Thr Cys Gln Ala Glu Gly Tyr
145                 150                 155                 160

ccc aag gcc gaa gtc atc tgg aca agc agt gac cat caa gtc ctg agt      586
Pro Lys Ala Glu Val Ile Trp Thr Ser Ser Asp His Gln Val Leu Ser
                165                 170                 175

ggt aag acc acc acc acc aat tcc aag aga gag gag aag ctt ttc aat      634
Gly Lys Thr Thr Thr Thr Asn Ser Lys Arg Glu Glu Lys Leu Phe Asn
            180                 185                 190

gtg acc agc aca ctg aga atc aac aca aca act aat gag att ttc tac      682
Val Thr Ser Thr Leu Arg Ile Asn Thr Thr Thr Asn Glu Ile Phe Tyr
        195                 200                 205

tgc act ttt agg aga tta gat cct gag gaa aac cat aca gct gaa ttg      730
Cys Thr Phe Arg Arg Leu Asp Pro Glu Glu Asn His Thr Ala Glu Leu
    210                 215                 220

gtc atc cca ggt aat att ctg aat gtg tcc att aaa ata tgt cta aca      778
Val Ile Pro Gly Asn Ile Leu Asn Val Ser Ile Lys Ile Cys Leu Thr
225                 230                 235                 240

ctg tcc cct agc acc tagcatgatg tctgcctatc atagtcattc agtgattgtt      833
Leu Ser Pro Ser Thr
                245

gaataaatga atgaatgaat aacactatgt ttacaaaata tatcctaatt cctcacctcc    893

attcatccaa accatattgt tacttaataa acattcagca gatatttatg gaataaaaaa    953

aaaaaaaaaa aaaaa                                                     968


<210> SEQ ID NO 42
<211> LENGTH: 245
```

```
<212> TYPE: PRT
<213> ORGANISM: Homo sapiens

<400> SEQUENCE: 42

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Gly Asn Ile Leu Asn Val Ser Ile Lys Ile Cys Leu Thr
225                 230                 235                 240

Leu Ser Pro Ser Thr
                245


<210> SEQ ID NO 43
<211> LENGTH: 1553
<212> TYPE: DNA
<213> ORGANISM: Homo sapiens
<220> FEATURE:
<221> NAME/KEY: CDS
<222> LOCATION: (53)..(922)

<400> SEQUENCE: 43

cgaggctccg caccagccgc gcttctgtcc gcctgcaggg cattccagaa ag atg agg      58
                                                          Met Arg
                                                          1

ata ttt gct gtc ttt ata ttc atg acc tac tgg cat ttg ctg aac gca      106
Ile Phe Ala Val Phe Ile Phe Met Thr Tyr Trp His Leu Leu Asn Ala
        5                   10                  15

ttt act gtc acg gtt ccc aag gac cta tat gtg gta gag tat ggt agc      154
Phe Thr Val Thr Val Pro Lys Asp Leu Tyr Val Val Glu Tyr Gly Ser
    20                  25                  30

aat atg aca att gaa tgc aaa ttc cca gta gaa aaa caa tta gac ctg      202
Asn Met Thr Ile Glu Cys Lys Phe Pro Val Glu Lys Gln Leu Asp Leu
35                  40                  45                  50
```

```
gct gca cta att gtc tat tgg gaa atg gag gat aag aac att att caa      250
Ala Ala Leu Ile Val Tyr Trp Glu Met Glu Asp Lys Asn Ile Ile Gln
                55                  60                  65

ttt gtg cat gga gag gaa gac ctg aag gtt cag cat agt agc tac aga      298
Phe Val His Gly Glu Glu Asp Leu Lys Val Gln His Ser Ser Tyr Arg
            70                  75                  80

cag agg gcc cgg ctg ttg aag gac cag ctc tcc ctg gga aat gct gca      346
Gln Arg Ala Arg Leu Leu Lys Asp Gln Leu Ser Leu Gly Asn Ala Ala
        85                  90                  95

ctt cag atc aca gat gtg aaa ttg cag gat gca ggg gtg tac cgc tgc      394
Leu Gln Ile Thr Asp Val Lys Leu Gln Asp Ala Gly Val Tyr Arg Cys
    100                 105                 110

atg atc agc tat ggt ggt gcc gac tac aag cga att act gtg aaa gtc      442
Met Ile Ser Tyr Gly Gly Ala Asp Tyr Lys Arg Ile Thr Val Lys Val
115                 120                 125                 130

aat gcc cca tac aac aaa atc aac caa aga att ttg gtt gtg gat cca      490
Asn Ala Pro Tyr Asn Lys Ile Asn Gln Arg Ile Leu Val Val Asp Pro
                135                 140                 145

gtc acc tct gaa cat gaa ctg aca tgt cag gct gag ggc tac ccc aag      538
Val Thr Ser Glu His Glu Leu Thr Cys Gln Ala Glu Gly Tyr Pro Lys
            150                 155                 160

gcc gaa gtc atc tgg aca agc agt gac cat caa gtc ctg agt ggt aag      586
Ala Glu Val Ile Trp Thr Ser Ser Asp His Gln Val Leu Ser Gly Lys
        165                 170                 175

acc acc acc acc aat tcc aag aga gag gag aag ctt ttc aat gtg acc      634
Thr Thr Thr Thr Asn Ser Lys Arg Glu Glu Lys Leu Phe Asn Val Thr
    180                 185                 190

agc aca ctg aga atc aac aca aca act aat gag att ttc tac tgc act      682
Ser Thr Leu Arg Ile Asn Thr Thr Thr Asn Glu Ile Phe Tyr Cys Thr
195                 200                 205                 210

ttt agg aga tta gat cct gag gaa aac cat aca gct gaa ttg gtc atc      730
Phe Arg Arg Leu Asp Pro Glu Glu Asn His Thr Ala Glu Leu Val Ile
                215                 220                 225

cca gaa cta cct ctg gca cat cct cca aat gaa agg act cac ttg gta      778
Pro Glu Leu Pro Leu Ala His Pro Pro Asn Glu Arg Thr His Leu Val
            230                 235                 240

att ctg gga gcc atc tta tta tgc ctt ggt gta gca ctg aca ttc atc      826
Ile Leu Gly Ala Ile Leu Leu Cys Leu Gly Val Ala Leu Thr Phe Ile
        245                 250                 255

ttc cgt tta aga aaa ggg aga atg atg gat gtg aaa aaa tgt ggc atc      874
Phe Arg Leu Arg Lys Gly Arg Met Met Asp Val Lys Lys Cys Gly Ile
    260                 265                 270

caa gat aca aac tca aag aag caa agt gat aca cat ttg gag gag acg      922
Gln Asp Thr Asn Ser Lys Lys Gln Ser Asp Thr His Leu Glu Glu Thr
275                 280                 285                 290

taatccagca ttggaacttc tgatcttcaa gcagggattc tcaacctgtg gtttaggggt    982

tcatcggggc tgagcgtgac aagaggaagg aatgggcccg tgggatgcag gcaatgtggg   1042

acttaaaagg cccaagcact gaaaatggaa cctggcgaaa gcagaggagg agaatgaaga   1102

aagatggagt caaacaggga gcctggaggg agaccttgat actttcaaat gcctgagggg   1162

ctcatcgacg cctgtgacag ggagaaagga tacttctgaa caaggagcct ccaagcaaat   1222

catccattgc tcatcctagg aagacgggtt gagaatccct aatttgaggg tcagttcctg   1282

cagaagtgcc ctttgcctcc actcaatgcc tcaatttgtt ttctgcatga ctgagagtct   1342

cagtgttgga acgggacagt atttatgtat gagtttttcc tatttatttt gagtctgtga   1402

ggtcttcttg tcatgtgagt gtggttgtga atgatttctt ttgaagatat attgtagtag   1462
```

```
atgttacaat tttgtcgcca aactaaactt gctgcttaat gatttgctca catctagtaa   1522

aacatggagt atttgtaaaa aaaaaaaaaa a                                  1553


<210> SEQ ID NO 44
<211> LENGTH: 290
<212> TYPE: PRT
<213> ORGANISM: Homo sapiens

<400> SEQUENCE: 44

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290


<210> SEQ ID NO 45
<211> LENGTH: 819
<212> TYPE: DNA
<213> ORGANISM: Homo sapiens
<220> FEATURE:
<221> NAME/KEY: CDS
<222> LOCATION: (1)..(819)

<400> SEQUENCE: 45
```

```
atg atc ttc ctc ctg cta atg ttg agc ctg gaa ttg cag ctt cac cag       48
Met Ile Phe Leu Leu Leu Met Leu Ser Leu Glu Leu Gln Leu His Gln
1               5                   10                  15

ata gca gct tta ttc aca gtg aca gtc cct aag gaa ctg tac ata ata       96
Ile Ala Ala Leu Phe Thr Val Thr Val Pro Lys Glu Leu Tyr Ile Ile
            20                  25                  30

gag cat ggc agc aat gtg acc ctg gaa tgc aac ttt gac act gga agt      144
Glu His Gly Ser Asn Val Thr Leu Glu Cys Asn Phe Asp Thr Gly Ser
        35                  40                  45

cat gtg aac ctt gga gca ata aca gcc agt ttg caa aag gtg gaa aat      192
His Val Asn Leu Gly Ala Ile Thr Ala Ser Leu Gln Lys Val Glu Asn
    50                  55                  60

gat aca tcc cca cac cgt gaa aga gcc act ttg ctg gag gag cag ctg      240
Asp Thr Ser Pro His Arg Glu Arg Ala Thr Leu Leu Glu Glu Gln Leu
65                  70                  75                  80

ccc cta ggg aag gcc tcg ttc cac ata cct caa gtc caa gtg agg gac      288
Pro Leu Gly Lys Ala Ser Phe His Ile Pro Gln Val Gln Val Arg Asp
                85                  90                  95

gaa gga cag tac caa tgc ata atc atc tat ggg gtc gcc tgg gac tac      336
Glu Gly Gln Tyr Gln Cys Ile Ile Ile Tyr Gly Val Ala Trp Asp Tyr
            100                 105                 110

aag tac ctg act ctg aaa gtc aaa gct tcc tac agg aaa ata aac act      384
Lys Tyr Leu Thr Leu Lys Val Lys Ala Ser Tyr Arg Lys Ile Asn Thr
        115                 120                 125

cac atc cta aag gtt cca gaa aca gat gag gta gag ctc acc tgc cag      432
His Ile Leu Lys Val Pro Glu Thr Asp Glu Val Glu Leu Thr Cys Gln
    130                 135                 140

gct aca ggt tat cct ctg gca gaa gta tcc tgg cca aac gtc agc gtt      480
Ala Thr Gly Tyr Pro Leu Ala Glu Val Ser Trp Pro Asn Val Ser Val
145                 150                 155                 160

cct gcc aac acc agc cac tcc agg acc cct gaa ggc ctc tac cag gtc      528
Pro Ala Asn Thr Ser His Ser Arg Thr Pro Glu Gly Leu Tyr Gln Val
                165                 170                 175

acc agt gtt ctg cgc cta aag cca ccc cct ggc aga aac ttc agc tgt      576
Thr Ser Val Leu Arg Leu Lys Pro Pro Pro Gly Arg Asn Phe Ser Cys
            180                 185                 190

gtg ttc tgg aat act cac gtg agg gaa ctt act ttg gcc agc att gac      624
Val Phe Trp Asn Thr His Val Arg Glu Leu Thr Leu Ala Ser Ile Asp
        195                 200                 205

ctt caa agt cag atg gaa ccc agg acc cat cca act tgg ctg ctt cac      672
Leu Gln Ser Gln Met Glu Pro Arg Thr His Pro Thr Trp Leu Leu His
    210                 215                 220

att ttc atc ccc tcc tgc atc att gct ttc att ttc ata gcc aca gtg      720
Ile Phe Ile Pro Ser Cys Ile Ile Ala Phe Ile Phe Ile Ala Thr Val
225                 230                 235                 240

ata gcc cta aga aaa caa ctc tgt caa aag ctg tat tct tca aaa gac      768
Ile Ala Leu Arg Lys Gln Leu Cys Gln Lys Leu Tyr Ser Ser Lys Asp
                245                 250                 255

aca aca aaa aga cct gtc acc aca aca aag agg gaa gtg aac agt gct      816
Thr Thr Lys Arg Pro Val Thr Thr Thr Lys Arg Glu Val Asn Ser Ala
            260                 265                 270

atc                                                                  819
Ile
```

<210> SEQ ID NO 46
<211> LENGTH: 273
<212> TYPE: PRT
<213> ORGANISM: Homo sapiens

<400> SEQUENCE: 46

```
Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
            20                  25                  30

Glu His Gly Ser Asn Val Thr Leu Glu Cys Asn Phe Asp Thr Gly Ser
        35                  40                  45

His Val Asn Leu Gly Ala Ile Thr Ala Ser Leu Gln Lys Val Glu Asn
    50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
        115                 120                 125

His Ile Leu Lys Val Pro Glu Thr Asp Glu Val Glu Leu Thr Cys Gln
    130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Pro Gly Arg Asn Phe Ser Cys
            180                 185                 190

Val Phe Trp Asn Thr His Val Arg Glu Leu Thr Leu Ala Ser Ile Asp
        195                 200                 205

Leu Gln Ser Gln Met Glu Pro Arg Thr His Pro Thr Trp Leu Leu His
    210                 215                 220

Ile Phe Ile Pro Ser Cys Ile Ile Ala Phe Ile Phe Ile Ala Thr Val
225                 230                 235                 240

Ile Ala Leu Arg Lys Gln Leu Cys Gln Lys Leu Tyr Ser Ser Lys Asp
                245                 250                 255

Thr Thr Lys Arg Pro Val Thr Thr Thr Lys Arg Glu Val Asn Ser Ala
            260                 265                 270

Ile
```

<210> SEQ ID NO 47
<211> LENGTH: 906
<212> TYPE: DNA
<213> ORGANISM: Homo sapiens

<400> SEQUENCE: 47

```
atgttttcac atcttccctt tgactgtgtc ctgctgctgc tgctgctact acttacaagg      60

tcctcagaag tggaatacag agcggaggtc ggtcagaatg cctatctgcc ctgcttctac     120

accccagccg ccccagggaa cctcgtgccc gtctgctggg gcaaaggagc ctgtcctgtg     180

tttgaatgtg gcaacgtggt gctcaggact gatgaaaggg atgtgaatta ttggacatcc     240

agatactggc taaatgggga tttccgcaaa ggagatgtgt ccctgaccat agagaatgtg     300

actctagcag acagtgggat ctactgctgc cggatccaaa tcccaggcat aatgaatgat     360

gaaaaattta acctgaagtt ggtcatcaaa ccagccaagg tcacccctgc accgactcgg     420

cagagagact tcactgcagc ctttccaagg atgcttacca ccaggggaca tggcccagca     480

gagacacaga cactggggag cctccctgat ataaatctaa cacaaatatc cacattggcc     540
```

```
aatgagttac gggactctag attggccaat gacttacggg actctggagc aaccatcaga    600

ataggcatct acatcggagc agggatctgt gctgggctgg ctctggctct tatcttcggc    660

gctttaattt tcaaatggta ttctcatagc aaagagaaga tacagaattt aagcctcatc    720

tctttggcca acctccctcc ctcaggattg gcaaatgcag tagcagaggg aattcgctca    780

gaagaaaaca tctataccat tgaagagaac gtatatgaag tggaggagcc caatgagtat    840

tattgctatg tcagcagcag gcagcaaccc tcacaacctt tgggttgtcg ctttgcaatg    900

ccatag                                                               906


<210> SEQ ID NO 48
<211> LENGTH: 301
<212> TYPE: PRT
<213> ORGANISM: Homo sapiens

<400> SEQUENCE: 48

Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Arg Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
        195                 200                 205

Ile Cys Ala Gly Leu Ala Leu Ala Leu Ile Phe Gly Ala Leu Ile Phe
    210                 215                 220

Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
                245                 250                 255

Gly Ile Arg Ser Glu Glu Asn Ile Tyr Thr Ile Glu Glu Asn Val Tyr
            260                 265                 270

Glu Val Glu Glu Pro Asn Glu Tyr Tyr Cys Tyr Val Ser Ser Arg Gln
        275                 280                 285

Gln Pro Ser Gln Pro Leu Gly Cys Arg Phe Ala Met Pro
    290                 295                 300
```

<210> SEQ ID NO 49
<211> LENGTH: 846
<212> TYPE: DNA
<213> ORGANISM: Mus musculus

<400> SEQUENCE: 49

```
atgttttcag gtcttaccct caactgtgtc ctgctgctgc tgcaactact acttgcaagg     60

tcattggaaa atgcttatgt gtttgaggtt ggtaagaatg cctatctgcc ctgcagttac    120

actctatcta cacctggggc acttgtgcct atgtgctggg gcaagggatt ctgtccttgg    180

tcacagtgta ccaacgagtt gctcagaact gatgaaagaa atgtgacata tcagaaatcc    240

agcagatacc agctaaaggg cgatctcaac aaaggagacg tgtctctgat cataaagaat    300

gtgactctgg atgaccatgg gacctactgc tgcaggatac agttccctgg tcttatgaat    360

gataaaaaat tagaactgaa attagacatc aaagcagcca aggtcactcc agctcagact    420

gcccatgggg actctactac agcttctcca agaaccctaa ccacggagag aaatggttca    480

gagacacaga cactggtgac cctccataat aacaatggaa caaaaatttc cacatgggct    540

gatgaaatta aggactctgg agaaacgatc agaactgcta tccacattgg agtgggagtc    600

tctgctgggt tgaccctggc acttatcatt ggtgtcttaa tccttaaatg gtattcctgt    660

aagaaaaaga agttatcgag tttgagcctt attacactgg ccaacttgcc tccaggaggg    720

ttggcaaatg caggagcagt caggattcgc tctgaggaaa atatctacac catcgaggag    780

aacgtatatg aagtggagaa ttcaaatgag tactactgct acgtcaacag ccagcagcca    840

tcctga                                                               846
```

<210> SEQ ID NO 50
<211> LENGTH: 281
<212> TYPE: PRT
<213> ORGANISM: Mus musculus

<400> SEQUENCE: 50

```
Met Phe Ser Gly Leu Thr Leu Asn Cys Val Leu Leu Leu Leu Gln Leu
1               5                   10                  15

Leu Leu Ala Arg Ser Leu Glu Asn Ala Tyr Val Phe Glu Val Gly Lys
            20                  25                  30

Asn Ala Tyr Leu Pro Cys Ser Tyr Thr Leu Ser Thr Pro Gly Ala Leu
        35                  40                  45

Val Pro Met Cys Trp Gly Lys Gly Phe Cys Pro Trp Ser Gln Cys Thr
    50                  55                  60

Asn Glu Leu Leu Arg Thr Asp Glu Arg Asn Val Thr Tyr Gln Lys Ser
65                  70                  75                  80

Ser Arg Tyr Gln Leu Lys Gly Asp Leu Asn Lys Gly Asp Val Ser Leu
                85                  90                  95

Ile Ile Lys Asn Val Thr Leu Asp Asp His Gly Thr Tyr Cys Cys Arg
            100                 105                 110

Ile Gln Phe Pro Gly Leu Met Asn Asp Lys Lys Leu Glu Leu Lys Leu
        115                 120                 125

Asp Ile Lys Ala Ala Lys Val Thr Pro Ala Gln Thr Ala His Gly Asp
    130                 135                 140

Ser Thr Thr Ala Ser Pro Arg Thr Leu Thr Thr Glu Arg Asn Gly Ser
145                 150                 155                 160

Glu Thr Gln Thr Leu Val Thr Leu His Asn Asn Asn Gly Thr Lys Ile
                165                 170                 175
```

```
Ser Thr Trp Ala Asp Glu Ile Lys Asp Ser Gly Glu Thr Ile Arg Thr
            180                 185                 190

Ala Ile His Ile Gly Val Gly Val Ser Ala Gly Leu Thr Leu Ala Leu
        195                 200                 205

Ile Ile Gly Val Leu Ile Leu Lys Trp Tyr Ser Cys Lys Lys Lys Lys
    210                 215                 220

Leu Ser Ser Leu Ser Leu Ile Thr Leu Ala Asn Leu Pro Pro Gly Gly
225                 230                 235                 240

Leu Ala Asn Ala Gly Ala Val Arg Ile Arg Ser Glu Glu Asn Ile Tyr
                245                 250                 255

Thr Ile Glu Glu Asn Val Tyr Glu Val Glu Asn Ser Asn Glu Tyr Tyr
            260                 265                 270

Cys Tyr Val Asn Ser Gln Gln Pro Ser
        275                 280
```

<210> SEQ ID NO 51
<211> LENGTH: 1578
<212> TYPE: DNA
<213> ORGANISM: Homo sapiens

<400> SEQUENCE: 51

```
atgtgggagg ctcagttcct gggcttgctg tttctgcagc cgctttgggt ggctccagtg     60

aagcctctcc agccaggggc tgaggtcccg gtggtgtggg cccaggaggg ggctcctgcc    120

cagctcccct gcagccccac aatccccctc caggatctca gccttctgcg aagagcaggg    180

gtcacttggc agcatcagcc agacagtggc ccgcccgctg ccgcccccgg ccatcccctg    240

gcccccggcc ctcacccggc ggcgccctcc tcctgggggc ccaggccccg ccgctacacg    300

gtgctgagcg tgggtcccgg aggcctgcgc agcgggaggc tgcccctgca gccccgcgtc    360

cagctggatg agcgcggccg gcagcgcggg gacttctcgc tatggctgcg cccagcccgg    420

cgcgcggacg ccggcgagta ccgcgccgcg gtgcacctca gggaccgcgc cctctcctgc    480

cgcctccgtc tgcgcctggg ccaggcctcg atgactgcca gcccccccagg atctctcaga    540

gcctccgact gggtcatttt gaactgctcc ttcagccgcc ctgaccgccc agcctctgtg    600

cattggttcc ggaaccgggg ccagggccga gtccctgtcc gggagtcccc ccatcaccac    660

ttagcggaaa gcttcctctt cctgccccaa gtcagcccca tggactctgg gccctggggc    720

tgcatcctca cctacagaga tggcttcaac gtctccatca tgtataacct cactgttctg    780

ggtctggagc ccccaactcc cttgacagtg tacgctggag caggttccag ggtggggctg    840

ccctgccgcc tgcctgctgg tgtggggacc cggtctttcc tcactgccaa gtggactcct    900

cctgggggag gccctgacct cctggtgact ggagacaatg gcgactttac ccttcgacta    960

gaggatgtga gccaggccca ggctgggacc tacacctgcc atatccatct gcaggaacag   1020

cagctcaatg ccactgtcac attggcaatc atcacagtga ctcccaaatc ctttgggtca   1080

cctggatccc tggggaagct gctttgtgag gtgactccag tatctggaca agaacgcttt   1140

gtgtggagct ctctggacac cccatcccag aggagtttct caggaccttg gctggaggca   1200

caggaggccc agctcctttc ccagccttgg caatgccagc tgtaccaggg ggagaggctt   1260

cttggagcag cagtgtactt cacagagctg tctagcccag gtgcccaacg ctctgggaga   1320

gccccaggtg ccctcccagc aggccacctc ctgctgtttc tcatccttgg tgtcctttct   1380

ctgctccttt tggtgactgg agcctttggc tttcaccttt ggagaagaca gtggcgacca   1440

agacgatttt ctgccttaga gcaagggatt caccctccgc aggctcagag caagatagag   1500
```

```
gagctggagc aagaaccgga gccggagccg gagccggaac cggagcccga gcccgagccc   1560

gagccggagc agctctga                                                 1578


<210> SEQ ID NO 52
<211> LENGTH: 525
<212> TYPE: PRT
<213> ORGANISM: Homo sapiens

<400> SEQUENCE: 52

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
    50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
    130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His His Leu Ala Glu Ser
    210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285

Gly Thr Arg Ser Phe Leu Thr Ala Lys Trp Thr Pro Pro Gly Gly Gly
    290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350
```

```
Val Thr Pro Lys Ser Phe Gly Ser Pro Gly Ser Leu Gly Lys Leu Leu
        355                 360                 365

Cys Glu Val Thr Pro Val Ser Gly Gln Glu Arg Phe Val Trp Ser Ser
    370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
        435                 440                 445

His Leu Leu Leu Phe Leu Ile Leu Gly Val Leu Ser Leu Leu Leu Leu
    450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
                485                 490                 495

Ser Lys Ile Glu Glu Leu Glu Gln Glu Pro Glu Pro Glu Pro Glu Pro
            500                 505                 510

Glu Pro Glu Pro Glu Pro Glu Pro Glu Pro Glu Gln Leu
        515                 520                 525


<210> SEQ ID NO 53
<211> LENGTH: 1566
<212> TYPE: DNA
<213> ORGANISM: Mus musculus

<400> SEQUENCE: 53

atgagggagg acctgctcct tggctttttg cttctgggac tgctttggga agctccagtt      60

gtgtcttcag ggcctgggaa agagctcccc gtggtgtggg cccaggaggg agctcccgtc     120

catcttccct gcagcctcaa atcccccaac ctggatccta actttctacg aagaggaggg     180

gttatctggc aacatcaacc agacagtggc caacccactc ccatcccggc ccttgacctt     240

caccagggga tgccctcgcc tagacaaccc gcacccggtc gctacacggt gctgagcgtg     300

gctccaggag gcctgcgcag cgggaggcag cccctgcatc cccacgtgca gctggaggag     360

cgcggcctcc agcgcgggga cttctctctg tggttgcgcc cagctctgcg caccgatgcg     420

ggcgagtacc acgccaccgt gcgcctcccg aaccgcgccc tctcctgcag tctccgcctg     480

cgcgtcggcc aggcctcgat gattgctagt ccctcaggag tcctcaagct gtctgattgg     540

gtccttttga actgctcctt cagccgtcct gaccgcccag tctctgtgca ctggttccag     600

ggccagaacc gagtgcctgt ctacaactca ccgcgtcatt ttttagctga aactttcctg     660

ttactgcccc aagtcagccc cctggactct gggacctggg gctgtgtcct cacctacaga     720

gatggcttca atgtctccat cacgtacaac ctcaaggttc tgggtctgga gcccgtagcc     780

cctctgacag tgtacgctgc tgaaggttct agggtggagc tgccctgtca tttgcccccca    840

ggagtgggga ccccttcttt gctcattgcc aagtggactc ctcctggagg aggtcctgag     900

ctccccgtgg ctggaaagag tggcaatttt acccttcacc ttgaggctgt gggtctggca     960

caggctggga cctacacctg tagcatccat ctgcagggac agcagctcaa tgccactgtc    1020

acgttggcgg tcatcacagt gactcccaaa tccttcgggt tacctggctc ccgggggaag    1080

ctgttgtgtg aggtaacccc ggcatctgga aaggaaagat ttgtgtggcg tcccctgaac    1140
```

```
aatctgtcca ggagttgccc gggccctgtg ctggagattc aggaggccag gctccttgct   1200

gagcgatggc agtgtcagct gtacgagggc cagaggcttc ttggagcgac agtgtacgcc   1260

gcagagtcta gctcaggcgc ccacagtgct aggagaatct caggtgacct taaaggaggc   1320

catctcgttc tcgttctcat ccttggtgcc ctctccctgt tccttttggt ggccggggcc   1380

tttggctttc actggtggag aaaacagttg ctactgagaa gattttctgc cttagaacat   1440

gggattcagc catttccggc tcagaggaag atagaggagc tggagcgaga actggagacg   1500

gagatgggac aggagccgga gcccgagccg gagccacagc tggagccaga gcccaggcag   1560

ctctga                                                              1566
```

```
<210> SEQ ID NO 54
<211> LENGTH: 521
<212> TYPE: PRT
<213> ORGANISM: Mus musculus

<400> SEQUENCE: 54

Met Arg Glu Asp Leu Leu Leu Gly Phe Leu Leu Leu Gly Leu Leu Trp
1               5                   10                  15

Glu Ala Pro Val Val Ser Ser Gly Pro Gly Lys Glu Leu Pro Val Val
            20                  25                  30

Trp Ala Gln Glu Gly Ala Pro Val His Leu Pro Cys Ser Leu Lys Ser
        35                  40                  45

Pro Asn Leu Asp Pro Asn Phe Leu Arg Arg Gly Gly Val Ile Trp Gln
    50                  55                  60

His Gln Pro Asp Ser Gly Gln Pro Thr Pro Ile Pro Ala Leu Asp Leu
65                  70                  75                  80

His Gln Gly Met Pro Ser Pro Arg Gln Pro Ala Pro Gly Arg Tyr Thr
                85                  90                  95

Val Leu Ser Val Ala Pro Gly Gly Leu Arg Ser Gly Arg Gln Pro Leu
            100                 105                 110

His Pro His Val Gln Leu Glu Glu Arg Gly Leu Gln Arg Gly Asp Phe
        115                 120                 125

Ser Leu Trp Leu Arg Pro Ala Leu Arg Thr Asp Ala Gly Glu Tyr His
    130                 135                 140

Ala Thr Val Arg Leu Pro Asn Arg Ala Leu Ser Cys Ser Leu Arg Leu
145                 150                 155                 160

Arg Val Gly Gln Ala Ser Met Ile Ala Ser Pro Ser Gly Val Leu Lys
                165                 170                 175

Leu Ser Asp Trp Val Leu Leu Asn Cys Ser Phe Ser Arg Pro Asp Arg
            180                 185                 190

Pro Val Ser Val His Trp Phe Gln Gly Gln Asn Arg Val Pro Val Tyr
        195                 200                 205

Asn Ser Pro Arg His Phe Leu Ala Glu Thr Phe Leu Leu Leu Pro Gln
    210                 215                 220

Val Ser Pro Leu Asp Ser Gly Thr Trp Gly Cys Val Leu Thr Tyr Arg
225                 230                 235                 240

Asp Gly Phe Asn Val Ser Ile Thr Tyr Asn Leu Lys Val Leu Gly Leu
                245                 250                 255

Glu Pro Val Ala Pro Leu Thr Val Tyr Ala Ala Glu Gly Ser Arg Val
            260                 265                 270

Glu Leu Pro Cys His Leu Pro Pro Gly Val Gly Thr Pro Ser Leu Leu
        275                 280                 285

Ile Ala Lys Trp Thr Pro Pro Gly Gly Gly Pro Glu Leu Pro Val Ala
```

-continued

```
    290                 295                 300

Gly Lys Ser Gly Asn Phe Thr Leu His Leu Glu Ala Val Gly Leu Ala
305                 310                 315                 320

Gln Ala Gly Thr Tyr Thr Cys Ser Ile His Leu Gln Gly Gln Gln Leu
                325                 330                 335

Asn Ala Thr Val Thr Leu Ala Val Ile Thr Val Thr Pro Lys Ser Phe
            340                 345                 350

Gly Leu Pro Gly Ser Arg Gly Lys Leu Leu Cys Glu Val Thr Pro Ala
        355                 360                 365

Ser Gly Lys Glu Arg Phe Val Trp Arg Pro Leu Asn Asn Leu Ser Arg
    370                 375                 380

Ser Cys Pro Gly Pro Val Leu Glu Ile Gln Glu Ala Arg Leu Leu Ala
385                 390                 395                 400

Glu Arg Trp Gln Cys Gln Leu Tyr Glu Gly Gln Arg Leu Leu Gly Ala
                405                 410                 415

Thr Val Tyr Ala Ala Glu Ser Ser Ser Gly Ala His Ser Ala Arg Arg
            420                 425                 430

Ile Ser Gly Asp Leu Lys Gly Gly His Leu Val Leu Val Leu Ile Leu
        435                 440                 445

Gly Ala Leu Ser Leu Phe Leu Leu Val Ala Gly Ala Phe Gly Phe His
    450                 455                 460

Trp Trp Arg Lys Gln Leu Leu Leu Arg Arg Phe Ser Ala Leu Glu His
465                 470                 475                 480

Gly Ile Gln Pro Phe Pro Ala Gln Arg Lys Ile Glu Glu Leu Glu Arg
                485                 490                 495

Glu Leu Glu Thr Glu Met Gly Gln Glu Pro Glu Pro Glu Pro Glu Pro
            500                 505                 510

Gln Leu Glu Pro Glu Pro Arg Gln Leu
        515                 520
```

METHODS FOR TREATING PTEN DEFICIENT EPITHELIAL CANCERS USING A COMBINATION OF ANTI-PI3KBETA AND ANTI-IMMUNE CHECKPOINT AGENTS

CROSS-REFERENCE TO RELATED APPLICATIONS

This application is the U.S. national phase of International Patent Application No. PCT/US2017/041490, filed on 11 Jul. 2017, which claims the benefit of priority to U.S. Provisional Application Ser. No. 62/360,596, filed on 11 Jul. 2016; the entire contents of each of said applications are incorporated herein in their entirety by this reference.

STATEMENT OF RIGHTS

This invention was made with government support under grant numbers CA172461, CA187918, AI056299, and CA009361 awarded by The National Institutes of Health. The government has certain rights in the invention.

BACKGROUND OF THE INVENTION

Breast cancer is one of the most common types of cancer, with over 230,000 new cases diagnosed annually and accounting for more than 40,000 deaths every year in the United States alone. For example, triple-negative breast cancers (TNBCs), as defined by the absence of estrogen receptor (ER), progesterone receptor (PR), and human epidermal growth factor receptor 2 (HER2) expression, account for 15 to 20% of breast cancer cases, are often clinically aggressive, and typically exhibit high rates of recurrence and mortality. In addition, they do not respond to current targeted therapies used in the clinic that are highly effective in the treatment of luminal or HER2-positive breast cancer. While standard chemotherapy can be effective for early stage TNBC, patients with advanced TNBC typically respond poorly and may progress to metastatic disease, in which cancer cells invade into other tissues. Of note, metastasis accounts for over 90% of breast cancer-related deaths and currently there are no effective treatments against metastatic TNBC. Despite the lack of a common genetic determinant, loss of phosphatase and tensin homolog (PTEN) tumor suppressor function is observed in 25 to 30% of TNBCs (Cancer Genome Atlas Network (2012) *Nature* 490:61-70). Since PTEN is the major negative regulator of PI3K activity in cells, PTEN-deficient cancers often exhibit oncogenic addiction to PI3K signaling. Thus, the PI3K pathway and, in particular, class I PI3K isoforms (including p110α, p110β, p110γ and p110δ) have emerged as attractive therapeutic targets (Thorpe et al. (2015) *Nat. Rev. Cancer* 15:7-24). Yet, clinical trials with pan-PI3K inhibitors have showed only limited efficacy and reduced therapeutic windows as monotherapies, largely due to off-target and on-target effects arising from inhibiting all PI3K isoforms (Fruman and Rommel (2014) *Nat. Rev. Drug Disc.* 13:140-156 and Brachmann et al. (2012) *Mol. Cancer Ther.* 11:1747-1757).

Pre-clinical studies and emerging clinical trial data suggest that selective targeting of individual isoforms may achieve greater efficacy with fewer side effects than using pan-PI3K inhibitors, and thus isoform-specific PI3K inhibitors are currently undergoing clinical trials as both mono- and combination therapies in multiple cancer types, including breast cancer (Fruman and Rommel (2014) *Nat. Rev. Drug Disc.* 13:140-156; Thorpe et al. (2015) *Nat. Rev. Cancer* 15:7-24). Compounds targeting PI3Kalpha (also known as p110α) have garnered much of the efforts from both academic and pharmaceutical research groups. This is largely because mutations in PIK3CA, the gene encoding PI3Kalpha, are found in a significant number of cancers (Cancer Genome Atlas Network (2012) Nature 490:61-70). Also, tumors driven by receptor tyrosine kinases, such as Her2+ breast cancers, or Ras hyperactivation, mainly require signaling via PI3Kalpha for survival (Schmit et al. (2014) *Proc. Natl. Acad. Sci. USA* 111:6395-400).

However, PTEN-deficient cancers often depend on the beta isoform of PI3 Kinase (PI3Kbeta; p110β) encoded by PIK3CB for survival, and pharmacological targeting of p110β can effectively decrease the growth of PTEN-deficient tumors in mouse models (Jia et al. (2008) *Nature* 454:776-779; Ni et al. (2012) *Cancer Discov.* 2:425-433; Peng et al. (2016) *Cancer Disc.* 6:202-216). In TNBC, activating mutations in PIK3CA encoding PI3Kalpha were found by The Cancer Genome Atlas (TCGA) in only 7% of cases, but genetic PTEN loss occurred in over 35% of cases (Cancer Genome Atlas Network (2012) *Nature* 490:61-70).

Aside from targeted therapies, additional modalities for treating cancer have been explored. For example, immune checkpoint blockade (ICB), whereby anti-tumor T-cell response is enhanced by blocking immuno-inhibitory signals. The two major targets of ICB agents developed to date are CTLA-4 (Cytotoxic T lymphocyte-associated protein 4) and PD-1 (Programmed death-1) receptors, which are expressed on the surface of activated T-cells and are responsible for dampening immune response. CTLA-4 blockade is thought to occur in secondary lymphoid organs, thereby affecting systemic immune function. By contrast, PD-1 ligands are often overexpressed by cancer cells. Therefore, PD-1 blockade takes place primarily within the tumor microenvironment and is associated with fewer side effects (Topalian et al. (2015) *Cancer Cell* 27:450-461). Although immune checkpoint blockade (ICB) immunotherapy has demonstrated promising results, ICB agents used as monotherapies have yielded therapeutic efficacy in only a limited percentage of patients. Accumulating evidence indicates that targeted therapies can synergize with immunotherapy in multiple cancer types, although which targeted therapies in combination with which immunotherapies are efficacious for treating which cancers is currently unknown and difficult to predict (Vannemann and Dranoff (2012) *Nat. Rev. Cancer* 12:237-251; Sagiv-Barfi et al. (2015) *Proc. Natl. Acad. Sci. USA* 112:e966-e972).

Accordingly, a great need exists in the art to identify particular therapeutic interventions to effectively treat cancers, such as epithelial cancers like TNBCs. Similarly, serous ovarian cancer (SOC), which has also historically been difficult to treat, has many underlying genetic similarities to TNBCs and which are quite different from those of other cancers, like melanoma. For example, both types of cancers are associated with high histologic grades and poor prognosis. At the genetic level, the two cancers contain similar types and frequencies of genomic mutations, e.g. high frequency of TP53 (encoding the p53 tumor suppressor in humans) mutations, inactivation of BRCA1, genetic and epigenetic loss of PTEN, and amplification and high expression of the cMYC oncogene. Because of the similarities between TNBC and SOC, researchers have proposed that the two cancers could possibly be targeted by similar therapies (Wang et al. (2012) *Clin. Cancer Res.* 18:5806-5815).

SUMMARY OF THE INVENTION

The present invention is based, at least in part, on the discovery that inhibiting or blocking both PI3Kbeta and an immune checkpoint overcomes traditional barriers to therapeutically treating cancers having PTEN deficiency, with or without additional p53 deficiency. Such results are unexpected given the previously unappreciated role of PI3Kbeta modulation in treating cancer due to the focus on other isoforms of PI3K, such as PI3Kalpha.

In one aspect, a method of treating a subject afflicted with a cancer that is deficient in phosphatase and tensin homolog (PTEN) comprising administering to the subject a therapeutically effective amount of at least one agent that inhibits or blocks both phosphoinositide 3-kinase isoform beta (PI3Kbeta) and an immune checkpoint, wherein the cancer is an epithelial cancer (e.g., a breast cancer, an ovarian cancer, a prostate cancer, etc.), is provided.

Numerous embodiments are further provided that can be applied to any aspect of the present invention and/or combined with any other embodiment described herein. For example, in one embodiment, the at least one agent is a single agent that inhibits or blocks both PI3Kbeta and the immune checkpoint. In another embodiment, the at least one agent comprises a first agent that selectively inhibits or blocks PI3Kbeta and a second agent that selectively inhibits or blocks the immune checkpoint. In still another embodiment, the first agent and the second agent comprise a small molecule that inhibits or blocks PI3Kbeta and/or the immune checkpoint. In yet another embodiment, the at least one agent comprises an RNA interfering agent which inhibits expression of PI3Kbeta and/or the immune checkpoint (e.g., the RNA interfering agent is a small interfering RNA (siRNA), small hairpin RNA (shRNA), or a microRNA (miRNA)). In another embodiment, the at least one agent comprises an antisense oligonucleotide complementary to PI3Kbeta and/or the immune checkpoint. In still another embodiment, the at least one agent comprises a peptide or peptidomimetic that inhibits or blocks PI3Kbeta and/or the immune checkpoint. In yet another embodiment, the at least one agent comprises an aptamer that inhibits or blocks PI3Kbeta and/or the immune checkpoint. In another embodiment, the at least one agent is an antibody and/or an intrabody, or an antigen binding fragment thereof, which specifically binds to PI3Kbeta protein and/or the immune checkpoint protein (e.g., the antibody and/or intrabody, or antigen binding fragment thereof, is murine, chimeric, humanized, composite, or human). In still another embodiment, the antibody and/or intrabody, or antigen binding fragment thereof, is detectably labeled, comprises an effector domain, comprises an Fc domain, and/or is selected from the group consisting of Fv, Fav, F(ab')2), Fab', dsFv, scFv, sc(Fv)2, and diabodies fragments. In yet another embodiment, the antibody and/or intrabody, or antigen binding fragment thereof, is conjugated to a cytotoxic agent (e.g., the cytotoxic agent is selected from the group consisting of a chemotherapeutic agent, a biologic agent, a toxin, and a radioactive isotope).

In another embodiment, the immune checkpoint is selected from the group consisting of CTLA-4, PD-1, VISTA, B7-H2, B7-H3, PD-L1, B7-H4, B7-H6, 2B4, ICOS, HVEM, PD-L2, CD160, gp49B, PIR-B, KIR family receptors, TIM-1, TIM-3, TIM-4, LAG-3, BTLA, SIRPalpha, CD47, CD48, 2B4 (CD244), B7.1, B7.2, ILT-2, ILT-4, TIGIT, IDO, CD39, arginase, CD73, and A2aR. In still another embodiment, the immune checkpoint is selected from the group consisting of CTLA-4, PD-1, PD-L1, PD-L2, TIM-3, and LAG-3. In yet another embodiment, the immune checkpoint is PD-1. In another embodiment, the at least one agent comprises a selective PI3Kbeta inhibitor (e.g., the selective PI3Kbeta inhibitor has at least 2-fold more selectivity for the PI3Kbeta isoform as compared to a non-PI3Kbeta isoform selected from the group consisting of PI3Kalpha, PI3Kdelta, and PI3Kgamma). In still another embodiment, the at least one agent comprises 5-(2,6-dimorpholin-4-ylpyrimidin-4-yl)-4-(trifluoromethyl)pyridin-2-amine (BKM120) and/or (−)-2-[[(1R)-1-[7-Methyl-2-(4-morpholinyl)-4-oxo-4H-pyrido[1,2-a]pyrimidin-9-yl]ethyl]amino]benzoic acid (KIN193). In yet another embodiment, the at least one agent reduces the number of proliferating cells in the cancer and/or reduces the volume or size of a tumor of the cancer. In another embodiment, the at least one agent increases the number of viable CD8+ T cells within a tumor of the cancer. In still another embodiment, the at least one agent is administered in a pharmaceutically acceptable formulation. In yet another embodiment, the method further comprises administering to the subject a therapeutic agent or regimen for treating the cancer.

In another embodiment, the cancer described herein further has a p53 deficiency. In still another embodiment, the p53 deficiency and/or PTEN deficiency is selected from the group consisting of a mutation to a genomic nucleic acid sequence encoding p53 and/or PTEN protein. In yet another embodiment, the mutation is selected from the group consisting of a missense mutation, a nonsense mutation, a frameshift mutation, an insertion mutation, a deletion mutation, and a rearrangement mutation. In another embodiment, the PTEN deficiency is determined to be very low or null, as assessed by immunohistochemistry, or is a mutation to a genomic nucleic acid sequence encoding PTEN protein and the mutation is a missense mutation, a nonsense mutation, a frameshift mutation, an insertion mutation, a deletion mutation, or a rearrangement mutation of a PTEN codon C71, R130, R233, D268, T319 or X70, or phosphatase or C2 domains. In still another embodiment, the PTEN deficiency is a null mutation. In yet another embodiment, the PTEN deficiency is a germline or somatic PTEN null mutation. In another embodiment, the p53 deficiency is a mutation to a genomic nucleic acid sequence encoding p53 protein and the mutation is a missense mutation, a nonsense mutation, a frameshift mutation, an insertion mutation, a deletion mutation, or a rearrangement mutation of a p53 codon L45, Y126, P151, S166, R175, C176, H179, G187, H193, L194, R196, R213, Y220, C242, G245, R248, R249, R273, R280, D281, R282, E286, E294, or transactivation, DNA-binding or oligomerization domains. In still another embodiment, the p53 deficiency is a null mutation. In yet another embodiment, the p53 deficiency is a germline or somatic p53 null mutation. In another embodiment, the epithelial cancer described herein is a breast cancer, an ovarian cancer, or a prostate cancer. In still another embodiment, the breast cancer is a triple-negative breast cancer (TNBC). In yet another embodiment, the TNBC is metastatic TNBC. In another embodiment, the ovarian cancer is serous ovarian cancer. In still another embodiment, the subject is an animal model of TNBC or ovarian cancer. In another embodiment, the animal model is an orthotopic xenograft animal model of a human-derived epithelial cancer. In still another embodiment, the animal model is a mouse model. In yet another embodiment, the subject is a mammal, such as a mouse or a human.

Note that for every figure containing a histogram, the bars from left to right for each discrete measurement correspond to the figure boxes from top to bottom in the figure legend as indicated.

DETAILED DESCRIPTION OF THE INVENTION

It has been determined herein based on genetic, pharmacologic, and molecular analyses of PTEN-deficient TNBC models, with or without additional p53 deficiency, that inhibiting or blocking PI3Kbeta in combination with inhibiting or blocking an immune checkpoint (ICB) overcomes traditional barriers to therapeutically treating cancers having PTEN deficiency. For example, KIN-193 (i.e., a PI3Kbeta-selective inhibitor), but not BYL719 (i.e., a PI3Kalpha-selective inhibitor), synergizes with ICB to inhibit PTEN/p53-null TNBC tumor growth.

The great majority of samples analyzed from a panel of TNBC patient-derived samples showed the absence of PTEN expression (see Table 1 below, at least three retained a wild type PTEN gene), suggesting that the percentage of TNBC with deficient PTEN expression may be higher than what has been determined based on genetic deletion.

TABLE 1

TNBC patient-derive sample data

| Orthotopic PDX models of TNBC brain metastases | | | | |
|---|---|---|---|---|
| PDX # | PTEN (IHC) | P-AKT | PTEN gene | Scoring scale: |
| DF-BM362 | 0 | na | na | 0 = Null |
| DF-BM456 | 0 | na | na | 1 = Low |
| DF-BM640 | 0 | na | na | 2 = Medium |
| DF-BM656 | 0 | na | na | 3 = High |
| **Patient-derived xenograft (PDX) models of TNBC (non-CNS)** | | | | |
| PDX # | PTEN (IHC) | P-AKT (IHC) | PTEN gene | Scoring scale: |
| DFBC-1501 | 0-1 | 1 | nd | 0 = Null |
| DFBC-1504 | 0 | 3 | nd | 1 = Low |
| DFBC-1507 | 0 | nd | WT | 2 = Medium |
| DFBC-1510 | 0 | 2 | WT | 3 = High |
| DFBC-1520 | 0 | 2-3 | WT | |
| DFBC-1524 | nd | nd | nd | |
| DFBC-1611 | nd | nd | nd | |
| DFBC-1613 | nd | nd | nd | |

The importance of PI3Kbeta for overcoming anti-tumor immune response and supporting growth of PTEN-deficient tumors is further demonstrated by the inability of PTEN/p53/PI3Kbeta triple-null tumor cells to form tumors in immunocompetent mice, while PTEN/p53/PI3Kalpha triple-null tumor cells grow aggressive tumors in immunocompetent mice. On the other hand, PTEN/p53 double-null, PTEN/p53/PI3Kbeta triple-null and PTEN/p53/PI3Kalpha triple-null tumor cells all form tumors in immunodeficient mice lacking T cells. Notably, combined ICB and PI3Kbeta-selective inhibition strongly increases CD8+ T cell infiltration into the tumor, indicating an important role for this combination treatment in immunomodulation of tumor growth. In addition, the results show that PI3Kbeta, but not PI3Kalpha, is required for inducing cell motility in primary breast cancer cells with PTEN/p53 co-loss. In line with these finding, PTEN is lost in all samples of distal metastases analyzed from patients with TNBC. Thus, it is believed that PI3Kbeta inhibitors are effective against advanced and metastatic TNBC.

Figure 12:
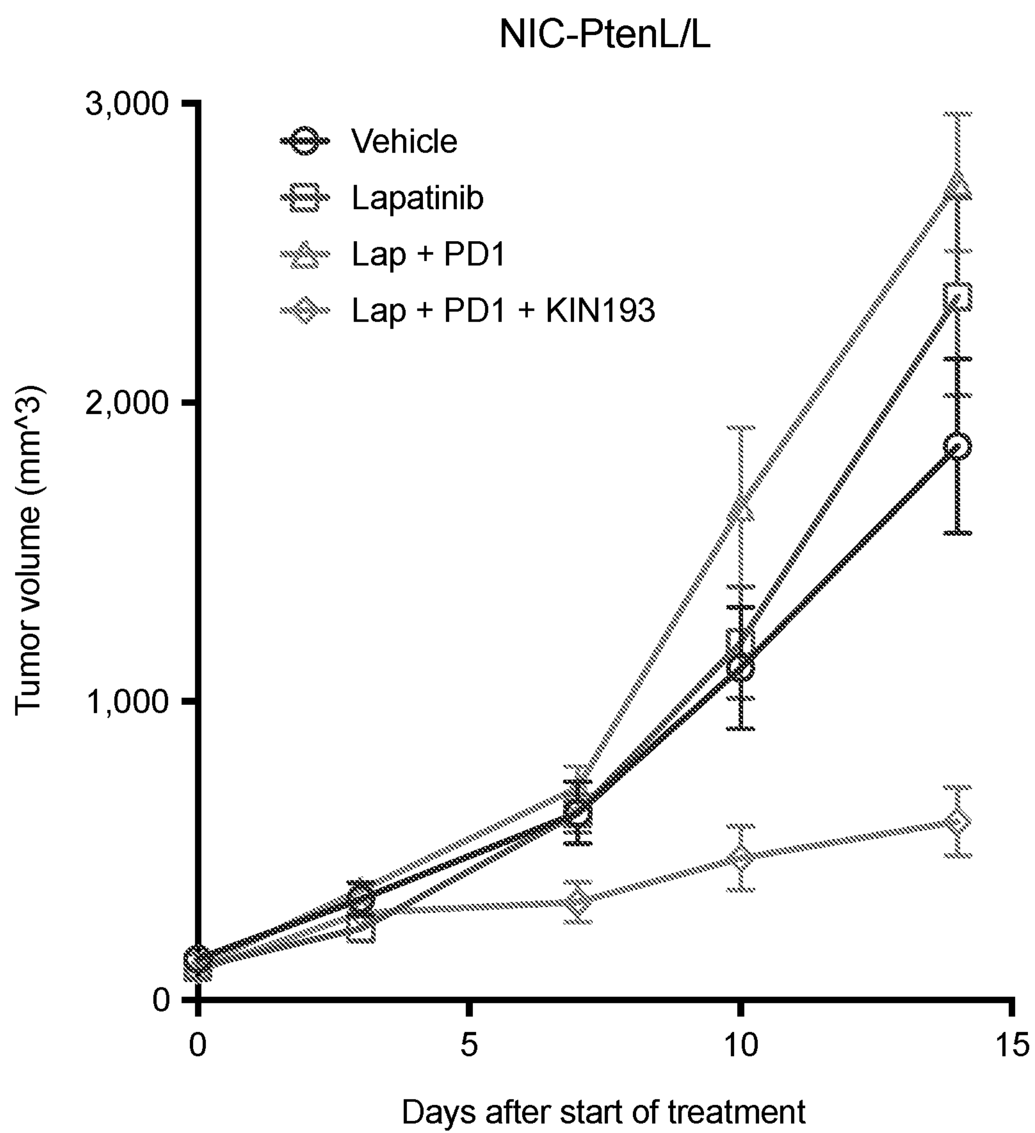
FIG. 12 shows that adding a PI3Kbeta targeted inhibitor to a treatment regimen of lapatinib (Lap; an EGFR and Her2/Neu dual inhibitor) leads to reduced tumor growth in a model of Her2-positive breast cancer.

In addition, PI3Kbeta inhibition combined with immune checkpoint blockade (ICB) also inhibits growth of a Her2-positive model of breast cancer driven by Her2/Neu over-expression and harboring wild type p53 (see at least FIG. 12). Moreover, combining a PI3Kbeta inhibitor and ICB led to stronger tumor growth inhibition than either agent alone in a model of serous ovarian cancer (SOC) with PTEN/p53 loss and Myc over-expression (see at least FIG. 14).

These results are surprising for at least several reasons. First, anti-cancer agents are generally focused on inhibiting or blocking PI3Kalpha or PI3K isoforms other than PI3Kbeta. Yet, a remarkable benefit of specifically targeting PI3Kbeta rather than all PI3K proteins or PI3Kalpha alone is that PI3Kbeta inhibition is less toxic than pan-PI3K or PI3Kalpha inhibition because PI3Kalpha is the major effector of insulin function in normal cells, and therefore inhibiting PI3Kalpha can lead to significant side effects. Second, TNBC and SOC are believed to be especially well-suited to the combination of PI3Kbeta inhibition/block and ICB because of their particular genotypic background regarding PTEN deficiencies, as distinguished from other cancer types. For example, TNBC and SOC are characterized by significant levels of PTEN deficiency and a high degree of PTEN/p53 co-deficiency. Also, unlike melanoma and lung cancer, for which ICB therapies are currently approved by the Food and Drug Administration (FDA), TNBC and SOC do not tend to have a high mutational load, and are therefore predicted to not respond well to IBC therapy alone. Finally, PI3Kbeta inhibition is known to generate resistance in some cancers, such as in PTEN-deficient prostate cancers (Schwartz et al. (2015) *Cancer Cell* 27:109-22), highlighting the need to find novel therapeutic targets to combine with PI3Kbeta inhibitors.

Accordingly, the present invention relates, in part, to methods for treating PTEN-deficient epithelial cancers (e.g., breast cancer and SOC) with a combination of PI3Kbeta and immune checkpoint inhibitors. In another aspect, the present invention provides diagnostic, prognostic, and prophylactic methods of stratifying patients and predicting responses of cancers to treatment with a combination of PI3Kbeta and immune checkpoint inhibitors based upon a determination and analysis of biomarkers described herein.

I. Definitions

The articles "a" and "an" are used herein to refer to one or to more than one (i.e. to at least one) of the grammatical object of the article. By way of example, "an element" means one element or more than one element.

The term "administering" is intended to include routes of administration which allow an agent to perform its intended function. Examples of routes of administration for treatment of a body which can be used include injection (subcutaneous, intravenous, parenterally, intraperitoneally, intrathecal, etc.), oral, inhalation, and transdermal routes. The injection can be bolus injections or can be continuous infusion. Depending on the route of administration, the agent can be coated with or disposed in a selected material to protect it from natural conditions which may detrimentally affect its ability to perform its intended function. The agent may be administered alone, or in conjunction with a pharmaceutically acceptable carrier. The agent also may be administered as a prodrug, which is converted to its active form in vivo.

The term "altered amount" or "altered level" refers to increased or decreased copy number (e.g., germline and/or somatic) of a biomarker nucleic acid, e.g., increased or decreased expression level in a cancer sample, as compared to the expression level or copy number of the biomarker nucleic acid in a control sample. The term "altered amount" of a biomarker also includes an increased or decreased protein level of a biomarker protein in a sample, e.g., a cancer sample, as compared to the corresponding protein level in a normal, control sample. Furthermore, an altered amount of a biomarker protein may be determined by detecting posttranslational modification such as methylation status of the marker, which may affect the expression or activity of the biomarker protein.

The amount of a biomarker in a subject is "significantly" higher or lower than the normal amount of the biomarker, if the amount of the biomarker is greater or less, respectively, than the normal level by an amount greater than the standard error of the assay employed to assess amount, and preferably at least 20%, 30%, 40%, 50%, 60%, 70%, 80%, 90%, 100%, 150%, 200%, 300%, 350%, 400%, 500%, 600%, 700%, 800%, 900%, 1000% or than that amount. Alternately, the amount of the biomarker in the subject can be considered "significantly" higher or lower than the normal amount if the amount is at least about two, and preferably at least about three, four, or five times, higher or lower, respectively, than the normal amount of the biomarker. Such "significance" can also be applied to any other measured parameter described herein, such as for expression, inhibition, cytotoxicity, cell growth, and the like.

The term "altered level of expression" of a biomarker refers to an expression level or copy number of the biomarker in a test sample, e.g., a sample derived from a patient suffering from cancer, that is greater or less than the standard error of the assay employed to assess expression or copy number, and is preferably at least twice, and more preferably three, four, five or ten or more times the expression level or copy number of the biomarker in a control sample (e.g., sample from a healthy subjects not having the associated disease) and preferably, the average expression level or copy number of the biomarker in several control samples. The altered level of expression is greater or less than the standard error of the assay employed to assess expression or copy number, and is preferably at least 20%, 30%, 40%, 50%, 60%, 70%, 80%, 90%, 100%, 150%, 200%, 300%, 350%, 400%, 500%, 600%, 700%, 800%, 900%, 1000% or more times the expression level or copy number of the biomarker in a control sample (e.g., sample from a healthy subjects not having the associated disease) and preferably, the average expression level or copy number of the biomarker in several control samples. In some embodiments, the level of the biomarker refers to the level of the biomarker itself, the level of a modified biomarker (e.g., phosphorylated biomarker), or to the level of a biomarker relative to another measured variable, such as a control (e.g., phosphorylated biomarker relative to an unphosphorylated biomarker).

The term "altered activity" of a biomarker refers to an activity of the biomarker which is increased or decreased in a disease state, e.g., in a cancer sample, as compared to the activity of the biomarker in a normal, control sample.

Altered activity of the biomarker may be the result of, for example, altered expression of the biomarker, altered protein level of the biomarker, altered structure of the biomarker, or, e.g., an altered interaction with other proteins involved in the same or different pathway as the biomarker or altered interaction with transcriptional activators or inhibitors.

The term "altered structure" of a biomarker refers to the presence of mutations or allelic variants within a biomarker nucleic acid or protein, e.g., mutations which affect expression or activity of the biomarker nucleic acid or protein, as compared to the normal or wild-type gene or protein. For example, mutations include, but are not limited to substitutions, deletions, or addition mutations. Mutations may be present in the coding or non-coding region of the biomarker nucleic acid.

Unless otherwise specified here within, the terms "antibody" and "antibodies" broadly encompass naturally-occurring forms of antibodies (e.g. IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., a biomarker polypeptide or fragment thereof). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a $F(ab')_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242:423-426; and Huston et al. (1988) *Proc. Natl. Acad. Sci. USA* 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov, S. M., et al. (1995) *Human Antibodies and Hybridomas* 6:93-101) and use of a cysteine residue, biomarker peptide and a C-terminal polyhistidine tag to make bivalent and biotinylated scFv polypeptides (Kipriyanov, S. M., et al. (1994) *Mol. Immunol.* 31:1047-1058). Antibody portions, such as Fab and $F(ab')_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

By contrast, antigen-binding portions can be adapted to be expressed within cells as "intracellular antibodies." (Chen et al. (1994) *Human Gene Ther.* 5:595-601). Methods are well-known in the art for adapting antibodies to target (e.g., inhibit) intracellular moieties, such as the use of single-chain antibodies (scFvs), modification of immunoglobulin VL domains for hyperstability, modification of antibodies to resist the reducing intracellular environment, generating fusion proteins that increase intracellular stability and/or modulate intracellular localization, and the like. Intracellular antibodies can also be introduced and expressed in one or more cells, tissues or organs of a multicellular organism, for example for prophylactic and/or therapeutic purposes (e.g., as a gene therapy) (see, at least PCT Publs. WO 08/020079, WO 94/02610, WO 95/22618, and WO 03/014960; U.S. Pat. No. 7,004,940; Cattaneo and Biocca (1997) *Intracellular Antibodies: Development and Applications* (Landes and Springer-Verlag publs.); Kontermann (2004) *Methods* 34:163-170; Cohen et al. (1998) *Oncogene* 17:2445-2456; Auf der Maur et al. (2001) *FEBS Lett.* 508:407-412; Shaki-Loewenstein et al. (2005) *J. Immunol. Meth.* 303:19-39).

Antibodies may be polyclonal or monoclonal; xenogeneic, allogeneic, or syngeneic; or modified forms thereof (e.g. humanized, chimeric, etc.). Antibodies may also be fully human. Preferably, antibodies of the present invention bind specifically or substantially specifically to a biomarker polypeptide or fragment thereof. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

Antibodies may also be "humanized", which is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the present invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

The term "assigned score" refers to the numerical value designated for each of the biomarkers after being measured in a patient sample. The assigned score correlates to the absence, presence or inferred amount of the biomarker in the sample. The assigned score can be generated manually (e.g., by visual inspection) or with the aid of instrumentation for image acquisition and analysis. In certain embodiments, the assigned score is determined by a qualitative assessment, for example, detection of a fluorescent readout on a graded scale, or quantitative assessment. In one embodiment, an "aggregate score," which refers to the combination of assigned scores from a plurality of measured biomarkers, is determined. In one embodiment the aggregate score is a summation of assigned scores. In another embodiment, combination of assigned scores involves performing mathematical operations on the assigned scores before combining them into an aggregate score. In certain, embodiments, the aggregate score is also referred to herein as the "predictive score."

The term "biomarker" refers to a measurable entity of the present invention that has been determined to be predictive of PI3K and mTOR combinatorial inhibitor therapy effects on a cancer. Biomarkers can include, without limitation, nucleic acids and proteins, including those shown in the Tables, the Examples, the Figures, and otherwise described herein. As described herein, any relevant characteristic of a biomarker can be used, such as the copy number, amount, activity, location, modification (e.g., phosphorylation), and the like.

A "blocking" antibody or an antibody "antagonist" is one which inhibits or reduces at least one biological activity of the antigen(s) it binds. In certain embodiments, the blocking antibodies or antagonist antibodies or fragments thereof described herein substantially or completely inhibit a given biological activity of the antigen(s).

The term "body fluid" refers to fluids that are excreted or secreted from the body as well as fluids that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit).

The terms "cancer" or "tumor" or "hyperproliferative" refer to the presence of cells possessing characteristics typical of cancer-causing cells, such as uncontrolled proliferation, immortality, metastatic potential, rapid growth and proliferation rate, and certain characteristic morphological features. Unless otherwise stated, the terms include metaplasias. In some embodiments, such cells exhibit such characteristics in part or in full due to the reduced expression, activity, and/or loss of PTEN. In other embodiments, such cells exhibit such characteristics in part or in full due to the reduced expression, activity, and/or loss of PTEN and p53. Cancer cells are often in the form of a tumor, but such cells may exist alone within an animal, or may be a non-tumorigenic cancer cell, such as a leukemia cell. As used herein, the term "cancer" includes premalignant as well as malignant cancers. Cancers include, but are not limited to, B cell cancer, e.g., multiple myeloma, Waldenström's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematologic tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, cancers are epithlelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated.

In some embodiments, the cancer is "an epithelial cancer," which refers to cancers developed from an epithelial cell/tissue (e.g., epithelium) origin. Epithelial tissues line the cavities and surfaces of blood vessels and organs throughout the body. There are three principal shapes of epithelial cell: squamous, columnar, and cuboidal. These can be arranged in a single layer of cells as simple epithelium, either squamous, columnar, cuboidal, pseudo-stratified columnar or in layers of two or more cells deep as stratified (layered), either squamous, columnar or cuboidal. All glands are made up of epithelial cells. Malfunction of any of these different types of epithelial cells may result in a carcinoma, or an epithelial cancer. Different types of epithelial cancers, according to their different cell origins, include, for example, squamous cell carcinoma (starting in squamous cells, which are the flat, surface covering cells found in areas such as the skin or the lining of the throat or food pipe (oesophagus)), adenocarcinoma (starting in glandular cells called adenomatous cells that produce fluids to keep tissues moist), transitional cell carcinoma (starting in cells that can stretch as an organ expands and make up tissues called transitional epithelium. An example is the lining of the bladder.), basal cell carcinoma (starting from the deepest layer of skin cells), etc. Among them, basal cell cancer grows slowly and can damage the tissue around it but is unlikely to spread to distant areas or result in death (Cakir et al. (2012) *Facial plastic surgery clinics of North America.* 20:419-422). It often appears as a painless raised area of skin, that may be shiny with small blood vessel running over it or may present as a raised area with an ulcer. Squamous-cell skin cancer is more likely to spread (Cakir et al. (2012), supra). It usually presents as a hard lump with a scaly top but may also form an ulcer. Exemplary epithelial cancers include, at least, lung cancers (e.g., non-small-cell lung cancer), nonpapillary renal cell carcinoma, cervical carcinoma, ovarian carcinoma (e.g., serous ovarian carcinoma), breast carcinoma, bladder cancers, colonrectal cancers, prostate cancers, etc. The epithelial cancers may be characterized in various other ways including, but not limited to, serous, endometrioid, mucinous, clear cell, Brenner, or undifferentiated. Epithelial cancers may be caused by exposure to ultraviolet radiation from the Sun. Decreasing exposure to ultraviolet radiation and the use of sunscreen (usually containing zinc oxide and/or titanium oxide) are appear to be effective methods of preventing squamous-cell skin cancer. The effect to basal cell cancer is unknown. Other treatments generally include surgical removal and, less commonly, radiation therapy or topical medications such as fluorouracil. Topical chemotherapy might be indicated for large superficial basal-cell carcinoma and other epithelial cancers. For low-risk diseases, radiation therapy (external beam radiotherapy or brachytherapy), topical chemotherapy (e.g., imiquimod or 5-fluorouracil) and cryotherapy (e.g., freezing the cancer off) can provide adequate control. However, they may have lower overall cure rates than certain type of surgery. Other modalities of treatment such as photodynamic therapy, topical chemotherapy, electrodesiccation and curettage can be found for basal-cell carcinomas and squamous-cell carcinomas. Mohs' micrographic surgery (Mohs surgery) is a technique used to remove the cancer with the least amount of surrounding tissue and the edges are checked immediately to see if tumor is found. In the case of disease that has spread (metastasized), further surgical procedures or chemotherapy may be required. Chimeric antigen receptor (CAR) or T cell receptor (TCR) gene therapies have been found promosing for epithelial cancers, performed by first harvesting mononuclear cells from the peripheral blood of the patient through a leukapheresis procedure. T cells from the leukapheresis product are then transduced with a viral vector other gene transfer platform encoding a CAR to TCR. The genetically engineered T cells are expanded in the laboratory and administered to the patient intravenously. Lymphocyte-depleting chemotherapy may be given prior to cell infusion to enhance engraftment and function of the engineered T cells. T cell infusion may be followed by systemic administration of cytokines, such as interleukin-2, to support the T cells. CARs are synthetic molecules composed of antibody single-chain variable fragments (ScFv) that bind to a target tumor antigen, and domains from CD3 signaling chains and T cell costimulatory receptor molecules that provide intracellular signaling. For a review of CARs and TCRs, see Hinrichs (2016) *Clin Cancer Res.* 22:1559-1564. Many types of epithelial derived tumors have an elevated level of Notch, which is also associated with poor outcomes. A new group of therapies target stem-like cells in epithelial cancers, identifying multiple druggable targets and pathways. For a review of exemplary treatments and clinical trials, see Ahmed et al. (2017) *Stem Cells* 35:839-850. For example, Wnt inhibitors affecting many cancer sten cekk (CSC) regulators (such as Hedgehog, Notch, PI3K/Akt/mTOR pathway, etc.), such as Curcumin, analog GO-Y030, and diflurinated curcumin (CDF), have been tested in Phase 2 for colon CSC, pancreatic CSC, and breast CSC (Naujokat and Laufer (2013) *J. Cancer Res. Updates* 2:36-67; Ramasamy et al. (2015) *Cancer Cell Int.* 15. doi: 10.1186/s12935-015-0241-x). Multiple compounds treating breast cancers, lung cancers, colonrectal cancers, and pancreatic cancers are also summarized in Ahmed et al. (2017), supra.

In some embodiments, the cancer is "triple negative breast cancer" or "TNBC," which refers to breast cancers that are estrogen receptor (ER) negative, progesterone receptor (PR) negative, and human epidermal growth factor receptor 2 (HER-2) negative (Pegram et al. (1998) *J. Clin. Oncol.* 16:2659-2671; Wiggans et al. (1979) *Cancer Chemother. Pharmacol.* 3:45-48; Carey et al. (2007) *Clin. Cancer Res.* 13:2329-2334). Several subtypes of TNBC are known, including 2 basal-like (BL1 and BL2), an immunomodulatory (IM), a mesenchymal (M), a mesenchymal stem-like (MSL), and a luminal androgen receptor (LAR) subtype (see, for example, U.S. Pat. Publ. 2014/0303133). Determination of TNBC or a subtype thereof can be pe accomplished using well-known and standard techniques, such as immunohistochemical and/or nucleic acid analysis of ER, PR, and HER-2 receptor status (Chebil et al. (2003) *Acta Oncol.* 42:43-47; Chebil et al. (2003) *Acta Oncol.* 42:719-725; Yamashita et al. (2006) *Rinsho Byori* 54:27-30; Schaller et al. (2001) *Ann. Oncol.* 12:S97-S100; and Kallioniemi et al. (1992) *Proc. Natl. Acad. Sci. U.S.A.* 89:5321-5325).

TNBCs constitute 10-20% of all breast cancers, more frequently affect younger patients, and are more prevalent in African-American women (Morris et al. (2007) *Cancer* 110:876-884). TNBC tumors are generally larger in size, are of higher grade, have lymph node involvement at diagnosis, and are biologically more aggressive (Haffty et al. (2006) *J. Clin. Oncol.* 24:5652-5657). Despite having higher rates of clinical response to presurgical (neoadjuvant) chemotherapy, TNBC patients have a higher rate of distant recurrence and a poorer prognosis than women with other breast cancer subtypes (Haffty et al. (2006) *J. Clin. Oncol.* 24:5652-5657; Dent et al. (2007) *Clin. Cancer Res.* 13:4429-4434). Less than 30% of women with metastatic TNBC survive 5 years, and almost all die of their disease despite adjuvant chemotherapy, which is the mainstay of treatment (Dent et al. (2007) *Clin. Cancer Res.* 13:4429-4434).

Two of the three major modalities for treating hormone receptor-positive breast cancers (i.e., endocrine and biologic) do not apply to TNBC due to the lack of hormone receptor expression. Thus, well-established therapies, such as selective ER modulation using tamoxifen or anti-estrogens, aromatase inhibitors, nonsteroidal drugs (e.g., letrozol, anastrozol, and vostrozol), steroidal drugs (e.g., exemestane), ovarian ablation surgery, ovarian ablation radiotherapy, LHRH analog therapy, anti-HER-2 antibodies, anti-ER antibodies, anti-PR antibodies, and the like, are generally ineffective against TNBC. The general standard of care for treating TNBC is therefore chemotherapy. Frequently applied chemotherapeutic drugs in breast cancer are drugs from the anthracycline class, the taxane class and to a lower extent antimetabolites (e.g., capecitabine, gemcitabine, alkylating agents, vinca alkaloids, and the like). These drugs are used in two basic applications schemes. The drugs can be applied as single agents in a sequential fashion or they can be used in a combination regime. The two treatment sub-modalities can be combined to some extent. The anthracyclines, and especially doxorubicin and epirubicin, have been shown to be active agents in the treatment of breast cancer and anthracycline-containing combination regimes are common first line treatments in patients who have not received anthracyclines in an adjuvant setting. Common combination treatment consists for example of doxorubicin/epirubicin plus cyclophosphamide, doxorubicin/epirubicin plus cyclophosphamide and 5-fluorouracil, or combinations of anthracyclines and capecitabine or gemcitabine. With the common use of anthracyclines in early stages of breast cancer treatment, the likelihood of anthracycline resistant forms of breast cancer, however, increases (Bernard-Marty et al. (2004) *Oncologist* 9:617-632).

In certain embodiments, the cancer is "ovarian cancer." The ovarian cancer can be a type of ovarian cancer, such as epithelial ovarian cancer, or a sub-type thereof, such as serous ovarian cancer. Ovarian cancer ranks as the fifth most common cancer in women and has the highest mortality rate among gynecologic malignancies (U.S. Pat. Publ. 2016/0097102 Suh et al. (2010) *Exp. Rev. Mol. Diagn.* 10:1069-1083; Landen et al. (2008) *J. Clin. Oncol.* 26:995-1005). Although the 5-year survival rate of ovarian cancer is around 90% when detected in early stages (I/II), nearly 80% of the new cases are diagnosed in advanced stages (III/IV) because of the asymptomatic nature of the disease at stage I and early stage II. Unfortunately, the 5-year survival rate of advanced ovarian cancer is as low as 11% (Altekruse et al., SEER Cancer Statistics Review, 1975-2007, National Cancer Institute. Bethesda, Md.).

Generally, ovarian cancers are grouped into 3 major categories: (1) epithelial tumors (tumors arising from cells that line or cover the ovaries); (2) germ cell tumors (tumors that originate from cells that are destined to form eggs within the ovaries; and (3) sex cord-stromal cell tumors (tumors that begin in connective cells that hold the ovaries together and produce female hormones). The most common ovarian cancers are epithelial tumors, which account for about 90% of all ovarian cancers. Ovarian epithelial tumors are divided into subtypes which include serous, papillary serous, endometrioid, mucinous and clear cell tumors.

The serous subtype of ovarian carcinoma accounts for approximately 60-80% of ovarian cancer cases and exhibits the most aggressive histology (Levanon et al. (2008) *J. Clin. Oncol.* 26:5284-5293). Fewer than 25% of serous ovarian cancer cases are detected at an early stage (stages I and II), which reflects grimly on survival figures (Seidman et al. (2004) *Int. J. Gynecol. Pathol.* 23:41-44). High-grade serous carcinoma involves the surface of the ovary, often bilaterally, and the peritoneal membranes, with rapid onset of carcinomatosis, a fact that restricts the surgical options to debulking only (Levanon et al. (2008) *J. Clin. Oncol.* 26:5284-5293). Despite the introduction of taxanes to therapeutic protocols and the prolonged survival with intraperitoneal chemotherapy administration, there has been little progress in improving cure rates, a parameter that is still solely dependent on the disease stage at the time of presentation (Levanon et al. (2008) *J. Clin. Oncol.* 26:5284-5293).

Papillary serous carcinoma of the ovary is one of the most common and lethal malignant tumors (Tong et al. (2007) *Modern Pathol.* 20:856-863).

Papillary serous histology accounts for 75% of ovarian cancers and its histological pattern simulates the lining of the fallopian tube (Jelovac and Armstrong (2011) CA 61:183-203). Most cases of papillary serous ovarian cancer are diagnosed at advanced stages, when the tumors have already metastasized (Kim et al. (2012) *Proc. Natl. Acad. Sci. USA* 109:3921-3926). Despite the steady improvement of surgery and chemotherapy, greater than 90% of women with advanced ovarian cancers die after relapse (Bukowski et al. (2007) *Semin. Oncol.* 34:S1-S15). Early detection of these high-grade serous carcinomas is thus key to reducing ovarian cancer deaths (Bast et al. (2009) *Nat. Rev. Cancer* 9:415-428).

Ovarian endometrioid carcinomas account for only 10% of ovarian carcinomas (McConechy et al. (2007) *Modern Pathol.* 27:128-134). The majority of ovarian endometrioid carcinomas are low-grade carcinomas with good prognosis (Chen et al. (2005) *Modern Pathol.* 18:903-911).

The mucinous cell type accounts for approximately 10% of all primary epithelial ovarian carcinomas (Chan et al. (2008) *Gynecol. Oncol.* 109:370-376). Most mucinous epithelial ovarian carcinomas are diagnosed early (International Federation of Gynecology and Obstetrics (FIGO) stages I-IIA) and confined to one ovary. In stage I, mucinous epithelial ovarian carcinomas, the 5-year disease-free survival rate is about 90%, which is slightly better than the 76% observed for patients with serous epithelial ovarian carcinomas (Vergote et al. (2001) Lancet 357:176-182). Less frequently, primary mucinous epithelial ovarian carcinoma is associated with peritoneal carcinomatosis and/or extraperitoneal metastases (FIGO stages IIB-IV). Unlike FIGO stage I tumors, advanced mucinous epithelial ovarian carcinomas reportedly have poorer prognoses than serous epithelial ovarian carcinomas (Omura et al. (1991) *J. Clin. Oncol.* 9:1138-1150; Teramukai et al. (2007) *J. Clin. Oncol.* 25:3302-3306).

Ovarian clear cell adenocarcinomas account for <5% of all ovarian malignancies and 3.7-12.1% of all epithelial ovarian carcinomas (Tan and Kaye (2007) *J. Clin. Pathol.* 60:355-360). Compared to other epithelial ovarian cancer (EOC) subtypes, when at an advanced stage, they are associated with a poorer prognosis and are relatively resistant to conventional platinum-based chemotherapy (Sugiyama et al. (2000) *Cancer* 88:2584-2589). By contrast, early-stage clear cell ovarian cancer carries a relatively good prognosis (Tan and Kaye (2007) *J. Clin. Pathol.* 60:355-360). Hence, early detection is the key to improve prognosis and reduce deaths associated with this type of ovarian cancer.

The process used to determine whether ovarian cancer has spread within the ovaries or to other parts of the body (i.e., metastasized) is called staging. It is important to determine the stage of ovarian cancer because the stage will determine the type of treatment plan selected to combat the disease. The results of tests used to diagnose ovarian cancer are often also used to stage the disease. Such tests include ultrasound, computerized tomography (CT) scan, positron emission tomography (PET) scan, magnetic resonance imaging (MRI), X-ray and biopsy. Ovarian cancer staging guidelines have been developed by the International Federation of Gynecologists and Obstetricians (FIGO). The FIGO staging system for ovarian cancer is well-known in the art.

In addition to staging, an ovarian tumor can also be described by grade (G) GX, GB, and G1-G4. Grading determines how similar ovarian cancer tissue is to normal tissue. Tumor grade is determined by microscopic examination of cancer tissue; with healthy cells appearing as well-differentiated. That is, the more differentiated the ovarian tumor, the better the prognosis. The ovarian cancer grading system is well-known in the art.

Serous ovarian cancer is not graded in this way and only considers a low-grade and a high-grade classification. Low-grade serous carcinomas exhibit low-grade nuclei with infrequent mitotic figures. They evolve from adenofibromas or borderline tumors, have frequent mutations of the KRAS, BRAF, or ERBB2 genes, and can lack TP53 mutations (Type I pathway). Low-grade tumors are indolent and have better outcome than high-grade tumors. In contrast, high-grade serous carcinomas have high-grade nuclei and numerous mitotic figures (Vang et al. (2009) *Adv. Anat. Pathol.* 16:267-282).

A number of well-known and standard-of-care therapies are available to treat ovarian cancer. Due to the lack of effective screening programs, ovarian cancer is diagnosed at an early stage only in about 25% of cases (Kim et al. (2012) *J. Exp. Clin. Cancer Res.* 31:14). In most of these cases, surgery is able to cure the disease, and the five-year survival rate for early-stage (stage I or II) ovarian cancer is around 90% (Hennessy et al. (2009) *Lancet* 374:1371-1382). Adjuvant chemotherapy for early stage ovarian cancer is still controversial, but some studies have shown its benefit under confined conditions. According to these studies, patients with IA or IB FIGO stage, non-clear-cell histology, well-differentiated (G1) tumors, and an "optimal" surgery (i.e., performed according to international guidelines, with pelvic and retroperitoneal assessment), appear not to benefit from chemotherapy (Trimbos et al. (2003) *J. Natl. Cancer Inst.* 95:105-112). Thus, it is commonly believed that, at least in these cases, chemotherapy can probably be avoided and patients can be advised to undergo clinical and instrumental follow-up. In all the other (early stage) patients, (adjuvant) chemotherapy is indicated (Hennessy et al. (2009) *Lancet* 374:1371-1382).

By contrast, the standard treatment for patients with advanced ovarian cancer is maximal surgical cytoreduction (i.e., total abdominal hysterectomy, bilateral salpingo-oophorectomy, pelvic and para-aortic lymphadenectomy and omentectomy) followed by systemic platinum-based chemotherapy (e.g., cisplatin followed by carboplatin-based combinations, cisplatin with paclitaxel, cisplatin with cyclophosphamide, cisplatin with doxorubicin, etc.). The expected 5-year survival for these patients is 10-30% (Hennessy et al. (2009) *Lancet* 374:1371-1382). The concept of primary debulking surgery is to diminish the residual tumor burden to a point at which adjuvant therapy will be optimally effective. The percentage of patients with advanced ovarian cancer who can optimally undergo cytoreductive surgery seems to range from 17%-87% (Ramirez et al. (2011) *Cancer Control* 18:22-30). This percentage can largely depend on the experience of the surgeon.

In addition, a deeper knowledge of ovarian cancer biology has led to the identification of multiple molecular targets, such as growth factor receptors, signal transduction pathways, cell cycle regulators, and angiogenic mechanisms (Kim et al. (2012) *J. Exp. Clin. Cancer Res.* 31:14). For example, VEGF expression is higher in ovarian cancer tumors than in normal ovarian tissue or benign ovarian tumors, and increasing VEGF expression in either cytosolic fractions derived from ovarian cancer tumors or serum VEGF levels in preoperative serum is considered to be associated with advanced stage and poor prognosis (Kim et al. (2012) *J. Exp. Clin. Cancer Res.* 31:14). In order to inhibit the VEGF pathway, there are two primary strategies: (1) inhibition of the VEGF ligand with antibodies or soluble receptors and (2) inhibition of the VEGF receptor (VEGFR) with tyrosine kinase inhibitors (TKIS), or receptor antibodies. Of the VEGF targeting therapies, the one most employed has been inhibition of the VEGF ligand with bevacizumab. However, oral inhibitors of the VEGF receptor (VEGFR) tyrosine kinase have been shown to have activity in patients with recurrent ovarian cancer, resulting in tumor responses and stabilization of disease, delaying tumor progression (Friedlander et al. (2010) *Gynecol. Oncol.* 119:32-37; Ledermann et al. (2011) *J. Clin. Oncol.* 29:3798-3804; Matulonis et al. (2009) *J. Clin. Oncol.* 27:5601-5606; Biagi et al. (2011) *Ann. Oncol.* 22:335-340; Matei et al. (2011) *J. Clin. Oncol.* 29:69-75).

Other targets to inhibit include the epidermal growth factor receptor (EGFR) overexpressed in up to 70% of ovarian cancer patients (Kohler et al. (1992) *Eur. J. Cancer* 28a:1432-1437) such as by erlotinib treatment; insulin growth factor 1 (IGF 1) is involved in the inhibition of apoptosis, tumor progression and metastase, such as by aMG479 monoclonal antibody or OSI-906 treatment; poly (ADP-ribose) polymerase (PARP) (Rouleau et al. (2010) *Nat. Rev. Cancer* 10:293-301), such as by olaparib treatment (Fong et al. (2010) *J. Clin. Oncol.* 28:2512-2519).

In some embodiments, the cancer is "prostate cancer," which refers to cancers that occur in male's prostate. Prostate cancer is one of the most common types of cancer in men. Prostate cancer usually grows slowly and initially remains confined to the prostate gland, where it may not cause serious harm. While some types of prostate cancer grow slowly and may need minimal or no treatment, other types are aggressive and can spread quickly. Prostate cancer that is detected early—when it's still confined to the prostate gland—has a better chance of successful treatment. In the vast majority of cases, the prostate cancer starts in the gland cells—this is called adenocarcinoma.

The stage of prostate cancers, or how far they have spread helps to define the prognosis and treatment. The most common system for determining cancer stages is the TNM (Tumor/Nodes/Metastases). This involves defining the size of the tumor, how many lymph nodes are involved, and whether there are any other metastases. When defining with the TNM system, it is crucial to distinguish between cancers that are still restricted just to the prostate, and those that have spread elsewhere. Clinical T1 and T2 cancers are found only in the prostate, and nowhere else, while T3 and T4 have spread outside the prostate. There are many ways to find out whether the cancer has spread. Computer tomography will check for spread inside the pelvis, bone scans will decide whether the cancer has spread to the bones, and endorectal coil magnetic resonance imaging will evaluate the prostatic capsule and the seminal vesicles.

Prostate cancer may cause no signs or symptoms in its early stages. Prostate cancer that is more advanced may cause signs and symptoms such as: trouble urinating (little or no urine output, difficulty starting (straining) or stopping the urine stream, decreased force in the stream of urine, increased frequency for urine), blood in urine or semen and/or deep back, discomfort in the hip, pelvic, or abdominal area, bone pain, erectile dysfunction, urinary problems, frequent urination, dribbling, pain or burning during urination), erectile dysfunction or painful ejaculation. Other symptoms may include weight loss, bone pain (often in the spine (vertebrae), pelvis, or ribs), leg weakness (if cancer has spread to the spine and compressed the spinal cord), urinary incontinence (if cancer has spread to the spine and compressed the spinal cord), fecal incontinence (if cancer has spread to the spine and compressed the spinal cord) and lower extremity swelling. In addition to tumor translocation, prostate cancer is related to, at least, BPH (benign prostatic hyperplasia), acute and chronic bacterial prostatitis and chronic prostatitis (non-bacterial).

The specific causes for prostate cancers are not well know, although both genetic and environmental factors may be relevant. There are so many possible factors, including age, race, lifestyle, medications, and genetics, to name a few. Age is considered as the primary risk factor. The older a man is, the higher is his risk. Prostate cancer is rare among men under the age of 45, but much more common after the age of 50. Among genetic factors, BRCA1 and BRCA2 have been reported as relevant genes for prostate cancers (Castro et al. (2013) *J. Clin. Oncol.* 31:1748-1757). Many other loci on chromosomes are also related to prostate cancers, including genes such as MSMB, TBP2, JAZF1, PNE3, IL16, LMTK2, KLK2, KLK3, and CDH13 (Thomas et al. (2008) *Nat Genet.* 40:310-315; Eeles et al. (2008) *Nat Genet.* 40:316-321). PRSS3/mesotrypsin is also a therapeutic target for metastatic prostate cancer (Hockla et al. (2008) *Mol Cancer Res.* 10:1555-1566). Men with chronic inflammation in non-cancerous prostate tissue were found to have nearly double the risk of developing prostate cancer, representing a clear association between prostate inflammation and prostate cancer (Gurel et al. (2014) *Cancer Epidemiol Biomarkers Prev.* 23:847-856). Diet, obesity, sexually transmitted diseases (STDs, such as gonorrhea) are also risk factors.

Prostate screening tests might include, at least, digital rectal exam (DRE) and prostate-specific antigen (PSA) test. Futher diagnostic methods include ultrasound detection and/or prostate biopsy. A Gleason score is used to represent the aggressiveness of the cancer, which combines two numbers and usually ranges from 2 (nonaggressive cancer) to 10 (very aggressive cancer). Further scans (such as bone scan, ultrasound, computerized tomography (CT) scan, magnetic resonance imaging (MRI), positron emission tomography (PET) scan, etc.) may be used to determine the degree of the prostate cancer spreading to other tissues and/or organs.

Treatment for the early stage of prostate cancers (e.g., when the cancer tissues are small and contained/localized) may include, at least: 1) watchful waiting—not immediate treatment is carried out. PSA blood levels are regularly monitored; 2) radical prostatectomy—the prostate is surgically removed; 3) brachytherapy—radioactive seeds are implanted into the prostate; 4) conformal radiotherapy—the radiation beams are shaped so that the region where they overlap is as close to the same shape as the organ or region that requires treatment, thus minimizing healthy tissue exposure to radiation; and 5) intensity modulated radiotherapy—beams with variable intensity are used. An advanced form of conformal radiotherapy usually delivered by a computer-controlled linear accelerator.

Treatment recommendations really depend on individual cases. In general, if there is a good prognosis and the cancer is in its early stages, all options can be considered. However, they all have their advantages and disadvantages. The patient should discuss available options thoroughly with his doctor. More aggressive, or advanced, prostate cancer may require a combination of radiotherapy and hormone therapy (e.g., preventing testosterone production). Other surgery methods include, at least, salvage radical prostatectomy, image-guided, intensity-modulated radiation therapy (IG-IMRT), stereotactic high-precision radiosurgery (similar to CyberKnife), stereotactic hypofractionated accelerated radiation therapy (SHARP), and low-dose-rate permanent seed implants and high-dose-rate temporary seed implants (both forms of brachytherapy). For men with small, localized prostate tumors, focal therapy, or partial gland ablation, can be used. Chemotherapies and immunotherapies are also important treatment methods. For example, Sipuleucel-T (APC8015, trade name Provenge®) is a cell-based cancer immunotherapy for prostate cancer. Other immunotherapies for prostate cancers include, at least, PROSTVAC (similar to Provenge® in that it uses re-engineered cells to attack prostate cancer cells. This vaccine is targeted to the PSA antigen and has been tested for treating prostate cancers alone or in combination with ipilimumab (Yervoy®)), GVAX (alone or in combination with ipilimumab (Yervoy®)), etc.

In certain embodiments, the cancer is a "PI3Kbeta-dependent cancer," which can refer to a cancer that is functionally dependent on PI3Kbeta. For instance, even if the expression level of PI3Kbeta (e.g., PI3Kbeta mRNA, PI3Kbeta protein, newly synthesized PI3Kbeta protein, etc.) in a tumor tissue is comparable to its expression level in normal tissue, a cancer is PI3Kbeta-dependent if inhibition of the PI3Kbeta mRNA and/or protein, directly or indirectly such as by using RNAi or any other means, or deletion of the PI3Kbeta gene (e.g., by knock-out or clustered regularly interspaced short palindromic repeats (CRISPR) technology) leads to inhibition of oncogenesis, tumor cell proliferation, tumor metastasis or induces tumor cell differentiation. The term "PI3Kbeta-dependent cancer" also refers to a cancer in which PI3Kbeta is expressed (e.g., PI3Kbeta mRNA, PI3Kbeta protein, newly synthesized PI3Kbeta protein, etc.) at a significantly higher level than the normal amount of PI3Kbeta expressed in a non-cancerous cell of the same cell type as the PI3Kbeta-dependent cancer. A significantly modulated amount of PI3Kbeta relative to the normal amount of PI3Kbeta is an amount less than or greater than, respectively, the standard error of the assay employed to assess amount, and preferably at least 5%, 10%, 15% 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, 200%, 250%, 300%, 350%, 400%, 500%, 600%, 700%, 800%, 900%, 1000% or more than the normal (control) amount. Alternately, the amount of the biomarker in the subject can be considered "significantly" modulated relative to the normal (control) amount if the amount is at least about 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, 200%, 250%, 300%, 350%, 400%, 500%, 600%, 700%, 800%, 900%, 1000% or more, higher or lower, respectively, than the normal (control) amount of PI3Kbeta.

The term "micrometastasis" as used herein is preferably defined as a group of confluent cancer cells measuring from greater than 0.2 mm and/or having greater than 200 cells to 2 mm in maximum width. More preferably "micrometastasis" is defined as a group of confluent cancer cells from 0.2 mm to 2 mm in maximum width (see Edge et al. (2010) *AJCC Cancer Staging Manual and Handbook* (7th ed.)). An alternative preferred definition of "micrometastasis" is a confluent group of at least 1000 cancer cells and at least 0.1 mm in widest dimension up to 1 mm in widest dimension. Micrometastasis is generally not visible in standard contrast Mill imaging or other clinical imaging techniques. However, in certain cancers, radioactive antibodies directed to tumor selective antigens (e.g., Her2 for breast cancer metastasis) allows for visualization of micrometastasis. Other indirect detection methods include contrast media leakage at brain micrometastasis sites due to VEGF induced vascular leakage (Yano et al. (2000) Cancer Res. 60:4959-49067; U.S. Pat. Publ. 2015/0352113). More sensitive imaging techniques may also be applied to detect micrometastases. For example, blood volume may be imaged by Mill using the alternative contrast agent, USPIO (Molday Iron, Biopal, Worcester, Mass.) to detect micrometastasis (Yin et al. (2009) *Clin. Exp. Metastasis.* 26:403-414).

The term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

The term "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from a control cancer patient (can be stored sample or previous sample measurement) with a known outcome; normal tissue or cells isolated from a subject, such as a normal patient or the cancer patient, cultured primary cells/tissues isolated from a subject such as a normal subject or the cancer patient, adjacent normal cells/tissues obtained from the same organ or body location of the cancer patient, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment (for example, standard of care cancer therapy). It will be understood by those of skill in the art that such control samples and reference standard expression product levels can be used in combination as controls in the methods of the present invention. In one embodiment, the control may comprise normal or non-cancerous cell/tissue sample. In another preferred embodiment, the control may comprise an expression level for a set of patients, such as a set of cancer patients, or for a set of cancer patients receiving a certain treatment, or for a set of patients with one outcome versus another outcome. In the former case, the specific expression product level of each patient can be assigned to a percentile level of expression, or expressed as either higher or lower than the mean or average of the reference standard expression level. In another preferred embodiment, the control may comprise normal cells, cells from patients treated with combination chemotherapy, and cells from patients having benign cancer. In another embodiment, the control may also comprise a measured value for example, average level of expression of a particular gene in a population compared to the level of expression of a housekeeping gene in the same population. Such a population may comprise normal subjects, cancer patients who have not undergone any treatment (i.e., treatment naive), cancer patients undergoing standard of care therapy, or patients having benign cancer. In another preferred embodiment, the control comprises a ratio transformation of expression product levels, including but not limited to determining a ratio of expression product levels of two genes in the test sample and comparing it to any suitable ratio of the same two genes in a reference standard; determining expression product levels of the two or more genes in the test sample and determining a difference in expression product levels in any suitable control; and determining expression product levels of the two or more genes in the test sample, normalizing their expression to expression of housekeeping genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all patients with cancer. In one embodiment a control expression product level is established wherein higher or lower levels of expression product relative to, for instance, a particular percentile, are used as the basis for predicting outcome. In another preferred embodiment, a control expression product level is established using expression product levels from cancer control patients with a known outcome, and the expression product levels from the test sample are compared to the control expression product level as the basis for predicting outcome. As demonstrated by the data below, the methods of the present invention are not limited to use of a specific cut-point in comparing the level of expression product in the test sample to the control.

The "copy number" of a biomarker nucleic acid refers to the number of DNA sequences in a cell (e.g., germline and/or somatic) encoding a particular gene product. Generally, for a given gene, a mammal has two copies of each gene. The copy number can be increased, however, by gene amplification or duplication, or reduced by deletion. For example, germline copy number changes include changes at one or more genomic loci, wherein said one or more genomic loci are not accounted for by the number of copies in the normal complement of germline copies in a control (e.g., the normal copy number in germline DNA for the same species as that from which the specific germline DNA and corresponding copy number were determined). Somatic copy number changes include changes at one or more genomic loci, wherein said one or more genomic loci are not accounted for by the number of copies in germline DNA of a control (e.g., copy number in germline DNA for the same subject as that from which the somatic DNA and corresponding copy number were determined).

The "normal" copy number (e.g., germline and/or somatic) of a biomarker nucleic acid or "normal" level of expression of a biomarker nucleic acid or protein is the activity/level of expression or copy number in a biological sample, e.g., a sample containing tissue, whole blood, serum, plasma, buccal scrape, saliva, cerebrospinal fluid, urine, stool, and bone marrow, from a subject, e.g., a human, not afflicted with cancer, or from a corresponding non-cancerous tissue in the same subject who has cancer.

As used herein, the term "costimulate" with reference to activated immune cells includes the ability of a costimulatory molecule to provide a second, non-activating receptor mediated signal (a "costimulatory signal") that induces proliferation or effector function. For example, a costimulatory signal can result in cytokine secretion, e.g., in a T cell that has received a T cell-receptor-mediated signal. Immune cells that have received a cell-receptor mediated signal, e.g., via an activating receptor are referred to herein as "activated immune cells."

The term "determining a suitable treatment regimen for the subject" is taken to mean the determination of a treatment regimen (i.e., a single therapy or a combination of different therapies that are used for the prevention and/or treatment of the cancer in the subject) for a subject that is started, modified and/or ended based or essentially based or at least partially based on the results of the analysis according to the present invention. One example is starting an adjuvant therapy after surgery whose purpose is to decrease the risk of recurrence, another would be to modify the dosage of a particular chemotherapy. The determination can, in addition to the results of the analysis according to the present invention, be based on personal characteristics of the subject to be treated. In most cases, the actual determination of the suitable treatment regimen for the subject will be performed by the attending physician or doctor.

The term "diagnosing cancer" includes the use of the methods, systems, and code of the present invention to determine the presence or absence of a cancer or subtype thereof in an individual. The term also includes methods, systems, and code for assessing the level of disease activity in an individual.

A molecule is "fixed" or "affixed" to a substrate if it is covalently or non-covalently associated with the substrate such that the substrate can be rinsed with a fluid (e.g. standard saline citrate, pH 7.4) without a substantial fraction of the molecule dissociating from the substrate.

The term "expression signature" or "signature" refers to a group of one or more coordinately expressed biomarkers related to a measured phenotype. For example, the genes, proteins, metabolites, and the like making up this signature may be expressed in a specific cell lineage, stage of differentiation, or during a particular biological response. The biomarkers can reflect biological aspects of the tumors in which they are expressed, such as the cell of origin of the cancer, the nature of the non-malignant cells in the biopsy, and the oncogenic mechanisms responsible for the cancer. Expression data and gene expression levels can be stored on computer readable media, e.g., the computer readable medium used in conjunction with a microarray or chip reading device. Such expression data can be manipulated to generate expression signatures.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

The term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes.

The term "immune checkpoint" refers to a group of molecules on the cell surface of CD4+ and/or CD8+ T cells that fine-tune immune responses by down-modulating or inhibiting an anti-tumor immune response. Immune checkpoint proteins are well-known in the art and include, without limitation, CTLA-4, PD-1, VISTA, B7-H2, B7-H3, PD-L1, B7-H4, B7-H6, 2B4, ICOS, HVEM, PD-L2, CD160, gp49B, PIR-B, KIR family receptors, TIM-1, TIM-3, TIM-4, LAG-3, BTLA, SIRPalpha, CD47, CD48, 2B4 (CD244), B7.1, B7.2, ILT-2, ILT-4, TIGIT, IDO, CD39, arginase, CD73, and A2aR (see, for example, WO 2012/177624). The term further encompasses biologically active protein fragment, as well as nucleic acids encoding full-length immune checkpoint proteins and biologically active protein fragments thereof. In some embodiment, the term further encompasses any fragment according to homology descriptions provided herein.

Immune checkpoints and their sequences are well-known in the art and representative embodiments are described below. For example, the term "PD-1" refers to a member of the immunoglobulin gene superfamily that functions as a coinhibitory receptor having PD-L1 and PD-L2 as known ligands. PD-1 was previously identified using a subtraction cloning based approach to select for genes upregulated during TCR-induced activated T cell death. PD-1 is a member of the CD28/CTLA-4 family of molecules based on its ability to bind to PD-L1. Like CTLA-4, PD-1 is rapidly induced on the surface of T-cells in response to anti-CD3 (Agata et al. 25 (1996) *Int. Immunol.* 8:765). In contrast to CTLA-4, however, PD-1 is also induced on the surface of B-cells (in response to anti-IgM). PD-1 is also expressed on a subset of thymocytes and myeloid cells (Agata et al. (1996) supra; Nishimura et al. (1996) *Int. Immunol.* 8:773).

The nucleic acid and amino acid sequences of a representative human PD-1 biomarker is available to the public at the GenBank database under NM_005018.2 and NP_005009.2 and is shown in Table 3 (see also Ishida et al. (1992) 20 *EMBO J* 11:3887; Shinohara et al. (1994) *Genom-*

*ics* 23:704; U.S. Pat. No. 5,698,520). PD-1 has an extracellular region containing immunoglobulin superfamily domain, a transmembrane domain, and an intracellular region including an immunoreceptor tyrosine-based inhibitory motif (ITIM) (Ishida et al. (1992) *EMBO J.* 11:3887; Shinohara et al. (1994) *Genomics* 23:704; and U.S. Pat. No. 5,698,520) and an immunoreceptor tyrosine-based switch motif (ITSM). These features also define a larger family of polypeptides, called the immunoinhibitory receptors, which also includes gp49B, PIR-B, and the killer inhibitory receptors (KIRs) (Vivier and Daeron (1997) *Immunol. Today* 18:286). It is often assumed that the tyrosyl phosphorylated ITIM and/or ITSM motif of these receptors interacts with SH2-domain containing phosphatases, which leads to inhibitory signals. A subset of these immunoinhibitory receptors bind to MHC polypeptides, for example the KIRs, and CTLA4 binds to B7-1 and B7-2. It has been proposed that there is a phylogenetic relationship between the MHC and B7 genes (Henry et al. (1999) *Immunol. Today* 20(6):285-8). Nucleic acid and polypeptide sequences of PD-1 orthologs in organisms other than humans are well known and include, for example, mouse PD-1 (NM_008798.2 and NP_032824.1), rat PD-1 (NM_001106927.1 and NP_001100397.1), dog PD-1 (XM_543338.3 and XP_543338.3), cow PD-1 (NM_001083506.1 and NP_001076975.1), and chicken PD-1 (XM_422723.3 and XP_422723.2).

PD-1 polypeptides are inhibitory receptors capable of transmitting an inhibitory signal to an immune cell to thereby inhibit immune cell effector function, or are capable of promoting costimulation (e.g., by competitive inhibition) of immune cells, e.g., when present in soluble, monomeric form. Preferred PD-1 family members share sequence identity with PD-1 and bind to one or more B7 family members, e.g., B7-1, B7-2, PD-1 ligand, and/or other polypeptides on antigen presenting cells.

The term "PD-1 activity," includes the ability of a PD-1 polypeptide to modulate an inhibitory signal in an activated immune cell, e.g., by engaging a natural PD-1 ligand on an antigen presenting cell, tumor cell or other cell in the tumor microenvironment. Modulation of an inhibitory signal in an immune cell results in modulation of proliferation of, and/or cytokine secretion by, an immune cell. Thus, the term "PD-1 activity" includes the ability of a PD-1 polypeptide to bind its natural ligand(s), the ability to modulate immune cell costimulatory or inhibitory signals, and the ability to modulate the immune response.

The term "PD-1 ligand" refers to binding partners of the PD-1 receptor and includes both PD-L1 (Freeman et al. (2000) *J. Exp. Med.* 192:1027) and PD-L2 (Latchman et al. (2001) *Nat. Immunol.* 2:261). At least two types of human PD-1 ligand polypeptides exist. PD-1 ligand proteins comprise a signal sequence, and an IgV domain, an IgC domain, a transmembrane domain, and a short cytoplasmic tail. Both PD-L1 (See Freeman et al. (2000) *J. Exp. Med.* 192:1027 for sequence data) and PD-L2 (See Latchman et al. (2001) *Nat. Immunol.* 2:261 for sequence data) are members of the B7 family of polypeptides. Both PD-L1 and PD-L2 are expressed in placenta, spleen, lymph nodes, thymus, and heart. Only PD-L2 is expressed in pancreas, lung and liver, while only PD-L1 is expressed in fetal liver. Both PD-1 ligands are upregulated on activated monocytes and dendritic cells, although PD-L1 expression is broader. For example, PD-L1 is known to be constitutively expressed and upregulated to higher levels on murine hematopoietic cells (e.g., T cells, B cells, macrophages, dendritic cells (DCs), and bone marrow-derived mast cells) and non-hematopoietic cells (e.g., endothelial, epithelial, and muscle cells), whereas PD-L2 is inducibly expressed on DCs, macrophages, and bone marrow-derived mast cells (see Butte et al. (2007) *Immunity* 27:111).

PD-1 ligands comprise a family of polypeptides having certain conserved structural and functional features. The term "family" when used to refer to proteins or nucleic acid molecules, is intended to mean two or more proteins or nucleic acid molecules having a common structural domain or motif and having sufficient amino acid or nucleotide sequence homology, as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics. PD-1 ligands are members of the B7 family of polypeptides. The term "B7 family" or "B7 polypeptides" as used herein includes costimulatory polypeptides that share sequence homology with B7 polypeptides, e.g., with B7-1, B7-2, B7h (Swallow et al. (1999) *Immunity* 11:423), and/or PD-1 ligands (e.g., PD-L1 or PD-L2). For example, human B7-1 and B7-2 share approximately 26% amino acid sequence identity when compared using the BLAST program at NCBI with the default parameters (Blosum62 matrix with gap penalties set at existence 11 and extension 1 (See the NCBI website). The term B7 family also includes variants of these polypeptides which are capable of modulating immune cell function. The B7 family of molecules share a number of conserved regions, including signal domains, IgV domains and the IgC domains. IgV domains and the IgC domains are art-recognized Ig superfamily member domains. These domains correspond to structural units that have distinct folding patterns called Ig folds. Ig folds are comprised of a sandwich of two β sheets, each consisting of anti-parallel β strands of 5-10 amino acids with a conserved disulfide bond between the two sheets in most, but not all, IgC domains of Ig, TCR, and MEW molecules share the same types of sequence patterns and are called the C1-set within the Ig superfamily. Other IgC domains fall within other sets. IgV domains also share sequence patterns and are called V set domains. IgV domains are longer than IgC domains and contain an additional pair of β strands.

Preferred B7 polypeptides are capable of providing costimulatory or inhibitory signals to immune cells to thereby promote or inhibit immune cell responses. For example, B7 family members that bind to costimulatory receptors increase T cell activation and proliferation, while B7 family members that bind to inhibitory receptors reduce costimulation. Moreover, the same B7 family member may increase or decrease T cell costimulation. For example, when bound to a costimulatory receptor, PD-1 ligand can induce costimulation of immune cells or can inhibit immune cell costimulation, e.g., when present in soluble form. When bound to an inhibitory receptor, PD-1 ligand polypeptides can transmit an inhibitory signal to an immune cell. Preferred B7 family members include B7-1, B7-2, B7h, PD-L1 or PD-L2 and soluble fragments or derivatives thereof. In one embodiment, B7 family members bind to one or more receptors on an immune cell, e.g., CTLA4, CD28, ICOS, PD-1 and/or other receptors, and, depending on the receptor, have the ability to transmit an inhibitory signal or a costimulatory signal to an immune cell, preferably a T cell.

Modulation of a costimulatory signal results in modulation of effector function of an immune cell. Thus, the term "PD-1 ligand activity" includes the ability of a PD-1 ligand polypeptide to bind its natural receptor(s) (e.g. PD-1 or B7-1), the ability to modulate immune cell costimulatory or inhibitory signals, and the ability to modulate the immune response.

The term "PD-L1" refers to a specific PD-1 ligand. Two forms of human PD-L1 molecules have been identified. One form is a naturally occurring PD-L1 soluble polypeptide, i.e., having a short hydrophilic domain and no transmembrane domain, and is referred to herein as PD-L1S (shown in Table 3). The second form is a cell-associated polypeptide, i.e., having a transmembrane and cytoplasmic domain, referred to herein as PD-L1M (shown in SEQ ID NO: 6). The nucleic acid and amino acid sequences of representative human PD-L1 biomarkers regarding PD-L1M are also available to the public at the GenBank database under NM_014143.3 and NP_054862.1. PD-L1 proteins comprise a signal sequence, and an IgV domain and an IgC domain. The signal sequence of SEQ ID NO: 4 is shown from about amino acid 1 to about amino acid 18. The signal sequence of SEQ ID NO: 6 is shown: from about amino acid 1 to about amino acid 18. The IgV domain of SEQ ID NO: 4 is shown from about amino acid 19 to about amino acid 134 and the IgV domain of SEQ ID NO: 6 is shown from about amino acid 19 to about amino acid 134. The IgC domain of SEQ ID NO: 4 is shown from about amino acid 135 to about amino acid 227 and the IgC domain of SEQ ID NO: 6 is shown from about amino acid 135 to about amino acid 227. The hydrophilic tail of the PD-L1 exemplified in SEQ ID NO: 4 comprises a hydrophilic tail shown from about amino acid 228 to about amino acid 245. The PD-L1 polypeptide exemplified in SEQ ID NO: 6 comprises a transmembrane domain shown from about amino acids 239 to about amino acid 259 of SEQ ID NO: 6 and a cytoplasmic domain shown from about 30 amino acid 260 to about amino acid 290 of SEQ ID NO: 6. In addition, nucleic acid and polypeptide sequences of PD-L1 orthologs in organisms other than humans are well known and include, for example, mouse PD-L1 (NM_021893.3 and NP_068693.1), rat PD-L1 (NM_001191954.1 and NP_001178883.1), dog PD-L1 (XM_541302.3 and XP_541302.3), cow PD-L1 (NM_001163412.1 and NP_001156884.1), and chicken PD-L1 (XM_424811.3 and XP_424811.3).

The term "PD-L2" refers to another specific PD-1 ligand. PD-L2 is a B7 family member expressed on various APCs, including dendritic cells, macrophages and bone-marrow derived mast cells (Zhong et al. (2007) Eur. J. Immunol. 37:2405). APC-expressed PD-L2 is able to both inhibit T cell activation through ligation of PD-1 and costimulate T cell activation, through a PD-1 independent mechanism (Shin et al. (2005) J. Exp. Med. 201:1531). In addition, ligation of dendritic cell-expressed PD-L2 results in enhanced dendritic cell cytokine expression and survival (Radhakrishnan et al. (2003) J. Immunol. 37:1827; Nguyen et al. (2002) J. Exp. Med. 196:1393). The nucleic acid and amino acid sequences of representative human PD-L2 biomarkers (e.g., SEQ ID NOs: 7 and 8) are well known in the art and are also available to the public at the GenBank database under NM_025239.3 and NP_079515.2. PD-L2 proteins are characterized by common structural elements. In some embodiments, PD-L2 proteins include at least one or more of the following domains: a signal peptide domain, a transmembrane domain, an IgV domain, an IgC domain, an extracellular domain, a transmembrane domain, and a cytoplasmic domain. For example, amino acids 1-19 of SEQ ID NO: 8 comprises a signal sequence. As used herein, a "signal sequence" or "signal peptide" serves to direct a polypeptide containing such a sequence to a lipid bilayer, and is cleaved in secreted and membrane bound polypeptides and includes a peptide containing about 15 or more amino acids which occurs at the N-terminus of secretory and membrane bound polypeptides and which contains a large number of hydrophobic amino acid residues. For example, a signal sequence contains at least about 10-30 amino acid residues, preferably about 15-25 amino acid residues, more preferably about 18-20 amino acid residues, and even more preferably about 19 amino acid residues, and has at least about 35-65%, preferably about 38-50%, and more preferably about 40-45% hydrophobic amino acid residues (e.g., valine, leucine, isoleucine or phenylalanine). In another embodiment, amino acid residues 220-243 of the native human PD-L2 polypeptide and amino acid residues 201-243 of the mature polypeptide comprise a transmembrane domain. As used herein, the term "transmembrane domain" includes an amino acid sequence of about 15 amino acid residues in length which spans the plasma membrane. More preferably, a transmembrane domain includes about at least 20, 25, 30, 35, 40, or 45 amino acid residues and spans the plasma membrane. Transmembrane domains are rich in hydrophobic residues, and typically have an alpha-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta, W. N. et al. (1996) Annu. Rev. Neurosci. 19: 235-263. In still another embodiment, amino acid residues 20-120 of the native human PD-L2 polypeptide and amino acid residues 1-101 of the mature polypeptide comprise an IgV domain. Amino acid residues 121-219 of the native human PD-L2 polypeptide and amino acid residues 102-200 of the mature polypeptide comprise an IgC domain. As used herein, IgV and IgC domains are recognized in the art as Ig superfamily member domains. These domains correspond to structural units that have distinct folding patterns called Ig folds. Ig folds are comprised of a sandwich of two ß sheets, each consisting of antiparallel (3 strands of 5-10 amino acids with a conserved disulfide bond between the two sheets in most, but not all, domains. IgC domains of Ig, TCR, and MHC molecules share the same types of sequence patterns and are called the Cl set within the Ig superfamily. Other IgC domains fall within other sets. IgV domains also share sequence patterns and are called V set domains. IgV domains are longer than C-domains and form an additional pair of strands. In yet another embodiment, amino acid residues 1-219 of the native human PD-L2 polypeptide and amino acid residues 1-200 of the mature polypeptide comprise an extracellular domain. As used herein, the term "extracellular domain" represents the N-terminal amino acids which extend as a tail from the surface of a cell. An extracellular domain of the present invention includes an IgV domain and an IgC domain, and may include a signal peptide domain. In still another embodiment, amino acid residues 244-273 of the native human PD-L2 polypeptide and amino acid residues 225-273 of the mature polypeptide comprise a cytoplasmic domain. As used herein, the term "cytoplasmic domain" represents the C-terminal amino acids which extend as a tail into the cytoplasm of a cell. In addition, nucleic acid and polypeptide sequences of PD-L2 orthologs in organisms other than humans are well known and include, for example, mouse PD-L2 (NM_021396.2 and NP_067371.1), rat PD-L2 (NM_001107582.2 and NP_001101052.2), dog PD-L2 (XM_847012.2 and XP_852105.2), cow PD-L2 (XM_586846.5 and XP_586846.3), and chimpanzee PD-L2 (XM_001140776.2 and XP_001140776.1).

The term "PD-L2 activity," "biological activity of PD-L2," or "functional activity of PD-L2," refers to an activity exerted by a PD-L2 protein, polypeptide or nucleic acid molecule on a PD-L2-responsive cell or tissue, or on a PD-L2 polypeptide binding partner, as determined in vivo, or in vitro, according to standard techniques. In one embodiment, a PD-L2 activity is a direct activity, such as an association with a PD-L2 binding partner. As used herein, a "target molecule" or "binding partner" is a molecule with which a PD-L2 polypeptide binds or interacts in nature, such that PD-L2-mediated function is achieved. In an exemplary embodiment, a PD-L2 target molecule is the receptor RGMb. Alternatively, a PD-L2 activity is an indirect activity, such as a cellular signaling activity mediated by interaction of the PD-L2 polypeptide with its natural binding partner (i.e., physiologically relevant interacting macromolecule involved in an immune function or other biologically relevant function), e.g., RGMb. The biological activities of PD-L2 are described herein. For example, the PD-L2 polypeptides of the present invention can have one or more of the following activities: 1) bind to and/or modulate the activity of the receptor RGMb, PD-1, or other PD-L2 natural binding partners, 2) modulate intra- or intercellular signaling, 3) modulate activation of immune cells, e.g., T lymphocytes, and 4) modulate the immune response of an organism, e.g., a mouse or human organism.

The term "TIM-3" refers to a type I cell-surface glycoprotein that comprises an N-terminal immunoglobulin (Ig)-like domain, a mucin domain with O-linked glycosylations and with N-linked glycosylations close to the membrane, a single transmembrane domain, and a cytoplasmic region with tyrosine phosphorylation motif(s) (see, for example, U.S. Pat. Publ. 2013/0156774). TIM-3 is a member of the T cell/transmembrane, immunoglobulin, and mucin (TIM) gene family. Nucleic acid and polypeptide sequences of human TIM-3 are well known in the art and are publicly available, for example, as described in NM_032782.4 and NP_116171.3. The term, as described above for useful markers such as PD-L1 and PD-1, encompasses any naturally occurring allelic, splice variants, and processed forms thereof. Typically, TIM-3 refers to human TIM-3 and can include truncated forms or fragments of the TIM-3 polypeptide. In addition, nucleic acid and polypeptide sequences of TIM-3 orthologs in organisms other than humans are well known and include, for example, mouse TIM-3 (NM_134250.2 and NP_599011.2), chimpanzee TIM-3 (XM_518059.4 and XP_518059.3), dog TIM-3 (NM_001254715.1 and NP_001241644.1), cow TIM-3 (NM_001077105.2 and NP_001070573.1), and rat TIM-3 (NM_001100762.1 and NP_001094232.1). In addition, neutralizing anti-TIM-3 antibodies are well known in the art (see, at least U.S. Pat. Publ. 2013/0183688, Ngiow et al. (2011) *Cancer Res.* 71:3540-3551; and antibody 344823 from R&D Biosystems, as well as clones 2C23, 5D12, 2E2, 4A4, and IG5, which are all published and thus publicly available).

TIM-3 was originally identified as a mouse Th1-specific cell surface protein that was expressed after several rounds of in vitro Th1 differentiation, and was later shown to also be expressed on Th17 cells. In humans, TIM-3 is expressed on a subset of activated CD4+ T cells, on differentiated Th1 cells, on some CD8+ T cells, and at lower levels on Th17 cells (Hastings et al. (2009) *Eur. J. Immunol.* 39:2492-2501). TIM-3 is also expressed on cells of the innate immune system including mouse mast cells, subpopulations of macrophages and dendritic cells (DCs), NK and NKT cells, human monocytes, human dendritic cells, and on murine primary bronchial epithelial cell lines. TIM-3 expression is regulated by the transcription factor T-bet. TIM-3 can generate an inhibitory signal resulting in apoptosis of Th1 and Tc1 cells, and can mediate phagocytosis of apoptotic cells and cross-presentation of antigen. Polymorphisms in TIM-1 and TIM-3 can reciprocally regulate the direction of T-cell responses (Freeman et al. (2010) *Immunol. Rev.* 235:172-89).

TIM-3 has several known ligands, including galectin-9, phosphatidylserine, and HMGB1. For example, galectin-9 is an S-type lectin with two distinct carbohydrate recognition domains joined by a long flexible linker, and has an enhanced affinity for larger poly-N-acetyllactosamine-containing structures. Galectin-9 does not have a signal sequence and is localized in the cytoplasm. However, it can be secreted and exerts its function by binding to glycoproteins on the target cell surface via their carbohydrate chains (Freeman et al. (2010) *Immunol. Rev.* 235:172-89). Engagement of TIM-3 by galectin-9 leads to Th1 cell death and a consequent decline in IFN-gamma production. When given in vivo, galectin-9 had beneficial effects in several murine disease models, including an EAE model, a mouse model of arthritis, in cardiac and skin allograft transplant models, and contact hypersensitivity and psoriatic models (Freeman et al. (2010) *Immunol. Rev.* 235:172-89). Residues important for TIM-3 binding to galectin-9 include TIM-3(44), TIM-3(74), and TIM-3(100), which undergo N- and/or O-glycosylation. It is also known that TIM-3 mediates T-cell dysfunction associated with chronic viral infections (Golden-Mason et al. (2009) *J. Virol.* 83:9122-9130; Jones et al. (2008) *J. Exp. Med.* 205:2763-2779) and increases HIV-1-specific T cell responses when blocked ex vivo (Golden-Mason et al. (2009) *J. Virol.* 83:9122-9130). In addition, in chronic HCV infection, TIM-3 expression was increased on CD4+ and CD8+ T cells, specifically HCV-specific CD8+ cytotoxic T cells (CTLs) in chronic HCV infection and treatment with a blocking monoclonal antibody to TIM-3 reversed HCV-specific T cell exhaustion (Jones et al. (2008) *J. Exp. Med.* 205:2763-2779).

The term "LAG-3," also known as CD223, refers to a member of the immunoglobulin supergene family and is structurally and genetically related to CD4 (see, U.S. Pat. Publ. 2011/0150892). LAG-3 is generally known as a membrane protein encoded by a gene located on the distal part of the short arm of chromosome 12, near the CD4 gene, suggesting that the LAG-3 gene may have evolved through gene duplication (Triebel et al. (1990) *J. Exp. Med.* 171: 1393-1405). However, secreted forms of the protein are known (e.g., for human and mouse TIM-3). Nucleic acid and polypeptide sequences of human LAG-3 are well known in the art and are publicly available, for example, as described in NM_002286.5 and NP_002277.4.

The term encompasses any naturally occurring allelic, splice variants, and processed forms thereof. Typically, LAG-3 refers to human LAG-3 and can include truncated forms or fragments of the LAG-3 polypeptide. In addition, nucleic acid and polypeptide sequences of LAG-3 orthologs in organisms other than humans are well known and include, for example, mouse LAG-3 (NM_008479.2 and NP_032505.1), chimpanzee LAG-3 (XM_508966.4 and XP_508966.2), monkey LAG-3 (XM_001108923.2 and XP_001108923.1), cow LAG-3 (NM_00124949.1 and NP_001232878.1), rat LAG-3 (NM_212513.2 and NP_997678.2), and chicken LAG-3 (XM_416510.3, XP_416510.2, XM_004938117.1, and XP_004938174.1). In addition, neutralizing anti-LAG-3 antibodies are well known in the art (see, at least U.S. Pat. Publs. 2011/0150892 and 2010/0233183; Macon-Lemaitre and Triebel (2005) *Immunology* 115:170-178; Drake et al. (2006) *J. Clin. Oncol.* 24:2573; Richter et al. (2010) *Int. Immunol.* 22:13-23).

LAG-3 is not expressed on resting peripheral blood lymphocytes but is expressed on activated T cells and NK cells and has a number of functions (see, U.S. Pat. Publ. 2011/0150892). Similar to CD4, LAG-3 has been demonstrated to interact with MHC Class II molecules but, unlike CD4, LAG-3 does not interact with the human immunodeficiency virus gp120 protein (Baixeras et al. (1992) *J. Exp. Med.* 176:327-337). Studies using a soluble LAG-3 immunoglobulin fusion protein (sLAG-3Ig) demonstrated direct and specific binding of LAG-3 to MHC class II on the cell surface (Huard et al. (1996) *Eur. J. Immunol.* 26:1180-1186). In in vitro studies of antigen-specific T cell responses, the addition of anti-LAG-3 antibodies led to increased T cell proliferation and higher expression of activation antigens such as CD25, supporting a role for the LAG-/MHC class II interaction in down-regulating antigen-dependent stimulation of CD4+ T lymphocytes (Huard et al. (1994) *Eur. J. Immunol.* 24:3216-3221). The intra-cytoplasmic region of LAG-3 has been demonstrated to interact with a protein termed LAP, which is thought to be a signal transduction molecule involved in the downregulation of the CD3/TCR activation pathway (Iouzalen et al. (2001) *Eur. J. Immunol.* 31:2885-2891). Furthermore, CD4+CD25+ regulatory T cells ($T_{reg}$) have been shown to express LAG-3 upon activation and antibodies to LAG-3 inhibit suppression by induced regulatory T cells, both in vitro and in vivo, suggesting that LAG-3 contributes to the suppressor activity of regulatory T cells (Huang et al. (2004) *Immunity* 21:503-513). Still further, LAG-3 has been shown to negatively regulate T cell homeostasis by regulatory T cells in both T cell-dependent and independent mechanisms (Workman and Vignali (2005) *J. Immunol.* 174:688-695).

In certain circumstances, LAG-3 also has been shown to have immunostimulatory effects. For example, LAG-3 transfected tumor cells transplanted into syngeneic mice showed marked growth reduction or complete regression as compared to untransfected tumor cells, suggesting that LAG-3 expression on the tumor cells stimulated an anti-tumor response by triggering antigen presenting cells via MEW class II molecules (Prigent et al. (1999) *Eur. J. Immunol.* 29:3867-3876). Additionally, soluble LAG-3 Ig fusion protein has been shown to stimulate both humoral and cellular immune responses when administered to mice together with an antigen, indicating that soluble LAG-3Ig can function as a vaccine adjuvant (El Mir and Triebel (2000) *J. Immunol.* 164:5583-5589). Furthermore, soluble human LAG-3Ig has been shown to amplify the in vitro generation of type I tumor-specific immunity (Casati et al. (2006) *Cancer Res.* 66:4450-4460). The functional activity of LAG-3 is reviewed further in Triebel (2003) *Trends Immunol.* 24:619-622.

"Anti-immune checkpoint" therapy refers to the use of agents that inhibit immune checkpoint nucleic acids and/or proteins. Immune checkpoints share the common function of providing inhibitory signals that suppress immune response and inhibition of one or more immune checkpoints can block or otherwise neutralize inhibitory signaling to thereby upregulate an immune response in order to more efficaciously treat cancer. Exemplary agents useful for inhibiting immune checkpoints include antibodies, small molecules, peptides, peptidomimetics, natural ligands, and derivatives of natural ligands, that can either bind and/or inactivate or inhibit immune checkpoint proteins, or fragments thereof; as well as RNA interference, antisense, nucleic acid aptamers, etc. that can downregulate the expression and/or activity of immune checkpoint nucleic acids, or fragments thereof. Exemplary agents for upregulating an immune response include antibodies against one or more immune checkpoint proteins block the interaction between the proteins and its natural receptor(s); a non-activating form of one or more immune checkpoint proteins (e.g., a dominant negative polypeptide); small molecules or peptides that block the interaction between one or more immune checkpoint proteins and its natural receptor(s); fusion proteins (e.g. the extracellular portion of an immune checkpoint inhibition protein fused to the Fc portion of an antibody or immunoglobulin) that bind to its natural receptor(s); nucleic acid molecules that block immune checkpoint nucleic acid transcription or translation; and the like. Such agents can directly block the interaction between the one or more immune checkpoints and its natural receptor(s) (e.g., antibodies) to prevent inhibitory signaling and upregulate an immune response. Alternatively, agents can indirectly block the interaction between one or more immune checkpoint proteins and its natural receptor(s) to prevent inhibitory signaling and upregulate an immune response. For example, a soluble version of an immune checkpoint protein ligand such as a stabilized extracellular domain can binding to its receptor to indirectly reduce the effective concentration of the receptor to bind to an appropriate ligand. In one embodiment, anti-PD-1 antibodies, anti-PD-L1 antibodies, and/or anti-PD-L2 antibodies, either alone or in combination, are used to inhibit immune checkpoints. These embodiments are also applicable to specific therapy against particular immune checkpoints, such as the PD-1 pathway (e.g., anti-PD-1 pathway therapy, otherwise known as PD-1 pathway inhibitor therapy). Numerous immune checkpoint inhibitors are known and publicly available including, for example, Keytruda® (pembrolizumab; anti-PD-1 antibody), Opdivo® (nivolumab; anti-PD-1 antibody), Tecentriq® (atezolizumab; anti-PD-L1 antibody), durvalumab (anti-PD-L1 antibody), and the like.

The term "immune response" includes T cell mediated and/or B cell mediated immune responses. Exemplary immune responses include T cell responses, e.g., cytokine production and cellular cytotoxicity. In addition, the term immune response includes immune responses that are indirectly affected by T cell activation, e.g., antibody production (humoral responses) and activation of cytokine responsive cells, e.g., macrophages.

The term "immunotherapeutic agent" can include any molecule, peptide, antibody or other agent which can stimulate a host immune system to generate an immune response to a tumor or cancer in the subject. Various immunotherapeutic agents are useful in the compositions and methods described herein.

The term "inhibit" or "deficient" includes the decrease, limitation, or blockage, of, for example a particular action, function, or interaction. In some embodiments, cancer is "inhibited" if at least one symptom of the cancer is alleviated, terminated, slowed, or prevented. As used herein, cancer is also "inhibited" if recurrence or metastasis of the cancer is reduced, slowed, delayed, or prevented. Similarly, a biological function, such as the function of a protein, is inhibited if it is decreased as compared to a reference state, such as a control like a wild-type state. For example, kinase activity of a mutant PI3 kinase or a PI3 kinase that is contacted with a PI3 kinase inhibitor is inhibited or deficient if the kinase activity is decreased due to the mutation and/or contact with the inhibitor, in comparison to the wild-type PI3 kinase and/or the PI3 kinase not contacted with the inhibitor. Such inhibition or deficiency can be induced, such as by application of agent at a particular time and/or place, or can be constitutive, such as by a heritable mutation. Such inhibition or deficiency can also be partial or complete (e.g., essentially no measurable activity in comparison to a reference state, such as a control like a wild-type state). Essentially complete inhibition or deficiency is referred to as blocked.

The term "interaction", when referring to an interaction between two molecules, refers to the physical contact (e.g., binding) of the molecules with one another. Generally, such an interaction results in an activity (which produces a biological effect) of one or both of said molecules.

An "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations of a biomarker polypeptide or fragment thereof, in which the protein is separated from cellular components of the cells from which it is isolated or recombinantly produced. In one embodiment, the language "substantially free of cellular material" includes preparations of a biomarker protein or fragment thereof, having less than about 30% (by dry weight) of non-biomarker protein (also referred to herein as a "contaminating protein"), more preferably less than about 20% of non-biomarker protein, still more preferably less than about 10% of non-biomarker protein, and most preferably less than about 5% non-biomarker protein. When antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

A "kit" is any manufacture (e.g. a package or container) comprising at least one reagent, e.g. a probe or small molecule, for specifically detecting and/or affecting the expression of a marker of the present invention. The kit may be promoted, distributed, or sold as a unit for performing the methods of the present invention. The kit may comprise one or more reagents necessary to express a composition useful in the methods of the present invention. In certain embodiments, the kit may further comprise a reference standard, e.g., a nucleic acid encoding a protein that does not affect or regulate signaling pathways controlling cell growth, division, migration, survival or apoptosis. One skilled in the art can envision many such control proteins, including, but not limited to, common molecular tags (e.g., green fluorescent protein and beta-galactosidase), proteins not classified in any of pathway encompassing cell growth, division, migration, survival or apoptosis by GeneOntology reference, or ubiquitous housekeeping proteins. Reagents in the kit may be provided in individual containers or as mixtures of two or more reagents in a single container. In addition, instructional materials which describe the use of the compositions within the kit can be included.

The term "neoadjuvant therapy" refers to a treatment given before the primary treatment. Examples of neoadjuvant therapy can include chemotherapy, radiation therapy, and hormone therapy. For example, in treating breast cancer, neoadjuvant therapy can allows patients with large breast cancer to undergo breast-conserving surgery.

The "normal" level of expression and/or activity of a biomarker is the level of expression and/or activity of the biomarker in cells of a subject, e.g., a human patient, not afflicted with a cancer. An "over-expression" or "significantly higher level of expression" of a biomarker refers to an expression level in a test sample that is greater than the standard error of the assay employed to assess expression, and is preferably at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples. The same determination can be made to determine overactivity or underactivity.

The term "PI3K signaling pathway" refers to one of the intracellular signaling pathways activated by the binding of growth factors to receptor tyrosine kinases. Alterations in the PI3K signaling pathway involved in the development and recurrence of cancer commonly occur due to mutations in the catalytic or regulatory PI3K subunits, activation or amplification of receptor tyrosine kinases, or loss or inactivation of PTEN.

In general, upon activation, PI3K phosphorylates phosphatidylinositol-4,5-bisphosphate (PIP2) to phosphatidylinositol-3,4,5-trisphosphate (PIP3), a process that is reversed by PTEN. PIP3 signals activate the kinase PDK1, which in turn activates the kinase AKT. The AKT protein family, which members are also called protein kinases B (PKB) plays an important role in mammalian cellular signaling. Akt kinase is a serine/threonine kinase which is a downstream effector molecule of phosphoinositide 3-kinase and is involved in protecting a cell from apoptosis. Akt kinase is thought to be involved in the progression of cancer because it stimulates cell proliferation and suppresses apoptosis. Akt1 is involved in cellular survival pathways, by inhibiting apoptotic processes. Akt1 is also able to induce protein synthesis pathways, and is therefore a key signaling protein in the cellular pathways that lead to skeletal muscle hypertrophy, and general tissue growth. Since it can block apoptosis, and thereby promote cell survival, Akt1 has been implicated as a major factor in many types of cancer. Akt is known to play a role in the cell cycle. Under various circumstances, activation of Akt was shown to overcome cell cycle arrest in G1 and G2 phases. Moreover, activated Akt may enable proliferation and survival of cells that have sustained a potentially mutagenic impact and, therefore, may contribute to acquisition of mutations in other genes. AKT (activation, amplification) and PTEN (mutation, deletion, epigenetic inactivation) are deregulated in many human cancers (Altomare et al. (2003) *J. Cell Biochem.* 88:470-476; Ruggeri et al. (1998) *Mol. Carcin.* 21:81-86; Cheng et al. (1996) *Proc. Natl. Acad. Sci. U.S.A.* 93:3636-3641; Staal et al. (1987) *Proc. Natl. Acad. Sci. U.S.A.* 84:5034-5037; Li et al. (2005) *World J. Gastroenterol.* 11:285-288; Li et al. (1997) *Science* 275:1943-1947; Goel et al. (2004) *Cancer Res.* 64:3014-3021). PI3K pathway activation can be assessed by immunohistochemical analysis of PTEN or phosphorylated AKT levels in clinical samples (Slipicevic et al. (2005)*Am. J. Clin. Pathol.* 124:528-536).

Molecular targets of such inhibitors include, but are not limited to, PI3K, AKT, S6K1, mTORC1, PDK1, MYC, cMET, FGFR2, growth factors (EGF, b-FGF, IGF1, Insulin, or Heregulin) and the like. For example, mTOR exists in at least 2 distinct multiprotein complexes described as raptor-mTOR complex (mTORC1) and rictor-mTOR complex (mTORC2) in mammalian cells (sometimes referred to as just TORC1 and TORC2) (Dowling et al. (2010) *Biochim. Biophys. Acta* 1804:433-439; Dunlop et al. (2009) *Cell. Signal.* 21:827-8735; Hoeffer et al. (2010) *Trends Neurosci.* 33:67-75; Laplante et al. (2012) *Cell* 149:274-293; Laplante et al. (2013) *J. Cell. Sci.* 126:1713-1719; Neufeld (2010) *Curr. Opin. Cell Biol.* 22:157-168; Zoncu et al. (2011) *Nat. Rev. Mol. Cell Biol.* 12:21-35). mTORC1 is composed of mTOR, GβL and raptor proteins and it binds to FKBP12-rapamycin. mTORC1 is a rapamycin-sensitive complex as its kinase activity is inhibited by FKB12-rapamycin in vitro and the mTORC1 complex positively regulates cell growth. The raptor branch of the mTOR pathway modulates number of processes, including mRNA translation, ribosome biogenesis, nutrient metabolism and autophagy. The two mammalian proteins, S6 Kinase 1 (S6K1) and 4E-BP1, which are linked to protein synthesis, are downstream targets of mTORC1. S6K1 also phosphorylates S6RP, which is the S6 component of the 40S ribosomal subunit involved in regulating translation, cell size, cell proliferation, and glucose homeostasis (Magnuson et al. (2012) *Biochem. J.* 441:1-21). mTORC1 has been shown to phosphorylate S6K1 at T389 and is inhibited by FKBP12-rapamycin in vitro and by rapamycin in vivo. mTORC1 can also phosphorylate 4E-BP1 at T37/46 in vitro and in vivo. Other molecular targets are well-known in the art and are described, for example, in U.S. Pat. Publ. 2011/0015869. In some embodiments, the PI3K signaling pathway is limited to subsets of biomolecules within the pathway, such as PI3K, PI3K isoforms, mTORC1, S6RP, and 4E-BP1, or individual biomolecules within the pathway, such as PI3K, PI3k isoforms, mTORC1, S6RP, or 4E-BP1.

Inhibitors of PI3K signaling pathway members are also well-known in the art and include, mTOR inhibitors, such as RAD001 (also known as Everolimus; Novartis), CCI-779 (also known as Temsirolimus; Pfizer), AP23573 (Ariad Pharmaceuticals), and KU-0059475 (Kudus Pharmaceuticals; Mita, M. M. et al. (2003) Cancer Biology & Therapy 2:4:Suppl.1, S169-S177); S6K1 inhibitors, such as PF-4708671 (Pearce et al., 2010, Biochem. J. 431:245-255) and DG2 (3-bromo-4-)4-)2-methoxyphenyl)piperazine-1-yl)-1H-pyrazolo[3,4-d]-pyrimidine (Axon Medchem); AKT antibodies (Shin et al., 2005, Cancer Res. 65:2815-2824) (see also Cheng et al., Oncogene, 2005, 24:7482-7492 for review on inhibitors of AKT pathway); PDK1 inhibitors, such as AR-12, BX-795, staurosporine, OSU-03012, celecoxib, and others described in U.S. Pat. Nos. 6,124,272; 7,344,870; and 7,041,687); and IGF1R inhibitors (such as monoclonal antibody MK-0646 U.S. Pat. No. 7,241,444).

As used herein, the term "PI3K" refers to a family of intracellular signal transducer enzymes capable of phosphorylating the 3 position hydroxyl group of the inositol ring of phosphatidylinositol (PtdIns). PI3Ks are divided into four different classes, known as class I, class II, class III, and class IV, based on the enzyme primary structure, enzymatic regulation, and lipid substrate specificity (Leevers et al. (1999) *Curr. Opin. Cell Biol.* 11:219-225). Class I PI3Ks are heterodimeric molecules composed of a regulatory and a catalytic subunit, are activated by G protein-coupled receptors (GPCRs) and tyrosine kinase receptors, and are responsible for the production of the following phosphatidylinositols: PI(3)P, PI(3,4)$P_2$, and PI(3,4,5)$P_3$. Class II PI3Ks do not contain a regulatory subunit, lack a critical Asp residue in the C-terminal C2 domain required for coordinate binding of calcium ions, can comprise one of three catalytic isoforms (C2alpha, C2beta, or C2gamma), and catalyze the production of PI(3)P from PI and PI(3,4)$P_2$ from PIP. Class III PI3Ks are similar to class II PI3Ks in structure, but only produce PI(3)P from PI. Finally, class IV PI3Ks is a more distantly related set of enzymes that are protein serine/threonine kinases and include the members, mTOR, DNA-PK, ATM, and ATR. In humans, the four class I catalytic PI3Ks are known as PIK3C alpha, PIK3C beta, PIK3C gamma, and PIK3C delta. The term "pan-PI3K" refers to the group of PIK3C alpha, PIK3C beta, PIK3C gamma, and PIK3C delta. For example, a "pan-PI3K inhibitor" inhibits PIK3C alpha, PIK3C beta, PIK3C gamma, and PIK3C delta.

Nucleic acid and amino acid sequences for each PI3K, including catalytic PI3Ks, are known in the art and are publicly available in the GenBank database maintained by the U.S. National Center for Biotechnology Information. For example, PIK3C alpha (PIK3CA) nucleic acid and amino acid sequences are well-known and include, for example, human PIK3CA (NM_006218.2 and NP_006209.2), monkey PIK3CA (NM_001260668.1 and NP_001247597.1), mouse PIK3CA (XM_006535409.2, XP_006535472.1, XM_006535410.2, and XP_006535473.1), and rat PIK3CA (NM_133399.2 and NP_596890.2). PIK3C beta (PIK3CB) nucleic acid and amino acid sequences are well-known and include, for example, human PIK3CB (NM_006219.2, NP_006210.1, NM_001256045.1, and NP_001242974.1), monkey PIK3CB (XM_015132082.1 and XP_014987568.1), mouse PIK3CB (NM_029094.3 and NP_083370.2), and rat PIK3CB (XM_008766567.1, XP_008764789.1, XM_006243642.2, and XP_006243704.1). PIK3C gamma (PIK3CG) nucleic acid and amino acid sequences are well-known and include, for example, human PIK3CG (NM_002649.3, NP_002640.2, NM_001282426.1, NP_001269355.1, NM_001282427.1, and NP_001269356.1), monkey PIK3CG (NM_001266758.1 and NP_001253687.1), mouse PIK3CG (NM_020272.2, NP_064668.2, NM_001146201.1, NP_001139673.1, NM_001146200.1, and NP_001139672.1), and rat PIK3CG (XM_006240004.2, XP_006240066.1, XM_006240005.2, XP_006240067.1, XM_006240003.2, and XP_006240065.1). PIK3C delta (PIK3CD) nucleic acid and amino acid sequences are well-known and include, for example, human PIK3CD (NM_005026.3 and NP_005017.3), chimpanzee PIK3CD (XM_009447951.1, XP_009446226.1, XM_009447957.1, and XP_009446232.1), mouse PIK3CD (NM_008840.3, NP_032866.2, NM_001164052.1, NP_001157524.1, NM_001164051.1, NP_001157523.1, NM_001164050.1, NP_001157522.1, NM_001164049.1, NP_001157521.1, NM_001029837.2, and NP_001025008.2), and rat PIK3CD (NM_0011089078.1 and NP_001102448.1). Anti-PI3K agents, including intrabodies, nucleic acids, and the like are well-known in the art and include, for example, pan-PI3K inhibitors having broad inhibitory activity against all catalytic PI3Ks (e.g., pan-Class I PI3K inhibitors) are known and include BKM120 (5-(2,6-dimorpholin-4-ylpyrimidin-4-yl)-4-(trifluoromethyl)pyridin-2-amine; Maira et al. (2011) *Mol. Cancer Ther.* 11:317-348), BEZ235 (Maira et al. (2011) *Mol. Cancer Ther.* 11:317-348), wortmannin (Wymann et al. (1996) *Mol. Cell. Biol.* 16:1722-1733), LY294002 (Vlahos et al. (1994) *J. Biol. Chem.* 269:5241-5248; Wetzker and Rommel (2004) *Curr. Pharm. Des.* 10:1915-1922), and BAY 80-80-6946 (copanlisib). In addition, PI3K isoform-specific small molecule inhibitors are known. For example, AZD6482 and GSK2636771 selectively inhibit PI3 KB, AS-252424 and AS-604850 selectively inhibit PI3KG, IC87114 selectively inhibits PI3KD, and GDC0941 selectively inhibits PI3KA and PI3KD (Finan and Thomas (2004) *Biochem. Soc. Trans.* 32:378-382; PCT Publ. WO01/81346; PCT Publ. WO01/372557; U.S. Pat. No. 6,403,588; and PCT Publ. WO01/43266). Other inhibitors of PI3Ks (e.g., other small molecules that are organic chemical molecules that are not peptides or nucleic acids) are known. In addition, antibodies that bind PI3Ks, such as, TA802118, TA801482, and TA303167 (PIK3CA; OriGene Technol., Inc.); TA308795, TA330901, and TA329903 (PIK3CB; OriGene Technol., Inc.); TA505226, TA505228, and TA505227 (PIK3CGl OriGene Technol., Inc.); and OTI2H3, TA325015, and TA307256 (PIK3CD; OriGene Technol., Inc.), and nucleic acids, such as SR303520, TF310428, SR421939, and TL501641 (PIK3CA-specific, OriGene Technol., Inc.); SR303521, TL310427, SR421863, TL515159, SR512202, and TL711892 (PIK3CB-specific, OriGene Technol., Inc.); SR303524, TL310425, SR422070, TL502804, TR705298 (PIK3CG-specific, OriGene Technol., Inc.); and SR303523, TL310426, SR421859, TL515984, SR500333, and TL707500 (PIK3CD-specific, OriGene Technol., Inc.), are well-known in the art. It is to be noted that the term can further be used to refer to any combination of features described herein regarding PI3Ks. For example, any combination of class, sequence composition, percentage identify, sequence length, domain structure, functional activity, etc. can be used to describe a PI3K of the present invention.

As used herein, the term "P53" refers to the well-known tumor suppressor, p53 (see, for example, Meek (2015) *Biochem J.* 469:325-346; Ballinger et al. (2015) *Curr. Opin. Oncol.* 27:332-337; Amelio and Melino (2015) *Trends Biochem. Sci.* 40:425-434; Saha et al. (2014) *Prog. Biophys. Mol. Biol.* 117:250-263; Tchelebit et al. (2014) *Subcell. Biochem.* 85:133-159; Yeudall (2014) *Subcell. Biochem.* 85:105-117; Santoro et al. (2014) *Subcell. Biochem.* 85:91-103; Girardini et al. (2014) *Subcell. Biochem.* 85:41-70; Soussi et al. (2014) *Hum. Mutat.* 35:766-778; Leroy et al. (2014) *Hum. Mutat.* 35:756-765; Leory et al. (2014) *Hum. Mutat.* 35:672-688; Nguyen et al. (2014) *Hum. Mutat.* 35:738-755; Bertheau et al. (2013) *Breast* 22:S27-S29; Brachova et al. (2013) *Int. J. Mol. Sci.* 14:19257-19275; Carvajal and Manfredi (2013) *EMBO Rep.* 14:414-421; Tornesello et al. (2013) *Gynecol. Oncol.* 128:442-448; Lehmann and Pietenpol (2012) *J. Clin. Oncol.* 30:3648-3650; Bellini et al. (2012) *J. Biomed. Biotechnol.* 2012:891961; Li et al. (2012) *Biochim. Biophys. Acta.* 1819:684-687; and Naccarati et al. (2012) *Mutagenesis* 27:211-218). The gene encoding the p53 protein is highly conserved among vertebrates and is mutated to cause deficiency of p53 protein function in greater than 50% of human cancers (Surget et al. (2013) *OncoTargets Therapy* 7:57-68). In humans, the p53 gene, which is located at 17p13.1, encodes at least 15 protein isoforms. The protein structure of the p53 protein is well-known and is characterized by certain domains. For example, in one embodiment, wild-type functional human p53 comprises:

1) an acidic N-terminus transcription-activation domain (TAD), also known as activation domain 1 (AD1), which activates transcription factors (e.g., residues 1-42). The N-terminus contains two complementary transcriptional activation domains, with a major one at residues 1-42 and a minor one at residues 55-75, specifically involved in the regulation of several pro-apoptotic genes (Venot et al. (1998) *EMBO J.* 17:4668-4679);

2) activation domain 2 (AD2), which is important for apoptotic activity (e.g., residues 43-63);

3) proline rich domain, which is important for the apoptotic activity of p53 by nuclear exportation via MAPK (e.g., residues 64-92);

4) central DNA-binding core domain (DBD), which contains one zinc atom and several arginine amino acids (e.g., residues 102-292). This region is responsible for binding the p53 co-repressor LMO3 (Larsen et al. (2010) *Biochem. Biophys. Res. Commun.* 392:252-257;

5) nuclear localization signaling domain (e.g., residues 316-325);

6) homo-oligomerization domain (OD) (e.g., residues 307-355). Tetramerization is essential for the activity of p53 in vivo; and 7) a C-terminal domain involved in downregulation of DNA binding of the central domain (e.g., residues 356-393) (Harms et al. (2005) *Mol. Cell. Biol.* 25:2014-2030).

Mutations that make p53 deficient in cancer usually occur in the DBD. Most of these mutations destroy the ability of the protein to bind to its target DNA sequences, and thus prevents transcriptional activation of these genes. As such, mutations in the DBD are recessive loss-of-function mutations. Molecules of p53 with mutations in the OD dimerize with wild-type p53, and prevent them from activating transcription. Therefore, OD mutations have a dominant negative effect on the function of p53. Mutations in p53 nucleic acids that either do not encode functional p53 protein or p53 protein having reduced function (collectively, p53 deficiency) are well-known in the art, as described above, and can be generated by any number of well-known types of mutation including, for example, a missense mutation (base change that alters the encoded amino acid), a nonsense mutation (base change that alters the encoded amino acid to a premature stop codon), a frameshift mutation (base addition or loss in a manner that is not a multiple of 3), an insertion mutation (any base addition, large or small in number, that alters the function of the encoded protein), a deletion mutation (any base deletion, large or small in number, that alters the function of the encoded protein), or a rearrangement mutation (any alteration, large or small, that alters the function of the encoded protein while retaining the starting amount of bases). In some embodiments, mutations can be combined, such as when rearrangements are accompanied by additions and/or deletions, or multiple missense mutations are combined. In some embodiments, the mutation is a genetic null (any mutation that completes ablates the function of the encoded protein) that arises in the germline, somatically, or both. This description of mutation types applies to any marker described herein.

Assays for determining p53 activity, or reduction thereof, are well-known and commercially available (see, for example, Qiagen Cignal® p53 reporter kit, Active Motif® TransAM® p53 reporter kit; Cayman Chemical p53 transcription factor assay kit item number 600020, Genecopoeia™ TF-Detect™ human p53 activity assay kit; Hiraki et al. (2015) *Cell Chem. Biol.* 22:1206-1216; Flaman et al. (1995) *Proc. Natl. Acad. Sci. USA* 92:3963-3967 (1995); and Kovvali et al. (2001) *Nucl. Acids Res.* 29:e28).

Nucleic acid and amino acid sequences for p53 nucleic acids and protein are known in the art and are publicly available in the GenBank database maintained by the U.S. National Center for Biotechnology Information. For example, human p53 nucleic acid and amino acid sequences are well-known and include, for example, NM_000546.5 (variant 1) and NP_000537.3 (isoform a); NM_001126112.2 (variant 2) and NP_001119584.1 (isoform a); NM_001126114.2 (variant 3) and NP_001119586.1 (isoform b); NM_001126113.2 (variant 4) and NP_001119585.1 (isoform c); NM_001126115.1 (variant 5) and NP_001119587.1 (isoform d); NM_001126116.1 (variant 6) and NP_001119588.1 (isoform e); NM_001126117.1 (variant 7) and NP_001119589.1 (isoform f); NM_001126118.1 (variant 8) and NP_001119590.1 (isoform g); NM_001276695.1 (variant 9) and NP_001263624.1 (isoform h); NM_001276696.1 (variant 10) and NP_001263625.1 (isoform i); NM_001276697.1 (variant 10) and NP_001263626.1 (isoform j); NM_001276698.1 (variant 11) and NP_001263627.1 (isoform k); NM_001276699.1 (variant 12) and NP_001263628.1 (isoform 1); NM_001276760.1 (variant 13) and NP_001263689.1 (isoform g); and NM_001276761.1 (variant 14) and NP_001263690.1 (isoform g). Nucleic acid and amino acid sequences of p53 orthologs in other species are also well-known and include, for example, mouse p53 (NM_001127233.1, NP_001120705.1, NM_011640.3, and NP_035770.2), chimpanzee p53 (XM_001172077.4 and XP_001172077.2), monkey p53 (NM_001047151.2 and NP_001040616.1), dog p53 (NM_001003210.1 and NP_001003210.1), cow p53 (NM_174201.2 and NP_776626.1), frog p53 (NM_001001903.1 and NP_001001903.1), and zebrafish p53 (NM_001271820.1, NP_001258749.1, NM_131327.3, and NP_571402.1). It is to be noted that the term can further be used to refer to any combination of features described herein regarding p53. For example, any combination of class, sequence composition, percentage identify, sequence length, domain structure, functional activity, etc. can be used to describe p53 as used according to the present invention.

The term "pre-determined" biomarker amount and/or activity measurement(s) may be a biomarker amount and/or activity measurement(s) used to, by way of example only, evaluate a subject that may be selected for a particular treatment, evaluate a response to a treatment such as combination PI3Kbeta and immune checkpoint inhibitor therapy, and/or evaluate the disease state. A pre-determined biomarker amount and/or activity measurement(s) may be determined in populations of patients with or without cancer. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements. In another embodiment, the amounts determined and/or compared in a method described herein are based on relative measurements, such as ratios (e.g., serum biomarker normalized to the expression of housekeeping or otherwise generally constant biomarker). The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

The term "predictive" includes the use of a biomarker nucleic acid and/or protein status, e.g., over- or under-activity, emergence, expression, growth, remission, recurrence or resistance of tumors before, during or after therapy, for determining the likelihood of response of a cancer to combination PI3Kbeta and immune checkpoint inhibitor therapy (e.g., treatment with a combination of a PI3Kbeta-selective inhibitor, such as KIN193, and an immune checkpoint inhibitor, such as an anti-PD-1 antibody). Such predictive use of the biomarker may be confirmed by, e.g., (1) increased or decreased copy number (e.g., by FISH, FISH plus SKY, single-molecule sequencing, e.g., as described in the art at least at J. Biotechnol., 86:289-301, or qPCR), overexpression or underexpression of a biomarker nucleic acid (e.g., by ISH, Northern Blot, or qPCR), increased or decreased biomarker protein (e.g., by IHC), or increased or decreased activity, e.g., in more than about 5%, 6%, 7%, 8%, 9%, 10%, 11%, 12%, 13%, 14%, 15%, 20%, 25%, 30%, 40%, 50%, 60%, 70%, 80%, 90%, 95%, 100%, or more of assayed human cancers types or cancer samples; (2) its absolute or relatively modulated presence or absence in a biological sample, e.g., a sample containing tissue, whole blood, serum, plasma, buccal scrape, saliva, cerebrospinal fluid, urine, stool, or bone marrow, from a subject, e.g. a human, afflicted with cancer; (3) its absolute or relatively modulated presence or absence in clinical subset of patients with cancer (e.g., those responding to a particular combination PI3Kbeta and immune checkpoint inhibitor therapy or those developing resistance thereto).

The term "pre-malignant lesions" as described herein refers to a lesion that, while not cancerous, has potential for becoming cancerous. It also includes the term "pre-malignant disorders" or "potentially malignant disorders." In particular this refers to a benign, morphologically and/or histologically altered tissue that has a greater than normal risk of malignant transformation, and a disease or a patient's habit that does not necessarily alter the clinical appearance of local tissue but is associated with a greater than normal risk of precancerous lesion or cancer development in that tissue (leukoplakia, erythroplakia, erytroleukoplakia lichen planus (lichenoid reaction) and any lesion or an area which histological examination showed atypia of cells or dysplasia. In one embodiment, a metaplasia is a pre-malignant lesion.

The terms "prevent," "preventing," "prevention," "prophylactic treatment," and the like refer to reducing the probability of developing a disease, disorder, or condition in a subject, who does not have, but is at risk of or susceptible to developing a disease, disorder, or condition.

The term "probe" refers to any molecule which is capable of selectively binding to a specifically intended target molecule, for example, a nucleotide transcript or protein encoded by or corresponding to a biomarker nucleic acid. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

The term "prognosis" includes a prediction of the probable course and outcome of cancer or the likelihood of recovery from the disease. In some embodiments, the use of statistical algorithms provides a prognosis of cancer in an individual. For example, the prognosis can be surgery, development of a clinical subtype of cancer (e.g., solid tumors, such as esophageal cancer and gastric cancer), development of one or more clinical factors, or recovery from the disease.

As used herein, the term "PTEN" or "phosphatase and tensin homolog" refers to the well-known tumor suppressor, pten (see, for example, Nakanishi et al. (2014) *Int. J. Oncol.* 44:1813-1819; Xu et al. (2014) *Drug Des. Devel. Ther.* 8:1745-1751; Shi et al. (2012) *J. Cell Sci.* 125:4687-4692; Leslie (2012) *Sci. Signal.* 5:pe50; Conde-Perez and Lame (2012) *Future Oncol.* 8:1109-1120; Zhang et al. (2012) *Biomed. Pharmacother.* 66:485-490; Song et al. (2012) *Nat. Rev. Mol. Cell Biol.* 13:283-296; Aguissa-Toure and Li (2012) *Cell Mol. Life Sci.* 69:1475-1491; Wallace et al. (2011) *Cancer Res.* 71:1203-1207; Liu et al. (2008) *Anticancer Res.* 28:3613-3619; Keniry and Parsons (2008) *Oncogene* 27:5477-5485; Yin and Shen (2008) *Oncogene* 27:5443-5453; Planchon et al. (2008) *J. Cell Sci.* 121:249-253; Maehama (2007) *Biol. Pharm. Bull.* 30:1624-1727; Vazquez and Devreotes (2006) *Cell Cycle* 5:1523-1527; Steelman et al. (2004) *Exp. Opin. Ther. Targets* 8:537-550; Parsons (2004) *Semin. Cell Dev. Biol.* 15:171-176; and Maehama et al. (2004) *Biochem. Soc. Trans.* 32:343-347). The gene encoding the PTEN protein, which is a phosphatidylinositol-3,4,5-trisphosphate 3-phosphatase, is highly conserved among vertebrates and is mutated to cause deficiency of PTEN protein function (e.g., negatively regulating phosphatidyl-3,4,5-trisphosphate (PtdIns (3,4,5)P3, also known as PIP3) levels in cells and negatively regulating AKT/PKB signaling). In particular, PTEN specifically catalyzes the dephosphorylation of the 3' phosphate of the inositol ring in PIP3 to generate the bisphosphate product, PtdIns(4,5)P2 (also known as PIP2), and whose dephosphorylation inhibits the AKT/PKB signaling pathway. In addition, PTEN has phosphatase activity of proteins, such as IRS1 and disheveled, involved in cell cycle regulation (Shi et al. (2014) *Nat. Struct. Mol. Biol.* 21:522-527; Shnitsar et al. (2015) *Nat. Comm.* 6:838). In humans, the pten gene, which is located at 10q23.3, encodes several different isoforms. The protein structure of the PTEN protein is well-known and is characterized by certain domains (see, for example, Lee et al. (1999) *Cell* 99:323-334; Haynie and Xue (2015) *Prot. Sci.* 24:874-882; Campbell et al. (2003) *J. Biol. Chem.* 278:33617-33620; Iijima et al. (2004) *J. Biol. Chem.* 279:16606-16613; McConnachie et al. (2003) *Biochem. J.* 371:947-955; Rahdar et al. (2009) *Proc. Natl. Acad. Sci. USA* 106:480-485; Masson et al. (2015) *Biochem. J.* 473:135-144; Hopkins et al. (2013) *Science* 341:399-402; Liang et al. (2014) *Cell Metabol.* 19:836-848; and Malaney et al. (2013) *Mol. Biosys.* 9:877-2888). For example, in one embodiment, wild-type functional human PTEN comprises a phosphatase domain, which contains the active enzymatic site, and a C2 domain, which binds the phospholipid membrane. PTEN binds cellular membranes through both the phosphatase and C2 domains in order to bring the active site in proximity to membrane-bound PIP3 for dephosphorylation. In addition, wild-type functional human PTEN comprises, but need not comprise for functionality, several additional domains. For example, a short 10-amino acid N-terminal region (residues 6-15) called the PIP2 binding domain (PBD), which increases PTEN's affinity for the cellular membrane. Similarly, a C-terminal domain spanning residues 353-403 is constitutively phosphorylated and enhances PTEN's ability to bind lipid membranes. Finally, PTEN can be expressed as a long version adding an additional ~173 amino acids to the N-terminus.

Mutations that make PTEN deficient in cancer cause inactivation of its enzymatic activity leading to increased cellular proliferation and decreased cell death. Assays for determining PTEN activity are well-known and commercially available (see, for example, Echelon® PTEN activity ELISA catalog number K-4700; Shi et al. (2014) *Nat. Struct. Mol. Biol.* 21:522-527; and Zhang et al. (2012) *Biochem. J.* 444:457-464).

Nucleic acid and amino acid sequences for PTEN nucleic acids and protein are known in the art and are publicly available in the GenBank database maintained by the U.S. National Center for Biotechnology Information. For example, human PTEN nucleic acid and amino acid sequences are well-known and include, for example, NM_000314.6 or NM_001304717.2 (variant 1), which encodes multiple isoforms due to the use of alternative translation initiation codons. The longest isoform is known as PTEN-L or PTENalpha, is derived from the use of an upstream non-AUG (CUG) start codon to initiate with a leucine, is believed to preferentially associated with the mitochondrial inner membrane, and has an amino acid sequence that is publicly available as NP_001291646.2. Two shorter isoforms are derived from downstream AUG start codons. The most abundant isoform (PTEN), is derived from the use of the 5'-most AUG start codon and has an amino acid sequence that is publicly available as NP_000305.3. Similarly, NM_001304718.1 (variant 2) both contains and lacks alternate exons in its 5' untranslated region (UTR) as compared to variant 1. Variant 2 represents translation initiation at a downstream AUG compared to the more upstream CUG and AUG start codons, as used in variant 1. Use of the more 5' initiation codons, as used in variant 1, is associated with a truncated ORF that would render the transcript a candidate for nonsense-mediated decay (NMD). Leaky scanning may allow translation initiation at the downstream AUG to encode an isoform, whose amino acid sequence is publicly available as NP_001291647.1, which has a shorter N-terminus, compared to isoform PTEN-L and PTEN described above.

Nucleic acid and amino acid sequences of PTEN orthologs in other species are also well-known and include, for example, mouse PTEN (NM_008960.2 and NP_032986.1), monkey PTEN (NM_001260965.1 and NP_001247894.1), dog PTEN (NM_001003192.1 and NP_001003192.1), rat PTEN (NM_031606.1 and NP_113794.1), frog PTEN (NM_001123471.1 and NP_001116943.1), chicken PTEN (XM_015278701.1 and XP_015134187.1), and zebrafish PTEN (NM_001001822.2 and NP_001001822.1). It is to be noted that the term can further be used to refer to any combination of features described herein regarding PTEN. For example, any combination of class, sequence composition, percentage identify, sequence length, domain structure, functional activity, etc. can be used to describe PTEN as used according to the present invention.

The term "response to anti-cancer therapy" or "response to combination PI3Kbeta and immune checkpoint inhibitor therapy" relates to any response of the hyperproliferative disorder (e.g., cancer) to an anti-cancer agent(s) such as treatment with a combination of a PI3Kbeta-selective inhibitor, such as KIN193, and an immune checkpoint inhibitor, such as an anti-PD-1 antibody, preferably to a change in tumor mass and/or volume after initiation of neoadjuvant or adjuvant therapy. Hyperproliferative disorder response may be assessed, for example for efficacy or in a neoadjuvant or adjuvant situation, where the size of a tumor after systemic intervention can be compared to the initial size and dimensions as measured by CT, PET, mammogram, ultrasound or palpation. Responses may also be assessed by caliper measurement or pathological examination of the tumor after biopsy or surgical resection. Response may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of hyperproliferative disorder response may be done early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed. This is typically three months after initiation of neoadjuvant therapy. In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular cancer therapeutic regimen is at least 25%, 30%, 35%, 40%, 45%, 50%, 55%, 60%, 65%, 70%, 75%, 80%, 85%, or more. Additional criteria for evaluating the response to cancer therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence. For example, in order to determine appropriate threshold values, a particular cancer therapeutic regimen can be administered to a population of subjects and the outcome can be correlated to biomarker measurements that were determined prior to administration of any cancer therapy. The outcome measurement may be pathologic response to therapy given in the neoadjuvant setting. Alternatively, outcome measures, such as overall survival and disease-free survival can be monitored over a period of time for subjects following cancer therapy for which biomarker measurement values are known. In certain embodiments, the doses administered are standard doses known in the art for cancer therapeutic agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of a cancer therapy can be determined using well-known methods in the art, such as those described in the Examples section.

The term "resistance" refers to an acquired or natural resistance of a cancer sample or a mammal to a cancer therapy (i.e., being nonresponsive to or having reduced or limited response to the therapeutic treatment), such as having a reduced response to a therapeutic treatment by 25% or more, for example, 30%, 40%, 50%, 60%, 70%, 80%, or more, to 2-fold, 3-fold, 4-fold, 5-fold, 10-fold, 15-fold, 20-fold or more. The reduction in response can be measured by comparing with the same cancer sample or mammal before the resistance is acquired, or by comparing with a different cancer sample or a mammal that is known to have no resistance to the therapeutic treatment. A typical acquired resistance to chemotherapy is called "multidrug resistance." The multidrug resistance can be mediated by P-glycoprotein or can be mediated by other mechanisms, or it can occur when a mammal is infected with a multi-drug-resistant microorganism or a combination of microorganisms. The determination of resistance to a therapeutic treatment is routine in the art and within the skill of an ordinarily skilled clinician, for example, can be measured by cell proliferative assays and cell death assays as described herein as "sensitizing." In some embodiments, the term "reverses resistance" means that the use of a second agent in combination with a primary cancer therapy (e.g., chemotherapeutic or radiation therapy) is able to produce a significant decrease in tumor volume at a level of statistical significance (e.g., $p<0.05$) when compared to tumor volume of untreated tumor in the circumstance where the primary cancer therapy (e.g., chemotherapeutic or radiation therapy) alone is unable to produce a statistically significant decrease in tumor volume compared to tumor volume of untreated tumor. This generally applies to tumor volume measurements made at a time when the untreated tumor is growing log rhythmically.

The terms "response" or "responsiveness" refers to an anti-cancer response, such as in the sense of reduction of tumor size or inhibiting tumor growth. The terms can also refer to an improved prognosis, for example, as reflected by an increased time to recurrence, which is the period to first recurrence censoring for second primary cancer as a first event or death without evidence of recurrence, or an increased overall survival, which is the period from treatment to death from any cause. To respond or to have a response means there is a beneficial endpoint attained when exposed to a stimulus. Alternatively, a negative or detrimental symptom is minimized, mitigated or attenuated on exposure to a stimulus. It will be appreciated that evaluating the likelihood that a tumor or subject will exhibit a favorable response is equivalent to evaluating the likelihood that the tumor or subject will not exhibit favorable response (i.e., will exhibit a lack of response or be non-responsive).

An "RNA interfering agent" as used herein, is defined as any agent which interferes with or inhibits expression of a target biomarker gene by RNA interference (RNAi). Such RNA interfering agents include, but are not limited to, nucleic acid molecules including RNA molecules which are homologous to the target biomarker gene of the present invention, or a fragment thereof, short interfering RNA (siRNA), and small molecules which interfere with or inhibit expression of a target biomarker nucleic acid by RNA interference (RNAi).

"RNA interference (RNAi)" is an evolutionally conserved process whereby the expression or introduction of RNA of a sequence that is identical or highly similar to a target biomarker nucleic acid results in the sequence specific degradation or specific post-transcriptional gene silencing (PTGS) of messenger RNA (mRNA) transcribed from that targeted gene (see Coburn and Cullen (2002) *J. Virol.* 76:9225), thereby inhibiting expression of the target biomarker nucleic acid. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs or RNA interfering agents, to inhibit or silence the expression of target biomarker nucleic acids. As used herein, "inhibition of target biomarker nucleic acid expression" or "inhibition of marker gene expression" includes any decrease in expression or protein activity or level of the target biomarker nucleic acid or protein encoded by the target biomarker nucleic acid. The decrease may be of at least 30%, 40%, 50%, 60%, 70%, 80%, 90%, 95% or 99% or more as compared to the expression of a target biomarker nucleic acid or the activity or level of the protein encoded by a target biomarker nucleic acid which has not been targeted by an RNA interfering agent.

The term "sample" used for detecting or determining the presence or level of at least one biomarker is typically brain tissue, cerebrospinal fluid, whole blood, plasma, serum, saliva, urine, stool (e.g., feces), tears, and any other bodily fluid (e.g., as described above under the definition of "body fluids"), or a tissue sample (e.g., biopsy) such as a small intestine, colon sample, or surgical resection tissue. In certain instances, the method of the present invention further comprises obtaining the sample from the individual prior to detecting or determining the presence or level of at least one marker in the sample.

The term "selective inhibition" or "selectively inhibit" as applied to a biologically active agent refers to the agent's ability to selectively reduce the target signaling activity as compared to off-target signaling activity, via direct or interact interaction with the target. For example, an agent that selectively inhibits one isoform of PI3K over another isoform of PI3K has an activity against a first isoform that is at least 2× (times) more than the compound's activity against the second isoform (e.g., at least about 3×, 4×, 5×, 6×, 7×, 8×, 9×, 10×, 15×, 20×, 25×, 30×, 35×, 40×, 45×, 50×, 55×, 60×, 65×, 70×, 75×, 80×, 85×, 90×, 95×, 100×, 105×, 110×, 120×, 125×, 150×, 200×, 250×, 300×, 350×, 400×, 450×, 500×, 600×, 700×, 800×, 900×, 1000×, or greater, or any range in between, inclusive) (Frazzetto et al. (2008) *Biochem J.* 414:383-390). The PI3Kbeta-selective inhibitor, AZD6482, has an IC50 for PI3Kbeta of 10 nM and is 8× (IC50 80 nM), 87× (IC50 870 nM), and 109× (IC50 1090 nM) more selective toward PI3Kbeta than to PI3Kdelta, PI3Kalpha, and PI3Kgamma, respectively, as determined in cell-free assays (PCT Publ. WO 2009/093972; Ni et al. (2012) *Cancer Discov.* 2:425-433; Nylander et al. (2012) *J. Thromb. Haemost.* 10:2127-2136). The PI3Kbeta-selective inhibitor, TGC-221 (7-methyl-2-morpholino-9-(1-(phenylamino)ethyl)-4H-pyrido[1,2-a]pyrimidin-4-one) has an IC50 of 5 nM, 0.1 uM, 5 uM, and less than 10 uM for PI3Kbeta, PI3Kdelta, PI3Kalpha, and PI3Kgamma, respectively (Jackson et al. (2005) *Nat. Med.* 11:507-514). GSK2636771 (2-methyl-1-[[2-methyl-3-(trifluoromethyl) phenyl]methyl]-6-(4-morpholinyl)-1H-benzimidazole-4-carboxylic acid) is also a PI3Kbeta-selective inhibitor (Macauley et al. (2012) *Drugs Fut.* 37:451; Weigelt et al. (2013) *Clin. Cancer Res.* 19:3533-3544).

TABLE 2

IC50 values for PI3K chemical inhibitors (adapted from the World Wide Web at selleckchem.com/pathways_PI3K.html)

| | IC50 (nM) | | | | |
|---|---|---|---|---|---|
| | Pan-PI3K | PI3K alpha | PI3K beta | PI3K delta | PI3K gamma |
| Omipalisib (GSK2126458, GSK458) | | 0.019 | 0.13 | 0.024 | 0.06 |
| GSK1059615 | | 0.4 | 0.6 | 2 | 5 |
| PF-04691502 | | 1.8 | 2.1 | 1.6 | 1.9 |
| PI-103 | | 2 | 3 | 3 | 15 |
| BAY 80-6946 (Copanlisib) | | 0.469 | 3.72 | 0.7 | 6.4 |
| AZD8186 | | 35 | 4 | 17 | 675 |
| TGX-221 | | 5000 | 5 | 100 | |
| PKI-402 | | 2 | 7 | 14 | 16 |
| GDC-0032 | | 0.29 | 9.1 | 0.12 | 0.97 |
| AZD6482 (KIN-193) | | 870 | 10 | 80 | 1090 |
| VS-5584 (SB2343) | | 2.6 | 21 | 2.7 | 3 |
| Apitolisib (GDC-0980, RG7422) | | 5 | 27 | 7 | 14 |
| Pictilisib (GDC-0941) | | 3 | 33 | 3 | 75 |
| Pilaralisib (XL147) | | 39 | 36 | 36 | 23 |
| ZSTK474 | 37 | 16 | 44 | 4.6 | 49 |
| CUDC-907 | | 19 | 54 | 39 | 311 |
| BGT226 (NVP-BGT226) | | 4 | 63 | | 38 |
| BEZ235 (NVP-BEZ235, Dactolisib) | | 4 | 75 | 7 | 5 |
| Voxtalisib (SAR245409, XL765) Analogue | | 39 | 113 | 43 | 9 |
| Voxtalisib (XL765, SAR245409) | | 39 | 113 | 43 | 9 |

TABLE 2-continued

IC50 values for PI3K chemical inhibitors (adapted from the World Wide Web at selleckchem.com/pathways_PI3K.html)

| | IC50 (nM) | | | | |
|---|---|---|---|---|---|
| | Pan-PI3K | PI3K alpha | PI3K beta | PI3K delta | PI3K gamma |
| CH5132799 | | 14 | 120 | 500 | 36 |
| PF-4989216 | | 2 | 142 | 1 | 65 |
| BKM120 (NVP-BKM120, Buparlisib) | | 52 | 166 | 116 | 262 |
| TG100713 | | 165 | 215 | 24 | 50 |
| AS-605240 | | 60 | 270 | 300 | 8 |
| PIK-90 | | 11 | 350 | 58 | 18 |
| XL147 analogue | | 39 | 383 | 36 | 23 |
| PIK-294 | | | 490 | 10 | 160 |
| CAL-101 (Idelalisib, GS-1101) | | 820 | 565 | 2.5 | 89 |
| PIK-93 | | 39 | 590 | 120 | 16 |
| LY294002 | | 500 | 970 | 570 | |
| PI-3065 | | 2299 | 1078 | 15 | 27542 |
| CZC24832 | | | 1100 | 8200 | 27 |
| TG100-115 | | 1300 | 1200 | 235 | 83 |
| PIK-75 | | 5.8 | 1300 | 510 | 76 |
| Duvelisib (IPI-145, INK1197) | | 25900 | 1564 | 23 | 243 |
| AMG319 | | 33000 | 2700 | 18 | 850 |
| Quercetin | | | 5400 | 3000 | 2400 |
| PIK-293 | | 100000 | 25000 | 240 | 10000 |
| IC-87114 | | | 75000 | 500 | 29000 |
| Gedatolisib (PF-05212384, PKI-587) | | 0.4 | | | 5.4 |
| HS-173 | | 0.8 | | | |
| Alpelisib (BYL719) | | 5 | | | |
| A66 | | 32 | | | 3480 |
| AS-252424 | | 935 | | | 33 |
| YM201636 | | 3300 | | | |
| AS-604850 | | 4500 | | | 250 |
| NU7441 (KU-57788) | 5000 | | | | |
| Wortmannin | 3 | | | | |
| 3-Methyladenine (3-MA) | | | | | 60 |

The term "sensitize" means to alter cancer cells or tumor cells in a way that allows for more effective treatment of the associated cancer with a cancer therapy (e.g., anti-immune checkpoint, chemotherapeutic, and/or radiation therapy). In some embodiments, normal cells are not affected to an extent that causes the normal cells to be unduly injured by the anti-immune checkpoint therapy. An increased sensitivity or a reduced sensitivity to a therapeutic treatment is measured according to a known method in the art for the particular treatment and methods described herein below, including, but not limited to, cell proliferative assays (Tanigawa et al. (1982) *Cancer Res.* 42:2159-2164), cell death assays (Weisenthal et al. (1984) *Cancer Res.* 94:161-173; Weisenthal et al. (1985) *Cancer Treat. Rep.* 69:615-632; Weisenthal L M, In: Kaspers et al. eds. Drug Resistance in Leukemia and Lymphoma. Langhorne, P A: Harwood Academic Publishers, 1993: 415-432; Weisenthal et al. (1994) *Contrib. Gynecol. Obstet.* 19:82-90). The sensitivity or resistance may also be measured in animal by measuring the tumor size reduction over a period of time, for example, 6 month for human and 4-6 weeks for mouse. A composition or a method sensitizes response to a therapeutic treatment if the increase in treatment sensitivity or the reduction in resistance is 25% or more, for example, 30%, 40%, 50%, 60%, 70%, 80%, or more, to 2-fold, 3-fold, 4-fold, 5-fold, 10-fold, 15-fold, 20-fold or more, compared to treatment sensitivity or resistance in the absence of such composition or method. The determination of sensitivity or resistance to a therapeutic treatment is routine in the art and within the skill of an ordinarily skilled clinician. It is to be understood that any method described herein for enhancing the efficacy of a cancer therapy can be equally applied to methods for sensitizing hyperproliferative or otherwise cancerous cells (e.g., resistant cells) to the cancer therapy.

The term "specific binding" refers to an agent, such as an antibody, binding to a pre-determined target, such as an antigen. Typically, the antibody binds with an affinity ($K_D$) of approximately less than $10^{-7}$M, such as approximately less than $10^{-8}$M, $10^{-9}$M or $10^{-10}$ M or even lower when determined by surface plasmon resonance (SPR) technology in a BIACORE® assay instrument using an antigen of interest as the analyte and the antibody as the ligand, and binds to the predetermined antigen with an affinity that is at least 1.1-, 1.2-, 1.3-, 1.4-, 1.5-, 1.6-, 1.7-, 1.8-, 1.9-, 2.0-, 2.5-, 3.0-, 3.5-, 4.0-, 4.5-, 5.0-, 6.0-, 7.0-, 8.0-, 9.0-, or 10.0-fold or greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen." Selective binding is a relative term referring to the ability of an antibody to discriminate the binding of one antigen over another.

The term "synergistic effect" refers to the combined effect of two or more anti-cancer agents (e.g., treatment with a combination of a PI3Kbeta-selective inhibitor, such as KIN193, and an immune checkpoint inhibitor, such as an anti-PD-1 antibody) can be greater than the sum of the separate effects of the anti-cancer agents alone.

"Short interfering RNA" (siRNA), also referred to herein as "small interfering RNA" is defined as an agent which functions to inhibit expression of a target biomarker nucleic acid, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

In another embodiment, an siRNA is a small hairpin (also called stem loop) RNA (shRNA). In one embodiment, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) *RNA* April; 9(4):493-501 incorporated by reference herein).

RNA interfering agents, e.g., siRNA molecules, may be administered to a patient having or at risk for having cancer, to inhibit expression of a biomarker gene which is overexpressed in cancer and thereby treat, prevent, or inhibit cancer in the subject.

The term "subject" refers to any healthy animal, mammal or human, or any animal, mammal or human afflicted with a cancer, e.g., an epithelial cancer, including brain metastasis, lung, ovarian, pancreatic, liver, breast, prostate, colon carcinomas, melanoma, multiple myeloma, and the like. The term "subject" is interchangeable with "patient."

The term "survival" includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to chemotherapy, probability of survival, probability of metastasis within a given time period, and probability of tumor recurrence.

The term "therapeutic effect" refers to a local or systemic effect in animals, particularly mammals, and more particularly humans, caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically effective amount of a compound will depend on its therapeutic index, solubility, and the like. For example, certain compounds discovered by the methods of the present invention may be administered in a sufficient amount to produce a reasonable benefit/risk ratio applicable to such treatment.

The terms "therapeutically-effective amount" and "effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment. Toxicity and therapeutic efficacy of subject compounds may be determined by standard pharmaceutical procedures in cell cultures or experimental animals, e.g., for determining the $LD_{50}$ and the $ED_{50}$. Compositions that exhibit large therapeutic indices are preferred. In some embodiments, the $LD_{50}$ (lethal dosage) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more reduced for the agent relative to no administration of the agent. Similarly, the $ED_{50}$ (i.e., the concentration which achieves a half-maximal inhibition of symptoms) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. Also, Similarly, the $IC_{50}$ (i.e., the concentration which achieves half-maximal cytotoxic or cytostatic effect on cancer cells) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. In some embodiments, cancer cell growth in an assay can be inhibited by at least about 10%, 15%, 20%, 25%, 30%, 35%, 40%, 45%, 50%, 55%, 60%, 65%, 70%, 75%, 80%, 85%, 90%, 95%, or even 100%. In another embodiment, at least about a 10%, 15%, 20%, 25%, 30%, 35%, 40%, 45%, 50%, 55%, 60%, 65%, 70%, 75%, 80%, 85%, 90%, 95%, or even 100% decrease in a solid malignancy can be achieved.

In one embodiment, a therapeutically effective amount of antibody (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an antibody can include a single treatment or, preferably, can include a series of treatments. In a preferred example, a subject is treated with antibody in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody used for treatment may increase or decrease over the course of a particular treatment. Changes in dosage may result from the results of diagnostic assays.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a biomarker nucleic acid and normal post-transcriptional processing (e.g. splicing), if any, of the RNA transcript, and reverse transcription of the RNA transcript.

As used herein, the term "unresponsiveness" includes refractivity of cancer cells to therapy or refractivity of therapeutic cells, such as immune cells, to stimulation, e.g., stimulation via an activating receptor or a cytokine. Unresponsiveness can occur, e.g., because of exposure to immunosuppressants or exposure to high doses of antigen. As used herein, the term "anergy" or "tolerance" includes refractivity to activating receptor-mediated stimulation. Such refractivity is generally antigen-specific and persists after exposure to the tolerizing antigen has ceased. For example, anergy in T cells (as opposed to unresponsiveness) is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory polypeptide) results in failure to produce cytokines and, thus, failure to proliferate. Anergic T cells can, however, proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the AP1 sequence that can be found within the enhancer (Kang et al. (1992) Science 257:1134).

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |

-continued

| GENETIC CODE | |
|---|---|
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well-known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA encoding a biomarker nucleic acid (or any portion thereof) can be used to derive the polypeptide amino acid sequence, using the genetic code to translate the DNA or RNA into an amino acid sequence. Likewise, for polypeptide amino acid sequence, corresponding nucleotide sequences that can encode the polypeptide can be deduced from the genetic code (which, because of its redundancy, will produce multiple nucleic acid sequences for any given amino acid sequence). Thus, description and/or disclosure herein of a nucleotide sequence which encodes a polypeptide should be considered to also include description and/or disclosure of the amino acid sequence encoded by the nucleotide sequence. Similarly, description and/or disclosure of a polypeptide amino acid sequence herein should be considered to also include description and/or disclosure of all possible nucleotide sequences that can encode the amino acid sequence.

Finally, nucleic acid and amino acid sequence information for the loci and biomarkers of the present invention (e.g., biomarkers listed in Table 3) are well-known in the art and readily available on publicly available databases, such as the National Center for Biotechnology Information (NCBI). For example, exemplary nucleic acid and amino acid sequences derived from publicly available sequence databases are provided below and include, for example, PCT Publ. WO 2014/022759, which is incorporated herein in its entirety by this reference.

TABLE 3

SEQ ID NO: 1 Human PIK3CA cDNA Acid Sequence

```
   1 atgcctccac gaccatcatc aggtgaactg tggggcatcc acttgatgcc cccaagaatc
  61 ctagtagaat gtttactacc aaatggaatg atagtgactt tagaatgcct ccgtgaggct
 121 acattaataa ccataaagca tgaactattt aaagaagcaa gaaaataccc cctccatcaa
 181 cttcttcaag atgaatcttc ttacattttc gtaagtgtta ctcaagaagc agaaagggaa
 241 gaatttttg  atgaaacaag acgactttgt gaccttcggc tttttcaacc ctttttaaaa
 301 gtaattgaac cagtaggcaa ccgtgaagaa aagatcctca atcgagaaat tggttttgct
 361 atcggcatgc cagtgtgtga atttgatatg gttaaagatc cagaagtaca ggacttccga
 421 agaaatattc tgaacgtttg taaagaagct gtggatctta gggacctcaa ttcacctcat
 481 agtagagcaa tgtatgtcta tcctccaaat gtagaatctt caccagaatt gccaaagcac
 541 atatataata aattagataa agggcaaata atagtggtga tctgggtaat agtttctcca
 601 aataatgaca agcagaagta tactctgaaa atcaaccatg actgtgtacc agaacaagta
 661 attgctgaag caatcaggaa aaaaactcga agtatgttgc tatcctctga acaactaaaa
 721 ctctgtgttt tagaatatca gggcaagtat attttaaaag tgtgtggatg tgatgaatac
 781 ttcctagaaa aatatcctct gagtcagtat aagtatataa gaagctgtat aatgcttggg
 841 aggatgccca atttgatgtt gatggctaaa gaaagccttt attctcaact gccaatggac
 901 tgttttacaa tgccatctta ttccagacgc atttccacag ctacaccata tatgaatgga
 961 gaaacatcta caaaatccct ttgggttata aatagtgcac tcagaataaa aattctttgt
1021 gcaacctacg tgaatgtaaa tattcgagac attgataaga tctatgttcg aacaggtatc
1081 taccatggag gagaaccctt atgtgacaat gtgaacactc aaagagtacc ttgttccaat
1141 cccaggtgga atgaatggct gaattatgat atatacattc ctgatcttcc tcgtgctgct
1201 cgactttgcc tttccatttg ctctgttaaa ggccgaaagg gtgctaaaga ggaacactgt
1261 ccattggcat ggggaaatat aaacttgttt gattacacag acactctagt atctggaaaa
1321 atggctttga atctttggcc agtacctcat ggattagaag atttgctgaa ccctattggt
1381 gttactggat caaatccaaa taaagaaact ccatgcttag agttggagtt tgactggttc
1441 agcagtgtgg taaagttccc agatatgtca gtgattgaag agcatgccaa ttggtctgta
1501 tcccgagaag caggatttag ctattcccac gcaggactga gtaacagact agctagagac
1561 aatgaattaa gggaaaatga caaagaacag ctcaaagcaa tttctacacg agatcctctc
1621 tctgaaatca ctgagcagga gaaagatttt ctatggagtc acagacacta ttgtgtaact
1681 atccccgaaa ttctacccaa attgcttctg tctgttaaat ggaattctag agatgaagta
1741 gcccagatgt attgcttggt aaaagattgg cctccaatca aacctgaaca ggctatggaa
1801 cttctggact gtaattaccc agatcctatg gttcgaggtt ttgctgttcg gtgcttggaa
1861 aaatatttaa cagatgacaa actttctcag tatttaattc agctagtaca ggtcctaaaa
1921 tatgaacaat atttggataa cttgcttgtg agatttttac tgaagaaagc attgactaat
1981 caaaggattg ggcacttttt cttttggcat ttaaaatctg agatgcacaa taaaacagtt
2041 agccagaggt ttggcctgct tttggagtcc tattgtcgtg catgtgggat gtatttgaag
2101 cacctgaata ggcaagtcga ggcaatggaa aagctcatta acttaactga cattctcaaa
2161 caggagaaga aggatgaaac acaaaaggta cagatgaagt ttttagttga gcaaatgagg
2221 cgaccagatt tcatggatgc tctacagggc tttctgtctc ctctaaaccc tgctcatcaa
2281 ctaggaaacc tcaggcttga agagtgtcga attatgtcct ctgcaaaaag gccactgtgg
2341 ttgaattggg agaacccaga catcatgtca gagttactgt ttcagaacaa tgagatcatc
2401 tttaaaaatg gggatgattt acggcaagat atgctaacac ttcaaattat tcgtattatg
2461 gaaaatatct ggcaaaatca aggtcttgat cttcgaatgt taccttatgg ttgtctgtca
2521 atcggtgact gtgtgggact tattgaggtg gtgcgaaatt ctcacactat tatgcaaatt
2581 cagtgcaaag gcggcttgaa aggtgcactg cagttcaaca gccacacact acatcagtgg
2641 ctcaaagaca agaacaaagg agaaatatat gatgcagcca ttgacctgtt tacacgttca
2701 tgtgctggat actgtgtagc taccttcatt ttgggaattg gagatcgtca caatagtaac
2761 atcatggtga aagacgatgg acaactgttt catatagatt ttggacactt tttggatcac
2821 aagaagaaaa aatttggtta taaacgagaa cgtgtgccat ttgttttgac acaggatttc
2881 ttaatagtga ttagtaaagg agcccaagaa tgcacaaaga caagagaatt tgagaggttt
2941 caggagatgt gttacaaggc ttatctagct attcgacagc atgccaatct cttcataaat
3001 cttttctcaa tgatgcttgg ctctggaatg ccagaactac aatcttttga tgacattgca
3061 tacattcgaa agaccctagc cttagataaa actgagcaag aggctttgga gtatttcatg
3121 aaacaaatga atgatgcaca tcatggtggc tggacaacaa aaatggattg gatcttccac
3181 acaattaaac agcatgcatt gaactga
```

SEQ ID NO: 2 Human PIK3CA Amino Acid Sequence

```
   1 mpprpssgel wgihlmppri lvecllpngm ivtleclrea tlitikhelf kearkyplhq
  61 llqdessyif vsvtqeaere effdetrrlc dlrlfqpflk viepvgnree kilnreigfa
 121 igmpvcefdm vkdpevqdfr rnilnvckea vdlrdlnsph sramyvyppn vesspelpkh
 181 iynkldkgqi ivviwvivsp nndkqkytlk inhdcvpeqv iaeairkktr smllsseqlk
 241 lcvleyqgky ilkvcgcdey flekyplsqy kyirscimlg rmpnlmlmak eslysqlpmd
 301 cftmpsysrr istatpymng etstkslwvi nsalrikilc atyvnvnird idkiyvrtgi
 361 yhggeplcdn vntqrvpcsn prwnewlnyd iyipdlpraa rlclsicsvk grkgakeehc
 421 plawgninlf dytdtlvsgk malnlwpvph gledllnpig vtgsnpnket pclelefdwf
 481 ssvvkfpdms vieehanwsv sreagfsysh aglsnrlard nelrendkeq lkaistrdpl
 541 seiteqekdf lwshrhycvt ipeilpklll svkwnsrdev aqmyclvkdw ppikpeqame
 601 lldcnypdpm vrgfavrcle kyltddklsq yliqlvqvlk yeqyldnllv rfllkkaltn
 661 qrighfffwh lksemhnktv sqrfgllles ycracgmylk hlnrqveame klinitdilk
 721 qekkdetqkv qmkflveqmr rpdfmdalqg flspinpahq lgnlrleecr imssakrplw
 781 lnwenpdims ellfqnneii fkngddlrqd mltlqiirim eniwqnqgld lrmlpygcls
 841 igdcvgliev vrnshtimqi qckgglkgal qfnshtlhqw lkdknkgeiy daaidlftrs
 901 cagycvatfi lgigdrhnsn imvkddgqlf hidfghfldh kkkkfgykre rvpfvltqdf
 961 liviskgaqe ctktreferf qemcykayla irqhanlfin lfsmmlgsgm pelqsfddia
1021 yirktlaldk teqealeyfm kqmndahhgg wttkmdwifh tikqhaln
```

TABLE 3-continued

SEQ ID NO: 3 Mouse PIK3CA (Transcript 1) cDNA Acid Sequence

```
   1 atgcctccac gaccatcttc gggtgaactg tggggcatcc acttgatgcc cccacgaatc
  61 ctagtggaat gtttactccc caatggaatg atagtgactt tagaatgcct ccgtgaggcc
 121 acactcgtca ccatcaaaca tgaactgttc agagaggcca ggaaataccc tctccatcag
 181 cttctgcaag acgaaacttc ttacattttc gtaagtgtca cccaagaagc agaaagggaa
 241 gaatttttg atgaaacaag acgactttgt gaccttcggc tttttcaacc ctttttaaaa
 301 gttattgaac cagtaggcaa ccgtgaagaa aagatcctca atcgagaaat tggttttgtt
 361 attggcatgc cagtgtgtga atttgatatg gttaaagatc cagaagtcca agactttcga
 421 aggaacattc tgaatgtttg caaagaagct gtggacctgc gggatctcaa ctcgcctcat
 481 agcagagcaa tgtatgtcta ccctccaaat gtcgagtctt ccccagaact gccaaagcac
 541 atctacaaca agttagataa aggacaaatc atagtggtga tttgggtaat agtctctcca
 601 aacaacgaca agcagaagta cactctgaag atcaatcatg actgtgtgcc agagcaagtc
 661 attgctgaag ccatcaggaa aaagactcgg agcatgttgt tgtcctctga gcagctgaaa
 721 ctctgtgtct tagaatatca gggcaagtat attctgaaag tgtgtggctg tgacgaatac
 781 ttcctggaaa agtaccctct gagtcagtac aagtacataa gaagctgtat aatgctgggg
 841 aggatgccca acttgatgct gatggccaaa gaaagcctat actctcagct gccgattgat
 901 agcttcacca tgccgtcata ctccaggcgc atctccacag ccacacccta catgaatgga
 961 gagacatcta cgaaatccct ctgggtcata aatagtgcgc tcagaataaa aattctttgt
1021 gcaacctatg taaatgtaaa tattcgagac attgataaga tctatgttcg aacaggtatc
1081 taccatggag gagaaccctt atgtgacaat gtgaacactc aaagagtacc ttgttccaat
1141 cctaggtgga atgaatggct gaattatgat atatacattc ctgatcttcc tcgtgctgcg
1201 cgcctttgcc tttcaatctg ctctgttaaa ggccgaaagg gtgctaagga ggagcactgt
1261 ccgttggcct ggggaaacat aaacttgttt gattatacag acaccctagt gtccgggaaa
1321 atggctttga atctctggcc tgtaccgcat gggttagaag atctgctgaa ccctattggt
1381 gttactgggt caaatccaaa taaagaaact ccatgcttag agttggagtt tgattggttc
1441 agcagtgtgg tgaagtttcc agacatgtct gtgatcgaag aacatgccaa ttggtccgtg
1501 tcccgagaag ctggattcag ttactcccat acaggactga gtaacagact agccagagac
1561 aatgagttaa gagaaaatga caaggaacag ctccgagcac tttgcacccg ggacccacta
1621 tctgaaatca ctgaacaaga gaaagacttc ctatggagcc acagacacta ctgcgtaact
1681 attcctgaaa tcctacccaa attgcttctg tctgtcaagt ggaattccag agacgaagtg
1741 gcccagatgt actgcttagt aaaagattgg cctccaatca aaccagagca agccatggaa
1801 ctcctggact gtaactatcc agatcctatg gttcggagtt ttgctgttcg gtgcttagaa
1861 aaatatttaa cagatgacaa actttctcag tacctcattc aacttgtaca ggtcttaaaa
1921 tatgaacagt atttggataa cctgcttgtg agatttttac tcaagaaagc attgacaaat
1981 caaaggattg gccatttttt cttttggcat ttaaaatctg agatgcacaa taagactgtc
2041 agtcagaggt ttggcctgct attggagtcc tactgccgtg cctgtgggat gtatctgaag
2101 cacctgaaca gacaagtaga ggccatggag aagctcatca acctaacgga catccttaag
2161 caggagaaga aggatgagac acaaaaggta cagatgaagt tttggttga acagatgaga
2221 cagccagact tcatggatgc tttgcagggt tttctgtccc ctctgaatcc tgctcaccaa
2281 ctaggaaacc tcaggcttga agagtgtcga attatgtcct ctgcaaaaag gccactgtgg
2341 ttgaattggg agaacccaga catcatgtca gagctactgt ttcagaacaa tgagatcatc
2401 tttaaaaatg gcgacgactt acggcaagat atgttaaccc ttcagatcat ccgaatcatg
2461 gagaacatct ggcaaaacca aggccttgac cttcgcatgc taccttatgg ctgtctatcc
2521 attggggact gtgtgggtct catcgaggtg gtgagaaact ctcacaccat catgcaaatc
2581 cagtgcaaag gaggcctgaa gggggcgctg cagttcaaca gccacacact gcatcaatgg
2641 ctcaaggaca agaacaaggg cgagatatat gatgcagcca ttgacctgtt cactcggtcc
2701 tgcgctgggt actgcgtggc aacctttatc ttgggaattg gagaccggca caacagcaac
2761 atcatggtga aagatgacgg acagctgttt catatagatt ttgggcactt tttggatcac
2821 aagaagaaaa aatttggcta taagcgggaa cgtgtgccat ttgtgttgac acaggatttc
2881 ttgattgtga ttagtaaggg agcacaagag tacaccaaga ccagagagtt tgagaggttt
2941 caggagatgt gttacaaggc ttacctagca attcggcagc atgccaatct cttcatcaac
3001 ctttttttcaa tgatgcttgg ctctggaatg ccagaactac aatcttttga tgacattgca
3061 tatatccgaa agactctagc cttggacaaa actgagcaag aagctttgga atatttcaca
3121 aagcaaatga atgatgcaca tcatggtgga tggacgacaa aaatggattg gatcttccac
3181 accatcaagc agcatgcttt gaactga
```

SEQ ID NO: 4 Mouse PIK3CA (Isoform 1) Amino Acid Sequence

```
   1 mpprpssgel wgihlmppri lvecllpngm ivtleclrea tlvtikhelf rearkyplhq
  61 llqdetsyif vsvtqeaere effdetrrlc dlrlfqpflk viepvgnree kilnreigfv
 121 igmpvcefdm vkdpevqdfr rnilnvckea vdlrdlnsph sramyvyppn vesspelpkh
 181 iynkldkgqi ivviwvivsp nndkqkytlk inhdcvpeqv iaeairkktr smllsseqlk
 241 lcvleyqgky ilkvcgcdey flekyplsqy kyirscimlg rmpnlmlmak eslysqlpid
 301 sftmpsysrr istatpymng etstkslwvi nsalrikilc atyvnvnird idkiyvrtgi
 361 yhggeplcdn vntqrvpcsn prwnewlnyd iyipdlpraa rlclsicsvk grkgakeehc
 421 plawgninlf dytdtlvsgk malnlwpvph gledllnpig vtgsnpnket pclelefdwf
 481 ssvvkfpdms vieehanwsv sreagfsysh tglsnrlard nelrendkeq lralctrdpl
 541 seiteqekdf lwshrhycvt ipeilpklll svkwnsrdev aqmyclvkdw ppikpeqame
 601 lldcnypdpm vrsfavrcle kyltddklsq yliqlvqvlk yeqyldnllv rfllkkaltn
 661 qrighfffwh lksemhnktv sqrfgllles ycracgmylk hlnrqveame klinltdilk
 721 qekkdetqkv qmkflveqmr qpdfmdalqg flsplnpahq lgnlrleecr imssakrplw
 781 lnwenpdims ellfqnneii fkngddlrqd mltlqiirim eniwqnqgld lrmlpygcls
 841 igdcvgliev vrnshtimqi qckgglkgal qfnshtlhqw lkdknkgeiy daaidlftrs
 901 cagycvatfi lgigdrhnsn imvkddgqlf hidfghfldh kkkkfgykre rvpfvltqdf
 961 liviskgaqe ytktreferf qemcykayla irqhanlfin lfsmmlgsgm pelqsfddia
1021 yirktlaldk teqealeyft kgmndahhgg wttkmdwifh tikqhaln
```

TABLE 3-continued

SEQ ID NO: 5 Mouse PIK3CA (Transcript 2) cDNA Acid Sequence

```
   1 atgcctccac gaccatcttc gggtgaactg tggggcatcc acttgatgcc cccacgaatc
  61 ctagtggaat gtttactccc caatggaatg atagtgactt tagaatgcct ccgtgaggcc
 121 acactcgtca ccatcaaaca tgaactgttc agagaggcca ggaaataccc tctccatcag
 181 cttctgcaag acgaaacttc ttacattttc gtaagtgtca cccaagaagc agaaagggaa
 241 gaatttttg atgaaacaag acgactttgt gaccttcggc tttttcaacc ctttttaaaa
 301 gttattgaac cagtaggcaa ccgtgaagaa aagatcctca atcgagaaat tggttttgtt
 361 attggcatgc cagtgtgtga atttgatatg gttaaagatc cagaagtcca agactttcga
 421 aggaacattc tgaatgtttg caaagaagct gtggacctgc gggatctcaa ctcgcctcat
 481 agcagagcaa tgtatgtcta ccctccaaat gtcgagtctt ccccagaact gccaaagcac
 541 atctacaaca agttagataa aggacaaatc atagtggtga tttgggtaat agtctctcca
 601 aacaacgaca agcagaagta cactctgaag atcaatcatg actgtgtgcc agagcaagtc
 661 attgctgaag ccatcaggaa aaagactcgg agcatgttgt tgtcctctga gcagctgaaa
 721 ctctgtgtct tagaatatca gggcaagtat attctgaaag tgtgtggctg tgacgaatac
 781 ttcctggaaa agtaccctct gagtcagtac aagtacataa gaagctgtat aatgctgggg
 841 aggatgccca acttgatgct gatggccaaa gaaagcctat actctcagct gccgattgat
 901 agcttcacca tgccgtcata ctccaggcgc atctccacag ccacacccta catgaatgga
 961 gagacatcta cgaaatccct ctgggtcata aatagtgcgc tcagaataaa aattctttgt
1021 gcaacctatg taaatgtaaa tattcgagac attgataaga tctatgttcg aacaggtatc
1081 taccatggag gagaaccctt atgtgacaat gtgaacactc aaagagtacc ttgttccaat
1141 cctaggtgga atgaatggct gaattatgat atatacattc ctgatcttcc tcgtgctgcg
1201 cgcctttgcc tttcaatctg ctctgttaaa ggccgaaagg gtgctaagga ggagcactgt
1261 ccgttggcct ggggaaacat aaacttgttt gattatacag acaccctagt gtccgggaaa
1321 atggctttga atctctggcc tgtaccgcat gggttagaag atctgctgaa ccctattggt
1381 gttactgggt caaatccaaa taaagaaact ccatgcttag agttggagtt tgattggttc
1441 agcagtgtgg tgaagtttcc agacatgtct gtgatcgaag aacatgccaa ttggtccgtg
1501 tcccgagaag ctggattcag ttactcccat acaggactga gtaacagact agccagagac
1561 aatgagttaa gagaaaatga caaggaacag ctccgagcac tttgcacccg ggacccacta
1621 tctgaaatca ctgaacaaga gaaagacttc ctatggagcc acagacacta ctgcgtaact
1681 attcctgaaa tcctacccaa attgcttctg tctgtcaagt ggaattccag agacgaagtg
1741 gcccagatgt actgcttagt aaaagattgg cctccaatca aaccagagca agccatggaa
1801 ctcctggact gtaactatcc agatcctatg gttcggagtt ttgctgttcg gtgcttagaa
1861 aaatatttaa cagatgacaa actttctcag tacctcattc aacttgtaca ggtcttaaaa
1921 tatgaacagt atttggataa cctgcttgtg agatttttac tcaagaaagc attgacaaat
1981 caaaggattg gccatttttt cttttggcat ttaaaatctg agatgcacaa taagactgtc
2041 agtcagaggt ttggcctgct attggagtcc tactgccgtg cctgtgggat gtatctgaag
2101 cacctgaaca gacaagtaga ggccatggag aagctcatca acctaacgga catccttaag
2161 caggagaaga aggatgagac acaaaaggta cagatgaagt tttggttgga acagatgaga
2221 cagccagact tcatggatgc tttgcagggt tttctgtccc ctctgaatcc tgctcaccaa
2281 ctaggaaacc tcaggcttga agagtgtcga attatgtcct ctgcaaaaag gccactgtgg
2341 ttgaattggg agaacccaga catcatgtca gagctactgt ttcagaacaa tgagatcatc
2401 tttaaaaatg gcgacgactt acggcaagat atgttaaccc ttcagatcat ccgaatcatg
2461 gagaacatct ggcaaaacca aggccttgac cttcgcatgc taccttatgg ctgtctatcc
2521 attggggact gtgtgggtct catcgaggtg gtgagaaact ctcacaccat catgcaaatc
2581 cagtgcaaag gaggcctgaa gggggcgctg cagttcaaca gccacacact gcatcaatgg
2641 ctcaaggaca agaacaaggg cgagatatat gatgcagcca ttgacctgtt cactcggtcc
2701 tgcgctgggt actgcgtggc aacctttatc ttgggaattg gagaccggca caacagcaac
2761 atcatggtga aagatgacgg acagctgttt catatagatt ttgggcactt tttggatcac
2821 aagaagaaaa aatttggcta taagcgggaa cgtgtgccat ttgtgttgac acaggatttc
2881 ttgattgtga ttagtaaggg agcacaagag tacaccaaga ccagagagtt tgagaggttt
2941 caggagatgt gttacaaggc ttacctagca attcggcagc atgccaatct cttcatcaac
3001 ctttttttcaa tgatgcttgg ctctggaatg ccagaactac aatcttttga tgacattgca
3061 tatatccgaa agactctagc cttggacaaa actgagcaag aagctttgga atatttcaca
3121 aagcaaatga atgatgcaca tcatggtgga tggacgacaa aaatggattg gatcttccac
3181 accatcaagc agcatgcttt gaactga
```

SEQ ID NO: 6 Mouse PIK3CA (Isoform 2) Amino Acid Sequence

```
   1 mpprpssgel wgihlmppri lvecllpngm ivtleclrea tlvtikhelf rearkyplhq
  61 llgdetsyif vsvtqeaere effdetrrlc dlrlfqpflk viepvgnree kilnreigfv
 121 igmpvcefdm vkdpevqdfr rnilnvckea vdlrdlnsph sramyvyppn vesspelpkh
 181 iynkldkgqi ivviwvivsp nndkqkytlk inhdcvpeqv iaeairkktr smllsseqlk
 241 lcvleyqgky ilkvcgcdey flekyplsqy kyirscimlg rmpnlmlmak eslysqlpid
 301 sftmpsysrr istatpymng etstkslwvi nsalrikilc atyvnvnird idkiyvrtgi
 361 yhggeplcdn vntqrvpcsn prwnewlnyd iyipdlpraa rlclsicsvk grkgakeehc
 421 plawgninlf dytdtlvsgk malnlwpvph gledllnpig vtgsnpnket pclelefdwf
 481 ssvvkfpdms vieehanwsv sreagfsysh tglsnrlard nelrendkeq lralctrdpl
 541 seiteqekdf lwshrhycvt ipeilpklll svkwnsrdev aqmyclvkdw ppikpeqame
 601 lldcnypdpm vrsfavrcle kyltddklsq yliqlvqvlk yegyldnllv rfllkkaltn
 661 qrighfffwh lksemhnktv sqrfgllles ycracgmylk hlnrqveame klinitdilk
 721 qekkdetqkv qmkflveqmr qpdfmdalqg flsplnpahq lgnlrleecr imssakrplw
 781 lnwenpdims ellfqnneii fkngddlrqd mltlqiirim eniwqnqgld lrmlpygcls
 841 igdcvgliev vrnshtimqi qckgglkgal qfnshtlhqw lkdknkgeiy daaidlftrs
 901 cagycvatfi lgigdrhnsn imvkddgqlf hidfghfldh kkkkfgykre rvpfvltqdf
 961 liviskgaqe ytktreferf qemcykayla irqhanlfin lfsmmlgsgm pelqsfddia
1021 yirktlaldk teqealeyft kqmndahhgg wttkmdwifh tikqhaln
```

TABLE 3-continued

SEQ ID NO: 7 Human PIK3CB (Transcript 1) cDNA Acid Sequence

```
   1 atgtgcttca gtttcataat gcctcctgct atggcagaca tccttgacat ctgggcggtg
  61 gattcacaga tagcatctga tggctccata cctgtggatt tcctttttgcc cactgggatt
 121 tatatccagt tggaggtacc tcgggaagct accatttctt atattaagca gatgttatgg
 181 aagcaagttc acaattaccc aatgttcaac ctccttatgg atattgactc ctatatgttt
 241 gcatgtgtga atcagactgc tgtatatgag gagcttgaag atgaaacacg aagactctgt
 301 gatgtcagac cttttcttcc agttctcaaa ttagtgacaa gaagttgtga cccaggggaa
 361 aaattagact caaaaattgg agtccttata ggaaaaggtc tgcatgaatt tgattccttg
 421 aaggatcctg aagtaaatga atttcgaaga aaaatgcgca aattcagcga ggaaaaaatc
 481 ctgtcacttg tgggattgtc ttggatggac tggctaaaac aaacatatcc accagagcat
 541 gaaccatcca tccctgaaaa cttagaagat aaactttatg gggaaagct catcgtagct
 601 gttcattttg aaaactgcca ggacgtgttt agctttcaag tgtctcctaa tatgaatcct
 661 atcaaagtaa atgaattggc aatccaaaaa cgtttgacta ttcatgggaa ggaagatgaa
 721 gttagcccct atgattatgt gttgcaagtc agcgggagag tagaatatgt tttggtgat
 781 catccactaa ttcagttcca gtatatccgg aactgtgtga tgaacagagc cctgccccat
 841 tttatacttg tggaatgctg caagatcaag aaaatgtatg aacaagaaat gattgccata
 901 gaggctgcca taaatcgaaa ttcatctaat cttcctcttc cattaccacc aaagaaaaca
 961 cgaattattt ctcatgtttg ggaaaataac aaccctttcc aaattgtctt ggttaaggga
1021 aataaactta acacagagga aactgtaaaa gttcatgtca gggctggtct ttttcatggt
1081 actgagctcc tgtgtaaaac catcgtaagc tcagaggtat cagggaaaaa tgatcatatt
1141 tggaatgaac cactggaatt tgatattaat atttgtgact taccaagaat ggctcgatta
1201 tgttttgctg tttatgcagt tttggataaa gtaaaaacga agaaatcaac gaaaactatt
1261 aatccctcta aatatcagac catcaggaaa gctggaaaag tgcattatcc tgtagcgtgg
1321 gtaaatacga tggtttttga ctttaaagga caattgagaa ctggagacat aatattacac
1381 agctggtctt catttcctga tgaactcgaa gaaatgttga atccaatggg aactgttcaa
1441 acaaatccat atactgaaaa tgcaacagct ttgcatgtta aatttccaga gaataaaaaa
1501 caaccttatt attaccctcc cttcgataag attattgaaa aggcagctga gattgcaagc
1561 agtgatagtg ctaatgtgtc aagtcgaggt ggaaaaaagt ttcttcctgt attgaaagaa
1621 atcttggaca gggatcccct gtctcaactg tgtgaaaatg aaatggatct tatttggact
1681 ttgcgacaag actgccgaga gattttccca caatcactgc caaaattact gctgtcaatc
1741 aagtggaata aacttgagga tgttgctcag cttcaggcgc tgcttcagat ttggcctaaa
1801 ctgccccccc gggaggccct agagcttctg gatttcaact atccagacca gtacgttcga
1861 gaatatgctg taggctgcct gcgacagatg agtgatgaag aactttctca atatctttta
1921 caactggtgc aagtgttaaa atatgagcct tttcttgatt gtgccctctc tagattccta
1981 ttagaaagag cacttggtaa tcggaggata gggcagtttc tattttggca tcttaggtca
2041 gaagtgcaca ttcctgctgt ctcagtacaa tttggtgtca tccttgaagc atactgccgg
2101 ggaagtgtgg ggcacatgaa agtgctttct aagcaggttg aagcactcaa taagttaaaa
2161 actttaaata gtttaatcaa actgaatgcc gtgaagttaa acagagccaa agggaaggag
2221 gccatgcata cctgtttaaa acagagtgct taccgggaag ccctctctga cctgcagtca
2281 cccctgaacc catgtgttat cctctcagaa ctctatgttg aaaagtgcaa atacatggat
2341 tccaaaatga agcctttgtg gctggtatac aataacaagg tatttggtga ggattcagtt
2401 ggagtgattt ttaaaaatgg tgatgattta cgacaggata tgttgacact ccaaatgttg
2461 cgcttgatgg atttactctg gaaagaagct ggtttggatc ttcggatgtt gccttatggc
2521 tgtttagcaa caggagatcg ctctggcctc attgaagttg tgagcacctc tgaaacaatt
2581 gctgacattc agctgaacag tagcaatgtg gctgctgcag cagccttcaa caaagatgcc
2641 cttctgaact ggcttaaaga atacaactct ggggatgacc tggaccgagc cattgaggaa
2701 tttacactgt cctgtgctgg ctactgtgta gcttcttatg tccttgggat tggtgacaga
2761 catagtgaca acatcatggt caaaaaaact ggccagctct tccacattga ctttggacat
2821 attcttggaa atttcaaatc taagtttggc attaaaaggg agcgagtgcc ttttattctt
2881 acctatgatt tcatccatgt cattcaacaa ggaaaaacag gaaatacaga aaagtttggc
2941 cggttccgcc agtgttgtga ggatgcatat ctgattttac gacggcatgg gaatctcttc
3001 atcactctct ttgcgctgat gttgactgca gggcttcctg aactcacatc agtcaaagat
3061 atacagtatc ttaaggactc tcttgcatta gggaagagtg aagaagaagc actcaaacag
3121 tttaagcaaa aatttgatga ggcgctcagg gaaagctgga ctactaaagt gaactggatg
3181 gcccacacag ttcggaaaga ctacagatct taa
```

SEQ ID NO: 8 Human PIK3CB (Isoform 1) Amino Acid Sequence

```
   1 mcfsfimppa madildiwav dsqiasdgsi pvdfllptgi yiqlevprea tisyikqmlw
  61 kqvhnypmfn llmdidsymf acvnqtavye eledetrrlc dvrpflpvlk lvtrscdpge
 121 kldskigvli gkglhefdsl kdpevnefrr kmrkfseeki lslvglswmd wlkqtyppeh
 181 epsipenled klyggkliva vhfencqdvf sfqvspnmnp ikvnelaiqk rltihgkede
 241 vspydyvlqv sgrveyvfgd hpliqfqyir ncvmnralph filvecckik kmyeqemiai
 301 eaainrnssn lplplppkkt riishvwenn npfqivlvkg nklnteetvk vhvraglfhg
 361 tellcktivs sevsgkndhi wneplefdin icdlprmarl cfavyavldk vktkkstkti
 421 npskyqtirk agkvhypvaw vntmvfdfkg qlrtgdiilh swssfpdele emlnpmgtvq
 481 tnpytenata lhvkfpenkk qpyyyppfdk iiekaaeias sdsanvssrg gkkflpvlke
 541 ildrdplsql cenemdliwt lrqdcreifp qslpklllsi kwnkledvaq lqallqiwpk
 601 lpprealell dfnypdqyvr eyavgclrqm sdeelsqyll qlvqvlkyep fldcalsrfl
 661 leralgnrri gqflfwhlrs evhipaysvq fgvileaycr gsvghmkvls kqvealnklk
 721 tlnsliklna vklnrakgke amhtclkqsa yrealsdlqs plnpcvilse lyvekckymd
 781 skmkplwlvy nnkvfgedsv gvifkngddl rqdmltlqml rlmdllwkea gldlrmlpyg
 841 clatgdrsgl ievvstseti adiqlnssnv aaaaafnkda llnwlkeyns gddldraiee
 901 ftlscagycv asyvlgigdr hsdnimvkkt gqlfhidfgh ilgnfkskfg ikrervpfil
 961 tydfihviqq gktgntekfg rfrqcceday lilrrhgnlf itlfalmlta glpeltsvkd
1021 iqylkdslal gkseeealkq fkqkfdealr eswttkvnwm ahtvrkdyrs
```

TABLE 3-continued

SEQ ID NO: 9 Human PIK3CB (Transcript 2) cDNA Acid Sequence

```
   1 atgttgaatc caatgggaac tgttcaaaca aatccatata ctgaaaatgc aacagctttg
  61 catgttaaat ttccagagaa taaaaaacaa ccttattatt accctccctt cgataagagt
 121 cgaggtggaa aaaagtttct tcctgtattg aaagaaatct tggacaggga tcccttgtct
 181 caactgtgtg aaaatgaaat ggatcttatt tggactttgc gacaagactg ccgagagatt
 241 ttcccacaat cactgccaaa attactgctg tcaatcaagt ggaataaact tgaggatgtt
 301 gctcagcttc aggcgctgct tcagatttgg cctaaactgc ccccccggga ggccctagag
 361 cttctggatt tcaactatcc agaccagtac gttcgagaat atgctgtagg ctgcctgcga
 421 cagatgagtg atgaagaact ttctcaatat cttttacaac tggtgcaagt gttaaaatat
 481 gagccttttc ttgattgtgc cctctctaga ttcctattag aaagagcact tggtaatcgg
 541 aggatagggc agtttctatt ttggcatctt aggtcagaag tgcacattcc tgctgtctca
 601 gtacaatttg gtgtcatcct tgaagcatac tgccggggaa gtgtggggca catgaaagtg
 661 ctttctaagc aggttgaagc actcaataag ttaaaaactt taaatagttt aatcaaactg
 721 aatgccgtga agttaaacag agccaaaggg aaggaggcca tgcatacctg tttaaaacag
 781 agtgcttacc gggaagccct ctctgacctg cagtcacccc tgaacccatg tgttatcctc
 841 tcagaactct atgttgaaaa gtgcaaatac atggattcca aaatgaagcc tttgtggctg
 901 gtatacaata acaaggtatt tggtgaggat tcagttggag tgatttttaa aaatggtgat
 961 gatttacgac aggatatgtt gacactccaa atgttgcgct tgatggattt actctggaaa
1021 gaagctggtt tggatcttcg gatgttgcct tatggctgtt tagcaacagg agatcgctct
1081 ggcctcattg aagttgtgag cacctctgaa acaattgctg acattcagct gaacagtagc
1141 aatgtggctg ctgcagcagc cttcaacaaa gatgcccttc tgaactggct taaagaatac
1201 aactctgggg atgacctgga ccgagccatt gaggaattta cactgtcctg tgctggctac
1261 tgtgtagctt cttatgtcct tgggattggt gacagacata gtgacaacat catggtcaaa
1321 aaaactggcc agctcttcca cattgacttt ggacatattc ttggaaattt caaatctaag
1381 tttggcatta aaagggagcg agtgcctttt attcttacct atgatttcat ccatgtcatt
1441 caacaaggaa aaacaggaaa tacagaaaag tttggccggt tccgccagtg ttgtgaggat
1501 gcatatctga ttttacgacg gcatgggaat ctcttcatca ctctctttgc gctgatgttg
1561 actgcagggc ttcctgaact cacatcagtc aaagatatac agtatcttaa ggactctctt
1621 gcattaggga agagtgaaga agaagcactc aaacagttta agcaaaaatt tgatgaggcg
1681 ctcagggaaa gctggactac taaagtgaac tggatggccc acacagttcg gaaagactac
1741 agatcttaa
```

SEQ ID NO: 10 Human PIK3CB (Isoform 2) Amino Acid Sequence

```
   1 mlnpmgtvqt npytenatal hvkfpenkkq pyyyppfdks rggkkflpvl keildrdpls
  61 qlcenemdli wtlrqdcrei fpgslpklll sikwnkledv aqlqallqiw pklppreale
 121 lldfnypdqy vreyavgclr qmsdeelsqy llqlvqvlky epfldcalsr flleralgnr
 181 rigqflfwhl rsevhipavs vqfgvileay crgsvghmkv lskqvealnk lktlnslikl
 241 navklnrakg keamhtclkq sayrealsdl qspinpcvil selyvekcky mdskmkplwl
 301 vynnkvfged svgvifkngd dlrqdmltlq mlrlmdllwk eagldlrmlp ygclatgdrs
 361 glievvstse tiadiqlnss nvaaaaafnk dallnwlkey nsgddldrai eeftlscagy
 421 cvasyvlgig drhsdnimvk ktgqlfhidf ghilgnfksk fgikrervpf iltydfihvi
 481 qqgktgntek fgrfrqcced aylilrrhgn lfitlfalml taglpeltsv kdiqylkdsl
 541 algkseeeal kqfkqkfdea lreswttkvn wmahtvrkdy rs
```

SEQ ID NO: 11 Mouse PIK3CB cDNA Acid Sequence

```
   1 atgcctcctg ctatggcaga caaccttgac atctgggcag tggactcaca gattgcatcc
  61 gatggcgcca tatccgtcga tttccttctg cccaccggga tttatatcca gttggaagta
 121 cctcgggaag ctaccatttc ttatattaaa cagatgttat ggaagcaagt tcacaactac
 181 ccgatgttta acctcctcat ggacattgac tcgtatatgt ttgcatgtgt gaatcaaact
 241 gctgtatatg aggaactgga agacgaaaca cgaagacttt gtgatgtcag acctttttctt
 301 ccagttctca aactagtgac tagaagctgt gaccccgcag aaaaattgga ctcaaaaatt
 361 ggggttctta taggaaaagg tcttcatgag tttgatgcct tgaaggatcc cgaagtgaat
 421 gaatttagaa gaaaaatgcg caaattcagt gaggccaaga ttcagtctct ggtagggttg
 481 tcttggatcg actggctaaa gcacacgtat ccgcctgagc acgagccgtc cgtcctggag
 541 aacttggaag ataaacttta tggaggaaag ctggttgtgg ctgtgcactt tgaaaatagc
 601 caggatgtat ttagttttca agtgtctccc aatttgaatc ctataaaaat aaatgaattg
 661 gcaatccaga aacgcctcac tattcgtgga aaggaagatg aagctagccc ctgtgactat
 721 gtgttacagg tcagtgggag agtggagtat gtgtttggcg atcatccact aattcagttc
 781 cagtacatcc ggaattgtgt gatgaataga accctgcccc acttcatcct tgtggaatgt
 841 tgtaagatca agaaaatgta tgaacaagaa atgattgcca tagaggctgc catcaaccga
 901 aactcatcca accttcctct ccctttacca ccaaagaaaa cgcgagttat ttctcatatc
 961 tgggacaaca acaacccttt ccaaattacc ttggttaaag gaaataagct taatacagaa
1021 gaaactgtga aagttcatgt ccgagctggg ctttttcacg gaaccgagct cctgtgtaaa
1081 accgtcgtaa gctcagagat atcaggaaag aacgaccata tttggaatga acaactggaa
1141 tttgatatta atatttgtga cttaccaaga atggctcgat tatgttttgc tgtttatgca
1201 gttttggata aagtaaaaac gaagaaatca acaaagacta ttaatccctc taagtatcag
1261 accatcagga aagccgggaa agtgcattat cctgtcgcat gggtaaatac catggttttt
1321 gacttcaaag gacagctgag gtctggagac gtcatattgc atagctggtc ttcgtttcct
1381 gatgagctgg aagaaatgct gaatcccatg ggactgtgc agacgaaccc atatgctgag
1441 aacgccaccg ccttgcacat tacgttccca gagaataaga agcagccgtg ttattatccc
1501 cccttcgata agatcattga gaaggcagct gagcttgcca gcggagacag tgctaatgtg
1561 tcaagtcgtg gtggaaaaaa atttcttgct gtgctgaaag aaatcttgga cagggacccc
1621 ctgtctcagc tgtgtgagaa cgaaatggac cttatttgga ctctacggca agactgccga
1681 gaaaatttcc ctcagtcact gccaaaacta ctcttgtcaa tcaagtggaa taaacttgaa
1741 gatgttgctc agcttcaggc gctcctgcag atatggccca aactgccccc cagggaagcc
1801 ctggaactcc tggatttcaa ctatccagac cagtatgtcc gggaatacgc tgtaggctgc
```

TABLE 3-continued

```
1861 cttcgacaga tgagtgatga agaactctct cagtatcttt tacaattggt gcaagttttg
1921 aaatatgagc cttttctcga ttgtgccctc tccagattcc tattagaaag agcacttgat
1981 aatcggagga ttgggcagtt tctgttttgg catcttaggt cagaggtgca cactcctgct
2041 gtgtccgtac agtttggtgt catcctggaa gcatactgtc gaggaagcgt ggggcacatg
2101 aaagtgcttt ccaaacaggt ggaagcactc aataagttaa aaactttaaa tagcttaatc
2161 aaactgaatg cggtgaagct gagcagagct aagggaaagg aggccatgca cacgtgcctg
2221 aaacagagtg cttaccggga ggcgctctct gacctgcagt cgccgctgaa cccctgcgtc
2281 atcctctcag agctctatgt tgaaaagtgc aaatacatgg actccaagat gaagcccctg
2341 tggctggtct acagcagcag agcctttgga gaggactcgg ttggagtgat ctttaaaaat
2401 ggtgacgatt tgcggcagga catgctgacg ctgcagatgt tgcgcctgat ggatctgctt
2461 tggaaagaag ctggcttgga cctgcggatg ctcccctatg gctgcttagc aacaggagat
2521 cgctctggcc tcattgaggt tgtgagcacc tctgagacaa tcgctgacat tcagctgaac
2581 agtagtaacg tggctgccac ggcagccttc aacaaagacg cactcctgaa ctggctcaag
2641 gagtacaact ctggggatga cctggaccga gcgattgagg agtttacctt gtcctgtgct
2701 ggctactgtg tagcctctta tgtcctcggc attggtgaca ggcacagtga caacatcatg
2761 gtgaagaaaa ccggccagct cttccacata gattttgggc atattcttgg aaatttcaaa
2821 tctaaatttg gcattaaaag ggagcgagta ccttttattc ttacttatga cttcattcat
2881 gtcattcaac aaggaaaaac gggaaacact gaaaaattgg gcagattccg ccagtgctgt
2941 gaagatgcgt atctgatttt acggcggcat gggaatctct tcatcaccct gtttgccctg
3001 atgttgactg cagggctgcc tgagctcaca tcggtcaaag atatacagta tcttaaggac
3061 tcgcttgcct tagggaagag cgaggaggaa gcactgaagc agttcaagca gaagtttgac
3121 gaggccctca gggaaagctg gactactaaa gtgaactgga tggctcacac agtacggaaa
3181 gactacaggt cctag
```

SEQ ID NO: 12 Mouse PIK3CB Amino Acid Sequence

```
   1 mppamadnld iwavdsqias dgaisvdfll ptgiyiqlev preatisyik qmlwkqvhny
  61 pmfnllmdid symfacvnqt avyeeledet rrlcdvrpfl pvlklvtrsc dpaekldski
 121 gvligkglhe fdalkdpevn efrrkmrkfs eakiqslvgl swidwlkhty ppehepsvle
 181 nledklyggk lvvavhfens qdvfsfqvsp nlnpikinel aiqkrltirg kedeaspcdy
 241 vlqvsgrvey vfgdhpliqf qyirncvmnr tlphfilvec ckikkmyeqe miaieaainr
 301 nssnlplplp pkktrvishi wdnnnpfqit lvkgnklnte etvkvhvrag lfhgtellck
 361 tvvsseisgk ndhiwneqle fdinicdlpr marlcfavya vldkvktkks tktinpskyq
 421 tirkagkvhy pvawvntmvf dfkgqlrsgd vilhswssfp deleemlnpm gtvqtnpyae
 481 natalhitfp enkkqpcyyp pfdkiiekaa elasgdsanv ssrggkkfla vlkeildrdp
 541 lsqlcenemd liwtlrqdcr enfpqslpkl llsikwnkle dvaqlqallq iwpklpprea
 601 lelldfnypd qyvreyavgc lrqmsdeels qyllqlvqvl kyepfldcal srfllerald
 661 nrrigqflfw hlrsevhtpa vsvqfgvile aycrgsvghm kvlskqveal nklktlnsli
 721 klnavklsra kgkeamhtcl kqsayreals dlqsplnpcv ilselyvekc kymdskmkpl
 781 wlvyssrafg edsvgvifkn gddlrqdmlt lqmlrlmdll wkeagldlrm lpygclatgd
 841 rsglievvst setiadiqln ssnvaataaf nkdallnwlk eynsgddldr aieeftlsca
 901 gycvasyvlg igdrhsdnim vkktgqlfhi dfghilgnfk skfgikrery pfiltydfih
 961 viqqgktgnt ekfgrfrqcc edaylilrrh gnlfitlfal mltaglpelt svkdiqylkd
1021 slalgkseee alkqfkqkfd ealreswttk vnwmahtvrk dyrs
```

SEQ ID NO: 13 Human PIK3CG (Transcript 1) cDNA Acid Sequence

```
   1 atggagctgg agaactataa acagcccgtg gtgctgagag aggacaactg ccgaaggcgc
  61 cggaggatga agccgcgcag tgctgcggcc agcctgtcct ccatggagct catccccatc
 121 gagttcgtgc tgcccaccag ccagcgcaaa tgcaagagcc ccgaaacggc gctgctgcac
 181 gtggccggcc acggcaacgt ggagcagatg aaggcccagg tgtggctgcg agcgctggag
 241 accagcgtgg cggcggactt ctaccaccgg ctgggaccgc atcacttcct cctgctctat
 301 cagaagaagg ggcagtggta cgagatctac gacaagtacc aggtggtgca gactctggac
 361 tgcctgcgct actggaaggc cacgcaccgg agcccgggcc agatccacct ggtgcagcgg
 421 cacccgccct ccgaggagtc ccaagccttc cagcggcagc tcacggcgct gattggctat
 481 gacgtcactg acgtcagcaa cgtgcacgac gatgagctgg agttcacgcg ccgtggcttg
 541 gtgaccccgc gcatggcgga ggtggccagc cgcgacccca agctctacgc catgcacccg
 601 tgggtgacgt ccaagcccct cccggagtac ctgtggaaga agattgccaa caactgcatc
 661 ttcatcgtca ttcaccgcag caccaccagc cagaccatta aggtctcacc cgacgacacc
 721 cccggcgcca tcctgcagag cttcttcacc aagatggcca agaagaaatc tctgatggat
 781 attcccgaaa gccaaagcga acaggatttt gtgctgcgcg tctgtggccg ggatgagtac
 841 ctggtgggcg aaacgcccat caaaaacttc cagtgggtga ggcactgcct caagaacgga
 901 gaagagattc acgtggtact ggacacgcct ccagacccgg ccctagacga ggtgaggaag
 961 gaagagtggc cactggtgga tgactgcacg ggagtcaccg gctaccatga gcagcttacc
1021 atccacggca aggaccacga gagtgtgttc accgtgtccc tgtgggactg cgaccgcaag
1081 ttcagggtca agatcagagg cattgatatc cccgtcctgc ctcggaacac cgacctcaca
1141 gtttttgtag aggcaaacat ccagcatggg caacaagtcc tttgccaaag gagaaccagc
1201 cccaaaccct tcacagagga ggtgctgtgg aatgtgtggc ttgagttcag tatcaaaatc
1261 aaagacttgc ccaaaggggc tctactgaac ctccagatct actgcggtaa agctccagca
1321 ctgtccagca aggcctctgc agagtccccc agttctgagt ccaagggcaa agttcagctt
1381 ctctattatg tgaacctgct gctgatagac caccgtttcc tcctgcgccg tggagaatac
1441 gtcctccaca tgtggcagat atctgggaag ggagaagacc aaggaagctt caatgctgac
1501 aaactcacgt ctgcaactaa cccagacaag gagaactcaa tgtccatctc cattcttctg
1561 gacaattact gccacccgat agccctgcct aagcatcagc ccacccctga cccggaaggg
1621 gaccgggttc gagcagaaat gcccaaccag cttcgcaagc aattggaggc gatcatagcc
1681 actgatccac ttaaccctct cacagcagag gacaaagaat tgctctggca ttttagatac
1741 gaaagcctta agcacccaaa agcatatcct aagctattta gttcagtgaa atggggacag
1801 caagaaattg tggccaaaac ataccaattg ttggccagaa gggaagtctg ggatcaaagt
1861 gctttggatg ttgggttaac aatgcagctc ctggactgca acttctcaga tgaaaatgta
1921 agagccattg cagttcagaa actggagagc ttggaggacg atgatgttct gcattacctt
```

TABLE 3-continued

```
1981 ctacaattgg tccaggctgt gaaatttgaa ccataccatg atagcgccct tgccagattt
2041 ctgctgaagc gtggtttaag aaacaaaaga attggtcact ttttgttttg gttcttgaga
2101 agtgagatag cccagtccag acactatcag cagaggttcg ctgtgattct ggaagcctat
2161 ctgaggggct gtggcacagc catgctgcac gactttaccc aacaagtcca agtaatcgag
2221 atgttacaaa aagtcaccct tgatattaaa tcgctctctg ctgaaaagta tgacgtcagt
2281 tcccaagtta tttcacaact taaacaaaag cttgaaaacc tgcagaattc tcaactcccc
2341 gaaagcttta gagttccata tgatcctgga ctgaaagcag gagcgctggc aattgaaaaa
2401 tgtaaagtaa tggcctccaa gaaaaaacca ctatggcttg agtttaaatg tgccgatcct
2461 acagccctat caaatgaaac aattggaatt atctttaaac atggtgatga tctgcgccaa
2521 gacatgctta ttttacagat tctacgaatc atggagtcta tttgggagac tgaatctttg
2581 gatctatgcc tcctgccata tggttgcatt tcaactggtg acaaaatagg aatgatcgag
2641 attgtgaaag acgccacgac aattgccaaa attcagcaaa gcacagtggg caacacggga
2701 gcatttaaag atgaagtcct gaatcactgg ctcaaagaaa aatcccctac tgaagaaaag
2761 tttcaggcag cagtggagag atttgtttat tcctgtgcag gctactgtgt ggcaaccttt
2821 gttcttggaa taggcgacag acacaatgac aatattatga tcaccgagac aggaaaccta
2881 tttcatattg acttcgggca cattcttggg aattacaaaa gtttcctggg cattaataaa
2941 gagagagtgc catttgtgct aacccctgac ttcctctttg tgatgggaac ttctggaaag
3001 aagacaagcc cacacttcca gaaatttcag gacatctgtg ttaaggctta tctagccctt
3061 cgtcatcaca caaacctact gatcatcctg ttctccatga tgctgatgac aggaatgccc
3121 cagttaacaa gcaaagaaga cattgaatat atccgggatg ccctcacagt ggggaaaaat
3181 gaggaggatg ctaaaaagta ttttcttgat cagatcgaag tttgcagaga caaaggatgg
3241 actgtgcagt ttaattggtt tctacatctt gttcttggca tcaaacaagg agagaaacat
3301 tcagcctaa
```

SEQ ID NO: 14 Human PIK3CG (Isoform 1) Amino Acid Sequence

```
   1 melenykqpv vlredncrrr rrmkprsaaa slssmelipi efvlptsqrk ckspetallh
  61 vaghgnveqm kaqvwlrale tsvaadfyhr lgphhflllly qkkgqwyeiy dkyqvvqtld
 121 clrywkathr spgqihlvqr hppseesqaf qrqltaligy dvtdvsnvhd deleftrrgl
 181 vtprmaevas rdpklyamhp wvtskplpey lwkkiannci fivihrstts qtikvspddt
 241 pgailqsfft kmakkkslmd ipesqseqdf vlrvcgrdey lvgetpiknf qwvrhclkng
 301 eeihvvldtp pdpaldevrk eewplvddct gvtgyheqlt ihgkdhesvf tvslwdcdrk
 361 frvkirgidi pvlprntdlt vfveaniqhg qqvlcqrrts pkpfteevlw nvwlefsiki
 421 kdlpkgalln lqiycgkapa lsskasaesp sseskgkvql lyyvnlllid hrfllrrgey
 481 vlhmwqisgk gedqgsfnad kltsatnpdk ensmsisill dnychpialp khqptpdpeg
 541 drvraempnq lrkqleaiia tdplnpltae dkellwhfry eslkhpkayp klfssvkwgq
 601 qeivaktyql larrevwdqs aldvgltmql ldcnfsdenv raiavqkles ledddvlhyl
 661 lqlvqavkfe pyhdsalarf llkrglrnkr ighflfwflr seiaqsrhyq qrfavileay
 721 lrgcgtamlh dftqqvqvie mlqkvtldik slsaekydvs sqvisqlkqk lenlqnsqlp
 781 esfrvpydpg lkagalaiek ckvmaskkkp lwlefkcadp talsnetigi ifkhgddlrq
 841 dmlilqilri mesiwetesl dlcllpygci stgdkigmie ivkdattiak iqqstvgntg
 901 afkdevlnhw lkekspteek fqaaverfvy scagycvatf vlgigdrhnd nimitetgnl
 961 fhidfghilg nyksflgink ervpfvltpd flfvmgtsgk ktsphfqkfq dicvkaylal
1021 rhhtnlliil fsmmlmtgmp qltskediey irdaltvgkn eedakkyfld qievcrdkgw
1081 tvqfnwflhl vlgikqgekh sa
```

SEQ ID NO: 15 Human PIK3CG (Transcript 2) cDNA Acid Sequence

```
   1 atggagctgg agaactataa acagcccgtg gtgctgagag aggacaactg ccgaaggcgc
  61 cggaggatga agccgcgcag tgctgcggcc agcctgtcct ccatggagct catccccatc
 121 gagttcgtgc tgcccaccag ccagcgcaaa tgcaagagcc ccgaaacggc gctgctgcac
 181 gtggccggcc acggcaacgt ggagcagatg aaggcccagg tgtggctgcg agcgctggag
 241 accagcgtgg cggcggactt ctaccaccgg ctgggaccgc atcacttcct cctgctctat
 301 cagaagaagg ggcagtggta cgagatctac gacaagtacc aggtggtgca gactctggac
 361 tgcctgcgct actggaaggc cacgcaccgg agcccgggcc agatccacct ggtgcagcgg
 421 cacccgccct ccgaggagtc ccaagccttc cagcggcagc tcacggcgct gattggctat
 481 gacgtcactg acgtcagcaa cgtgcacgac gatgagctgg agttcacgcg ccgtggcttg
 541 gtgaccccgc gcatggcgga ggtggccagc cgcgacccca agctctacgc catgcacccg
 601 tgggtgacgt ccaagcccct cccggagtac ctgtggaaga agattgccaa caactgcatc
 661 ttcatcgtca ttcaccgcag caccaccagc cagaccatta aggtctcacc cgacgacacc
 721 cccggcgcca tcctgcagag cttcttcacc aagatggcca agaagaaatc tctgatggat
 781 attcccgaaa gccaaagcga acaggatttt gtgctgcgcg tctgtggccg ggatgagtac
 841 ctggtgggcg aaacgcccat caaaaacttc cagtgggtga ggcactgcct caagaacgga
 901 gaagagattc acgtggtact ggacacgcct ccagacccgg ccctagacga ggtgaggaag
 961 gaagagtggc cactggtgga tgactgcacg ggagtcaccg gctaccatga gcagcttacc
1021 atccacggca aggaccacga gagtgtgttc accgtgtccc tgtgggactg cgaccgcaag
1081 ttcaggtca agatcagagg cattgatatc cccgtcctgc ctcggaacac cgacctcaca
1141 gtttttgtag aggcaaacat ccagcatggg caacaagtcc tttgccaaag gagaaccagc
1201 cccaaaccct tcacagagga ggtgctgtgg aatgtgtggc ttgagttcag tatcaaaatc
1261 aaagacttgc ccaaaggggc tctactgaac ctccagatct actgcggtaa agctccagca
1321 ctgtccagca aggcctctgc agagtccccc agttctgagt ccaagggcaa agttcagctt
1381 ctctattatg tgaacctgct gctgatagac caccgtttcc tcctgcgccg tggagaatac
1441 gtcctccaca tgtggcagat atctgggaag ggagaagacc aaggaagctt caatgctgac
1501 aaactcacgt ctgcaactaa cccagacaag gagaactcaa tgtccatctc cattcttctg
1561 gacaattact gccacccgat agccctgcct aagcatcagc ccacccctga cccggaaggg
1621 gaccgggttc gagcagaaat gcccaaccag cttcgcaagc aattggaggc gatcatagcc
1681 actgatccac ttaaccctct cacagcagag gacaaagaat tgctctggca ttttagatac
1741 gaaagcctta agcacccaaa agcatatcct aagctattta gttcagtgaa atggggacag
1801 caagaaattg tggccaaaac ataccaattg ttggccagaa gggaagtctg ggatcaaagt
1861 gctttggatg ttgggttaac aatgcagctc ctggactgca acttctcaga tgaaaatgta
```

TABLE 3-continued

```
1921 agagccattg cagttcagaa actggagagc ttggaggacg atgatgttct gcattacctt
1981 ctacaattgg tccaggctgt gaaatttgaa ccataccatg atagcgccct tgccagattt
2041 ctgctgaagc gtggtttaag aaacaaaaga attggtcact tttgttttg gttcttgaga
2101 agtgagatag cccagtccag acactatcag cagaggttcg ctgtgattct ggaagcctat
2161 ctgaggggct gtggcacagc catgctgcac gactttaccc aacaagtcca agtaatcgag
2221 atgttacaaa aagtcaccct tgatattaaa tcgctctctg ctgaaaagta tgacgtcagt
2281 tcccaagtta tttcacaact taaacaaaag cttgaaaacc tgcagaattc tcaactcccc
2341 gaaagcttta gagttccata tgatcctgga ctgaaagcag gagcgctggc aattgaaaaa
2401 tgtaaagtaa tggcctccaa gaaaaaacca ctatggcttg agtttaaatg tgccgatcct
2461 acagccctat caaatgaaac aattggaatt atctttaaac atggtgatga tctgcgccaa
2521 gacatgctta ttttacagat tctacgaatc atggagtcta tttgggagac tgaatctttg
2581 gatctatgcc tcctgccata tggttgcatt tcaactggtg acaaaatagg aatgatcgag
2641 attgtgaaag acgccacgac aattgccaaa attcagcaaa gcacagtggg caacacggga
2701 gcatttaaag atgaagtcct gaatcactgg ctcaaagaaa aatcccctac tgaagaaaag
2761 tttcaggcag cagtggagag atttgtttat tcctgtgcag gctactgtgt ggcaaccttt
2821 gttcttggaa taggcgacag acacaatgac aatattatga tcaccgagac aggaaaccta
2881 tttcatattg acttcgggca cattcttggg aattacaaaa gtttcctggg cattaataaa
2941 gagagagtgc catttgtgct aacccctgac ttcctctttg tgatgggaac ttctggaaag
3001 aagacaagcc cacacttcca gaaatttcag gacatctgtg ttaaggctta tctagccctt
3061 cgtcatcaca caaacctact gatcatcctg ttctccatga tgctgatgac aggaatgccc
3121 cagttaacaa gcaaagaaga cattgaatat atccgggatg ccctcacagt ggggaaaaat
3181 gaggaggatg ctaaaaagta ttttcttgat cagatcgaag tttgcagaga caaaggatgg
3241 actgtgcagt ttaattggtt tctacatctt gttcttggca tcaaacaagg agagaaacat
3301 tcagcctaa
```

SEQ ID NO: 16 Human PIK3CG (Isoform 2) Amino Acid Sequence

```
   1 melenykqpv vlredncrrr rrmkprsaaa slssmelipi efvlptsqrk ckspetallh
  61 vaghgnveqm kaqvwlrale tsvaadfyhr lgphhfllly qkkgqwyeiy dkyqvvqtld
 121 clrywkathr spgqihlvqr hppseesqaf qrqltaligy dvtdvsnvhd deleftrrgl
 181 vtprmaevas rdpklyamhp wvtskplpey lwkkiannci fivihrstts qtikvspddt
 241 pgailqsfft kmakkkslmd ipesqseqdf vlrvcgrdey lvgetpiknf qwvrhclkng
 301 eeihvvldtp pdpaldevrk eewplvddct gvtgyheqlt ihgkdhesvf tvslwdcdrk
 361 frvkirgidi pvlprntdlt vfveaniqhg qqvlcqrrts pkpfteevlw nvwlefsiki
 421 kdlpkgalln lqiycgkapa lsskasaesp sseskgkvql lyyvnlllid hrfllrrgey
 481 vlhmwqisgk gedqgsfnad kltsatnpdk ensmsisill dnychpialp khqptpdpeg
 541 drvraempnq lrkqleaiia tdplnpltae dkellwhfry eslkhpkayp klfssvkwgq
 601 qeivaktyql larrevwdqs aldvgltmql ldcnfsdenv raiavqkles ledddvlhyl
 661 lqlvqavkfe pyhdsalarf llkrglrnkr ighflfwflr seiaqsrhyq qrfavileay
 721 lrgcgtamlh dftqqvqvie mlqkvtldik slsaekydvs sqvisqlkqk lenlqnsqlp
 781 esfrvpydpg lkagalaiek ckvmaskkkp lwlefkcadp talsnetigi ifkhgddlrq
 841 dmlilqilri mesiwetesl dlcllpygci stgdkigmie ivkdattiak iqqstvgntg
 901 afkdevlnhw lkekspteek fqaaverfvy scagycvatf vlgigdrhnd nimitetgnl
 961 fhidfghilg nyksflgink ervpfvltpd flfvmgtsgk ktsphfqkfq dicvkaylal
1021 rhhtnlliil fsmmlmtgmp qltskediey irdaltvgkn eedakkyfld qievcrdkgw
1081 tvqfnwflhl vlgikqgekh sa
```

SEQ ID NO: 17 Human PIK3CG (Transcript 3) cDNA Acid Sequence

```
   1 atggagctgg agaactataa acagcccgtg gtgctgagag aggacaactg ccgaaggcgc
  61 cggaggatga agccgcgcag tgctgcggcc agcctgtcct ccatggagct catccccatc
 121 gagttcgtgc tgcccaccag ccagcgcaaa tgcaagagcc ccgaaacggc gctgctgcac
 181 gtggccggcc acggcaacgt ggagcagatg aaggcccagg tgtggctgcg agcgctggag
 241 accagcgtgg cggcggactt ctaccaccgg ctgggaccgc atcacttcct cctgctctat
 301 cagaagaagg ggcagtggta cgagatctac gacaagtacc aggtggtgca gactctggac
 361 tgcctgcgct actggaaggc cacgcaccgg agcccgggcc agatccacct ggtgcagcgg
 421 cacccgccct ccgaggagtc ccaagccttc cagcggcagc tcacggcgct gattggctat
 481 gacgtcactg acgtcagcaa cgtgcacgac gatgagctgg agttcacgcg ccgtggcttg
 541 gtgaccccgc gcatggcgga ggtggccagc cgcgacccca agctctacgc catgcacccg
 601 tgggtgacgt ccaagcccct cccggagtac ctgtggaaga agattgccaa caactgcatc
 661 ttcatcgtca ttcaccgcag caccaccagc cagaccatta aggtctcacc cgacgacacc
 721 cccggcgcca tcctgcagag cttcttcacc aagatggcca agaagaaatc tctgatggat
 781 attcccgaaa gccaaagcga acaggatttt gtgctgcgcg tctgtggccg ggatgagtac
 841 ctggtgggcg aaacgcccat caaaaacttc cagtgggtga ggcactgcct caagaacgga
 901 gaagagattc acgtggtact ggacacgcct ccagacccgg ccctagacga ggtgaggaag
 961 gaagagtggc cactggtgga tgactgcacg ggagtcaccg gctaccatga gcagcttacc
1021 atccacggca aggaccacga gagtgtgttc accgtgtccc tgtgggactg cgaccgcaag
1081 ttcagggtca agatcagagg cattgatatc cccgtcctgc ctcggaacac cgacctcaca
1141 gtttttgtag aggcaaacat ccagcatggg caacaagtcc tttgccaaag gagaaccagc
1201 cccaaaccct tcacagagga ggtgctgtgg aatgtgtggc ttgagttcag tatcaaaatc
1261 aaagacttgc ccaaaggggc tctactgaac ctccagatct actgcggtaa agctccagca
1321 ctgtccagca aggcctctgc agagtccccc agttctgagt ccaagggcaa agttcagctt
1381 ctctattatg tgaacctgct gctgatagac caccgtttcc tcctgcgccg tggagaatac
1441 gtcctccaca tgtggcagat atctgggaag ggagaagacc aaggaagctt caatgctgac
1501 aaactcacgt ctgcaactaa cccagacaag gagaactcaa tgtccatctc cattcttctg
1561 gacaattact gccacccgat agccctgcct aagcatcagc ccacccctga cccggaaggg
1621 gaccgggttc gagcagaaat gcccaaccag cttcgcaagc aattggaggc gatcatagcc
1681 actgatccac ttaaccctct cacagcagag gacaaagaat tgctctggca ttttagatac
1741 gaaagcctta agcacccaaa agcatatcct aagctattta gttcagtgaa atggggacag
1801 caagaaattg tggccaaaac ataccaattg ttggccagaa gggaagtctg ggatcaaagt
```

TABLE 3-continued

```
1861 gctttggatg ttgggttaac aatgcagctc ctggactgca acttctcaga tgaaaatgta
1921 agagccattg cagttcagaa actggagagc ttggaggacg atgatgttct gcattacctt
1981 ctacaattgg tccaggctgt gaaatttgaa ccataccatg atagcgccct tgccagattt
2041 ctgctgaagc gtggtttaag aaacaaaaga attggtcact tttttgtttttg gttcttgaga
2101 agtgagatag cccagtccag acactatcag cagaggttcg ctgtgattct ggaagcctat
2161 ctgaggggct gtggcacagc catgctgcac gactttaccc aacaagtcca agtaatcgag
2221 atgttacaaa aagtcaccct tgatattaaa tcgctctctg ctgaaaagta tgacgtcagt
2281 tcccaagtta tttcacaact taaacaaaag cttgaaaacc tgcagaattc tcaactcccc
2341 gaaagcttta gagttccata tgatcctgga ctgaaagcag gagcgctggc aattgaaaaa
2401 tgtaaagtaa tggcctccaa gaaaaaacca ctatggcttg agtttaaatg tgccgatcct
2461 acagccctat caaatgaaac aattggaatt atctttaaac atggtgatga tctgcgccaa
2521 gacatgctta ttttacagat tctacgaatc atggagtcta tttgggagac tgaatctttg
2581 gatctatgcc tcctgccata tggttgcatt tcaactggtg acaaaatagg aatgatcgag
2641 attgtgaaag acgccacgac aattgccaaa attcagcaaa gcacagtggg caacacggga
2701 gcatttaaag atgaagtcct gaatcactgg ctcaaagaaa aatcccctac tgaagaaaag
2761 tttcaggcag cagtggagag atttgtttat tcctgtgcag gctactgtgt ggcaaccttt
2821 gttcttggaa taggcgacag acacaatgac aatattatga tcaccgagac aggaaaccta
2881 tttcatattg acttcgggca cattcttggg aattacaaaa gtttcctggg cattaataaa
2941 gagagagtgc catttgtgct aacccctgac ttcctctttg tgatgggaac ttctggaaag
3001 aagacaagcc cacacttcca gaaatttcag gacatctgtg ttaaggctta tctagccctt
3061 cgtcatcaca caaacctact gatcatcctg ttctccatga tgctgatgac aggaatgccc
3121 cagttaacaa gcaaagaaga cattgaatat atccgggatg ccctcacagt ggggaaaaat
3181 gaggaggatg ctaaaaagta ttttcttgat cagatcgaag tttgcagaga caaaggatgg
3241 actgtgcagt ttaattggtt tctacatctt gttcttggca tcaaacaagg agagaaacat
3301 tcagcctaa
```

SEQ ID NO: 18 Human PIK3CG (Isoform 3) Amino Acid Sequence

```
   1 melenykqpv vlredncrrr rrmkprsaaa slssmelipi efvlptsqrk ckspetallh
  61 vaghgnveqm kaqvwlrale tsvaadfyhr lgphhfllly qkkgqwyeiy dkyqvvqtld
 121 clrywkathr spgqihlvqr hppseesqaf qrqltaligy dvtdvsnvhd deleftrrgl
 181 vtprmaevas rdpklyamhp wvtskplpey lwkkiannci fivihrstts qtikvspddt
 241 pgailqsfft kmakkkslmd ipesqseqdf vlrvcgrdey lvgetpiknf qwvrhclkng
 301 eeihvvldtp pdpaldevrk eewplvddct gvtgyheqlt ihgkdhesvf tvslwdcdrk
 361 frvkirgidi pvlprntdlt vfveaniqhg qqvlcqrrts pkpfteevlw nvwlefsiki
 421 kdlpkgalln lqiycgkapa lsskasaesp sseskgkvql lyyvnlllid hrfllrrgey
 481 vlhmwqisgk gedqgsfnad kltsatnpdk ensmsisill dnychpialp khqptpdpeg
 541 drvraempnq lrkqleaiia tdplnpltae dkellwhfry eslkhpkayp klfssvkwgq
 601 qeivaktyql larrevwdqs aldvgltmql ldcnfsdenv raiavqkles ledddvlhyl
 661 lqlvqavkfe pyhdsalarf llkrglrnkr ighflfwflr seiaqsrhyq qrfavileay
 721 lrgcgtamlh dftqqvqvie mlqkvtldik slsaekydvs sqvisqlkqk lenlqnsqlp
 781 esfrvpydpg lkagalaiek ckvmaskkkp lwlefkcadp talsnetigi ifkhgddlrq
 841 dmlilqilri mesiwetesl dlcllpygci stgdkigmie ivkdattiak iqqstvgntg
 901 afkdevlnhw lkekspteek fqaaverfvy scagycvatf vlgigdrhnd nimitetgnl
 961 fhidfghilg nyksflgink ervpfvltpd flfvmgtsgk ktsphfqkfq dicvkaylal
1021 rhhtnllliil fsmmlmtgmp qltskediey irdaltvgkn eedakkyfld qievcrdkgw
1081 tvqfnwflhl vlgikqgekh sa
```

SEQ ID NO: 19 Mouse PIK3CG (Transcript 1) cDNA Acid Sequence

```
   1 atggagctgg agaactatga acaaccggtg gttctaagag aggacaacct ccgccggcgc
  61 cggaggatga agccacgcag cgcagcaggc agcctgtctt ccatggagct catccccatt
 121 gagttcgtac tgcccaccag ccagcgcatc agcaagactc cagaaacagc gctgctgcat
 181 gtggctggcc atggcaatgt ggaacagatg aaagctcagg tgtggctgcg cgcactggag
 241 accagtgtgg ctgcggagtt ctaccaccga ttgggcccgg accaattcct cctgctctac
 301 cagaagaaag gacaatggta tgagatctat gacaggtacc aagtggtgca gaccctagac
 361 tgcctgcatt actggaagtt gatgcacaag agccctggcc agatccacgt ggtacagcga
 421 cacgtacctt ctgaggagac cttggctttc cagaagcagc tcacctccct gattggctat
 481 gacgtcactg acatcagcaa tgtgcacgat gatgagctag agttcactcg ccgccgtctg
 541 gttacgcccc gcatggctga agtggctggc cgggatgcca aactctatgc tatgcaccct
 601 tgggtaacgt ccaaacctct cccagactac ctgtcaaaaa agattgccaa caactgcatc
 661 ttcatcgtca tccaccgcgg taccaccagc caaaccatca aggtctccgc agatgatact
 721 cctggtacca tcctccagag cttcttcacc aagatggcca agaagaagtc cctaatgaat
 781 atctcagaaa gtcaaagtga gcaggatttt gtattgcggg tttgtggccg cgatgagtac
 841 ctggtgggtg aaacacccct caaaaatttc cagtgggtga ggcagtgcct caagaacgga
 901 gatgaaatac acctggtgct cgacacgcct ccagacccag cccttgatga ggtgaggaag
 961 gaagaatggc cgctggtgga tgactgcact ggagtcaccg gctaccacga gcagctgacc
1021 atccatggca aggaccacga gagtgtgttc acagtgtctt tgtgggactg cgaccgaaag
1081 ttcagggtca agatcagagg cattgatatc cctgtcctgc ctcggaacac cgacctcact
1141 gtgtttgtgg aagcgaacat ccagcacggg caacaagtcc tctgccaaag gagaaccagc
1201 cctaagccct tcgcagaaga ggtactctgg aatgtgtggc tggagtttgg catcaaaatc
1261 aaagacttgc ccaaaggggc tctattgaac ctacagatct actgctgcaa aaccccatca
1321 ctgtccagca aggcttctgc agagactcca ggctccgagt ccaagggcaa agcccagctt
1381 ctctattacg tgaacttgct gttaatagac caccgtttcc tcctccgcca cggggactat
1441 gtgctccaca tgtggcagat atctggcaag gcagaggagc agggcagctt caatgctgac
1501 aagctcacat ccgcaaccaa tcctgacaag gagaactcaa tgtccatttc catcctgctg
1561 gacaattact gtcaccccat agctttgcct aagcaccggc ccacccctga cccagaggga
1621 gacagggttc gggctgaaat gcccaatcag cttcgaaagc aattggaggc gatcatagcc
1681 acagatccac ttaacccccct cacagcagag gacaaagaat tgctctggca ttttcgatat
1741 gaaagcctga agcatccgaa ggcttaccct aagctattca gctcagtgaa atgggggcag
```

TABLE 3-continued

```
1801 caagaaattg ttgccaaaac gtaccagctg ttagccagaa gggagatctg ggatcaaagt
1861 gctttggacg ttggcttaac catgcagctc ctggactgca acttttcaga cgagaatgtc
1921 cgggccattg cagttcagaa actggagagc ttagaggacg atgacgtttt acattacctt
1981 ctccagctgg tacaggctgt gaaatttgaa ccgtaccacg acagtgcgct ggccagattc
2041 ctgctgaagc gtggcttgag gaacaaaaga atcggtcact tcttgttctg gttcctgcga
2101 agtgagatcg cacagtccag acactatcag cagaggttcg ctgtgatcct ggaggcgtac
2161 ctgcgaggct gtggcacagc catgttgcag gacttcacac agcaggtcca tgtgattgag
2221 atgttacaga aagtcaccat tgatattaaa tcgctctcgg cagagaagta tgacgtcagt
2281 tcccaagtta tttcacagct taagcaaaag cttgaaagcc ttcagaactc caatctcccc
2341 gagagcttta gagttcccta tgatcctgga ctaaaagccg gtaccctggt gatcgagaaa
2401 tgcaaagtga tggcctccaa gaagaagccc ctgtggcttg agtttaagtg tgctgatccc
2461 acagtcctat ccaacgaaac cattggaatc atctttaaac atggtgatga tctgcgccaa
2521 gacatgttga tcttgcagat tctacgcatc atggagtcca tttgggagac tgaatctctg
2581 gacctgtgcc ttctgcctta cggttgcatc tcaactggtg acaaaatagg aatgatcgag
2641 attgtaaagg atgccacaac gatcgctcaa attcagcaaa gcacagtggg taacacgggg
2701 gcattcaaag atgaagtcct gaatcactgg ctcaaggaaa aatgtcctat tgaagaaaag
2761 tttcaggccg cagtggaaag gtttgtttac tcctgtgcag gctactgtgt ggccacattt
2821 gttcttggga tcggtgacag gcacaacgac aacattatga tctcagagac aggaaaccta
2881 tttcatatag acttcggaca cattcttggg aattacaaga gtttcctggg catcaataaa
2941 gagagagtgc ccttcgtcct aaccccagac ttcttgtttg tgatgggatc ttctggaaaa
3001 aagacaagtc cacacttcca gaaattccag gatgtctgtg ttagagctta cctagctctt
3061 cgccatcaca caaacctgtt gatcatcttg ttctccatga tgctgatgac aggaatgccc
3121 cagctgacaa gcaaagagga cattgaatat atccgggatg ccctcaccgt gggaaaaagc
3181 gaggaggacg ctaagaaata tttccttgat cagatcgaag tctgcagaga caaaggatgg
3241 actgtgcagt ttaactggtt cctacatctt gttcttggca tcaaacaagg agaaaagcac
3301 tccgcttga
```

SEQ ID NO: 20 Mouse PIK3CG (Isoform 1) Amino Acid Sequence

```
   1 melenyeqpv vlrednlrrr rrmkprsaag slssmelipi efvlptsqri sktpetallh
  61 vaghgnveqm kaqvwlrale tsvaaefyhr lgpdqflllу qkkgqwyeiy dryqvvqtld
 121 clhywklmhk spgqihvvqr hvpseetlaf qkqltsligy dvtdisnvhd deleftrrrl
 181 vtprmaevag rdaklyamhp wvtskplpdy lskkiannci fivihrgtts qtikvsaddt
 241 pgtilqsfft kmakkkslmn isesqseqdf vlrvcgrdey lvgetplknf qwvrqclkng
 301 deihlvldtp pdpaldevrk eewplvddct gvtgyheqlt ihgkdhesvf tvslwdcdrk
 361 frvkirgidi pvlprntdlt vfveaniqhg qqvlcqrrts pkpfaeevlw nvwlefgiki
 421 kdlpkgalln lqiyccktps lsskasaetp gseskgkaql lyyvnllliid hrfllrhgdy
 481 vlhmwqisgk aeeqgsfnad kltsatnpdk ensmsisill dnychpialp khrptpdpeg
 541 drvraempnq lrkqleaiia tdplnpltae dkellwhfry eslkhpkayp klfssvkwgq
 601 qeivaktyql larreiwdqs aldvgltmql ldcnfsdenv raiavqkles ledddvlhyl
 661 lqlvqavkfe pyhdsalarf llkrglrnkr ighflfwflr seiaqsrhyq qrfavileay
 721 lrgcgtamlq dftqqvhvie mlqkvtidik slsaekydvs sqvisqlkqk leslqnsnlp
 781 esfrvpydpg lkagtlviek ckvmaskkkp lwlefkcadp tvlsnetigi ifkhgddlrq
 841 dmlilqilri mesiwetesl dlcllpygci stgdkigmie ivkdattiaq iqqstvgntg
 901 afkdevlnhw lkekcpieek fqaaverfvy scagycvatf vlgigdrhnd nimisetgnl
 961 fhidfghilg nyksflgink ervpfvltpd flfvmgssgk ktsphfqkfq dvcvraylal
1021 rhhtnlliil fsmmlmtgmp qltskediey irdaltvgks eedakkyfld qievcrdkgw
1081 tvqfnwflhl vlgikqgekh sa
```

SEQ ID NO: 21 Mouse PIK3CG (Transcript 2) cDNA Acid Sequence

```
   1 atggagctgg agaactatga acaaccggtg gttctaagag aggacaacct ccgccggcgc
  61 cggaggatga agccacgcag cgcagcaggc agcctgtctt ccatggagct catccccatt
 121 gagttcgtac tgcccaccag ccagcgcatc agcaagactc cagaaacagc gctgctgcat
 181 gtggctggcc atggcaatgt ggaacagatg aaagctcagg tgtggctgcg cgcactggag
 241 accagtgtgg ctgcggagtt ctaccaccga ttgggcccgg accaattcct cctgctctac
 301 cagaagaaag gacaatggta tgagatctat gacaggtacc aagtggtgca gaccctagac
 361 tgcctgcatt actggaagtt gatgcacaag agccctggcc agatccacgt ggtacagcga
 421 cacgtacctt ctgaggagac cttggctttc cagaagcagc tcacctccct gattggctat
 481 gacgtcactg acatcagcaa tgtgcacgat gatgagctag agttcactcg ccgccgtctg
 541 gttacgcccc gcatggctga agtggctggc cgggatgcca aactctatgc tatgcaccct
 601 tgggtaacgt ccaaacctct cccagactac ctgtcaaaaa agattgccaa caactgcatc
 661 ttcatcgtca tccaccgcgg taccaccagc caaaccatca aggtctccgc agatgatact
 721 cctggtacca tcctccagag cttcttcacc aagatggcca agaagaagtc cctaatgaat
 781 atctcagaaa gtcaaagtga gcaggatttt gtattgcggg tttgtggccg cgatgagtac
 841 ctggtgggtg aaacacccct caaaaatttc cagtgggtga ggcagtgcct caagaacgga
 901 gatgaaatac acctggtgct cgacacgcct ccagacccag cccttgatga ggtgaggaag
 961 gaagaatggc cgctggtgga tgactgcact ggagtcaccg gctaccacga gcagctgacc
1021 atccatggca aggaccacga gagtgtgttc acagtgtctt tgtgggactg cgaccgaaag
1081 ttcagggtca agatcagagg cattgatatc cctgtcctgc ctcggaacac cgacctcact
1141 gtgtttgtgg aagcgaacat ccagcacggg caacaagtcc tctgccaaag gagaaccagc
1201 cctaagccct tcgcagaaga ggtactctgg aatgtgtggc tggagtttgg catcaaaatc
1261 aaagacttgc ccaaaggggc tctattgaac ctacagatct actgctgcaa aaccccatca
1321 ctgtccagca aggcttctgc agagactcca ggctccgagt ccaagggcaa agcccagctt
1381 ctctattacg tgaacttgct gttaatagac caccgtttcc tcctccgcca cggggactat
1441 gtgctccaca tgtggcagat atctggcaag gcagaggagc agggcagctt caatgctgac
1501 aagctcacat ccgcaaccaa tcctgacaag gagaactcaa tgtccatttc catcctgctg
1561 gacaattact gtcaccccat agctttgcct aagcaccggc ccacccctga cccagaggga
1621 gacagggttc gggctgaaat gcccaatcag cttcgaaagc aattggaggc gatcatagcc
1681 acagatccac ttaaccccct cacagcagag gacaaagaat tgctctggca ttttcgatat
```

TABLE 3-continued

```
1741 gaaagcctga agcatccgaa ggcttaccct aagctattca gctcagtgaa atgggggcag
1801 caagaaattg ttgccaaaac gtaccagctg ttagccagaa gggagatctg ggatcaaagt
1861 gctttggacg ttggcttaac catgcagctc ctggactgca acttttcaga cgagaatgtc
1921 cgggccattg cagttcagaa actggagagc ttagaggacg atgacgtttt acattacctt
1981 ctccagctgg tacaggctgt gaaatttgaa ccgtaccacg acagtgcgct ggccagattc
2041 ctgctgaagc gtggcttgag gaacaaaaga atcggtcact tcttgttctg gttcctgcga
2101 agtgagatcg cacagtccag acactatcag cagaggttcg ctgtgatcct ggaggcgtac
2161 ctgcgaggct gtggcacagc catgttgcag gacttcacac agcaggtcca tgtgattgag
2221 atgttacaga aagtcaccat tgatattaaa tcgctctcgg cagagaagta tgacgtcagt
2281 tcccaagtta tttcacagct taagcaaaag cttgaaagcc ttcagaactc caatctcccc
2341 gagagcttta gagttcccta tgatcctgga ctaaaagccg gtaccctggt gatcgagaaa
2401 tgcaaagtga tggcctccaa gaagaagccc ctgtggcttg agtttaagtg tgctgatccc
2461 acagtcctat ccaacgaaac cattggaatc atctttaaac atggtgatga tctgcgccaa
2521 gacatgttga tcttgcagat tctacgcatc atggagtcca tttgggagac tgaatctctg
2581 gacctgtgcc ttctgcctta cggttgcatc tcaactggtg acaaaatagg aatgatcgag
2641 attgtaaagg atgccacaac gatcgctcaa attcagcaaa gcacagtggg taacacgggg
2701 gcattcaaag atgaagtcct gaatcactgg ctcaaggaaa aatgtcctat tgaagaaaag
2761 tttcaggccg cagtggaaag gtttgtttac tcctgtgcag gctactgtgt ggccacattt
2821 gttcttggga tcggtgacag gcacaacgac aacattatga tctcagagac aggaaaccta
2881 tttcatatag acttcggaca cattcttggg aattacaaga gtttcctggg catcaataaa
2941 gagagagtgc ccttcgtcct aaccccagac ttcttgtttg tgatgggatc ttctggaaaa
3001 aagacaagtc cacacttcca gaaattccag gatgtctgtg ttagagctta cctagctctt
3061 cgccatcaca caaacctgtt gatcatcttg ttctccatga tgctgatgac aggaatgccc
3121 cagctgacaa gcaaagagga cattgaatat atccgggatg ccctcaccgt gggaaaaagc
3181 gaggaggacg ctaagaaata tttccttgat cagatcgaag tctgcagaga caaaggatgg
3241 actgtgcagt ttaactggtt cctacatctt gttcttggca tcaaacaagg agaaaagcac
3301 tccgcttga
```

SEQ ID NO: 22 Mouse PIK3CG (Isoform 2) Amino Acid Sequence

```
   1 melenyeqpv vlrednlrrr rrmkprsaag slssmelipi efvlptsqri sktpetallh
  61 vaghgnveqm kaqvwlrale tsvaaefyhr lgpdqfllly qkkgqwyeiy dryqvvqtld
 121 clhywklmhk spgqihvvqr hvpseetlaf qkqltsligy dvtdisnvhd deleftrrrl
 181 vtprmaevag rdaklyamhp wvtskplpdy lskkiannci fivihrgtts qtikvsaddt
 241 pgtilqsfft kmakkkslmn isesgseqdf vlrvcgrdey lvgetplknf qwvrqclkng
 301 deihlvldtp pdpaldevrk eewplvddct gvtgyheqlt ihgkdhesvf tvslwdcdrk
 361 frvkirgidi pvlprntdlt vfveaniqhg qqvlcqrrts pkpfaeevlw nvwlefgiki
 421 kdlpkgalln lqiyccktps lsskasaetp gseskgkaql lyyvnlllid hrfllrhgdy
 481 vlhmwqisgk aeeqgsfnad kltsatnpdk ensmsisill dnychpialp khrptpdpeg
 541 drvraempnq lrkqleaiia tdplnpltae dkellwhfry eslkhpkayp klfssvkwgq
 601 qeivaktyql larreiwdqs aldvgltmql ldcnfsdenv raiavqkles ledddvlhyl
 661 lqlvqavkfe pyhdsalarf llkrglrnkr ighflfwflr seiaqsrhyq qrfavileay
 721 lrgcgtamlq dftqqvhvie mlqkvtidik slsaekydvs sqvisqlkqk leslqnsnlp
 781 esfrvpydpg lkagtlviek ckvmaskkkp lwlefkcadp tvlsnetigi ifkhgddlrq
 841 dmlilqilri mesiwetesl dlcllpygci stgdkigmie ivkdattiaq iqqstvgntg
 901 afkdevlnhw lkekcpieek fqaaverfvy scagycvatf vlgigdrhnd nimisetgnl
 961 fhidfghilg nyksflgink ervpfvltpd flfvmgssgk ktsphfqkfq dvcvraylal
1021 rhhtnlliil fsmmlmtgmp qltskediey irdaltvgks eedakkyfld qievcrdkgw
1081 tvqfnwflhl vlgikqgekh sa
```

SEQ ID NO: 23 Mouse PIK3CG (Transcript 3) cDNA Acid Sequence

```
   1 atggagctgg agaactatga acaaccggtg gttctaagag aggacaacct ccgccggcgc
  61 cggaggatga agccacgcag cgcagcaggc agcctgtctt ccatggagct catccccatt
 121 gagttcgtac tgcccaccag ccagcgcatc agcaagactc cagaaacagc gctgctgcat
 181 gtggctggcc atggcaatgt ggaacagatg aaagctcagg tgtggctgcg cgcactggag
 241 accagtgtgg ctgcggagtt ctaccaccga ttgggcccgg accaattcct cctgctctac
 301 cagaagaaag gacaatggta tgagatctat gacaggtacc aagtggtgca gaccctagac
 361 tgcctgcatt actggaagtt gatgcacaag agccctggcc agatccacgt ggtacagcga
 421 cacgtacctt ctgaggagac cttggctttc cagaagcagc tcacctccct gattggctat
 481 gacgtcactg acatcagcaa tgtgcacgat gatgagctag agttcactcg ccgccgtctg
 541 gttacgcccc gcatggctga agtggctggc cgggatgcca aactctatgc tatgcaccct
 601 tgggtaacgt ccaaacctct cccagactac ctgtcaaaaa agattgccaa caactgcatc
 661 ttcatcgtca tccaccgcgg taccaccagc caaaccatca aggtctccgc agatgatact
 721 cctggtacca tcctccagag cttcttcacc aagatggcca agaagaagtc cctaatgaat
 781 atctcagaaa gtcaaagtga gcaggatttt gtattgcggg tttgtggccg cgatgagtac
 841 ctggtgggtg aaacacccct caaaaatttc cagtgggtga ggcagtgcct caagaacgga
 901 gatgaaatac acctggtgct cgacacgcct ccagacccag cccttgatga ggtgaggaag
 961 gaagaatggc cgctggtgga tgactgcact ggagtcaccg gctaccacga gcagctgacc
1021 atccatggca aggaccacga gagtgtgttc acagtgtctt tgtgggactg cgaccgaaag
1081 ttcagggtca agatcagagg cattgatatc cctgtcctgc ctcggaacac cgacctcact
1141 gtgtttgtgg aagcgaacat ccagcacggg caacaagtcc tctgccaaag gagaaccagc
1201 cctaagccct tcgcagaaga ggtactctgg aatgtgtggc tggagtttgg catcaaaatc
1261 aaagacttgc ccaaaggggc tctattgaac ctacagatct actgctgcaa aaccccatca
1321 ctgtccagca aggcttctgc agagactcca ggctccgagt ccaagggcaa agcccagctt
1381 ctctattacg tgaacttgct gttaatagac caccgtttcc tcctccgcca cggggactat
1441 gtgctccaca tgtggcagat atctggcaag gcagaggagc agggcagctt caatgctgac
1501 aagctcacat ccgcaaccaa tcctgacaag gagaactcaa tgtccatttc catcctgctg
1561 gacaattact gtcaccccat agctttgcct aagcaccggc ccacccctga cccagaggga
1621 gacagggttc gggctgaaat gcccaatcag cttcgaaagc aattggaggc gatcatagcc
```

TABLE 3-continued

```
1681 acagatccac ttaacccccct cacagcagag gacaaagaat tgctctggca ttttcgatat
1741 gaaagcctga agcatccgaa ggcttaccct aagctattca gctcagtgaa atgggggcag
1801 caagaaattg ttgccaaaac gtaccagctg ttagccagaa gggagatctg ggatcaaagt
1861 gctttggacg ttggcttaac catgcagctc ctggactgca acttttcaga cgagaatgtc
1921 cgggccattg cagttcagaa actggagagc ttagaggacg atgacgtttt acattacctt
1981 ctccagctgg tacaggctgt gaaatttgaa ccgtaccacg acagtgcgct ggccagattc
2041 ctgctgaagc gtggcttgag gaacaaaaga atcggtcact tcttgttctg gttcctgcga
2101 agtgagatcg cacagtccag acactatcag cagaggttcg ctgtgatcct ggaggcgtac
2161 ctgcgaggct gtggcacagc catgttgcag gacttcacac agcaggtcca tgtgattgag
2221 atgttacaga aagtcaccat tgatattaaa tcgctctcgg cagagaagta tgacgtcagt
2281 tcccaagtta tttcacagct taagcaaaag cttgaaaagcc ttcagaactc caatctcccc
2341 gagagcttta gagttcccta tgatcctgga ctaaaagccg gtaccctggt gatcgagaaa
2401 tgcaaagtga tggcctccaa gaagaagccc ctgtggcttg agtttaagtg tgctgatccc
2461 acagtcctat ccaacgaaac cattggaatc atctttaaac atggtgatga tctgcgccaa
2521 gacatgttga tcttgcagat tctacgcatc atggagtcca tttgggagac tgaatctctg
2581 gacctgtgcc ttctgcctta cggttgcatc tcaactggtg acaaaatagg aatgatcgag
2641 attgtaaagg atgccacaac gatcgctcaa attcagcaaa gcacagtggg taacacgggg
2701 gcattcaaag atgaagtcct gaatcactgg ctcaaggaaa aatgtcctat tgaagaaaag
2761 tttcaggccg cagtggaaag gtttgtttac tcctgtgcag gctactgtgt ggccacattt
2821 gttcttggga tcggtgacag gcacaacgac aacattatga tctcagagac aggaaaccta
2881 tttcatatag acttcggaca cattcttggg aattacaaga gtttcctggg catcaataaa
2941 gagagagtgc ccttcgtcct aaccccagac ttcttgtttg tgatgggatc ttctggaaaa
3001 aagacaagtc cacacttcca gaaattccag gatgtctgtg ttagagctta cctagctctt
3061 cgccatcaca caaacctgtt gatcatcttg ttctccatga tgctgatgac aggaatgccc
3121 cagctgacaa gcaaagagga cattgaatat atccgggatg ccctcaccgt gggaaaaagc
3181 gaggaggacg ctaagaaata tttccttgat cagatcgaag tctgcagaga caaaggatgg
3241 actgtgcagt ttaactggtt cctacatctt gttcttggca tcaaacaagg agaaaagcac
3301 tccgcttga
```

SEQ ID NO: 24 Mouse PIK3CG (Isoform 3) Amino Acid Sequence

```
   1 melenyeqpv vlrednlrrr rrmkprsaag slssmelipi efvlptsqri sktpetallh
  61 vaghgnveqm kaqvwlrale tsvaaefyhr lgpdqflllly qkkgqwyeiy dryqvvqtld
 121 clhywklmhk spgqihvvqr hvpseetlaf qkqltsligy dvtdisnvhd deleftrrrl
 181 vtprmaevag rdaklyamhp wvtskplpdy lskkiannci fivihrgtts qtikvsaddt
 241 pgtilqsfft kmakkkslmn isesqseqdf vlrvcgrdey lvgetplknf qwvrqclkng
 301 deihlvldtp pdpaldevrk eewplvddct gvtgyheqlt ihgkdhesvf tvslwdcdrk
 361 frvkirgidi pvlprntdlt vfveaniqhg qqvlcqrrts pkpfaeevlw nvwlefgiki
 421 kdlpkgalln lqiyccktps lsskasaetp gseskgkaql lyyvnllllid hrfllrhgdy
 481 vlhmwqisgk aeeqgsfnad kltsatnpdk ensmsisill dnychpialp khrptpdpeg
 541 drvraempnq lrkqleaiia tdplnpltae dkellwhfry eslkhpkayp klfssvkwgq
 601 qeivaktyql larreiwdqs aldvgltmql ldcnfsdenv raiavqkles ledddvlhyl
 661 lqlvqavkfe pyhdsalarf llkrglrnkr ighflfwflr seiaqsrhyq qrfavileay
 721 lrgcgtamlq dftqqvhvie mlqkvtidik slsaekydvs sqvisqlkqk leslqnsnlp
 781 esfrvpydpg lkagtlviek ckvmaskkkp lwlefkcadp tvlsnetigi ifkhgddlrq
 841 dmlilqilri mesiwetesl dlcllpygci stgdkigmie ivkdattiaq iqqstvgntg
 901 afkdevlnhw lkekcpieek fqaaverfvy scagycvatf vlgigdrhnd nimisetgnl
 961 fhidfghilg nyksflgink ervpfvltpd flfvmgssgk ktsphfqkfq dvcvraylal
1021 rhhtnllill fsmmlmtgmp qltskediey irdaltvgks eedakkyfld qievcrdkgw
1081 tvqfnwflhl vlgikqgekh sa
```

SEQ ID NO: 25 Human PIK3CD cDNA Acid Sequence

```
   1 atgccccctg gggtggactg ccccatggaa ttctggacca aggaggagaa tcagagcgtt
  61 gtggttgact tcctgctgcc cacaggggtc tacctgaact tccctgtgtc ccgcaatgcc
 121 aacctcagca ccatcaagca gctgctgtgg caccgcgccc agtatgagcc gctcttccac
 181 atgctcagtg gccccgaggc ctatgtgttc acctgcatca accagacagc ggagcagcaa
 241 gagctggagg acgagcaacg gcgtctgtgt gacgtgcagc ccttcctgcc cgtcctgcgc
 301 ctggtggccc gtgagggcga ccgcgtgaag aagctcatca actcacagat cagcctcctc
 361 atcggcaaag gcctccacga gtttgactcc ttgtgcgacc cagaagtgaa cgactttcgc
 421 gccaagatgt gccaattctg cgaggaggcg gccgcccgcc ggcagcagct gggctgggag
 481 gcctggctgc agtacagttt cccccctgcag ctggagccct cggctcaaac ctggggggcct
 541 ggtaccctgc ggctcccgaa ccgggccctt ctggtcaacg ttaagtttga gggcagcgag
 601 gagagcttca ccttccaggt gtccaccaag gacgtgccgc tggcgctgat ggcctgtgcc
 661 ctgcggaaga aggccacagt gttccggcag ccgctggtgg agcagccgga agactacacg
 721 ctgcaggtga acggcaggca tgagtacctg tatggcagct acccgctctg ccagttccag
 781 tacatctgca gctgcctgca cagtgggttg acccctcacc tgaccatggt ccattcctcc
 841 tccatcctcg ccatgcggga tgagcagagc aaccctgccc cccaggtcca gaaaccgcgt
 901 gccaaaccac ctcccattcc tgcgaagaag ccttcctctg tgtccctgtg gtccctggag
 961 cagccgttcc gcatcgagct catccagggc agcaaagtga acgccgacga gcggatgaag
1021 ctggtggtgc aggccgggct tttccacggc aacgagatgc tgtgcaagac ggtgtccagc
1081 tcggaggtga gcgtgtgctc ggagcccgtg tggaagcagc ggctggagtt cgacatcaac
1141 atctgcgacc tgccccgcat ggcccgtctc tgctttgcgc tgtacgccgt gatcgagaaa
1201 gccaagaagg ctcgctccac caagaagaag tccaagaagg cggactgccc cattgcctgg
1261 gccaacctca tgctgtttga ctacaaggac cagcttaaga ccggggaacg ctgcctctac
1321 atgtggccct ccgtcccaga tgagaagggc gagctgctga accccacggg cactgtgcgc
1381 agtaacccca acacggatag cgccgctgcc ctgctcatct gcctgcccga ggtggccccg
1441 caccccgtgt actacccgc cctggagaag atcttggagc tggggcgaca cagcgagtgt
1501 gtgcatgtca ccgaggagga gcagctgcag ctgcgggaaa tcctggagcg gcgggggtct
1561 ggggagctgt atgagcacga gaaggacctg gtgtggaagc tgcggcatga agtccaggag
```

TABLE 3-continued

```
1621 cacttcccgg aggcgctagc ccggctgctg ctggtcacca agtggaacaa gcatgaggat
1681 gtggcccaga tgctctacct gctgtgctcc tggccggagc tgcccgtcct gagcgccctg
1741 gagctgctag acttcagctt ccccgattgc cacgtaggct ccttcgccat caagtcgctg
1801 cggaaactga cggacgatga gctgttccag tacctgctgc agctggtgca ggtgctcaag
1861 tacgagtcct acctggactg cgagctgacc aaattcctgc tggaccgggc cctggccaac
1921 cgcaagatcg gccacttcct tttctggcac ctccgctccg agatgcacgt gccgtcggtg
1981 gccctgcgct tcggcctcat cctggaggcc tactgcaggg gcagcaccca ccacatgaag
2041 gtgctgatga agcaggggga agcactgagc aaactgaagg ccctgaatga cttcgtcaag
2101 ctgagctctc agaagacccc caagccccag accaaggagc tgatgcactt gtgcatgcgg
2161 caggaggcct acctagaggc cctctcccac ctgcagtccc cactcgaccc cagcaccctg
2221 ctggctgaag tctgcgtgga gcagtgcacc ttcatggact ccaagatgaa gcccctgtgg
2281 atcatgtaca gcaacgagga ggcaggcagc ggcggcagcg tgggcatcat ctttaagaac
2341 ggggatgacc tccggcagga catgctgacc ctgcagatga tccagctcat ggacgtcctg
2401 tggaagcagg aggggctgga cctgaggatg acccccatg gctgcctccc caccggggac
2461 cgcacaggcc tcattgaggt ggtactccgt tcagacacca tcgccaacat ccaactcaac
2521 aagagcaaca tggcagccac agccgccttc aacaaggatg ccctgctcaa ctggctgaag
2581 tccaagaacc cgggggaggc cctggatcga gccattgagg agttcaccct ctcctgtgct
2641 ggctattgtg tggccacata tgtgctgggc attggcgatc ggcacagcga caacatcatg
2701 atccgagaga gtgggcagct gttccacatt gattttggcc actttctggg gaatttcaag
2761 accaagtttg gaatcaaccg cgagcgtgtc ccattcatcc tcacctacga ctttgtccat
2821 gtgattcagc aggggaagac taataatagt gagaaatttg aacggttccg ggctactgt
2881 gaaagggcct acaccatcct gcggcgccac gggcttctct tcctccacct ctttgccctg
2941 atgcgggcgg caggcctgcc tgagctcagc tgctccaaag acatccagta tctcaaggac
3001 tccctggcac tggggaaaac agaggaggag gcactgaagc acttccgagt gaagtttaac
3061 gaagccctcc gtgagagctg gaaaaccaaa gtgaactggc tggcccacaa cgtgtccaaa
3121 gacaacaggc agtag
```

SEQ ID NO: 26 Human PIK3CD Amino Acid Sequence

```
   1 mppgvdcpme fwtkeenqsv vvdfllptgv ylnfpvsrna nlstikqllw hraqyeplfh
  61 mlsgpeayvf tcinqtaeqq eledeqrrlc dvqpflpvlr lvaregdrvk klinsqisll
 121 igkglhefds lcdpevndfr akmcqfceea aarrqqlgwe awlqysfplq lepsaqtwgp
 181 gtlrlpnral lvnvkfegse esftfqvstk dvplalmaca lrkkatvfrq plveqpedyt
 241 lqvngrheyl ygsyplcqfq yicsclhsgl tphltmvhss silamrdeqs npapqvqkpr
 301 akpppipakk pssyslwsle qpfrieliqg skvnadermk lvvqaglfhg nemlcktvss
 361 sevsvcsepv wkqrlefdin icdlprmarl cfalyaviek akkarstkkk skkadcpiaw
 421 anlmlfdykd qlktgercly mwpsvpdekg ellnptgtvr snpntdsaaa llicl pevap
 481 hpvyypalek ilelgrhsec vhvteeeqlq lreilerrgs gelyehekdl vwklrhevqe
 541 hfpealarll lvtkwnkhed vaqmlyllcs wpelpvlsal elldfsfpdc hvgsfaiksl
 601 rkltddelfq yllqlvqvlk yesyldcelt kflldralan rkighflfwh lrsemhvpsv
 661 alrfglilea ycrgsthhmk vlmkqgeals klkalndfvk lssqktpkpq tkelmhlcmr
 721 qeaylealsh lqspldpstl laevcveqct fmdskmkplw imysneeags ggsvgiifkn
 781 gddlrqdmlt lqmiqlmdvl wkqegldlrm tpygclptgd rtglievvlr sdtianiqln
 841 ksnmaataaf nkdallnwlk sknpgealdr aieeftlsca gycvatyvlg igdrhsdnim
 901 iresgqlfhi dfghflgnfk tkfginrerv pfiltydfvh viqqgktnns ekferfrgyc
 961 eraytilrrh gllflhlfal mraaglpels cskdiqylkd slalgkteee alkhfrvkfn
1021 ealreswktk vnwlahnvsk dnrq
```

SEQ ID NO: 27 Mouse PIK3CD (Transcript 1) cDNA Acid Sequence

```
   1 atgccccctg gggtggactg ccccatggag ttctggacca aagaggagag ccagagcgtg
  61 gttgttgact tcttgctgcc cacaggggtc tacttgaact tccccgtgtc ccgcaatgcc
 121 aacctcagca ccatcaagca ggtgctgtgg caccgtgcac agtatgagcc actcttccac
 181 atgctcagtg accccgaggc ctatgtgttc acctgtgtga accagacggc ggagcagcag
 241 gagttggagg atgagcagcg gaggctgtgc gacatccagc ccttcctgcc cgtgctgcgc
 301 ctcgtggccc gagaggggga ccgcgtgaag aagctcatta actcccagat cagcctcctc
 361 attggcaaag gtctccatga gtttgattcc ctgcgggacc cggaagtaaa cgacttccgc
 421 actaagatgc gccagttttg tgaagaggct gctgctcacc gccagcagct gggctgggtg
 481 gaatggctgc agtacagctt cccccctgcag ctggagccct cagcaagggg ttggcgggcc
 541 ggcttattgc gtgtcagcaa ccgagccctg ctggtcaacg tgaagttcga gggcagtgag
 601 gagagcttca ccttccaggt atccaccaag gacatgcccc tggcactgat ggcctgtgcc
 661 ctccgaaaaa aggccacagt gttccggcag cctctggtgg agcagcctga ggaatatgcc
 721 ctgcaggtga acgggaggca cgaatacctc tacggcaact acccgctctg ccactttcag
 781 tacatctgca gctgcctaca cagcgggctg acccctcatc tgaccatggt ccactcctcc
 841 tccatccttg ctatgcggga tgagcagagc aatcctgccc cccaagtaca gaaaccacgt
 901 gccaaacctc ccccgatccc tgccaagaag ccctcctctg tgtccctgtg gtccctggaa
 961 cagccattct ccattgagct gatcgagggc cgaaaagtga atgctgacga gcggatgaag
1021 ctggttgttc aggccgggct cttccatggc aatgagatgc tgtgcaagac tgtgtcaagc
1081 tcggaggtga atgtatgctc agagcccgtg tggaagcagc gactggagtt cgatatcagc
1141 gtctgtgacc tcccgcgcat ggctcgactc tgttttgctc tctatgccgt cgtggagaag
1201 gctaagaagg cacgctccac aaagaagaag tctaagaagg cggactgccc catcgcttgg
1261 gccaacctca tgctattcga ctacaaagat cagctcaaga cgggggagcg ctgcctctac
1321 atgtggccct ctgtcccaga tgagaaggga gagctgctga atcctgcggg tacagtgcgc
1381 gggaacccca acacggagag tgccgctgcc ctggtcatct acctgcctga ggtggccccc
1441 caccctgtgt acttccccgc tctggagaag atcctggagc tggggcgtca cggggagcgt
1501 gggcgcatca cggaggagga gctgcagctg cgggagatcc tggaacggcg gggatccggg
1561 gaactgtacg aacatgagaa ggacctggtg tggaagatgc gccacgaagt ccaggagcat
1621 ttcccagagg cgctggcccg cctgctgctg gtcaccaagt ggaataaaca cgaggatgtg
1681 gcccagatgc tctatttgct gtgctcctgg cccgagctgc ctgtgctgag cgccctggaa
1741 cttctggact ttagctttcc cgactgctac gtgggctcct tcgccatcaa gtcccttcgg
```

TABLE 3-continued

```
1801 aagctgacgg acgatgagct cttccagtac cttctgcagc tggtgcaagt gctcaaatat
1861 gagtcctacc tggactgcga gctgaccaaa ttcttgctgg gccgagccct ggctaaccgc
1921 aagatcggac acttcctgtt ctggcacctc cgctctgaga tgcacgtacc atcagtggct
1981 ctgcggtttg gtctcatcat ggaagcctac tgcagaggca gcacccacca catgaaggtg
2041 ctgatgaagc agggggaagc actgagcaag cttaaggcac tgaatgactt tgtgaaggtg
2101 agttcccaga agaccaccaa gccccaaacc aaggagatga tgcatatgtg catgcgccag
2161 gagacctaca tggaggccct gtcccacctg cagtctccac tcgaccccag caccctgctg
2221 gaggaagtct gtgtggagca gtgcaccttc atggactcca aaatgaagcc cctgtggatc
2281 atgtacagca gcgaggaggc gggcagtgct ggcaacgtgg gcatcatctt taagaacggg
2341 gatgacctcc gccaggacat gctgactctg cagatgatcc agctcatgga cgtcctgtgg
2401 aagcaggagg gcctggacct gaggatgacg ccctacggct gcctccccac cggggaccgc
2461 acaggtctca tcgaggtggt cctccactcg gacaccatcg ccaacatcca gctgaacaaa
2521 agcaacatgg cggccacagc tgccttcaac aaggacgccc tgctcaactg gctcaagtcc
2581 aagaaccctg gggaggccct ggatcgggcc attgaggaat tcaccctctc ctgtgctggc
2641 tactgtgtgg ccacatatgt tctgggcatc ggtgaccggc acagcgacaa catcatgatc
2701 agagagagtg ggcagctctt ccacattgat tttggccact ttctggggaa cttcaagacc
2761 aagtttggaa tcaaccgaga gcgcgtcccc ttcattctca cctacgactt tgtccacgtg
2821 atccagcagg ggaagactaa caacagtgag aagtttgaaa ggttccgcgg ctactgtgaa
2881 cgagcctata ccatcctgcg gcgccacggg ctgcttttcc tccatctctt cgccctgatg
2941 cgggccgcag gtctgcctga gcttagctgc tccaaagata tccagtatct caaggactct
3001 ctggcactgg ggaagacgga ggaagaggcg ctaaagcact tccgggtgaa gttcaacgaa
3061 gctctccgag aaagctggaa aaccaaagtc aactggctgg cgcacaatgt gtccaaggat
3121 aaccgacagt ag
```

SEQ ID NO: 28 Mouse PIK3CD (Isoform 1) Amino Acid Sequence

```
   1 mppgvdcpme fwtkeesqsv vvdfllptgv ylnfpvsrna nlstikqvlw hraqyeplfh
  61 mlsdpeayvf tcvnqtaegq eledeqrrlc diqpflpvlr lvaregdrvk klinsqisll
 121 igkglhefds lrdpevndfr tkmrqfceea aahrqqlgwv ewlqysfplq lepsargwra
 181 gllrvsnral lvnvkfegse esftfqvstk dmplalmaca lrkkatvfrq plveqpeeya
 241 lqvngrheyl ygnyplchfq yicsclhsgl tphltmvhss silamrdeqs npapqvqkpr
 301 akpppipakk pssyslwsle qpfsielieg rkvnadermk lvvqaglfhg nemlcktvss
 361 sevnvcsepv wkqrlefdis vcdlprmarl cfalyavvek akkarstkkk skkadcpiaw
 421 anlmlfdykd qlktgercly mwpsvpdekg ellnpagtvr gnpntesaaa lviylpevap
 481 hpvyfpalek ilelgrhger griteeelql reilerrgsg elyehekdlv wkmrhevqeh
 541 fpealarlll vtkwnkhedv aqmlyllcsw pelpvlsale lldfsfpdcy vgsfaikslr
 601 kltddelfqy llqlvqvlky esyldceltk fllgralanr kighflfwhl rsemhvpsva
 661 lrfglimeay crgsthhmkv lmkqgealsk lkalndfvkv ssqkttkpqt kemmhmcmrq
 721 etymealshl qspldpstll eevcveqctf mdskmkplwi mysseeagsa gnvgiifkng
 781 ddlrqdmltl qmiqlmdvlw kqegldlrmt pygclptgdr tglievvlhs dtianiqlnk
 841 snmaataafn kdallnwlks knpgealdra ieeftlscag ycvatyvlgi gdrhsdnimi
 901 resgqlfhid fghflgnfkt kfginrervp filtydfvhv iqqgktnnse kferfrgyce
 961 raytilrrhg llflhlfalm raaglpelsc skdiqylkds lalgkteeea lkhfrvkfne
1021 alreswktkv nwlahnvskd nrq
```

SEQ ID NO: 29 Mouse PIK3CD (Transcript 2) cDNA Acid Sequence

```
   1 atgccccctg gggtggactg ccccatggag ttctggacca aagaggagag ccagagcgtg
  61 gttgttgact tcttgctgcc cacaggggtc tacttgaact tccccgtgtc ccgcaatgcc
 121 aacctcagca ccatcaagca ggtgctgtgg caccgtgcac agtatgagcc actcttccac
 181 atgctcagtg accccgaggc ctatgtgttc acctgtgtga accagacggc ggagcagcag
 241 gagttggagg atgagcagcg gaggctgtgc gacatccagc ccttcctgcc cgtgctgcgc
 301 ctcgtggccc gagaggggga ccgcgtgaag aagctcatta actcccagat cagcctcctc
 361 attggcaaag gtctccatga gtttgattcc ctgcgggacc cggaagtaaa cgacttccgc
 421 actaagatgc gccagttttg tgaagaggct gctgctcacc gccagcagct gggctgggtg
 481 gaatggctgc agtacagctt ccccctgcag ctggagccct cagcaagggg ttggcgggcc
 541 ggcttattgc gtgtcagcaa ccgagccctg ctggtcaacg tgaagttcga gggcagtgag
 601 gagagcttca ccttccaggt atccaccaag gacatgcccc tggcactgat ggcctgtgcc
 661 ctccgaaaaa aggccacagt gttccggcag cctctggtgg agcagcctga ggaatatgcc
 721 ctgcaggtga acgggaggca cgaatacctc tacggcaact acccgctctg ccactttcag
 781 tacatctgca gctgcctaca cagcgggctg acccctcatc tgaccatggt ccactcctcc
 841 tccatccttg ctatgcggga tgagcagagc aatcctgccc cccaagtaca gaaaccacgt
 901 gccaaacctc ccccgatccc tgccaagaag ccctcctctg tgtccctgtg gtccctggaa
 961 cagccattct ccattgagct gatcgagggc cgaaaagtga atgctgacga gcggatgaag
1021 ctggttgttc aggccgggct cttccatggc aatgagatgc tgtgcaagac tgtgtcaagc
1081 tcggaggtga atgtatgctc agagcccgtg tggaagcagc gactggagtt cgatatcagc
1141 gtctgtgacc tcccgcgcat ggctcgactc tgttttgctc tctatgccgt cgtggagaag
1201 gctaagaagg cacgctccac aaagaagaag tctaagaagg cggactgccc catcgcttgg
1261 gccaacctca tgctattcga ctacaaagat cagctcaaga cgggggagcg ctgcctctac
1321 atgtggccct ctgtcccaga tgagaaggga gagctgctga atcctgcggg tacagtgcgc
1381 gggaacccca acacggagag tgccgctgcc ctggtcatct acctgcctga ggtggccccc
1441 caccctgtgt acttccccgc tctggagaag atcctggagc tggggcgtca cggggagcgt
1501 gggcgcatca cggaggagga gcagctgcag ctgcgggaga tcctggaacg gcggggatcc
1561 ggggaactgt acgaacatga gaaggacctg gtgtggaaga tgcgccacga agtccaggag
1621 catttcccag aggcgctggc ccgcctgctg ctggtcacca agtggaataa acacgaggat
1681 gtggcccagc tgtcccagat gctctatttg ctgtgctcct ggcccgagct gcctgtgctg
1741 agcgccctgg aacttctgga ctttagcttt cccgactgct acgtgggctc cttcgccatc
1801 aagtcccttc ggaagctgac ggacgatgag ctcttccagt accttctgca gctggtgcaa
1861 gtgctcaaat atgagtccta cctggactgc gagctgacca aattcttgct gggccgagcc
1921 ctggctaacc gcaagatcgg acacttcctg ttctggcacc tccgctctga gatgcacgta
```

TABLE 3-continued

```
1981 ccatcagtgg ctctgcggtt tggtctcatc atggaagcct actgcagagg cagcacccac
2041 cacatgaagg tgctgatgaa gcaggggaa gcactgagca agcttaaggc actgaatgac
2101 tttgtgaagg tgagttccca gaagaccacc aagccccaaa ccaaggagat gatgcatatg
2161 tgcatgcgcc aggagaccta catggaggcc ctgtcccacc tgcagtctcc actcgacccc
2221 agcaccctgc tggaggaagt ctgtgtggag cagtgcacct tcatggactc caaaatgaag
2281 cccctgtgga tcatgtacag cagcgaggag gcgggcagtg ctggcaacgt gggcatcatc
2341 tttaagaacg gggatgacct ccgccaggac atgctgactc tgcagatgat ccagctcatg
2401 gacgtcctgt ggaagcagga gggcctggac ctgaggatga cgccctacgg ctgcctcccc
2461 accggggacc gcacaggtct catcgaggtg gtcctccact cggacaccat cgccaacatc
2521 cagctgaaca aaagcaacat ggcggccaca gctgccttca acaaggacgc cctgctcaac
2581 tggctcaagt ccaagaaccc tggggaggcc ctggatcggg ccattgagga attcaccctc
2641 tcctgtgctg gctactgtgt ggccacatat gttctgggca tcggtgaccg gcacagcgac
2701 aacatcatga tcagagagag tgggcagctc ttccacattg attttggcca ctttctgggg
2761 aacttcaaga ccaagtttgg aatcaaccga gagcgcgtcc ccttcattct cacctacgac
2821 tttgtccacg tgatccagca ggggaagact aacaacagtg agaagtttga aaggttccgc
2881 ggctactgtg aacgagccta taccatcctg cggcgccacg ggctgctttt cctccatctc
2941 ttcgccctga tgcgggccgc aggtctgcct gagcttagct gctccaaaga tatccagtat
3001 ctcaaggact ctctggcact ggggaagacg gaggaagagg cgctaaagca cttccgggtg
3061 aagttcaacg aagctctccg agaaagctgg aaaaccaaag tcaactggct ggcgcacaat
3121 gtgtccaagg ataaccgaca gtag
```

SEQ ID NO: 30 Mouse PIK3CD (Isoform 2) Amino Acid Sequence

```
   1 mppgvdcpme fwtkeesqsv vvdfllptgv ylnfpvsrna nlstikqvlw hraqyeplfh
  61 mlsdpeayvf tcvnqtaeqq eledeqrrlc diqpflpvlr lvaregdrvk klinsqisll
 121 igkglhefds lrdpevndfr tkmrqfceea aahrqqlgwv ewlqysfplq lepsargwra
 181 gllrvsnral lvnvkfegse esftfqvstk dmplalmaca lrkkatvfrq plveqpeeya
 241 lqvngrheyl ygnyplchfq yicsclhsgl tphltmvhss silamrdeqs npapqvqkpr
 301 akpppipakk pssvslwsle qpfsielieg rkvnadermk lvvqaglfhg nemlcktvss
 361 sevnvcsepv wkqrlefdis vcdlprmarl cfalyavvek akkarstkkk skkadcpiaw
 421 anlmlfdykd qlktgercly mwpsvpdekg ellnpagtvr gnpntesaaa lviylpevap
 481 hpvyfpalek ilelgrhger griteeeqlq lreilerrgs gelyehekdl vwkmrhevqe
 541 hfpealarll lvtkwnkhed vaqlsgmlyl lcswpelpvl salelldfsf pdcyvgsfai
 601 kslrkltdde lfqyllqlvq vlkyesyldc eltkfllgra lanrkighfl fwhlrsemhv
 661 psvalrfgli meaycrgsth hmkvlmkqge alsklkalnd fvkvssqktt kpqtkemmhm
 721 cmrqetymea lshlqspldp stlleevcve qctfmdskmk plwimyssee agsagnvgii
 781 fkngddlrqd mltlqmiqlm dvlwkqegld lrmtpygclp tgdrtgliev vlhsdtiani
 841 qlnksnmaat aafnkdalln wlksknpgea ldraieeftl scagycvaty vlgigdrhsd
 901 nimiresgql fhidfghflg nfktkfginr ervpfiltyd fvhviqqgkt nnsekferfr
 961 gyceraytil rrhgllflhl falmraaglp elscskdiqy lkdslalgkt eeealkhfrv
1021 kfnealresw ktkvnwlahn vskdnrq
```

SEQ ID NO: 31 Mouse PIK3CD (Transcript 3) cDNA Acid Sequence

```
   1 atgccccctg gggtggactg ccccatggag ttctggacca aagaggagag ccagagcgtg
  61 gttgttgact tcttgctgcc cacaggggtc tacttgaact tccccgtgtc ccgcaatgcc
 121 aacctcagca ccatcaagca ggtgctgtgg caccgtgcac agtatgagcc actcttccac
 181 atgctcagtg accccgaggc ctatgtgttc acctgtgtga accagacggc ggagcagcag
 241 gagttggagg atgagcagcg gaggctgtgc gacatccagc ccttcctgcc cgtgctgcgc
 301 ctcgtggccc gagaggggga ccgcgtgaag aagctcatta actcccagat cagcctcctc
 361 attggcaaag gtctccatga gtttgattcc ctgcgggacc cggaagtaaa cgacttccgc
 421 actaagatgc gccagttttg tgaagaggct gctgctcacc gccagcagct gggctgggtg
 481 gaatggctgc agtacagctt ccccctgcag ctggagccct cagcaagggg ttggcgggcc
 541 ggcttattgc gtgtcagcaa ccgagccctg ctggtcaacg tgaagttcga gggcagtgag
 601 gagagcttca ccttccaggt atccaccaag gacatgcccc tggcactgat ggcctgtgcc
 661 ctccgaaaaa aggccacagt gttccggcag cctctggtgg agcagcctga ggaatatgcc
 721 ctgcaggtga acgggaggca cgaatacctc tacggcaact acccgctctg ccactttcag
 781 tacatctgca gctgcctaca cagcgggctg acccctcatc tgaccatggt ccactcctcc
 841 tccatccttg ctatgcggga tgagcagagc aatcctgccc cccaagtaca gaaaccacgt
 901 gccaaacctc cccgatccc tgccaagaag ccctcctctg tgtccctgtg gtccctggaa
 961 cagccattct ccattgagct gatcgagggc cgaaaagtga atgctgacga gcggatgaag
1021 ctggttgttc aggccgggct cttccatggc aatgagatgc tgtgcaagac tgtgtcaagc
1081 tcggaggtga atgtatgctc agagcccgtg tggaagcagc gactggagtt cgatatcagc
1141 gtctgtgacc tcccgcgcat ggctcgactc tgttttgctc tctatgccgt cgtggagaag
1201 gctaagaagg cacgctccac aaagaagaag tctaagaagg cggactgccc catcgcttgg
1261 gccaacctca tgctattcga ctacaaagat cagctcaaga cgggggagcg ctgcctctac
1321 atgtggccct ctgtcccaga tgagaaggga gagctgctga atcctgcggg tacagtgcgc
1381 gggaacccca acacggagag tgccgctgcc ctggtcatct acctgcctga ggtggccccc
1441 caccctgtgt acttccccgc tctggagaag atcctggagc tggggcgtca cggggagcgt
1501 gggcgcatca cggaggagga gcagctgcag ctgcgggaga tcctggaacg gcggggatcc
1561 ggggaactgt acgaacatga gaaggacctg gtgtggaaga tgcgccacga agtccaggag
1621 catttcccag aggcgctggc ccgcctgctg ctggtcacca agtggaataa acacgaggat
1681 gtggcccagc tgtcccagat gctctatttg ctgtgctcct ggcccgagct gcctgtgctg
1741 agcgccctgg aacttctgga ctttagcttt cccgactgct acgtgggctc cttcgccatc
1801 aagtcccttc ggaagctgac ggacgatgag ctcttccagt accttctgca gctggtgcaa
1861 gtgctcaaat atgagtccta cctggactgc gagctgacca aattcttgct gggccgagcc
1921 ctggctaacc gcaagatcgg acacttcctg ttctggcacc tccgctctga gatgcacgta
1981 ccatcagtgg ctctgcggtt tggtctcatc atggaagcct actgcagagg cagcacccac
2041 cacatgaagg tgctgatgaa gcaggggaa gcactgagca agcttaaggc actgaatgac
2101 tttgtgaagg tgagttccca gaagaccacc aagccccaaa ccaaggagat gatgcatatg
```

TABLE 3-continued

```
2161 tgcatgcgcc aggagaccta catggaggcc ctgtcccacc tgcagtctcc actcgacccc
2221 agcaccctgc tggaggaagt ctgtgtggag cagtgcacct tcatggactc caaaatgaag
2281 cccctgtgga tcatgtacag cagcgaggag gcgggcagtg ctggcaacgt gggcatcatc
2341 tttaagaacg gggatgacct ccgccaggac atgctgactc tgcagatgat ccagctcatg
2401 gacgtcctgt ggaagcagga gggcctggac ctgaggatga cgccctacgg ctgcctcccc
2461 accggggacc gcacaggtct catcgaggtg gtcctccact cggacaccat cgccaacatc
2521 cagctgaaca aaagcaacat ggcggccaca gctgccttca acaaggacgc cctgctcaac
2581 tggctcaagt ccaagaaccc tggggaggcc ctggatcggg ccattgagga attcaccctc
2641 tcctgtgctg gctactgtgt ggccacatat gttctgggca tcggtgaccg gcacagcgac
2701 aacatcatga tcagagagag tgggcagctc ttccacattg attttggcca ctttctgggg
2761 aacttcaaga ccaagtttgg aatcaaccga gagcgcgtcc ccttcattct cacctacgac
2821 tttgtccacg tgatccagca ggggaagact aacaacagtg agaagtttga aaggttccgc
2881 ggctactgtg aacgagccta taccatcctg cggcgccacg ggctgctttt cctccatctc
2941 ttcgccctga tgcgggccgc aggtctgcct gagcttagct gctccaaaga tatccagtat
3001 ctcaaggact ctctggcact ggggaagacg gaggaagagg cgctaaagca cttccgggtg
3061 aagttcaacg aagctctccg agaaagctgg aaaaccaaag tcaactggct ggcgcacaat
3121 gtgtccaagg ataaccgaca gtag
```

SEQ ID NO: 32 Mouse PIK3CD (Isoform 3) Amino Acid Sequence

```
   1 mppgvdcpme fwtkeesqsv vvdfllptgv ylnfpvsrna nlstikqvlw hraqyeplfh
  61 mlsdpeayvf tcvnqtaeqq eledeqrrlc diqpflpvlr lvaregdrvk klinsqisll
 121 igkglhefds lrdpevndfr tkmrqfceea aahrqqlgwv ewlqysfplq lepsargwra
 181 gllrvsnral lvnvkfegse esftfqvstk dmplalmaca lrkkatvfrq plveqpeeya
 241 lqvngrheyl ygnyplchfq yicsclhsgl tphltmvhss silamrdeqs npapqvqkpr
 301 akpppipakk pssyslwsle qpfsielieg rkvnadermk lvvqaglfhg nemlcktvss
 361 sevnvcsepv wkqrlefdis vcdlprmarl cfalyavvek akkarstkkk skkadcpiaw
 421 anlmlfdykd qlktgercly mwpsvpdekg ellnpagtvr gnpntesaaa lviylpevap
 481 hpvyfpalek ilelgrhger griteeeqlq lreilerrgs gelyehekdl vwkmrhevqe
 541 hfpealarll lvtkwnkhed vaqlsgmlyl lcswpelpvl salelldfsf pdcyvgsfai
 601 kslrkltdde lfqyllqlvq vlkyesyldc eltkfllgra lanrkighfl fwhlrsemhv
 661 psvalrfgli meaycrgsth hmkvlmkqge alsklkalnd fvkvssqktt kpqtkemmhm
 721 cmrqetymea lshlqspldp stlleevcve qctfmdskmk plwimyssee agsagnvgii
 781 fkngddlrqd mltlqmiqlm dvlwkqegld lrmtpygclp tgdrtgliev vlhsdtiani
 841 qlnksnmaat aafnkdalln wlksknpgea ldraieeftl scagycvaty vlgigdrhsd
 901 nimiresgql fhidfghflg nfktkfginr ervpfiltyd fvhviqqgkt nnsekferfr
 961 gyceraytil rrhgllflhl falmraaglp elscskdiqy lkdslalgkt eeealkhfrv
1021 kfnealresw ktkvnwlahn vskdnrq
```

SEQ ID NO: 33 Mouse PIK3CD (Transcript 4) cDNA Acid Sequence

```
   1 atgccccctg gggtggactg ccccatggag ttctggacca aagaggagag ccagagcgtg
  61 gttgttgact tcttgctgcc cacaggggtc tacttgaact tccccgtgtc ccgcaatgcc
 121 aacctcagca ccatcaagca ggtgctgtgg caccgtgcac agtatgagcc actcttccac
 181 atgctcagtg accccgaggc ctatgtgttc acctgtgtga accagacggc ggagcagcag
 241 gagttggagg atgagcagcg gaggctgtgc gacatccagc ccttcctgcc cgtgctgcgc
 301 ctcgtggccc gagaggggga ccgcgtgaag aagctcatta actcccagat cagcctcctc
 361 attggcaaag gtctccatga gtttgattcc ctgcgggacc cggaagtaaa cgacttccgc
 421 actaagatgc gccagttttg tgaagaggct gctgctcacc gccagcagct gggctgggtg
 481 gaatggctgc agtacagctt cccccctgcag ctggagccct cagcaagggg ttggcgggcc
 541 ggcttattgc gtgtcagcaa ccgagccctg ctggtcaacg tgaagttcga gggcagtgag
 601 gagagcttca ccttccaggt atccaccaag gacatgcccc tggcactgat ggcctgtgcc
 661 ctccgaaaaa aggccacagt gttccggcag cctctggtgg agcagcctga ggaatatgcc
 721 ctgcaggtga acgggaggca cgaatacctc tacggcaact acccgctctg ccactttcag
 781 tacatctgca gctgcctaca cagcgggctg acccctcatc tgaccatggt ccactcctcc
 841 tccatccttg ctatgcggga tgagcagagc aatcctgccc cccaagtaca gaaaccacgt
 901 gccaaacctc cccccgatccc tgccaagaag ccctcctctg tgtccctgtg gtccctggaa
 961 cagccattct ccattgagct gatcgagggc cgaaaagtga atgctgacga gcggatgaag
1021 ctggttgttc aggccgggct cttccatggc aatgagatgc tgtgcaagac tgtgtcaagc
1081 tcggaggtga atgtatgctc agagcccgtg tggaagcagc gactggagtt cgatatcagc
1141 gtctgtgacc tcccgcgcat ggctcgactc tgttttgctc tctatgccgt cgtggagaag
1201 gctaagaagg cacgctccac aaagaagaag tctaagaagg cggactgccc catcgcttgg
1261 gccaacctca tgctattcga ctacaaagat cagctcaaga cgggggagcg ctgcctctac
1321 atgtggccct ctgtcccaga tgagaaggga gagctgctga atcctgcggg tacagtgcgc
1381 gggaacccca acacggagag tgccgctgcc ctggtcatct acctgcctga ggtggccccc
1441 caccctgtgt acttccccgc tctggagaag atcctggagc tggggcgtca cggggagcgt
1501 gggcgcatca cggaggagga gcagctgcag ctgcgggaga tcctggaacg gcggggatcc
1561 ggggaactgt acgaacatga gaaggacctg gtgtggaaga tgcgccacga agtccaggag
1621 catttcccag aggcgctggc ccgcctgctg ctggtcacca agtggaataa acacgaggat
1681 gtggcccaga tgctctattt gctgtgctcc tggcccgagc tgcctgtgct gagcgccctg
1741 gaacttctgg actttagctt tcccgactgc tacgtgggct ccttcgccat caagtccctt
1801 cggaagctga cggacgatga gctcttccag taccttctgc agctggtgca agtgctcaaa
1861 tatgagtcct acctggactg cgagctgacc aaattcttgc tgggccgagc cctggctaac
1921 cgcaagatcg gacacttcct gttctggcac ctccgctctg agatgcacgt accatcagtg
1981 gctctgcggt ttggtctcat catggaagcc tactgcagag gcagcaccca ccacatgaag
2041 gtgctgatga agcaggggga agcactgagc aagcttaagg cactgaatga ctttgtgaag
2101 gtgagttccc agaagaccac caagccccaa accaaggaga tgatgcatat gtgcatgcgc
2161 caggagacct acatggaggc cctgtcccac ctgcagtctc cactcgaccc cagcaccctg
2221 ctggaggaag tctgtgtgga gcagtgcacc ttcatggact ccaaaatgaa gcccctgtgg
2281 atcatgtaca gcagcgagga ggcgggcagt gctggcaacg tgggcatcat ctttaagaac
```

TABLE 3-continued

```
2341 ggggatgacc tccgccagga catgctgact ctgcagatga tccagctcat ggacgtcctg
2401 tggaagcagg agggcctgga cctgaggatg acgccctacg gctgcctccc caccggggac
2461 cgcacaggtc tcatcgaggt ggtcctccac tcggacacca tcgccaacat ccagctgaac
2521 aaaagcaaca tggcggccac agctgccttc aacaaggacg ccctgctcaa ctggctcaag
2581 tccaagaacc ctggggaggc cctggatcgg gccattgagg aattcaccct ctcctgtgct
2641 ggctactgtg tggccacata tgttctgggc atcggtgacc ggcacagcga caacatcatg
2701 atcagagaga gtgggcagct cttccacatt gattttggcc actttctggg gaacttcaag
2761 accaagtttg gaatcaaccg agagcgcgtc cccttcattc tcacctacga ctttgtccac
2821 gtgatccagc aggggaagac taacaacagt gagaagtttg aaaggttccg cggctactgt
2881 gaacgagcct ataccatcct gcggcgccac gggctgcttt tcctccatct cttcgccctg
2941 atgcgggccg caggtctgcc tgagcttagc tgctccaaag atatccagta tctcaaggac
3001 tctctggcac tggggaagac ggaggaagag gcgctaaagc acttccgggt gaagttcaac
3061 gaagctctcc gagaaagctg gaaaaccaaa gtcaactggc tggcgcacaa tgtgtccaag
3121 gataaccgac agtag
```

SEQ ID NO: 34 Mouse PIK3CD (Isoform 4) Amino Acid Sequence

```
   1 mppgvdcpme fwtkeesqsv vvdfllptgv ylnfpvsrna nlstikqvlw hraqyeplfh
  61 mlsdpeayvf tcvnqtaeqq eledeqrrlc diqpflpvlr lvaregdrvk klinsqisll
 121 igkglhefds lrdpevndfr tkmrqfceea aahrqqlgwv ewlqysfplq lepsargwra
 181 gllrvsnral lvnvkfegse esftfqvstk dmplalmaca lrkkatvfrq plveqpeeya
 241 lqvngrheyl ygnyplchfq yicsclhsgl tphltmvhss silamrdeqs npapqvqkpr
 301 akpppipakk psscslwsle qpfsielieg rkvnadermk lvvqaglfhg nemlcktvss
 361 sevnvcsepv wkqrlefdis vcdlprmarl cfalyavvek akkarstkkk skkadcpiaw
 421 anlmlfdykd qlktgercly mwpsvpdekg ellnpagtvr gnpntesaaa lviylpevap
 481 hpvyfpalek ilelgrhger griteeeqlq lreilerrgs gelyehekdl vwkmrhevqe
 541 hfpealarll lvtkwnkhed vaqmlyllcs wpelpvlsal elldfsfpdc yvgsfaiksl
 601 rkltddelfq yllqlvqvlk yesyldcelt kfllgralan rkighflfwh lrsemhvpsv
 661 alrfglimea ycrgsthhmk vlmkqgeals klkalndfvk vssqkttkpq tkemmhmcmr
 721 qetymealsh lqspldpstl leevcveqct fmdskmkplw imysseeags agnvgiifkn
 781 gddlrqdmlt lqmiqlmdvl wkqegldlrm tpygclptgd rtglievvlh sdtianiqln
 841 ksnmaataaf nkdallnwlk sknpgealdr aieeftlsca gycvatyvlg igdrhsdnim
 901 iresgqlfhi dfghflgnfk tkfginrerc pfiltydfvh viqqgktnns ekferfrgyc
 961 eraytilrrh gllflhlfal mraaglpels cskdiqylkd slalgkteee alkhfrvkfn
1021 ealreswktk vnwlahnvsk dnrq
```

SEQ ID NO: 35 Mouse PIK3CD (Transcript 5) cDNA Acid Sequence

```
   1 atgccccctg ggtggactg ccccatggag ttctggacca aagaggagag ccagagcgtg
  61 gttgttgact tcttgctgcc cacaggggtc tacttgaact tccccgtgtc ccgcaatgcc
 121 aacctcagca ccatcaagca ggtgctgtgg caccgtgcac agtatgagcc actcttccac
 181 atgctcagtg accccgaggc ctatgtgttc acctgtgtga accagacggc ggagcagcag
 241 gagttggagg atgagcagcg gaggctgtgc gacatccagc ccttcctgcc cgtgctgcgc
 301 ctcgtggccc gagaggggga ccgcgtgaag aagctcatta actcccagat cagcctcctc
 361 attggcaaag gtctccatga gtttgattcc ctgcgggacc cggaagtaaa cgacttccgc
 421 actaagatgc gccagttttg tgaagaggct gctgctcacc gccagcagct gggctgggtg
 481 gaatggctgc agtacagctt ccccctgcag ctggagccct cagcaagggg ttggcgggcc
 541 ggcttattgc gtgtcagcaa ccgagccctg ctggtcaacg tgaagttcga gggcagtgag
 601 gagagcttca ccttccaggt atccaccaag gacatgcccc tggcactgat ggcctgtgcc
 661 ctccgaaaaa aggccacagt gttccggcag cctctggtgg agcagcctga ggaatatgcc
 721 ctgcaggtga acgggaggca cgaatacctc tacggcaact acccgctctg ccactttcag
 781 tacatctgca gctgcctaca cagcgggctg acccctcatc tgaccatggt ccactcctcc
 841 tccatccttg ctatgcggga tgagcagagc aatcctgccc cccaagtaca gaaaccacgt
 901 gccaaacctc ccccgatccc tgccaagaag ccctcctctg tgtccctgtg gtccctggaa
 961 cagccattct ccattgagct gatcgagggc cgaaaagtga atgctgacga gcggatgaag
1021 ctggttgttc aggccgggct cttccatggc aatgagatgc tgtgcaagac tgtgtcaagc
1081 tcggaggtga atgtatgctc agagcccgtg tggaagcagc gactggagtt cgatatcagc
1141 gtctgtgacc tcccgcgcat ggctcgactc tgttttgctc tctatgccgt cgtggagaag
1201 gctaagaagg cacgctccac aaagaagaag tctaagaagg cggactgccc catcgcttgg
1261 gccaacctca tgctattcga ctacaaagat cagctcaaga cgggggagcg ctgcctctac
1321 atgtggccct ctgtcccaga tgagaaggga gagctgctga atcctgcggg tacagtgcgc
1381 gggaacccca acacggagag tgccgctgcc ctggtcatct acctgcctga ggtggccccc
1441 caccctgtgt acttccccgc tctggagaag atcctggagc tggggcgtca cggggagcgt
1501 gggcgcatca cggaggagga gcagctgcag ctgcgggaga tcctggaacg gcggggatcc
1561 ggggaactgt acgaacatga gaaggacctg gtgtggaaga tgcgccacga agtccaggag
1621 catttcccag aggcgctggc ccgcctgctg ctggtcacca agtggaataa acacgaggat
1681 gtggcccaga tgctctattt gctgtgctcc tggcccgagc tgcctgtgct gagcgccctg
1741 gaacttctgg actttagctt tcccgactgc tacgtgggct ccttcgccat caagtccctt
1801 cggaagctga cggacgatga gctcttccag taccttctgc agctggtgca agtgctcaaa
1861 tatgagtcct acctggactg cgagctgacc aaattcttgc tgggccgagc cctggctaac
1921 cgcaagatcg gacacttcct gttctggcac ctccgctctg agatgcacgt accatcagtg
1981 gctctgcggt ttggtctcat catggaagcc tactgcagag gcagcaccca ccacatgaag
2041 gtgctgatga agcaggggga agcactgagc aagcttaagg cactgaatga ctttgtgaag
2101 gtgagttccc agaagaccac caagccccaa accaaggaga tgatgcatat gtgcatgcgc
2161 caggagacct acatggaggc cctgtcccac ctgcagtctc cactcgaccc cagcaccctg
2221 ctggaggaag tctgcagtgt ggagcagtgc accttcatgg actccaaaat gaagcccctg
2281 tggatcatgt acagcagcga ggaggcgggc agtgctggca acgtgggcat catctttaag
2341 aacggggatg acctccgcca ggacatgctg actctgcaga tgatccagct catggacgtc
2401 ctgtggaagc aggagggcct ggacctgagg atgacgccct acggctgcct ccccaccggg
2461 gaccgcacag gtctcatcga ggtggtcctc cactcggaca ccatcgccaa catccagctg
```

TABLE 3-continued

```
2521 aacaaaagca acatggcggc cacagctgcc ttcaacaagg acgccctgct caactggctc
2581 aagtccaaga accctgggga ggccctggat cgggccattg aggaattcac cctctcctgt
2641 gctggctact gtgtggccac atatgttctg ggcatcggtg accggcacag cgacaacatc
2701 atgatcagag agagtgggca gctcttccac attgattttg gccactttct ggggaacttc
2761 aagaccaagt ttggaatcaa ccgagagcgc gtccccttca ttctcaccta cgactttgtc
2821 cacgtgatcc agcaggggaa gactaacaac agtgagaagt ttgaaaggtt ccgcggctac
2881 tgtgaacgag cctataccat cctgcggcgc cacgggctgc ttttcctcca tctcttcgcc
2941 ctgatgcggg ccgcaggtct gcctgagctt agctgctcca aagatatcca gtatctcaag
3001 gactctctgg cactggggaa gacggaggaa gaggcgctaa agcacttccg ggtgaagttc
3061 aacgaagctc tccgagaaag ctggaaaacc aaagtcaact ggctggcgca caatgtgtcc
3121 aaggataacc gacagtag
```

SEQ ID NO: 36 Mouse PIK3CD (Isoform 5) Amino Acid Sequence

```
   1 mppgvdcpme fwtkeesqsv vvdfllptgv ylnfpvsrna nlstikqvlw hraqyeplfh
  61 mlsdpeayvf tcvnqtaeqq eledeqrrlc diqpflpvlr lvaregdrvk klinsqisll
 121 igkglhefds lrdpevndfr tkmrqfceea aahrqqlgwv ewlqysfplq lepsargwra
 181 gllrvsnral lvnvkfegse esftfqvstk dmplalmaca lrkkatvfrq plveqpeeya
 241 lqvngrheyl ygnyplchfq yicsclhsgl tphltmvhss silamrdeqs npapqvqkpr
 301 akpppipakk pssyslwsle qpfsielieg rkvnadermk lvvqaglfhg nemlcktvss
 361 sevnvcsepv wkqrlefdis vcdlprmarl cfalyavvek akkarstkkk skkadcpiaw
 421 anlmlfdykd qlktgercly mwpsvpdekg ellnpagtvr gnpntesaaa lviylpevap
 481 hpvyfpalek ilelgrhger griteeeqlq lreilerrgs gelyehekdl vwkmrhevqe
 541 hfpealarll lvtkwnkhed vaqmlyllcs wpelpvlsal elldfsfpdc yvgsfaiksl
 601 rkltddelfq yllqlvqvlk yesyldcelt kfllgralan rkighflfwh lrsemhvpsv
 661 alrfglimea ycrgsthhmk vlmkqgeals klkalndfvk vssqkttkpq tkemmhmcmr
 721 qetymealsh lqspldpstl leevcsveqc tfmdskmkpl wimysseeag sagnvgiifk
 781 ngddlrqdml tlqmiqlmdv lwkqegldlr mtpygclptg drtglievvl hsdtianiql
 841 nksnmaataa fnkdallnwl ksknpgeald raieeftlsc agycvatyvl gigdrhsdni
 901 miresgqlfh idfghflgnf ktkfginrer vpfiltydfv hviqqgktnn sekferfrgy
 961 ceraytilrr hgllflhlfa lmraaglpel scskdiqylk dslalgktee ealkhfrvkf
1021 nealreswkt kvnwlahnvs kdnrq
```

SEQ ID NO: 37 Mouse PIK3CD (Transcript 6) cDNA Acid Sequence

```
   1 atgccccctg gggtggactg ccccatggag ttctggacca aagaggagag ccagagcgtg
  61 gttgttgact tcttgctgcc cacaggggtc tacttgaact tccccgtgtc ccgcaatgcc
 121 aacctcagca ccatcaagca ggtgctgtgg caccgtgcac agtatgagcc actcttccac
 181 atgctcagtg accccgaggc ctatgtgttc acctgtgtga accagacggc ggagcagcag
 241 gagttggagg atgagcagcg gaggctgtgc gacatccagc ccttcctgcc cgtgctgcgc
 301 ctcgtggccc gagaggggga ccgcgtgaag aagctcatta actcccagat cagcctcctc
 361 attggcaaag gtctccatga gtttgattcc ctgcgggacc cggaagtaaa cgacttccgc
 421 actaagatgc gccagttttg tgaagaggct gctgctcacc gccagcagct gggctgggtg
 481 gaatggctgc agtacagctt cccccctgcag ctggagccct cagcaagggg ttggcgggcc
 541 ggcttattgc gtgtcagcaa ccgagccctg ctggtcaacg tgaagttcga gggcagtgag
 601 gagagcttca ccttccaggt atccaccaag gacatgcccc tggcactgat ggcctgtgcc
 661 ctccgaaaaa aggccacagt gttccggcag cctctggtgg agcagcctga ggaatatgcc
 721 ctgcaggtga acgggaggca cgaatacctc tacggcaact acccgctctg ccactttcag
 781 tacatctgca gctgcctaca cagcgggctg acccctcatc tgaccatggt ccactcctcc
 841 tccatccttg ctatgcggga tgagcagagc aatcctgccc cccaagtaca gaaaccacgt
 901 gccaaacctc ccccgatccc tgccaagaag ccctcctctg tgtccctgtg gtccctggaa
 961 cagccattct ccattgagct gatcgagggc cgaaaagtga atgctgacga gcggatgaag
1021 ctggttgttc aggccgggct cttccatggc aatgagatgc tgtgcaagac tgtgtcaagc
1081 tcggaggtga atgtatgctc agagcccgtg tggaagcagc gactggagtt cgatatcagc
1141 gtctgtgacc tcccgcgcat ggctcgactc tgttttgctc tctatgccgt cgtggagaag
1201 gctaagaagg cacgctccac aaagaagaag tctaagaagg cggactgccc catcgcttgg
1261 gccaacctca tgctattcga ctacaaagat cagctcaaga cgggggagcg ctgcctctac
1321 atgtggccct ctgtcccaga tgagaaggga gagctgctga atcctgcggg tacagtgcgc
1381 gggaacccca acacggagag tgccgctgcc ctggtcatct acctgcctga ggtggccccc
1441 caccctgtgt acttccccgc tctggagaag atcctggagc tggggcgtca cggggagcgt
1501 gggcgcatca cggaggagga gctgcagctg cgggagatcc tggaacggcg gggatccggg
1561 gaactgtacg aacatgagaa ggacctggtg tggaagatgc gccacgaagt ccaggagcat
1621 ttcccagagg cgctggcccg cctgctgctg gtcaccaagt ggaataaaca cgaggatgtg
1681 gcccagctgt cccagatgct ctatttgctg tgctcctggc ccgagctgcc tgtgctgagc
1741 gccctggaac ttctggactt tagctttccc gactgctacg tgggctcctt cgccatcaag
1801 tcccttcgga agctgacgga cgatgagctc ttccagtacc ttctgcagct ggtgcaagtg
1861 ctcaaatatg agtcctacct ggactgcgag ctgaccaaat tcttgctggg ccgagccctg
1921 gctaaccgca agatcggaca cttcctgttc tggcacctcc gctctgagat gcacgtacca
1981 tcagtggctc tgcggtttgg tctcatcatg gaagcctact gcagaggcag cacccaccac
2041 atgaaggtgc tgatgaagca gggggaagca ctgagcaagc ttaaggcact gaatgacttt
2101 gtgaaggtga gttcccagaa gaccaccaag ccccaaacca aggagatgat gcatatgtgc
2161 atgcgccagg agacctacat ggaggccctg tcccacctgc agtctccact cgaccccagc
2221 accctgctgg aggaagtctg tgtggagcag tgcaccttca tggactccaa aatgaagccc
2281 ctgtggatca tgtacagcag cgaggaggcg ggcagtgctg gcaacgtggg catcatcttt
2341 aagaacgggg atgacctccg ccaggacatg ctgactctgc agatgatcca gctcatggac
2401 gtcctgtgga agcaggaggg cctggacctg aggatgacgc cctacggctg cctccccacc
2461 ggggaccgca caggtctcat cgaggtggtc ctccactcgg acaccatcgc caacatccag
2521 ctgaacaaaa gcaacatggc ggccacagct gccttcaaca aggacgccct gctcaactgg
2581 ctcaagtcca agaaccctgg ggaggccctg gatcgggcca ttgaggaatt caccctctcc
2641 tgtgctggct actgtgtggc cacatatgtt ctgggcatcg gtgaccggca cagcgacaac
2701 atcatgatca gagagagtgg gcagctcttc cacattgatt ttggccactt tctggggaac
2761 ttcaagacca agtttggaat caaccgagag cgcgtcccct tcattctcac ctacgacttt
```

TABLE 3-continued

```
2821 gtccacgtga tccagcaggg gaagactaac aacagtgaga agtttgaaag gttccgcggc
2881 tactgtgaac gagcctatac catcctgcgg cgccacgggc tgcttttcct ccatctcttc
2941 gccctgatgc gggccgcagg tctgcctgag cttagctgct ccaaagatat ccagtatctc
3001 aaggactctc tggcactggg gaagacggag gaagaggcgc taaagcactt ccgggtgaag
3061 ttcaacgaag ctctccgaga aagctggaaa accaaagtca actggctggc gcacaatgtg
3121 tccaaggata accgacagta g
```

SEQ ID NO: 38 Mouse PIK3CD (Isoform 6) Amino Acid Sequence

```
   1 mppgvdcpme fwtkeesqsv vvdfllptgv ylnfpvsrna nlstikqvlw hraqyeplfh
  61 mlsdpeayvf tcvnqtaeqq eledeqrrlc diqpflpvlr lvaregdrvk klinsqisll
 121 igkglhefds lrdpevndfr tkmrqfceea aahrqqlgwv ewlqysfplq lepsargwra
 181 gllrvsnral lvnvkfegse esftfqvstk dmplalmaca lrkkatvfrq plveqpeeya
 241 lqvngrheyl ygnyplchfq yicsclhsgl tphltmvhss silamrdeqs npapqvqkpr
 301 akpppipakk pssyslwsle qpfsielieg rkvnadermk lvvqaglfhg nemlcktvss
 361 sevnvcsepv wkqrlefdis vcdlprmarl cfalyavvek akkarstkkk skkadcpiaw
 421 anlmlfdykd qlktgercly mwpsvpdekg ellnpagtvr gnpntesaaa lviylpevap
 481 hpvyfpalek ilelgrhger griteeelql reilerrgsg elyehekdlv wkmrhevqeh
 541 fpealarlll vtkwnkhedv aqlsgmlyll cswpelpvls alelldfsfp dcyvgsfaik
 601 slrkltddel fqyllqlvqv lkyesyldce ltkfllgral anrkighflf whlrsemhvp
 661 svalrfglim eaycrgsthh mkvlmkqgea lsklkalndf vkvssqkttk pqtkemmhmc
 721 mrqetymeal shlqspldps tlleevcveq ctfmdskmkp lwimysseea gsagnvgiif
 781 kngddlrqdm ltlqmiqlmd vlwkqegldl rmtpygclpt gdrtglievv lhsdtianiq
 841 lnksnmaata afnkdallnw lksknpgeal draieeftls cagycvatyv lgigdrhsdn
 901 imiresgqlf hidfghflgn fktkfginre rvpfiltydf vhviqqgktn nsekferfrg
 961 yceraytilr rhgllflhlf almraaglpe lscskdiqyl kdslalgkte eealkhfrvk
1021 fnealreswk tkvnwlahnv skdnrq
```

SEQ ID NO: 39 Human PD-1 cDNA Sequence

```
cactctggtg gggctgctcc aggc atg cag atc cca cag gcg ccc tgg cca      51
                           Met Gln Ile Pro Gln Ala Pro Trp Pro
                             1               5

gtc gtc tgg gcg gtg cta caa ctg ggc tgg cgg cca gga tgg ttc tta      99
Val Val Trp Ala Val Leu Gln Leu Gly Trp Arg Pro Gly Trp Phe Leu
 10                  15                  20                  25

gac tcc cca gac agg ccc tgg aac ccc ccc acc ttc tcc cca gcc ctg     147
Asp Ser Pro Asp Arg Pro Trp Asn Pro Pro Thr Phe Ser Pro Ala Leu
                 30                  35                  40

ctc gtg gtg acc gaa ggg gac aac gcc acc ttc acc tgc agc ttc tcc     195
Leu Val Val Thr Glu Gly Asp Asn Ala Thr Phe Thr Cys Ser Phe Ser
             45                  50                  55

aac aca tcg gag agc ttc gtg cta aac tgg tac cgc atg agc ccc agc     243
Asn Thr Ser Glu Ser Phe Val Leu Asn Trp Tyr Arg Met Ser Pro Ser
         60                  65                  70

aac cag acg gac aag ctg gcc gcc ttc ccc gag gac cgc agc cag ccc     291
Asn Gln Thr Asp Lys Leu Ala Ala Phe Pro Glu Asp Arg Ser Gln Pro
     75                  80                  85

ggc cag gac tgc cgc ttc cgt gtc aca caa ctg ccc aac ggg cgt gac     339
Gly Gln Asp Cys Arg Phe Arg Val Thr Gln Leu Pro Asn Gly Arg Asp
 90                  95                 100                 105

ttc cac atg agc gtg gtc agg gcc cgg cgc aat gac agc ggc acc tac     387
Phe His Met Ser Val Val Arg Ala Arg Arg Asn Asp Ser Gly Thr Tyr
                110                 115                 120

ctc tgt ggg gcc atc tcc ctg gcc ccc aag gcg cag atc aaa gag agc     435
Leu Cys Gly Ala Ile Ser Leu Ala Pro Lys Ala Gln Ile Lys Glu Ser
            125                 130                 135

ctg cgg gca gag ctc agg gtg aca gag aga agg gca gaa gtg ccc aca     483
Leu Arg Ala Glu Leu Arg Val Thr Glu Arg Arg Ala Glu Val Pro Thr
        140                 145                 150

gcc cac ccc agc ccc tca ccc agg tca gcc ggc cag ttc caa acc ctg     531
Ala His Pro Ser Pro Ser Pro Arg Ser Ala Gly Gln Phe Gln Thr Leu
    155                 160                 165

gtg gtt ggt gtc gtg ggc ggc ctg ctg ggc agc ctg gtg ctg cta gtc     579
Val Val Gly Val Val Gly Gly Leu Leu Gly Ser Leu Val Leu Leu Val
170                 175                 180                 185

tgg gtc ctg gcc gtc atc tgc tcc cgg gcc gca cga ggg aca ata gga     627
Trp Val Leu Ala Val Ile Cys Ser Arg Ala Ala Arg Gly Thr Ile Gly
                190                 195                 200

gcc agg cgc acc ggc cag ccc ctg aag gag gac ccc tca gcc gtg cct     675
Ala Arg Arg Thr Gly Gln Pro Leu Lys Glu Asp Pro Ser Ala Val Pro
            205                 210                 215

gtg ttc tct gtg gac tat ggg gag ctg gat ttc cag tgg cga gag aag     723
Val Phe Ser Val Asp Tyr Gly Glu Leu Asp Phe Gln Trp Arg Glu Lys
        220                 225                 230

acc ccg gag ccc ccc gtg ccc tgt gtc cct gag cag acg gag tat gcc     771
Thr Pro Glu Pro Pro Val Pro Cys Val Pro Glu Gln Thr Glu Tyr Ala
    235                 240                 245
```

TABLE 3-continued

```
acc att gtc ttt cct agc gga atg ggc acc tca tcc ccc gcc cgc agg    819
Thr Ile Val Phe Pro Ser Gly Met Gly Thr Ser Ser Pro Ala Arg Arg
250                 255                 260                 265
ggc tca gct gac ggc cct cgg agt gcc cag cca ctg agg cct gag gat    867
Gly Ser Ala Asp Gly Pro Arg Ser Ala Gln Pro Leu Arg Pro Glu Asp
                270                 275                 280
gga cac tgc tot tgg ccc ctc tgaccggctt ccttggccac cagtgttctg cag   921
Gly His Cys Ser Trp Pro Leu
            285
```

SEQ ID NO: 40 Human PD-1 Amino Acid Sequence

```
Met Gln Ile Pro Gln Ala Pro Trp Pro Val Val Trp Ala Val Leu Gln
  1               5                  10                  15
Leu Gly Trp Arg Pro Gly Trp Phe Leu Asp Ser Pro Asp Arg Pro Trp
            20                  25                  30
Asn Pro Pro Thr Phe Ser Pro Ala Leu Leu Val Val Thr Glu Gly Asp
        35                  40                  45
Asn Ala Thr Phe Thr Cys Ser Phe Ser Asn Thr Ser Glu Ser Phe Val
    50                  55                  60
Leu Asn Trp Tyr Arg Met Ser Pro Ser Asn Gln Thr Asp Lys Leu Ala
 65                  70                  75                  80
Ala Phe Pro Glu Asp Arg Ser Gln Pro Gly Gln Asp Cys Arg Phe Arg
                85                  90                  95
Val Thr Gln Leu Pro Asn Gly Arg Asp Phe His Met Ser Val Val Arg
            100                 105                 110
Ala Arg Arg Asn Asp Ser Gly Thr Tyr Leu Cys Gly Ala Ile Ser Leu
        115                 120                 125
Ala Pro Lys Ala Gln Ile Lys Glu Ser Leu Arg Ala Glu Leu Arg Val
    130                 135                 140
Thr Glu Arg Arg Ala Glu Val Pro Thr Ala His Pro Ser Pro Ser Pro
145                 150                 155                 160
Arg Ser Ala Gly Gln Phe Gln Thr Leu Val Val Gly Val Val Gly Gly
                165                 170                 175
Leu Leu Gly Ser Leu Val Leu Leu Val Trp Val Leu Ala Val Ile Cys
            180                 185                 190
Ser Arg Ala Ala Arg Gly Thr Ile Gly Ala Arg Arg Thr Gly Gln Pro
        195                 200                 205
Leu Lys Glu Asp Pro Ser Ala Val Pro Val Phe Ser Val Asp Tyr Gly
    210                 215                 220
Glu Leu Asp Phe Gln Trp Arg Glu Lys Thr Pro Glu Pro Pro Val Pro
225                 230                 235                 240
Cys Val Pro Glu Gln Thr Glu Tyr Ala Thr Ile Val Phe Pro Ser Gly
                245                 250                 255
Met Gly Thr Ser Ser Pro Ala Arg Arg Gly Ser Ala Asp Gly Pro Arg
            260                 265                 270
Ser Ala Gln Pro Leu Arg Pro Glu Asp Gly His Cys Ser Trp Pro Leu
        275                 280                 285
```

SEQ ID NO: 41 Human PD-L1S cDNA Acid Sequence

```
gcttcccgag gctccgcacc agccgcgctt ctgtccgcct gcagggcatt ccagaaag     58
atg agg ata ttt got gtc ttt ata ttc atg acc tac tgg cat ttg ctg    106
Met Arg Ile Phe Ala Val Phe Ile Phe Met Thr Tyr Trp His Leu Leu
  1               5                  10                  15
aac gca ttt act gtc acg gtt ccc aag gac cta tat gtg gta gag tat    154
Asn Ala Phe Thr Val Thr Val Pro Lys Asp Leu Tyr Val Val Glu Tyr
            20                  25                  30
ggt agc aat atg aca att gaa tgc aaa ttc cca gta gaa aaa caa tta    202
Gly Ser Asn Met Thr Ile Glu Cys Lys Phe Pro Val Glu Lys Gln Leu
        35                  40                  45
gac ctg gct gca cta att gtc tat tgg gaa atg gag gat aag aac att    250
Asp Leu Ala Ala Leu Ile Val Tyr Trp Glu Met Glu Asp Lys Asn Ile
    50                  55                  60
att caa ttt gtg cat gga gag gaa gac ctg aag gtt cag cat agt agc    298
Ile Gln Phe Val His Gly Glu Glu Asp Leu Lys Val Gln His Ser Ser
 65                  70                  75                  80
tac aga cag agg gcc cgg ctg ttg aag gac cag ctc tcc ctg gga aat    346
Tyr Arg Gln Arg Ala Arg Leu Leu Lys Asp Gln Leu Ser Leu Gly Asn
                85                  90                  95
gct gca ctt cag atc aca gat gtg aaa ttg cag gat gca ggg gtg tac    394
Ala Ala Leu Gln Ile Thr Asp Val Lys Leu Gln Asp Ala Gly Val Tyr
            100                 105                 110
cgc tgc atg atc agc tat ggt ggt gcc gac tac aag cga att act gtg    442
Arg Cys Met Ile Ser Tyr Gly Gly Ala Asp Tyr Lys Arg Ile Thr Val
        115                 120                 125
aaa gtc aat gcc cca tac aac aaa atc aac caa aga att ttg gtt gtg    490
Lys Val Asn Ala Pro Tyr Asn Lys Ile Asn Gln Arg Ile Leu Val Val
    130                 135                 140
```

TABLE 3-continued

```
gat cca gtc acc tct gaa cat gaa ctg aca tgt cag gct gag ggc tac    538
Asp Pro Val Thr Ser Glu His Glu Leu Thr Cys Gln Ala Glu Gly Tyr
145                 150                 155                 160
ccc aag gcc gaa gtc atc tgg aca agc agt gac cat caa gtc ctg agt    586
Pro Lys Ala Glu Val Ile Trp Thr Ser Ser Asp His Gln Val Leu Ser
                165                 170                 175
ggt aag acc acc acc acc aat tcc aag aga gag gag aag ctt ttc aat    634
Gly Lys Thr Thr Thr Thr Asn Ser Lys Arg Glu Glu Lys Leu Phe Asn
            180                 185                 190
gtg acc agc aca ctg aga atc aac aca aca act aat gag att ttc tac    682
Val Thr Ser Thr Leu Arg Ile Asn Thr Thr Thr Asn Glu Ile Phe Tyr
        195                 200                 205
tgc act ttt agg aga tta gat cct gag gaa aac cat aca gct gaa ttg    730
Cys Thr Phe Arg Arg Leu Asp Pro Glu Glu Asn His Thr Ala Glu Leu
    210                 215                 220
gtc atc cca ggt aat att ctg aat gtg tcc att aaa ata tgt cta aca    778
Val Ile Pro Gly Asn Ile Leu Asn Val Ser Ile Lys Ile Cys Leu Thr
225                 230                 235                 240
ctg tcc cct agc acc tagcatgatg tctgcctatc atagtcattc agtgattgtt    833
Leu Ser Pro Ser Thr
                245
gaataaatga atgaatgaat aacactatgt ttacaaaata tatcctaatt cctcacctcc  893
attcatccaa accatattgt tacttaataa acattcagca gatatttatg gaataaaaaa  953
aaaaaaaaaa aaaaa                                                   968
```

SEQ ID NO: 42 Human PD-L1S Amino Acid Sequence

```
Met Arg Ile Phe Ala Val Phe Ile Phe Met Thr Tyr Trp His Leu Leu
  1               5                  10                  15
Asn Ala Phe Thr Val Thr Val Pro Lys Asp Leu Tyr Val Val Glu Tyr
            20                  25                  30
Gly Ser Asn Met Thr Ile Glu Cys Lys Phe Pro Val Glu Lys Gln Leu
        35                  40                  45
Asp Leu Ala Ala Leu Ile Val Tyr Trp Glu Met Glu Asp Lys Asn Ile
    50                  55                  60
Ile Gln Phe Val His Gly Glu Glu Asp Leu Lys Val Gln His Ser Ser
 65                  70                  75                  80
Tyr Arg Gln Arg Ala Arg Leu Leu Lys Asp Gln Leu Ser Leu Gly Asn
                85                  90                  95
Ala Ala Leu Gln Ile Thr Asp Val Lys Leu Gln Asp Ala Gly Val Tyr
            100                 105                 110
Arg Cys Met Ile Ser Tyr Gly Gly Ala Asp Tyr Lys Arg Ile Thr Val
        115                 120                 125
Lys Val Asn Ala Pro Tyr Asn Lys Ile Asn Gln Arg Ile Leu Val Val
    130                 135                 140
Asp Pro Val Thr Ser Glu His Glu Leu Thr Cys Gln Ala Glu Gly Tyr
145                 150                 155                 160
Pro Lys Ala Glu Val Ile Trp Thr Ser Ser Asp His Gln Val Leu Ser
                165                 170                 175
Gly Lys Thr Thr Thr Thr Asn Ser Lys Arg Glu Glu Lys Leu Phe Asn
            180                 185                 190
Val Thr Ser Thr Leu Arg Ile Asn Thr Thr Thr Asn Glu Ile Phe Tyr
        195                 200                 205
Cys Thr Phe Arg Arg Leu Asp Pro Glu Glu Asn His Thr Ala Glu Leu
    210                 215                 220
Val Ile Pro Gly Asn Ile Leu Asn Val Ser Ile Lys Ile Cys Leu Thr
225                 230                 235                 240
Leu Ser Pro Ser Thr
                245
```

SEQ ID NO: 43 Human PD-L1M cDNA Acid Sequence

```
cgaggctccg caccagccgc gcttctgtcc gcctgcaggg cattccagaa agatgagg     58
                                                        Met Arg
                                                          1
ata ttt gct gtc ttt ata ttc atg acc tac tgg cat ttg ctg aac gca    106
Ile Phe Ala Val Phe Ile Phe Met Thr Tyr Trp His Leu Leu Asn Ala
        5                  10                  15
ttt act gtc acg gtt ccc aag gac cta tat gtg gta gag tat ggt agc    154
Phe Thr Val Thr Val Pro Lys Asp Leu Tyr Val Val Glu Tyr Gly Ser
    20                  25                  30
aat atg aca att gaa tgc aaa ttc cca gta gaa aaa caa tta gac ctg    202
Asn Met Thr Ile Glu Cys Lys Phe Pro Val Glu Lys Gln Leu Asp Leu
 35                  40                  45                  50
gct gca cta att gtc tat tgg gaa atg gag gat aag aac att att caa    250
Ala Ala Leu Ile Val Tyr Trp Glu Met Glu Asp Lys Asn Ile Ile Gln
                55                  60                  65
ttt gtg cat gga gag gaa gac ctg aag gtt cag cat agt agc tac aga    298
Phe Val His Gly Glu Glu Asp Leu Lys Val Gln His Ser Ser Tyr Arg
            70                  75                  80
```

TABLE 3-continued

```
cag agg gcc cgg ctg ttg aag gac cag ctc tcc ctg gga aat gct gca    346
Gln Arg Ala Arg Leu Leu Lys Asp Gln Leu Ser Leu Gly Asn Ala Ala
         85                  90                  95
ctt cag atc aca gat gtg aaa ttg cag gat gca ggg gtg tac cgc tgc    394
Leu Gln Ile Thr Asp Val Lys Leu Gln Asp Ala Gly Val Tyr Arg Cys
    100                 105                 110
atg atc agc tat ggt ggt gcc gac tac aag cga att act gtg aaa gtc    442
Met Ile Ser Tyr Gly Gly Ala Asp Tyr Lys Arg Ile Thr Val Lys Val
115                 120                 125                 130
aat gcc cca tac aac aaa atc aac caa aga att ttg gtt gtg gat cca    490
Asn Ala Pro Tyr Asn Lys Ile Asn Gln Arg Ile Leu Val Val Asp Pro
                135                 140                 145
gtc acc tct gaa cat gaa ctg aca tgt cag gct gag ggc tac ccc aag    538
Val Thr Ser Glu His Glu Leu Thr Cys Gln Ala Glu Gly Tyr Pro Lys
            150                 155                 160
gcc gaa gtc atc tgg aca agc agt gac cat caa gtc ctg agt ggt aag    586
Ala Glu Val Ile Trp Thr Ser Ser Asp His Gln Val Leu Ser Gly Lys
        165                 170                 175
acc acc acc acc aat tcc aag aga gag gag aag ctt ttc aat gtg acc    634
Thr Thr Thr Thr Asn Ser Lys Arg Glu Glu Lys Leu Phe Asn Val Thr
    180                 185                 190
agc aca ctg aga atc aac aca aca act aat gag att ttc tac tgc act    682
Ser Thr Leu Arg Ile Asn Thr Thr Thr Asn Glu Ile Phe Tyr Cys Thr
195                 200                 205                 210
ttt agg aga tta gat cct gag gaa aac cat aca gct gaa ttg gtc atc    730
Phe Arg Arg Leu Asp Pro Glu Glu Asn His Thr Ala Glu Leu Val Ile
                215                 220                 225
cca gaa cta cct ctg gca cat cct cca aat gaa agg act cac ttg gta    778
Pro Glu Leu Pro Leu Ala His Pro Pro Asn Glu Arg Thr His Leu Val
            230                 235                 240
att ctg gga gcc atc tta tta tgc ctt ggt gta gca ctg aca ttc atc    826
Ile Leu Gly Ala Ile Leu Leu Cys Leu Gly Val Ala Leu Thr Phe Ile
        245                 250                 255
ttc cgt tta aga aaa ggg aga atg atg gat gtg aaa aaa tgt ggc atc    874
Phe Arg Leu Arg Lys Gly Arg Met Met Asp Val Lys Lys Cys Gly Ile
    260                 265                 270
caa gat aca aac tca aag aag caa agt gat aca cat ttg gag gag acg    922
Gln Asp Thr Asn Ser Lys Lys Gln Ser Asp Thr His Leu Glu Glu Thr
275                 280                 285                 290
taatccagca ttggaacttc tgatcttcaa gcagggattc tcaacctgtg gtttaggggt  982
tcatcggggc tgagcgtgac aagaggaagg aatgggcccg tgggatgcag gcaatgtggg 1042
acttaaaagg cccaagcact gaaaatggaa cctggcgaaa gcagaggagg agaatgaaga 1102
aagatggagt caaacaggga gcctggaggg agaccttgat actttcaaat gcctgagggg 1162
ctcatcgacg cctgtgacag ggagaaagga tacttctgaa caaggagcct ccaagcaaat 1222
catccattgc tcatcctagg aagacgggtt gagaatccct aatttgaggg tcagttcctg 1282
cagaagtgcc ctttgcctcc actcaatgcc tcaatttgtt ttctgcatga ctgagagtct 1342
cagtgttgga acgggacagt atttatgtat gagtttttcc tatttatttt gagtctgtga 1402
ggtcttcttg tcatgtgagt gtggttgtga atgatttctt ttgaagatat attgtagtag 1462
atgttacaat tttgtcgcca aactaaactt gctgcttaat gatttgctca catctagtaa 1522
aacatggagt atttgtaaaa aaaaaaaaaa a                                1553
```

SEQ ID NO: 44 Human PD-L1M Amino Acid Sequence

```
Met Arg Ile Phe Ala Val Phe Ile Phe Met Thr Tyr Trp His Leu Leu
  1               5                  10                  15
Asn Ala Phe Thr Val Thr Val Pro Lys Asp Leu Tyr Val Val Glu Tyr
            20                  25                  30
Gly Ser Asn Met Thr Ile Glu Cys Lys Phe Pro Val Glu Lys Gln Leu
        35                  40                  45
Asp Leu Ala Ala Leu Ile Val Tyr Trp Glu Met Glu Asp Lys Asn Ile
    50                  55                  60
Ile Gln Phe Val His Gly Glu Glu Asp Leu Lys Val Gln His Ser Ser
 65                  70                  75                  80
Tyr Arg Gln Arg Ala Arg Leu Leu Lys Asp Gln Leu Ser Leu Gly Asn
                 85                  90                  95
Ala Ala Leu Gln Ile Thr Asp Val Lys Leu Gln Asp Ala Gly Val Tyr
            100                 105                 110
Arg Cys Met Ile Ser Tyr Gly Gly Ala Asp Tyr Lys Arg Ile Thr Val
        115                 120                 125
Lys Val Asn Ala Pro Tyr Asn Lys Ile Asn Gln Arg Ile Leu Val Val
    130                 135                 140
Asp Pro Val Thr Ser Glu His Glu Leu Thr Cys Gln Ala Glu Gly Tyr
145                 150                 155                 160
Pro Lys Ala Glu Val Ile Trp Thr Ser Ser Asp His Gln Val Leu Ser
                165                 170                 175
Gly Lys Thr Thr Thr Thr Asn Ser Lys Arg Glu Glu Lys Leu Phe Asn
            180                 185                 190
Val Thr Ser Thr Leu Arg Ile Asn Thr Thr Thr Asn Glu Ile Phe Tyr
        195                 200                 205
Cys Thr Phe Arg Arg Leu Asp Pro Glu Glu Asn His Thr Ala Glu Leu
```

TABLE 3-continued

```
    210                 215                 220
Val Ile Pro Glu Leu Pro Leu Ala His Pro Pro Asn Glu Arg Thr His
225                 230                 235                 240
Leu Val Ile Leu Gly Ala Ile Leu Leu Cys Leu Gly Val Ala Leu Thr
                245                 250                 255
Phe Ile Phe Arg Leu Arg Lys Gly Arg Met Met Asp Val Lys Lys Cys
            260                 265                 270
Gly Ile Gln Asp Thr Asn Ser Lys Lys Gln Ser Asp Thr His Leu Glu
        275                 280                 285
Glu Thr
    290
```

SEQ ID NO: 45 Human PD-L2 cDNA Acid Sequence

```
atg atc ttc ctc ctg cta atg ttg agc ctg gaa ttg cag ctt cac cag      48
Met Ile Phe Leu Leu Leu Met Leu Ser Leu Glu Leu Gln Leu His Gln
 1               5                  10                  15
ata gca gct tta ttc aca gtg aca gtc cct aag gaa ctg tac ata ata      96
Ile Ala Ala Leu Phe Thr Val Thr Val Pro Lys Glu Leu Tyr Ile Ile
            20                  25                  30
gag cat ggc agc aat gtg acc ctg gaa tgc aac ttt gac act gga agt     144
Glu His Gly Ser Asn Val Thr Leu Glu Cys Asn Phe Asp Thr Gly Ser
        35                  40                  45
cat gtg aac ctt gga gca ata aca gcc agt ttg caa aag gtg gaa aat     192
His Val Asn Leu Gly Ala Ile Thr Ala Ser Leu Gln Lys Val Glu Asn
    50                  55                  60
gat aca tcc cca cac cgt gaa aga gcc act ttg ctg gag gag cag ctg     240
Asp Thr Ser Pro His Arg Glu Arg Ala Thr Leu Leu Glu Glu Gln Leu
 65                 70                  75                  80
ccc cta ggg aag gcc tcg ttc cac ata cct caa gtc caa gtg agg gac     288
Pro Leu Gly Lys Ala Ser Phe His Ile Pro Gln Val Gln Val Arg Asp
                85                  90                  95
gaa gga cag tac caa tgc ata atc atc tat ggg gtc gcc tgg gac tac     336
Glu Gly Gln Tyr Gln Cys Ile Ile Ile Tyr Gly Val Ala Trp Asp Tyr
            100                 105                 110
aag tac ctg act ctg aaa gtc aaa gct tcc tac agg aaa ata aac act     384
Lys Tyr Leu Thr Leu Lys Val Lys Ala Ser Tyr Arg Lys Ile Asn Thr
        115                 120                 125
cac atc cta aag gtt cca gaa aca gat gag gta gag ctc acc tgc cag     432
His Ile Leu Lys Val Pro Glu Thr Asp Glu Val Glu Leu Thr Cys Gln
    130                 135                 140
gct aca ggt tat cct ctg gca gaa gta tcc tgg cca aac gtc agc gtt     480
Ala Thr Gly Tyr Pro Leu Ala Glu Val Ser Trp Pro Asn Val Ser Val
145                 150                 155                 160
cct gcc aac acc agc cac tcc agg acc cct gaa ggc ctc tac cag gtc     528
Pro Ala Asn Thr Ser His Ser Arg Thr Pro Glu Gly Leu Tyr Gln Val
                165                 170                 175
acc agt gtt ctg cgc cta aag cca ccc cct ggc aga aac ttc agc tgt     576
Thr Ser Val Leu Arg Leu Lys Pro Pro Pro Gly Arg Asn Phe Ser Cys
            180                 185                 190
gtg ttc tgg aat act cac gtg agg gaa ctt act ttg gcc agc att gac     624
Val Phe Trp Asn Thr His Val Arg Glu Leu Thr Leu Ala Ser Ile Asp
        195                 200                 205
ctt caa agt cag atg gaa ccc agg acc cat cca act tgg ctg ctt cac     672
Leu Gln Ser Gln Met Glu Pro Arg Thr His Pro Thr Trp Leu Leu His
    210                 215                 220
att ttc atc ccc tcc tgc atc att gct ttc att ttc ata gcc aca gtg     720
Ile Phe Ile Pro Ser Cys Ile Ile Ala Phe Ile Phe Ile Ala Thr Val
225                 230                 235                 240
ata gcc cta aga aaa caa ctc tgt caa aag ctg tat tct tca aaa gac     768
Ile Ala Leu Arg Lys Gln Leu Cys Gln Lys Leu Tyr Ser Ser Lys Asp
                245                 250                 255
aca aca aaa aga cct gtc acc aca aca aag agg gaa gtg aac agt gct     816
Thr Thr Lys Arg Pro Val Thr Thr Thr Lys Arg Glu Val Asn Ser Ala
                260                 265                 270
atc                                                                 819
Ile
```

SEQ ID NO: 46 Human PD-L2 Amino Acid Sequence

```
Met Ile Phe Leu Leu Leu Met Leu Ser Leu Glu Leu Gln Leu His Gln
 1               5                  10                  15
Ile Ala Ala Leu Phe Thr Val Thr Val Pro Lys Glu Leu Tyr Ile Ile
            20                  25                  30
Glu His Gly Ser Asn Val Thr Leu Glu Cys Asn Phe Asp Thr Gly Ser
        35                  40                  45
His Val Asn Leu Gly Ala Ile Thr Ala Ser Leu Gln Lys Val Glu Asn
    50                  55                  60
Asp Thr Ser Pro His Arg Glu Arg Ala Thr Leu Leu Glu Glu Gln Leu
65                  70                  75                  80
```

TABLE 3-continued

```
Pro Leu Gly Lys Ala Ser Phe His Ile Pro Gln Val Gln Val Arg Asp
                85                  90                  95
Glu Gly Gln Tyr Gln Cys Ile Ile Ile Tyr Gly Val Ala Trp Asp Tyr
            100                 105                 110
Lys Tyr Leu Thr Leu Lys Val Lys Ala Ser Tyr Arg Lys Ile Asn Thr
        115                 120                 125
His Ile Leu Lys Val Pro Glu Thr Asp Glu Val Glu Leu Thr Cys Gln
    130                 135                 140
Ala Thr Gly Tyr Pro Leu Ala Glu Val Ser Trp Pro Asn Val Ser Val
145                 150                 155                 160
Pro Ala Asn Thr Ser His Ser Arg Thr Pro Glu Gly Leu Tyr Gln Val
                165                 170                 175
Thr Ser Val Leu Arg Leu Lys Pro Pro Pro Gly Arg Asn Phe Ser Cys
            180                 185                 190
Val Phe Trp Asn Thr His Val Arg Glu Leu Thr Leu Ala Ser Ile Asp
        195                 200                 205
Leu Gln Ser Gln Met Glu Pro Arg Thr His Pro Thr Trp Leu Leu His
    210                 215                 220
Ile Phe Ile Pro Ser Cys Ile Ile Ala Phe Ile Phe Ile Ala Thr Val
225                 230                 235                 240
Ile Ala Leu Arg Lys Gln Leu Cys Gln Lys Leu Tyr Ser Ser Lys Asp
                245                 250                 255
Thr Thr Lys Arg Pro Val Thr Thr Thr Lys Arg Glu Val Asn Ser Ala
            260                 265                 270
Ile
```

SEQ ID NO: 47 Human TIM-3 cDNA Sequence

```
  1 atgttttcac atcttccctt tgactgtgtc ctgctgctgc tgctgctact acttacaagg
 61 tcctcagaag tggaatacag agcggaggtc ggtcagaatg cctatctgcc ctgcttctac
121 accccagccg ccccagggaa cctcgtgccc gtctgctggg gcaaaggagc ctgtcctgtg
181 tttgaatgtg gcaacgtggt gctcaggact gatgaaaggg atgtgaatta ttggacatcc
241 agatactggc taaatgggga tttccgcaaa ggagatgtgt ccctgaccat agagaatgtg
301 actctagcag acagtgggat ctactgctgc cggatccaaa tcccaggcat aatgaatgat
361 gaaaaattta acctgaagtt ggtcatcaaa ccagccaagg tcacccctgc accgactcgg
421 cagagagact tcactgcagc ctttccaagg atgcttacca ccaggggaca tggcccagca
481 gagacacaga cactggggag cctccctgat ataaatctaa cacaaatatc cacattggcc
541 aatgagttac gggactctag attggccaat gacttacggg actctggagc aaccatcaga
601 ataggcatct acatcggagc agggatctgt gctgggctgg ctctggctct tatcttcggc
661 gctttaattt tcaaatggta ttctcatagc aaagagaaga tacagaattt aagcctcatc
721 tctttggcca acctccctcc ctcaggattg gcaaatgcag tagcagaggg aattcgctca
781 gaagaaaaca tctataccat tgaagagaac gtatatgaag tggaggagcc caatgagtat
841 tattgctatg tcagcagcag gcagcaaccc tcacaacctt tgggttgtcg ctttgcaatg
901 ccatag
```

SEQ ID NO: 48 Human TIM-3 Amino Acid Sequence

```
  1 mfshlpfdcv llllllllltr sseveyraev gqnaylpcfy tpaapgnlvp vcwgkgacpv
 61 fecgnvvlrt derdvnywts rywlngdfrk gdvsltienv tladsgiycc riqipgimnd
121 ekfnlklvik pakvtpaptr qrdftaafpr mlttrghgpa etqtlgslpd initqistla
181 nelrdsrlan dlrdsgatir igiyigagic aglalalifg alifkwyshs kekiqnlsli
241 slanlppsgl anavaegirs eeniytieen vyeveepney ycyvssrqqp sqplgcrfam
301 p
```

SEQ ID NO: 49 Mouse TIM-3 cDNA Sequence

```
  1 atgttttcag gtcttaccct caactgtgtc ctgctgctgc tgcaactact acttgcaagg
 61 tcattggaaa atgcttatgt gtttgaggtt ggtaagaatg cctatctgcc ctgcagttac
121 actctatcta cacctggggc acttgtgcct atgtgctggg gcaagggatt ctgtccttgg
181 tcacagtgta ccaacgagtt gctcagaact gatgaaagaa atgtgacata tcagaaatcc
241 agcagatacc agctaaaggg cgatctcaac aaaggagacg tgtctctgat cataaagaat
301 gtgactctgg atgaccatgg gacctactgc tgcaggatac agttccctgg tcttatgaat
361 gataaaaaat tagaactgaa attagacatc aaagcagcca aggtcactcc agctcagact
421 gcccatgggg actctactac agcttctcca agaaccctaa ccacggagag aaatggttca
481 gagacacaga cactggtgac cctccataat aacaatggaa caaaaatttc cacatgggct
541 gatgaaatta aggactctgg agaaacgatc agaactgcta tccacattgg agtgggagtc
601 tctgctgggt tgaccctggc acttatcatt ggtgtcttaa tccttaaatg gtattcctgt
661 aagaaaaaga agttatcgag tttgagcctt attacactgg ccaacttgcc tccaggaggg
721 ttggcaaatg caggagcagt caggattcgc tctgaggaaa atatctacac catcgaggag
781 aacgtatatg aagtggagaa ttcaaatgag tactactgct acgtcaacag ccagcagcca
841 tcctga
```

SEQ ID NO: 50 Mouse TIM-3 Amino Acid Sequence

```
  1 mfsgltlncv llllqlllar slenayvfev gknaylpcsy tlstpgalvp mcwgkgfcpw
 61 sqctnellrt dernvtyqks sryqlkgdln kgdvsliikn vtlddhgtyc criqfpglmn
121 dkklelkldi kaakvtpaqt ahgdsttasp rtltterngs etqtlvtlhn nngtkistwa
181 deikdsgeti rtaihigvgv sagltlalii gvlilkwysc kkkklsslsl itlanlppgg
241 lanagavrir seeniytiee nvyevensne yycyvnsqqp s
```

TABLE 3-continued

SEQ ID NO: 51 Human LAG-3 cDNA Sequence

```
   1 atgtgggagg ctcagttcct gggcttgctg tttctgcagc cgctttgggt ggctccagtg
  61 aagcctctcc agccaggggc tgaggtcccg gtggtgtggg cccaggaggg ggctcctgcc
 121 cagctcccct gcagccccac aatcccccte caggatctca gccttctgcg aagagcaggg
 181 gtcacttggc agcatcagcc agacagtggc ccgcccgctg ccgcccccgg ccatcccctg
 241 gcccccggcc ctcacccggc ggcgccctcc tcctgggggc ccaggccccg ccgctacacg
 301 gtgctgagcg tgggtcccgg aggcctgcgc agcgggaggc tgcccctgca gccccgcgtc
 361 cagctggatg agcgcggccg gcagcgcggg gacttctcgc tatggctgcg cccagcccgg
 421 cgcgcggacg ccggcgagta ccgcgccgcg gtgcacctca gggaccgcgc cctctcctgc
 481 cgcctccgtc tgcgcctggg ccaggcctcg atgactgcca gcccccc agg atctctcaga
 541 gcctccgact gggtcatttt gaactgctcc ttcagccgcc ctgaccgccc agcctctgtg
 601 cattggttcc ggaaccgggg ccagggccga gtccctgtcc gggagtcccc ccatcaccac
 661 ttagcggaaa gcttcctctt cctgccccaa gtcagcccca tggactctgg gccctggggc
 721 tgcatcctca cctacagaga tggcttcaac gtctccatca tgtataacct cactgttctg
 781 ggtctggagc ccccaactcc cttgacagtg tacgctggag caggttccag ggtggggctg
 841 ccctgccgcc tgcctgctgg tgtggggacc cggtctttcc tcactgccaa gtggactcct
 901 cctgggggag gccctgacct cctggtgact ggagacaatg gcgactttac ccttcgacta
 961 gaggatgtga gccaggccca ggctgggacc tacacctgcc atatccatct gcaggaacag
1021 cagctcaatg ccactgtcac attggcaatc atcacagtga ctcccaaatc ctttgggtca
1081 cctggatccc tggggaagct gctttgtgag gtgactccag tatctggaca agaacgcttt
1141 gtgtggagct ctctggacac ccatcccag aggagtttct caggaccttg gctggaggca
1201 caggaggccc agctcctttc ccagccttgg caatgccagc tgtaccaggg ggagaggctt
1261 cttggagcag cagtgtactt cacagagctg tctagcccag gtgcccaacg ctctgggaga
1321 gccccaggtg ccctcccagc aggccacctc ctgctgtttc tcatccttgg tgtcctttct
1381 ctgctccttt tggtgactgg agcctttggc tttcaccttt ggagaagaca gtggcgacca
1441 agacgatttt ctgccttaga gcaagggatt caccctccgc aggctcagag caagatagag
1501 gagctggagc aagaaccgga gccggagccg gagccggaac cggagcccga gcccgagccc
1561 gagccggagc agctctga
```

SEQ ID NO: 52 Human LAG-3 Amino Acid Sequence

```
   1 mweaqflgll flqplwvapv kplqpgaevp vvwaqegapa qlpcsptipl qdlsllrrag
  61 vtwqhqpdsg ppaaapghpl apgphpaaps swgprprryt vlsvgpgglr sgrlplqprv
 121 qldergrqrg dfslwlrpar radageyraa vhlrdralsc rlrlrlgqas mtasppgslr
 181 asdwvilncs fsrpdrpasv hwfrnrgqgr vpvresphhh laesflflpq vspmdsgpwg
 241 ciltyrdgfn vsimynltvl glepptpltv yagagsrvgl pcrlpagvgt rsfltakwtp
 301 pgggpdllvt gdngdftlrl edvsqaqagt ytchihlqeg qlnatvtlai itvtpksfgs
 361 pgslgkllce vtpvsgqerf vwssldtpsq rsfsgpwlea qeaqllsqpw qcqlyqgerl
 421 lgaavyftel sspgaqrsgr apgalpaghl llflilgvls llllvtgafg fhlwrrqwrp
 481 rrfsaleqgi hppqaqskie eleqepepep epepepepep epeql
```

SEQ ID NO: 53 Mouse LAG-3 cDNA Sequence

```
   1 atgagggagg acctgctcct tggctttttg cttctgggac tgctttggga agctccagtt
  61 gtgtcttcag ggcctgggaa agagctcccc gtggtgtggg cccaggaggg agctcccgtc
 121 catcttccct gcagcctcaa atcccccaac ctggatccta actttctacg aagaggaggg
 181 gttatctggc aacatcaacc agacagtggc caacccactc ccatcccggc ccttgacctt
 241 caccagggga tgccctcgcc tagacaaccc gcacccggtc gctacacggt gctgagcgtg
 301 gctccaggag gcctgcgcag cgggaggcag cccctgcatc cccacgtgca gctggaggag
 361 cgcggcctcc agcgcgggga cttctctctg tggttgcgcc cagctctgcg caccgatgcg
 421 ggcgagtacc acgccaccgt gcgcctcccg aaccgcgccc tctcctgcag tctccgcctg
 481 cgcgtcggcc aggcctcgat gattgctagt ccctcaggag tcctcaagct gtctgattgg
 541 gtcctttga actgctcctt cagccgtcct gaccgcccag tctctgtgca ctggttccag
 601 ggccagaacc gagtgcctgt ctacaactca ccgcgtcatt ttttagctga aactttcctg
 661 ttactgcccc aagtcagccc cctggactct gggacctggg gctgtgtcct cacctacaga
 721 gatggcttca atgtctccat cacgtacaac ctcaaggttc tgggtctgga gcccgtagcc
 781 cctctgacag tgtacgctgc tgaaggttct agggtggagc tgccctgtca tttgcccca
 841 ggagtgggga ccccttcttt gctcattgcc aagtggactc ctcctggagg aggtcctgag
 901 ctccccgtgg ctggaaagag tggcaatttt acccttcacc ttgaggctgt gggtctggca
 961 caggctggga cctacacctg tagcatccat ctgcagggac agcagctcaa tgccactgtc
1021 acgttggcgg tcatcacagt gactcccaaa tccttcgggt tacctggctc ccgggggaag
1081 ctgttgtgtg aggtaacccc ggcatctgga aaggaaagat ttgtgtggcg tcccctgaac
1141 aatctgtcca ggagttgccc gggccctgtg ctggagattc aggaggccag gctccttgct
1201 gagcgatggc agtgtcagct gtacgagggc cagaggcttc ttggagcgac agtgtacgcc
1261 gcagagtcta gctcaggcgc ccacagtgct aggagaatct caggtgacct taaaggaggc
1321 catctcgttc tcgttctcat ccttggtgcc ctctccctgt tccttttggt ggccggggcc
1381 tttggctttc actggtggag aaaacagttg ctactgagaa gattttctgc cttagaacat
1441 gggattcagc catttccggc tcagaggaag atagaggagc tggagcgaga actggagacg
1501 gagatgggac aggagccgga gcccgagccg gagccacagc tggagccaga gcccaggcag
1561 ctctga
```

SEQ ID NO: 54 Mouse LAG-3 Amino Acid Sequence

```
   1 mredlllgfl llgllweapv vssgpgkelp vvwaqegapv hlpcslkspn ldpnflrrgg
  61 viwqhqpdsg qptpipaldl hqgmpsprqp apgrytvlsv apgglrsgrq plhphvqlee
 121 rglqrgdfsl wlrpalrtda geyhatvrlp nralscslrl rvgqasmias psgvlklsdw
 181 vllncsfsrp drpvsvhwfq gqnrvpvyns prhflaetfl llpqvsplds gtwgcvltyr
 241 dgfnvsityn lkvlglepva pltvyaaegs rvelpchlpp gvgtpsllia kwtppgggpe
 301 lpvagksgnf tlhleavgla qagtytcsih lqgqqlnatv tlavitvtpk sfglpgsrgk
```

TABLE 3-continued

```
361 llcevtpasg kerfvwrpln nlsrscpgpv leiqearlla erwqcqlyeg qrllgatvya
421 aesssgahsa rrisgdlkgg hlvlvlilga lslfllvaga fgfhwwrkql llrrfsaleh
481 giqpfpagrk ieelerelet emggepepep epqlepeprq l
```

* Included in Table 3 are RNA nucleic acid molecules (e.g., thymines replaced with uredines), nucleic acid molecules encoding orthologs of the encoded proteins, as well as DNA or RNA nucleic acid sequences comprising a nucleic acid sequence haying at least 80%, 81%, 82%, 83%, 84%, 85%, 86%, 87%, 88%, 89%, 90%, 91%, 92%, 93%, 94%, 95%, 96%, 97%, 98%, 99%, 09.5%, or more identity across their full length with the nucleic acid sequence of any SEQ ID NO listed in Table 3, or a portion thereof. Such nucleic acid molecules can have a function of the full-length nucleic acid as described further herein.

* Included in Table 3 are orthologs of the proteins, as well as polypeptide molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of any SEQ ID NO listed in Table 3, or a portion thereof. Such polypeptides can have a function of the full-length polypeptide as described further herein.

II. Subjects

In one embodiment, the subject for whom combination PI3Kbeta and immune checkpoint inhibitor therapy is administered, is a mammal (e.g., mouse, rat, primate, non-human mammal, domestic animal, such as a dog, cat, cow, horse, and the like), and is preferably a human. In another embodiment, the subject is an animal model of an epithelial cancer (e.g., a breast cancer (such as TNBC), an ovarian cancer, or a prostate cancer). For example, the animal model can be an orthotopic xenograft animal model of a human-derived epithelial cancer (e.g., a breast cancer (such as TNBC), an ovarian cancer, or a prostate cancer).

In another embodiment of the methods of the present invention, the subject has not undergone treatment, such as chemotherapy, radiation therapy, targeted therapy, and/or anti-immune checkpoint therapy. In still another embodiment, the subject has undergone treatment, such as chemotherapy, radiation therapy, targeted therapy, and/or anti-immune checkpoint therapy.

In certain embodiments, the subject has had surgery to remove cancerous or pre-cancerous tissue. In other embodiments, the cancerous tissue has not been removed, e.g., the cancerous tissue may be located in an inoperable region of the body, such as in a tissue that is essential for life, or in a region where a surgical procedure would cause considerable risk of harm to the patient.

The methods of the present invention can be used to treat and/or determine the responsiveness to combination PI3Kbeta and immune checkpoint inhibitor therapy of many different cancers in subjects such as those described herein.

III. Anti-Cancer Therapies

In one aspect, combination PI3Kbeta and immune checkpoint inhibitor therapy or combinations of therapies (e.g., one or more PI3Kbeta-selective inhibitors, such as KIN193, in combination with one or more immune checkpoint inhibitors, such as an anti-PD-1 antibody, either alone or in combination with yet additional anti-cancer therapies, such as targeted therapy) can be administered, particularly if a subject has first been indicated as being a likely responder to combination PI3Kbeta and immune checkpoint inhibitor therapy, such as through selection for p53 and/or PTEN deficiency in their target cancer cells. In another embodiment, such combination PI3Kbeta and immune checkpoint inhibitor therapy can be avoided once a subject is indicated as not being a likely responder to such therapy and an alternative treatment regimen, such as targeted and/or untargeted anti-cancer therapies can be administered.

Combination therapies are also contemplated and can comprise, for example, one or more chemotherapeutic agents and radiation, one or more chemotherapeutic agents and immunotherapy, or one or more chemotherapeutic agents, radiation and chemotherapy, each combination of which can be with anti-immune checkpoint therapy. As described below, agents can be administered in combination therapy with, e.g., chemotherapeutic agents, hormones, antiangiogens, radiolabelled, compounds, or with surgery, cryotherapy, and/or radiotherapy. The preceding treatment methods can be administered in conjunction with other forms of conventional therapy (e.g., standard-of-care treatments for cancer well-known to the skilled artisan), either consecutively with, pre- or post-conventional therapy. For example, these modulatory agents can be administered with a therapeutically effective dose of chemotherapeutic agent. In another embodiment, these modulatory agents are administered in conjunction with chemotherapy to enhance the activity and efficacy of the chemotherapeutic agent. The Physicians' Desk Reference (PDR) discloses dosages of chemotherapeutic agents that have been used in the treatment of various cancers. The dosing regimen and dosages of these aforementioned chemotherapeutic drugs that are therapeutically effective will depend on the particular melanoma, being treated, the extent of the disease and other factors familiar to the physician of skill in the art and can be determined by the physician.

The term "targeted therapy" refers to administration of agents that selectively interact with a chosen biomolecule to thereby treat cancer. One example includes epithelial cancer antigens, such as breast, ovarian, or prostate cancer antigens.

The terms "PI3Kbeta therapy" and "immune checkpoint inhibitor" are described above. However, for additional illustration of immune checkpoint inhibition, description of anti-PD-1 pathway agents is illustrative of the class of targets and their inhibitors. Anti-PD-1 pathway agents, such as therapeutic monoclonal blocking antibodies, are well-known in the art and described above, can be used to target tumor microenvironments and cells expressing unwanted components of the PD-1 pathway, such as the PD-1 receptor and its ligands, PD-L1 and PD-L2. "PD-1 pathway inhibitors" block or otherwise reduce the interaction between PD-1 and one or both of its ligands such that the immunoinhibitory signaling otherwise generated by the interaction is blocked or otherwise reduced. Anti-immune checkpoint inhibitors can be direct or indirect. Direct anti-immune checkpoint inhibitors block or otherwise reduce the interaction between an immune checkpoint and at least one of its ligands. For example, PD-1 inhibitors can block PD-1 binding with one or both of its ligands. Direct PD-1 combination inhibitors are well-known in the art, especially since the natural binding partners of PD-1 (e.g., PD-L1 and PD-L2), PD-L1 (e.g., PD-1 and B7-1), and PD-L2 (e.g., PD-1 and RGMb) are known.

For example, agents which directly block the interaction between PD-1 and PD-L1, PD-1 and PD-L2, PD-1 and both PD-L1 and PD-L2, such as a bispecific antibody, can prevent inhibitory signaling and upregulate an immune response (i.e., as a PD-1 pathway inhibitor). Alternatively, agents that indirectly block the interaction between PD-1 and one or both of its ligands can prevent inhibitory signaling and upregulate an immune response. For example, B7-1 or a soluble form thereof, by binding to a PD-L1 polypeptide indirectly reduces the effective concentration of PD-L1 polypeptide available to bind to PD-1. Exemplary agents include monospecific or bispecific blocking antibodies against PD-1, PD-L1, and/or PD-L2 that block the interaction between the receptor and ligand(s); a non-activating form of PD-1, PD-L1, and/or PD-L2 (e.g., a dominant negative or soluble polypeptide), small molecules or peptides that block the interaction between PD-1, PD-L1, and/or PD-L2; fusion proteins (e.g. the extracellular portion of PD-1, PD-L1, and/or PD-L2, fused to the Fc portion of an antibody or immunoglobulin) that bind to PD-1, PD-L1, and/or PD-L2 and inhibit the interaction between the receptor and ligand(s); a non-activating form of a natural PD-1, PD-L2, and/or PD-L2 ligand, and a soluble form of a natural PD-1, PD-L2, and/or PD-L2 ligand.

Indirect anti-immune checkpoint inhibitors block or otherwise reduce the immunoinhibitory signaling generated by the interaction between the immune checkpoint and at least one of its ligands. For example, an inhibitor can block the interaction between PD-1 and one or both of its ligands without necessarily directly blocking the interaction between PD-1 and one or both of its ligands. For example, indirect inhibitors include intrabodies that bind the intracellular portion of PD-1 and/or PD-L1 required to signal to block or otherwise reduce the immunoinhibitory signaling. Similarly, nucleic acids that reduce the expression of PD-1, PD-L1, and/or PD-L2 can indirectly inhibit the interaction between PD-1 and one or both of its ligands by removing the availability of components for interaction. Such nucleic acid molecules can block PD-L1, PD-L2, and/or PD-L2 transcription or translation.

Alternatively, immunotherapy is one form of targeted therapy that may comprise, for example, the use of cancer vaccines and/or sensitized antigen presenting cells. For example, an oncolytic virus is a virus that is able to infect and lyse cancer cells, while leaving normal cells unharmed, making them potentially useful in cancer therapy. Replication of oncolytic viruses both facilitates tumor cell destruction and also produces dose amplification at the tumor site. They may also act as vectors for anticancer genes, allowing them to be specifically delivered to the tumor site. The immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer.

The term "untargeted therapy" refers to administration of agents that do not selectively interact with a chosen biomolecule yet treat cancer. Representative examples of untargeted therapies include, without limitation, chemotherapy, gene therapy, and radiation therapy.

In one embodiment, chemotherapy is used. Chemotherapy includes the administration of a chemotherapeutic agent. Such a chemotherapeutic agent may be, but is not limited to, those selected from among the following groups of compounds: platinum compounds, cytotoxic antibiotics, antimetabolites, anti-mitotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: cisplatin, treosulfan, and trofosfamide; plant alkaloids: vinblastine, paclitaxel, docetaxol; DNA topoisomerase inhibitors: teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiments, PARP (e.g., PARP-1 and/or PARP-2) inhibitors are used and such inhibitors are well-known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1,8-naphthalimide; (Trevigen); 6(5H)-phenanthridinone (Trevigen); benzamide (U.S. Pat. Re. 36,397); and NU1025 (Bowman et al.). The mechanism of action is generally related to the ability of PARP inhibitors to bind PARP and decrease its activity. PARP catalyzes the conversion of .beta.-nicotinamide adenine dinucleotide (NAD+) into nicotinamide and poly-ADP-ribose (PAR). Both poly (ADP-ribose) and PARP have been linked to regulation of transcription, cell proliferation, genomic stability, and carcinogenesis (Bouchard V. J. et. al. Experimental Hematology, Volume 31, Number 6, June 2003, pp. 446-454(9); Herceg Z.; Wang Z.-Q. Mutation Research/Fundamental and Molecular Mechanisms of Mutagenesis, Volume 477, Number 1, 2 Jun. 2001, pp. 97-110(14)). Poly(ADP-ribose) polymerase 1 (PARP1) is a key molecule in the repair of DNA single-strand breaks (SSBs) (de Murcia J. et al. 1997. Proc Natl Acad Sci USA 94:7303-7307; Schreiber V, Dantzer F, Ame J C, de Murcia G (2006) Nat Rev Mol Cell Biol 7:517-528; Wang Z Q, et al. (1997) Genes Dev 11:2347-2358). Knockout of SSB repair by inhibition of PARP1 function induces DNA double-strand breaks (DSBs) that can trigger synthetic lethality in cancer cells with defective homology-directed DSB repair (Bryant H E, et al. (2005) Nature 434:913-917; Farmer H, et al. (2005) Nature 434:917-921). The foregoing examples of chemotherapeutic agents are illustrative, and are not intended to be limiting.

In another embodiment, radiation therapy is used. The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In another embodiment, surgical intervention can occur to physically remove cancerous cells and/or tissues.

In still another embodiment, hormone therapy is used. Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

In yet another embodiment, hyperthermia, a procedure in which body tissue is exposed to high temperatures (up to 106° F.) is used. Heat may help shrink tumors by damaging cells or depriving them of substances they need to live. Hyperthermia therapy can be local, regional, and whole-body hyperthermia, using external and internal heating devices. Hyperthermia is almost always used with other forms of therapy (e.g., radiation therapy, chemotherapy, and biological therapy) to try to increase their effectiveness. Local hyperthermia refers to heat that is applied to a very small area, such as a tumor. The area may be heated externally with high-frequency waves aimed at a tumor from a device outside the body. To achieve internal heating, one of several types of sterile probes may be used, including thin, heated wires or hollow tubes filled with warm water; implanted microwave antennae; and radiofrequency electrodes. In regional hyperthermia, an organ or a limb is heated. Magnets and devices that produce high energy are placed over the region to be heated. In another approach, called perfusion, some of the patient's blood is removed, heated, and then pumped (perfused) into the region that is to be heated internally. Whole-body heating is used to treat metastatic cancer that has spread throughout the body. It can be accomplished using warm-water blankets, hot wax, inductive coils (like those in electric blankets), or thermal chambers (similar to large incubators). Hyperthermia does not cause any marked increase in radiation side effects or complications. Heat applied directly to the skin, however, can cause discomfort or even significant local pain in about half the patients treated. It can also cause blisters, which generally heal rapidly.

In still another embodiment, photodynamic therapy (also called PDT, photoradiation therapy, phototherapy, or photochemotherapy) is used for the treatment of some types of cancer. It is based on the discovery that certain chemicals known as photosensitizing agents can kill one-celled organisms when the organisms are exposed to a particular type of light. PDT destroys cancer cells through the use of a fixed-frequency laser light in combination with a photosensitizing agent. In PDT, the photosensitizing agent is injected into the bloodstream and absorbed by cells all over the body. The agent remains in cancer cells for a longer time than it does in normal cells. When the treated cancer cells are exposed to laser light, the photosensitizing agent absorbs the light and produces an active form of oxygen that destroys the treated cancer cells. Light exposure must be timed carefully so that it occurs when most of the photosensitizing agent has left healthy cells but is still present in the cancer cells. The laser light used in PDT can be directed through a fiber-optic (a very thin glass strand). The fiber-optic is placed close to the cancer to deliver the proper amount of light. The fiber-optic can be directed through a bronchoscope into the lungs for the treatment of lung cancer or through an endoscope into the esophagus for the treatment of esophageal cancer. An advantage of PDT is that it causes minimal damage to healthy tissue. However, because the laser light currently in use cannot pass through more than about 3 centimeters of tissue (a little more than one and an eighth inch), PDT is mainly used to treat tumors on or just under the skin or on the lining of internal organs. Photodynamic therapy makes the skin and eyes sensitive to light for 6 weeks or more after treatment. Patients are advised to avoid direct sunlight and bright indoor light for at least 6 weeks. If patients must go outdoors, they need to wear protective clothing, including sunglasses. Other temporary side effects of PDT are related to the treatment of specific areas and can include coughing, trouble swallowing, abdominal pain, and painful breathing or shortness of breath. In December 1995, the U.S. Food and Drug Administration (FDA) approved a photosensitizing agent called porfimer sodium, or Photofrin®, to relieve symptoms of esophageal cancer that is causing an obstruction and for esophageal cancer that cannot be satisfactorily treated with lasers alone. In January 1998, the FDA approved porfimer sodium for the treatment of early non-small cell lung cancer in patients for whom the usual treatments for lung cancer are not appropriate. The National Cancer Institute and other institutions are supporting clinical trials (research studies) to evaluate the use of photodynamic therapy for several types of cancer, including cancers of the bladder, brain, larynx, and oral cavity.

In yet another embodiment, laser therapy is used to harness high-intensity light to destroy cancer cells. This technique is often used to relieve symptoms of cancer such as bleeding or obstruction, especially when the cancer cannot be cured by other treatments. It may also be used to treat cancer by shrinking or destroying tumors. The term "laser" stands for light amplification by stimulated emission of radiation. Ordinary light, such as that from a light bulb, has many wavelengths and spreads in all directions. Laser light, on the other hand, has a specific wavelength and is focused in a narrow beam. This type of high-intensity light contains a lot of energy. Lasers are very powerful and may be used to cut through steel or to shape diamonds. Lasers also can be used for very precise surgical work, such as repairing a damaged retina in the eye or cutting through tissue (in place of a scalpel). Although there are several different kinds of lasers, only three kinds have gained wide use in medicine: Carbon dioxide ($CO_2$) laser—This type of laser can remove thin layers from the skin's surface without penetrating the deeper layers. This technique is particularly useful in treating tumors that have not spread deep into the skin and certain precancerous conditions. As an alternative to traditional scalpel surgery, the $CO_2$ laser is also able to cut the skin. The laser is used in this way to remove skin cancers. Neodymium:yttrium-aluminum-garnet (Nd:YAG) laser—Light from this laser can penetrate deeper into tissue than light from the other types of lasers, and it can cause blood to clot quickly. It can be carried through optical fibers to less accessible parts of the body. This type of laser is sometimes used to treat throat cancers. Argon laser—This laser can pass through only superficial layers of tissue and is therefore useful in dermatology and in eye surgery. It also is used with light-sensitive dyes to treat tumors in a procedure known as photodynamic therapy (PDT). Lasers have several advantages over standard surgical tools, including: Lasers are more precise than scalpels. Tissue near an incision is protected, since there is little contact with surrounding skin or other tissue. The heat produced by lasers sterilizes the surgery site, thus reducing the risk of infection. Less operating time may be needed because the precision of the laser allows for a smaller incision. Healing time is often shortened; since laser heat seals blood vessels, there is less bleeding, swelling, or scarring. Laser surgery may be less complicated. For example, with fiber optics, laser light can be directed to parts of the body without making a large incision. More procedures may be done on an outpatient basis. Lasers can be used in two ways to treat cancer: by shrinking or destroying a tumor with heat, or by activating a chemical—known as a photosensitizing agent—that destroys cancer cells. In PDT, a photosensitizing agent is retained in cancer cells and can be stimulated by light to cause a reaction that kills cancer cells. $CO_2$ and Nd:YAG lasers are used to shrink or destroy tumors. They may be used with endoscopes, tubes that allow physicians to see into certain areas of the body, such as the bladder. The light from some lasers can be transmitted through a flexible endoscope fitted with fiber optics. This allows physicians to see and work in parts of the body that could not otherwise be reached except by surgery and therefore allows very precise aiming of the laser beam. Lasers also may be used with low-power microscopes, giving the doctor a clear view of the site being treated. Used with other instruments, laser systems can produce a cutting area as small as 200 microns in diameter—less than the width of a very fine thread. Lasers are used to treat many types of cancer. Laser surgery is a standard treatment for certain stages of glottis (vocal cord), cervical, skin, lung, vaginal, vulvar, and penile cancers. In addition to its use to destroy the cancer, laser surgery is also used to help relieve symptoms caused by cancer (palliative care). For example, lasers may be used to shrink or destroy a tumor that is blocking a patient's trachea (windpipe), making it easier to breathe. It is also sometimes used for palliation in colorectal and anal cancer. Laser-induced interstitial thermotherapy (LITT) is one of the most recent developments in laser therapy. LITT uses the same idea as a cancer treatment called hyperthermia; that heat may help shrink tumors by damaging cells or depriving them of substances they need to live. In this treatment, lasers are directed to interstitial areas (areas between organs) in the body. The laser light then raises the temperature of the tumor, which damages or destroys cancer cells.

The duration and/or dose of treatment with therapies may vary according to the particular therapeutic agent or combination thereof. An appropriate treatment time for a particular cancer therapeutic agent will be appreciated by the skilled artisan. The present invention contemplates the continued assessment of optimal treatment schedules for each cancer therapeutic agent, where the phenotype of the cancer of the subject as determined by the methods of the present invention is a factor in determining optimal treatment doses and schedules.

Any means for the introduction of a polynucleotide into mammals, human or non-human, or cells thereof may be adapted to the practice of this invention for the delivery of the various constructs of the present invention into the intended recipient. In one embodiment of the present invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Felgner, et al., Ann NY Acad Sci 126-139, 1995). Formulation of DNA, e.g. with various lipid or liposome materials, may then be effected using known methods and materials and delivered to the recipient mammal. See, e.g., Canonico et al, Am J Respir Cell Mol Biol 10:24-29, 1994; Tsan et al, Am J Physiol 268; Alton et al., Nat Genet. 5:135-142, 1993 and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below).

Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest may be in a plasmid or viral vector, or other vector as is known in the art. Such vectors are well-known and any can be selected for a particular application. In one embodiment of the present invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter may be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., Hum. Gene. Ther. 3:147-154, 1992. Other vehicles which can optionally be used include DNA-ligand (Wu et al., J. Biol. Chem. 264:16985-16987, 1989), lipid-DNA combinations (Felgner et al., Proc. Natl. Acad. Sci. USA 84:7413 7417, 1989), liposomes (Wang et al., Proc. Natl. Acad. Sci. 84:7851-7855, 1987) and microprojectiles (Williams et al., Proc. Natl. Acad. Sci. 88:2726-2730, 1991).

A gene delivery vehicle can optionally comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al., Cell 33:153, 1983, Cane and Mulligan, Proc. Nat'l. Acad. Sci. USA 81:6349, 1984, Miller et al., Human Gene Therapy 1:5-14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Ram et al., Cancer Res. 53:83-88, 1993; Takamiya et al., J. Neurosci. Res. 33:493-503, 1992; Baba et al., J. Neurosurg. 79:729-735, 1993 (U.S. Pat. No. 4,777,127, GB 2,200,651, EP 0,345,242 and WO91/02805).

Other viral vector systems that can be used to deliver a polynucleotide of the present invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxivirus, an arena virus, a vaccinia virus, a polio virus, and the like. They offer several attractive features for various mammalian cells (Friedmann (1989) Science, 244:1275-1281; Ridgeway, 1988, supra; Baichwal and Sugden, 1986, supra; Coupar et al., 1988; Horwich et al. (1990) J. Virol., 64:642-650).

In other embodiments, target DNA in the genome can be manipulated using well-known methods in the art. For example, the target DNA in the genome can be manipulated by deletion, insertion, and/or mutation are retroviral insertion, artificial chromosome techniques, gene insertion, random insertion with tissue specific promoters, gene targeting, transposable elements and/or any other method for introducing foreign DNA or producing modified DNA/modified nuclear DNA. Other modification techniques include deleting DNA sequences from a genome and/or altering nuclear DNA sequences. Nuclear DNA sequences, for example, may be altered by site-directed mutagenesis.

In other embodiments, recombinant biomarker polypeptides, and fragments thereof, can be administered to subjects. In some embodiments, fusion proteins can be constructed and administered which have enhanced biological properties. In addition, the biomarker polypeptides, and fragment thereof, can be modified according to well-known pharmacological methods in the art (e.g., pegylation, glycosylation, oligomerization, etc.) in order to further enhance desirable biological activities, such as increased bioavailability and decreased proteolytic degradation.

Clinical efficacy can be measured by any method known in the art. For example, the response to a therapy, such as combination PI3Kbeta and immune checkpoint inhibitor therapy, relates to any response of the cancer, e.g., a tumor, to the therapy, preferably to a change in tumor mass and/or volume after initiation of neoadjuvant or adjuvant chemotherapy. Tumor response may be assessed in a neoadjuvant or adjuvant situation where the size of a tumor after systemic intervention can be compared to the initial size and dimensions as measured by CT, PET, mammogram, ultrasound or palpation and the cellularity of a tumor can be estimated histologically and compared to the cellularity of a tumor biopsy taken before initiation of treatment. Response may also be assessed by caliper measurement or pathological examination of the tumor after biopsy or surgical resection. Response may be recorded in a quantitative fashion like percentage change in tumor volume or cellularity or using a semi-quantitative scoring system such as residual cancer burden (Symmans et al., *J. Clin. Oncol.* (2007) 25:4414-4422) or Miller-Payne score (Ogston et al., (2003) *Breast* (Edinburgh, Scotland) 12:320-327) in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of tumor response may be performed early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed.

In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular anti-immune checkpoint therapeutic regimen is at least 25%, 30%, 35%, 40%, 45%, 50%, 55%, 60%, 65%, 70%, 75%, 80%, 85%, or more.

Additional criteria for evaluating the response to anti-immune checkpoint therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence.

For example, in order to determine appropriate threshold values, a particular anti-cancer therapeutic regimen can be administered to a population of subjects and the outcome can be correlated to biomarker measurements that were determined prior to administration of any combination PI3Kbeta and immune checkpoint inhibitor therapy. The outcome measurement may be pathologic response to therapy given in the neoadjuvant setting. Alternatively, outcome measures, such as overall survival and disease-free survival can be monitored over a period of time for subjects following anti-immune checkpoint therapy for whom biomarker measurement values are known. In certain embodiments, the same doses of anti-immune checkpoint agents are administered to each subject. In related embodiments, the doses administered are standard doses known in the art for anti-immune checkpoint agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of an anti-immune checkpoint therapy can be determined using methods such as those described in the Examples section.

3. Pharmaceutical Compositions

The present invention provides pharmaceutically acceptable compositions which comprise a therapeutically-effective amount of an agent that modulates (e.g., decreases) biomarker expression and/or activity, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of an agent that modulates (e.g., inhibits) biomarker expression and/or activity, or expression and/or activity of the complex, or composition comprising an agent that modulates (e.g., inhibits) biomarker expression and/or activity, or expression and/or activity of the complex, which is effective for producing some desired therapeutic effect, e.g., cancer treatment, at a reasonable benefit/risk ratio.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents that modulates (e.g., inhibits) biomarker expression and/or activity, or expression and/or activity of the complex encompassed by the present invention. These salts can be prepared in situ during the final isolation and purification of the therapeutic agents, or by separately reacting a purified therapeutic agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (See, for example, Berge et al. (1977) "Pharmaceutical Salts", *J. Pharm. Sci.* 66:1-19).

In other cases, the agents useful in the methods of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of agents that modulates (e.g., inhibits) biomarker expression and/or activity, or expression and/or activity of the complex. These salts can likewise be prepared in situ during the final isolation and purification of the therapeutic agents, or by separately reacting the purified therapeutic agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well-known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent that modulates (e.g., inhibits) biomarker expression and/or activity, with the carrier and, optionally, one or more accessory ingredients. In general, the formulations are prepared by uniformly and intimately bringing into association a therapeutic agent with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a therapeutic agent as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well-known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more therapeutic agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an agent that modulates (e.g., inhibits) biomarker expression and/or activity include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a therapeutic agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an agent that modulates (e.g., inhibits) biomarker expression and/or activity, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The agent that modulates (e.g., inhibits) biomarker expression and/or activity, can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a therapeutic agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more therapeutic agents in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the present invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of an agent that modulates (e.g., inhibits) biomarker expression and/or activity, in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

When the therapeutic agents of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions of this invention may be determined by the methods of the present invention so as to obtain an amount of the active ingredient, which is effective to achieve the desired therapeutic response for a particular subject, composition, and mode of administration, without being toxic to the subject.

The nucleic acid molecules of the present invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054 3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The present invention also encompasses kits for detecting and/or modulating biomarkers described herein. A kit of the present invention may also include instructional materials disclosing or describing the use of the kit or an antibody of the disclosed invention in a method of the disclosed invention as provided herein. A kit may also include additional components to facilitate the particular application for which the kit is designed. For example, a kit may additionally contain means of detecting the label (e.g., enzyme substrates for enzymatic labels, filter sets to detect fluorescent labels, appropriate secondary labels such as a sheep anti-mouse-HRP, etc.) and reagents necessary for controls (e.g., control biological samples or standards). A kit may additionally include buffers and other reagents recognized for use in a method of the disclosed invention. Non-limiting examples include agents to reduce non-specific binding, such as a carrier protein or a detergent.

4. Further Uses and Methods of the Present Invention

The compositions described herein can be used in a variety of diagnostic, prognostic, and therapeutic applications. In any method described herein, such as a diagnostic method, prognostic method, therapeutic method, or combination thereof, all steps of the method can be performed by a single actor or, alternatively, by more than one actor. For example, diagnosis can be performed directly by the actor providing therapeutic treatment. Alternatively, a person providing a therapeutic agent can request that a diagnostic assay be performed. The diagnostician and/or the therapeutic interventionist can interpret the diagnostic assay results to determine a therapeutic strategy. Similarly, such alternative processes can apply to other assays, such as prognostic assays.

1. Predictive Medicine

The present invention can pertain to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining the amount and/or activity level of a biomarker described herein, such as p53 and/or PTEN deficiency status, in the context of a biological sample (e.g., blood, serum, cells, or tissue) to thereby determine whether an individual afflicted with a cancer is likely to respond to combination PI3Kbeta and immune checkpoint inhibitor therapy, such as in epithelial cancers (e.g., breast cancers, ovarian cancers, or prostate cancers). Such assays can be used for prognostic or predictive purpose alone, or can be coupled with a therapeutic intervention to thereby prophylactically treat an individual prior to the onset or after recurrence of a disorder characterized by or associated with biomarker polypeptide, nucleic acid expression or activity. The skilled artisan will appreciate that any method can use one or more (e.g., combinations) of biomarkers described herein, such as those in the tables, figures, examples, and otherwise described in the specification.

Another aspect of the present invention pertains to monitoring the influence of agents (e.g., drugs, compounds, and small nucleic acid-based molecules) on the expression or activity of a biomarker or cancer state described herein. These and other agents are described in further detail in the following sections.

The skilled artisan will also appreciated that, in certain embodiments, the methods of the present invention implement a computer program and computer system. For example, a computer program can be used to perform algorithms described herein. A computer system can also store and manipulate data generated by the methods of the present invention which comprises a plurality of biomarker signal changes/profiles which can be used by a computer system in implementing the methods of this invention. In certain embodiments, a computer system receives biomarker expression data; (ii) stores the data; and (iii) compares the data in any number of ways described herein (e.g., analysis relative to appropriate controls) to determine the state of informative biomarkers from cancerous or pre-cancerous tissue. In other embodiments, a computer system (i) compares the determined expression biomarker level to a threshold value; and (ii) outputs an indication of whether said biomarker level is significantly modulated (e.g., above or below) the threshold value, or a phenotype based on said indication.

In certain embodiments, such computer systems are also considered part of the present invention. Numerous types of computer systems can be used to implement the analytic methods of this invention according to knowledge possessed by a skilled artisan in the bioinformatics and/or computer arts. Several software components can be loaded into memory during operation of such a computer system. The software components can comprise both software components that are standard in the art and components that are special to the present invention (e.g., dCHIP software described in Lin et al. (2004) Bioinformatics 20, 1233-1240; radial basis machine learning algorithms (RBM) known in the art).

The methods of the present invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus from MathSoft (Seattle, Wash.).

In certain embodiments, the computer comprises a database for storage of biomarker data. Such stored profiles can be accessed and used to perform comparisons of interest at a later point in time. For example, biomarker expression profiles of a sample derived from the non-cancerous tissue of a subject and/or profiles generated from population-based distributions of informative loci of interest in relevant populations of the same species can be stored and later compared to that of a sample derived from the cancerous tissue of the subject or tissue suspected of being cancerous of the subject.

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

2. Diagnostic Assays

The present invention provides, in part, methods, systems, and code for accurately classifying whether a biological sample is associated with a cancer that is likely to respond to combination PI3Kbeta and immune checkpoint inhibitor therapy. In some embodiments, the present invention is useful for classifying a sample (e.g., from a subject) as associated with or at risk for responding to or not responding to combination PI3Kbeta and immune checkpoint inhibitor therapy using a statistical algorithm and/or empirical data (e.g., the amount or activity of a biomarker described herein, such as in the tables, figures, examples, and otherwise described in the specification).

An exemplary method for detecting the amount or activity of a biomarker described herein, and thus useful for classifying whether a sample is likely or unlikely to respond to combination PI3Kbeta and immune checkpoint inhibitor therapy involves obtaining a biological sample from a test subject and contacting the biological sample with an agent, such as a protein-binding agent like an antibody or antigen-binding fragment thereof, or a nucleic acid-binding agent like an oligonucleotide, capable of detecting the amount or activity of the biomarker, such as a p53 and/or PTEN nucleic acid or protein of interest, in the biological sample. In some embodiments, at least one antibody or antigen-binding fragment thereof is used, wherein two, three, four, five, six, seven, eight, nine, ten, or more such antibodies or antibody fragments can be used in combination (e.g., in sandwich ELISAs) or in serial. In certain instances, the statistical algorithm is a single learning statistical classifier system. For example, a single learning statistical classifier system can be used to classify a sample as a based upon a prediction or probability value and the presence or level of the biomarker. The use of a single learning statistical classifier system typically classifies the sample as, for example, a likely anti-immune checkpoint therapy responder or progressor sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Other suitable statistical algorithms are well-known to those of skill in the art. For example, learning statistical classifier systems include a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ). In certain embodiments, the method of the present invention further comprises sending the sample classification results to a clinician, e.g., an oncologist.

In another embodiment, the diagnosis of a subject is followed by administering to the individual a therapeutically effective amount of a defined treatment based upon the diagnosis.

In one embodiment, the methods further involve obtaining a control biological sample (e.g., biological sample from a subject who does not have a cancer or whose cancer is susceptible to combination PI3Kbeta and immune checkpoint inhibitor therapy), a biological sample from the subject during remission, or a biological sample from the subject during treatment for developing a cancer progressing despite combination PI3Kbeta and immune checkpoint inhibitor therapy.

3. Prognostic Assays

The diagnostic methods described herein can furthermore be utilized to identify subjects having or at risk of developing a cancer that is likely or unlikely to be responsive to combination PI3Kbeta and immune checkpoint inhibitor therapy. The assays described herein, such as the preceding diagnostic assays or the following assays, can be utilized to identify a subject having or at risk of developing a disorder associated with a misregulation of the amount or activity of at least one biomarker described herein, such as in cancer. Alternatively, the prognostic assays can be utilized to identify a subject having or at risk for developing a disorder associated with a misregulation of the at least one biomarker described herein, such as in cancer. Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat a disease or disorder associated with the aberrant biomarker expression or activity.

4. Biomarker Nucleic Acids and Polypeptides

The therapeutic and other methods of the present invention uses biomarkers of interest. In some embodiments, the biomarkers of itnerst are isolated nucleic acid molecules that correspond to biomarker nucleic acids that encode a biomarker polypeptide or a portion of such a polypeptide. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. Preferably, an "isolated" nucleic acid molecule is free of sequences (preferably protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

A biomarker nucleic acid molecule of the present invention can be isolated using standard molecular biology techniques and the sequence information in the database records described herein. Using all or a portion of such nucleic acid sequences, nucleic acid molecules of the present invention can be isolated using standard hybridization and cloning techniques (e.g., as described in Sambrook et al., ed., *Molecular Cloning: A Laboratory Manual,* 2nd ed., Cold Spring Harbor Laboratory Press, Cold Spring Harbor, N.Y., 1989).

A nucleic acid molecule of the present invention can be amplified using cDNA, mRNA, or genomic DNA as a template and appropriate oligonucleotide primers according to standard PCR amplification techniques. The nucleic acid molecules so amplified can be cloned into an appropriate vector and characterized by DNA sequence analysis. Furthermore, oligonucleotides corresponding to all or a portion of a nucleic acid molecule of the present invention can be prepared by standard synthetic techniques, e.g., using an automated DNA synthesizer.

Moreover, a nucleic acid molecule of the present invention can comprise only a portion of a nucleic acid sequence, wherein the full length nucleic acid sequence comprises a marker of the present invention or which encodes a polypeptide corresponding to a marker of the present invention. Such nucleic acid molecules can be used, for example, as a probe or primer. The probe/primer typically is used as one or more substantially purified oligonucleotides. The oligonucleotide typically comprises a region of nucleotide sequence that hybridizes under stringent conditions to at least about 7, preferably about 15, more preferably about 25, 50, 75, 100, 125, 150, 175, 200, 250, 300, 350, or 400 or more consecutive nucleotides of a biomarker nucleic acid sequence. Probes based on the sequence of a biomarker nucleic acid molecule can be used to detect transcripts or genomic sequences corresponding to one or more markers of the present invention. The probe comprises a label group attached thereto, e.g., a radioisotope, a fluorescent compound, an enzyme, or an enzyme co-factor.

A biomarker nucleic acid molecules that differ, due to degeneracy of the genetic code, from the nucleotide sequence of nucleic acid molecules encoding a protein which corresponds to the biomarker, and thus encode the same protein, are also contemplated.

In addition, it will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

The term "allele," which is used interchangeably herein with "allelic variant," refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene or allele. For example, biomarker alleles can differ from each other in a single nucleotide, or several nucleotides, and can include substitutions, deletions, and insertions of nucleotides. An allele of a gene can also be a form of a gene containing one or more mutations.

The term "allelic variant of a polymorphic region of gene" or "allelic variant", used interchangeably herein, refers to an alternative form of a gene having one of several possible nucleotide sequences found in that region of the gene in the population. As used herein, allelic variant is meant to encompass functional allelic variants, non-functional allelic variants, SNPs, mutations and polymorphisms.

The term "single nucleotide polymorphism" (SNP) refers to a polymorphic site occupied by a single nucleotide, which is the site of variation between allelic sequences. The site is usually preceded by and followed by highly conserved sequences of the allele (e.g., sequences that vary in less than 1/100 or 1/1000 members of a population). A SNP usually arises due to substitution of one nucleotide for another at the polymorphic site. SNPs can also arise from a deletion of a nucleotide or an insertion of a nucleotide relative to a reference allele. Typically the polymorphic site is occupied by a base other than the reference base. For example, where the reference allele contains the base "T" (thymidine) at the polymorphic site, the altered allele can contain a "C" (cytidine), "G" (guanine), or "A" (adenine) at the polymorphic site. SNP's may occur in protein-coding nucleic acid sequences, in which case they may give rise to a defective or otherwise variant protein, or genetic disease. Such a SNP may alter the coding sequence of the gene and therefore specify another amino acid (a "missense" SNP) or a SNP may introduce a stop codon (a "nonsense" SNP). When a SNP does not alter the amino acid sequence of a protein, the SNP is called "silent." SNP's may also occur in noncoding regions of the nucleotide sequence. This may result in defective protein expression, e.g., as a result of alternative spicing, or it may have no effect on the function of the protein.

As used herein, the terms "gene" and "recombinant gene" refer to nucleic acid molecules comprising an open reading frame encoding a polypeptide corresponding to a marker of the present invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the present invention.

In another embodiment, a biomarker nucleic acid molecule is at least 7, 15, 20, 25, 30, 40, 60, 80, 100, 150, 200, 250, 300, 350, 400, 450, 550, 650, 700, 800, 900, 1000, 1100, 1200, 1300, 1400, 1500, 1600, 1700, 1800, 1900, 2000, 2200, 2400, 2600, 2800, 3000, 3500, 4000, 4500, or more nucleotides in length and hybridizes under stringent conditions to a nucleic acid molecule corresponding to a marker of the present invention or to a nucleic acid molecule encoding a protein corresponding to a marker of the present invention. As used herein, the term "hybridizes under stringent conditions" is intended to describe conditions for hybridization and washing under which nucleotide sequences at least 60% (65%, 70%, 75%, 80%, preferably 85%) identical to each other typically remain hybridized to each other. Such stringent conditions are known to those skilled in the art and can be found in sections 6.3.1-6.3.6 of *Current Protocols in Molecular Biology*, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50-65° C.

In addition to naturally-occurring allelic variants of a nucleic acid molecule of the present invention that can exist in the population, the skilled artisan will further appreciate that sequence changes can be introduced by mutation thereby leading to changes in the amino acid sequence of the encoded protein, without altering the biological activity of the protein encoded thereby. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

Accordingly, another aspect of the present invention pertains to nucleic acid molecules encoding a polypeptide of the present invention that contain changes in amino acid residues that are not essential for activity. Such polypeptides differ in amino acid sequence from the naturally-occurring proteins which correspond to the markers of the present invention, yet retain biological activity. In one embodiment, a biomarker protein has an amino acid sequence that is at least about 40% identical, 50%, 60%, 70%, 75%, 80%, 83%, 85%, 87.5%, 90%, 91%, 92%, 93%, 94%, 95%, 96%, 97%, 98%, 99% or identical to the amino acid sequence of a biomarker protein described herein.

An isolated nucleic acid molecule encoding a variant protein can be created by introducing one or more nucleotide substitutions, additions or deletions into the nucleotide sequence of nucleic acids of the present invention, such that one or more amino acid residue substitutions, additions, or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

In some embodiments, the present invention further contemplates the use of anti-biomarker antisense nucleic acid molecules, i.e., molecules which are complementary to a sense nucleic acid of the present invention, e.g., complementary to the coding strand of a double-stranded cDNA molecule corresponding to a marker of the present invention or complementary to an mRNA sequence corresponding to a marker of the present invention. Accordingly, an antisense nucleic acid molecule of the present invention can hydrogen bond to (i.e. anneal with) a sense nucleic acid of the present invention. The antisense nucleic acid can be complementary to an entire coding strand, or to only a portion thereof, e.g., all or part of the protein coding region (or open reading frame). An antisense nucleic acid molecule can also be antisense to all or part of a non-coding region of the coding strand of a nucleotide sequence encoding a polypeptide of the present invention. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45, or 50 or more nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been sub-cloned in an antisense orientation (i.e., RNA transcribed from the inserted nucleic acid will be of an antisense orientation to a target nucleic acid of interest, described further in the following subsection).

The antisense nucleic acid molecules of the present invention are typically administered to a subject or generated in situ such that they hybridize with or bind to cellular mRNA and/or genomic DNA encoding a polypeptide corresponding to a selected marker of the present invention to thereby inhibit expression of the marker, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. Examples of a route of administration of antisense nucleic acid molecules of the present invention includes direct injection at a tissue site or infusion of the antisense nucleic acid into a blood- or bone marrow-associated body fluid. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the present invention can be an α-anomeric nucleic acid molecule. An α-anomeric nucleic acid molecule forms specific double-stranded hybrids with complementary RNA in which, contrary to the usual α-units, the strands run parallel to each other (Gaultier et al., 1987, *Nucleic Acids Res.* 15:6625-6641). The antisense nucleic acid molecule can also comprise a 2'-o-methylribonucleotide (Inoue et al., 1987, *Nucleic Acids Res.* 15:6131-6148) or a chimeric RNA-DNA analogue (Inoue et al., 1987, *FEBS Lett.* 215:327-330).

The present invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes as described in Haselhoff and Gerlach, 1988, *Nature* 334:585-591) can be used to catalytically cleave mRNA transcripts to thereby inhibit translation of the protein encoded by the mRNA. A ribozyme having specificity for a nucleic acid molecule encoding a polypeptide corresponding to a marker of the present invention can be designed based upon the nucleotide sequence of a cDNA corresponding to the marker. For example, a derivative of a Tetrahymena L-19 IVS RNA can be constructed in which the nucleotide sequence of the active site is complementary to the nucleotide sequence to be cleaved (see Cech et al. U.S. Pat. No. 4,987,071; and Cech et al. U.S. Pat. No. 5,116,742). Alternatively, an mRNA encoding a polypeptide of the present invention can be used to select a catalytic RNA having a specific ribonuclease activity from a pool of RNA molecules (see, e.g., Bartel and Szostak, 1993, *Science* 261:1411-1418).

The present invention also encompasses nucleic acid molecules which form triple helical structures. For example, expression of a biomarker protein can be inhibited by targeting nucleotide sequences complementary to the regulatory region of the gene encoding the polypeptide (e.g., the promoter and/or enhancer) to form triple helical structures that prevent transcription of the gene in target cells. See generally Helene (1991) *Anticancer Drug Des.* 6(6):569-84; Helene (1992) *Ann. N.Y. Acad. Sci.* 660:27-36; and Maher (1992) *Bioassays* 14(12):807-15.

In various embodiments, the nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acid molecules (see Hyrup et al., 1996, *Bioorganic & Medicinal Chemistry* 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670-675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup, 1996, supra; Perry-O'Keefe et al., 1996, *Proc. Natl. Acad. Sci. USA* 93:14670-675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNASE H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup (1996), supra, and Finn et al. (1996) *Nucleic Acids Res.* 24(17):3357-63. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al., 1989, *Nucleic Acids Res.* 17:5973-88). PNA monomers are then coupled in a step-wise manner to produce a chimeric molecule with a 5' PNA segment and a 3' DNA segment (Finn et al., 1996, *Nucleic Acids Res.* 24(17):3357-63). Alternatively, chimeric molecules can be synthesized with a 5' DNA segment and a 3' PNA segment (Peterser et al., 1975, *Bioorganic Med. Chem. Lett.* 5:1119-11124).

In other embodiments, the oligonucleotide can include other appended groups such as peptides (e.g., for targeting host cell receptors in vivo), or agents facilitating transport across the cell membrane (see, e.g., Letsinger et al., 1989, *Proc. Natl. Acad. Sci. USA* 86:6553-6556; Lemaitre et al., 1987, *Proc. Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al., 1988, *Bio/Techniques* 6:958-976) or intercalating agents (see, e.g., Zon, 1988, *Pharm. Res.* 5:539-549). To this end, the oligonucleotide can be conjugated to another molecule, e.g., a peptide, hybridization triggered cross-linking agent, transport agent, hybridization-triggered cleavage agent, etc.

Another aspect of the present invention pertains to the use of biomarker proteins and biologically active portions thereof. In one embodiment, the native polypeptide corresponding to a marker can be isolated from cells or tissue sources by an appropriate purification scheme using standard protein purification techniques. In another embodiment, polypeptides corresponding to a marker of the present invention are produced by recombinant DNA techniques. Alternative to recombinant expression, a polypeptide corresponding to a marker of the present invention can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a biomarker polypeptide include polypeptides comprising amino acid sequences sufficiently identical to or derived from a biomarker protein amino acid sequence described herein, but which includes fewer amino acids than the full length protein, and exhibit at least one activity of the corresponding full-length protein. Typically, biologically active portions comprise a domain or motif with at least one activity of the corresponding protein. A biologically active portion of a protein of the present invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide of the present invention.

Preferred polypeptides have an amino acid sequence of a biomarker protein encoded by a nucleic acid molecule described herein. Other useful proteins are substantially identical (e.g., at least about 40%, preferably 50%, 60%, 70%, 75%, 80%, 83%, 85%, 88%, 90%, 91%, 92%, 93%, 94%, 95%, 96%, 97%, 98%, or 99%) to one of these sequences and retain the functional activity of the protein of the corresponding naturally-occurring protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J. Mol. Biol.* 215:403-410. BLAST nucleotide searches can be performed with the NBLAST program, score=100, wordlength=12 to obtain nucleotide sequences homologous to a nucleic acid molecules of the present invention. BLAST protein searches can be performed with the XBLAST program, score=50, wordlength=3 to obtain amino acid sequences homologous to a protein molecules of the present invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, (1988) *Comput Appl Biosci,* 4:11-7. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

The present invention also provides chimeric or fusion proteins corresponding to a biomarker protein. As used herein, a "chimeric protein" or "fusion protein" comprises all or part (preferably a biologically active part) of a polypeptide corresponding to a marker of the present invention operably linked to a heterologous polypeptide (i.e., a polypeptide other than the polypeptide corresponding to the marker). Within the fusion protein, the term "operably linked" is intended to indicate that the polypeptide of the present invention and the heterologous polypeptide are fused in-frame to each other. The heterologous polypeptide can be fused to the amino-terminus or the carboxyl-terminus of the polypeptide of the present invention.

One useful fusion protein is a GST fusion protein in which a polypeptide corresponding to a marker of the present invention is fused to the carboxyl terminus of GST sequences. Such fusion proteins can facilitate the purification of a recombinant polypeptide of the present invention.

In another embodiment, the fusion protein contains a heterologous signal sequence, immunoglobulin fusion protein, toxin, or other useful protein sequence. Chimeric and fusion proteins of the present invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the present invention can be cloned into such an expression vector such that the fusion moiety is linked in-frame to the polypeptide of the present invention.

A signal sequence can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the present invention pertains to the described polypeptides having a signal sequence, as well as to polypeptides from which the signal sequence has been proteolytically cleaved (i.e., the cleavage products). In one embodiment, a nucleic acid sequence encoding a signal sequence can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

The present invention also pertains to variants of the biomarker polypeptides described herein. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a biomarker protein which function as either agonists (mimetics) or as antagonists can be identified by screening combinatorial libraries of mutants, e.g., truncation mutants, of the protein of the present invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the present invention from a degenerate oligonucleotide sequence. Methods for synthesizing degenerate oligonucleotides are known in the art (see, e.g., Narang, 1983, *Tetrahedron* 39:3; Itakura et al., 1984, *Annu. Rev. Biochem.* 53:323; Itakura et al., 1984, *Science* 198:1056; Ike et al., 1983 *Nucleic Acid Res.* 11:477).

In addition, libraries of fragments of the coding sequence of a polypeptide corresponding to a marker of the present invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes amino terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the present invention (Arkin and Yourvan, 1992, *Proc. Natl. Acad. Sci. USA* 89:7811-7815; Delgrave et al., 1993, *Protein Engineering* 6(3):327-331).

The production and use of biomarker nucleic acid and/or biomarker polypeptide molecules described herein can be facilitated by using standard recombinant techniques. In some embodiments, such techniques use vectors, preferably expression vectors, containing a nucleic acid encoding a biomarker polypeptide or a portion of such a polypeptide. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, namely expression vectors, are capable of directing the expression of genes to which they are operably linked. In general, expression vectors of utility in recombinant DNA techniques are often in the form of plasmids (vectors). However, the present invention is intended to include such other forms of expression vectors, such as viral vectors (e.g., replication defective retroviruses, adenoviruses and adeno-associated viruses), which serve equivalent functions.

The recombinant expression vectors of the present invention comprise a nucleic acid of the present invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Methods in Enzymology: Gene Expression Technology* vol. 185, Academic Press, San Diego, Calif. (1991). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the present invention can be introduced into host cells to thereby produce proteins or peptides, including fusion proteins or peptides, encoded by nucleic acids as described herein.

The recombinant expression vectors for use in the present invention can be designed for expression of a polypeptide corresponding to a marker of the present invention in prokaryotic (e.g., *E. coli*) or eukaryotic cells (e.g., insect cells {using baculovirus expression vectors}, yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988, *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., 1988, *Gene* 69:301-315) and pET 11d (Studier et al., p. 60-89, In *Gene Expression Technology: Methods in Enzymology* vol. 185, Academic Press, San Diego, Calif., 1991). Target biomarker nucleic acid expression from the pTrc vector relies on host RNA polymerase transcription from a hybrid trp-lac fusion promoter. Target biomarker nucleic acid expression from the pET 11d vector relies on transcription from a T7 gn10-lac fusion promoter mediated by a co-expressed viral RNA polymerase (T7 gn1). This viral polymerase is supplied by host strains BL21 (DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacterium with an impaired capacity to proteolytically cleave the recombinant protein (Gottesman, p. 119-128, In *Gene Expression Technology: Methods in Enzymology* vol. 185, Academic Press, San Diego, Calif., 1990. Another strategy is to alter the nucleic acid sequence of the nucleic acid to be inserted into an expression vector so that the individual codons for each amino acid are those preferentially utilized in *E. coli* (Wada et al., 1992, *Nucleic Acids Res.* 20:2111-2118). Such alteration of nucleic acid sequences of the present invention can be carried out by standard DNA synthesis techniques.

In another embodiment, the expression vector is a yeast expression vector. Examples of vectors for expression in yeast *S. cerevisiae* include pYepSecl (Baldari et al., 1987, *EMBO J.* 6:229-234), pMFa (Kurjan and Herskowitz, 1982, *Cell* 30:933-943), pJRY88 (Schultz et al., 1987, Gene 54:113-123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith et al., 1983, *Mol. Cell Biol.* 3:2156-2165) and the pVL series (Lucklow and Summers, 1989, *Virology* 170:31-39).

In yet another embodiment, a nucleic acid of the present invention is expressed in mammalian cells using a mammalian expression vector. Examples of mammalian expression vectors include pCDM8 (Seed, 1987, *Nature* 329:840) and pMT2PC (Kaufman et al., 1987, *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, *Genes Dev.* 1:268-277), lymphoid-specific promoters (Calame and Eaton, 1988, *Adv. Immunol.* 43:235-275), in particular promoters of T cell receptors (Winoto and Baltimore, 1989, *EMBO J.* 8:729-733) and immunoglobulins (Banerji et al., 1983, *Cell* 33:729-740; Queen and Baltimore, 1983, *Cell* 33:741-748), neuron-specific promoters (e.g., the neurofilament promoter; Byrne and Ruddle, 1989, *Proc. Natl. Acad. Sci. USA* 86:5473-5477), pancreas-specific promoters (Edlund et al., 1985, *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss, 1990, *Science* 249:374-379) and the α-fetoprotein promoter (Camper and Tilghman, 1989, *Genes Dev.* 3:537-546).

The present invention further provides a recombinant expression vector comprising a DNA molecule cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the present invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue-specific or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes (see Weintraub et al., 1986, *Trends in Genetics*, Vol. 1(1)).

Another aspect of the present invention pertains to host cells into which a recombinant expression vector of the present invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

5. Analyzing Biomarker Nucleic Acids and Polypeptides

For any method described herein, biomarker nucleic acids and/or biomarker polypeptides can be analyzed according to the methods described herein and techniques known to the skilled artisan to identify such genetic or expression alterations useful for the present invention including, but not limited to, 1) an alteration in the level of a biomarker transcript or polypeptide, 2) a deletion or addition of one or more nucleotides from a biomarker gene, 4) a substitution of one or more nucleotides of a biomarker gene, 5) aberrant modification of a biomarker gene, such as an expression regulatory region, and the like.

a. Methods for Detection of Biomarker Copy Number

Methods of evaluating the copy number of a biomarker nucleic acid are well-known to those of skill in the art. The presence or absence of chromosomal gain or loss can be evaluated simply by a determination of copy number of the regions or markers identified herein.

In one embodiment, a biological sample is tested for the presence of copy number changes in genomic loci containing the genomic marker. A copy number of at least 3, 4, 5, 6, 7, 8, 9, or 10 is predictive of poorer outcome of PI3K/mTOR combination inhibitor treatment.

Methods of evaluating the copy number of a biomarker locus include, but are not limited to, hybridization-based assays. Hybridization-based assays include, but are not limited to, traditional "direct probe" methods, such as Southern blots, in situ hybridization (e.g., FISH and FISH plus SKY) methods, and "comparative probe" methods, such as comparative genomic hybridization (CGH), e.g., cDNA-based or oligonucleotide-based CGH. The methods can be used in a wide variety of formats including, but not limited to, substrate (e.g. membrane or glass) bound methods or array-based approaches.

In one embodiment, evaluating the biomarker gene copy number in a sample involves a Southern Blot. In a Southern Blot, the genomic DNA (typically fragmented and separated on an electrophoretic gel) is hybridized to a probe specific for the target region. Comparison of the intensity of the hybridization signal from the probe for the target region with control probe signal from analysis of normal genomic DNA (e.g., a non-amplified portion of the same or related cell, tissue, organ, etc.) provides an estimate of the relative copy number of the target nucleic acid. Alternatively, a Northern blot may be utilized for evaluating the copy number of encoding nucleic acid in a sample. In a Northern blot, mRNA is hybridized to a probe specific for the target region. Comparison of the intensity of the hybridization signal from the probe for the target region with control probe signal from analysis of normal RNA (e.g., a non-amplified portion of the same or related cell, tissue, organ, etc.) provides an estimate of the relative copy number of the target nucleic acid. Alternatively, other methods well-known in the art to detect RNA can be used, such that higher or lower expression relative to an appropriate control (e.g., a non-amplified portion of the same or related cell tissue, organ, etc.) provides an estimate of the relative copy number of the target nucleic acid.

An alternative means for determining genomic copy number is in situ hybridization (e.g., Angerer (1987) *Meth. Enzymol* 152: 649). Generally, in situ hybridization comprises the following steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application. In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained. The probes are typically labeled, e.g., with radioisotopes or fluorescent reporters. In one embodiment, probes are sufficiently long so as to specifically hybridize with the target nucleic acid(s) under stringent conditions. Probes generally range in length from about 200 bases to about 1000 bases. In some applications it is necessary to block the hybridization capacity of repetitive sequences. Thus, in some embodiments, tRNA, human genomic DNA, or Cot-I DNA is used to block non-specific hybridization.

An alternative means for determining genomic copy number is comparative genomic hybridization. In general, genomic DNA is isolated from normal reference cells, as well as from test cells (e.g., tumor cells) and amplified, if necessary. The two nucleic acids are differentially labeled and then hybridized in situ to metaphase chromosomes of a reference cell. The repetitive sequences in both the reference and test DNAs are either removed or their hybridization capacity is reduced by some means, for example by prehybridization with appropriate blocking nucleic acids and/or including such blocking nucleic acid sequences for said repetitive sequences during said hybridization. The bound, labeled DNA sequences are then rendered in a visualizable form, if necessary. Chromosomal regions in the test cells which are at increased or decreased copy number can be identified by detecting regions where the ratio of signal from the two DNAs is altered. For example, those regions that have decreased in copy number in the test cells will show relatively lower signal from the test DNA than the reference compared to other regions of the genome. Regions that have been increased in copy number in the test cells will show relatively higher signal from the test DNA. Where there are chromosomal deletions or multiplications, differences in the ratio of the signals from the two labels will be detected and the ratio will provide a measure of the copy number. In another embodiment of CGH, array CGH (aCGH), the immobilized chromosome element is replaced with a collection of solid support bound target nucleic acids on an array, allowing for a large or complete percentage of the genome to be represented in the collection of solid support bound targets. Target nucleic acids may comprise cDNAs, genomic DNAs, oligonucleotides (e.g., to detect single nucleotide polymorphisms) and the like. Array-based CGH may also be performed with single-color labeling (as opposed to labeling the control and the possible tumor sample with two different dyes and mixing them prior to hybridization, which will yield a ratio due to competitive hybridization of probes on the arrays). In single color CGH, the control is labeled and hybridized to one array and absolute signals are read, and the possible tumor sample is labeled and hybridized to a second array (with identical content) and absolute signals are read. Copy number difference is calculated based on absolute signals from the two arrays. Methods of preparing immobilized chromosomes or arrays and performing comparative genomic hybridization are well-known in the art (see, e.g., U.S. Pat. Nos. 6,335,167; 6,197,501; 5,830,645; and 5,665,549 and Albertson (1984) *EMBO J.* 3: 1227-1234; Pinkel (1988) *Proc. Natl. Acad. Sci. USA* 85: 9138-9142; EPO Pub. No. 430,402; *Methods in Molecular Biology*, Vol. 33: In situ Hybridization Protocols, Choo, ed., Humana Press, Totowa, N.J. (1994), etc.) In another embodiment, the hybridization protocol of Pinkel, et al. (1998) *Nature Genetics* 20: 207-211, or of Kallioniemi (1992) *Proc. Natl Acad Sci USA* 89:5321-5325 (1992) is used.

In still another embodiment, amplification-based assays can be used to measure copy number. In such amplification-based assays, the nucleic acid sequences act as a template in an amplification reaction (e.g., Polymerase Chain Reaction (PCR). In a quantitative amplification, the amount of amplification product will be proportional to the amount of template in the original sample. Comparison to appropriate controls, e.g. healthy tissue, provides a measure of the copy number.

Methods of "quantitative" amplification are well-known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) PCR Protocols, *A Guide to Methods and Applications*, Academic Press, Inc. N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR may also be used in the methods of the present invention. In fluorogenic quantitative PCR, quantitation is based on amount of fluorescence signals, e.g., TaqMan and SYBR green.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

Loss of heterozygosity (LOH) and major copy proportion (MCP) mapping (Wang, Z. C., et al. (2004) *Cancer Res* 64(1):64-71; Seymour, A. B., et al. (1994) *Cancer Res* 54, 2761-4; Hahn, S. A., et al. (1995) *Cancer Res* 55, 4670-5; Kimura, M., et al. (1996) *Genes Chromosomes Cancer* 17, 88-93; Li et al., (2008) *MBC Bioinform.* 9, 204-219) may also be used to identify regions of amplification or deletion.

b. Methods for Detection of Biomarker Nucleic Acid Expression

Biomarker expression may be assessed by any of a wide variety of well-known methods for detecting expression of a transcribed molecule or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In preferred embodiments, activity of a particular gene is characterized by a measure of gene transcript (e.g. mRNA), by a measure of the quantity of translated protein, or by a measure of gene product activity. Marker expression can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In another embodiment, detecting or determining expression levels of a biomarker and functionally similar homologs thereof, including a fragment or genetic alteration thereof (e.g., in regulatory or promoter regions thereof) comprises detecting or determining RNA levels for the marker of interest. In one embodiment, one or more cells from the subject to be tested are obtained and RNA is isolated from the cells. In a preferred embodiment, a sample of breast tissue cells is obtained from the subject.

In one embodiment, RNA is obtained from a single cell. For example, a cell can be isolated from a tissue sample by laser capture microdissection (LCM). Using this technique, a cell can be isolated from a tissue section, including a stained tissue section, thereby assuring that the desired cell is isolated (see, e.g., Bonner et al. (1997) Science 278: 1481; Emmert-Buck et al. (1996) Science 274:998; Fend et al. (1999) Am. J. Path. 154: 61 and Murakami et al. (2000) Kidney Int. 58:1346). For example, Murakami et al., supra, describe isolation of a cell from a previously immunostained tissue section.

It is also be possible to obtain cells from a subject and culture the cells in vitro, such as to obtain a larger population of cells from which RNA can be extracted. Methods for establishing cultures of non-transformed cells, i.e., primary cell cultures, are known in the art.

When isolating RNA from tissue samples or cells from individuals, it may be important to prevent any further changes in gene expression after the tissue or cells has been removed from the subject. Changes in expression levels are known to change rapidly following perturbations, e.g., heat shock or activation with lipopolysaccharide (LPS) or other reagents. In addition, the RNA in the tissue and cells may quickly become degraded. Accordingly, in a preferred embodiment, the tissue or cells obtained from a subject is snap frozen as soon as possible.

RNA can be extracted from the tissue sample by a variety of methods, e.g., the guanidium thiocyanate lysis followed by CsCl centrifugation (Chirgwin et al., 1979, Biochemistry 18:5294-5299). RNA from single cells can be obtained as described in methods for preparing cDNA libraries from single cells, such as those described in Dulac, C. (1998) Curr. Top. Dev. Biol. 36, 245 and Jena et al. (1996) J. Immunol. Methods 190:199. Care to avoid RNA degradation must be taken, e.g., by inclusion of RNAsin.

The RNA sample can then be enriched in particular species. In one embodiment, poly(A)+ RNA is isolated from the RNA sample. In general, such purification takes advantage of the poly-A tails on mRNA. In particular and as noted above, poly-T oligonucleotides may be immobilized within on a solid support to serve as affinity ligands for mRNA. Kits for this purpose are commercially available, e.g., the MessageMaker kit (Life Technologies, Grand Island, N.Y.).

In a preferred embodiment, the RNA population is enriched in marker sequences. Enrichment can be undertaken, e.g., by primer-specific cDNA synthesis, or multiple rounds of linear amplification based on cDNA synthesis and template-directed in vitro transcription (see, e.g., Wang et al. (1989) PNAS 86, 9717; Dulac et al., supra, and Jena et al., supra).

The population of RNA, enriched or not in particular species or sequences, can further be amplified. As defined herein, an "amplification process" is designed to strengthen, increase, or augment a molecule within the RNA. For example, where RNA is mRNA, an amplification process such as RT-PCR can be utilized to amplify the mRNA, such that a signal is detectable or detection is enhanced. Such an amplification process is beneficial particularly when the biological, tissue, or tumor sample is of a small size or volume.

Various amplification and detection methods can be used. For example, it is within the scope of the present invention to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR) as described by R. L. Marshall, et al., PCR Methods and Applications 4: 80-84 (1994). Real time PCR may also be used.

Other known amplification methods which can be utilized herein include but are not limited to the so-called "NASBA" or "3SR" technique described in PNAS USA 87: 1874-1878 (1990) and also described in Nature 350 (No. 6313): 91-92 (1991); Q-beta amplification as described in published European Patent Application (EPA) No. 4544610; strand displacement amplification (as described in G. T. Walker et al., Clin. Chem. 42: 9-13 (1996) and European Patent Application No. 684315; target mediated amplification, as described by PCT Publication WO9322461; PCR; ligase chain reaction (LCR) (see, e.g., Wu and Wallace, Genomics 4, 560 (1989), Landegren et al., Science 241, 1077 (1988)); self-sustained sequence replication (SSR) (see, e.g., Guatelli et al., Proc. Nat. Acad. Sci. USA, 87, 1874 (1990)); and transcription amplification (see, e.g., Kwoh et al., Proc. Natl. Acad. Sci. USA 86, 1173 (1989)).

Many techniques are known in the state of the art for determining absolute and relative levels of gene expression, commonly used techniques suitable for use in the present invention include Northern analysis, RNase protection assays (RPA), microarrays and PCR-based techniques, such as quantitative PCR and differential display PCR. For example, Northern blotting involves running a preparation of RNA on a denaturing agarose gel, and transferring it to a suitable support, such as activated cellulose, nitrocellulose or glass or nylon membranes. Radiolabeled cDNA or RNA is then hybridized to the preparation, washed and analyzed by autoradiography.

In situ hybridization visualization may also be employed, wherein a radioactively labeled antisense RNA probe is hybridized with a thin section of a biopsy sample, washed, cleaved with RNase and exposed to a sensitive emulsion for autoradiography. The samples may be stained with hematoxylin to demonstrate the histological composition of the sample, and dark field imaging with a suitable light filter shows the developed emulsion. Non-radioactive labels such as digoxigenin may also be used.

Alternatively, mRNA expression can be detected on a DNA array, chip or a microarray. Labeled nucleic acids of a test sample obtained from a subject may be hybridized to a solid surface comprising biomarker DNA. Positive hybridization signal is obtained with the sample containing biomarker transcripts. Methods of preparing DNA arrays and their use are well-known in the art (see, e.g., U.S. Pat. Nos. 6,618,6796; 6,379,897; 6,664,377; 6,451,536; 548,257; U.S. 20030157485 and Schena et al. (1995) *Science* 20, 467-470; Gerhold et al. (1999) *Trends In Biochem. Sci.* 24, 168-173; and Lennon et al. (2000) *Drug Discovery Today* 5, 59-65, which are herein incorporated by reference in their entirety). Serial Analysis of Gene Expression (SAGE) can also be performed (See for example U.S. Patent Application 20030215858).

To monitor mRNA levels, for example, mRNA is extracted from the biological sample to be tested, reverse transcribed, and fluorescently-labeled cDNA probes are generated. The microarrays capable of hybridizing to marker cDNA are then probed with the labeled cDNA probes, the slides scanned and fluorescence intensity measured. This intensity correlates with the hybridization intensity and expression levels.

Types of probes that can be used in the methods described herein include cDNA, riboprobes, synthetic oligonucleotides and genomic probes. The type of probe used will generally be dictated by the particular situation, such as riboprobes for in situ hybridization, and cDNA for Northern blotting, for example. In one embodiment, the probe is directed to nucleotide regions unique to the RNA. The probes may be as short as is required to differentially recognize marker mRNA transcripts, and may be as short as, for example, 15 bases; however, probes of at least 17, 18, 19 or 20 or more bases can be used. In one embodiment, the primers and probes hybridize specifically under stringent conditions to a DNA fragment having the nucleotide sequence corresponding to the marker. As herein used, the term "stringent conditions" means hybridization will occur only if there is at least 95% identity in nucleotide sequences. In another embodiment, hybridization under "stringent conditions" occurs when there is at least 97% identity between the sequences.

The form of labeling of the probes may be any that is appropriate, such as the use of radioisotopes, for example, $^{32}P$ and $^{35}S$. Labeling with radioisotopes may be achieved, whether the probe is synthesized chemically or biologically, by the use of suitably labeled bases.

In one embodiment, the biological sample contains polypeptide molecules from the test subject. Alternatively, the biological sample can contain mRNA molecules from the test subject or genomic DNA molecules from the test subject.

In another embodiment, the methods further involve obtaining a control biological sample from a control subject, contacting the control sample with a compound or agent capable of detecting marker polypeptide, mRNA, genomic DNA, or fragments thereof, such that the presence of the marker polypeptide, mRNA, genomic DNA, or fragments thereof, is detected in the biological sample, and comparing the presence of the marker polypeptide, mRNA, genomic DNA, or fragments thereof, in the control sample with the presence of the marker polypeptide, mRNA, genomic DNA, or fragments thereof in the test sample.

c. Methods for Detection of Biomarker Protein Expression

The activity or level of a biomarker protein can be detected and/or quantified by detecting or quantifying the expressed polypeptide. The polypeptide can be detected and quantified by any of a number of means well-known to those of skill in the art. Aberrant levels of polypeptide expression of the polypeptides encoded by a biomarker nucleic acid and functionally similar homologs thereof, including a fragment or genetic alteration thereof (e.g., in regulatory or promoter regions thereof) are associated with the likelihood of response of a cancer to PI3K/mTOR combination inhibitor therapy. Any method known in the art for detecting polypeptides can be used. Such methods include, but are not limited to, immunodiffusion, immunoelectrophoresis, radioimmunoassay (MA), enzyme-linked immunosorbent assays (ELISAs), immunofluorescent assays, Western blotting, binder-ligand assays, immunohistochemical techniques, agglutination, complement assays, high performance liquid chromatography (HPLC), thin layer chromatography (TLC), hyperdiffusion chromatography, and the like (e.g., Basic and Clinical Immunology, Sites and Terr, eds., Appleton and Lange, Norwalk, Conn. pp 217-262, 1991 which is incorporated by reference). Preferred are binder-ligand immunoassay methods including reacting antibodies with an epitope or epitopes and competitively displacing a labeled polypeptide or derivative thereof.

For example, ELISA and RIA procedures may be conducted such that a desired biomarker protein standard is labeled (with a radioisotope such as $^{125}I$ or $^{35}S$, or an assayable enzyme, such as horseradish peroxidase or alkaline phosphatase), and, together with the unlabeled sample, brought into contact with the corresponding antibody, whereon a second antibody is used to bind the first, and radioactivity or the immobilized enzyme assayed (competitive assay). Alternatively, the biomarker protein in the sample is allowed to react with the corresponding immobilized antibody, radioisotope- or enzyme-labeled anti-biomarker protein antibody is allowed to react with the system, and radioactivity or the enzyme assayed (ELISA-sandwich assay). Other conventional methods may also be employed as suitable.

The above techniques may be conducted essentially as a "one-step" or "two-step" assay. A "one-step" assay involves contacting antigen with immobilized antibody and, without washing, contacting the mixture with labeled antibody. A "two-step" assay involves washing before contacting, the mixture with labeled antibody. Other conventional methods may also be employed as suitable.

In one embodiment, a method for measuring biomarker protein levels comprises the steps of: contacting a biological specimen with an antibody or variant (e.g., fragment) thereof which selectively binds the biomarker protein, and detecting whether said antibody or variant thereof is bound to said sample and thereby measuring the levels of the biomarker protein.

Enzymatic and radiolabeling of biomarker protein and/or the antibodies may be effected by conventional means. Such means will generally include covalent linking of the enzyme to the antigen or the antibody in question, such as by glutaraldehyde, specifically so as not to adversely affect the activity of the enzyme, by which is meant that the enzyme must still be capable of interacting with its substrate, although it is not necessary for all of the enzyme to be active, provided that enough remains active to permit the assay to be effected. Indeed, some techniques for binding enzyme are non-specific (such as using formaldehyde), and will only yield a proportion of active enzyme.

It is usually desirable to immobilize one component of the assay system on a support, thereby allowing other components of the system to be brought into contact with the component and readily removed without laborious and time-consuming labor. It is possible for a second phase to be immobilized away from the first, but one phase is usually sufficient.

It is possible to immobilize the enzyme itself on a support, but if solid-phase enzyme is required, then this is generally best achieved by binding to antibody and affixing the antibody to a support, models and systems for which are well-known in the art. Simple polyethylene may provide a suitable support.

Enzymes employable for labeling are not particularly limited, but may be selected from the members of the oxidase group, for example. These catalyze production of hydrogen peroxide by reaction with their substrates, and glucose oxidase is often used for its good stability, ease of availability and cheapness, as well as the ready availability of its substrate (glucose). Activity of the oxidase may be assayed by measuring the concentration of hydrogen peroxide formed after reaction of the enzyme-labeled antibody with the substrate under controlled conditions well-known in the art.

Other techniques may be used to detect biomarker protein according to a practitioner's preference based upon the present disclosure. One such technique is Western blotting (Towbin et at., Proc. Nat. Acad. Sci. 76:4350 (1979)), wherein a suitably treated sample is run on an SDS-PAGE gel before being transferred to a solid support, such as a nitrocellulose filter. Anti-biomarker protein antibodies (unlabeled) are then brought into contact with the support and assayed by a secondary immunological reagent, such as labeled protein A or anti-immunoglobulin (suitable labels including $^{125}$I, horseradish peroxidase and alkaline phosphatase). Chromatographic detection may also be used.

Immunohistochemistry may be used to detect expression of biomarker protein, e.g., in a biopsy sample. A suitable antibody is brought into contact with, for example, a thin layer of cells, washed, and then contacted with a second, labeled antibody. Labeling may be by fluorescent markers, enzymes, such as peroxidase, avidin, or radiolabeling. The assay is scored visually, using microscopy.

Anti-biomarker protein antibodies, such as intrabodies, may also be used for imaging purposes, for example, to detect the presence of biomarker protein in cells and tissues of a subject. Suitable labels include radioisotopes, iodine ($^{125}$I, $^{121}$I) carbon ($^{14}$C), sulphur ($^{35}$S), tritium ($^{3}$H), indium ($^{112}$In), and technetium ($^{99}$mTc), fluorescent labels, such as fluorescein and rhodamine, and biotin.

For in vivo imaging purposes, antibodies are not detectable, as such, from outside the body, and so must be labeled, or otherwise modified, to permit detection. Markers for this purpose may be any that do not substantially interfere with the antibody binding, but which allow external detection. Suitable markers may include those that may be detected by X-radiography, NMR or MM. For X-radiographic techniques, suitable markers include any radioisotope that emits detectable radiation but that is not overtly harmful to the subject, such as barium or cesium, for example. Suitable markers for NMR and MM generally include those with a detectable characteristic spin, such as deuterium, which may be incorporated into the antibody by suitable labeling of nutrients for the relevant hybridoma, for example.

The size of the subject, and the imaging system used, will determine the quantity of imaging moiety needed to produce diagnostic images. In the case of a radioisotope moiety, for a human subject, the quantity of radioactivity injected will normally range from about 5 to 20 millicuries of technetium-99. The labeled antibody or antibody fragment will then preferentially accumulate at the location of cells which contain biomarker protein. The labeled antibody or antibody fragment can then be detected using known techniques.

Antibodies that may be used to detect biomarker protein include any antibody, whether natural or synthetic, full length or a fragment thereof, monoclonal or polyclonal, that binds sufficiently strongly and specifically to the biomarker protein to be detected. An antibody may have a $K_d$ of at most about $10^{-6}$M, $10^{-7}$M, $10^{-8}$M, $10^{-9}$M, $10^{-10}$M, $10^{-11}$M, $10^{-12}$M. The phrase "specifically binds" refers to binding of, for example, an antibody to an epitope or antigen or antigenic determinant in such a manner that binding can be displaced or competed with a second preparation of identical or similar epitope, antigen or antigenic determinant. An antibody may bind preferentially to the biomarker protein relative to other proteins, such as related proteins.

Antibodies are commercially available or may be prepared according to methods known in the art.

Antibodies and derivatives thereof that may be used encompass polyclonal or monoclonal antibodies, chimeric, human, humanized, primatized (CDR-grafted), veneered or single-chain antibodies as well as functional fragments, i.e., biomarker protein binding fragments, of antibodies. For example, antibody fragments capable of binding to a biomarker protein or portions thereof, including, but not limited to, Fv, Fab, Fab' and F(ab') 2 fragments can be used. Such fragments can be produced by enzymatic cleavage or by recombinant techniques. For example, papain or pepsin cleavage can generate Fab or F(ab') 2 fragments, respectively. Other proteases with the requisite substrate specificity can also be used to generate Fab or F(ab') 2 fragments. Antibodies can also be produced in a variety of truncated forms using antibody genes in which one or more stop codons have been introduced upstream of the natural stop site. For example, a chimeric gene encoding a F(ab') 2 heavy chain portion can be designed to include DNA sequences encoding the CH, domain and hinge region of the heavy chain.

Synthetic and engineered antibodies are described in, e.g., Cabilly et al., U.S. Pat. No. 4,816,567 Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0451216 B1; and Padlan, E. A. et al., EP 0519596 A1. See also, Newman, R. et al., BioTechnology, 10: 1455-1460 (1992), regarding primatized antibody, and Ladner et al., U.S. Pat. No. 4,946,778 and Bird, R. E. et al., Science, 242: 423-426 (1988)) regarding single-chain antibodies. Antibodies produced from a library, e.g., phage display library, may also be used.

In some embodiments, agents that specifically bind to a biomarker protein other than antibodies are used, such as peptides. Peptides that specifically bind to a biomarker protein can be identified by any means known in the art. For example, specific peptide binders of a biomarker protein can be screened for using peptide phage display libraries.

d. Methods for Detection of Biomarker Structural Alterations

The following illustrative methods can be used to identify the presence of a structural alteration in a biomarker nucleic acid and/or biomarker polypeptide molecule in order to, for example, identify PI3K/mTOR pathway proteins that are overexpressed, overfunctional, and the like.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in a biomarker nucleic acid such as a biomarker gene (see Abravaya et al. (1995) Nucleic Acids Res. 23:675-682). This method can include the steps of collecting a sample of cells from a subject, isolating nucleic acid (e.g., genomic, mRNA or both) from the cells of the sample, contacting the nucleic acid sample with one or more primers which specifically hybridize to a biomarker gene under conditions such that hybridization and amplification of the biomarker gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self-sustained sequence replication (Guatelli, J. C. et al. (1990) Proc. Natl. Acad. Sci. USA 87:1874-1878), transcriptional amplification system (Kwoh, D. Y. et al. (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques well-known to those of skill in the art. These detection schemes are especially useful for the detection of nucleic acid molecules if such molecules are present in very low numbers.

In an alternative embodiment, mutations in a biomarker nucleic acid from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in biomarker nucleic acid can be identified by hybridizing a sample and control nucleic acids, e.g., DNA or RNA, to high density arrays containing hundreds or thousands of oligonucleotide probes (Cronin, M. T. et al. (1996) Hum. Mutat. 7:244-255; Kozal, M. J. et al. (1996) Nat. Med. 2:753-759). For example, biomarker genetic mutations can be identified in two dimensional arrays containing light-generated DNA probes as described in Cronin et al. (1996) supra. Briefly, a first hybridization array of probes can be used to scan through long stretches of DNA in a sample and control to identify base changes between the sequences by making linear arrays of sequential, overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene. Such biomarker genetic mutations can be identified in a variety of contexts, including, for example, germline and somatic mutations.

In yet another embodiment, any of a variety of sequencing reactions known in the art can be used to directly sequence a biomarker gene and detect mutations by comparing the sequence of the sample biomarker with the corresponding wild-type (control) sequence. Examples of sequencing reactions include those based on techniques developed by Maxam and Gilbert (1977) *Proc. Natl. Acad. Sci. USA* 74:560 or Sanger (1977) *Proc. Natl. Acad Sci. USA* 74:5463. It is also contemplated that any of a variety of automated sequencing procedures can be utilized when performing the diagnostic assays (Naeve (1995) *Biotechniques* 19:448-53), including sequencing by mass spectrometry (see, e.g., PCT International Publication No. WO 94/16101; Cohen et al. (1996) *Adv. Chromatogr.* 36:127-162; and Griffin et al. (1993) *Appl. Biochem. Biotechnol.* 38:147-159).

Other methods for detecting mutations in a biomarker gene include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes formed by hybridizing (labeled) RNA or DNA containing the wild-type biomarker sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with SI nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Natl. Acad. Sci. USA 85:4397 and Saleeba et al. (1992) Methods Enzymol. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in biomarker cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662). According to an exemplary embodiment, a probe based on a biomarker sequence, e.g., a wild-type biomarker treated with a DNA mismatch repair enzyme, and the cleavage products, if any, can be detected from electrophoresis protocols or the like (e.g., U.S. Pat. No. 5,459,039.)

In other embodiments, alterations in electrophoretic mobility can be used to identify mutations in biomarker genes. For example, single strand conformation polymorphism (SSCP) may be used to detect differences in electrophoretic mobility between mutant and wild type nucleic acids (Orita et al. (1989) *Proc Natl. Acad. Sci USA* 86:2766; see also Cotton (1993) *Mutat. Res.* 285:125-144 and Hayashi (1992) *Genet. Anal. Tech. Appl.* 9:73-79). Single-stranded DNA fragments of sample and control biomarker nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163; Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

e. Sampling Methods

In some embodiments, biomarker amount and/or activity measurement(s) in a sample from a subject is compared to a predetermined control (standard) sample. The sample from the subject is typically from a diseased tissue, such as cancer cells or tissues. The control sample can be from the same subject or from a different subject. The control sample is typically a normal, non-diseased sample. However, in some embodiments, such as for staging of disease or for evaluating the efficacy of treatment, the control sample can be from a diseased tissue. The control sample can be a combination of samples from several different subjects. In some embodiments, the biomarker amount and/or activity measurement (s) from a subject is compared to a pre-determined level. This pre-determined level is typically obtained from normal samples. As described herein, a "pre-determined" biomarker amount and/or activity measurement(s) may be a biomarker amount and/or activity measurement(s) used to, by way of example only, evaluate a subject that may be selected for treatment (e.g., based on the number of genomic mutations and/or the number of genomic mutations causing non-functional proteins for DNA repair genes), evaluate a response to a PI3K/mTOR combination inhibitor therapy, and/or evaluate a response to a PI3K/mTOR combination inhibitor therapy with one or more additional anti-cancer therapies. A pre-determined biomarker amount and/or activity measurement(s) may be determined in populations of patients with or without cancer. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements.

In another embodiment, the amounts determined and/or compared in a method described herein are based on relative measurements, such as ratios (e.g., biomarker copy numbers, level, and/or activity before a treatment vs. after a treatment, such biomarker measurements relative to a spiked or man-made control, such biomarker measurements relative to the expression of a housekeeping gene, and the like). For example, the relative analysis can be based on the ratio of pre-treatment biomarker measurement as compared to post-treatment biomarker measurement. Pre-treatment biomarker measurement can be made at any time prior to initiation of anti-cancer therapy. Post-treatment biomarker measurement can be made at any time after initiation of anti-cancer therapy. In some embodiments, post-treatment biomarker measurements are made 1, 2, 3, 4, 5, 6, 7, 8, 9, 10, 11, 12, 13, 14, 15, 16, 17, 18, 19, 20 weeks or more after initiation of anti-cancer therapy, and even longer toward indefinitely for continued monitoring. Treatment can comprise anti-cancer therapy, such as a therapeutic regimen comprising one or more PI3K/mTOR combination inhibitors alone or in combination with other anti-cancer agents, such as with immune checkpoint inhibitors.

The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

In some embodiments of the present invention the change of biomarker amount and/or activity measurement(s) from the pre-determined level is about 0.1, 0.2, 0.3, 0.4, 0.5, 0.6, 0.7, 0.8, 0.9, 1.0, 1.5, 2.0, 2.5, 3.0, 3.5, 4.0, 4.5, or 5.0 fold or greater, or any range in between, inclusive. Such cutoff values apply equally when the measurement is based on relative changes, such as based on the ratio of pre-treatment biomarker measurement as compared to post-treatment biomarker measurement.

Biological samples can be collected from a variety of sources from a patient including a body fluid sample, cell sample, or a tissue sample comprising nucleic acids and/or proteins. "Body fluids" refer to fluids that are excreted or secreted from the body as well as fluids that are normally not (e.g., amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit). In a preferred embodiment, the subject and/or control sample is selected from the group consisting of cells, cell lines, histological slides, paraffin embedded tissues, biopsies, whole blood, nipple aspirate, serum, plasma, buccal scrape, saliva, cerebrospinal fluid, urine, stool, and bone marrow. In one embodiment, the sample is serum, plasma, or urine. In another embodiment, the sample is serum.

The samples can be collected from individuals repeatedly over a longitudinal period of time (e.g., once or more on the order of days, weeks, months, annually, biannually, etc.). Obtaining numerous samples from an individual over a period of time can be used to verify results from earlier detections and/or to identify an alteration in biological pattern as a result of, for example, disease progression, drug treatment, etc. For example, subject samples can be taken and monitored every month, every two months, or combinations of one, two, or three month intervals according to the present invention. In addition, the biomarker amount and/or activity measurements of the subject obtained over time can be conveniently compared with each other, as well as with those of normal controls during the monitoring period, thereby providing the subject's own values, as an internal, or personal, control for long-term monitoring.

Sample preparation and separation can involve any of the procedures, depending on the type of sample collected and/or analysis of biomarker measurement(s). Such procedures include, by way of example only, concentration, dilution, adjustment of pH, removal of high abundance polypeptides (e.g., albumin, gamma globulin, and transferrin, etc.), addition of preservatives and calibrants, addition of protease inhibitors, addition of denaturants, desalting of samples, concentration of sample proteins, extraction and purification of lipids.

The sample preparation can also isolate molecules that are bound in non-covalent complexes to other protein (e.g., carrier proteins). This process may isolate those molecules bound to a specific carrier protein (e.g., albumin), or use a more general process, such as the release of bound molecules from all carrier proteins via protein denaturation, for example using an acid, followed by removal of the carrier proteins.

Removal of undesired proteins (e.g., high abundance, uninformative, or undetectable proteins) from a sample can be achieved using high affinity reagents, high molecular weight filters, ultracentrifugation and/or electrodialysis. High affinity reagents include antibodies or other reagents (e.g., aptamers) that selectively bind to high abundance proteins. Sample preparation could also include ion exchange chromatography, metal ion affinity chromatography, gel filtration, hydrophobic chromatography, chromatofocusing, adsorption chromatography, isoelectric focusing and related techniques. Molecular weight filters include membranes that separate molecules on the basis of size and molecular weight. Such filters may further employ reverse osmosis, nanofiltration, ultrafiltration and microfiltration.

Ultracentrifugation is a method for removing undesired polypeptides from a sample. Ultracentrifugation is the centrifugation of a sample at about 15,000-60,000 rpm while monitoring with an optical system the sedimentation (or lack thereof) of particles. Electrodialysis is a procedure which uses an electromembrane or semipermable membrane in a process in which ions are transported through semi-permeable membranes from one solution to another under the influence of a potential gradient. Since the membranes used in electrodialysis may have the ability to selectively transport ions having positive or negative charge, reject ions of the opposite charge, or to allow species to migrate through a semipermable membrane based on size and charge, it renders electrodialysis useful for concentration, removal, or separation of electrolytes.

Separation and purification in the present invention may include any procedure known in the art, such as capillary electrophoresis (e.g., in capillary or on-chip) or chromatography (e.g., in capillary, column or on a chip). Electrophoresis is a method which can be used to separate ionic molecules under the influence of an electric field. Electrophoresis can be conducted in a gel, capillary, or in a microchannel on a chip. Examples of gels used for electrophoresis include starch, acrylamide, polyethylene oxides, agarose, or combinations thereof. A gel can be modified by its cross-linking, addition of detergents, or denaturants, immobilization of enzymes or antibodies (affinity electrophoresis) or substrates (zymography) and incorporation of a pH gradient. Examples of capillaries used for electrophoresis include capillaries that interface with an electrospray.

Capillary electrophoresis (CE) is preferred for separating complex hydrophilic molecules and highly charged solutes. CE technology can also be implemented on microfluidic chips. Depending on the types of capillary and buffers used, CE can be further segmented into separation techniques such as capillary zone electrophoresis (CZE), capillary isoelectric focusing (CIEF), capillary isotachophoresis (cITP) and capillary electrochromatography (CEC). An embodiment to couple CE techniques to electrospray ionization involves the use of volatile solutions, for example, aqueous mixtures containing a volatile acid and/or base and an organic such as an alcohol or acetonitrile.

Capillary isotachophoresis (cITP) is a technique in which the analytes move through the capillary at a constant speed but are nevertheless separated by their respective mobilities. Capillary zone electrophoresis (CZE), also known as free-solution CE (FSCE), is based on differences in the electrophoretic mobility of the species, determined by the charge on the molecule, and the frictional resistance the molecule encounters during migration which is often directly proportional to the size of the molecule. Capillary isoelectric focusing (CIEF) allows weakly-ionizable amphoteric molecules, to be separated by electrophoresis in a pH gradient. CEC is a hybrid technique between traditional high performance liquid chromatography (HPLC) and CE.

Separation and purification techniques used in the present invention include any chromatography procedures known in the art. Chromatography can be based on the differential adsorption and elution of certain analytes or partitioning of analytes between mobile and stationary phases. Different examples of chromatography include, but not limited to, liquid chromatography (LC), gas chromatography (GC), high performance liquid chromatography (HPLC), etc.

EXAMPLES

Example 1: Materials and Methods for Examples 2-5 a. Mice

K14Cre, $Pten^{L/L}$, $Pik3ca^{L/L}$, $Pik3cb^{L/L}$, $Trp53^{L/L}$, and MMTV-Neu-IRES-Cre (NIC) mice of FVB/N background were intercrossed to generate mice for this study. All animals were housed and treated in accordance with protocols approved by the Institutional Animal Care and Use Committees at Dana-Farber Cancer Institute and Harvard Medical School.

b. Breast Tumors

In order to obtain K14Cre; $Pten^{L/L}$; $Trp53^{L/L}$ with or without additional $Pik3ca^{L/L}$ or $Pik3cb^{L/L}$ mammary tumors while avoiding epidermal complications arising from Pten deletion in K14-positive basal cells (Wang et al. (2013) *Genes and Development* 27:1568-1580), mammary glands from genetically-engineered K14Cre; $Pten^{L/L}$; $Trp53^{L/L}$ with or without additional $Pik3ca^{L/L}$ or $Pik3cb^{L/L}$ mice were excised, and fragments transplanted orthotopically into cleared mammary fat pads of four week-old female nude mice (CrTac:NCr-$Foxn1^{nu}$). Mice were monitored until mammary tumors formed. Tumors were excised and transplanted into additional nude mice for expansion. To obtain NIC-$Pten^{L/L}$ tumors for experimentation, tumors formed de novo in GEM models were excised and transplanted into the $3^{rd}$ and $4^{th}$ fat pad of additional six week-old FVB/NJ (Taconic) mice. Orthotopic tumors were obtained by injecting $1.0\times10^5$ primary cells in 40% matrigel into the 3rd mammary fat pad of six week-old FVB/NJ (Taconic). Tumors growth was assessed by measuring the long and short axes with digital calipers, and tumor volume was calculated by use of the modified ellipsoid formula (long× short×0.52). For all experiments involving tumor transplantations, all mice were transplanted from single cell pools on the same day. Mice were tagged two to three days later and randomly assigned to treatment or control groups. All tumor measurements were performed by the same researcher in order to avoid variation due to methodology. All analyses were conducted by a second researcher, who was blinded to tumor measurements.

c. Derivation of Primary Breast Cancer Cells

Primary K14Cre; $Pten^{L/L}$; $Trp53^{L/L}$ with or without additional $Pik3ca^{L/L}$ or $Pik3cb^{L/L}$ breast tumors or NIC-$Pten^{L/L}$ tumors were excised, minced and dissociated in collagenase/hyaluronidase buffer (10 mM HEPES, 5% FBS, 20 ug/mL DNase I [Stem Cell Technologies], collagenase/hyaluronidase [Stem Cell Technologies] to 1×) for 45 minutes at 37° C., followed by red blood cell lysis (4 volumes of 0.8% $NH_4Cl$ 0.1 mM EDTA [Stem Cell Technologies] plus 1 volume PBS), and strained through a 40 um strainer into a cell culture dish. Primary cells from K14Cre; $Pten^{L/L}$; $Trp53^{L/L}$ with or without additional $Pik3ca^{L/L}$ or $Pik3cb^{L/L}$ breast tumors were grown at 37° C. in a humidified incubator under 5% $CO_2$ in F12/DMEM (1:3) media supplemented with 25 ng/mL hydrocortisone, 5 ug/mL insulin, 8.5 ng/mL cholera toxin, 0.125 ng/mL EGF, 10 ug/mL gentamicin and 5 uM Y-27632. Primary cells derived from NIC-$Pten^{L/L}$ tumors were grown in F12/DMEM (1:1) media supplemented with 0.6% FBS, 0.5 ug/mL hydrocortisone, 2.5 ug/mL insulin, 1.0 ng/mL cholera toxin, 20 ng/mL EGF, 10 ug/mL gentamicin and 5 uM Y-27632.

d. Ovarian Tumors

To obtain serous ovarian cancer (SOC) tumors, we isolated ovarian surface epithelial (OSE) cells from $Pten^{L/L}$; $Trp53^{L/L}$ mouse ovaries and introduced Cre and Myc expression via adenoviral and lentiviral transduction in vitro, respectively. Transduced OSE cells were subsequently injected into the ovarian bursa of recipient nude mice. Resulting tumors were excised, minced and dissociated as outlined above. In order to evaluate tumor growth in vivo, Firefly luciferase expression was introduced by lentiviral transduction of pLenti-Blasticidin-Luciferase in vitro, prior to injecting the cells back into the ovarian bursa of recipient FVB/NJ mice. The resulting Luciferase-expressing SOC tumors were used for orthotopic transplants into experimental cohorts of FVB/NJ mice.

e. In Vivo Drug Treatment

BKM120, BYL719 and KIN193 were reconstituted in one volume of NMP (1-methyl-2-pyrrolidone; Sigma) and 9 volumes of PEG-300 (polyethylene glycol 300; Fluka Analytical). Mice were dosed at 30 mg/kg once daily via oral gavage. Monoclonal antibody specific to mouse PD-1 (clone 332.8H3) was administered at 250 ug per mouse once every three days via intraperitoneal injection.

f. Flow Cytometry

Single-cell tumor suspensions in PBS containing 0.2% BSA and 5 mM EDTA were incubated with αCD16/32 antibody for 10 minutes at 4° C. to block Fc receptors, and subsequently incubated with fluorophore-labeled primary antibodies as appropriate for 20 minutes at 4° C. Cell sorting was performed on LSR II and analyzed with FloJo software.

g. Histology and Immunohistochemistry

For histology analyses, formalin-fixed tissue sections were embedded in paraffin, sectioned, and stained with hematoxylin and eosin by the Dana Farber/Harvard Cancer Center Rodent Histopathology Core. For immunohistochemistry, sections were de-paraffinized, incubated in primary antibody overnight, followed by secondary antibody and DAB incubation, and counterstained with hematoxylin.

h. Cell Viability and Cell Invasion Assays

For cell viability assays, one thousand primary cells were seeded in ultra-low attachment 96-well plates and incubated with the appropriate drug concentration for five days. Viability was determined by incubating with CellTiter-Glo® (Promega). Briefly, cells were lysed by adding CellTiter-Glo®, and then transferred to opaque plates to measure luminescence. Cell invasion assays were carried out using 6.5 mm, 8.0 μm-pore polycarbonate membrane transwell inserts (BD Biosciences) by seeding $1.0\times10^5$ cells in serum-free media into the inner chamber, and adding normal growth media to the outer chamber. Cells were incubated overnight. Non-migrating cells were carefully removed with a cotton swab. Migrating cells were stained with 0.5% crystal violet in 70% ethanol for ten minutes at room temperature, and photographed under a Zeiss light microscope. At least five random fields were counted and averaged.

i. Western Blotting

Cells were lysed in $EBC_{250}$ lysis buffer (250 mM NaCl, 50 mM Tris-HCl, pH 8.0, 0.5% Nonidet P-40, 0.2 mM PMSF, 2 μg/mL aprotinin, and 2 μg/mL leupeptin, 5 mM NaF, and 0.5 mM $NaVO_4$). Equal amounts of protein were resolved by SDS-polyacrylamide gel electrophoresis (SDS-PAGE), transferred to polyvinylidene difluoride membranes (PVDF), and hybridized to an appropriate primary antibody and fluorophore-conjugated secondary antibody for subsequent detection by Odyssey® Scanner (Li-Cor).

j. Analysis of Gene Expression and Quantitative-Polymerase Chain Reaction (Q-PCR)

Total RNA was isolated using RNeasy® Mini Kit (Qiagen) and reverse transcribed using SuperScript® III First-Strand Synthesis System (ThermoFisher). Q-PCR was performed in a 7300 Real-Time PCR System (Applied Biosystems, CA) using QuantiTect® SYBR® Green PCR Kit (Qiagen). Reactions were carried out in 96-well plates at 95° C. for 15 minutes, followed by 40 cycles of 94° C. for 15 seconds, 51° C. for 30 seconds and 72° C. for 30 seconds. Gene expression was normalized to GAPDH expression by the ΔΔCt method. For RNA sequencing (RNA Seq), RNA was isolated from bulk tumor fragments using TRIzol reagent according to manufacturer's specifications. RNA Seq was carried out by Ion Torrent (Thermo Fisher) using a panel of 3,826 mouse-specific genes. Gene set expression analysis (GSEA) was carried out by GSEA software (The Broad Institute of MIT and Harvard).

Example 2: Experimental TNBC Animal Model

Figure 1:
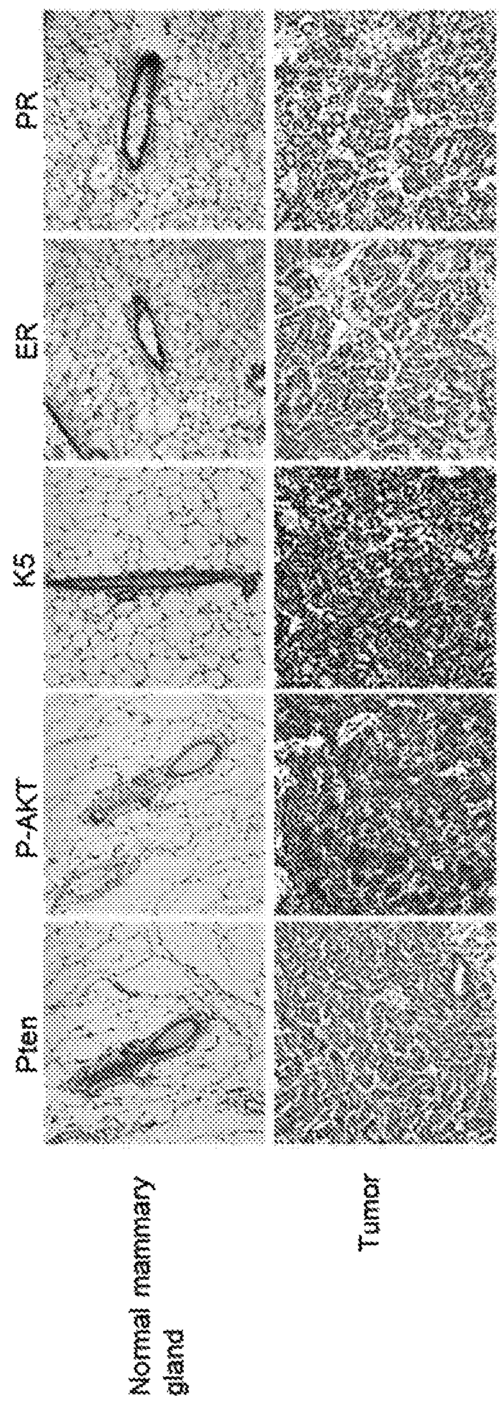
FIG. 1 includes 2 panels, identified as panels A and B, which show that Pten deletion in mammary cells causes breast tumor formation (Panel A) that is dependent on Pik3cb, but not on Pik3ca (Panel B).
Figure 1:
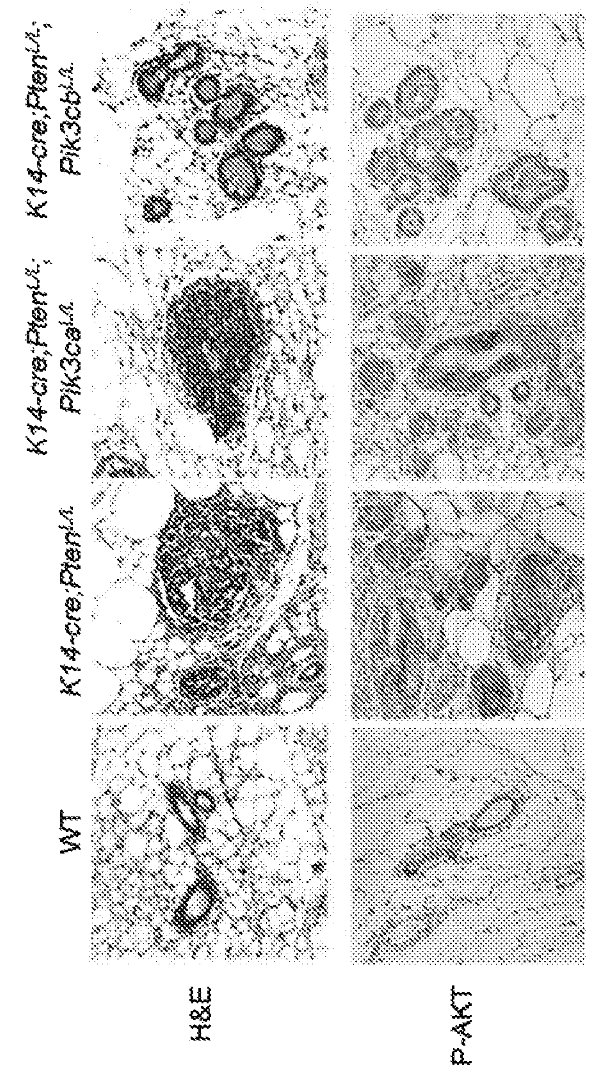

In order to investigate the role of p110β in PTEN-deficient TNBC and to develop novel therapeutic strategies, a genetically-engineered mouse (GEM) model of Pten-null TNBC was generated (FIG. 1A). Consistent with previous results in genetic models of prostate and ovarian cancer (Jia et al. (2008) *Nature* 454:776-9; Schmit et al (2014) *Proc. Natl. Acad. Sci. USA* 111:6395-400), Pten deletion led to tumor formation, which was prevented by additional loss of Pik3cb, but not by Pik3ca deletion (FIG. 1B). These initial findings confirmed the hypothesis that PTEN-deficient TNBC depends on p110β for survival, and supports the hypothesis that PI3Kβ-based combination therapies could lead to more effective treatments against PTEN-deficient TNBC.

Figure 2:
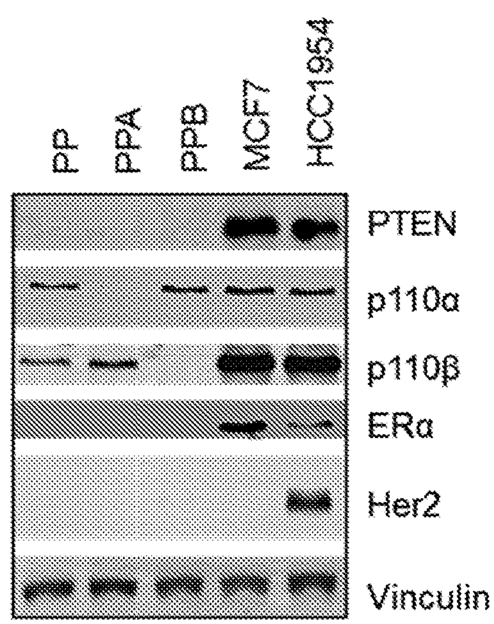
FIG. 2 includes 3 panels, identified as panels A, B, and C, which show that Pten; Trp53-null (PP; Trp53 encodes p53 in mice) TNBC primary cells with additional deletion of either Pik3ca (PPA) or Pik3cb maintain biochemical and phenotypic characteristics of parental tumors, including expression of diagnostic markers (Panel A) and sensitivity to isoform-specific PI3K inhibition using a pan-PI3K inhibitor (BKM120), a p110a inhibitor (BYL719) and a p110β inhibitor (KIN-193) (Panels B-C).
Figure 2:
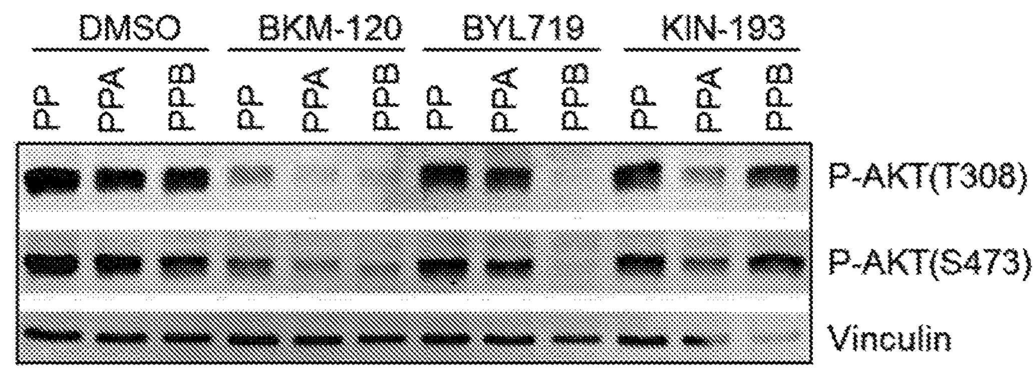
Figure 2:
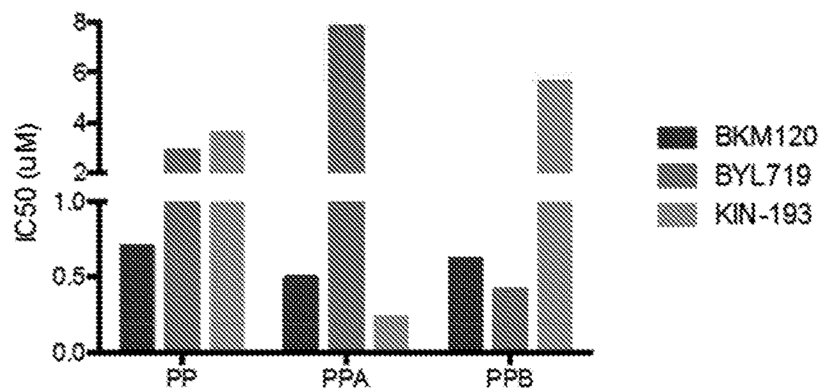

In order to obtain a more robust phenotype suitable for studying TNBC, the tumor suppressor p53 (encoded by TP53 in humans and Trp53 in mice) was concomitantly deleted by crossing K14-Cre; $Pten^{L/L}$ mice with $Trp53^{L/L}$ mice to obtain K14-Cre; $Pten^{L/L}$; $Trp53^{L/L}$ mice. Of note, approximately 84% of TNBC exhibit deleted or mutant p53. From the resulting tumors, early-passage primary Pten; Trp53-null (PP) TNBC cells were obtained that maintained the biochemical and phenotypic characteristics of the parental tumors, including expression of diagnostic markers (FIG. 2A) and sensitivity to isoform-specific PI3K inhibition, as shown by treatment with a pan-PI3K inhibitor (BKM120), a p110α inhibitor (BYL719) or a p110β inhibitor (KIN-193) (FIGS. 2B-2C). This system constitutes a durable research tool allowing the analysis of PI3K isoform-specific signaling networks within a Pten-null TNBC context, and further allowing the analysis of the impact of targeting these pathways on tumor growth and cancer progression.

Figure 3:
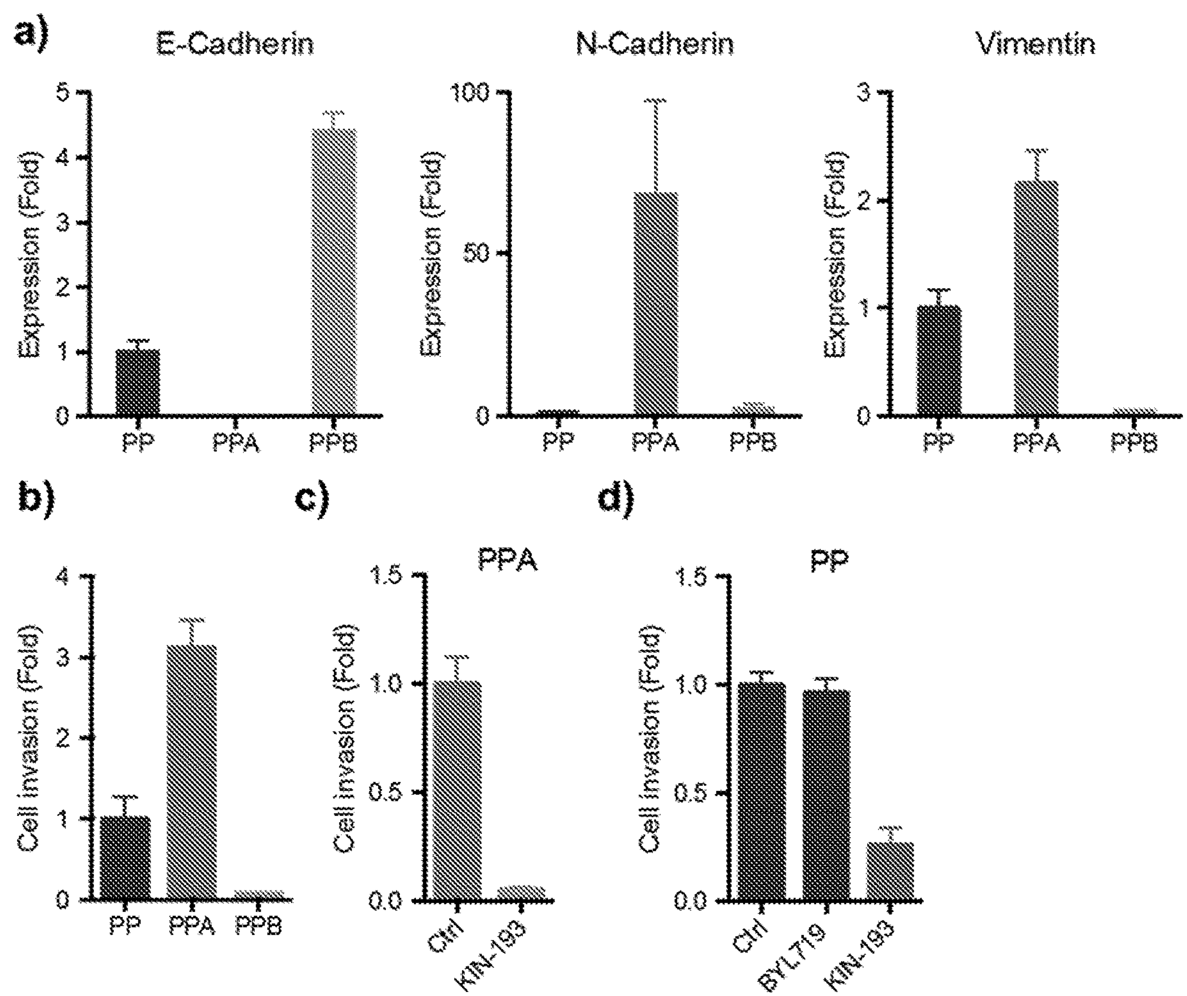
FIG. 3 includes 4 panels, identified as panels A, B, C, and D, which show that PI3Kbeta signaling regulates a cell invasion and motility program (Panels A-D).

Clear differences between p110α- and p110β-specific signaling pathways have been observed. For example, primary Pten; Trp53; Pik3ca-null (PPA) cells exhibit clear signs of epithelial to mesenchymal transition (EMT), including increased expression of mesenchymal markers (N-Cadherin and Vimentin) and undetectable levels of the epithelial marker, E-Cadherin. Conversely, primary Pten; Trp53; Pik3cb-null (PPB) cells express higher levels of E-Cadherin and undetectable levels of Vimentin (FIG. 3A). It has previously been shown that p110α and p110β compete for binding to the p85 PI3K regulatory subunit, so that deletion of one PI3K catalytic isoform results in increased signaling output through the other isoform (Utermark et al (2012). *Genes Dev* 26:1573-86). In other words, PPA cells contain upregulated p110β signaling, while PPB cells contain upregulated p110α activity. In addition, primary PPA cells display increased ability to invade through matrigel, compared to primary PP and PPB cells (FIG. 3B), which can be blocked by specific p110β inhibition (KIN-193; FIG. 3C). Likewise, primary PP cell invasion could be prevented by inhibiting p110β, but not by p110α inhibition (BYL719; FIG. 3D). These results indicate that p110β signaling may regulate a cell invasion and motility program that could potentially impact on a susceptibility axis to combine with p110β inhibition.

Figure 4:
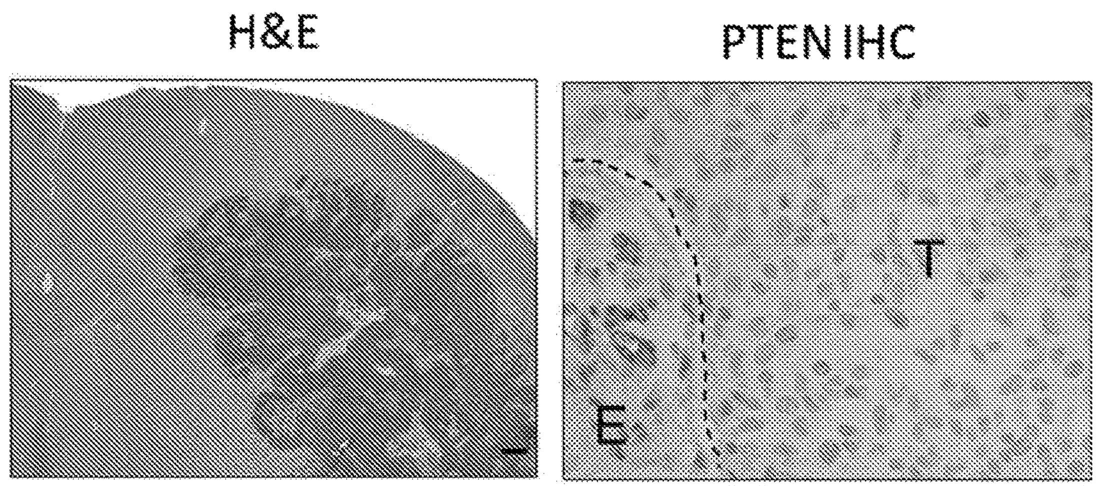
FIG. 4 shows a representative image of tumor (T) and endothelial (E) cells in sections of a distal TNBC metastasis having PTEN deficiency stained with hematoxylin and eosin (H&E) or analyzed using immunohistochemistry (IHC) with a PTEN antibody.

The experimental model indicates that PTEN loss could promote metastatic spread via sustained p110β signaling. In support of this hypothesis, loss of PTEN expression in the majority of samples of distal metastases analyzed from patients with advanced TNBC was confirmed (n=20) (FIG. 4). In addition, a case study was recently reported in which an initially responsive patient eventually developed resistance to p110α inhibition and presented numerous metastatic lesions that had all lost PTEN expression (Juric et al (2014) *Nature* 518:240-44). Taken together, these results and clinical observations suggest that a PI3Kβ-based treatment regimen could prevent TNBC from progressing into metastatic disease, or could be effective for targeting metastatic TNBC lesions even if the primary tumor were not PTEN-deficient. Interestingly, we observed that primary PP cells grow at a faster rate in immunocompromised mice (athymic nude) than in syngeneic immunocompetent mice (FVB strain; FIG. 5A). Furthermore, when injected intravenously into nude mice, primary PP cells formed numerous metastatic nodules in the lungs, while no metastatic nodules could be observed in the immunocompetent FVB mice (FIGS. 5B-5C). These results indicate that the growth of these tumors could be subject to initial rejection by the immune system, but that eventual resistance develops. Moreover, primary PPA tumor cells grow at an aggressively fast pace in immunocompetent FVB mice, while primary PPB tumor cells fail to form tumors in immunocompetent mice (FIG. 6) but do form tumors in immunodeficient nude mice. Together, these results indicate that PI3Kβ activity is required by Pten/p53-deficient breast cancer cells to inhibit anti-tumor immune activity.

Figure 7:
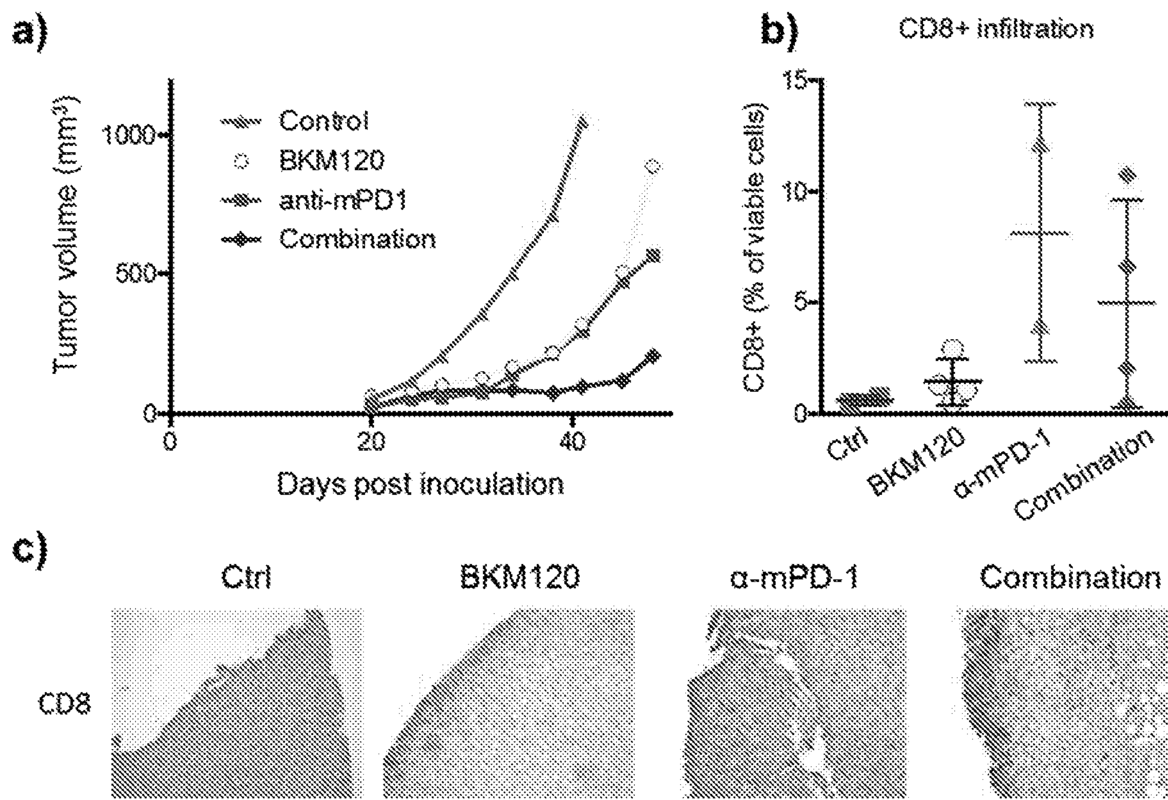
FIG. 7 includes 3 panels, identified as panels A, B, and C, which show the results of combined PI3K targeted therapy and ICB therapy toward inhibiting PP tumor growth (Panel A) and increasing CD8+ T cell infiltration (Panels B-C).

Example 3: Combined PI3Kbeta and Immune Checkpoint Blockade Delays Breast Cancer Tumor Growth The combination of isoform-selective PI3K inhibition and ICB immunotherapy in the model of PTEN-deficient breast cancer described in Example 2 was evaluated. Specifically, immunocompetent FVB mice bearing orthotopic Pten; Trp53-null tumors were treated with the immune checkpoint blocker (ICB) anti-mouse PD-1 monoclonal antibody (α-mPD-1) either alone or in combination with BKM120, a pan-PI3K inhibitor. A robust response to the combination treatment that significantly delayed tumor growth was observed (FIG. 7A). Moreover, fluorescence-activated cell sorting (FACS) analysis revealed increased CD8+ T-cell infiltration into the tumors in the combination treatment (FIGS. 7B-7C).

Figure 8:
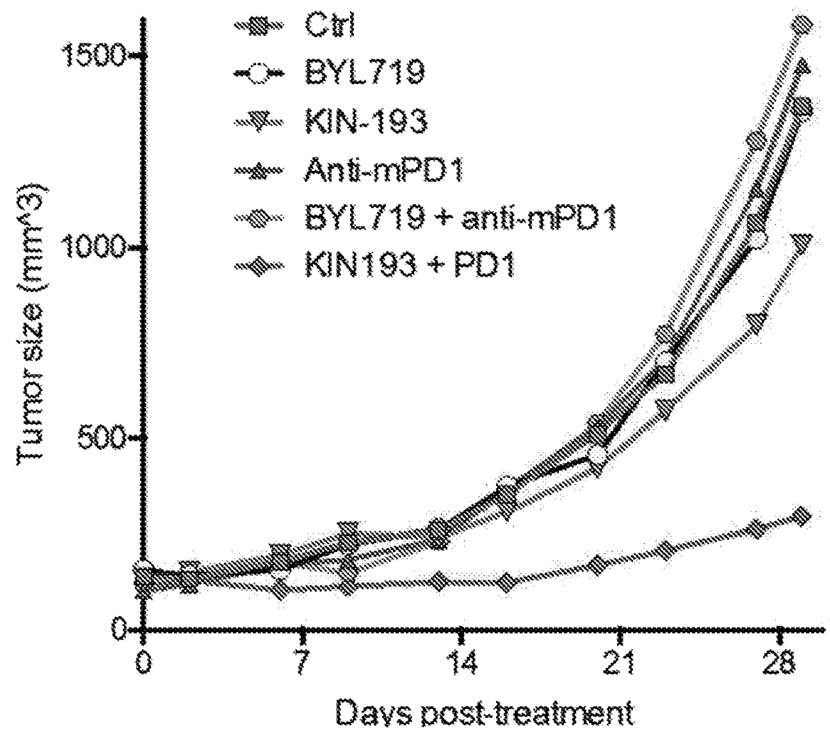
FIG. 8 includes 4 panels, identified as panels A, B, C, and D, which show the results of combined PI3Kbeta targeted therapy and ICB therapy synergizing to inhibit PP TNBC tumor growth (Panels A-C) and increasing CD8+ T cell infiltration (Panel D) on cohort 1.
Figure 8:
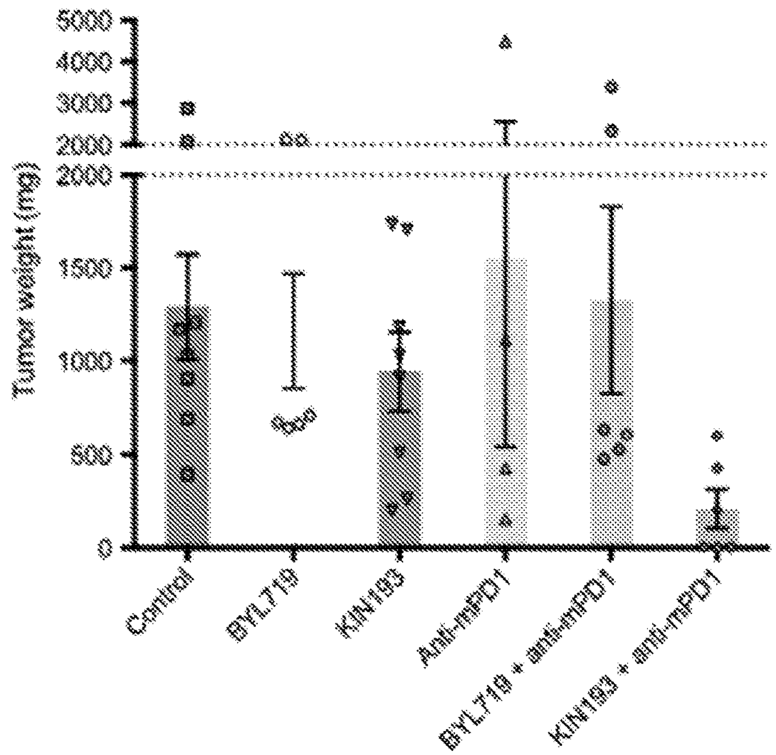
Figure 8:
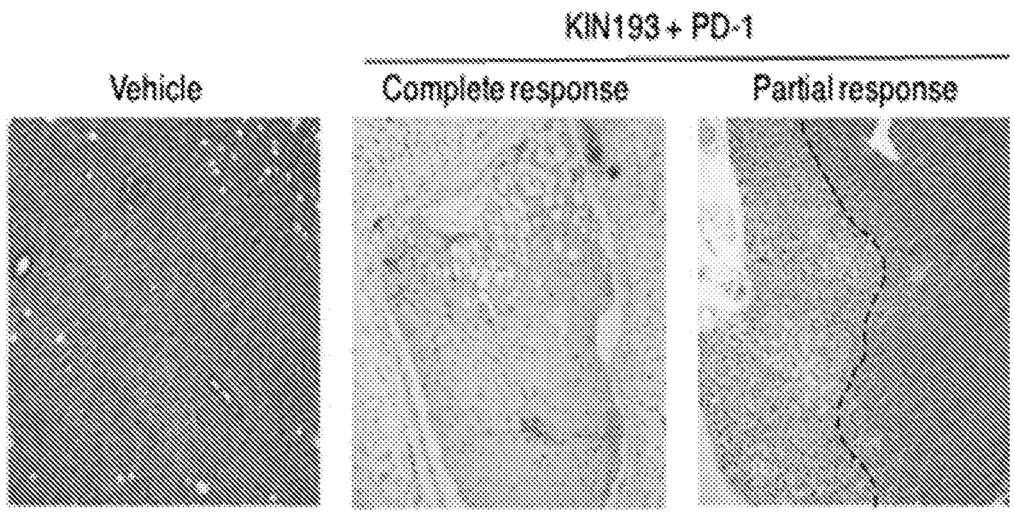
Figure 8:
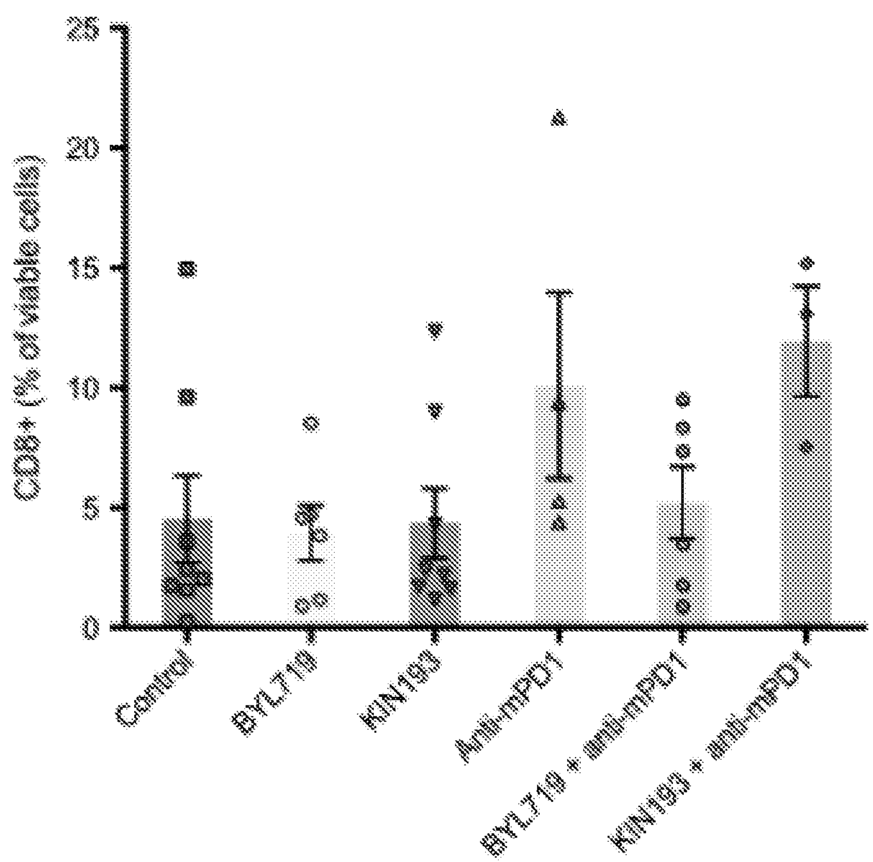

Next, isoform-specific combination treatments using either BYL719, a PI3Kalpha-specific inhibitor, and KIN193, a PI3Kbeta-specific inhibitor, (Ni et al. (2012) *Cancer Discov.* 2:425-433; Nylander et al (2012) *J. Thromb. Haemost.* 10:2127-36) in combination with the anti-mouse PD-1 monoclonal antibody (α-mPD-1) were tested as described above. It was determined that BYL719 treatment, either alone or in combination with anti-mouse PD-1, did not affect tumor growth. Similarly, KIN-193 treatment alone only marginally affected tumor growth. By contrast, KIN-193 in combination with ICB surprisingly inhibited tumor growth in a strong fashion (FIG. 8A). Notably, three of the six tumors treated with this combination therapy regressed to undetectable levels (FIG. 8B). This was confirmed by histological analysis, which demonstrated a complete loss of tumor cellularity (FIG. 8C). Increased CD8+ T-cell infiltration in tumors from mice treated with combined PI3Kbeta inhibition and ICB, as assessed by FACS, was also consistently observed (FIG. 8D).

Figure 9:
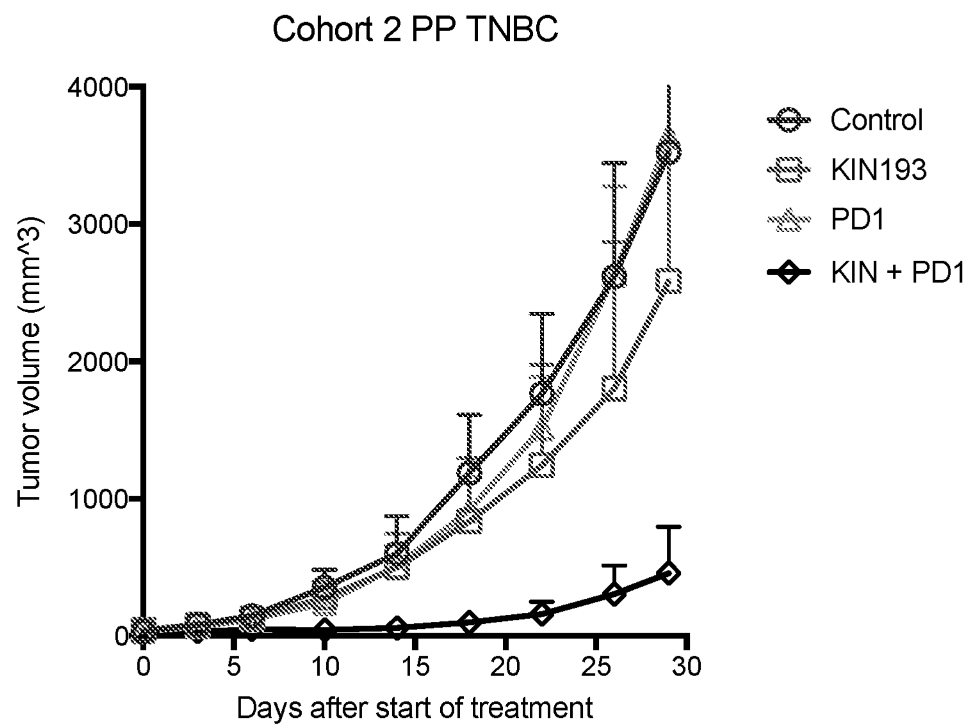
FIG. 9 includes 2 panels, identified as panels A and B, which show the results of combined PI3Kbeta targeted therapy and ICB therapy synergizing to inhibit PP TNBC tumor growth on cohort 2.
Figure 9:
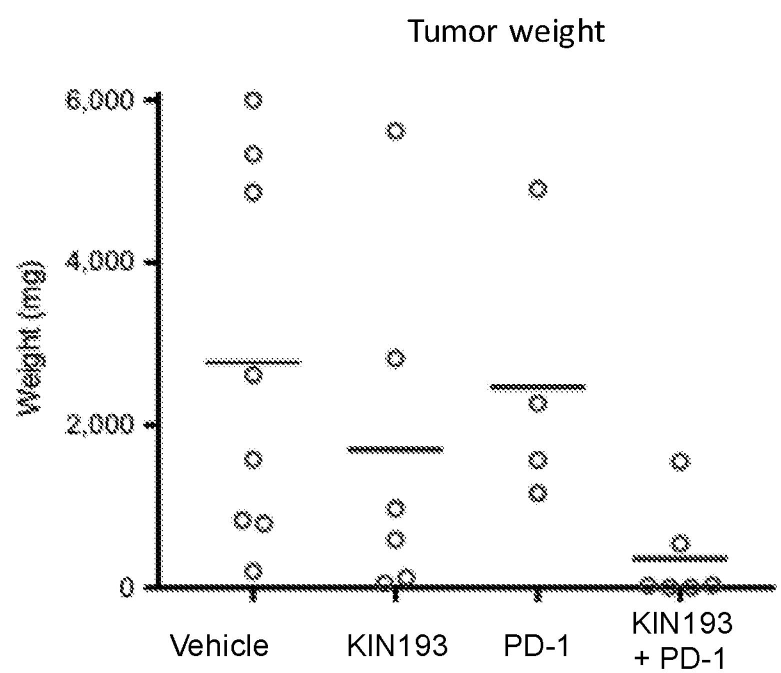

These results were confirmed on a second cohort of mice, which yielded similar results. Combined PI3Kbeta inhibition and ICB with an anti-mouse PD-1 monoclonal antibody strongly inhibited tumor growth, while neither agent alone led to a significant decrease in tumor growth compared to the vehicle control (FIG. 9A). In this second cohort, complete responses were observed in two out of six cases treated with the combined treatment, and an additional two cases showed almost complete responses (FIG. 9B).

The analysis can be furthered by characterizing the tumors by IHC for expression of markers of interest, including staining for CD8+ cells, Foxp3+ regulatory T cells that can dampen immune response, and PD-1 Ligand 1 (PD-L1), which is often over-expressed by tumor cells to inhibit anti-tumor immune response. It is believed that the results allow inference of whether immune suppression is due to increased Treg infiltration or an adaptive tumor response.

In addition, ablation of PD-L1 expression in PP primary TNBC cells using lentiviral-based GIPZ shRNA constructs obtained from Dharmacon, which allow selection by puromycin resistance and GFP expression, is performed. Without being bound by theory, it is believed that PP cells with silenced PD-L1 expression display slower and reduced tumor growth upon orthotopic transplantation into FVB mice.

Since a complete remission in 40-50% of the tumors treated with combined p110β inhibition and ICB immunotherapy was observed, robustness of this response is determined by continuing treatment for an additional two months, and then discontinuing treatment. Tumor growth and recurrence is monitored during this time and for an additional ten months. In the event of tumor recurrence, treatment is reinstated and responsiveness and/or resistance is evaluated.

Figure 10:
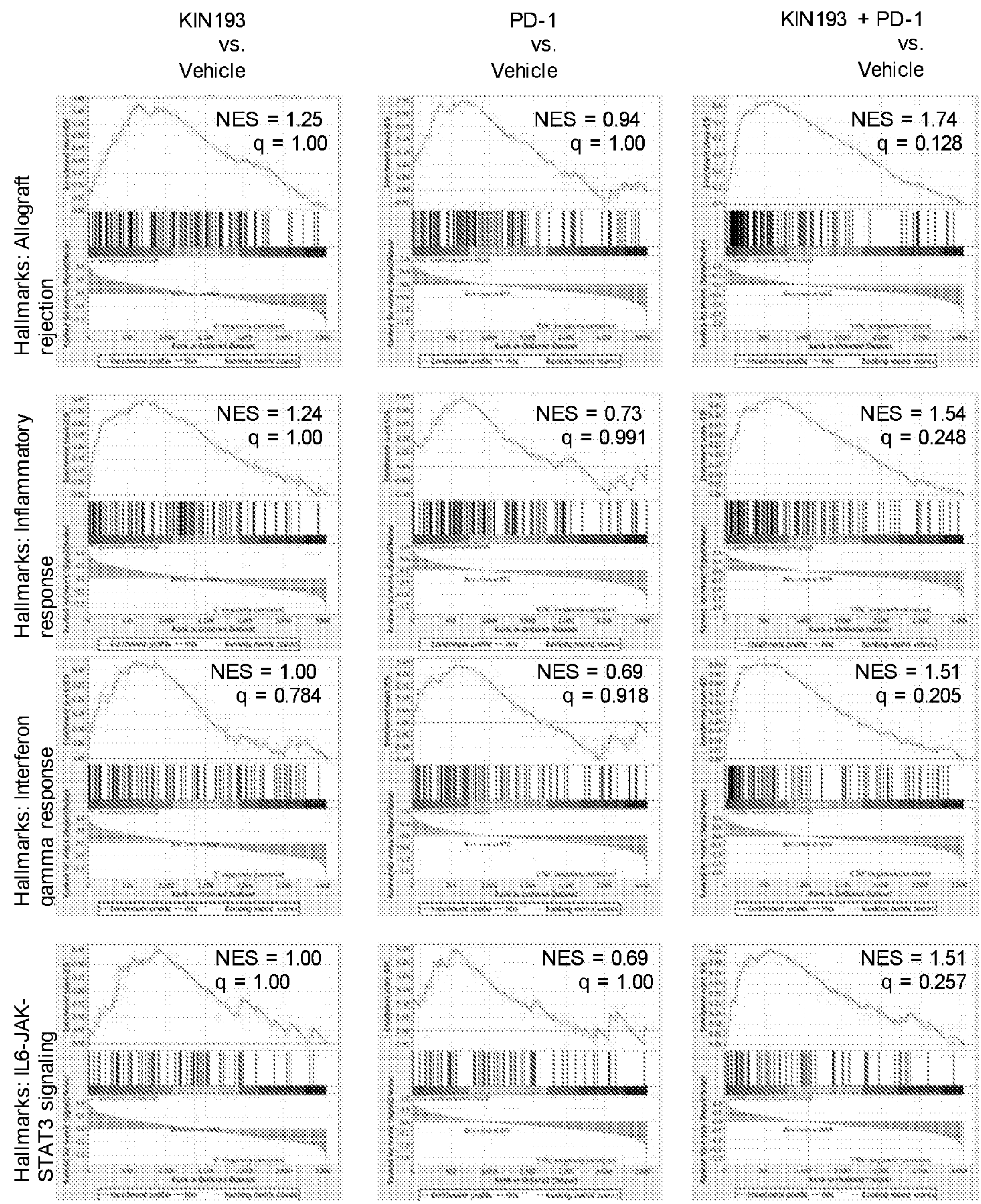
FIG. 10 shows that gene signatures involved in anti-tumor immune response are enriched to a much greater extent (represented by a greater normalized enrichment score (NES) value) and with a much greater degree of statistical significance (represented by a lower q-value) in combined PI3Kbeta targeted therapy and ICB therapy compared to the vehicle control than either agent alone compared to the vehicle control.

In order to investigate changes in genes expression induced by combined PI3Kbeta and ICB, gene expression levels were analyzed in tumors from mice treated with each agent alone or in combination for 96 hours. The results showed that combined treatment results in enriched gene signatures related to anti-tumor immune response to a much greater and significant extent than either agent alone (FIG. 10).

Figure 11:
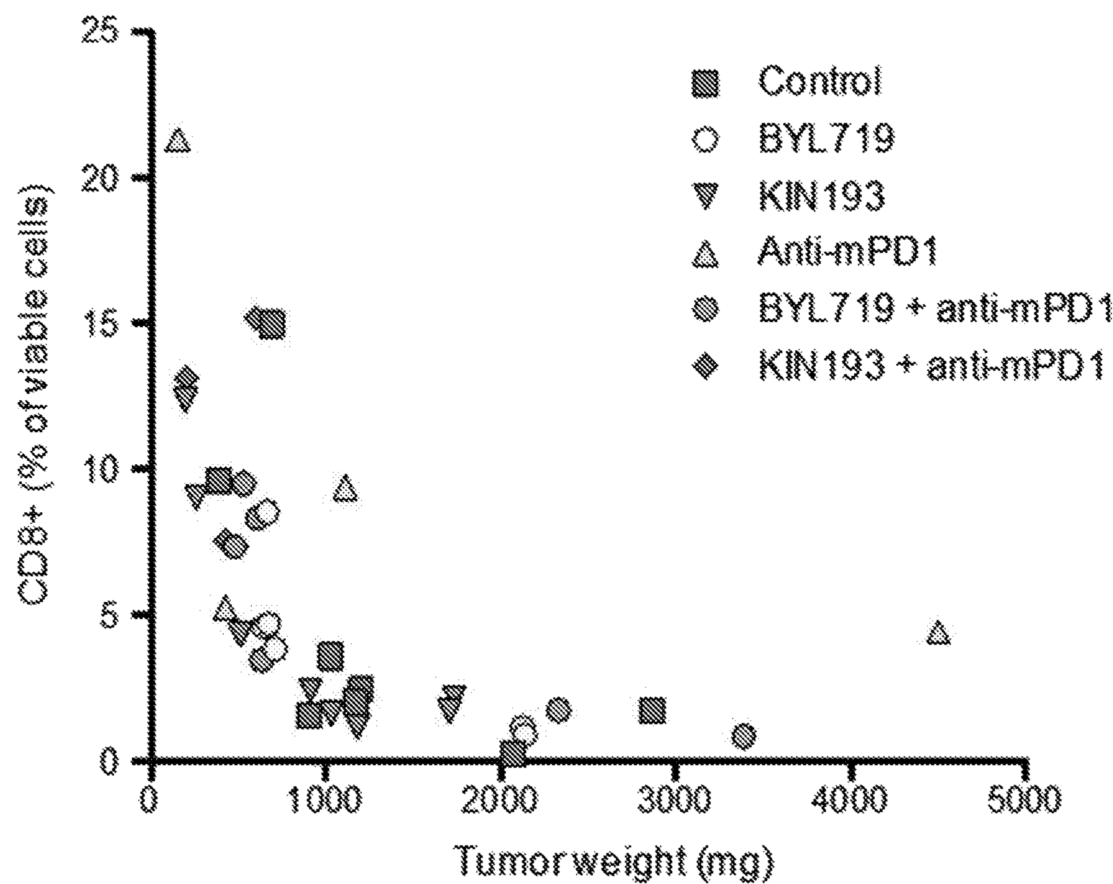
FIG. 11 shows that CD8+ T cell infiltration negatively correlates with tumor size.

In addition, a clear correlation between response and CD8+ T-cell infiltration has been observed (FIG. 11) with different responses between tumors from the same mouse indicating that treatment efficacy is not necessarily due to systemic factors.

In order to extend these results to other types of breast cancer with PTEN loss, combined PI3Kbeta inhibition and ICB was evaluated in a Her2-positive model of breast cancer driven by Her2/Neu over-expression and harboring wild type p53 expression. In this model, treatment with lapatinib alone, a small molecule EGFR/Her2 inhibitor used in clinical settings, did not significantly affect tumor growth. Similarly, treatment with lapatinib and anti-mouse PD-1 ICB did not affect tumor growth. However, treatment with lapatinib plus anti-mouse PD-1 and KIN-193 (a PI3Kbeta inhibitor) significantly inhibited tumor growth (FIG. 12). These results indicate that combined PI3Kbeta inhibition and ICB inhibits PTEN-null tumor growth in multiple breast cancer models.

In order to determine whether CD8+ T-cell infiltration prior to treatment correlates with response to therapy, PP tumors are biopsied prior to, during, and after treatment, and CD8+ infiltration is determined by FACS. Furthermore, to investigate if transcriptional differences between T-cell populations account for differences in response, CD8+ T-cells are isolated from the tumors and spleen (which represent systemic lymphocyte levels) from mice treated with or without combined p110β targeted therapy and ICB and gene expression is analyzed by transcriptome analysis.

Gene expression is also analyzed in purified tumor and stromal cells. Tumor and T cells are isolated using magnetic cell isolation and cell separation kits (Miltenyi Biotec). Without being bound by theory, it is believed that these analyses indicate how the tumor microenvironment affects response to immunotherapy. These results inform the rational design of adjuvant therapies to potentiate anti-tumor immune response.

For statistical analyses involving only two groups, a Student's t-test is used to assess statistical significance. The majority of analyses, however, involve at least three groups (e.g., differences in gene expression between PP, PPA and PPB primary TNBC cells). For statistical analyses involving three or more groups, one-way ANOVA followed by Tukey's HSD post-hoc analysis is used. Based on preliminary results, orthotopically transplanted PP tumors in FVB mice reach a mean volume of 1,365 $mm^3$ at endpoint (n=8; SD=702 $mm^3$). In order to achieve a reduction of 60% by the combination PI3Kbeta selective inhibitor and ICB treatment, assuming similar variance, the following power calculation is believed to apply:

TABLE 4

| Anticipated values | | | |
|---|---|---|---|
| | Mean ($mm^3$) | St. Dev. ($mm^3$) | St. Dev. (% of mean) |
| Control | 1365 | 702 | 51.4 |
| Combination | 546 | 280 | 51.3 |

Difference in means: 60%

TABLE 5

| Sample size needed in each group | | | | |
|---|---|---|---|---|
| | Power | | | |
| Alpha level | 95% | 90% | 80% | 50% |
| 0.1 | 9 | 7 | 5 | 2 |
| 0.05 | 11 | 9 | 7 | 3 |
| 0.02 | 13 | 11 | 9 | 5 |
| 0.01 | 15 | 13 | 10 | 6 |

Thus, to observe a statistically significant difference with a P-value of 0.05 and power level of 95%, at least 11 tumors per condition are analyzed. Since a mean reduction of 72% between control mice and mice treated with KIN-193 and anti-mouse PD-1 described above, it is believed that a 60% difference in means for our power calculation is a conservative suitable estimate. For all experiments involving tumor transplantations, all mice are transplanted from single cell pools on the same day. Mice are tagged two to three days later and randomly assigned to treatment or control groups. All tumor measurements are performed by the same research technician in order to avoid variation due to methodology. All analyses are conducted by the same investigator, who is blinded to tumor measurements. In the unlikely case of death before endpoint unrelated to tumor burden, data from the mouse are discarded, as post-mortem analysis of the tumors is compromised.

Example 4: Patient-Derived Xenograft (PD) TNBC Models

The combination of isoform-selective PI3K inhibition and ICB immunotherapy in the model of PTEN-deficient breast cancer described in Examples 2 and 3 are extended to analysis of pre-clinical cancer models using a panel of orthotopic patient-derived xenografts from advanced TNBC. One of the major advantages of PDX models is that they provide a clinically-relevant system, as genetic and epigenetic alterations found within these models correspond to alterations actually found in the clinic. Likewise, PDX models recapitulate the heterogeneity found within a single tumor and between patients. Since PDX models are amenable to molecular and pharmacological manipulations, this system can be used to evaluate response to novel cancer therapies, examine genetic and epigenetic differences between responder and non-responder tumors, investigate molecular mechanisms of resistance or recurrence, and even help in the design of personalized therapeutic options for patients. Therefore, PDX models provide a uniquely strong tool to evaluate novel cancer therapies, and an excellent system to validate results obtained from genetically engineered mouse (GEM) models.

Figure 13:
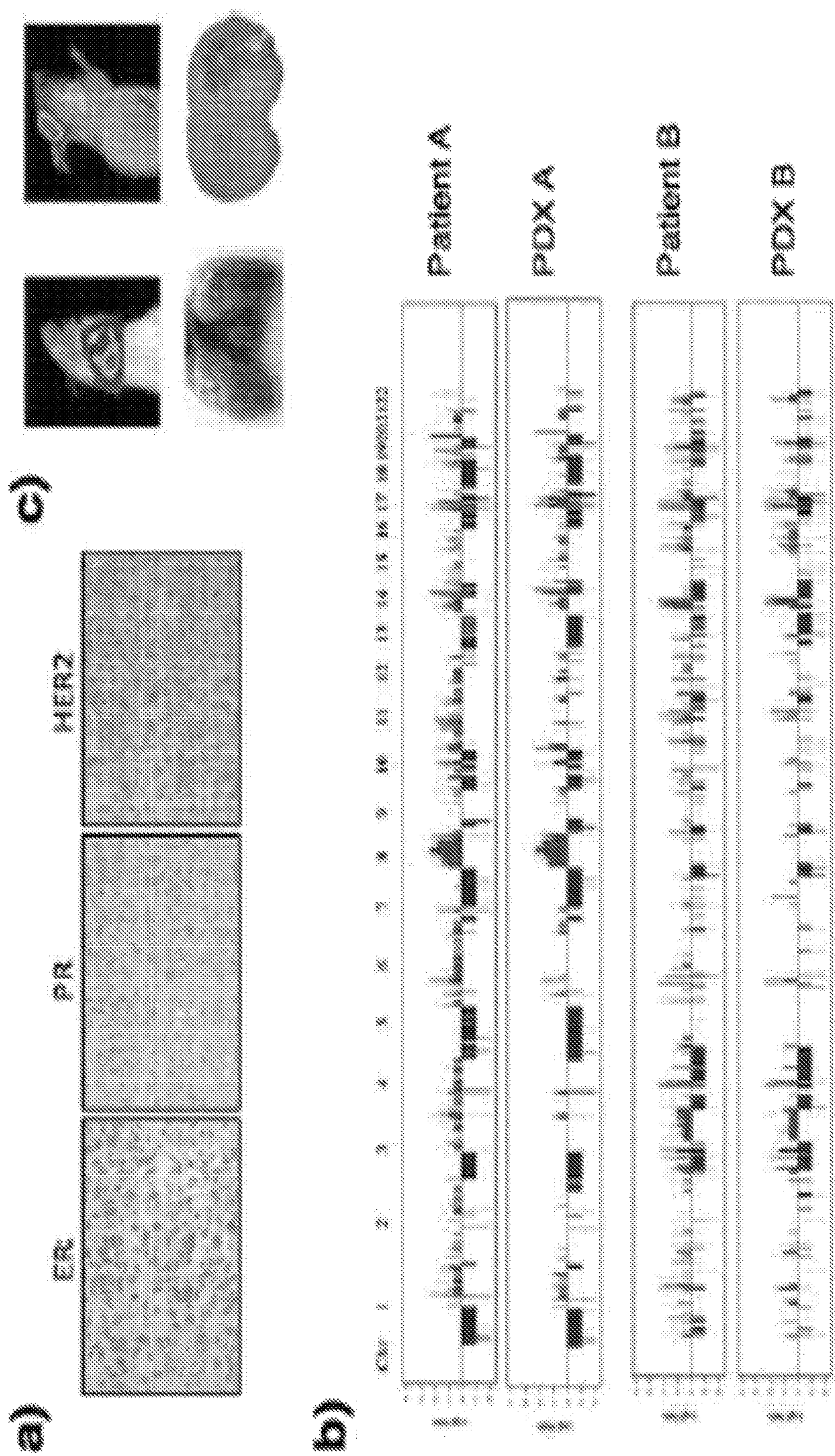
FIG. 13 includes 3 panels, identified as panels A, B, and C, which show that PDX models faithfully recapitulate patient-derived samples as shown by IHC analyses (Panel A), whole-exome sequencing (Panel B), and live imaging of metastatic lesions (Panel C).

Over twenty PDX models of TNBC from primary tumors and distal metastases (i.e., lungs, liver and brain) that faithfully recapitulate ER, PR and HER2 status, as shown by immunohistochemistry (IHC), have been established (FIG. 13A). This collection is under continuous expansion via tissue collection from newly diagnosed cases. Initial analyses of two PDX models by whole-exome sequencing demonstrate that these models retain the genetic features of patient-matched tumors (FIG. 13B). In addition, a luciferase gene can be introduced into the tumor cells to allow for live imaging of metastatic lesions (FIG. 13C).

IHC staining for PTEN and phosphorylated AKT, a major downstream target and effector of PI3K, are performed. IHC slides are scored blindly by two independent pathologists and potential mutations and copy number alterations in PTEN, as well as in other relevant genes, are identified such as by whole-exome sequencing. RNA-Seq is also used to examine gene expression profiles. PI3Kbeta-selective inhibitors, such as KIN-193, are tested on the PDX metastatic TNBC models. For example, early-passage, luciferase-tagged metastatic PDX tumors are transplanted into the third mammary fat pad of NODSCIDgamma (NSG) mice and treated as described above. Tumor growth is assessed as described above and metastatic dissemination is examined using luciferase imaging. Responses to PI3Kbeta inhibition are monitored and combination treatments using inhibitors to putative targets, such as immune checkpoints, are evaluated.

Without being bound by theory, it is believed that the majority of metastatic TNBC PDX models exhibit loss of PTEN expression, keeping in line with results described above. Based on the described genetically engineered mouse (GEM) models and in vivo studies on tumors derived from human PTEN-null cell lines, it is believed that PTEN-deficient PDX models are sensitive to PI3Kbeta inhibition. It is further believed that the combination of two pre-clinical approaches (i.e., a pure genetic model in immunocompetent mice and patient-derived samples in immunodeficient mice), effectively complement each other to assay therapeutic effects of the combination of isoform-selective PI3K inhibition and ICB immunotherapy.

Example 5: Combined PI3Kbeta and Immune Checkpoint Blockade Delays Ovarian Cancer Tumor Growth A previously generated GEM model of ovarian cancer (OvCa) driven by co-loss of p53 and PTEN (PP OvCa) demonstrated that PP OvCa tumors depend on PI3Kbeta for survival, as PP OvCa tumors with additional p110β deletion (PPB OvCa) exhibit significantly reduced tumor growth in vivo, while additional p110α deletion (PPA OvCa) does not affect tumor growth (Schmit et al (2014) *Proc. Natl. Acad. Sci. USA* 111:6395-400). Consistently, pharmacological p110β-specific inhibition (KIN193), but not p110α-specific (BYL719) inhibition, significantly inhibited tumor growth (Schmit et al (2014) *Proc. Natl. Acad. Sci. USA* 111:6395-400).

Figure 14:
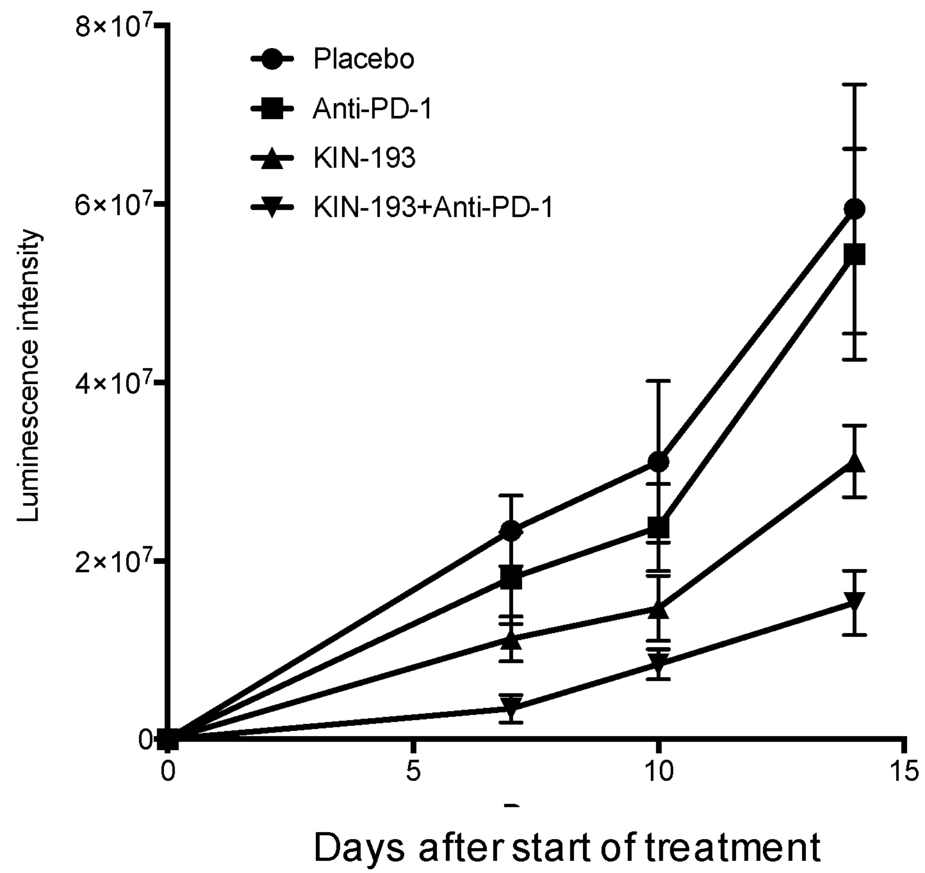
FIG. 14 shows that combined PI3Kbeta targeted therapy and ICB therapy synergize to inhibit PTEN/p53-deficient ovarian cancer tumor growth.

Hence, a serous ovarian cancer model suitable for experimental evaluation of combined PI3Kbeta and ICB was developed by deleting PTEN and p53, and over-expressing Myc. The combination of isoform-selective PI3Kbeta inhibition and ICB immunotherapy in this model of PTEN-deficient serous ovarian cancer was evaluated. PD-1 blockade by anti-mouse PD-1 monoclonal antibody did not affect tumor growth. Although PI3Kbeta inhibition by KIN193 delayed tumor growth compared to the vehicle control, combined PI3Kbeta inhibition and ICB significantly inhibited ovarian cancer tumor growth (FIG. 14). These results indicate that combined PI3Kbeta inhibition and ICB inhibits PTEN-null tumor growth in ovarian cancer with PTEN deficiency.

Example 6: Treating PTEN-Deficient Prostate Cancers

Since PTEN lesions are so common in primary prostate cancer (PCA), and become even more common (and focal) in advanced PCA, the PTEN pathway makes an attractive treatment target in this disease. However, the early clinical trials were not promising at all. One likely reason for this failure was due to a lack of understanding of the key catalytic isoforms of PI3K (see, for example, Lu et al. (2017) *Nature* 728-735). Using GEM models, it was demonstrated that, while tumors driven by oncogenes or receptor tyrosine kinases are dependent on p110α, those driven by PTEN loss are uniquely dependent on the p110β isoform. Notably, the prostate trials used so-called pan-PI3K inhibitors, which actually fail to sufficiently dampen the action of p110β. It is believed that PTEN loss, in addition to driving p110β activation, also activates pathways that render cells at least partially resistant to PI3K therapies. The mechanistic findings suggest novel targets that should be complementary to p110β inhibition. The main thrust is to initiate a clinical trial using p110β inhibitors to confirm the hypothesis and gain valuable information from the resulting patient derived data about markers for tumor sensitivity and both initial and acquired resistance. In addition, the mechanisms linking PTEN loss to p110β activation to obtain sufficient additional pre-clinical data has been investigated to prepare for trials attacking the novel mechanistic targets in combination with p110β-directed therapies and immunotherapies.

Specifically, the molecular details that uniquely couple PTEN loss to p110β activation are believed to be illustrated below, which not only explains how p110β is activated in response to PTEN loss, but also suggests why the same tumors might quickly become partially or even totally resistant to PI3K inhibition. The same mechanisms clearly suggest other therapeutic targets, under the same treatment or in combination with PI3K/p110β in PTEN-null tumors.

Step 1: Localizing p110β to Lipid Rafts

Figure 15:
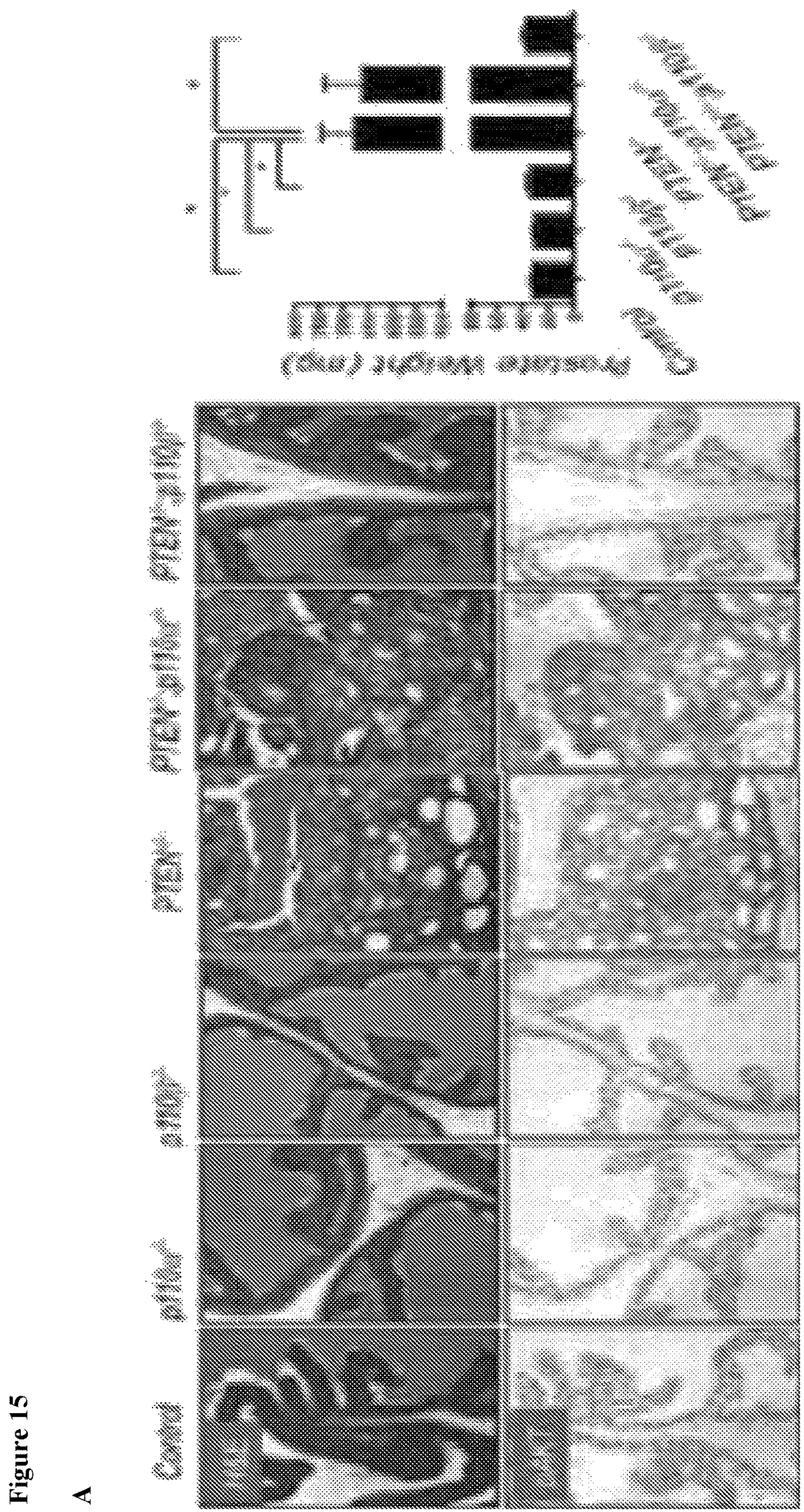
FIG. 15 includes 2 panels, identified as panels A, and B, which show the unique role of p110β in PTEN-null tumors (Panel A) and the cycle of Rac/p110β activation.
Figure 15:
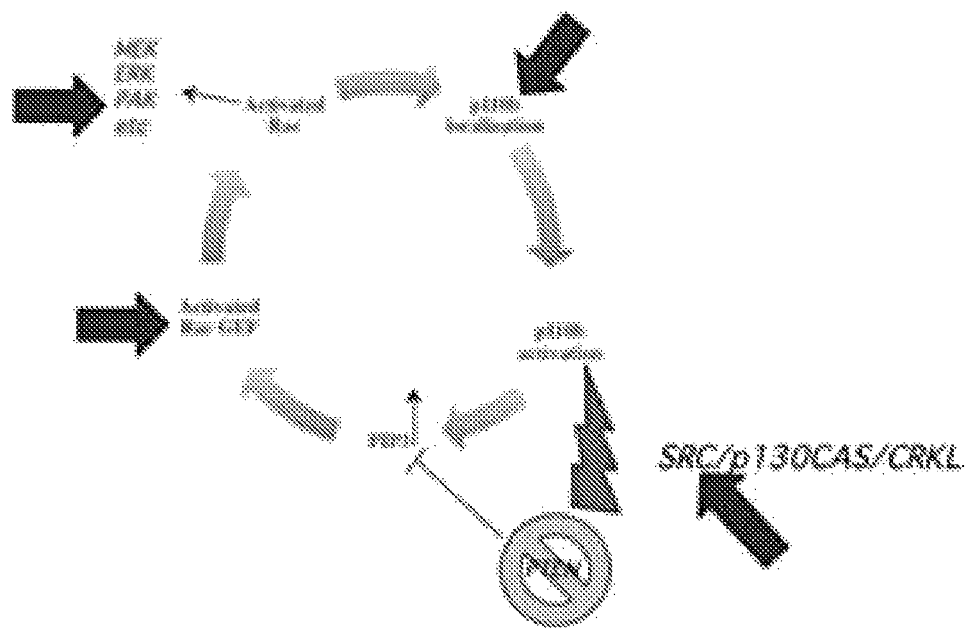

The first question to be addressed is how p110β is activated under physiological conditions by GPCRs. Since the plasma membrane is the major site of PI3K activation and integration of divergent growth factor signals, it was initially aimed to understand how spatial compartmentalization in the plasma membrane might contribute to the functions of the ubiquitous class IA phosphoinositide 3-kinase (PI3K) isoforms, p110α and p110β. Notably, GPCRs are known to be localized in lipid rafts. It was found that p110β also localizes to membrane rafts in a Rac1-dependent manner. This localization is required for Akt activation by G-protein-coupled receptors (GPCRs). Thus, genetic targeting of a Rac1 binding-deficient allele of p110β to rafts alleviated the requirement for p110β-Rac1 association for GPCR signaling, cell growth and migration. In contrast, p110α, which does not play a role in physiological GPCR signaling, is found to reside exclusively in nonraft regions of the plasma membrane. However it was shown that raft targeting of p110α by fusing a raft targeting motif from c-Lyn allows GPCR mediated activation of Akt by p110α. The discovery that Rac plays a key role in p110β activation via localization in lipid rafts led to a question about Rac's role in PTEN-null tumors. Notably, Rac interacts exclusively with p110β but not with p110α (Fritsch et al. (2013) *Cell* 153(5):1050-63). p110α is known to interact instead with Ras (Rodriguez-Viciana et al. (1994) *Nature* 370: 527-32; Rodriguez-Viciana et al. (1996) *EMBO J.* 15:2442-51). Thus, Rac activation is a necessary prelude to p110β activation, making Rac an upstream activator of p110β. However, Rac family members are unique in that their activators, the Rac GEFs, are known to be activated by the phosphoinositide products of PI3Ks. Thus, Rac is also a downstream effector of PI3Ks. Hence, the interactions of Rac and p110β constitute the very definition of a positive feedback loop. In the absence of PTEN, there is nothing to keep this positive feedback loop in check—a classic vicious cycle. This means that Rac inhibitors might be very useful in PTEN null tumors (see below) and might be ideal combination partners with p110β inhibitors. This has been proven and recently published (Yuzugullu et al. (2015) *Nat Commun.* 6:8501), diagrammed in FIG. 15.

Notably, p110β-dependent, PTEN null tumor cells critically also rely upon the integrity of their lipid rafts. As discussed below, lowering cholesterol can block both PI3K signaling and cell growth both in tissue culture and in tumors in vivo. Collectively, these findings provide a mechanistic account of how membrane raft localization regulates differential activation of distinct PI3K isoforms and offer insight into therapeutic approaches to complement p110b inhibition in PTEN null tumors.

Step 2 Activation of p110β

The data on the Rac/p110β feedback loop described above (see Yuzugullu et al. (2015) Nat Commun. 6:8501 for details) leaves open a big question: how the feedback loop is activated in the first place. While, in theory, p100β could be activated via its interactions with $G_{\beta\gamma}$ subunits of GPCRs, the current data suggest this is generally not the case. There must be something more to the activation process in the absence of PTEN. Novel p110β binding proteins is believed to solve the mechanism. Using taptag technology, CRKL was identified as a novel PI3Kβ interacting protein. Silencing endogenous CRKL expression in PTEN null human cancer cells led to a decrease in p110β-dependent PI3K signaling and cell proliferation. In contrast, CRKL depletion did not impair p110α-mediated signaling or growth. In addition, CRKL in turn binds to tyrosine-phosphorylated p130Cas in PTEN-null cancer cells. FAK/SRC family kinases have already been shown both to be negatively regulated by PTEN and to phosphorylate and activate p130Cas (Zhang et al. (2017) *Cell Reports* 20:1-9). Notably, both p130 CAS and CRKL also bind the very GEFs which activate Rac (Zhang et al. (2017), supra). These GEFs are in turn activated by the 3' phosphorylated phosphoinositides produced by p110β. This leads to the model shown in FIG. 11.

This model makes testable predictions. In this model, the PTEN loss leads to the activation of a number of signaling molecules in addition to PI3K. Two of these molecules, SRC and the MEK/ERK, are known to render cells resistant to PI3K inhibition (Cheng et al. (2016) *Oncogene.* 35:2961-2970). Further, inhibiting these pathways could synergize with PI3K inhibitors. As shown below, both predictions are believed to be true.

Pre-Clinical Testing of p110β Inhibitors in Combination with Compounds Targeting Candidates Discovered in Mechanistic Studies As targeted therapies are rarely effective as single agents, novel combinations of targeted therapies were investigated. Although inhibitor combinations that are successful in mice are often too toxic in clinical trials, p110β inhibitors are proving to have much lower on-target toxicity than pan-PI3K or p110α inhibitors. This is, in part, because p110β plays a lesser role in insulin action than p110α (Hill et al. (2009) *Endocrinology* 150:4874-4882; Sopasakis et al. (2010) *Cell Metabolism* 11:220-230; Xu et al. (2010) *Cell Metabolism* 12:88-95). Indeed, it is possible to have a healthy adult mouse with no p110β activity in any tissue in its body. For example, the tissue-specific p110β deletion in the bone marrow (Gritsman et al. (2014) *J Clin Invest.* 124:1794-1809; Yuzugullu et al. (2015) *Nat Commun.* 6:8501), liver (Sopasakis et al. (2010) *Cell Metabolism.* 11:220-230), mammary gland (Utermark et al. (2012) *Genes & Development.* 26:1573-1586), ovary (Schmit et al. (2014) *Proc Natl Acad Sci USA.* 111:6395-6400) or prostate (Jia et al. (2008) *Nature* 454:776-779) had little effect on the targeted tissue or the whole animal. Thus, efficacious combinations comprising p110β inhibitors are believed to be possible treatment options. The following examples illustrate identification of inhibitors targeting p110β localization, as well as its activation mode and/or novel downstream targets. In addition, clinical samples are used to test involvement of this pathway in human tumors (as outlined below). Established protocols are used, including animal studies and organoid tests, using various organoid models.

Targeting p110β Localization

Figure 16:
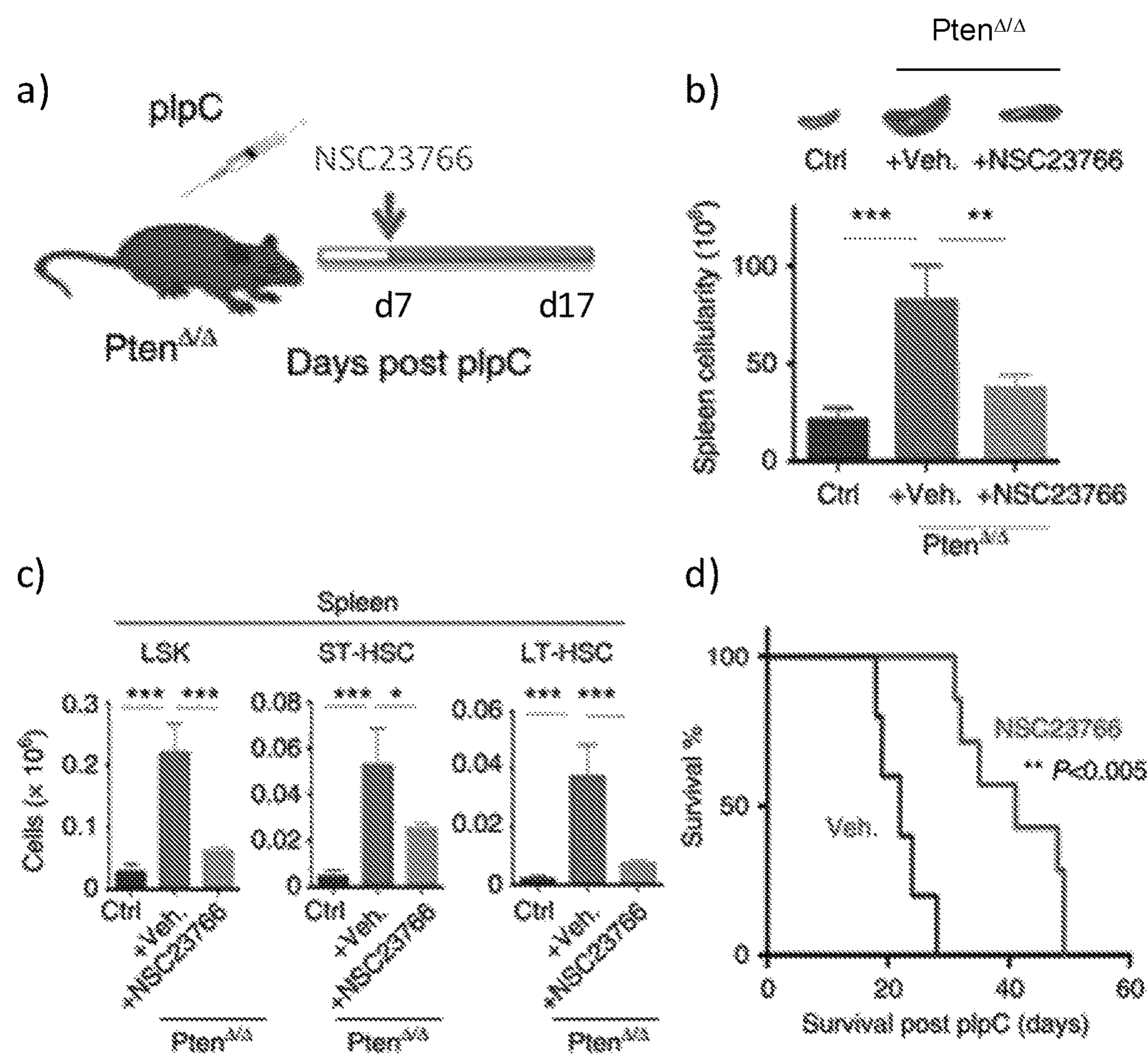
FIG. 16 includes 4 panels, identified as panels A, B, C, and D, which show the efficacy of Rac inhibitors in p110β-dependent tumors arising from PTEN-null hematopoietic stem cells.
Figure 17:
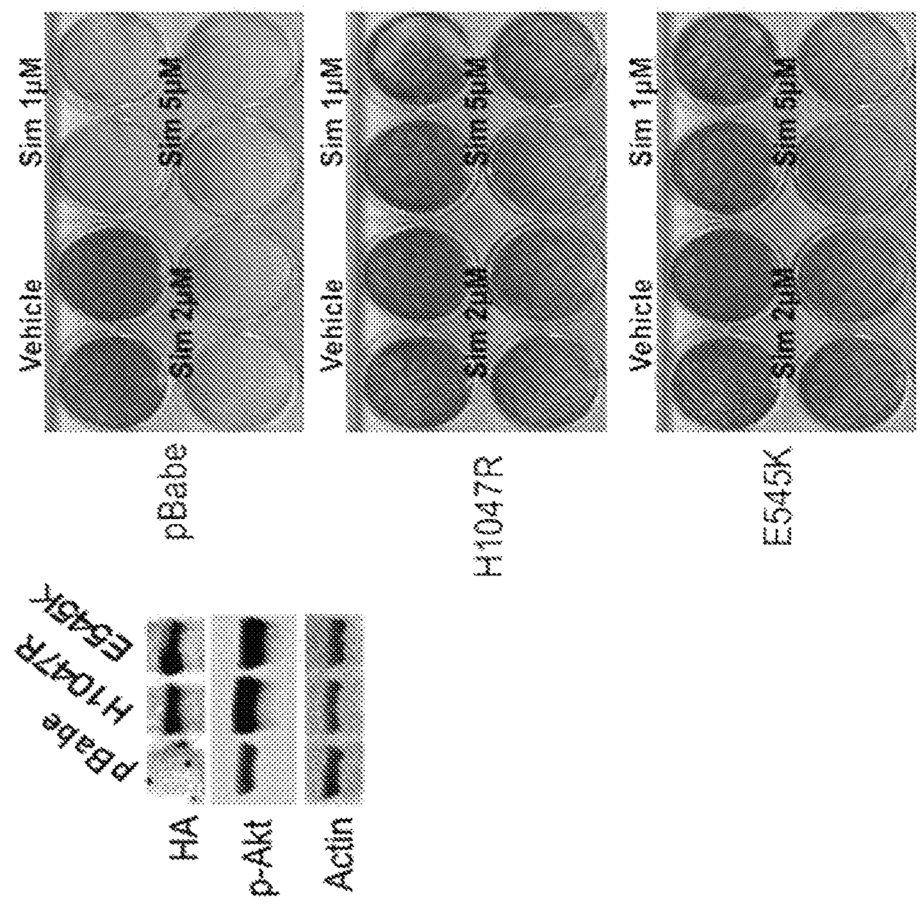
FIG. 17 includes 3 panels, identified as panels A, B, and C, which show that p110β-dependent PTEN-null tumor cell lines are sensitive to statins but can be rescued by activated alleles of p110α PC3 cells. Cells with wild-type Pten and PTEN-null cells that have had PTEN expression restored are not sensitive.
Figure 17:
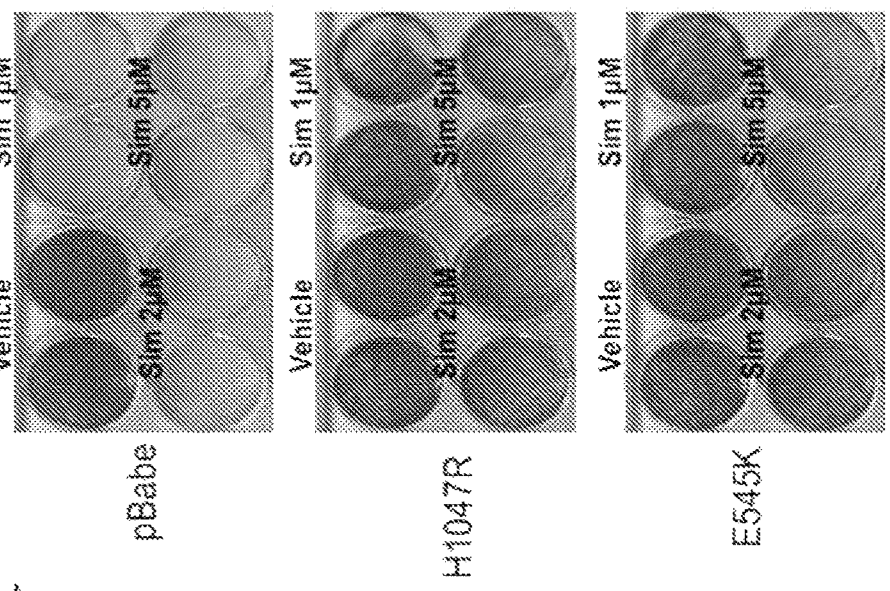
Figure 17:
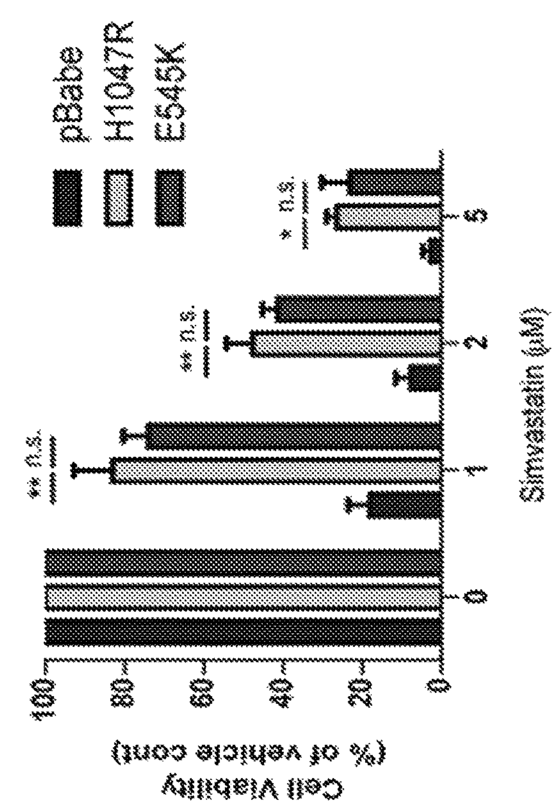

There are a large number of possible inhibitor combinations targeting p110β localization. Preliminary data indicated that inhibitors of the interaction between Rac and its GEFs effectively block the growth of PTEN-null human tumor cell lines and genetically engineered mouse (GEM) tumor models (FIG. 16; Yuzugullu et al. (2015) *Nat Commun.* 6:8501). However, lipid raft integrity was also required for the growth of PTEN null tumors (FIG. 17). It has been already found that statins are effective in vitro in a number of models (FIG. 17 and Cizmecioglu et al. (2016) *eLIFE* 5:e17635). Furthermore, the preliminary data showed that statins are effective in PTEN-null tumor models, in agreement with existing literature (Platz et al. (2006) *J Natl Cancer Inst.* 98(24):1819-25). Effective in vitro genetic controls are used to demonstrate that the effects of statins are actually occurring via p110β (FIG. 17 and Cizmecioglu et al. (2016) *eLIFE* 5:e17635). Since statins can only achieve relatively small reductions in cholesterol levels, other agents are also tested, including LXR agonists as well as antibodies targeting PCSK9, which can lower cholesterol to a much greater extent. In addition, prevention models will be examined, particularly in prostate cancer models.

Targeting p110β Activation and Downstream Signaling

It has been shown that in some cases the mechanism of activation of p110β via PTEN loss involves Src family members. Notably, published data showed that Src family kinases are activated by PTEN loss (Dey et al. (2008) *Cancer Res.* 68(6):1862-71). Src inhibitors, such as dasatinib, synergize with p110β inhibition in vitro. The same is true for inhibitors of PAK and MEK kinases that are activated downstream from Rac. In vivo validation of such inhibitors will be done accordingly. Combinations of PI3K or Akt inhibitors with MEK inhibitors have been poorly tolerated in clinical studies. However, since neither p110β nor Src inhibition nor cholesterol lowering is intrinsically toxic, further combinations may also be tolerated and be more effective. Optimal dosing schedules will be tested and found with similar protocols.

Testing of Immunotherapies Plus p110β Inhibitors

Figure 5:
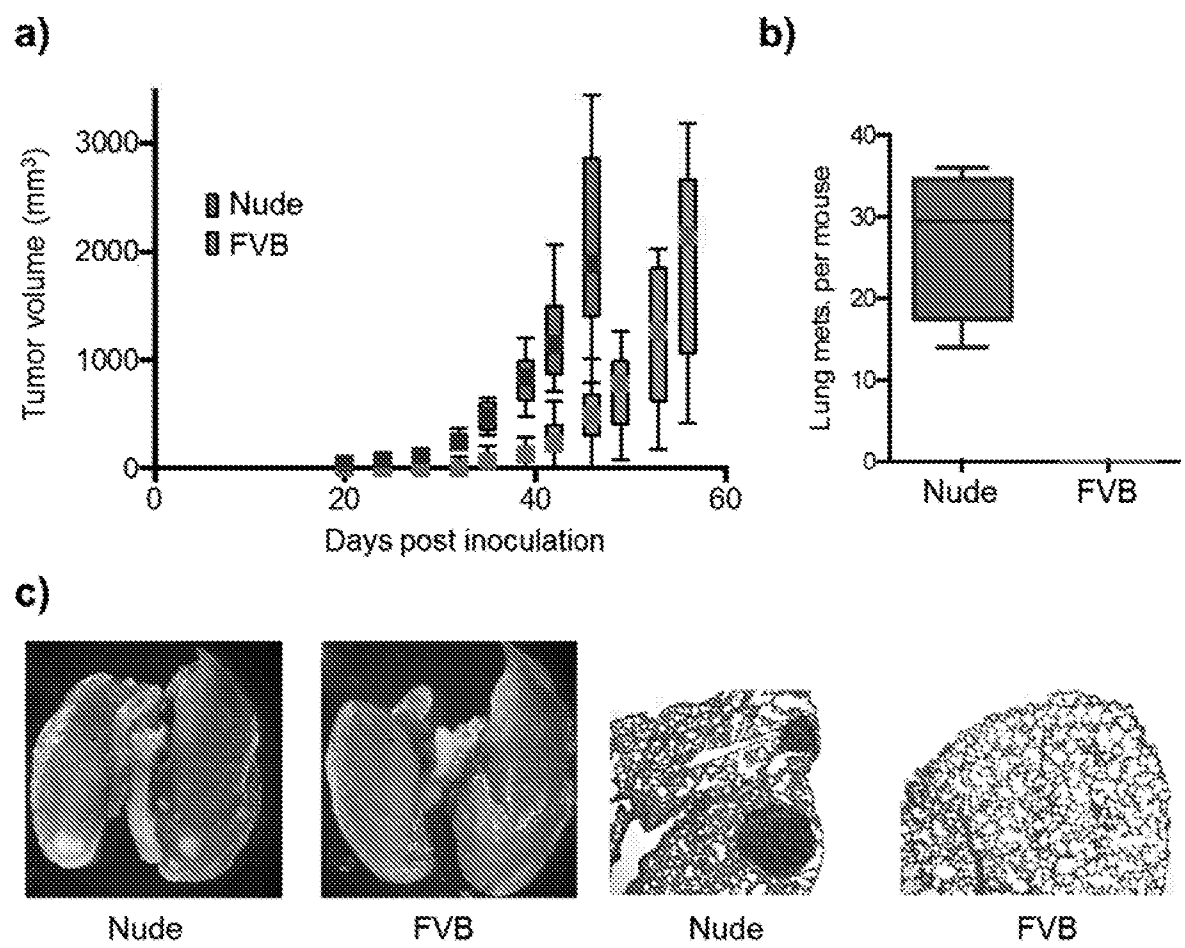
FIG. 5 includes 3 panels, identified as panels A, B, and C, which show that PP TNBC tumors grow faster (Panel A) and form metastatic nodules (Panels B-C) in immunocompromised (nude) mice.
Figure 6:
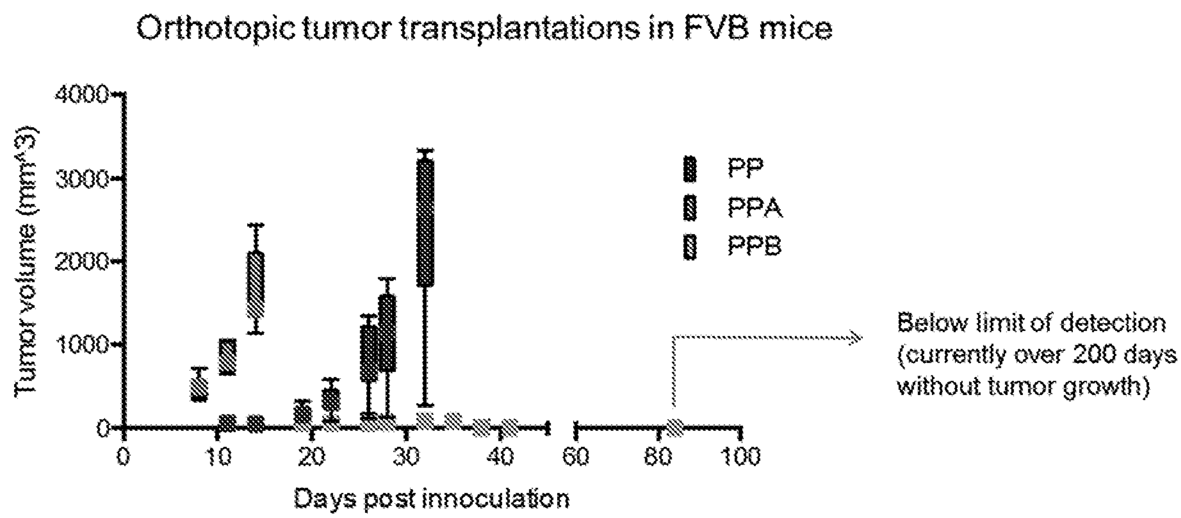
FIG. 6 shows that PP and PPA TNBC tumors grow in immunocompetent mice, while PPB tumors do not form tumors in immunocompetent mice.
Figure 18:
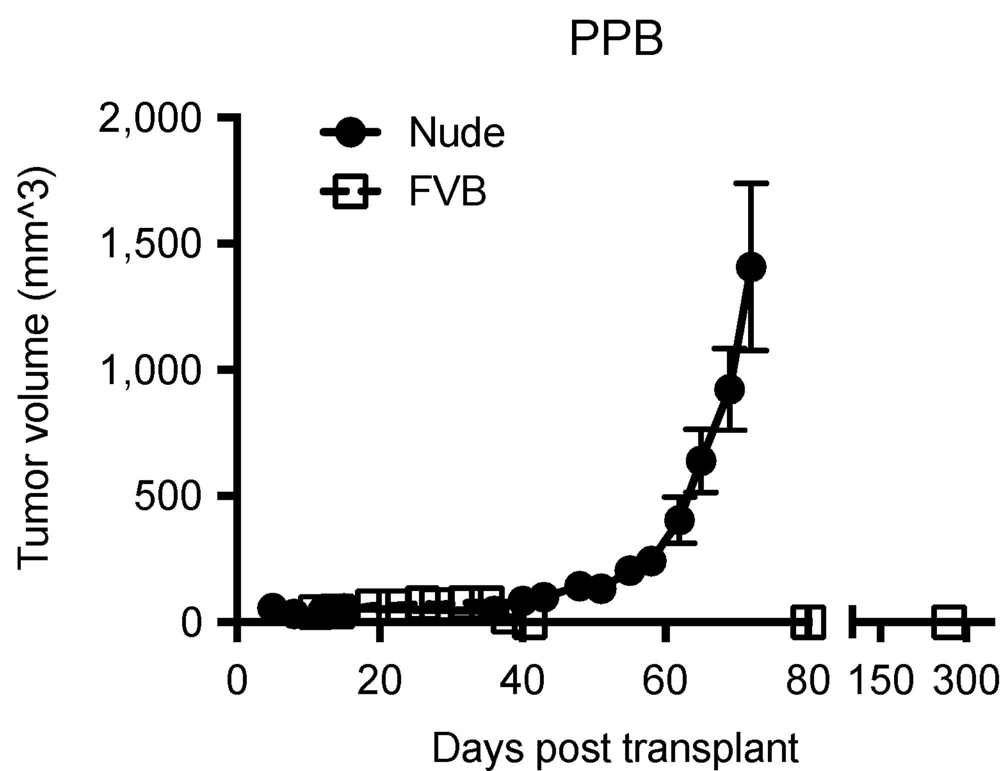
FIG. 18 shows that PP TNBC tumors with additional deletion of p110β (PPB TNBC) failed to grow in immunocompetent mice, but did form tumors in immunodeficient mice.

Immuno-oncology represents a huge opportunity in cancer therapy. At this point in time several so-called "checkpoint inhibitors" have been approved for melanoma and lung cancers. They also showing promise in prostate breast and brain cancers (e.g., Klein et al. (2015) *J. Immunol.* 194: 213.10). The beauty of this inhibitor class is that it offers much longer remissions than targeted inhibitors have usually been able to achieve. However, only a fraction of a given type of tumors respond. This is the opposite of targeted therapies that give broad responses in tumors of the correct genotype, but for which responses are usually of limited duration. Thus, current research is aimed at combining the best of both therapies to achieve broad and lasting tumor responses in susceptible tumor types. Notably, PTEN loss has been suggested to be a mode of resistance to checkpoint inhibitors, which may explain why prostate tumors have responded to ICB less well than melanomas. One worry with targeted therapies is that they might adversely alter immune function. However, it was shown that knocking out p110β in hematopoietic stem cells had no effect on the immune system. Moreover, since PTEN loss appears to frequently function via p110β inhibiting, p110β is expected to increase sensitivity to checkpoint inhibition. As described above, promising data have been built up on the effects of combining p110b knockout and inhibition with anti-PD1 in a PTEN/P53 (PP) knockout GEMN model of triple negative beast cancer. As shown in FIG. 5, PP TNBC tumors grow at a faster rate in immunocompromised mice (athymic nude) than in syngeneic immunocompetent mice (FVB strain). Signaling through PI3K-p110β is critical to mediate immune evasion, as PP TNBC tumors with additional deletion of p110β (PPB TNBC) fail to grow in immunocompetent mice, but do form tumors in immunodeficient mice (FIG. 18). A PTEN null/Erg allograft model of prostate cancer is generated to test these results in prostate cancer models.

The optimal timing of the administration of the two therapies (current theory suggests treating tumors with targeted therapy first to elicit tumor cell killing, which generates innate immune responses and primes later adaptive immune therapy) is tested. For example, different sequences of, and/or timings between, combinational therapies are to be tested. The most effective sequence(s)/timing(s) of combination therapies are arrived at by comparing the therapeutic results of each tested therapy. Similarly, the effectiveness of p110β inhibitors with other immunotherapies, such as anti-PDL1/2, is also tested. Other drugs targeting p110β localization, activation, and signaling discussed above, in combination with immunotherapies, are tested similarly. Moreover, the effect of increasing the burden of "neoantigens" is also tested in the same models. For example, the mutator alleles of DNA polymerase ε, Polε (P286R) are exogenously expressed (Kane et al. (2014) *Cancer Res.* 74(7): 1895-901; Shinbrot et al. (2014) *Genome Res.* 24(11): 1740-50) to generate matched tumors in which the numbers of neoantigens ranges from quite low to very high. As described herein, multiple approaches are to be used to maximize the therapeutic efficacy of combining immunotherapies with PI3Kbeta-directed directed therapies in the very large class of PTEN deficient human tumor.

Clinical Trial of a p110β Inhibitor in Combination with AR Targeted Therapy

An approved clinical trial for the SPORE project is ongoing. Organoid and slice cultures are to be established from the trial. Samples from the trial and existing samples are used to test mechanistic hypotheses and to validate preclinical discovery of combinational therapies. To measure pathway activation in pathology samples, multiplexed methods for pathway analysis are used in both frest tissue and fixed samples from previous trial. For example, validation of mechanisms underlying any effects of PI3K pathway activation on responses to checkpoint blockade, seen in preclinical studies, is to be performed with trial samples. This work forms the basis for a second trial combining p110β inhibition with checkpoint blockade. In addition to testing the effects of p110β inhibition on the tumors visibility to the immune system, the effects of inhibitors on the immune system itself are also to be tested. Pre-clinical studies showed that knockout of p110β has little effect on immune system function. However, after testing clinical candidate p110β inhibitors, the inhibition may be effective in vivo.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web at tigr.org and/or the National Center for Biotechnology Information (NCBI) on the World Wide Web at ncbi.nlm.nih.gov.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating a subject afflicted with an epithelial cancer that is deficient in phosphatase and tensin homolog (PTEN) comprising administering to the subject a combination therapy comprising a therapeutically effective amount of 5-(2,6-dimorpholin-4-ylpyrimidin-4-yl)-4-(trifluoromethyl)pyridin-2-amine (BKM120) and/or (−)-2-[[(1R)-1-[7-Methyl-2-(4-morpholinyl)-4-oxo-4H-pyrido[1,2-a]pyrimidin-9-yl]ethyl]amino]benzoic acid (KIN193); and an anti-PD1 monoclonal antibody, that inhibits or blocks both phosphoinositide 3-kinase isoform beta (PI3Kbeta) and an immune checkpoint, wherein the epithelial cancer is selected from a breast cancer, an ovarian cancer, or a prostate cancer.

2. The method of claim 1, wherein the anti-PD1 monoclonal antibody is murine, chimeric, humanized, composite, or human.

3. The method of claim 2, wherein the anti-PD1 monoclonal antibody is detectably labeled.

4. The method of claim 2, wherein the anti-PD1 monoclonal antibody is conjugated to a cytotoxic agent.

5. The method of claim 1, wherein the combination therapy a) reduces the number of proliferating cells in the cancer and/or reduces the volume or size of a tumor of the cancer;

b) increases the number of viable CD8+ T cells within a tumor of the cancer; and/or c) is administered in a pharmaceutically acceptable formulation.

6. The method of claim 1, further comprising administering to the subject a therapeutic agent or regimen for treating the cancer.

7. The method of claim 1, wherein the PTEN deficiency comprises a mutation to a genomic nucleic acid sequence encoding PTEN.

8. The method of claim 1, wherein the PTEN deficiency is determined to be very low or null, as assessed by immunohistochemistry, or is a mutation to a genomic nucleic acid sequence encoding PTEN protein and the mutation is a missense mutation, a nonsense mutation, a frameshift mutation, an insertion mutation, a deletion mutation, or a rearrangement mutation of a PTEN codon C71, R130, R233, D268, T319 or X70, or phosphatase or C2 domains.

9. The method of claim 1, wherein the cancer has a p53 deficiency.

10. The method of claim 9, wherein the p53 deficiency is a mutation to a genomic nucleic acid sequence encoding p53 protein and the mutation is a missense mutation, a nonsense mutation, a frameshift mutation, an insertion mutation, a deletion mutation, or a rearrangement mutation of a p53 codon L45, Y126, P151, 5166, R175, C176, H179, G187, H193, L194, R196, R213, Y220, C242, G245, R248, R249, R273, R280, D281, R282, E286, E294, or transactivation, DNA-binding or oligomerization domains.

11. The method of claim 10, wherein the p53 deficiency is a germline or somatic p53 null mutation.

12. The method of claim 1, wherein a) the breast cancer is triple negative breast cancer (TNBC) and/or metastatic TNBC, or b) wherein the ovarian cancer is serous ovarian cancer.

13. The method of claim 1, wherein the subject is a) an animal model of the epithelial cancer; or b) a mammal.

14. The method of claim 4, wherein the cytotoxic agent is selected from the group consisting of a chemotherapeutic agent, a biologic agent, a toxin, and a radioactive isotope.

15. The method of claim 7, wherein the mutation is selected from the group consisting of a missense mutation, a nonsense mutation, a frameshift mutation, an insertion mutation, a deletion mutation, and a rearrangement mutation.

16. The method of claim 8, wherein the PTEN deficiency is a) a null mutation and/or 2) a germline or somatic null mutation.

17. The method of claim 10, wherein the p53 deficiency is a) a null mutation and/or 2) a germline or somatic null mutation.

18. The method of claim 13, wherein a) the animal model of the epithelial cancer is an orthotopic xenograft animal model of a human-derived epithelial cancer and/or a mouse model; or b) the mammal is a mouse or a human.

* * * * *